US012459929B2

(12) United States Patent
Du

(10) Patent No.: US 12,459,929 B2
(45) Date of Patent: Nov. 4, 2025

(54) GPCR RECEPTOR AGONISTS, PHARMACEUTICAL COMPOSITIONS COMPRISING THE SAME, AND METHODS FOR THEIR USE

(71) Applicant: Carmot Therapeutics Inc., South San Francisco, CA (US)

(72) Inventor: Xiaohui Du, Belmont, CA (US)

(73) Assignee: Carmot Therapeutics Inc., South San Francisco, CA (US)

( * ) Notice: Subject to any disclaimer, the term of this patent is extended or adjusted under 35 U.S.C. 154(b) by 0 days.

(21) Appl. No.: 19/020,628

(22) Filed: Jan. 14, 2025

(65) Prior Publication Data

US 2025/0154137 A1 May 15, 2025

Related U.S. Application Data

(63) Continuation of application No. 18/262,956, filed as application No. PCT/US2022/014156 on Jan. 27, 2022, now abandoned.

(60) Provisional application No. 63/274,893, filed on Nov. 2, 2021, provisional application No. 63/183,612, filed on May 3, 2021, provisional application No. 63/143,025, filed on Jan. 28, 2021.

(51) Int. Cl.

| | |
|---|---|
| ***C07D 405/14*** | (2006.01) |
| ***A61K 31/4439*** | (2006.01) |
| ***A61K 31/444*** | (2006.01) |
| ***A61K 31/496*** | (2006.01) |
| ***A61K 31/506*** | (2006.01) |
| ***A61K 31/55*** | (2006.01) |
| ***A61P 3/08*** | (2006.01) |
| ***A61P 5/50*** | (2006.01) |
| ***C07D 401/14*** | (2006.01) |
| ***C07D 403/06*** | (2006.01) |
| ***C07D 403/14*** | (2006.01) |
| ***C07D 405/06*** | (2006.01) |
| ***C07D 405/12*** | (2006.01) |
| ***C07D 409/14*** | (2006.01) |
| ***C07D 413/14*** | (2006.01) |
| ***C07D 471/04*** | (2006.01) |
| ***C07D 487/08*** | (2006.01) |

(52) U.S. Cl.

CPC ........ *C07D 405/14* (2013.01); *A61K 31/4439* (2013.01); *A61K 31/444* (2013.01); *A61K 31/496* (2013.01); *A61K 31/506* (2013.01); *A61K 31/55* (2013.01); *A61P 3/08* (2018.01); *A61P 5/50* (2018.01); *C07D 401/14* (2013.01); *C07D 403/06* (2013.01); *C07D 403/14* (2013.01); *C07D 405/06* (2013.01); *C07D 405/12* (2013.01); *C07D 409/14* (2013.01); *C07D 413/14* (2013.01); *C07D 471/04* (2013.01); *C07D 487/08* (2013.01)

(58) Field of Classification Search

CPC .................................................... C07D 405/14

See application file for complete search history.

(56) References Cited

U.S. PATENT DOCUMENTS

| | | | |
|---|---|---|---|
| 10,844,049 | B2 | 11/2020 | Zhong |
| 2018/0170908 | A1 | 6/2018 | Aspnes et al. |
| 2019/0382384 | A1 | 12/2019 | Aspnes et al. |
| 2020/0325121 | A1 | 10/2020 | Zhong et al. |
| 2020/0407347 | A1 | 12/2020 | Coates et al. |

FOREIGN PATENT DOCUMENTS

| | | | | |
|---|---|---|---|---|
| CA | 3045644 | A1 | 12/2019 | |
| WO | WO-2018109607 | A1 * | 6/2018 | ......... A61K 31/4545 |
| WO | 2020103815 | A1 | 5/2020 | |
| WO | 2020207474 | A1 | 10/2020 | |
| WO | 2020234726 | A1 | 11/2020 | |
| WO | 2021096284 | A1 | 5/2021 | |
| WO | 2022042691 | A1 | 3/2022 | |
| WO | 2023029380 | A1 | 3/2023 | |

OTHER PUBLICATIONS

International Search Report for PCT/US2022/014156 issued on Aug. 4, 2022.

International Search Report for PCT/US2022/027535 dated Sep. 6, 2022.

* cited by examiner

*Primary Examiner* — Jeffrey S Lundgren
*Assistant Examiner* — Eric Tran

(57) ABSTRACT

Provided herein are GLP-1 receptor modulator compounds, pharmaceutical compositions, methods of their preparation, and methods of their use in treatment, and/or diagnosis.

6 Claims, 1 Drawing Sheet

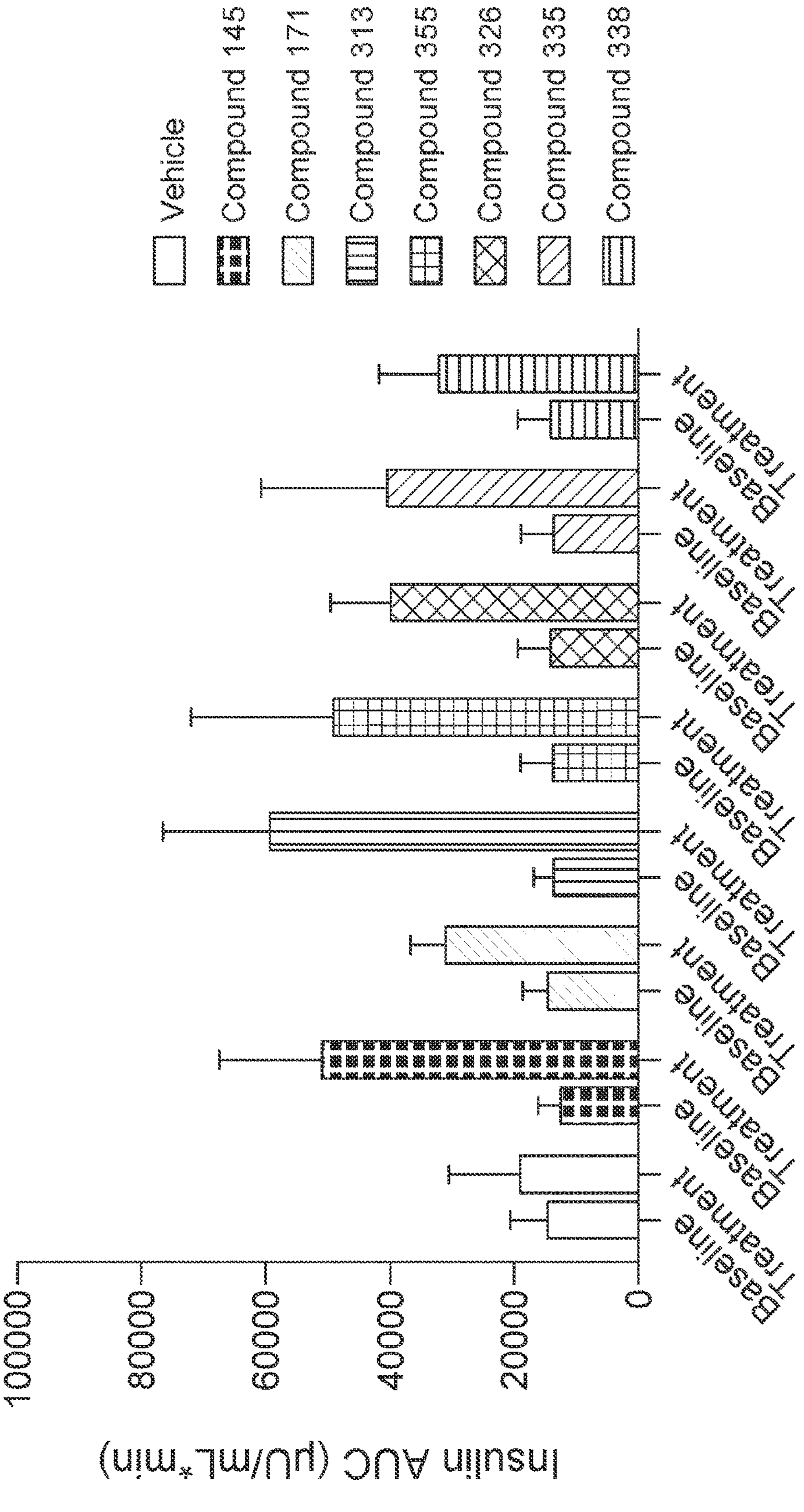
Insulin AUC (μU/mL*min)
100000
80000
60000
40000
20000
0
Baseline
Treatment
Vehicle
Compound 145
Compound 171
Compound 313
Compound 355
Compound 326
Compound 335
Compound 338

GPCR RECEPTOR AGONISTS, PHARMACEUTICAL COMPOSITIONS COMPRISING THE SAME, AND METHODS FOR THEIR USE

CROSS-REFERENCES TO RELATED APPLICATIONS

This application is a continuation of U.S. application Ser. No. 18/262,956, filed Jul. 26, 2023, which is a national stage application under U.S.C. § 371 of International Application No. PCT/US2022/014156, filed Jan. 27, 2022, claiming the benefit of U.S. Provisional Application No. 63/274,893, filed on Nov. 2, 2021, U.S. Provisional Application No. 63/183,162, filed on May 3, 2021, U.S. Provisional Application No. 63/143,025, filed Jan. 28, 2021, the entire contents of which are incorporated by reference herein.

FIELD

Provided herein are GLP-1 receptor modulator compounds; pharmaceutical compositions comprising the compounds; methods of producing the compounds; and methods of using the compounds, and compositions for therapy. The compounds, and compositions are useful, for instance, in methods of treatment, and prevention of metabolic diseases or conditions, methods of detection of metabolic diseases or conditions, and methods of diagnosis of metabolic diseases or conditions.

BACKGROUND

Diabetes is a serious chronic disease that occurs when the pancreas does not produce enough insulin, or when the body cannot effectively use the insulin it produces. Complications of diabetes include, damage to the heart, blood vessels, eyes, kidneys, and nerves. Diabetes can increase risk of heart disease, and stroke. The results include serious effects on quality of life, health, and mortality. *WHO Global Report on Diabetes,* 2016, World Health Organization. As of 2017, approximately 462 million individuals worldwide, about 6.28% of the population was affected by type 2 diabetes, and this prevalence was increasing measurably. Khan et al., 2020*, J. Epidemiol. Glob. Health* 10 (1): 107-111. The global economic burden of diabetes in 2015 was estimated to be $1.3T, and estimated to increase to $2.1T by 2030. Bommer et al., 2018*, Diabetes Care* 41 (5): 963-970. Approximately 90-95% of all diabetes cases are type 2 diabetes. Tripathi & Srivastava, 2016*, Med. Sci. Monit.* 12 (7): RA130-147.

The glucagon-like peptide-1 receptor (GLP-1 receptor, or GLP1R) has emerged as a potential target for treating type 2 diabetes. Its ligand, glucagon-like peptide-1 (GLP-1) enhances glucose-induced insulin secretion, and increases insulin synthesis among many other effects. Doyle and Egan, 2007*, Pharmacol. Ther.* 113 (3): 546-593. GLP-1 is known to delay gastric emptying, suppress food intake, increase satiety, and reduce weight in humans. Shah and Vella, 2014 *Rev Endocr Metab Disord.* 15 (3): 181-187. Activating the GLP-1 receptor has been shown to have beneficial effects on insulin secretion and the maintenance of beta cell glucose sensing, transcription, synthesis, proliferation, and survival. Doyle and Egan, 2007, supra. While the GLP-1 receptor is a promising therapeutic target, only a handful of GLP-1 receptor drugs have been approved to date, and most, or all of these are peptide, or polypeptide drugs.

There is a need for additional therapies for treating metabolic diseases, and conditions, like type 2 diabetes. Small molecules targeting GLP-1 receptor should provide safe, stable, and easy to administer therapeutics for metabolic diseases, and conditions such as type 2 diabetes.

SUMMARY

Provided herein are GLP-1 receptor modulator compounds of Formulas (I)-(XVIII), (XXV)-(XXVII), (XXX), (XXXI), (XXXIX), and (XL-XLVII), and sub-formulas thereof, compositions comprising the compounds, methods of producing the compounds, and methods of using the compounds, and compositions in treatment, and diagnosis. The compounds of Formula (I)-(XVIII), (XXV)-(XXVII), (XXX), (XXXI), (XXXIX), and (XL-XLVII), and sub-formulas and embodiments thereof, are useful for modulating the activity of GLP-1 receptor. In certain embodiments, the compounds can be used to agonize the activity of GLP-1 receptor. In certain embodiments, the compounds can be used for treating diseases, or conditions modulated by GLP-1 receptor.

In one aspect, provided is a compound of Formula (I), or a pharmaceutically acceptable salt, or stereoisomer thereof:

I

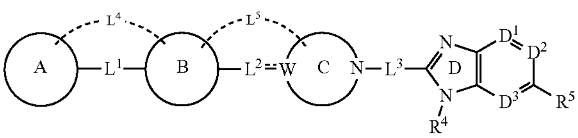

wherein, A is substituted or unsubstituted aryl, substituted or unsubstituted heteroaryl, substituted or unsubstituted cycloalkyl, —$NMe_2$, or —$CF_3$;

Ring B is substituted or unsubstituted aryl, substituted or unsubstituted heteroaryl, or substituted or unsubstituted bicyclic;

Ring C is substituted or unsubstituted heterocycloalkyl, or substituted or unsubstituted heterocycloalkenyl, each comprising at least one N, linked to $L^3$ as depicted;

zero, one, or two of $D^1$, $D^2$, and $D^3$ are N, and the rest are CH, or $CR^6$;

W is N, $CR^{14}$, or C; when W is $CR^{14}$, the adjacent dashed line indicates a single bond; when W is C, the adjacent dashed line indicates a double bond or $L^2$ is —C(H)═;

$L^1$ is selected from the group consisting of a bond, —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—;

$L^2$ is selected from the group consisting of a bond, —C(O)—, —$CH_2$—, —C(H)═, —$SO_2$—, —O—, —$CF_2$—. —CHF—, —CH(OH)—, —NH—, —N(Me)-, and

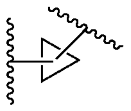

;

$L^3$ is —$CH_2$—, or —C(O)—;

$L^4$ is absent, or $L^4$ together with $L^1$ and Rings A and B form a fused tricycle, and $L^5$ is absent;

$L^5$ is absent, or $L^5$ together with $L^2$ and Rings B and C form a fused tricycle, and $L^4$ is absent;

$R^4$ is unsubstituted alkyl, substituted alkyl, unsubstituted arylalkylene, substituted arylalkylene, unsubstituted heteroalkyl, substituted heteroalkyl, unsubstituted heteroarylalkylene, substituted heteroarylalkylene, unsubstituted heterocycloalkylalkylene, or substituted heterocycloalkylalkylene;

$R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

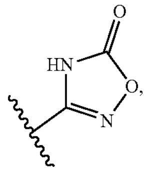

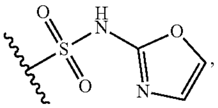
,

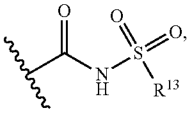
,

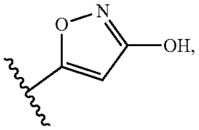
,

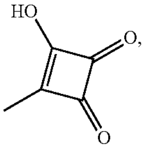
, and tetrazolyl;

each $R^6$ is independently selected from the group consisting of alkyl, substituted alkyl, halo, hydroxyl, alkoxyl, $R^{11}R^{12}NCO$—, and $R^{11}R^{12}N$—;

$R^{11}$ is hydrogen, or alkyl;

$R^{12}$ is hydrogen, or alkyl;

$R^{13}$ is hydrogen, or alkyl;

$R^{14}$ is hydrogen, cyano, halo, hydroxyl, alkyl, haloalklyl, methyl, $CH_2F$, or $CH_2OH$;

wherein when $L^1$ is a —$CH_2O$—, $L^4$ is absent, and $L^5$ is absent, then either $L^2$ is —C(O)—, —$CH_2$—, —C(H)═, —$SO_2$—, —O—, —NH—, —N(Me)-, or

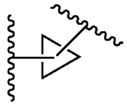
, or $L^3$ is —C(O)—, or both.

In one aspect, provided is a compound of Formula (Ia), or a pharmaceutically acceptable salt, or stereoisomer thereof:

Ia

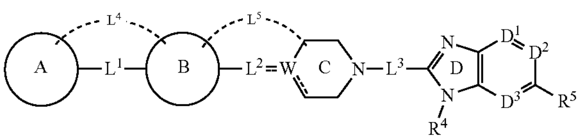

wherein, A is substituted or unsubstituted aryl, substituted or unsubstituted heteroaryl, substituted or unsubstituted cycloalkyl, —$NMe_2$, or —$CF_3$;

Ring B is substituted or unsubstituted aryl, or substituted or unsubstituted heteroaryl;

Ring C is further unsubstituted or further substituted, and/or bridged;

zero, one, or two of $D^1$, $D^2$, and $D^3$ are N, and the rest are CH or $CR^6$;

W is N, CH, or C; when W is CH the adjacent dashed lines indicate single bonds;

when W is C, one adjacent dashed line indicates a double bond, for instance $L^2$ is —C(H)═;

$L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—;

$L^2$ is selected from the group consisting of a bond, —C(O)—, —$CH_2$—, —C(H)═, —$CF_2$—, —$SO_2$—, —O—, —NH—, —N(Me)-, and

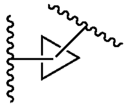
;

$L^3$ is —$CH_2$—, or —C(O)—;

$L^4$ is absent, or $L^4$ together with $L^1$ and Rings A and B form a fused tricycle, and $L^5$ is absent;

$L^5$ is absent, or $L^5$ together with $L^2$ and Rings B and C form a fused tricycle, and $L^4$ is absent;

$R^4$ is unsubstituted alkyl, substituted alkyl, unsubstituted arylalkylene, substituted arylalkylene, unsubstituted heteroalkyl, substituted heteroalkyl, unsubstituted heteroarylalkylene, substituted heteroarylalkylene, unsubstituted heterocycloalkylalkylene, or substituted heterocycloalkylalkylene;

$R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

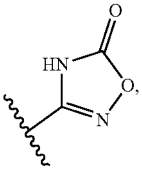
,

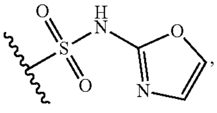
,

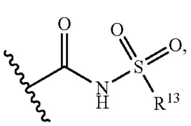
,

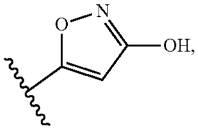
,

-continued

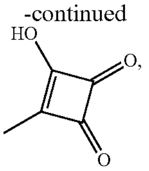

and tetrazolyl;

each $R^6$ is independently selected from the group consisting of alkyl, substituted alkyl, halo, hydroxyl, alkoxyl, $R^{11}R^{12}NCO$—, and $R^{11}R^{12}N$—;

$R^{11}$ is hydrogen or alkyl;

$R^{12}$ is hydrogen or alkyl; and $R^{13}$ is hydrogen or alkyl;

wherein, when $L^1$ is —$CH_2O$—, $L^4$ is absent, and $L^5$ is absent, then either $L^2$ is —C(O)—, —$CH_2$—, —C(H)═, —$SO_2$—, —O—, —NH—, —N(Me)-, or

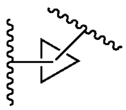

, or $L^3$ is —C(O)—, or both.

In one aspect, provided is a compound of Formula (XXX), or a pharmaceutically acceptable salt, or stereoisomer thereof:

XXX

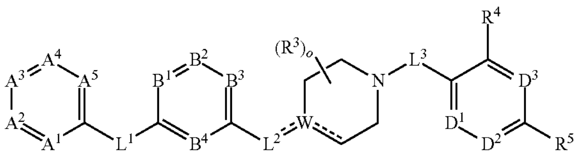

Wherein, W is N, CH, or C; when W is CH, the adjacent dashed lines indicate single bonds;

when W is C, one adjacent dashed line indicates a double bond, for instance $L^2$ is —C(H)═;

zero, one, or two of $A^1$, $A^2$, $A^3$, $A^4$, and $A^5$ are N, and the rest are CH or $CR^1$;

zero, one, or two of $B^1$, $B^2$, $B^3$, and $B^4$ are N, and the rest are CH or $CR^2$;

zero, one, or two of $D^1$, $D^2$, and $D^3$ are N, and the rest are CH or $CR^6$;

$L^1$ is selected from the group consisting of —O—, —$CH_2$—, —NH—, —N(Me)-, —N(Et)-, —$OCH_2$—, —$CH_2O$—, —$NHCH_2$—, —N(Me)$CH_2$—, and —$SO_2NH$—;

$L^2$ is selected from the group consisting of a bond, —C(O)—, —$CH_2$—, —C(H)═, —$SO_2$—, —O—, —$CF_2$—, —CHF—, —CH(OH)—, —NH—, —N(Me)-, and

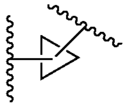

;

$L^3$ is —$CH_2$—, or —C(O)—;

each $R^1$ is independently selected from the group consisting of alkyl, substituted alkyl, halo, cyano, azido, alkoxy, haloalkoxy, and $R^{11}R^{12}NCO$—;

each $R^2$ is independently selected from the group consisting of alkyl, substituted alkyl, halo, cyano, azido, alkoxy, haloalkoxy, and $R^{11}R^{12}NCO$—;

each $R^3$ is independently selected from the group consisting of alkyl, substituted alkyl, halo, cyano, azido, alkoxy, haloalkoxy, and $R^{11}R^{12}NCO$—;

$R^4$ is unsubstituted alkyl, substituted alkyl, unsubstituted heteroalkyl, substituted heteroalkyl, unsubstituted heterocycloalkylalkylene, or substituted heterocycloalkylalkylene;

$R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

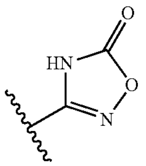

,

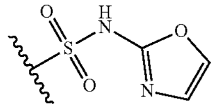

,

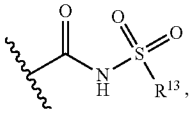

,

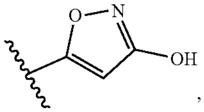

,

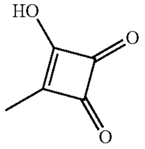

, and tetrazolyl;

each $R^6$ is independently selected from the group consisting of alkyl, substituted alkyl, halo, hydroxyl, alkoxyl, $R^{11}R^{12}NCO$—, and $R^{11}R^{12}N$—;

$R^{11}$ is hydrogen, or alkyl;

$R^{12}$ is hydrogen, or alkyl;

$R^{13}$ is hydrogen, or alkyl; and o is an integer from 0 to 4.

In one aspect provided herein is a compound of Formula XXXI, or a pharmaceutically acceptable salt, or stereoisomer thereof:

XXXI

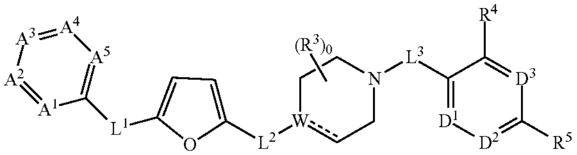

wherein W is N, CH, or C; when W is CH, the adjacent dashed lines indicate single; zero, one, or two of $A^1$, $A^2$, $A^3$, $A^4$, and $A^5$ are N, and the rest are CH, or $CR^1$;

zero, one, or two of $D^1$, $D^2$, and $D^3$ are N, and the rest are CH, or $CR^6$;

each $R^1$ is independently selected from the group consisting of alkyl, substituted alkyl, halo, cyano, azido, alkoxy, haloalkoxy, and $R^{11}R^{12}NCO$—;

$L^1$ is selected from the group consisting of —O—, —$CH_2$—, —NH—, —N(Me)-, —N(Et)-, —$OCH_2$—, —$CH_2O$—, —$NHCH_2$—, —N(Me)$CH_2$—, and —$SO_2NH$—;

$L^2$ is selected from the group consisting of a bond, —C(O)—, —$CH_2$—, —C(H)═, —$SO_2$—, —O—, —$CF_2$—, —CHF—, —CH(OH)—, —NH—, —N(Me)-, and

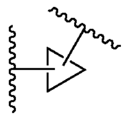

;

$L^3$ is —$CH_2$—, or —C(O)—;

each $R^3$ is independently selected from the group consisting of alkyl, substituted alkyl, halo, cyano, azido, alkoxy, haloalkoxy, and $R^{11}R^{12}NCO$—;

$R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene;

$R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

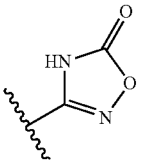

,

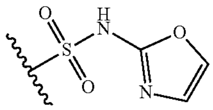

,

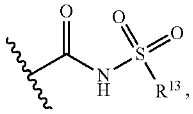

,

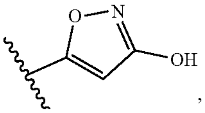

,

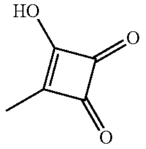

, and tetrazolyl;

each $R^6$ is independently selected from the group consisting of F, and methyl;

$R^{11}$ is hydrogen, or alkyl;

$R^{12}$ is hydrogen, or alkyl;

$R^{13}$ is hydrogen, or alkyl; and o is 1, 2, 3, or 4.

In certain aspects, the compounds are useful in methods of treatment and prevention of metabolic diseases, and conditions, methods of detection of metabolic diseases, and conditions, and methods of diagnosis of metabolic diseases, and conditions.

In another aspect, provided are compositions comprising a compound of Formula (I), (Ia), (XXX), or (XXXI). In some embodiments, the compositions are pharmaceutical compositions. Any suitable pharmaceutical composition may be used. In a further aspect, provided herein is a kit comprising the compound of Formula (I), (Ia), (XXX), or (XXXI), or embodiments thereof, or a pharmaceutical composition thereof.

In another aspect, provided herein are methods of using the compounds or the compositions described herein. In some embodiments, the methods are for treatment. In some embodiments, the methods are diagnostic methods. In some embodiments, the methods are analytical methods. In some embodiments, the compounds, or compositions described herein are used to treat a disease, or condition. In some aspects, the disease, or condition is selected from metabolic diseases, or conditions. In certain embodiments, the disease is type 2 diabetes.

Also provided herein is the use of compounds described herein, and compositions thereof, for the treatment of a metabolic disease, or condition. Also provided herein is the use of compounds described herein, and compositions thereof, for the treatment of type 2 diabetes.

BRIEF DESCRIPTION OF THE FIGURES

FIG. 1 provides intravenous glucose tolerance test (IVGTT) in cynomolgus monkeys.

DESCRIPTION OF EXEMPLARY EMBODIMENTS

Described herein are GLP-1 receptor compounds useful for treating metabolic diseases or conditions, such as type 2 diabetes.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity, and/or ready reference. The techniques and procedures described or referenced herein are generally well understood, and are commonly employed using conventional methodologies by those skilled in the art. As appropriate, procedures involving the use of commercially available kits, and reagents are generally carried out in accordance with manufacturer-defined protocols, and conditions unless otherwise noted.

As used herein, the singular forms "a," "an," and "the" include the plural referents unless the context clearly indicates otherwise.

The term "about" indicates and encompasses an indicated value, and a range above and below that value. In certain embodiments, the term "about" indicates the designated value ±10%, ±5%, or ±1%. In certain embodiments, the term "about" indicates the designated value±one standard deviation of that value. In certain embodiments, for example, logarithmic scales (e.g., pH), the term "about" indicates the designated value ±0.3, ±0.2, or ±0.1.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

"Alkoxy" and "alkoxyl," refer to the group —OR" where R" is alkyl or cycloalkyl. Alkoxy groups include, in certain embodiments, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkoxyamine," as used herein, refers to the group-alkylene-O—$NH_2$, wherein alkylene is as defined herein. In some embodiments, alkoxyamine groups can react with aldehydes to form oxime residues. Examples of alkoxyamine groups include —$CH_2CH_2$—O—$NH_2$ and —$CH_2$—O—$NH_2$.

The term "alkyl," as used herein, unless otherwise specified, refers to a saturated straight, or branched hydrocarbon. In certain embodiments, the alkyl group is a primary, secondary, or tertiary hydrocarbon. In certain embodiments, the alkyl group includes one to ten carbon atoms (i.e., $C_1$ to $C_{10}$ alkyl). In certain embodiments, the alkyl is a lower alkyl, for example, $C_{1-6}$ alkyl, and the like. In certain embodiments, the alkyl group is selected from the group consisting of methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl. In certain embodiments, "substituted alkyl" refers to an alkyl substituted with one, two, or three groups independently selected from a halogen (e.g., fluoro (F), chloro (Cl), bromo (Br), or iodo (I)), alkyl, haloalkyl, hydroxyl, amino, alkylamino, alkoxy, aryl, heteroaryl, cycloalkyl, cyano, oxo, alkyne, and heterocycloalkylalkylene. In some embodiments, alkyl is unsubstituted.

The term "alkylene," as used herein, unless otherwise specified, refers to a divalent alkyl group, as defined herein. "Substituted alkylene" refers to an alkylene group substituted as described herein for alkyl. In some embodiments, alkylene is unsubstituted.

"Alkenyl" refers to an olefinically unsaturated hydrocarbon group, in certain embodiments, having up to about eleven carbon atoms, or from two to six carbon atoms (e.g., "lower alkenyl"), which can be straight-chained or branched, and having at least one, or from one to two sites of olefinic unsaturation. "Substituted alkenyl" refers to an alkenyl group substituted as described herein for alkyl.

"Alkenylene" refers to a divalent alkenyl as defined herein. Lower alkenylene is, for example, $C_2$-$C_6$-alkenylene.

"Alkynyl" refers to acetylenically unsaturated hydrocarbon groups, in certain embodiments, having up to about eleven carbon atoms, or from two to six carbon atoms (e.g., "lower alkynyl"), which can be straight-chained or branched, and having at least one, or from one to two sites of acetylenic unsaturation. Non-limiting examples of alkynyl groups include acetylene (—C≡CH), propargyl (—$CH_2$C≡CH), and the like. "Substituted alkynyl" refers to an alkynyl group substituted as described herein for alkyl.

"Alkynylene" refers to a divalent alkynyl as defined herein. Lower alkynylene is, for example, $C_2$-$C_6$-alkynylene.

"Amino" refers to —$NH_2$.

The term "alkylamino," as used herein, and unless otherwise specified, refers to the group —NHR" where R" is, for example, $C_{1-10}$alkyl, as defined herein. In certain embodiments, alkylamino is $C_{1-6}$alkylamino.

The term "dialkylamino," as used herein, and unless otherwise specified, refers to the group —NR"R" where, each R" is independently $C_{1-10}$alkyl, as defined herein. In certain embodiments, dialkylamino is di-$C_{1-6}$alkylamino.

The term "aryl," as used herein, and unless otherwise specified, refers to phenyl, biphenyl, or naphthyl. The term includes both substituted and unsubstituted moieties. An aryl group can be substituted with any described moiety including, but not limited to, one or more moieties (e.g., in some embodiments one, two, or three moieties) selected from the group consisting of halogen (e.g., fluoro (F), chloro (Cl), bromo (Br), or iodo (I)), alkyl, haloalkyl, hydroxyl, amino, alkylamino, arylamino, alkoxy, aryloxy, nitro, cyano, sulfonic acid, sulfate, phosphonic acid, phosphate, and phosphonate, wherein each moiety is independently either unprotected, or protected as necessary, as would be appreciated by those skilled in the art (e.g., Greene, et al., *Protective Groups in Organic Synthesis*, John Wiley and Sons, Second Edition, 1991); and wherein the aryl in the arylamino and aryloxy substituents are not further substituted.

The term "arylamino," as used herein, and unless otherwise specified, refers to an —NR'R" group where R' is hydrogen, or $C_1$-$C_6$-alkyl; and R" is aryl, as defined herein.

The term "arylene," as used herein, and unless otherwise specified, refers to a divalent aryl group, as defined herein.

The term "aryloxy," as used herein, and unless otherwise specified, refers to an —OR group where R is aryl, as defined herein.

"Alkarylene" refers to an arylene group, as defined herein, wherein the aryl ring is substituted with one or two alkyl groups. "Substituted alkarylene" refers to an alkarylene, as defined herein, where the arylene group is further substituted, as defined herein for aryl.

"Aralkylene" refers to an -alkyl-arylene- or arylene-alkyl, for instance, a —$C_1$-$C_2$ alkyl-arylene-, -arylene-$C_1$-$C_2$ alkyl-, or —$C_1$-$C_2$ alkyl-arylene-$C_1$-$C_2$ alkyl-group, where arylene is as defined herein. "Substituted aralkylene" refers to an aralkylene, as defined herein, where the aralkylene group is substituted, as defined herein for aryl. "Substituted $C_1$-$C_2$ alkyl" refers to a $C_1$-$C_2$ alkyl group that is substituted as defined herein for an alkyl.

"Arylalkylene" refers to -alkyl-arylene- or arylene-alkyl, for instance, a —$C_1$-$C_2$ alkyl-arylene-, -arylene-$C_1$-$C_2$ alkyl-, or —$C_1$-$C_2$ alkyl-arylene-$C_1$-$C_2$ alkyl-group, where arylene is as defined herein. "Substituted arylalkylene" refers to an arylalkylene, as defined herein, where the arylalkylene group is substituted, as defined herein for aryl. "Substituted $C_1$-$C_2$ alkyl" refers to a $C_1$-$C_2$ alkyl group that is substituted as defined herein for an alkyl.

"Carboxyl" or "carboxy" refers to —C(O) OH or —COOH.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms (i.e., $C_3$ to $C_{10}$ cycloalkyl). In some embodiments, the cycloalkyl has from three to fifteen carbons ($C_{3-15}$), from three to ten carbons ($C_{3-10}$), from three to seven carbons ($C_{3-7}$), or from three to six carbons ($C_3$-$C_6$) (i.e., "lower cycloalkyl"). In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl.

The term "cycloalkylene," as used herein refers to a divalent cycloalkyl group, as defined herein. In certain embodiments, the cycloalkylene group is cyclopropylene

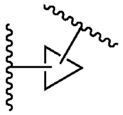

, cyclobutylene,

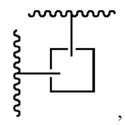

, cyclopentylene

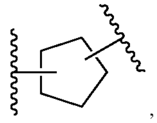

, cyclohexylene

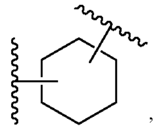

, cycloheptylene

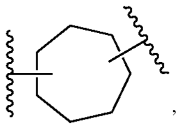

, and the like. Lower cycloalkylene refers to a $C_3$-$C_6$-cycloalkylene.

The term "cycloalkylalkyl," as used herein, unless otherwise specified, refers to an alkyl group, as defined herein, substituted with one or two cycloalkyl, as defined herein.

The term "ester," as used herein, refers to —C(O) OR, or —COOR, where R is alkyl, as defined herein.

The term "haloalkyl" refers to an alkyl group, as defined herein, substituted with one, or more halogen atoms (e.g., in some embodiments one, two, three, four, or five) which are independently selected.

The term "heteroalkyl" refers to an alkyl, as defined herein, in which one or more carbon atoms are replaced by heteroatoms. As used herein, "heteroalkenyl" refers to an alkenyl, as defined herein, in which one, or more carbon atoms are replaced by heteroatoms. As used herein, "heteroalkynyl" refers to an alkynyl, as defined herein, in which one, or more carbon atoms are replaced by heteroatoms. Suitable heteroatoms include, but are not limited to, nitrogen (N), oxygen (O), and sulfur(S) atoms. Heteroalkyl, heteroalkenyl, and heteroalkynyl are optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl. "Substituted heteroalkyl" refers to heteroalkyl substituted with one, two, or three groups independently selected from halogen (e.g., fluoro (F), chloro (Cl), bromo (Br), or iodo (I)), alkyl, haloalkyl, hydroxyl, amino, alkylamino, and alkoxy. In some embodiments, a heteroalkyl group may comprise one, two, three, or four heteroatoms. Those of skill in the art will recognize that a 4-membered heteroalkyl may generally comprise one, or two heteroatoms, a 5- or 6-membered heteroalkyl may generally comprise one, two, or three heteroatoms, and a 7- to 10-membered heteroalkyl may generally comprise one, two, three, or four heteroatoms.

The term "heteroalkylene," as used herein, refers to a divalent heteroalkyl, as defined herein. "Substituted heteroalkylene" refers to a divalent heteroalkyl, as defined herein, substituted as described for heteroalkyl.

The term "heterocycloalkyl" refers to a monovalent, monocyclic, or multicyclic non-aromatic ring system, wherein one, or more of the ring atoms are heteroatoms independently selected from oxygen (O), sulfur(S), and nitrogen (N) (e.g., where the nitrogen, or sulfur atoms may be optionally oxidized, and the nitrogen atoms may be optionally quaternized) and the remaining ring atoms of the non-aromatic ring are carbon atoms. In certain embodiments, heterocycloalkyl is a monovalent, monocyclic, or multicyclic fully-saturated ring system. In certain embodiments, the heterocycloalkyl group has from three to twenty, from three to fifteen, from three to ten, from three to eight, from four to seven, from four to eleven, or from five to six ring atoms. The heterocycloalkyl may be attached to a core structure at any heteroatom or carbon atom which results in the creation of a stable compound. In certain embodiments, the heterocycloalkyl is a monocyclic, bicyclic, tricyclic, or tetracyclic ring system, which may include a fused or bridged ring system and in which the nitrogen or sulfur atoms may be optionally oxidized, and/or the nitrogen atoms may be optionally quaternized. In some embodiments, heterocycloalkyl radicals include, but are not limited to, 2,5-diazabicyclo[2.2.2]octanyl, decahydroisoquinolinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocycloalkyl may also be optionally substituted as described herein. In certain embodiments, heterocycloalkyl is substituted with one, two, or three groups independently selected from halogen (e.g., fluoro (F), chloro (Cl), bromo (Br), or iodo (I)), alkyl, haloalkyl, hydroxyl, amino, alkylamino, oxo, cyano, and alkoxy. In some embodiments, a heterocycloalkyl group may comprise one, two, three, or four heteroatoms. Those of skill in the art will recognize that a 4-membered heterocycloalkyl may generally comprise one or two heteroatoms, a 5 or 6-membered heterocycloalkyl may generally comprise one, two, or three heteroatoms, and a 7- to 10-membered heterocycloalkyl may generally comprise one, two, three, or four heteroatoms.

"Heterocycloalkylene" refers to a divalent heterocycloalkyl as defined herein.

The term "heteroaryl" refers to a monovalent monocyclic aromatic group, and/or multicyclic aromatic group, wherein at least one aromatic ring contains one, or more heteroatoms independently selected from oxygen, sulfur, and nitrogen in the ring. Each ring of a heteroaryl group can contain one, or two oxygen atoms, one, or two sulfur atoms, and/or one to four nitrogen atoms, provided that the total number of heteroatoms in each ring is four, or less and each ring contains at least one carbon atom. In certain embodiments, the heteroaryl has from five to twenty, from five to fifteen, or from five to ten ring atoms. A heteroaryl may be attached to the rest of the molecule via a nitrogen or a carbon atom. In some embodiments, monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, triazolyl, thiadiazolyl, thiazolyl, thienyl, tetrazolyl, and triazinyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein. "Substituted heteroaryl" is a heteroaryl substituted as defined for aryl.

The term "heteroarylene" refers to a divalent heteroaryl group, as defined herein. "Substituted heteroarylene" is a heteroarylene substituted as defined for aryl.

The term "heteroarylalkylene" refers to -alkyl-heteroarylene- or -heteroarylene-alkyl, for instance, a a —$C_1$-$C_2$ alkyl-heteroarylene-, -heteroarylene-$C_1$-$C_2$ alkyl-, or —$C_1$-$C_2$ alkyl-heteroarylene-$C_1$-$C_2$ alkyl-group, where heteroarylene is as defined herein. "Substituted heteroarylalkylene" refers to a heteroarylalkylene, as defined herein, where the heteroarylalkylene group is substituted, as defined herein for aryl. "Substituted $C_1$-$C_2$ alkyl" refers to a $C_1$-$C_2$ alkyl group that is substituted as defined herein for an alkyl.

As used herein, an "oxo" refers to =O.

The term "protecting group," as used herein, and unless otherwise specified, refers to a group that is added to an oxygen, nitrogen, or phosphorus atom to prevent its further reaction, or for other purposes. A wide variety of oxygen, and nitrogen protecting groups are known to those skilled in the art of organic synthesis. (See, e.g., Greene, et al., Protective Groups in Organic Synthesis, John Wiley and Sons, Fourth Edition, 2006, which is incorporated herein by reference).

"Pharmaceutically acceptable salt" refers to any salt of a compound provided herein which retains its biological properties, and which is not toxic or otherwise undesirable for pharmaceutical use. Such salts may be derived from a variety of organic, and inorganic counter-ions well known in the art. Such salts include, but are not limited to (1) acid addition salts formed with organic, or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, glutamic, hydroxynaphthoic, salicylic, stearic, cyclohexylsulfamic, quinic, muconic acid, and the like; or (2) salts formed when an acidic proton present in the parent compound either (a) is replaced by a metal ion, for example, an alkali metal ion, an alkaline earth ion, or an aluminum ion, or alkali metal, or alkaline earth metal hydroxides, such as sodium, potassium, calcium, magnesium, aluminum, lithium, zinc, and barium hydroxide, or ammonia; or (b) coordinates with an organic base, such as aliphatic, alicyclic, or aromatic organic amines, including, without limitation, ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example and without limitation, sodium, potassium, calcium, magnesium, ammonium, and tetraalkylammonium salts, and the like, and when the compound contains a basic functionality, salts of non-toxic organic, or inorganic acids, such as hydrohalides, for example, hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, glutamate, hydroxynaphthoate, salicylate, stearate, cyclohexylsulfamate, quinate, muconate, and the like.

The term "substantially free of" or "substantially in the absence of" with respect to a composition refers to a composition that includes at least 85%, or 90% by weight, in certain embodiments 95%, 98%, 99%, or 100% by weight; or in certain embodiments, 95%, 98%, 99%, or 100% of the designated enantiomer or diastereomer of a compound. In certain embodiments, in the methods and compounds provided herein, the compounds are substantially free of one of two enantiomers. In certain embodiments, in the methods and compounds provided herein, the compounds are substantially free of one of two diastereomers. In certain embodiments, in the methods, and compounds provided herein, the compounds are substantially free of enantiomers (i.e., a racemic, or 50:50 mixture of compounds).

Similarly, the term "isolated" with respect to a composition refers to a composition that includes at least 85%, 90%, 95%, 98%, or 99% to 100% by weight, of the compound, the remainder comprising other chemical species, enantiomers or diastereomers.

"Solvate" refers to a compound provided herein, or a salt thereof, that further includes a stoichiometric, or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition, or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as hydrogen (H), the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium (D) enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "alkylene," "alkylamino," "dialkylamino," "cycloalkyl," "aryl," "arylene," "alkoxy," "amino," "carboxyl," "heterocycloalkyl," "heteroaryl," "heteroarylene," "carboxyl," and "amino acid" groups optionally comprise deuterium (D) at one, or more positions where hydrogen (H) atoms are present, and wherein the deuterium composition of the atom or atoms is other than the natural isotopic composition.

Also as used herein, "alkyl," "alkylene," "alkylamino," "dialkylamino," "cycloalkyl," "aryl," "arylene," "alkoxy," "amino," "carboxyl," "heterocycloalkyl," "heteroaryl," "heteroarylene," "carboxyl," and "amino acid" groups optionally comprise carbon-13 ($^{13}C$) at an amount other than the natural isotopic composition.

As used herein, term "$EC_{50}$" refers to a dosage, concentration, or amount of a particular test compound that elicits a dose-dependent response at 50% of maximal expression of a particular response that is induced, provoked, or potentiated by the particular test compound.

As used herein, and unless otherwise specified, the term "$IC_{50}$" refers to an amount, concentration, or dosage of a particular test compound that achieves a 50% inhibition of a maximal response in an assay that measures such response.

As used herein, the terms "subject", and "patient" are used interchangeably. The terms "subject", and "subjects" refer to an animal, such as a mammal including a non-primate (e.g., a cow, pig, horse, cat, dog, rat, and mouse), and a primate (e.g., a monkey, such as a cynomolgous monkey, a chimpanzee, and a human), and in certain embodiments, a human. In certain embodiments, the subject is a farm animal (e.g., a horse, a cow, a pig, etc.), or a pet (e.g., a dog or a cat). In certain embodiments, the subject is a human.

As used herein, the terms "therapeutic agent", and "therapeutic agents" refer to any agent(s) which can be used in the treatment, or prevention of a disorder, or one or more symptoms thereof. In certain embodiments, the term "therapeutic agent" includes a compound provided herein. In certain embodiments, a therapeutic agent is an agent which is known to be useful for, or has been, or is currently being used for the treatment, or prevention of a disorder, or one, or more symptoms thereof.

"Therapeutically effective amount" refers to an amount of a compound, or composition that, when administered to a subject for treating a condition, is sufficient to effect such treatment for the condition. A "therapeutically effective amount" can vary depending on, inter alia, the compound, the disease or disorder, and its severity, and the age, weight, etc., of the subject to be treated.

"Treating" or "treatment" of any disease, or disorder refers, in certain embodiments, to ameliorating a disease, or disorder that exists in a subject. In another embodiment, "treating", or "treatment" includes ameliorating at least one physical parameter, which may be indiscernible by the subject. In yet another embodiment, "treating", or "treatment" includes modulating the disease, or disorder, either physically (e.g., stabilization of a discernible symptom), or physiologically (e.g., stabilization of a physical parameter), or both. In yet another embodiment, "treating", or "treatment" includes delaying, or preventing the onset of the disease, or disorder, or delaying, or preventing recurrence of the disease, or disorder. In yet another embodiment, "treating", or "treatment" includes the reduction or elimination of either the disease, or disorder, or retarding the progression of the disease, or disorder, or of one, or more symptoms of the disease, or disorder, or reducing the severity of the disease, or disorder, or of one, or more symptoms of the disease, or disorder.

As used herein, the terms "prophylactic agent", and "prophylactic agents" as used refer to any agent(s) which can be used in the prevention of a disorder, or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent, or impede the onset, development, progression, and/or severity of a disorder.

As used herein, the phrase "prophylactically effective amount" refers to the amount of a therapy (e.g., prophylactic agent) which is sufficient to result in the prevention, or reduction of the development, recurrence, or onset of one or more symptoms associated with a disorder, or to enhance or improve the prophylactic effect(s) of another therapy (e.g., another prophylactic agent).

Compounds of Formulae (I)-(XVIII), (XXV)-(XXVII), (XXX), (XXXI), (XXXIX), and (XL-XLVII)

Provided herein are GLP-1 receptor compounds useful for modulating one, or more properties of GLP-1 receptor. The compounds can be prepared as described herein and used for therapy, or diagnosis. In certain embodiments, the therapy is the treatment of a metabolic disease or condition. In certain embodiments, the therapy is the treatment of type 2 diabetes.

The embodiments described herein include the recited compounds as well as pharmaceutically acceptable salts, hydrates, solvates, stereoisomers, tautomers, and/or mixtures thereof.

In certain embodiments, provided is a compound of Formula (I), or a pharmaceutically acceptable salt, tautomer, stereoisomer, and/or mixture of stereoisomers thereof; wherein A is substituted or unsubstituted aryl, substituted or unsubstituted heteroaryl, substituted or unsubstituted cycloalkyl, —$NMe_2$, or —$CF_3$; Ring B is substituted or unsubstituted aryl, or substituted or unsubstituted heteroaryl; Ring C is further unsubstituted or further substituted, and/or bridged; zero, one, or two of $D^1$, $D^2$, and $D^3$ are N, and the rest are CH, or $CR^6$; $L^1$ is selected from the group consisting of a bond, —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$CF_2$—, —$SO_2$—, —O—, —$CF_2$—, —CHF—, —CH (OH)—, —NH—, —N(Me)-, and

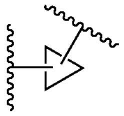

;

$L^3$ is —$CH_2$— or —C(O)—; $L^4$ is absent, or $L^4$ together with $L^1$ and Rings A and B form a fused tricycle, and $L^5$ is absent; $L^5$ is absent, or $L^5$ together with $L^2$ and Rings B and C form a fused tricycle, and $L^4$ is absent; $R^4$ is unsubstituted alkyl, substituted alkyl, unsubstituted arylalkylene, substituted arylalkylene, unsubstituted heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

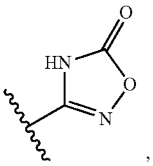

,

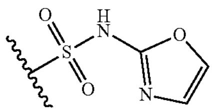

,

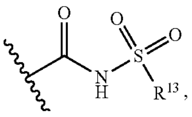

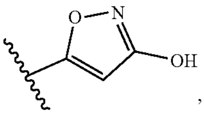

,

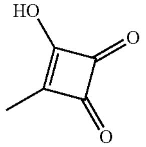

, and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; $R^{11}$ is hydrogen, or alkyl; $R^{12}$ is hydrogen, or alkyl; and $R^{13}$ is hydrogen, or alkyl. In certain embodiments, $L^2$ is selected from the group consisting of a bond, —C(O)—, —$CH_2$—, —C(H)═, —$CF_2$—, —$SO_2$—, —O—, —$CF_2$—, —CHF—, —CH (OH)—, and

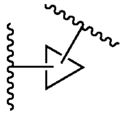

.

In certain embodiments, $L^2$ is selected from the group consisting of —NH— and —N(Me)-.

In certain embodiments of Formula (I), when $L^1$ is —$CH_2O$—, $L^4$ is absent, and $L^5$ is absent, then either $L^2$ is —C(O)—, —$CH_2$—, —C(H)═, —$SO_2$—, —O—, —$CF_2$—, CHF—, —CHOH—, —NH—, —N(Me)-, or

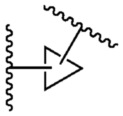

, or $L^3$ is —C(O)—, or both. In certain embodiments, when $L^1$ is —$CH_2O$—, $L^4$ is absent, and $L^5$ is absent, then $L^2$ is —C(O)—, —$CH_2$—, —C(H)═, —$SO_2$—, —O—, —NH—, —N(Me)-, or

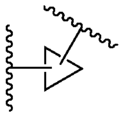

.

In certain embodiments, when $L^1$ is —$CH_2O$—, $L^4$ is absent, and $L^5$ is absent, then $L^3$ is —C(O)—. In certain embodiments, when $L^1$ is —$CH_2O$—, $L^4$ together with $L^1$ and Rings A and B form a fused tricycle. In certain embodiments, when $L^1$ is —$CH_2O$—, $L^5$ together with $L^2$ and Rings B and C form a fused tricycle. In certain embodiments, when $L^1$ is —$CH_2O$—, Ring C is substituted or unsubstituted azetidinyl, substituted or unsubstituted pyrrolidinyl, or substituted or unsubstituted piperidinyl.

In certain embodiments, A is a ring selected from phenyl and cyclohexyl. In certain embodiments, Ring C is selected from piperidine and piperazine. In certain embodiments, Ring B is selected from phenyl, furan, pyridine, pyrimidine, thiophene, oxazole, and benzofuran. In certain embodiments, A is phenyl and Ring C is piperazine. In certain embodiments, A is phenyl, and Ring C is piperidine. In certain embodiments, A is phenyl, and Ring C is piperazine, and Ring B is phenyl. In certain embodiments, A is phenyl, and Ring C is piperazine, and Ring B is furan. In certain embodiments, A is phenyl, and Ring C is piperidine, and Ring B is phenyl. In certain embodiments, A is phenyl, and Ring C is piperidine, and Ring B is furan.

In certain embodiments, A is a ring selected from phenyl and cyclohexyl. In certain embodiments, Ring C is selected from substituted piperidine, azetidine, and pyrrolidine. In certain embodiments, Ring B is selected from phenyl, furan, pyridine, pyrimidine, thiophene, oxazole, and benzofuran. In certain embodiments, A is phenyl and Ring C is piperazine. In certain embodiments, A is phenyl, and Ring C is piperidine. In certain embodiments, A is phenyl, and Ring C is substituted piperidine. In certain embodiments, A is phenyl, and Ring C is azetidine. In certain embodiments, A is phenyl, and Ring C is pyrrolidine. In certain embodiments, A is phenyl, Ring C is piperazine, and Ring B is phenyl. In certain embodiments, A is phenyl, Ring C is piperazine, and Ring B is furan. In certain embodiments, A is phenyl, Ring C is piperidine, and Ring B is phenyl. In certain embodiments, A is phenyl, Ring C is piperidine, and Ring B is furan. In certain embodiments, A is phenyl, Ring C is substituted piperidine, and Ring B is phenyl. In certain embodiments, A is phenyl, Ring C is substituted piperidine, and Ring B is furan. In certain embodiments, A is phenyl, Ring C is azetidine, and Ring B is phenyl. In certain embodiments, A is phenyl, Ring C is azetidine, and Ring B is furan. In certain embodiments, A is phenyl, Ring C is pyrrolidine, and Ring B is phenyl. In certain embodiments, A is phenyl, Ring C is pyrrolidine, and Ring B is furan.

In certain embodiments, provided is a compound of Formula (Ia), or a pharmaceutically acceptable salt, tautomer, stereoisomer, and/or mixture of stereoisomers thereof; wherein A is substituted or unsubstituted aryl, substituted or unsubstituted heteroaryl, substituted or unsubstituted cycloalkyl, —$NMe_2$, or —$CF_3$; Ring B is substituted or unsubstituted aryl, or substituted or unsubstituted heteroaryl; Ring C is further unsubstituted or further substituted, and/or bridged; zero, one, or two of $D^1$, $D^2$, and $D^3$ are N, and the rest are CH, or $CR^6$; W is N, CH, or C; when W is CH, the adjacent dashed lines indicate single bonds; when W is C, one adjacent dashed line indicates a double bond, for instance $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

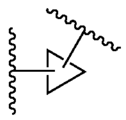

;

$L^3$ is —$CH_2$— or —C(O)—; $L^4$ is absent, or $L^4$ together with $L^1$ and Rings A and B form a fused tricycle, and $L^5$ is absent; $L^5$ is absent, or $L^5$ together with $L^2$ and Rings B and C form a fused tricycle, and $L^4$ is absent; $R^4$ is unsubstituted alkyl, substituted alkyl, unsubstituted arylalkylene, substituted arylalkylene, unsubstituted heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

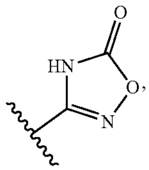
,
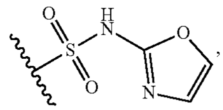
,
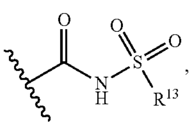
,
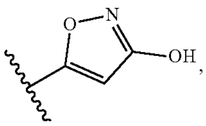
,
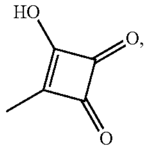
, and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; $R^{11}$ is hydrogen, or alkyl; $R^{12}$ is hydrogen, or alkyl; and $R^{13}$ is hydrogen, or alkyl. In certain embodiments, $L^2$ is selected from the group consisting of a bond, —C(O)—, —$CH_2$—, —C(H)═, —$CF_2$—, —$SO_2$—, —O—, —$CF_2$—, —CHF—, —CH(OH)—, and

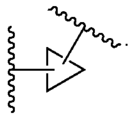
.

In certain embodiments, $L^2$ is selected from the group consisting of —NH— and —N(Me)-.

In certain embodiments of Formula (Ia), when $L^1$ is —$CH_2O$—, $L^4$ is absent, and $L^5$ is absent, then either $L^2$ is —C(O)—, —$CH_2$—, —C(H)═, —$SO_2$—, —O—, —NH—, —N(Me)-, or

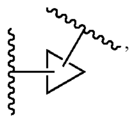
, or $L^3$ is —C(O)—, or both. In certain embodiments, when $L^1$ is —$CH_2O$—, $L^4$ is absent, and $L^5$ is absent, then $L^2$ is —C(O)—, —$CH_2$—, —C(H)═, —$SO_2$—, —O—, —NH—, —N(Me)-, or

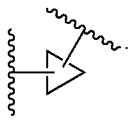
.

In certain embodiments, when $L^1$ is —$CH_2O$—, $L^4$ is absent, and $L^5$ is absent, then $L^2$ is —C(O)—, —$CH_2$—, —C(H)═, —$SO_2$—, —O—, or

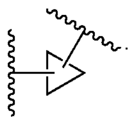
.

In certain embodiments, when $L^1$ is —$CH_2O$—, $L^4$ is absent, and $L^5$ is absent, then $L^3$ is —C(O)—. In certain embodiments, when $L^1$ is —$CH_2O$—, $L^4$ together with $L^1$ and Rings A and B form a fused tricycle. In certain embodiments, when $L^1$ is —$CH_2O$—, $L^5$ together with $L^2$ and Rings B and C form a fused tricycle.

In certain embodiments, A is a ring selected from phenyl, and cyclohexyl. In certain embodiments, Ring C is selected from piperidine, and piperazine. In certain embodiments, Ring B is selected from phenyl, furan, pyridine, pyrimidine, thiophene, oxazole, and benzofuran. In certain embodiments, A is phenyl and Ring C is piperazine. In certain embodiments, A is phenyl, and Ring C is piperidine. In certain embodiments, A is phenyl, and Ring C is piperazine, and Ring B is phenyl. In certain embodiments, A is phenyl, and Ring C is piperazine, and Ring B is furan. In certain embodiments, A is phenyl, and Ring C is piperidine, and Ring B is phenyl. In certain embodiments, A is phenyl, and Ring C is piperidine, and Ring B is furan.

In certain embodiments, provided is a compound of Formula (XXX), or a pharmaceutically salt, tautomer, stereoisomer, and/or mixture of stereoisomers thereof; wherein W is N, CH, or C; when W is CH, the adjacent dashed lines indicate single bonds; when W is C, one adjacent dashed line indicates a double bond, for instance $L^2$ is —C(H)═; zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH, or $CR^2$; zero, one, or two of $D^1$, $D^2$, and $D^3$ are N, and the rest are CH, or $CR^6$; $L^1$ is selected from the group consisting of —O—, —$CH_2$—, —NH—, —N(Me)-, —N(Et)-, —$OCH_2$—, —$CH_2O$—, —$NHCH_2$—, —N(Me)$CH_2$—, and —$SO_2NH$—;

$L^2$ is selected from the group consisting of a bond, —C(O)—, —$CH_2$—, —C(H)═, —$SO_2$—, —O—, —NH—, —N(Me)-, and

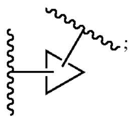;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted heteroalkyl, substituted heteroalkyl, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

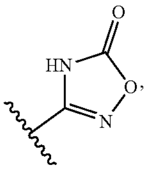 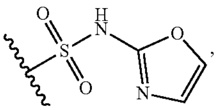,

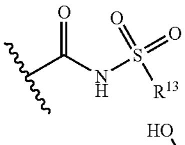, 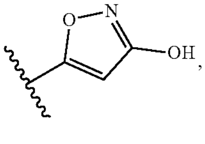,

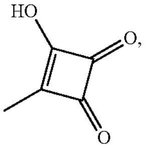

and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; $R^{11}$ is hydrogen or alkyl; $R^{12}$ is hydrogen, or alkyl; $R^{13}$ is hydrogen, or alkyl; and o is an integer from 0 to 4.

In certain embodiments, the compound of Formula (XXX) is selected from compounds 82, 83, 91, 92, and 110, in Table 1.

In certain embodiments, provided is a compound of Formula (XXXI), or a pharmaceutically salt, tautomer, stereoisomer, and/or mixture of stereoisomers thereof;

wherein W is N, CH, or C; when W is CH, the adjacent dashed lines indicate single; zero, one, or two of $A^1$, $A^2$, $A^3$, $A^4$, and $A^5$ are N, and the rest are CH, or $CR^1$;

zero, one, or two of $D^1$, $D^2$, and $D^3$ are N, and the rest are CH, or $CR^6$;

each $R^1$ is independently selected from the group consisting of alkyl, substituted alkyl, halo, cyano, azido, alkoxy, haloalkoxy, and $R^{11}R^{12}NCO$—;

$L^1$ is selected from the group consisting of —O—, —$CH_2$—, —NH—, —N(Me)-, —N(Et)-, —$OCH_2$—, —$CH_2O$—, —$NHCH_2$—, —N(Me)$CH_2$—, and —$SO_2NH$—;

$L^2$ is selected from the group consisting of a bond, —C(O)—, —$CH_2$—, —C(H)═, —$SO_2$—, —O—, —NH—, —N(Me)-, and

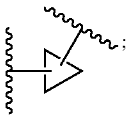;

$L^3$ is —$CH_2$—, or —C(O)—;

each $R^3$ is independently selected from the group consisting of alkyl, substituted alkyl, halo, cyano, azido, alkoxy, haloalkoxy, and $R^{11}R^{12}NCO$—;

$R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene;

$R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

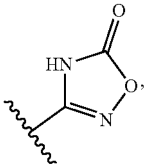 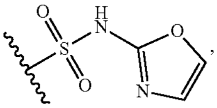,

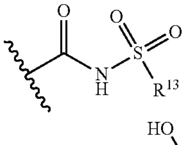, 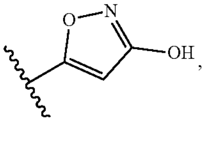,

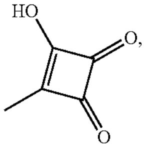

and tetrazolyl;

each $R^6$ is independently selected from the group consisting of F, and methyl;

$R^{11}$ is hydrogen, or alkyl;

$R^{12}$ is hydrogen, or alkyl;

$R^{13}$ is hydrogen, or alkyl; and o is 1, 2, 3, or 4. In certain embodiments, the compound of Formula (XXXI) is selected from compounds 97 and 107 in Table 1.

In certain embodiments, the compound of Formula (I) is according to Formula (IIa), or a pharmaceutically acceptable salt, tautomer, stereoisomer, and/or mixture of stereoisomers thereof:

IIa

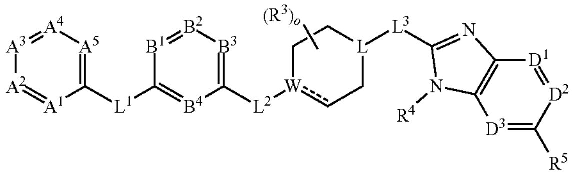

wherein zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH, or $CR^2$, wherein, in Formula IIa $B^4$ is absent; zero, one, or two of $D^1$, $D^2$, and $D^3$ are N, and the rest are CH, or $CR^6$; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

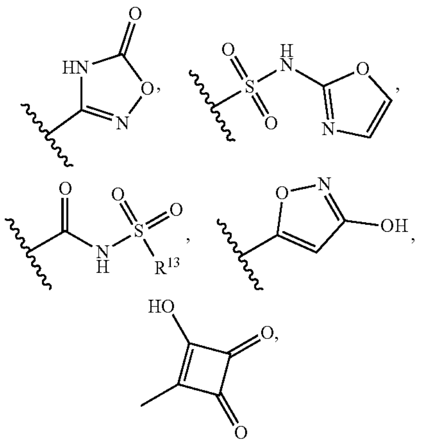

and tetrazolyl; each $R^6$ is independently selected from the group consisting of F, and methyl; each $R^{11}$ is hydrogen, or alkyl; each $R^{12}$ is hydrogen or alkyl; each $R^{13}$ is hydrogen or alkyl; and o is 1, 2, 3, or 4.

In certain embodiments, the compound of Formula (I) is according to Formula (IIb), or a pharmaceutically acceptable salt, tautomer, stereoisomer, and/or mixture of stereoisomers thereof:

IIb

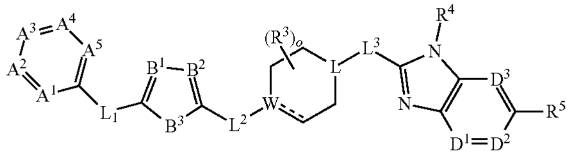

wherein zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH or $CR^2$, wherein, in Formula IIb, $B^4$ is absent; zero, one, or two of $D^1$, $D^2$, and $D^3$ are N, and the rest are CH, or $CR^6$; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

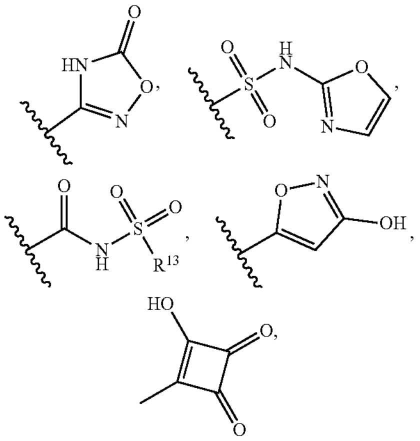

and tetrazolyl; each $R^6$ is independently selected from the group consisting of F, and methyl; each $R^{11}$ is hydrogen, or alkyl; each $R^{12}$ is hydrogen, or alkyl; each $R^{13}$ is hydrogen, or alkyl; and o is 1, 2, 3, or 4.

In certain embodiments, the compound of Formula (I) is according to Formula (IIc), or a pharmaceutically acceptable salt, tautomer, stereoisomer, and/or mixture of stereoisomers thereof:

IIc

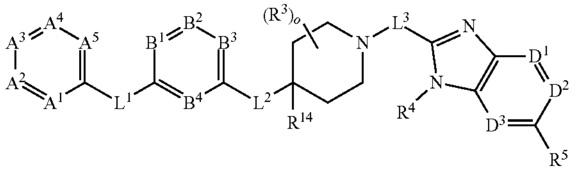

wherein zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH or $CR^2$, wherein, in Formula IIc $B^4$ is absent; zero, one, or two of $D^1$, $D^2$, and $D^3$ are N, and the rest are CH, or $CR^6$; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

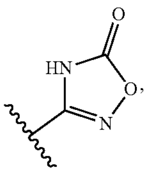
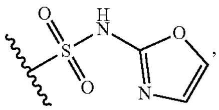
,
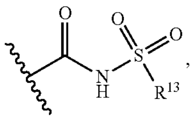
,
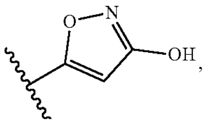
,
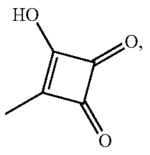

and tetrazolyl; each $R^6$ is independently selected from the group consisting of F, and methyl; each $R^{11}$ is hydrogen, or alkyl; each $R^{12}$ is hydrogen, or alkyl; each $R^{13}$ is hydrogen, or alkyl; $R^{14}$ is hydrogen, cyano, halo, hydroxyl, or methyl; and o is 1, 2, 3, or 4.

In certain embodiments, the compound of Formula (I) is according to Formula (IId), or a pharmaceutically acceptable salt, tautomer, stereoisomer, and/or mixture of stereoisomers thereof:

IId

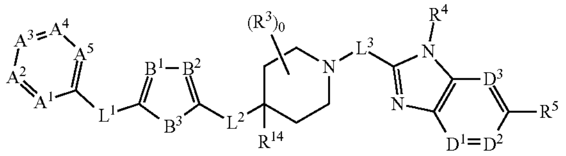

wherein zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH or $CR^2$, wherein, in Formula IId $B^4$ is absent; zero, one, or two of $D^1$, $D^2$, and $D^3$ are N, and the rest are CH, or $CR^6$; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

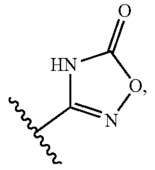
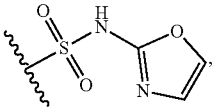
,
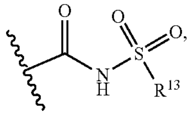
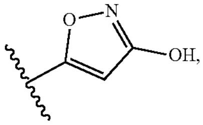
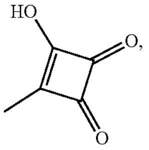

and tetrazolyl; each $R^6$ is independently selected from the group consisting of F, and methyl; each $R^{11}$ is hydrogen, or alkyl; each $R^{12}$ is hydrogen, or alkyl; each $R^{13}$ is hydrogen, or alkyl; $R^{14}$ is hydrogen, cyano, halo, hydroxyl, or methyl; and o is 1, 2, 3, or 4.

In certain embodiments, the compound of Formula (I) is according to Formula (IIg), or a pharmaceutically acceptable salt, tautomer, stereoisomer, and/or mixture of stereoisomers thereof:

IIg

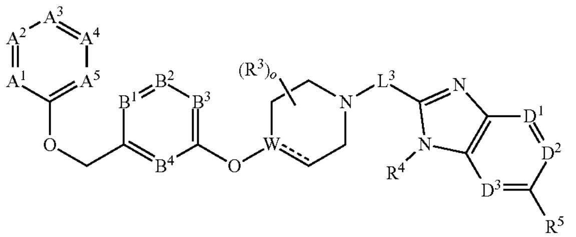

wherein zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH or $CR^2$, wherein, in Formula IIg, $B^4$ is absent; zero, one, or two of $D^1$, $D^2$, and $D^3$ are N, and the rest are CH, or $CR^6$; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

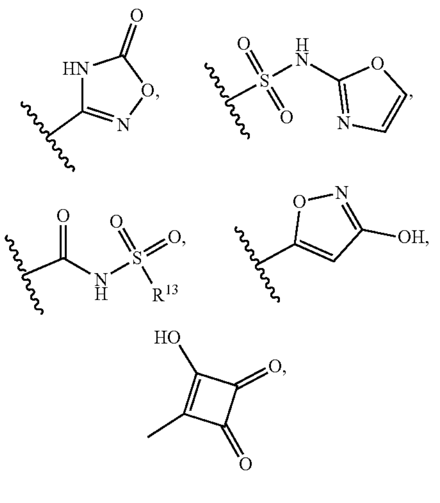

and tetrazolyl; each $R^6$ is independently selected from the group consisting of F, and methyl; each $R^{11}$ is hydrogen, or alkyl; each $R^{12}$ is hydrogen, or alkyl; each $R^{13}$ is hydrogen, or alkyl.

In certain embodiments, the compound of Formula (I) is according to Formula (IIh), or a pharmaceutically acceptable salt, tautomer, stereoisomer, and/or mixture of stereoisomers thereof:

IIh

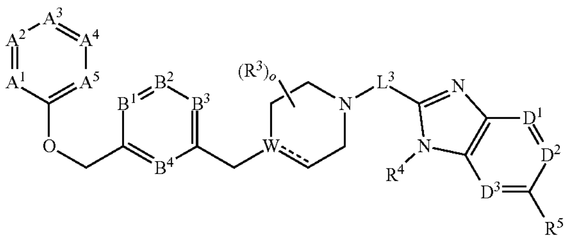

wherein zero, one, or two of $A^1$, $A^2$, $A^3$, $A^4$, and $A^5$ are N, and the rest are CH, or $CR^1$; zero, one, or two of $B^1$, $B^2$, $B^3$, and $B^4$ are N, and the rest are CH or $CR^2$, wherein, in Formula IIg, $B^4$ is absent; zero, one, or two of $D^1$, $D^2$, and $D^3$ are N, and the rest are CH, or $CR^6$; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is unsubstituted alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

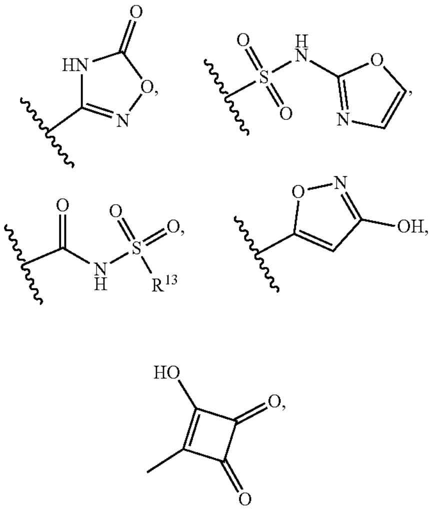

and tetrazolyl; each $R^6$ is independently selected from the group consisting of F, and methyl; each $R^{11}$ is hydrogen, or alkyl; each $R^{12}$ is hydrogen, or alkyl; each $R^{13}$ is hydrogen, or alkyl.

In certain embodiments, provided is a compound of Formula (III), or a pharmaceutically salt, tautomer, stereoisomer, and/or mixture of stereoisomers thereof:

III

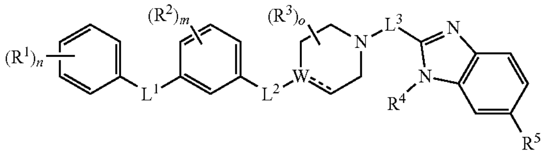

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$CF_2$—, —$SO_2$—, —O—, —NH—, —N(Me)-, and

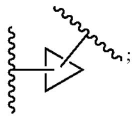

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

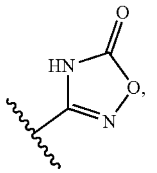

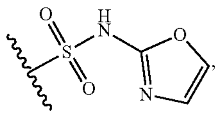

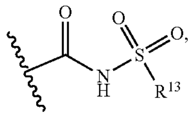

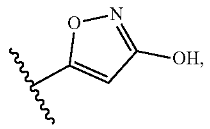

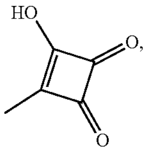

and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH (OH)—, and

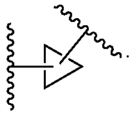

In certain embodiments, $L^2$ is selected from the group consisting of —NH— and —N(Me)-. In certain embodiments, $L^2$ is O. In certain embodiments, the compound of Formula (III) is selected from compounds 2, 3, 5-7, 10-18, 21-23, 25, 29, 32, 33, 35, 45, 46, 48, 50-52, 54, 56-58, 64-70, 75-80, 86, 89, 93, 95, 98, 100, 103-105, 111, 112, 115, 116, 122, 126, 130-133, 135, 137, 148, 149, 151, 157-159, 161, 162, 165, 166, 174, 187, 188, 202-208, 215-217, 221, 231, 232, 242, 243, 254, 255, 260, 263, 288, 294, 301, 318, 319, and 321 in Table 1.

In certain embodiments, provided is a compound of Formula (IIIa), or a pharmaceutically salt, tautomer, stereoisomer, and/or mixture of stereoisomers thereof:

IIIa

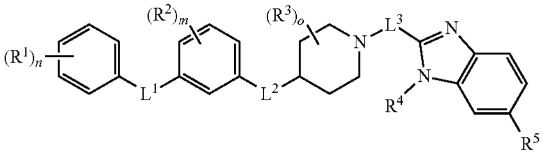

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —$CF_2$—, —CHF—, or —CH(OH)—, —NH—, —N(Me)-, and

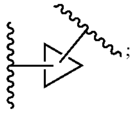

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me) (OH), —$SO_3H$, —$SO_2NH_2$, —$SO_2NHMe$, —$B(OH)_2$,

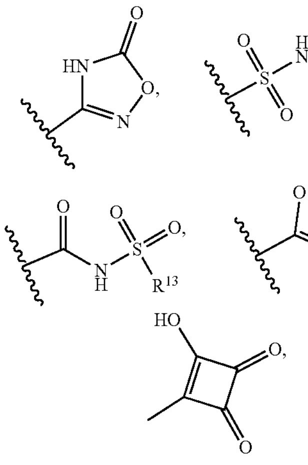

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; o is an integer from 0 to 4. In certain embodiments, $L^2$ is selected from the group consisting of —NH— and —N(Me)-. In certain embodiments, $L^2$ is O. In certain embodiments, the compound of Formula (IIIa) is selected from compounds 103, 104, 111, 116, 126, 130-133, 135, 137, 148, 149, 151, 157-159, 161, 162, 165, 166, 174, 187, 188, 202-208, 215-217, 221, 231, 232, 242, 243, 254, 255, 260, 263, 288, 294, 301, 318, 319, and 321 in Table 1.

In certain embodiments, provided is a compound of Formula (IV), or a pharmaceutically salt, tautomer, stereoisomer, and/or mixture of stereoisomers thereof:

IV

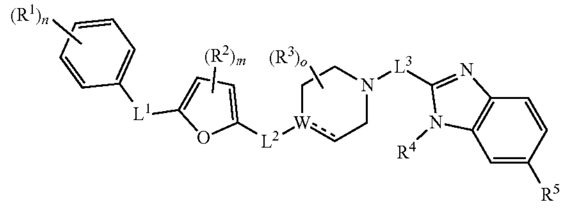

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

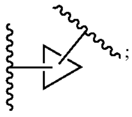

;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

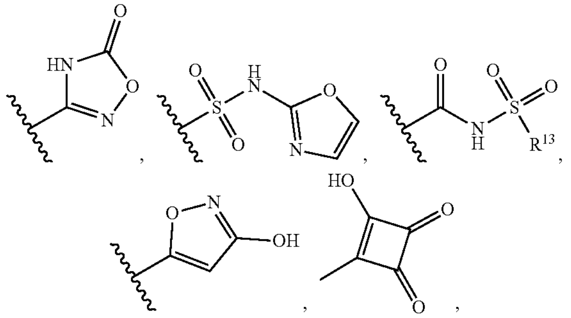

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

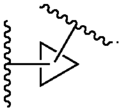

.

In certain embodiments, $L^2$ is selected from the group consisting of —NH— and —N(Me)-. In certain embodiments, the compound of Formula (IV) is selected from compounds 8, 9, 19, 20, 24, 26, 30, 31, 36-43, 47, 49, 55, 59, 63, 72-74, 81, 84, 94, 96, 108, and 109 in Table 1.

In certain embodiments, provided is a compound of Formula (V), or a pharmaceutically salt, tautomer, stereoisomer, and/or mixture of stereoisomers thereof:

V

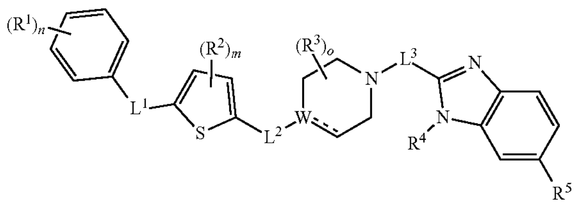

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

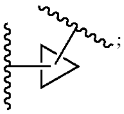;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

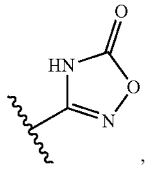, 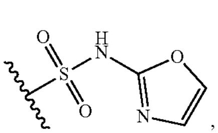, 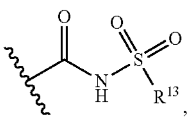, 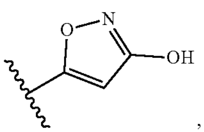, 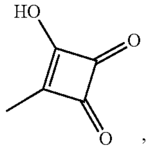, and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

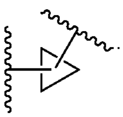.

In certain embodiments, $L^2$ is selected from the group consisting of —NH— and —N(Me)-. In certain embodiments, the compound of Formula (V) is selected from compound 71 in Table 1.

In certain embodiments, provided is a compound of Formula (VI) or a pharmaceutically salt, tautomer, stereoisomer, and/or mixture of stereoisomers thereof:

VI

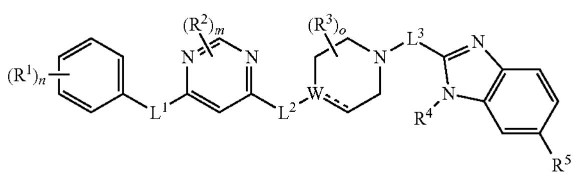

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

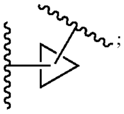;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

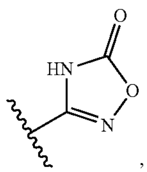, 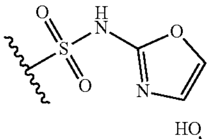, 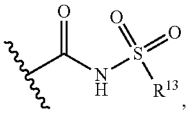, 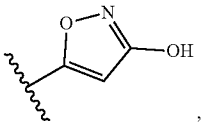, 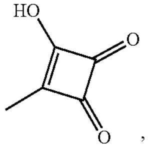, and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

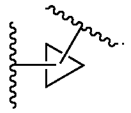

In certain embodiments, $L^2$ is selected from the group consisting of —NH— and —N(Me)-. In certain embodiments, the compound of Formula (VI) is selected from compounds 34, 62, and 331 in Table 1.

In certain embodiments, provided is a compound of Formula (VII), or a pharmaceutically salt, tautomer, stereoisomer, and/or mixture of stereoisomers thereof:

VII

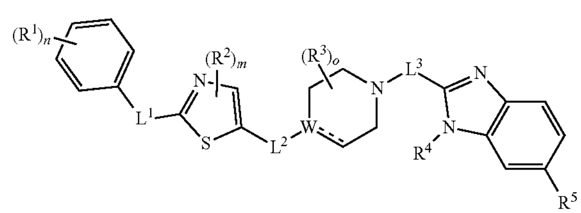

wherein W is N, $CR^{14}$, or C; when W is $CR^{14}$, the adjacent dashed line indicates a single bond; when W is C, the adjacent dashed line indicates a double bond or $L^2$ is —C(H)=; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)=, —$SO_2$—, —O—, —NH—, —N(Me)-, and

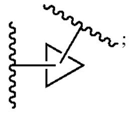;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

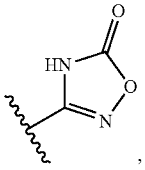, 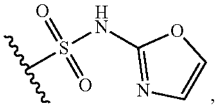, 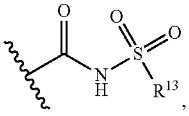,

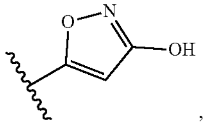, 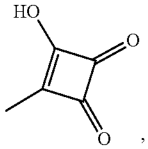, and tetrazolyl; each $R^{11}$ is hydrogen, or alkyl; each $R^{12}$ is hydrogen, or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)=, —$SO_2$—, —O—, —$CF_2$—, —CHF—, or —CH(OH)—, and

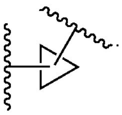

In certain embodiments, $L^2$ is selected from the group consisting of —NH— and —N(Me)-. In certain embodiments, the compound of Formula (VII) is selected from compounds 60, 102, 113, 124, 136, 138, 141, 144, 154, 156, 160, 186, 214, 256, 278, and 279 in Table 1.

In certain embodiments, provided is a compound of Formula (VIII), or a pharmaceutically salt, tautomer, stereoisomer, and/or mixture of stereoisomers thereof:

VIII

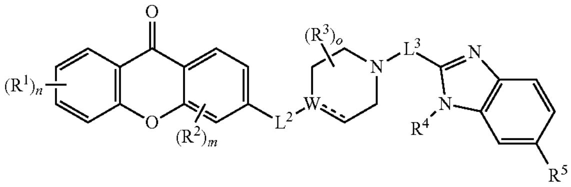

wherein W is N, $CR^{14}$, or C; when W is $CR^{14}$, the adjacent dashed line indicates a single bond; when W is C, the adjacent dashed line indicates a double bond or $L^2$ is —C(H)=; $L^2$ is selected from the group consisting of a bond, —C(O)—, —$CH_2$—, —C(H)=, —$SO_2$—, —O—, —NH—, —N(Me)-, and

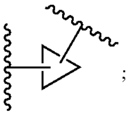;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

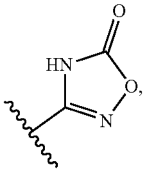
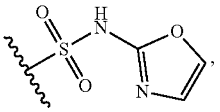,
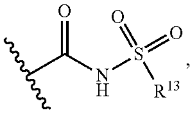,
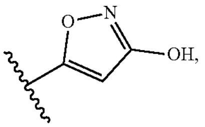
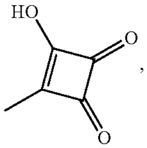, and tetrazolyl; each $R^{11}$ is hydrogen or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

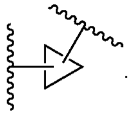.

In certain embodiments, $L^2$ is selected from the group consisting of —NH— and —N(Me)-. In certain embodiments, the compound of Formula (VIII) is selected from compound 44 in Table 1.

In certain embodiments, provided is a compound of Formula (IX), or a pharmaceutically salt, tautomer, stereoisomer, and/or mixture of stereoisomers thereof:

IX

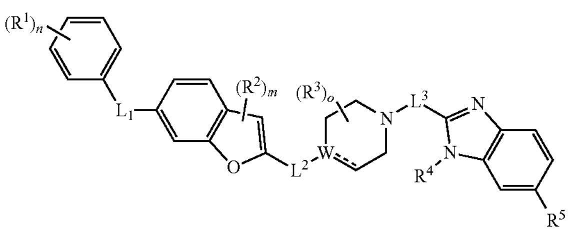

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —$N(Me)CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

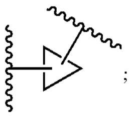;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

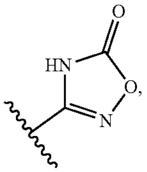
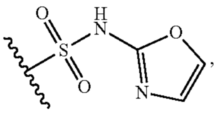,
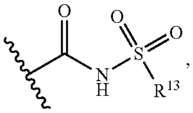,
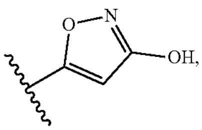
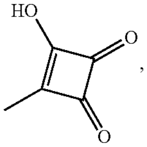, and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

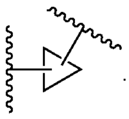.

In certain embodiments, $L^2$ is selected from the group consisting of —NH— and —N(Me)-. In certain embodiments, the compound of Formula (IX) is selected from compounds 27 and 28 in Table 1.

In certain embodiments, provided is a compound of Formula (X), or a pharmaceutically salt, tautomer, stereoisomer, and/or mixture of stereoisomers thereof:

X

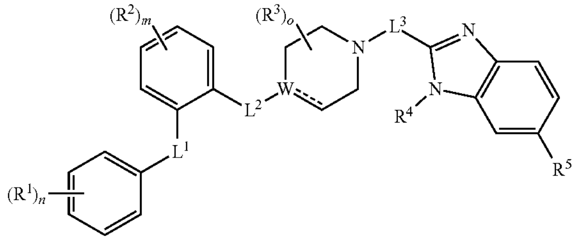

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

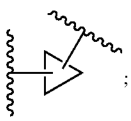

;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

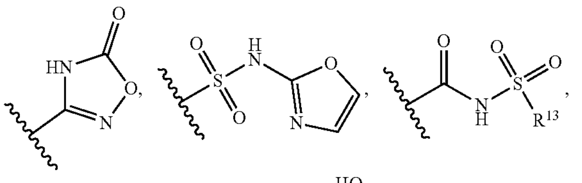

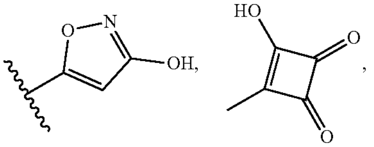

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

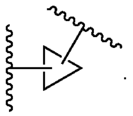

.

In certain embodiments, $L^2$ is selected from the group consisting of —NH— and —N(Me)-. In certain embodiments, the compound of Formula (X) is selected from compound 4, 272, and 284 in Table 1.

In certain embodiments, provided is a compound of Formula (XI), or a pharmaceutically salt, tautomer, stereoisomer, and/or mixture of stereoisomers thereof:

XI

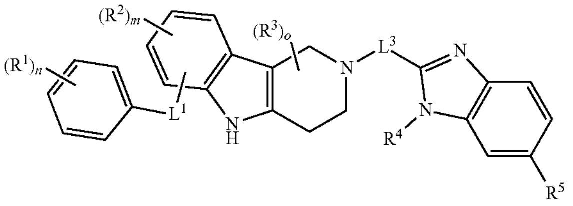

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

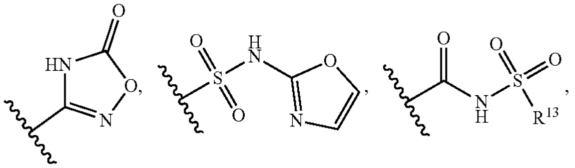

-continued

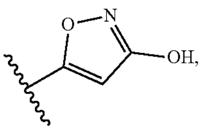

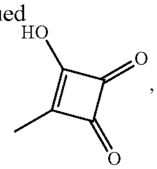

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

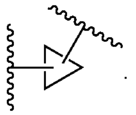

In certain embodiments, $L^2$ is selected from the group consisting of —NH— and —N(Me)-. In certain embodiments, the compound of Formula (XI) is selected from compounds 53, 90, 121, 142, and 143 in Table 1.

In certain embodiments, provided is a compound of Formula (XII), or a pharmaceutically salt, tautomer, stereoisomer, and/or mixture of stereoisomers thereof:

XII

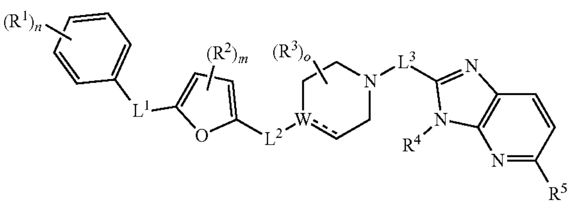

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

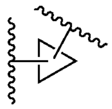

;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

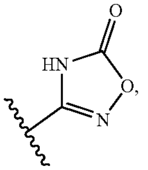

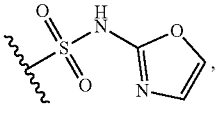

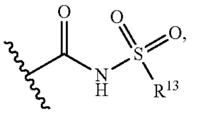

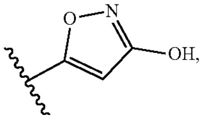

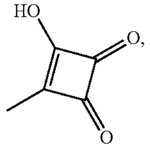

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

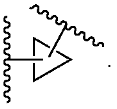

In certain embodiments, $L^2$ is selected from the group consisting of —NH— and —N(Me)-. In certain embodiments, the compound of Formula (XII) is compound 108 in Table 1.

In certain embodiments, provided is a compound of Formula (XIII), or a pharmaceutically salt, tautomer, stereoisomer, and/or mixture of stereoisomers thereof:

XIII

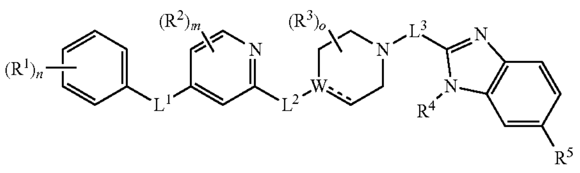

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

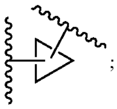
;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

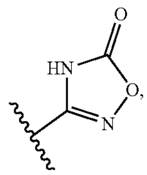
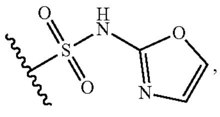
,

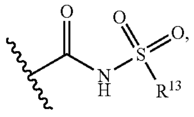
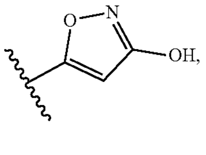
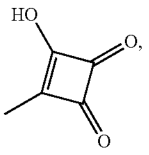

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)=, —$SO_2$—, —O—, —$CF_2$—, —CHF—, or —CH(OH)—, and

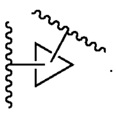
.

In certain embodiments, $L^2$ is selected from the group consisting of —NH— and —N(Me)-. In certain embodiments, the compound of Formula (XIII) is selected from compounds 88, 178, and 179 in Table 1.

In certain embodiments, provided is a compound of Formula (XIV), or a pharmaceutically salt, tautomer, stereoisomer, and/or mixture of stereoisomers thereof:

XIV

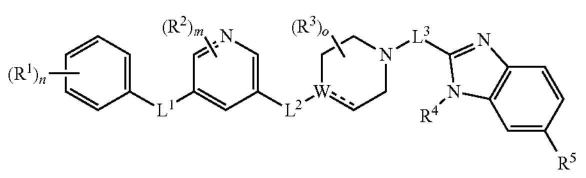

wherein W is N, $CR^{14}$, or C; when W is $CR^{14}$, the adjacent dashed line indicates a single bond; when W is C, the adjacent dashed line indicates a double bond or $L^2$ is —C(H)=; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)=, —$SO_2$—, —O—, —NH—, —N(Me)-, and

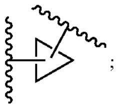
;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

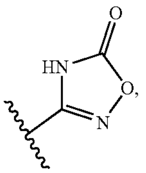
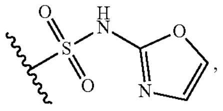
,

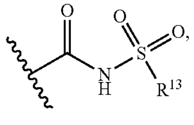
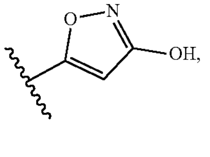
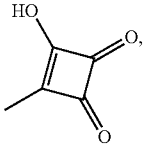

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)=, —$SO_2$—, —O—, —$CF_2$—, —CHF—, or —CH(OH)—, and

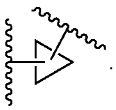

In certain embodiments, $L^2$ is selected from the group consisting of —NH— and —N(Me)-. In certain embodiments, the compound of Formula (XIV) is selected from compounds 85, 139, and 220 in Table 1.

In certain embodiments, provided is a compound of Formula (XV), or a pharmaceutically salt, tautomer, stereoisomer, and/or mixture of stereoisomers thereof:

XV

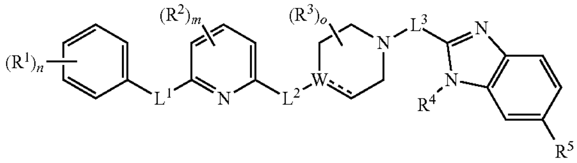

wherein W is N, $CR^{14}$, or C; when W is $CR^{14}$, the adjacent dashed line indicates a single bond; when W is C, the adjacent dashed line indicates a double bond or $L^2$ is —C(H)=; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)=, —$SO_2$—, —O—, —NH—, —N(Me)-, and

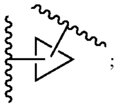

;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

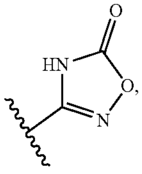

,

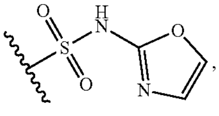

,

-continued

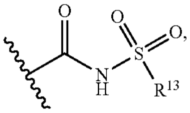

,

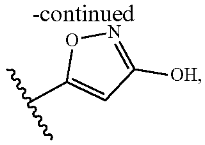

,

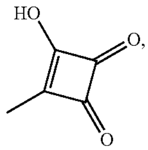

, and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)=, —$SO_2$—, —O—, —$CF_2$—, —CHF—, or —CH(OH)—, and

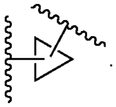

In certain embodiments, $L^2$ is selected from the group consisting of —NH— and —N(Me)-. In certain embodiments, $L^2$ is O. In certain embodiments, the compound of Formula (XV) is selected from compounds 101, 114, 118, 120, 123, 140, 146, 152, 153, 198-200, 246-249, 251-253, 264, 268-271, 285, 290, 291, 330, and 347 in Table 1.

In certain embodiments, provided is a compound of Formula (XVI), or a pharmaceutically salt, tautomer, stereoisomer, and/or mixture of stereoisomers thereof:

XVI

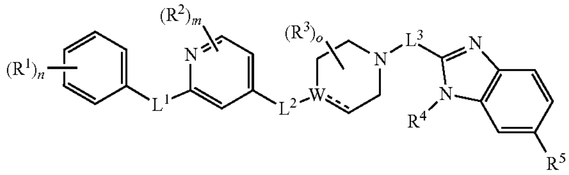

wherein W is N, $CR^{14}$, or C; when W is $CR^{14}$, the adjacent dashed line indicates a single bond; when W is C, the adjacent dashed line indicates a double bond or $L^2$ is —C(H)=; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)=, —$SO_2$—, —O—, —NH—, —N(Me)-, and

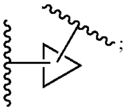

;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

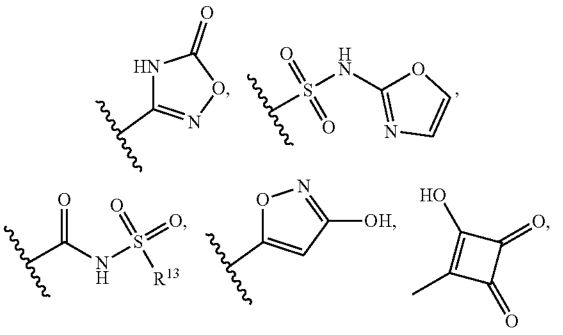

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

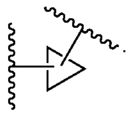

In certain embodiments, $L^2$ is selected from the group consisting of —NH— and —N(Me)-. In certain embodiments, $L^2$ is O. In certain embodiments $R^{14}$ is $CH_2F$ or $CH_2OH$. In certain embodiments, the compound of Formula (XVI) is selected from compounds 99, 128, 145, 150, 155, 163, 164, 168-171, 182, 183, 189, 227, 230, 239-241, 250, 257-259, 265-267, 274-277, 280, 283, 287, 292, 295, 297, 299, 308, 316, 321, 322, 333, 335, 337, 345, 346, 352, 354, 356-358, 362-364, 366-368, 378, and 380 in Table 1.

In certain embodiments, provided is a compound of Formula (XVIa), or a pharmaceutically salt, tautomer, stereoisomer, and/or mixture of stereoisomers thereof:

XVIa

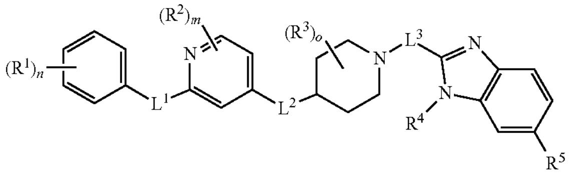

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —$CF_2$—, —CHF—, or —CH(OH)—, —NH—, —N(Me)-, and

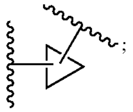

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

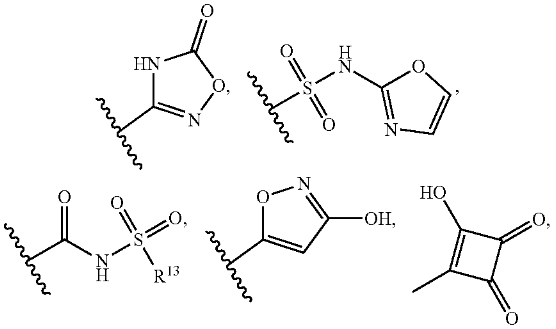

and tetrazolyl; each $R^{11}$ is hydrogen or alkyl; each $R^{12}$ is hydrogen or alkyl; each $R^{13}$ is hydrogen or alkyl; $R^{14}$ is hydrogen, cyano, halo, hydroxyl, or methyl; n is an integer from 0 to 5; m is an integer from 0 to 4. In certain embodiments, $L^2$ is selected from the group consisting of a bond, —C(O)—, —$CH_2$—, —C(H)═, —$CF_2$—, —$SO_2$—, —O—, —$CF_2$—, —CHF—, —CH(OH)—, and

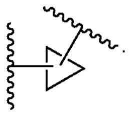

In certain embodiments, $L^2$ is selected from the group consisting of —NH— and —N(Me)-. In certain embodiments, $L^2$ is O. In certain embodiments, the compound of Formula (XVI) is selected from compounds 128, 145, 168-171, 182, 183, 227, 230, 239-241, 250, 257-259, 265-267, 274-277, 280, 283, 287, 292, 295, 297, 299, 302, 308, 316, 321, 322, 333, 335-337, 344-346, 352, 354, 356-359, 362-368, 378, and 380 in Table 1.

In certain embodiments, provided is a compound of Formula (XVII), or a pharmaceutically salt, tautomer, stereoisomer, and/or mixture of stereoisomers thereof:

XVII

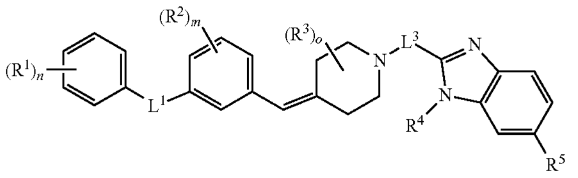

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

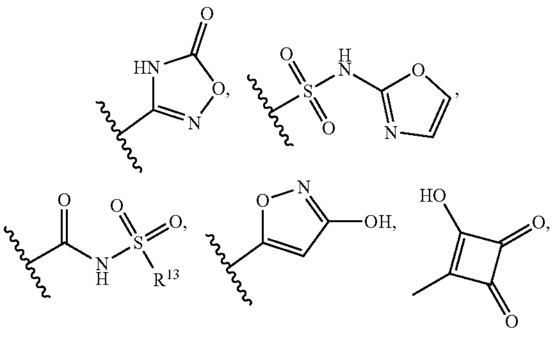

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

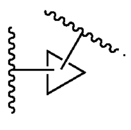

In certain embodiments, $L^2$ is selected from the group consisting of —NH— and —N(Me)-. In certain embodiments, the compound of Formula (XVII) is selected from compound 106 in Table 1.

In certain embodiments, provided is a compound of Formula (XVIII), or a pharmaceutically salt, tautomer, stereoisomer, and/or mixture of stereoisomers thereof:

XVIII

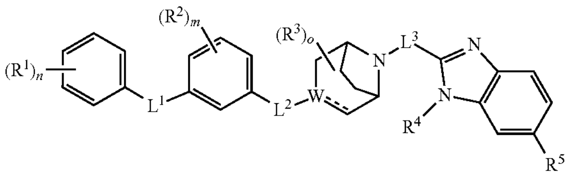

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

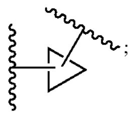

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

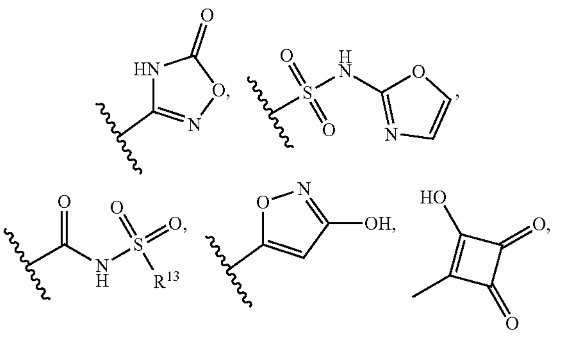

and tetrazolyl; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

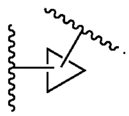

In certain embodiments, $L^2$ is selected from the group consisting of —NH— and —N(Me)-. In certain embodiments, the compound of Formula (XVIII) is compound 87 in Table 1.

In certain embodiments, provided is a compound of Formula (XXV), or a pharmaceutically salt, tautomer, stereoisomer, and/or mixture of stereoisomers thereof:

XXV

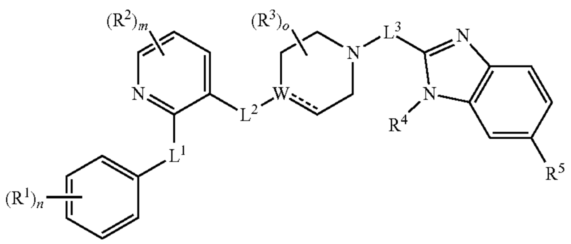

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —$CF_2$—, —CHF—, or —CH(OH)—, —NH—, —N(Me)-, and

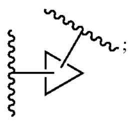

;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}$NCO—; each $R^3$ is independently selected from the group consisting of alkyl, substituted alkyl, halo, cyano, azido, alkoxy, haloalkoxy, and $R^{11}R^{12}$NCO—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

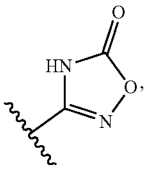

,

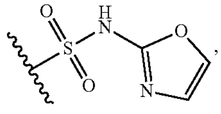

,

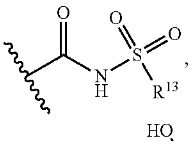

,

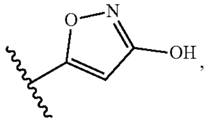

,

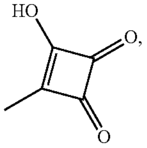

, and tetrazolyl; each $R^{11}$ is hydrogen or alkyl; each $R^{12}$ is hydrogen or alkyl; each $R^{13}$ is hydrogen or alkyl; $R^{14}$ is hydrogen, cyano, halo, hydroxyl, or methyl; n is an integer from 0 to 5; m is an integer from 0 to 4; o is an integer from 0 to 4; p is an integer from 0 or 1; q is an integer from 0 or 1. In certain embodiments, p is 0; and q is 0. In certain embodiments, p is 1; and q is 0. In certain embodiments, p is 0; and q is 1. In certain embodiments, p is 1; and q is 1. In certain embodiments, $L^2$ is selected from the group consisting of a bond, —C(O)—, —$CH_2$—, —C(H)═, —$CF_2$—, —$SO_2$—, —O—, —$CF_2$—, —CHF—, —CH(OH)—, and

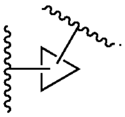

.

In certain embodiments, $L^2$ is selected from the group consisting of —NH— and —N(Me)-. In certain embodiments, the compound of Formula (XXV) is compound 286 in Table 1.

In certain embodiments, provided is a compound of Formula (XXVI), or a pharmaceutically salt, tautomer, stereoisomer, and/or mixture of stereoisomers thereof:

XXVI

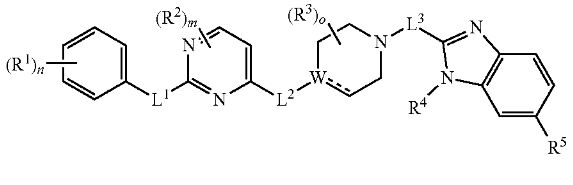

wherein W is N, $CR^{14}$, or C; when W is $CR^{14}$, the adjacent dashed line indicates a single bond; when W is C, the adjacent dashed line indicates a double bond or $L^2$ is —C(H)═; $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

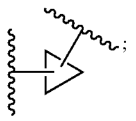

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

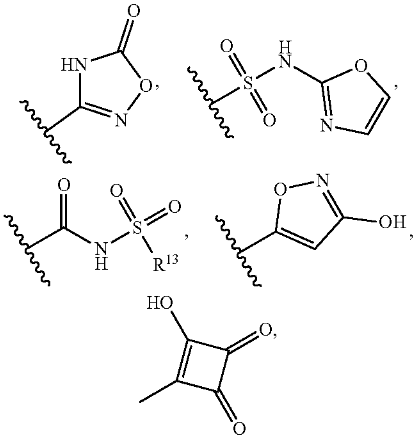

and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

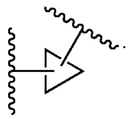

In certain embodiments, $L^2$ is selected from the group consisting of —NH— and —N(Me)-. In certain embodiments, $L^2$ is O. In certain embodiments, the compound of Formula (XXVI) is selected from compounds 261, 262, 296, 304, 306, 307, 311, 313, 315, 325, 326, 331, 338, 340, 342, 343, 348, 353, 354, 355, 369, 374-, 376, 475-481, 483, 485, 489, 490, 492, 493, 495, 498, 504, 510, 512, 514, and 515 in Table 1.

In certain embodiments, provided is a compound of Formula (XXVII), or a pharmaceutically salt, tautomer, stereoisomer, and/or mixture of stereoisomers thereof:

XXVII

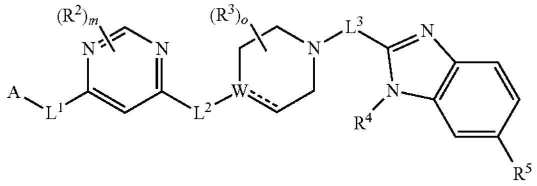

wherein A is —$NMe_2$ or —N($CH_3$)cylcohexane; $L^1$ is absent; W is N, $CR^{14}$, or C; when W is $CR^{14}$, the adjacent dashed line indicates a single bond; when W is C, the adjacent dashed line indicates a double bond or $L^2$ is —C(H)═; $L^2$ is selected from the group consisting of a bond, —C(O)—, —$CH_2$—, —C(H)═, —$SO_2$—, —O—, —NH—, —N(Me)-, and

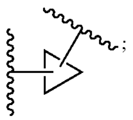

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

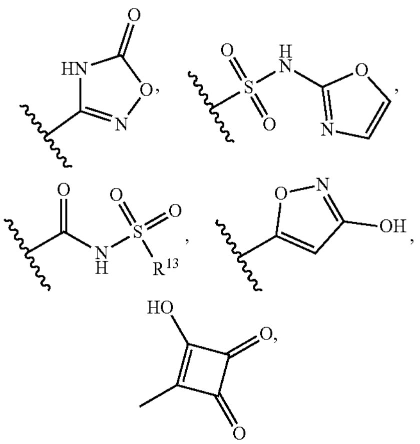

and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

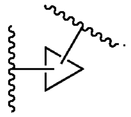

In certain embodiments, the compound of Formula (XXVII) is selected from compounds 1 and 62 in Table 1.

In certain embodiments, provided is a compound of Formula (XXXIX), or a pharmaceutically salt, tautomer, stereoisomer, and/or mixture of stereoisomers thereof:

XXXIX

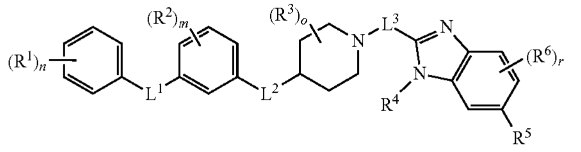

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

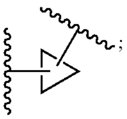

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

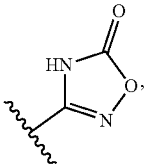,
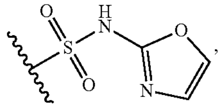,
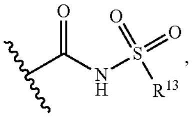,
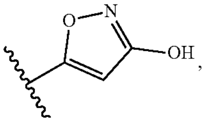,

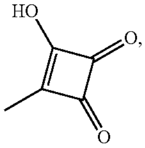

and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; o is an integer from 0 to 4; and r is an integer from 0 to 3. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

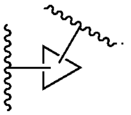

In certain embodiments, each $R^6$ is independently selected from the group consisting of F, and methyl. In certain embodiments, each $R^6$ is F. In certain embodiments, the compound of Formula (XXXIX) is selected from compounds 224, 300, 303, 309, 310, 317, and 320 in Table 1.

In certain embodiments, provided is a compound of Formula (XL), or a pharmaceutically salt, tautomer, stereoisomer, and/or mixture of stereoisomers thereof:

XL

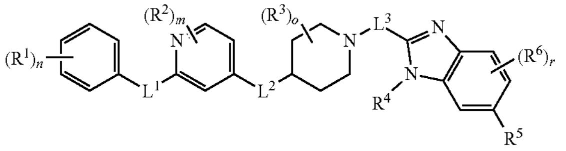

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)—, —$SO_2$—, —O—, —NH—, —N(Me)-, and

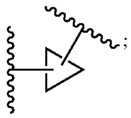

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

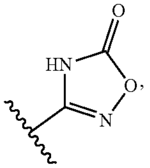 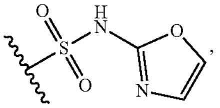

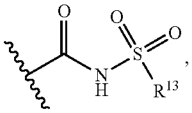 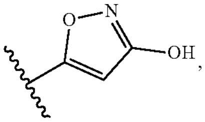

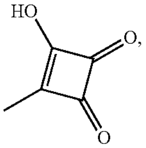

and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; o is an integer from 0 to 4; and r is an integer from 0 to 3. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

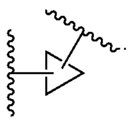

In certain embodiments, each $R^6$ is independently selected from the group consisting of F, and methyl. In certain embodiments, each $R^6$ is F. In certain embodiments, the compound of Formula (XL) is selected from compounds 302, 325, 336, 344, 359, and 365 in Table 1.

In certain embodiments, provided is a compound of Formula (XLI), or a pharmaceutically salt, tautomer, stereoisomer, and/or mixture of stereoisomers thereof:

XLI

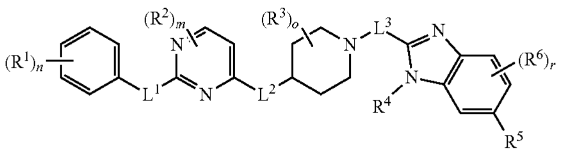

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —$N(Me)CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

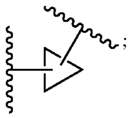

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

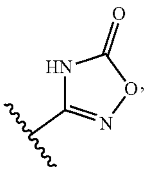 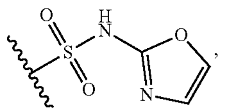

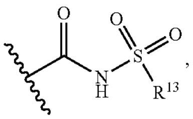 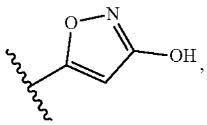

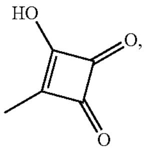

and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; o is an integer from 0 to 4; and r is an integer from 0 to 3. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

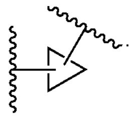

.

In certain embodiments, each $R^6$ is independently selected from the group consisting of F, and methyl. In certain embodiments, each $R^6$ is F. In certain embodiments, each $R^6$ is methyl. In certain embodiments, the compound of Formula (XLI) is selected from compounds 302, 325, 336, 344, 359, 365, 478, 482, 484, 494, 496, 500-503, 505, 508, 509, and 511 in Table 1.

In certain embodiments, provided is a compound of Formula (XLII), or a pharmaceutically salt, tautomer, stereoisomer, and/or mixture of stereoisomers thereof:

XLII

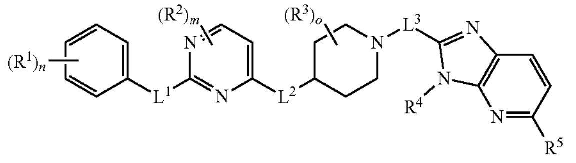

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

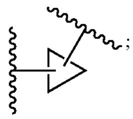

;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

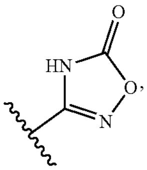

,

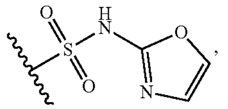

,

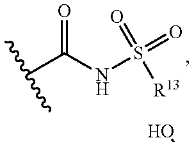

,

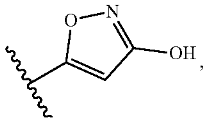

,

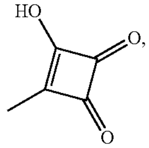

, and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

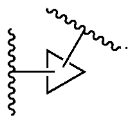

.

In certain embodiments, $L^2$ is —O—. In certain embodiments, the compound of Formula (XLII) is selected from compounds 370, 371, 373, 375, 377, 378, 486, and 513 in Table 1.

In certain embodiments, provided is a compound of Formula (XLIII), or a pharmaceutically salt, tautomer, stereoisomer, and/or mixture of stereoisomers thereof:

XLIII

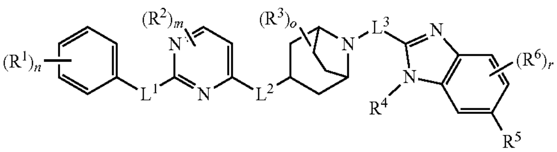

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

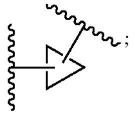

;

$L^3$ is —$CH_2$—, or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkylalkylene, or substituted heterocycloalkylalkylene; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

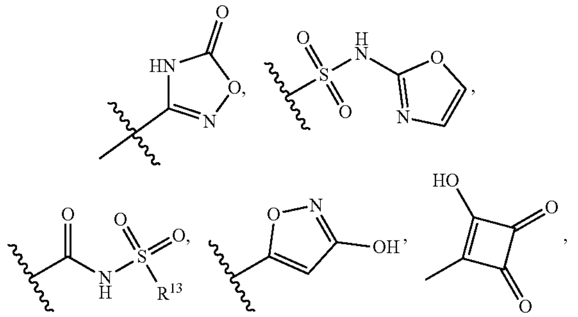

and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; each $R^{11}$ is hydrogen or alkyl; each $R^{12}$ is hydrogen or alkyl; each $R^{13}$ is hydrogen or alkyl; n is an integer from 0 to 5; m is an integer from 0 to 4; o is an integer from 0 to 4; r is an integer from 0 to 3. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

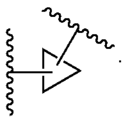

In certain embodiments, $L^2$ is —O—. In certain embodiments, each $R^6$ is independently selected from the group consisting of F, and methyl. In certain embodiments, each $R^6$ is F. In certain embodiments, each $R^6$ is methyl. In certain embodiments, the compound of Formula (XLIII) is c selected from compounds 487 and 488 in Table 1.

In certain embodiments, provided is a compound of Formula (XLII), or a pharmaceutically salt, tautomer, stereoisomer, and/or mixture of stereoisomers thereof:

XLIV

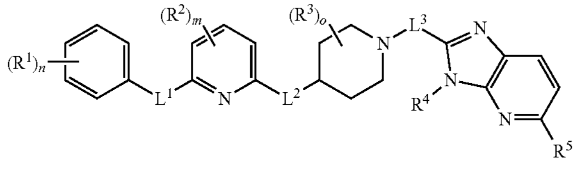

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —$N(Me)CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

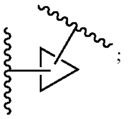

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —$C(OH)CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

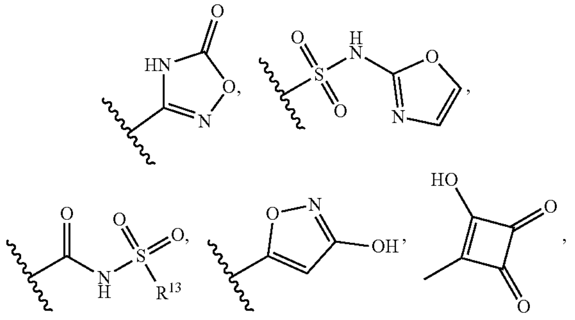

and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

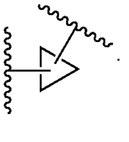

In certain embodiments, $L^2$ is —O—. In certain embodiments, the compound of Formula (XLIV) is compound 372 in Table 1.

In certain embodiments, provided is a compound of Formula (XLV), or a pharmaceutically salt, tautomer, stereoisomer, and/or mixture of stereoisomers thereof:

XLV

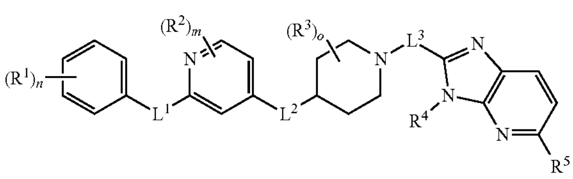

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

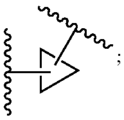

;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

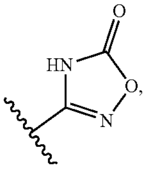

,

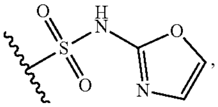

,

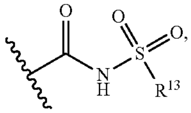

,

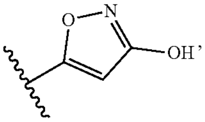

,

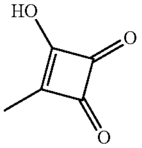

, and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

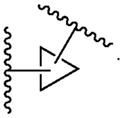

.

In certain embodiments, $L^2$ is —O—. In certain embodiments, the compound of Formula (XLV) is compound 379 in Table 1.

In certain embodiments, provided is a compound of Formula (XLVI), or a pharmaceutically salt, tautomer, stereoisomer, and/or mixture of stereoisomers thereof:

VLVI

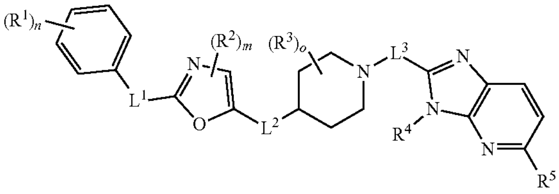

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

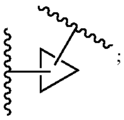

;

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

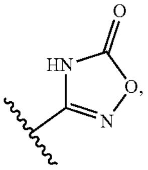

,

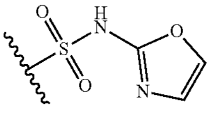

,

-continued

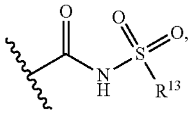

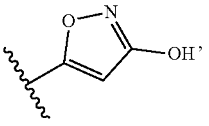

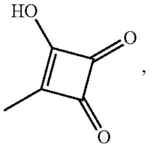

and tetrazolyl; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; and o is an integer from 0 to 4. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

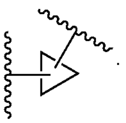

In certain embodiments, $L^2$ is —O—. In certain embodiments, the compound of Formula (XLVI) is selected from compounds 125 and 129 in Table 1.

In certain embodiments, provided is a compound of Formula (XLI), or a pharmaceutically salt, tautomer, stereoisomer, and/or mixture of stereoisomers thereof:

XLVII

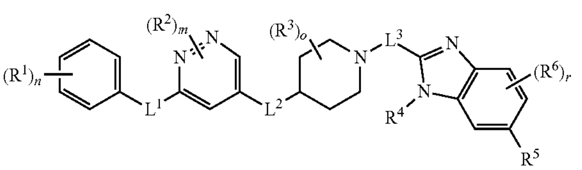

wherein $L^1$ is selected from the group consisting of —O—, —$CH_2$—, —NH—, —N(Me)-, —N(Et)-, —$OCH_2$—, —OC(H,Me)-, —$CH_2O$—, —$NHCH_2$—, —N(Me)$CH_2$—, and —$SO_2NH$—; $L^2$ is selected from the group consisting of a bond, —C(O)—, —$CH_2$—, —C(H)═, —$SO_2$—, —O—, —NH—, —N(Me)-, and

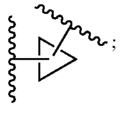

$L^3$ is —$CH_2$— or —C(O)—; each $R^1$ is independently selected from the group consisting of alkyl, substituted alkyl, halo, cyano, azido, alkoxy, haloalkoxy, and $R^{11}R^{12}NCO$—; each $R^2$ is independently selected from the group consisting of alkyl, substituted alkyl, halo, cyano, azido, alkoxy, haloalkoxy, and $R^{11}R^{12}NCO$—; each $R^3$ is independently selected from the group consisting of alkyl, substituted alkyl, halo, cyano, azido, alkoxy, haloalkoxy, and $R^{11}R^{12}NCO$—; $R^4$ is alkyl, substituted alkyl, unsubstituted arylalkylene, substituted arylalkylene, heteroalkyl, substituted heteroalkyl, unsubstituted heteroarylalkylene, substituted heteroarylalkylene, unsubstituted heterocycloalkyl, or substituted heterocycloalkyl; $R^5$ is selected from the group consisting of —COOH, —$COCF_3$, —C(OH)$CF_3$, —CONHCN, —CONHOH, CONHOMe, —$CONHSO_2N(Me)_2$, —$PO_3H_2$, —PO(Me)(OH), —$SO_3H$, —$SO_2NH_2$, —$SO_2NHMe$, —$B(OH)_2$,

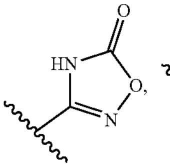

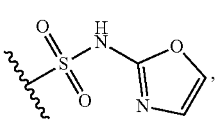

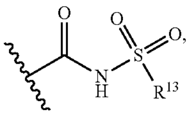

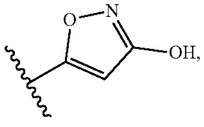

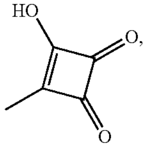

and tetrazolyl; each $R^6$ is independently selected from the group consisting of alkyl, substituted alkyl, halo, hydroxyl, alkoxyl, $R^{11}R^{12}NCO$—, and $R^{11}R^{12}N$—; each $R^{11}$ is hydrogen, or alkyl; each $R^{12}$ is hydrogen, or alkyl; each $R^{13}$ is hydrogen, or alkyl; n is an integer from 0 to 5; m is an integer from 0 to 4; o is an integer from 0 to 4; and r is an integer from 0 to 3. In certain embodiments, $L^2$ is selected from the group consisting of a bond, —C(O)—, —$CH_2$—, —C(H)═, —$SO_2$—, —O—, —$CF_2$—, —CHF—, or —CH(OH)—, and

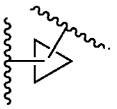

In certain embodiments, each $R^6$ is independently selected from the group consisting of F, and methyl. In certain embodiments, each $R^6$ is F. In certain embodiments, each $R^6$ is methyl. In certain embodiments, the compound of Formula (XLVII) is compound 491 in Table 1.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein each $R^2$ and $R^3$ is H, or F.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein m is 0; and o is 0.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein W is N, or CH.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein W is C.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein W is CH.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein W is N.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein W is $CR^{14}$.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^4$ is selected from the group consisting of oxetan-2-yl-methyl, (1-ethyl-1H-imidazol-5-yl)-methyl, oxelan-3-yl-methyl and 1,3-oxazol-2-yl-methyl.

In certain embodiments, provided is a compound of any of Formulas (XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^4$ is selected from the group consisting of oxetan-2-yl-methyl, and (1-ethyl-1H-imidazol-5-yl)-methyl.

In certain embodiments, provided is a compound of any of Formulas (XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^4$ is oxetan-2-yl-methyl.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^4$ is (2S)-oxetan-2-yl-methyl.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^4$ is (1-ethyl-1H-imidazol-5-yl)-methyl.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^4$ is selected from the group consisting of(S)-buta-4-yl-1,3-diol, butan-1-yl-one, 1-(cyanomethyl)-cycloprop-1-yl-methyl, 1-(Fluoromethyl)-cycloprop-1-yl-methyl, 1-hydroxyl-cycloprop-1-yl-methyl, isoxazol-5-yl-methyl, (1-methyl-1H-imidazol-5-yl)-methyl, 1-methoxy-cycloprop-1yl-methyl, methoxyethan-2-yl, 1-(2-methoxyethyl)-cycloprop-1-yl-methyl, and 2-oxabicyclo [2.1.1]hexa-1-yl-methyl.

In certain embodiments, provided is a compound of Formula (XXX), or a pharmaceutically salt, tautomer, stereoisomer, and/or mixture of stereoisomers thereof, wherein $R^4$ is H.

In certain embodiments, provided is a compound of Formula (XXX), or a pharmaceutically salt, tautomer, stereoisomer, and/or mixture of stereoisomers thereof, wherein $R^4$ is selected from the group consisting of oxelan-3-yl-methyl and 1,3-oxazol-2-yl-methyl.

In certain embodiments, provided is a compound of Formula (XXX) and (XXXI), or a pharmaceutically salt, tautomer, stereoisomer, and/or mixture of stereoisomers thereof, wherein $R^4$ is (3R)-oxelan-3-yl-methyl.

In certain embodiments, provided is a compound of Formula (XXX) and (XXXI), or a pharmaceutically salt, tautomer, stereoisomer, and/or mixture of stereoisomers thereof, wherein $R^4$ is 1,3-oxazol-2-yl-methyl.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^5$ is —COOH, or —COOMe.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^5$ is —COOH In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^5$ is tetrazolyl.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $R^5$ is 1H-1,2,3,4-tetrazol-5-yl.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is $—CH_2—$, —C(O)—, or $—SO_2—$.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is a bond, —C(O)—, $—CH_2—$, —C(H)═, $—SO_2—$, —O—, $—CF_2—$, —CHF—, or —CH(OH)—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —CH═ or —O—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is $—CF_2—$, —CHF—, or —CH(OH)—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH— or —N(Me)-.

In certain embodiments, provided is a compound of Formula (XXX), or a pharmaceutically salt, tautomer, stereoisomer, and/or mixture of stereoisomers thereof, wherein $L^2$ is a bond.

In certain embodiments, provided is a compound of Formula (XXXI), or a pharmaceutically salt, tautomer, stereoisomer, and/or mixture of stereoisomers thereof, wherein $L^2$ is $—CH_2—$.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^3$ is $—CH_2—$.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^3$ is —C(O)—.

In certain embodiments, provided is a compound of Formulas (XXX), or a pharmaceutically salt, tautomer, stereoisomer, and/or mixture of stereoisomers thereof, wherein $L^1$ is —$CH_2O$—, or —$OCH_2$—.

In certain embodiments, provided is a compound of Formula (XXXI), or a pharmaceutically salt, tautomer, stereoisomer, and/or mixture of stereoisomers thereof, wherein $L^1$ is —$CH_2O$—, or —$OCH_2$.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$CH_2O$—; and $L^2$ is —$CH_2$— or —CO—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$CH_2O$—; and $L^3$ is —C(O)—.

In certain embodiments, provided is a compound of any of Formulas (I)-(XVIII), (XXV)-(XXVII), (XXX), and (XXXI), or a pharmaceutically salt, tautomer, stereoisomer, and/or mixture of stereoisomers thereof, wherein $L^1$ is —O—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$CH_2$—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —NH—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —N(Me)-.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —N(Et)-.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$OCH_2$—.

In certain embodiments, provided is a compound of any of Formulas (I)-(XVIII), (XXV)-(XXVII), (XXX), and (XXXI), or a pharmaceutically salt, tautomer, stereoisomer, and/or mixture of stereoisomers thereof, wherein $L^1$ is —OC(H,Me)-.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$CH_2O$—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$NHCH_2$—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —N(Me)$CH_2$—.

In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^1$ is —$SO_2NH$—.

In certain embodiments of any of Formulas (I)-(XVIII), (XXV)-(XXVII), (XXX), a (XXXI), (XXXIX), and (XL-XLVII), $L^1$ is —O—; and $L^2$ is —C(O)—. In certain embodiments of any of Formulas (I)-(XVIII), (XXV)-(XXVII), (XXX), (XXXI), (XXXIX), and (XL-XLVII), $L^1$ is —O—; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —O—; and $L^2$ is —C(H)=. In certain embodiments of any of Formulas (I)-(XVIII), (XXV)-(XXVII), (XXX), (XXXI), (XXXIX), and (XL-XLVII), $L^1$ is —O—; and $L^2$ is —$SO_2$—. In certain embodiments of any of Formulas (I)-(XVIII), (XXV)-(XXVII), (XXX), (XXXI), (XXXIX), and (XL-XLVII), $L^1$ is —O—; and $L^2$ is —NH—. In certain embodiments of any of Formulas (I)-(XVIII), (XXV)-(XXVII), (XXX), (XXXI), (XXXIX), and (XL-XLVII), $L^1$ is —O—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —C(H)=; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLICI), $L^1$ is —O—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —C(H)=; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), and (XXXI), $L^1$ is —O—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is (1-ethyl-1H-imidazol- 5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLIIV), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), and (XXXI) $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —C(O)—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —C(H)═. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —$SO_2$—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —NH—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; and $L^3$ is —$CH_2$—. In certain embodiments of any of Formulas (I)-(XVIII), (XXV)-(XXVII), (XXX), and (XXXI), $L^1$ is —$CH_2O$—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLIII), $L^1$ is —$CH_2O$—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (2) XI), (XXXIX), and (XL-XLVII), $L^1$ is —$CH_2O$—; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—;

$R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), XXXIX), and (XL-XLVII), $L^1$ is —$CH_2O$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; and $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; and $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)=; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1, 3-diol. In certain embodiments of any of Formulas (I)-(XVIII), (XXV)-(XXVII), (XXX), and (XXXI) $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), and (XXXI) $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), and (XXXI) $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl) azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (2), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —C(O)—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —C(H)=. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —$SO_2$—. In certain embodiments of any of Formulas (I)-(XVIII), (XXV)-(XXVII), (XXX), and (XXXI), $L^1$ is —$OCH_2$—; and $L^2$ is —NH—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLIVII), $L^1$ is —$OCH_2$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLIII), $L^1$ is —$OCH_2$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLIII), $L^1$ is —$OCH_2$—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLIVII), $L^1$ is —$OCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLIII), $L^1$ is —$OCH_2$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), and (XXXI) $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLIII), $R^4$ is 1-(Fluoromethyl)-cycloprop-1-yl-methyl. In certain embodiments of any of Formulas (I)-(XVIII), (XXV)-(XXVII), (XXX), and (XXXI) $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), and (XXXI) $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (2), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —NH— and $L^2$ is —C(O)—. In certain embodiments of any of Formulas (I)-(XVIII), (XXV)-(XXVII), (XXX), (XXXI), (XXXIX), and (XL-XLVII), $L^1$ is —NH— and $L^2$ is —$CH_2$—. In certain embodiments of any of Formulas (I)-(XVIII), (XXV)-(XXVII), (XXX), and (XXXI), $L^1$ is —NH—; and $L^2$ is —C(H)═. In certain embodiments of any of Formulas (I)-(XVIII), (XXV)-(XXVII), (XXX), (XXXI), (XXXIX), and (XL-XLVII), $L^1$ is —NH—; and $L^2$ is —$SO_2$—. In certain embodiments of any of Formulas (I)-(XVIII), (XXV)-(XXVII), (XXX), (XXXI), (XXXIX), and (XL-XLVII), $L^1$ is —NH—; and $L^2$ is —NH—In certain embodiments of any of Formulas (I)-(XVIII), (XXV)-(XXVII), (XXX), (XXXI), (XXXIX), and (XL-XLVII), $L^1$ is —NH—; and $L^2$ is —N(Me)-. In certain embodiments of any of Formulas (I)-(XVIII), (XXV)-(XXVII), (XXX), (XXXI), (XXXIX), and (XL-XLIII), $L^1$ is —NH—; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), ((XX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLIII), $L^1$ is —NH—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-;

$L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)- and $L^2$ is —C(O)—. In certain embodiments of any of Formulas (I)-(XVIII), (XXV)-(XXVII), (XXX), (XXXI), (XXXIX), and (XL-XLVII), $L^1$ is —N(Me)- and $L^2$ is —$CH_2$—. In certain embodiments of any of Formulas (I)-(XVIII), (XXV)-(XXVII), (XXX), (XXXI), (XXXIX), and (XL-XLVII), $L^1$ is —N(Me)- and $L^2$ is —$SO_2$—. In certain embodiments of any of Formulas (I)-(XVIII), (XXV)-(XXVII), (XXX), (XXXI), (XXXIX), and (XL-XLVII), $L^1$ is —N(Me)-; and $L^2$ is —NH—. In certain embodiments of any of Formulas (I)-(XVIII), (XXV)-(XXVII), (XXX), (XXXI), (XXXIX), and (XL-XLVII), $L^1$ is —N(Me)-; and $L^2$ is —N(Me)-. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXI), (XXXIX), and (XL-XLIII), $L^1$ is —N(Me)-; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLIII), $L^1$ is —N(Me)-; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is (2S)-oxetan-2-yl-methyl; (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XVII), $L^1$ is —N(Me)-; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), and (XXXI), $L^1$ is —N(Me)-; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV) (XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI) (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLIII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Et)-; and $L^2$ is —C(O)—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —C(H)═. In certain embodiments of any of Formulas (I)-(XVIII), (XXV)-(XXVII), (XXX), (XXXI), (XXXIX), and (XL-XLVII), $L^1$ is —N(Et)-; and $L^2$ is —$SO_2$—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —NH—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —N(Me)-. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLIVI), $L^1$ is —N(Et)-; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLIII), $L^1$ is —N(Et)-; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLIII), $L^1$ is —N(Et)-; $L^2$ is —C(H)=; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), and (XXXI) $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), and (XXXI) $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), and (XXXI) $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), and (XXXI) $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl] methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —C(O)—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —C(H)=. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —$SO_2$—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —NH—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)=; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; and $L^3$ is —$CH_2$—. In certain embodiments of any of Formulas (I)-(XVIII), (XXV) (XXVII), (XXX), (XXXI), (XXXIX), and (XL-XLVII), $L^1$ is —$NHCH_2$—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), and (XXXI), $L^1$ is —$NHCH_2$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLIII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —C(O)—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —C(H)═. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —$SO_2$—. In certain embodiments of any of Formulas (I)-(XVIII), (XXV)-(XXVII), (XXX), and (XXXI), $L^1$ is —N(Me)$CH_2$—; and $L^2$ is —NH—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLIII), $L^1$ is —N(Me)$CH_2$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV) (XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is-$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXII), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX)), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —C(O)—. In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —C(H)═. In certain embodiments of any of Formulas (I)-(XVIII), (XXV)-(XXVII), (XXX), (XXXI), (XXXIX), and (XL-XLVII), $L^1$ is —OC(H,Me)- and $L^2$ is —$SO_2$—. In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —NH—. In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —N(Me)-. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; and $L^3$ is —$CH_2$—. In certain embodiments of any of Formulas (I)-(XVIII), (XXV)-(XXVII), (XXX), a (XXXI), (XXXIX), and (XL-XLVII), $L^1$ is —OC(H,Me)-; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; and $L^3$ is —$CH_2$—. In certain embodiments of any of Formulas (I)-(XVIII), (XXV)-(XXVII), (XXX), and (XXXI), $L^1$ is —OC(H,Me)-; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL- XLVII), $L^1$ is —OC(H,Me)-; $L^2$ is-$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is-$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), and (XXXI) $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl] methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL- XLVII), $L^1$ is —$SO_2NH$—; and $L^2$ is —C(O)—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —C(H)═. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —$SO_2$—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —NH—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; and $L^3$ is —$CH_2$—. In certain embodiments of any of Formulas (I)-(XVIII), (XXV)-(XXVII), (XXX), (XXXI), (XXXIX), and (XL-XVII), $L^1$ is —$SO_2NH$—; $L^2$ is —C(H)═; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XVII), $L^1$ is —$SO_2NH$—; $L^2$ is —C(O)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXX), (XXXIX), and (XL-XLVII), $L^1$ is —$SO_2NH$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLIVII), $L^1$ is —$SO_2NH$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), and (XXXI), $L^1$ is —$SO_2NH$—; $L^2$ is —C(O)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV) (XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1, 3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), and (XXXI) $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), and (XXXI) $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl] methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XX)), (XXXIX), and (XL-XLVII), $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV) (XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is-$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLIII), $L^1$ is —O—; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX)), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl.

In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLIII), $L^1$ is —$OCH_2$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLIII), $L^1$ is —$OCH_2$—; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —C(H)=; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLIII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLIVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—;

$L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), and (XXXI) $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —C(H)=; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), is —N(Me)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —C(H)=; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), and (XXXI) $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL- XLIII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxy-ethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV) (XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), and (XXXI) $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxy-ethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), and (XXXI) $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC (H,Me)-; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLIVII), $L^1$ is —OC(H,Me)-; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX) (XXXI), (XXXIX), and (XL-XLVII), $L^1$ is —$SO_2$NH—; $L^2$ is —C(O)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$CH_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(H)═; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$SO_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLIII), $L^1$ is —$SO_2$NH—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(O)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$CH_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(H)═; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$SO_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(O)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$CH_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(H)═; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$SO_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(O)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$CH_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(H)═; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$SO_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —C(O)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2$NH—; $L^2$ is —$CH_2$—; $L^3$ is —$CH_2$—;

$R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(O)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CH_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —C(H)═; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$SO_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl] methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —O—; and $L^2$ is —O—. In certain embodiments of any of Formulas (I)-(XVIII), (XXV)-(XXVII), (XXX), (XXXI), (XXXIX), and (XL-XLVII), $L^1$ is —O—; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —O—; and $L^2$ is —CHF—. In certain embodiments of any of Formulas (I)-(XVIII), (XXV)-(XXVII), (XXX), (XXXI), (XXXIX), and (XL-XLVII), $L^1$ is —O—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —O—; and $L^2$ is —NH—. In certain embodiments of any of Formulas (I)-(XVIII), (XXV)-(XXVII), (XXX), (XXXI), (XXXIX), and (XL-XVII), $L^1$ is —O—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —O—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLIII), $L^1$ is —O—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XX) XI), (XXXIX), and (XL-XLVII), $L^1$ is —O—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI) (XXXIX), and (XL-XLVII), $L^1$ is —O—; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), v$R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI) (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —O—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —CHF—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —NH—. In certain embodiments of any of Formulas (I)-(XVIII), (XXV)-(XXVII), (XXX), (XXXI), (XXXIX), and (XL-XLVII), $L^1$ is —$CH_2O$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; and $L^3$ is —$CH_2$—. In certain embodiments of any of Formulas (I)-(XVIII), (XXV)-(XXVII), (XXX), and (XXXI), $L^1$ is —$CH_2O$—; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH (OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH (OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (2) XX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), and (XXXI) $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl) azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), and (XXXI), $L^1$ is —$OCH_2$—; and $L^2$ is —O—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —CHF—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —NH—. In certain embodiments of any of Formulas (I)-(XVIII), (XXV)-(XXVII), (XXX), (XXXI), (XXXIX), and (XL-XLVII), $L^1$ is —$OCH_2$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; and $L^3$ is —$CH_2$—. In certain embodiments of any of Formulas (I)-(XVIII), (XXV)-(XXVII), (XXX), and (XXXI), $L^1$ is —$OCH_2$—; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXI), (XXXIX), and (XL-XLVII), $L^1$ is —$OCH_2$—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH (OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH (OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI) (XXXIX), and (XL-XLVII), $L^1$ is —$OCH_2$—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), and (XXXI), $L^1$ is —$OCH_2$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV) (XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), and (XXXI) $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl] methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —NH— and $L^2$ is —O—. In certain embodiments of any of Formulas (I)-(XVIII), (XXV)-(XXVII), (XXX), (XXXI), (XXXIX), and (XL-XLVII), $L^1$ is —NH— and $L^2$ is —$CF_2$—. In certain embodiments of any of Formulas (I)-(XVIII), (XXV)-(XXVII), (XXX), (XXXI), (XXXIX), and (XL-XLVII), $L^1$ is —NH—; and $L^2$ is —CHF—. In certain embodiments of any of Formulas (I)-(XVIII), (XXV)-(XXVII), (XXX), (XXXI), (XXXIX), and (XL-XLVII), $L^1$ is —NH—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —NH—; and $L^2$ is —NH—. In certain embodiments of any of Formulas (I)-(XVIII), (XXV)-(XXVII), (XXX), (XXXI), (XXXIX), and (XL-XLVII), $L^1$ is —NH—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —NH—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —CH (OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —CH (OH)—; $L^3$ is —$CH_2$—; and $R^2$ and $R^3$ are each H. In certain embodiments of any of Formulas (I)-(XVIII), (XXV)-(XXVII), (XXX), and (XXXI), $L^1$ is —NH—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV) (XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CH (OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—;

$R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1, 3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), and (XXXI) $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI) (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl) azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), o (XXXIX), and (XL-XLVII), r a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)- and $L^2$ is —O—. In certain embodiments of any of Formulas (I)-(XVIII), (XXV)-(XXVII), (XXX), and (XXXI), $L^1$ is —N(Me)- and $L^2$ is —$CF_2$—. In certain embodiments of any of Formulas (I)-(XVIII), (XXV)-(XXVII), (XXX), (XXXI), (XXXIX), and (XL-XLVII), $L^1$ is —N(Me)- and $L^2$ is —CHF—. In certain embodiments of any of Formulas (I)-(XVIII), (XXV)-(XXVII), (XXX), (XXXI), (XXXIX), and (XL-XLVII), $L^1$ is —N(Me)- and $L^2$ is —CH(OH)—. In certain embodiments of any of Formulas (I)-(XVIII), (XXV)-(XXVII), (XXX), (XXXI), (XXXIX), and (XL-XLVII), $L^1$ is —N(Me)- and $L^2$ is —NH—. In certain embodiments of any of Formulas (I)-(XVIII), (XXV)-(XXVII), (XXX), (XXXI), (XXXIX), and (XL-XLVII), $L^1$ is —N(Me)- and $L^2$ is —N(Me)-. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH (OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXXIX), and (XL-XLVII), $R^4$ is butan-1-yl-one. In certain (XXVII), (XXX), (XXX embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), and (XXXI) $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl] methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo [2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Et)-; and $L^2$ is —O—. In certain embodiments of any of Formulas (I)-(XVIII), (XXV)-(XXVII), (XXX), and (XXXI), $L^1$ is —N(Et)-; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —CHF—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —NH—. In certain embodiments of any of Formulas (I)-(XVIII), (XXV)-(XXVII), (XXX), (XXXI), (XXXIX), and (XL-XLVII), $L^1$ is —N(Et)-; and $L^2$ is —N(Me)-. In certain embodiments of any of Formulas (I)-(XVIII), (XXV)-(XXVII), (XXX), and (XXXI), $L^1$ is —N(Et)-; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH (OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(ME)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), and (XXXI) $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), and (XXXI) $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XVII), $R^4$ is methoxy-ethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-

(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —O—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —CHF—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —NH—. In certain embodiments of any of Formulas (I)-(XVIII), (XXV)-(XXVII), (XXX), (XXXI), (XXXIX), and (XL-XLVII), $L^1$ is —$NHCH_2$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; and $L^3$ is —$CH_2$—. In certain embodiments of any of Formulas (I)-(XVIII), (XXV)-(XXVII), (XXX), and (XXXI), $L^1$ is —$NHCH_2$—; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; and $L^3$ is —$CH_2$—. In certain embodiments of any of Formulas (I)-(XVIII), (XXV)-(XXVII), (XXX), and (XXXI), $L^1$ is —$NHCH_2$—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH (OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI) (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —O—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —CHF—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —NH—. In certain embodiments of any of Formulas (I)-(XVIII), (XXV)-(XXVII), (XXX), (XXXI), (XXXIX), and (XL-XLVII), $L^1$ is —N(Me)$CH_2$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; and $L^3$ is —$CH_2$—. In certain embodiments of any of Formulas (I)-(XVIII), (XXV) (XXVII), (XXX), (XXXI), (XXXIX), and (XL-XLVII), $L^1$ is —N(Me)$CH_2$—; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV) (XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), and (XXXI), $L^1$ is —N(Me)$CH_2$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), and (XXXI), $L^1$ is —N(Me)$CH_2$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), $R^4$ is 1-(cyanomethyl)-cycloprop-1-yl-methyl. In certain embodiments of any of Formulas (I(XXXIX), and (XL-XLVII), )-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl) azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —O—. In certain embodiments of any of Formulas (I)-(XVIII), (XXV)-(XXVII), (XXX), (XXXI), (XXXIX), and (XL-XLVII), $L^1$ is —OC(H,Me)-; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —OC (H,Me)-; and $L^2$ is —CHF—. In certain embodiments of any of Formulas (I)-(XVIII), (XXV)-(XXVII), (XXX), (XXXI), (XXXIX), and (XL-XLVII), $L^1$ is —OC(H,Me)- and $L^2$ is —CH(OH)—. In certain embodiments of any of Formulas (I)-(XVIII), (XXV)-(XXVII), (XXX), (XXXI), (XXXIX), and (XL-XLVII), $L^1$ is —OC(H,Me)- and $L^2$ is —NH—. In certain embodiments of any of Formulas (I)-(XVIII), (XXV)-(XXVII), (XXX), (XXXI), (XXXIX), and (XL-XLVII), $L^1$ is —OC(H,Me)- and $L^2$ is —N(Me)-. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH (Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC (H,Me)-; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), and (XXXI), $L^1$ is —OC(H,Me)-; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxy-ethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —O—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —$CF_2$—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —CHF—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —CH(OH)—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —NH—. In certain embodiments of any of Formulas (I)-(XVIII), (XXV)-(XXVII), (XXX), (XXXI), (XXXIX), and (XL-XLVII), $L^1$ is —$SO_2NH$—; and $L^2$ is —N(Me)-. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; and $L^3$ is —$CH_2$—. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; and $R^2$ and $R^3$ are each H. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; and $R^4$ is (2S)-oxetan-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; and $R^4$ is (1-ethyl-1H-imidazol-5-yl)-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XX) (XXXIX), and (XL-XLVII), $L^1$ is —$SO_2NH$—; $L^2$ is —CHF—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH (OH)—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (2S)-oxetan-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH (OH)—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (2S)-oxetan-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is (1-ethyl-1H-imidazol-5-yl)-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxy-ethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI) XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV) (XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV) (XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), and (XXXI), $L^1$ is —O—; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —O—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (2 (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$CH_2$O—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; and $R^4$ is oxelan-3-yl-methyl. In certain embodiments of any of Formulas Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), and (XXXI), $L^1$ is —$CH_2O$—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$CH_2O$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV) (XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX) (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH (OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$OCH_2$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)- methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV) (XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL- XLVII), $L^1$ is —NH—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —NH—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (2), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH (OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1, 3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), and (XXXI) $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl) azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH (OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL- XLVII), $L^1$ is —N(Et)-; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Et)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-

(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$NHCH_2$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV) (XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX) (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —N(Me)$CH_2$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is 1,3-oxazol-2-yl-methyl; (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —CH(OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —OC(H,Me)-; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxyethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXXI), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; and $R^4$ is oxelan-3-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; and $R^4$ is 1,3-oxazol-2-yl-methyl. In certain embodiments of any of Formulas Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; and $R^4$ is 1,3-oxazol-2-yl-methyl. In certain embodiments of any of Formulas Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; and $R^4$ is 1,3-oxazol-2-yl-methyl. In certain embodiments of any of Formulas Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; and $R^4$ is 1,3-oxazol-2-yl-methyl. In certain embodiments of any of Formulas Formulas (I)-(XVIII), (XXV) (XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; and $R^4$ is 1,3-oxazol-2-yl-methyl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is oxelan-3-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is 1,3-oxazol-2-yl-methyl; and $R^5$ is —COOH. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is 1,3-oxazol-2-yl-methyl; (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH(OH)—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is oxelan-3-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is oxelan-3-yl-methyl; and $R^5$ is tetrazolyl, for instance 1H-1, 2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —O—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —$CF_2$—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CHF—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —CH (OH)—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —NH—; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In certain embodiments of any of Formulas (I)-(XVIII), (XXV)-(XXVII), (XXX), (XXXI), (XXXIX), and (XL-XLVII), $L^1$ is —$SO_2NH$—; $L^2$ is —N(Me)-; $L^3$ is —$CH_2$—; $R^2$ and $R^3$ are each H; $R^4$ is 1,3-oxazol-2-yl-methyl; and $R^5$ is tetrazolyl, for instance 1H-1,2,3,4-tetrazol-5-yl. In any embodiment according to this paragraph, $R^1$ can be selected from H, Cl, F, Me, —$CF_3$, —OMe, —CN, —C(O)$NMe_2$, alkyl, propyl, isopropyl, and cyclopropyl. In certain embodiments of any of Formulas (I)-(XVIII), (XXV)-(XXVII), (XXX), (XXXI), (XXXIX), and (XL-XLVII), $R^4$ is azetidine-3-yl-methyl. In certain embodiments of any of Formulas (I)-(XVIII), (XXV)-(XXVII), (XXX), (XXXI), (XXXIX), and (XL-XLVII), $R^4$ is (3R)-azetidine-3-yl-methyl. In certain embodiments of any of Formulas (I)-(XVIII), (XXV)-(XXVII), (XXX), (XXXI), (XXXIX), and (XL-XLVII), $R^4$ is (3S)-azetidine-3-yl-methyl. In certain embodiments of any of Formulas (I)-(XVIII), (XXV)-(XXVII), (XXX), (XXXI), (XXXIX), and (XL-XLVII), $R^4$ is(S)-buta-4-yl-1,3-diol. In certain embodiments of any of Formulas (I)-(XVIII), (XXV)-(XXVII), (XXX), (XXXI), (XXXIX), and (XL-XLVII), $R^4$ is butan-1-yl-one. In certain embodiments of any of Formulas (I)-(XVIII), (XXV)-(XXVII), (XXX), (XXXI), (XXXIX), and (XL-XLVII), $R^4$ is 1-(cyanomethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-(Fluoromethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is 1-hydroxyl-cycloprop-1-yl-methyl. In certain embodiments of any of Formulas (I)-(XVIII), (XXV)-(XXVII), (XXX), (XXXI), (XXXIX), and (XL-XLVII), $R^4$ is isoxazol-5-yl-methyl. In certain embodiments of any of Formulas (I)-(XVIII), (XXV)-(XXVII), (XXX), (XXXI), (XXXIX), and (XL-XLVII), $R^4$ is (1-methyl-1H-imidazol-5-yl)-methyl. In certain embodiments of any of Formulas (XXXIX), and (XL-XLVII), (I)-(XVIII), (XXV)-(XXVII), (XXX), (XXXI), (XXXIX), and (XL-XLVII), $R^4$ is 1-methoxy-cycloprop-1yl-methyl. In certain embodiments of any of Formulas (I)-(XVIII), (XXV)-(XXVII), (XXX), (XXXI), (XXXIX), and (XL-XLVII), $R^4$ is methoxyethan-2-yl. In certain embodiments of any of Formulas (I)-(XVIII), (XXV)-(XXVII), (XXX), (XXXI), (XXXIX), and (XL-XLVII), $R^4$ is 1-(2-methoxy-ethyl)-cycloprop-1-yl-methyl. In certain embodiments of any of Formulas (I)-(XVIII), (XXV)-(XXVII), (XXX), (XXXI), (XXXIX), and (XL-XLVII), $R^4$ is {[1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2R)-1-(1,2-oxazole-3-carbonyl)azetidin-2-yl]methyl}. In certain embodiments of any of Formulas (I)-(XVIII), (XXV)-(XXVII), (XXX), (XXXI), (XXXIX), and (XL-XLVII), $R^4$ is {[(2S)-1-(1,2-oxazole-3-carbonyl)azetidin-2-yl]methyl. In certain embodiments of any of Formulas (I)-(XVIII), (XXV)-(XXVII), (XXX), (XXX), (XXXIX), and (XL-XLVII), $R^4$ is 2-oxabicyclo[2.1.1]hexa-1-yl-methyl. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —NH—. In certain embodiments, provided is a compound of any of Formulas (I)-(XVIII), (XXV)-(XXVII), (XXX), (XXXI), (XXXIX), and (XL-XLVII), or a pharmaceutically salt, tautomer, stereoisomer, and/or mixture of stereoisomers thereof, wherein $L^2$ is —N(Me)-.

In certain embodiments, provided is a compound of Table 1 below, or a pharmaceutically salt, tautomer, stereoisomer, and/or mixture of stereoisomers thereof.

| Compound | Structure | IUPAC |
|---|---|---|
| 1 | 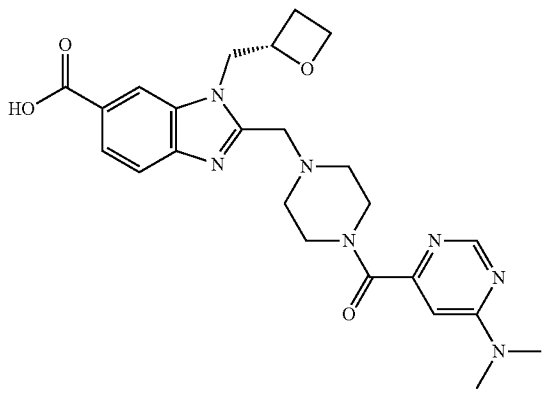 [SMILES: CN(C)c1cc(C(=O)N2CCN(Cc3nc4ccc(C(=O)O)cc4n3C[C@@H]3CCO3)CC2)ncn1] | 2-({4-[6-(dimethylamino) pyrimidine-4-carbonyl]piperazin-1-yl}methyl)-1-{[(2S)-oxetan-2-yl]methyl}-1H-1,3-benzodiazole-6-carboxylic acid |

-continued
| Compound | Structure | IUPAC |
|---|---|---|
| 2 | 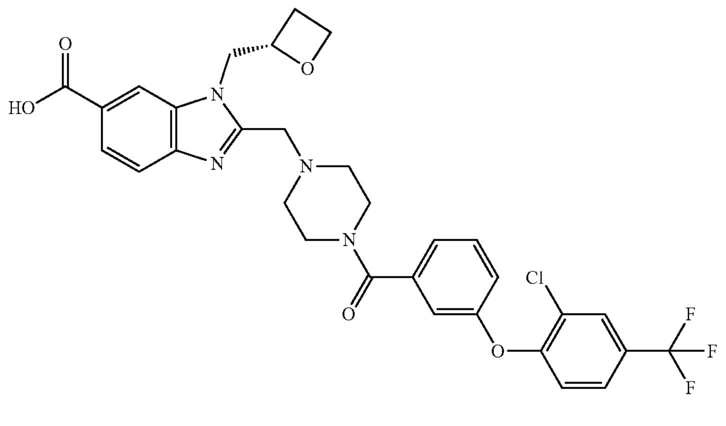 [SMILES: O=C(O)c1ccc2nc(CN3CCN(C(=O)c4cccc(Oc5ccc(C(F)(F)F)cc5Cl)c4)CC3)n(C[C@@H]3CCO3)c2c1] | 2-[(4-{3-[2-chloro-4-(trifluoromethyl)phenoxy]benzoyl}piperazin-1-yl)methyl]-1-{[(2S)-oxetan-2-yl]methyl}-1H-1,3-benzodiazole-6-carboxylic acid |
| 3 | 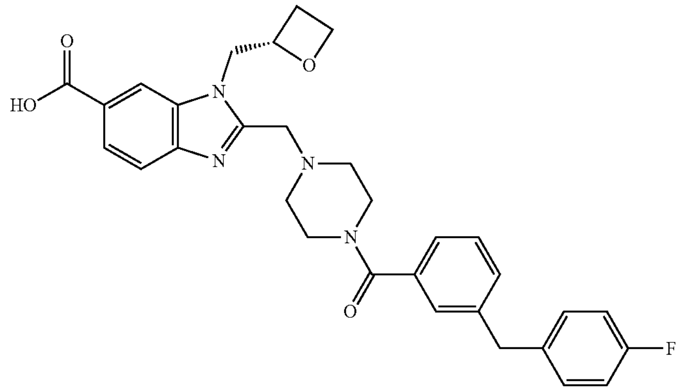 [SMILES: O=C(O)c1ccc2nc(CN3CCN(C(=O)c4cccc(Cc5ccc(F)cc5)c4)CC3)n(C[C@@H]3CCO3)c2c1] | 2-[(4-{3-[(4-fluorophenyl)methyl]benzoyl}piperazin-1-yl)methyl]-1-{[(2S)-oxetan-2-yl]methyl}-1H-1,3-benzodiazole-6-carboxylic acid |
| 4 | 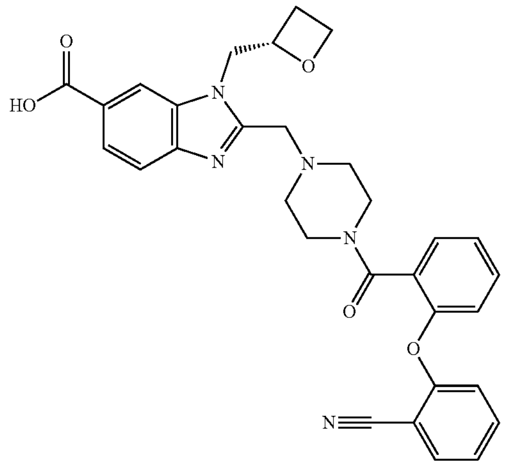 [SMILES: N#Cc1ccccc1Oc1ccccc1C(=O)N1CCN(Cc2nc3ccc(C(=O)O)cc3n2C[C@@H]2CCO2)CC1] | 2-({4-[2-(2-cyanophenoxy)benzoyl]piperazin-1-yl}methyl)-1-{[(2S)-oxetan-2-yl]methyl}-1H-1,3-benzodiazole-6-carboxylic acid |

-continued

| Compound | Structure | IUPAC |
|---|---|---|
| 5 | 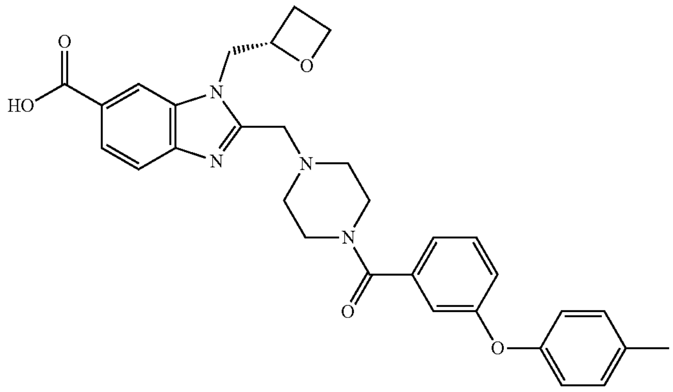 [SMILES: Cc1ccc(Oc2cccc(C(=O)N3CCN(Cc4nc5ccc(C(=O)O)cc5n4C[C@@H]4CCO4)CC3)c2)cc1] | 2-({4-[3-(4-methylphenoxy)benzoyl]piperazin-1-yl}methyl)-1-{[(2S)-oxetan-2-yl]methyl}-1H-1,3-benzodiazole-6-carboxylic acid |
| 6 | 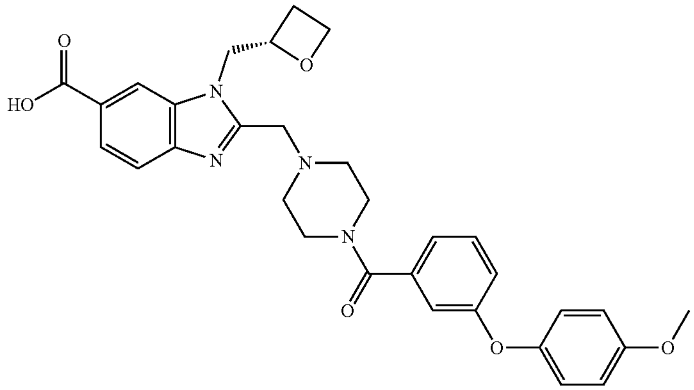 [SMILES: COc1ccc(Oc2cccc(C(=O)N3CCN(Cc4nc5ccc(C(=O)O)cc5n4C[C@@H]4CCO4)CC3)c2)cc1] | 2-({4-[3-(4-methoxyphenoxy)benzoyl]piperazin-1-yl}methyl)-1-{[(2S)-oxetan-2-yl]methyl}-1H-1,3-benzodiazole-6-carboxylic acid |
| 7 | 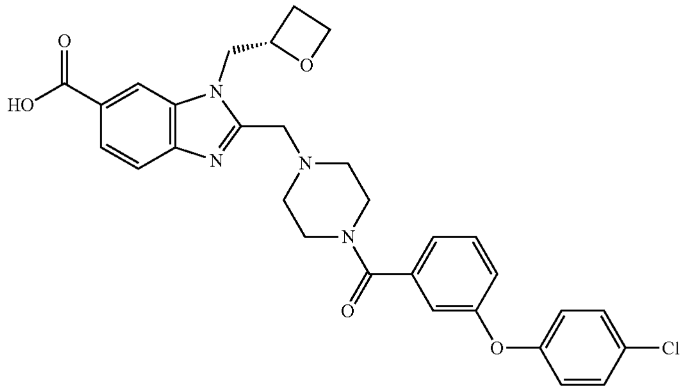 [SMILES: O=C(O)c1ccc2nc(CN3CCN(C(=O)c4cccc(Oc5ccc(Cl)cc5)c4)CC3)n(C[C@@H]3CCO3)c2c1] | 2-({4-[3-(4-chlorophenoxy)benzoyl]piperazin-1-yl}methyl)-1-{[(2S)-oxetan-2-yl]methyl}-1H-1,3-benzodiazole-6-carboxylic acid |
| 8 | 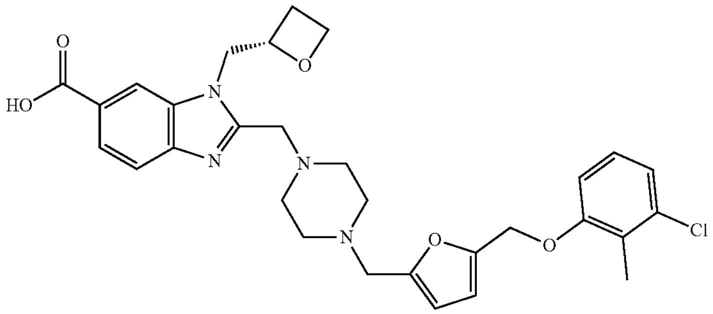 [SMILES: Cc1c(Cl)cccc1OCc1ccc(CN2CCN(Cc3nc4ccc(C(=O)O)cc4n3C[C@@H]3CCO3)CC2)o1] | 2-{[4-({5-[(3-chloro-2-methylphenoxy)methyl]furan-2-yl}methyl)piperazin-1-yl]methyl}-1-{[(2S)-oxetan-2-yl]methyl}-1H-1,3-benzodiazole-6-carboxylic acid |

-continued
| Compound | Structure | IUPAC |
| --- | --- | --- |
| 9 | 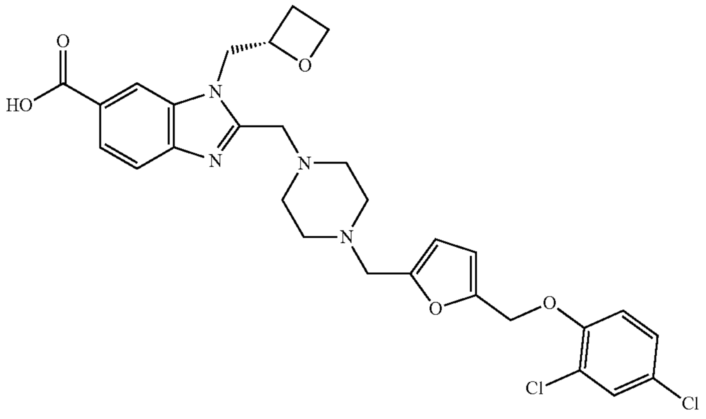 | 2-{[4-({5-[(2,4-dichlorophenoxy) methyl]furan-2-yl}methyl)piperazin-1-yl]methyl}-1-{[(2S)-oxetan-2-yl]methyl}-1H-1,3-benzodiazole-6-carboxylic acid |
| 10 | 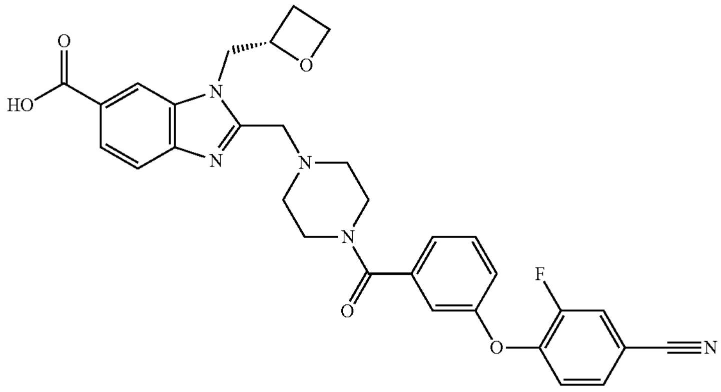 [SMILES: N#Cc1ccc(Oc2cccc(C(=O)N3CCN(Cc4nc5ccc(C(=O)O)cc5n4C[C@@H]4CCO4)CC3)c2)c(F)c1] | 2-({4-[3-(4-cyano-2-fluorophenoxy)benzoyl] piperazin-1-yl}methyl)-1-{[(2S)-oxetan-2-yl]methyl}-1H-1,3-benzodiazole-6-carboxylic acid |
| 11 | 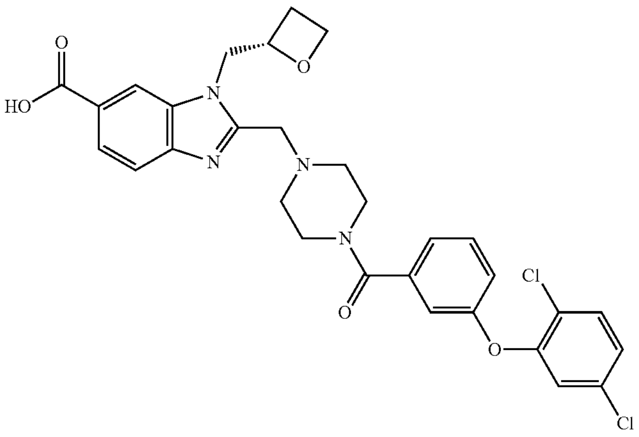 [SMILES: O=C(O)c1ccc2nc(CN3CCN(C(=O)c4cccc(Oc5cc(Cl)ccc5Cl)c4)CC3)n(C[C@@H]3CCO3)c2c1] | 2-({4-[3-(2,5-dichlorophenoxy)benzoyl] piperazin-1-yl}methyl)-1-{[(2S)-oxetan-2-yl]methyl}-1H-1,3-benzodiazole-6-carboxylic acid |

-continued
| Compound | Structure | IUPAC |
|---|---|---|
| 12 | 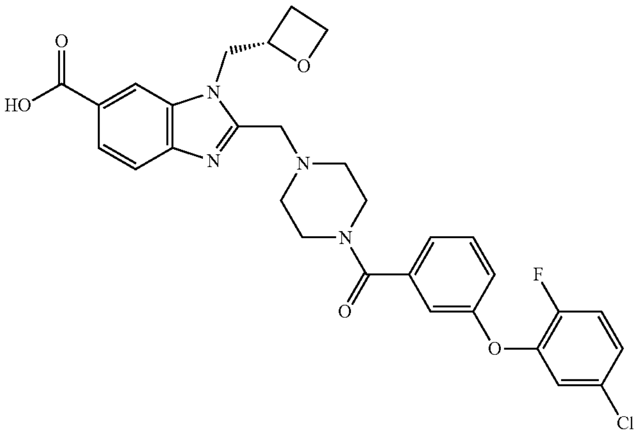 | 2-({4-[3-(5-chloro-2-fluorophenoxy)benzoyl]piperazin-1-yl}methyl)-1-{[(2S)-oxetan-2-yl]methyl}-1H-1,3-benzodiazole-6-carboxylic acid |
| 13 | 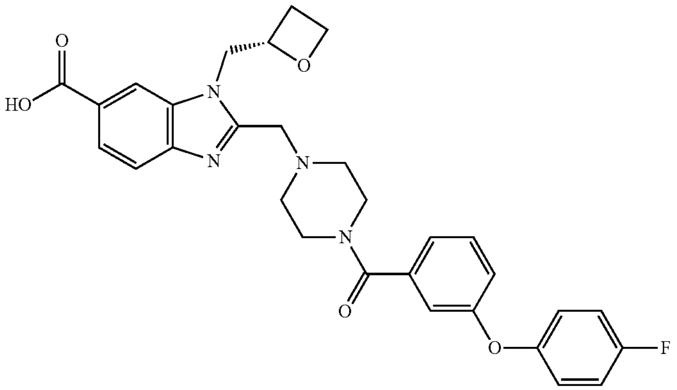 | 2-({4-[3-(4-fluorophenoxy)benzoyl]piperazin-1-yl}methyl)-1-{[(2S)-oxetan-2-yl]methyl}-1H-1,3-benzodiazole-6-carboxylic acid |
| 14 | 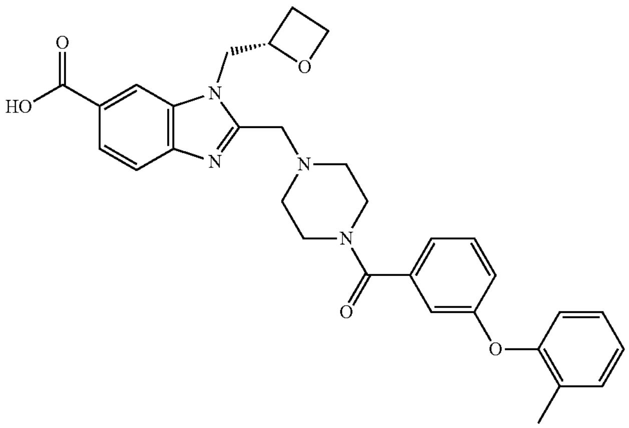 [SMILES: Cc1ccccc1Oc1cccc(C(=O)N2CCN(Cc3nc4ccc(C(=O)O)cc4n3C[C@@H]3CCO3)CC2)c1] | 2-({4-[3-(2-methylphenoxy)benzoyl]piperazin-1-yl}methyl)-1-{[(2S)-oxetan-2-yl]methyl}-1H-1,3-benzodiazole-6-carboxylic acid |

-continued
| Compound | Structure | IUPAC |
|---|---|---|
| 15 | 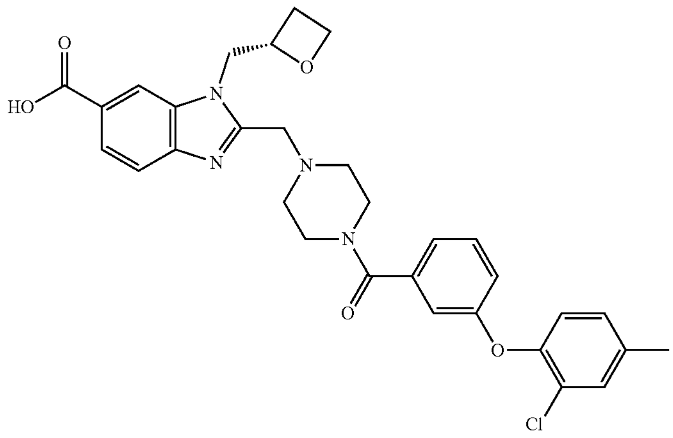 | 2-({4-[3-(2-chloro-4-methylphenoxy)benzoyl]piperazin-1-yl}methyl)-1-{[(2S)-oxetan-2-yl]methyl}-1H-1,3-benzodiazole-6-carboxylic acid |
| 16 | 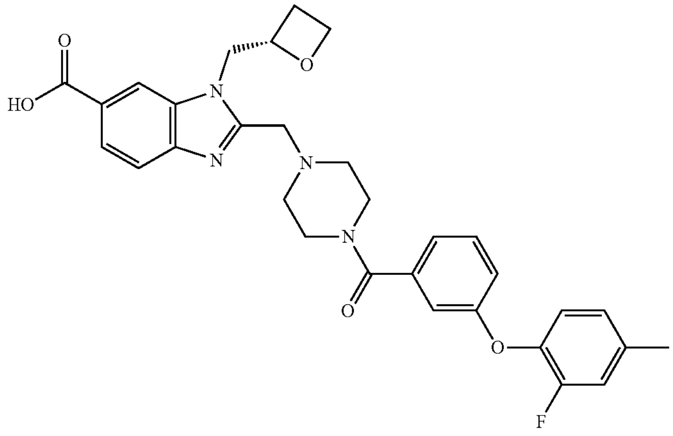 [SMILES: Cc1ccc(Oc2cccc(C(=O)N3CCN(Cc4nc5ccc(C(=O)O)cc5n4C[C@@H]4CCO4)CC3)c2)c(F)c1] | 2-({4-[3-(2-fluoro-4-methylphenoxy)benzoyl]piperazin-1-yl}methyl)-1-{[(2S)-oxetan-2-yl]methyl}-1H-1,3-benzodiazole-6-carboxylic acid |
| 17 | 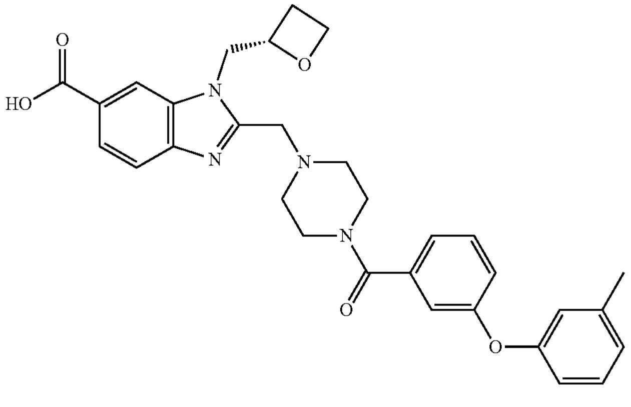 [SMILES: Cc1cccc(Oc2cccc(C(=O)N3CCN(Cc4nc5ccc(C(=O)O)cc5n4C[C@@H]4CCO4)CC3)c2)c1] | 2-({4-[3-(3-methylphenoxy)benzoyl]piperazin-1-yl}methyl)-1-{[(2S)-oxetan-2-yl]methyl}-1H-1,3-benzodiazole-6-carboxylic acid |

-continued

| Compound | Structure | IUPAC |
|---|---|---|
| 18 | 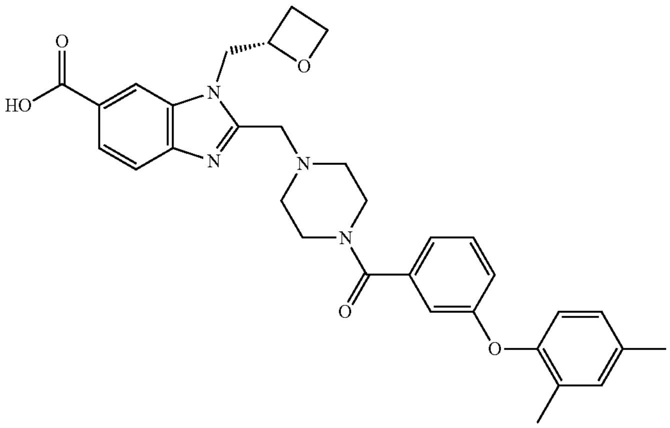 [SMILES: Cc1ccc(Oc2cccc(C(=O)N3CCN(Cc4nc5ccc(C(=O)O)cc5n4C[C@@H]4CCO4)CC3)c2)c(C)c1] | 2-({4-[3-(2,4-dimethylphenoxy)benzoyl]piperazin-1-yl}methyl)-1-{[(2S)-oxetan-2-yl]methyl}-1H-1,3-benzodiazole-6-carboxylic acid |
| 19 | 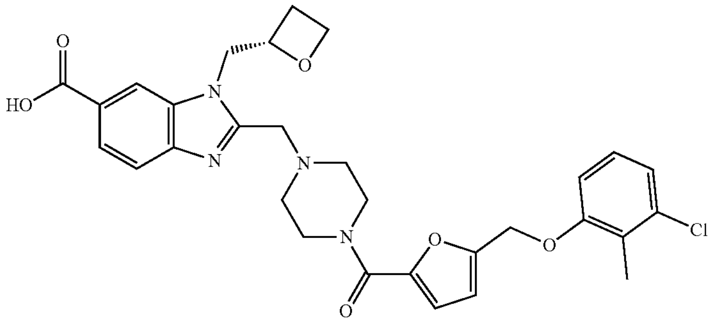 [SMILES: Cc1c(Cl)cccc1OCc1ccc(C(=O)N2CCN(Cc3nc4ccc(C(=O)O)cc4n3C[C@@H]3CCO3)CC2)o1] | 2-[(4-{5-[(3-chloro-2-methylphenoxy)methyl]furan-2-carbonyl}piperazin-1-yl)methyl]-1-{[(2S)-oxetan-2-yl]methyl}-1H-1,3-benzodiazole-6-carboxylic acid |
| 20 | 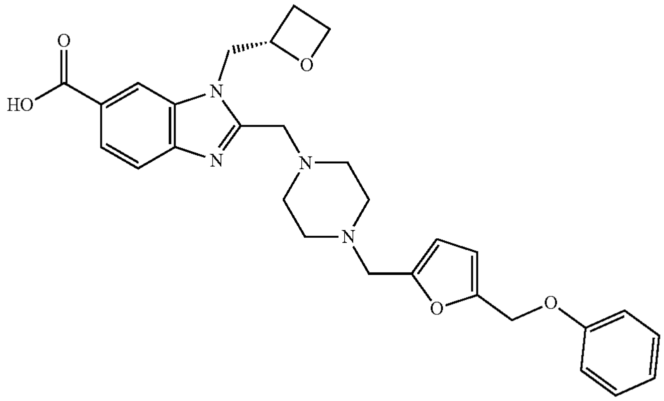 [SMILES: O=C(O)c1ccc2nc(CN3CCN(Cc4ccc(COc5ccccc5)o4)CC3)n(C[C@@H]3CCO3)c2c1] | 1-{[(2S)-oxetan-2-yl]methyl}-2-[(4-{[5-(phenoxymethyl)furan-2-yl]methyl}piperazin-1-yl)methyl]-1H-1,3-benzodiazole-6-carboxylic acid |
| 21 | 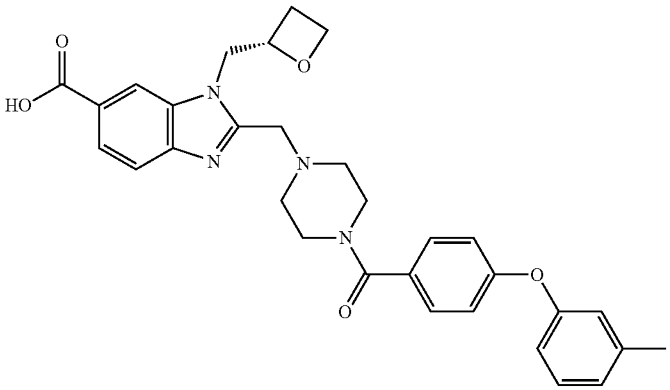 [SMILES: Cc1cccc(Oc2ccc(C(=O)N3CCN(Cc4nc5ccc(C(=O)O)cc5n4C[C@@H]4CCO4)CC3)cc2)c1] | 2-({4-[4-(3-methylphenoxy)benzoyl]piperazin-1-yl}methyl)-1-{[(2S)-oxetan-2-yl]methyl}-1H-1,3-benzodiazole-6-carboxylic acid |

-continued
| Compound | Structure | IUPAC |
|---|---|---|
| 22 | 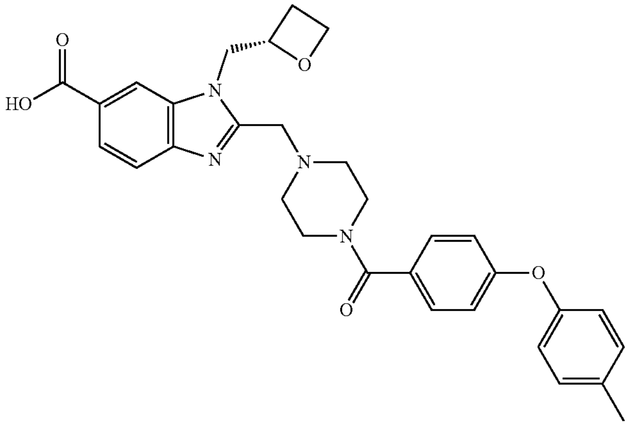 [SMILES: Cc1ccc(Oc2ccc(C(=O)N3CCN(Cc4nc5ccc(C(=O)O)cc5n4C[C@@H]4CCO4)CC3)cc2)cc1] | 2-({4-[4-(4-methylphenoxy)benzoyl]piperazin-1-yl}methyl)-1-{[(2S)-oxetan-2-yl]methyl}-1H-1,3-benzodiazole-6-carboxylic acid |
| 23 | 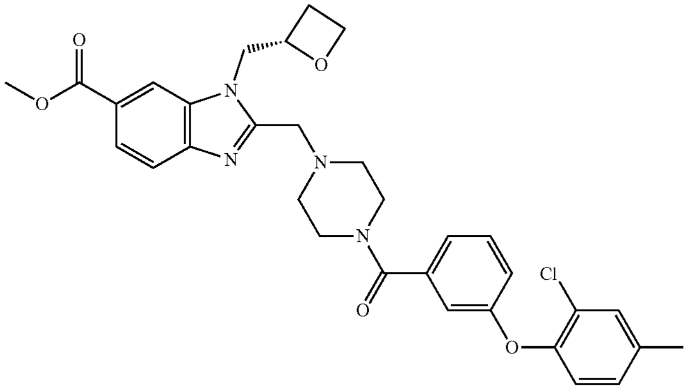 | methyl 2-({4-[3-(2-chloro-4-methylphenoxy)benzoyl]piperazin-1-yl}methyl)-1-{[(2S)-oxetan-2-yl]methyl}-1H-1,3-benzodiazole-6-carboxylate |
| 24 | 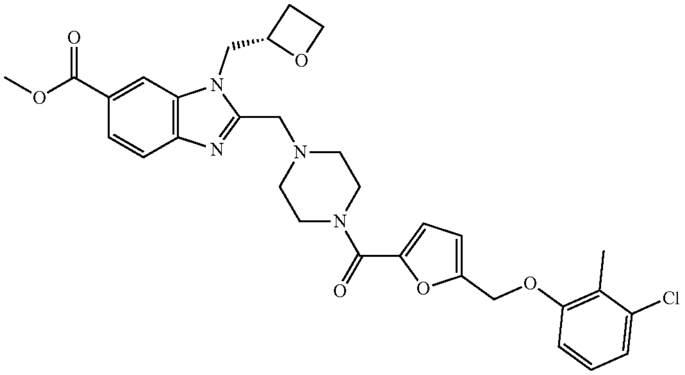 [SMILES: COC(=O)c1ccc2nc(CN3CCN(C(=O)c4ccc(COc5cccc(Cl)c5C)o4)CC3)n(C[C@@H]3CCO3)c2c1] | methyl 2-[(4-{5-[(3-chloro-2-methylphenoxy)methyl]furan-2-carbonyl}piperazin-1-yl)methyl]-1-{[(2S)-oxetan-2-yl]methyl}-1H-1,3-benzodiazole-6-carboxylate |

-continued

| Compound | Structure | IUPAC |
|---|---|---|
| 25 | 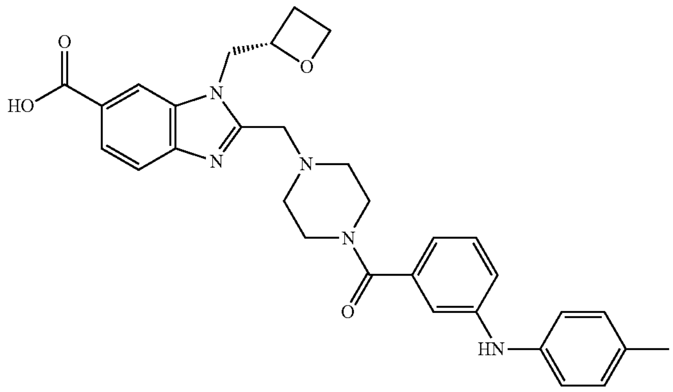 [SMILES: Cc1ccc(Nc2cccc(C(=O)N3CCN(Cc4nc5ccc(C(=O)O)cc5n4C[C@@H]4CCO4)CC3)c2)cc1] | 2-[(4-{3-[(4-methylphenyl) amino]benzoyl}piperazin-1-yl)methyl]-1-{[(2S)-oxetan-2-yl]methyl}-1H-1,3-benzodiazole-6-carboxylic acid |
| 26 | 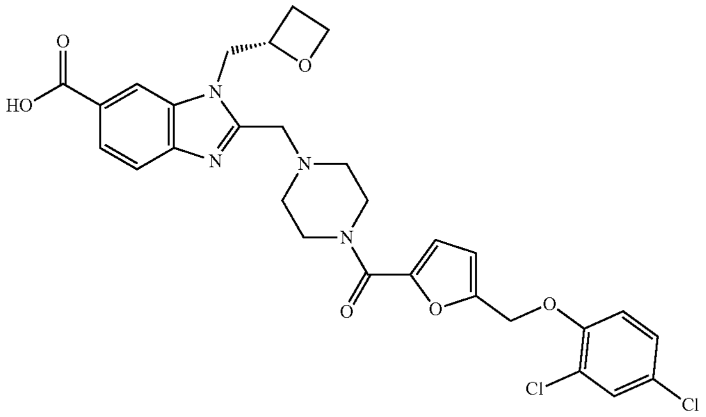 [SMILES: O=C(O)c1ccc2nc(CN3CCN(C(=O)c4ccc(COc5ccc(Cl)cc5Cl)o4)CC3)n(C[C@@H]3CCO3)c2c1] | 2-[(4-{5-[(2,4-dichlorophenoxy) methyl]furan-2-carbonyl}piperazin-1-yl)methyl]-1-{[(2S)-oxetan-2-yl]methyl}-1H-1,3-benzodiazole-6-carboxylic acid |
| 27 | 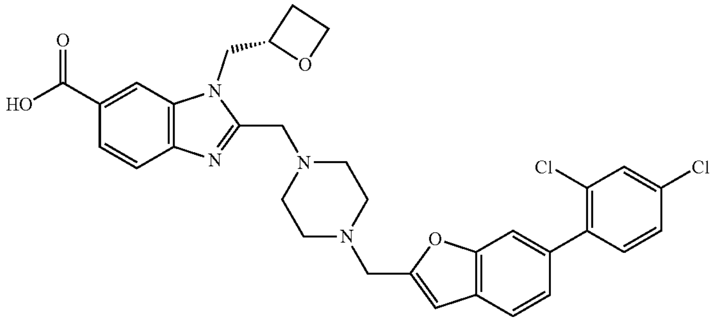 | 2-[(4-{[6-(2,4-dichlorophenyl)-1-benzofuran-2-yl]methyl}piperazin-1-yl)methyl]-1-{[(2S)-oxetan-2-yl]methyl}-1H-1,3-benzodiazole-6-carboxylic acid |
| 28 | 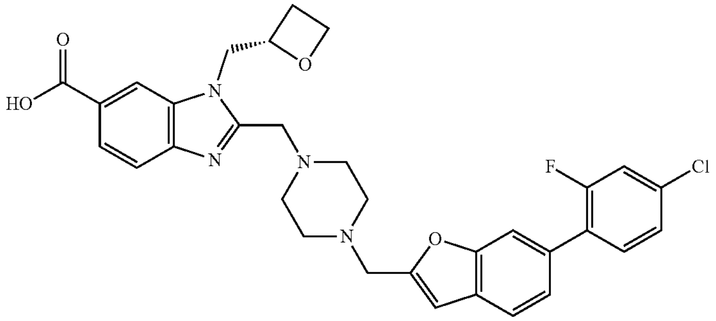 [SMILES: O=C(O)c1ccc2nc(CN3CCN(Cc4cc5ccc(-c6ccc(Cl)cc6F)cc5o4)CC3)n(C[C@@H]3CCO3)c2c1] | 2-[(4-{[6-(4-chloro-2-fluorophenyl)-1-benzofuran-2-yl] methyl}piperazin-1-yl)methyl]-1-{[(2S)-oxetan-2-yl]methyl}-1H-1,3-benzodiazole-6-carboxylic acid |

-continued
| Compound | Structure | IUPAC |
|---|---|---|
| 29 | 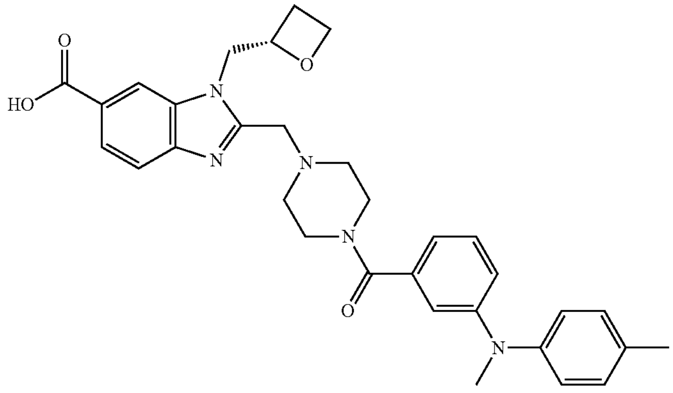 [SMILES: Cc1ccc(N(C)c2cccc(C(=O)N3CCN(Cc4nc5ccc(C(=O)O)cc5n4C[C@@H]4CCO4)CC3)c2)cc1] | 2-[(4-{3-[methyl(4-methylphenyl)amino]benzoyl}piperazin-1-yl)methyl]-1-{[(2S)-oxetan-2-yl]methyl}-1H-1,3-benzodiazole-6-carboxylic acid |
| 30 | 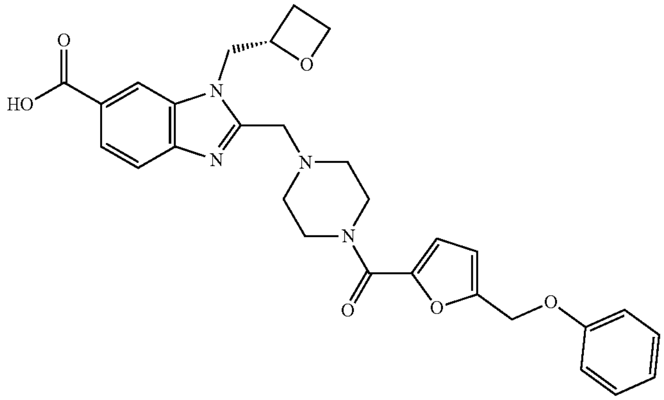 [SMILES: O=C(O)c1ccc2nc(CN3CCN(C(=O)c4ccc(COc5ccccc5)o4)CC3)n(C[C@@H]3CCO3)c2c1] | 1-{[(2S)-oxetan-2-yl]methyl}-2-({4-[5-(phenoxymethyl)furan-2-carbonyl]piperazin-1-yl}methyl)-1H-1,3-benzodiazole-6-carboxylic acid |
| 31 | 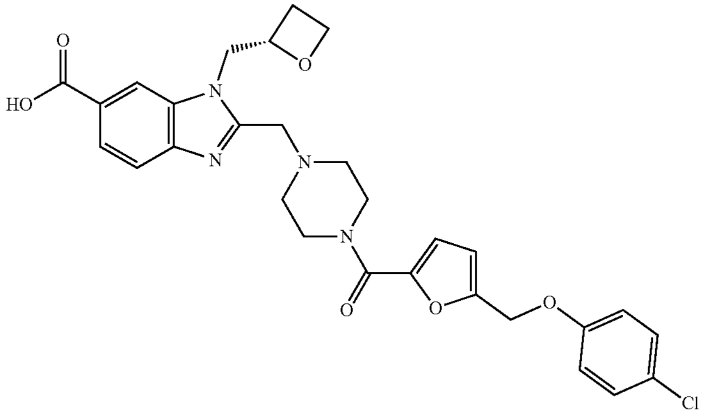 [SMILES: O=C(O)c1ccc2nc(CN3CCN(C(=O)c4ccc(COc5ccc(Cl)cc5)o4)CC3)n(C[C@@H]3CCO3)c2c1] | 2-[(4-{5-[(4-chlorophenoxy)methyl]furan-2-carbonyl}piperazin-1-yl)methyl]-1-{[(2S)-oxetan-2-yl]methyl}-1H-1,3-benzodiazole-6-carboxylic acid |

-continued
| Compound | Structure | IUPAC |
| --- | --- | --- |
| 32 | 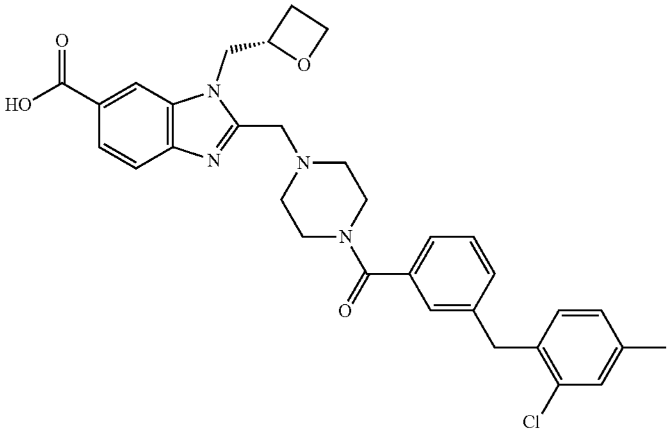 [SMILES: Cc1ccc(Cc2cccc(C(=O)N3CCN(Cc4nc5ccc(C(=O)O)cc5n4C[C@@H]4CCO4)CC3)c2)c(Cl)c1] | 2-[(4-{3-[(2-chloro-4-methylphenyl)methyl]benzoyl}piperazin-1-yl)methyl]-1-{[(2S)-oxetan-2-yl]methyl}-1H-1,3-benzodiazole-6-carboxylic acid |
| 33 | 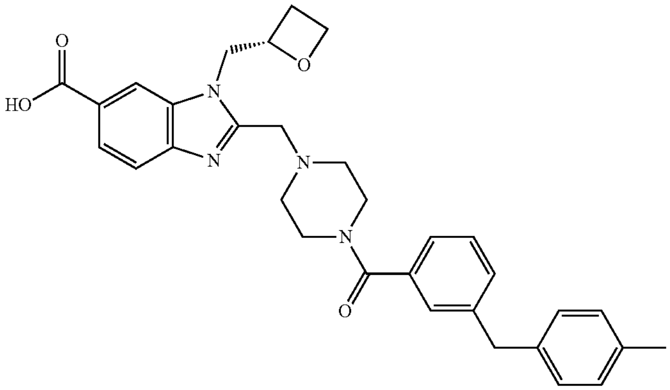 [SMILES: Cc1ccc(Cc2cccc(C(=O)N3CCN(Cc4nc5ccc(C(=O)O)cc5n4C[C@@H]4CCO4)CC3)c2)cc1] | 2-[(4-{3-[(4-methylphenyl)methyl]benzoyl}piperazin-1-yl)methyl]-1-{[(2S)-oxetan-2-yl]methyl}-1H-1,3-benzodiazole-6-carboxylic acid |
| 34 | 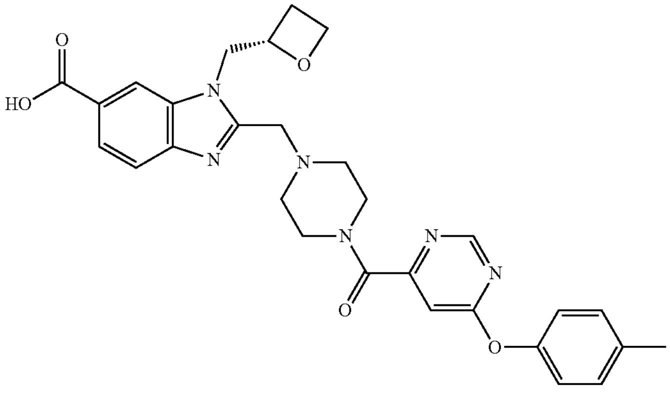 [SMILES: Cc1ccc(Oc2cc(C(=O)N3CCN(Cc4nc5ccc(C(=O)O)cc5n4C[C@@H]4CCO4)CC3)ncn2)cc1] | 2-({4-[6-(4-methylphenoxy)pyrimidine-4-carbonyl]piperazin-1-yl}methyl)-1-{[(2S)-oxetan-2-yl]methyl}-1H-1,3-benzodiazole-6-carboxylic acid |

-continued

| Compound | Structure | IUPAC |
|---|---|---|
| 35 | 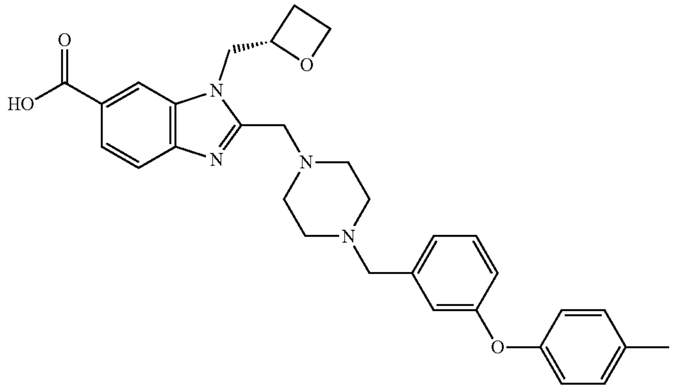 [SMILES: Cc1ccc(Oc2cccc(CN3CCN(Cc4nc5ccc(C(=O)O)cc5n4C[C@@H]4CCO4)CC3)c2)cc1] | 2-[(4-{[3-(4-methylphenoxy)phenyl]methyl}piperazin-1-yl)methyl]-1-{[(2S)-oxetan-2-yl]methyl}-1H-1,3-benzodiazole-6-carboxylic acid |
| 36 | 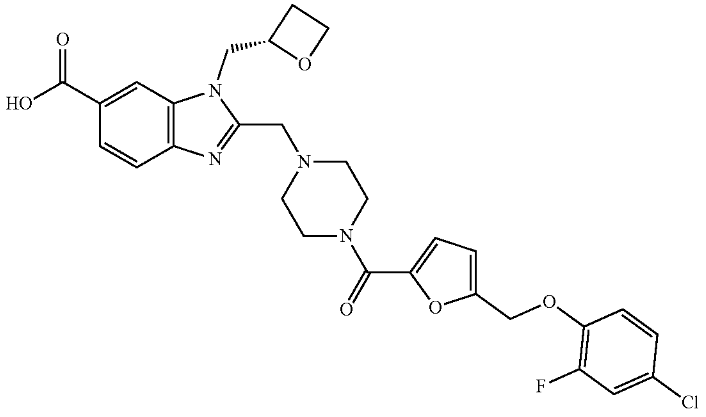 [SMILES: O=C(O)c1ccc2nc(CN3CCN(C(=O)c4ccc(COc5ccc(Cl)cc5F)o4)CC3)n(C[C@@H]3CCO3)c2c1] | 2-[(4-{5-[(4-chloro-2-fluorophenoxy)methyl]furan-2-carbonyl}piperazin-1-yl)methyl]-1-{[(2S)-oxetan-2-yl]methyl}-1H-1,3-benzodiazole-6-carboxylic acid |
| 37 | 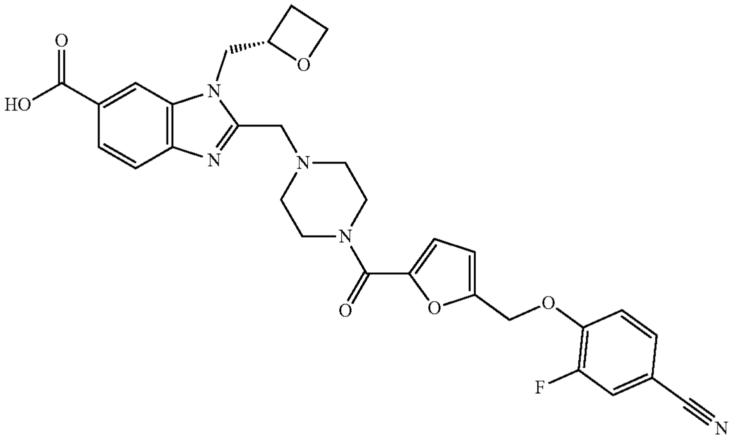 [SMILES: N#Cc1ccc(OCc2ccc(C(=O)N3CCN(Cc4nc5ccc(C(=O)O)cc5n4C[C@@H]4CCO4)CC3)o2)c(F)c1] | 2-[(4-{5-[(4-cyano-2-fluorophenoxy)methyl]furan-2-carbonyl}piperazin-1-yl)methyl]-1-{[(2S)-oxetan-2-yl]methyl}-1H-1,3-benzodiazole-6-carboxylic acid |
| 38 | 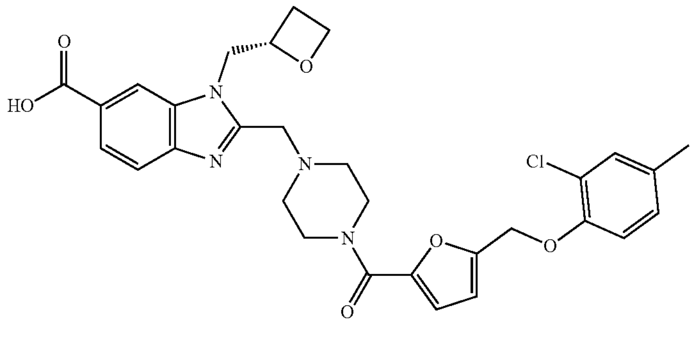 [SMILES: Cc1ccc(OCc2ccc(C(=O)N3CCN(Cc4nc5ccc(C(=O)O)cc5n4C[C@@H]4CCO4)CC3)o2)c(Cl)c1] | 2-[(4-{5-[(2-chloro-4-methylphenoxy)methyl]furan-2-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
| --- | --- | --- |
| 39 | 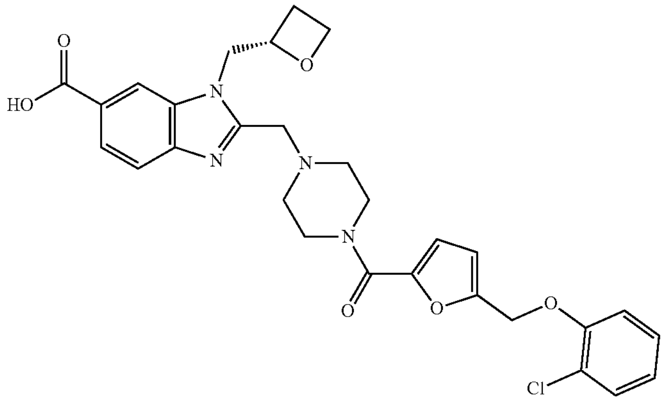 [SMILES: O=C(O)c1ccc2nc(CN3CCN(C(=O)c4ccc(COc5ccccc5Cl)o4)CC3)n(C[C@@H]3CCO3)c2c1] | 2-[(4-{5-[(2-chlorophenoxy)methyl]furan-2-carbonyl}piperazin-1-yl)methyl]-1-{[(2S)-oxetan-2-yl]methyl}-1H-1,3-benzodiazole-6-carboxylic acid |
| 40 | 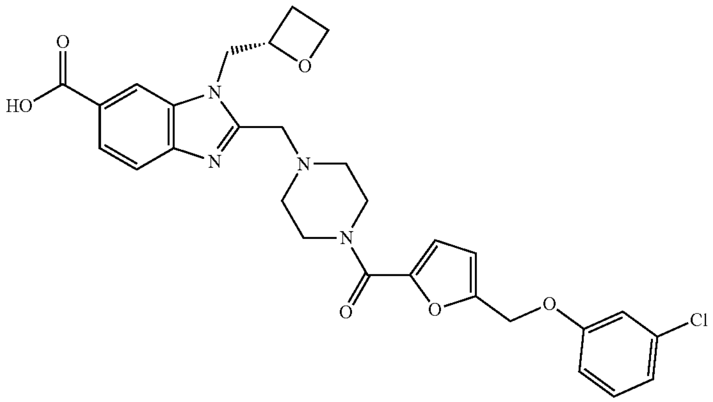 [SMILES: O=C(O)c1ccc2nc(CN3CCN(C(=O)c4ccc(COc5cccc(Cl)c5)o4)CC3)n(C[C@@H]3CCO3)c2c1] | 2-[(4-{5-[(3-chlorophenoxy)methyl]furan-2-carbonyl}piperazin-1-yl)methyl]-1-{[(2S)-oxetan-2-yl]methyl}-1H-1,3-benzodiazole-6-carboxylic acid |
| 41 | 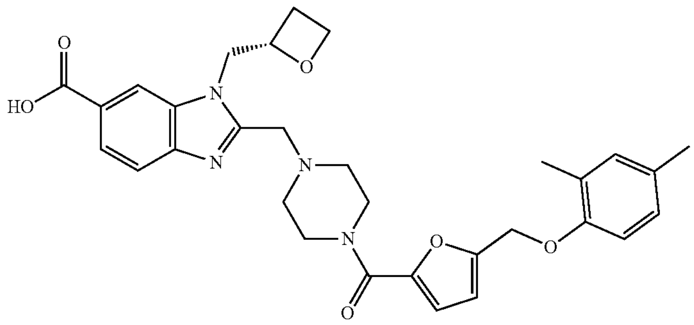 [SMILES: Cc1ccc(OCc2ccc(C(=O)N3CCN(Cc4nc5ccc(C(=O)O)cc5n4C[C@@H]4CCO4)CC3)o2)c(C)c1] | 2-[(4-{5-[(2,4-dimethylphenoxy)methyl]furan-2-carbonyl}piperazin-1-yl)methyl]-1-{[(2S)-oxetan-2-yl]methyl}-1H-1,3-benzodiazole-6-carboxylic acid |
| 42 | 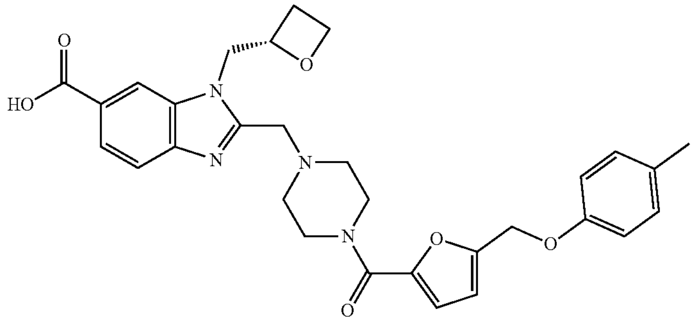 [SMILES: Cc1ccc(OCc2ccc(C(=O)N3CCN(Cc4nc5ccc(C(=O)O)cc5n4C[C@@H]4CCO4)CC3)o2)cc1] | 2-[(4-{5-[(4-methylphenoxy)methyl]furan-2-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
|---|---|---|
| 43 | 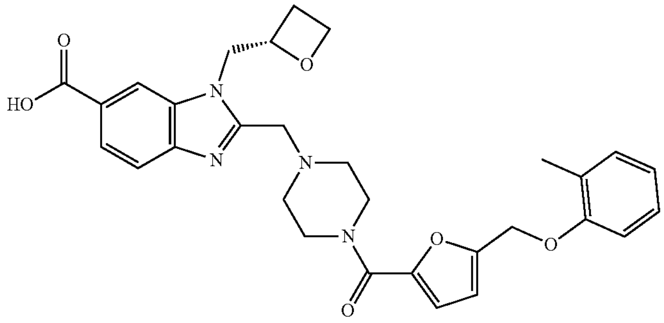 [SMILES: Cc1ccccc1OCc1ccc(C(=O)N2CCN(Cc3nc4ccc(C(=O)O)cc4n3C[C@@H]3CCO3)CC2)o1] | 2-[(4-{5-[(2-methylphenoxy)methyl]furan-2-carbonyl}piperazin-1-yl)methyl]-1-{[(2S)-oxetan-2-yl]methyl}-1H-1,3-benzodiazole-6-carboxylic acid |
| 44 | 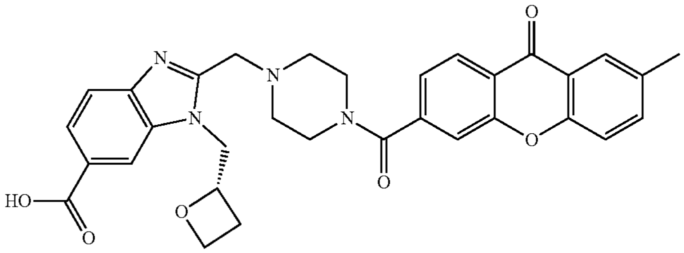 [SMILES: Cc1ccc2oc3cc(C(=O)N4CCN(Cc5nc6ccc(C(=O)O)cc6n5C[C@@H]5CCO5)CC4)ccc3c(=O)c2c1] | 2-{[4-(7-methyl-9-oxo-9H-xanthene-3-carbonyl)piperazin-1-yl]methyl}-1-{[(2S)-oxetan-2-yl]methyl}-1H-1,3-benzodiazole-6-carboxylic acid |
| 45 | 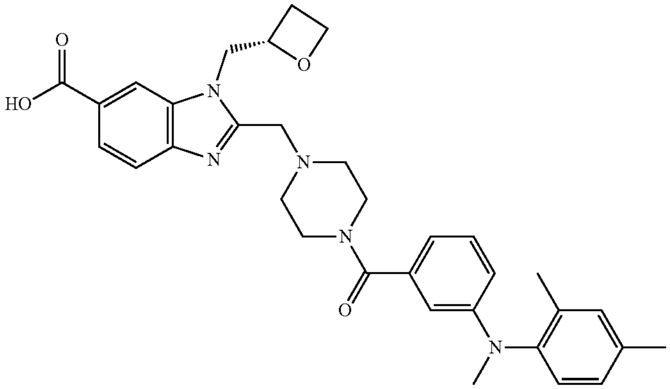 [SMILES: Cc1ccc(N(C)c2cccc(C(=O)N3CCN(Cc4nc5ccc(C(=O)O)cc5n4C[C@@H]4CCO4)CC3)c2)c(C)c1] | 2-[(4-{3-[(2,4-dimethylphenyl)(methyl)amino]benzoyl}piperazin-1-yl)methyl]-1-{[(2S)-oxetan-2-yl]methyl}-1H-1,3-benzodiazole-6-carboxylic acid |
| 46 | 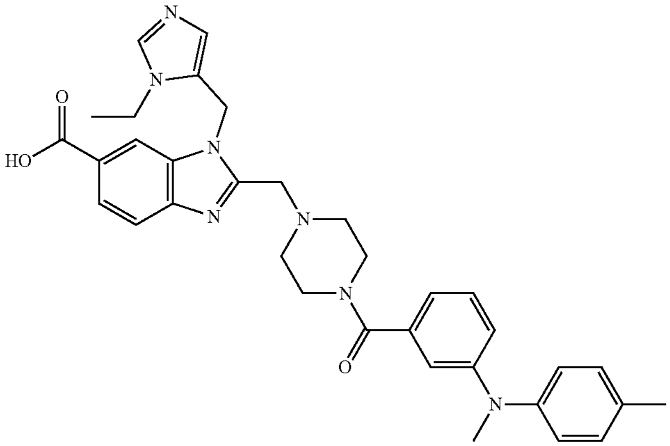 [SMILES: CCn1cncc1Cn1c(CN2CCN(C(=O)c3cccc(N(C)c4ccc(C)cc4)c3)CC2)nc2ccc(C(=O)O)cc21] | 1-[(1-ethyl-1H-imidazol-5-yl)methyl]-2-[(4-{3-[methyl(4-methylphenyl)amino]benzoyl}piperazin-1-yl)methyl]-1H-1,3-benzodiazole-6-carboxylic acid |

-continued

| Compound | Structure | IUPAC |
| --- | --- | --- |
| 47 | 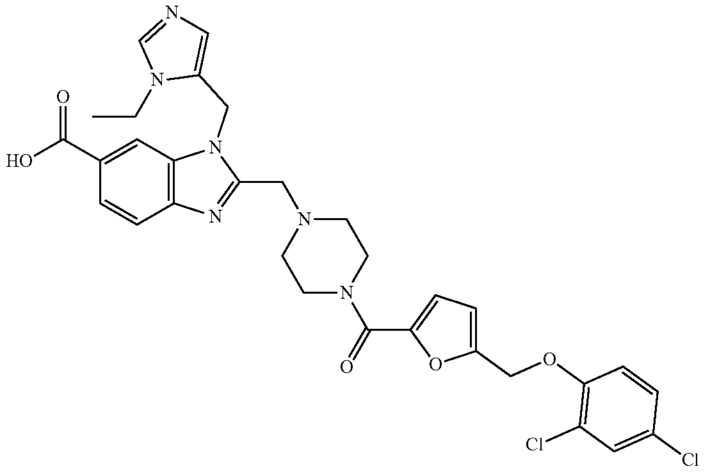 [SMILES: CCn1cncc1Cn1c(CN2CCN(C(=O)c3ccc(COc4ccc(Cl)cc4Cl)o3)CC2)nc2ccc(C(=O)O)cc21] | 2-[(4-{5-[(2,4-dichlorophenoxy)methyl]furan-2-carbonyl}piperazin-1-yl)methyl]-1-[(1-ethyl-1H-imidazol-5-yl)methyl]-1H-1,3-benzodiazole-6-carboxylic acid |
| 48 | 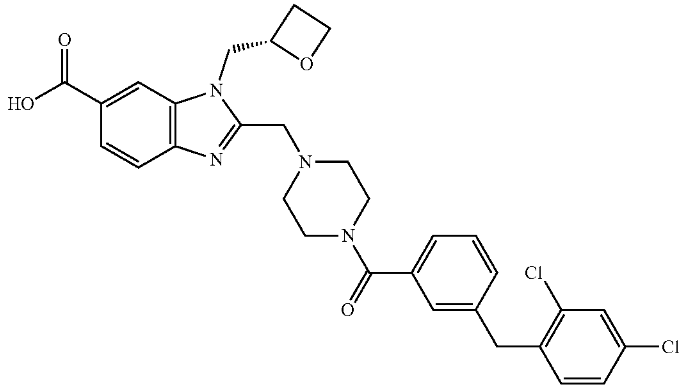 [SMILES: O=C(O)c1ccc2nc(CN3CCN(C(=O)c4cccc(Cc5ccc(Cl)cc5Cl)c4)CC3)n(C[C@@H]3CCO3)c2c1] | 2-[(4-{3-[(2,4-dichlorophenyl)methyl]benzoyl}piperazin-1-yl)methyl]-1-{[(2S)-oxetan-2-yl]methyl}-1H-1,3-benzodiazole-6-carboxylic acid |
| 49 | 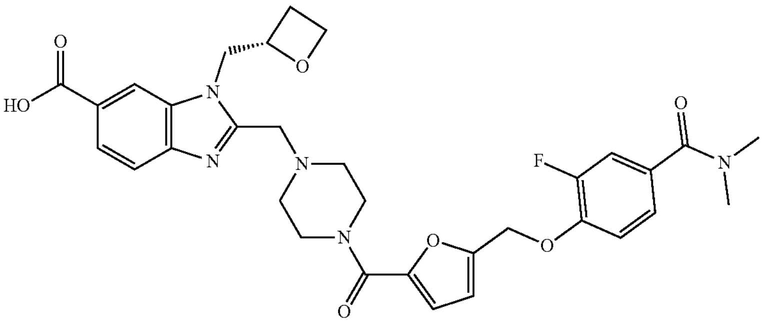 [SMILES: CN(C)C(=O)c1ccc(OCc2ccc(C(=O)N3CCN(Cc4nc5ccc(C(=O)O)cc5n4C[C@@H]4CCO4)CC3)o2)c(F)c1] | 2-{[4-(5-{[4-(dimethylcarbamoyl)-2-fluorophenoxy]methyl}furan-2-carbonyl)piperazin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 50 | 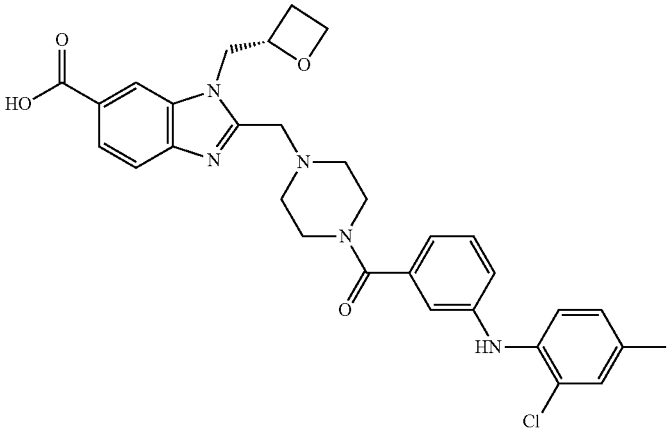 [SMILES: Cc1ccc(Nc2cccc(C(=O)N3CCN(Cc4nc5ccc(C(=O)O)cc5n4C[C@@H]4CCO4)CC3)c2)c(Cl)c1] | 2-[(4-{3-[(2-chloro-4-methylphenyl)amino]benzoyl}piperazin-1-yl)methyl]-1-{[(2S)-oxetan-2-yl]methyl}-1H-1,3-benzodiazole-6-carboxylic acid |
| 51 | 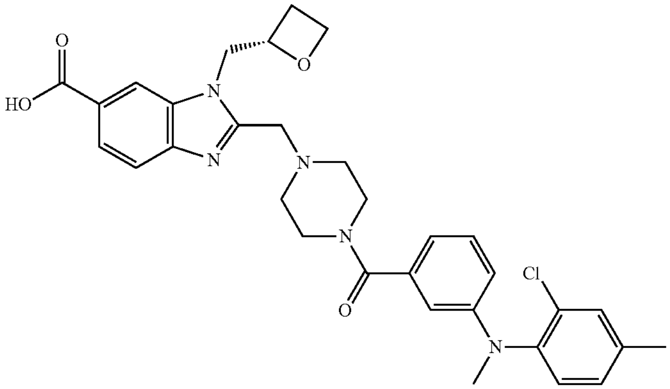 | 2-[(4-{3-[(2-chloro-4-methylphenyl)(methyl)amino]benzoyl}piperazin-1-yl)methyl]-1-{[(2S)-oxetan-2-yl]methyl}-1H-1,3-benzodiazole-6-carboxylic acid |
| 52 | 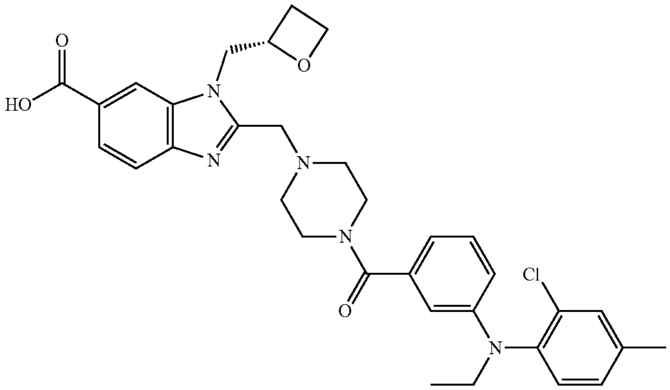 [SMILES: CCN(c1cccc(C(=O)N2CCN(Cc3nc4ccc(C(=O)O)cc4n3C[C@@H]3CCO3)CC2)c1)c1ccc(C)cc1Cl] | 2-[(4-{3-[(2-chloro-4-methylphenyl)(ethyl)amino]benzoyl}piperazin-1-yl)methyl]-1-{[(2S)-oxetan-2-yl]methyl}-1H-1,3-benzodiazole-6-carboxylic acid |
| 53 | 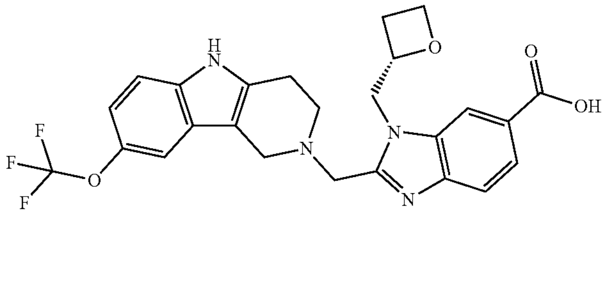 [SMILES: O=C(O)c1ccc2nc(CN3CCc4[nH]c5ccc(OC(F)(F)F)cc5c4C3)n(C[C@@H]3CCO3)c2c1] | 1-{[(2S)-oxetan-2-yl]methyl}-2-{[8-(trifluoromethoxy)-1H,2H,3H,4H,5H-pyrido[4,3-b]indol-2-yl]methyl}-1H-1,3-benzodiazole-6-carboxylic acid |

-continued

| Compound | Structure | IUPAC |
|---|---|---|
| 54 | 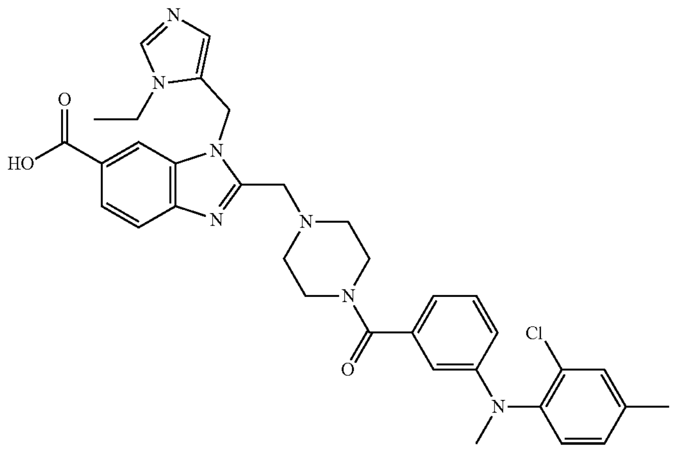 [SMILES: CCn1cncc1Cn1c(CN2CCN(C(=O)c3cccc(N(C)c4ccc(C)cc4Cl)c3)CC2)nc2ccc(C(=O)O)cc21] | 2-[(4-{3-[(2-chloro-4-methylphenyl)(methyl)amino]benzoyl}piperazin-1-yl)methyl]-1-[(1-ethyl-1H-imidazol-5-yl)methyl]-1H-1,3-benzodiazole-6-carboxylic acid |
| 55 | 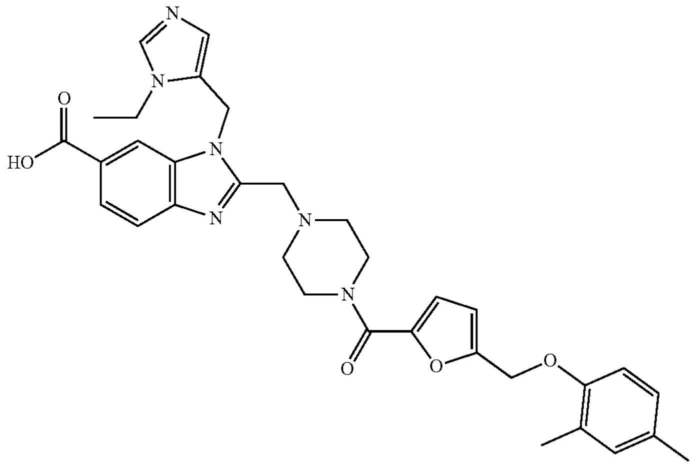 [SMILES: CCn1cncc1Cn1c(CN2CCN(C(=O)c3ccc(COc4ccc(C)cc4C)o3)CC2)nc2ccc(C(=O)O)cc21] | 2-[(4-{5-[(2,4-dimethylphenoxy)methyl]furan-2-carbonyl}piperazin-1-yl)methyl]-1-[(1-ethyl-1H-imidazol-5-yl)methyl]-1H-1,3-benzodiazole-6-carboxylic acid |
| 56 | 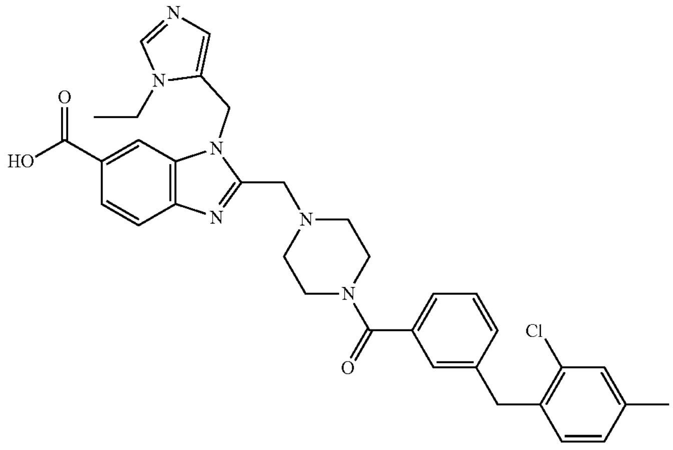 [SMILES: CCn1cncc1Cn1c(CN2CCN(C(=O)c3cccc(Cc4ccc(C)cc4Cl)c3)CC2)nc2ccc(C(=O)O)cc21] | 2-[(4-{3-[(2-chloro-4-methylphenyl)methyl]benzoyl}piperazin-1-yl)methyl]-1-[(1-ethyl-1H-imidazol-5-yl)methyl]-1H-1,3-benzodiazole-6-carboxylic acid |

-continued

| Compound | Structure | IUPAC |
| --- | --- | --- |
| 57 | 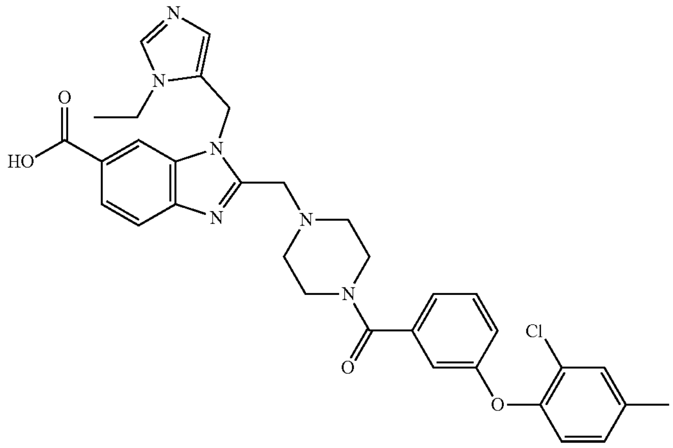 [SMILES: CCn1cncc1Cn1c(CN2CCN(C(=O)c3cccc(Oc4ccc(C)cc4Cl)c3)CC2)nc2ccc(C(=O)O)cc21] | 2-({4-[3-(2-chloro-4-methylphenoxy)benzoyl]piperazin-1-yl}methyl)-1-[(1-ethyl-1H-imidazol-5-yl)methyl]-1H-1,3-benzodiazole-6-carboxylic acid |
| 58 | 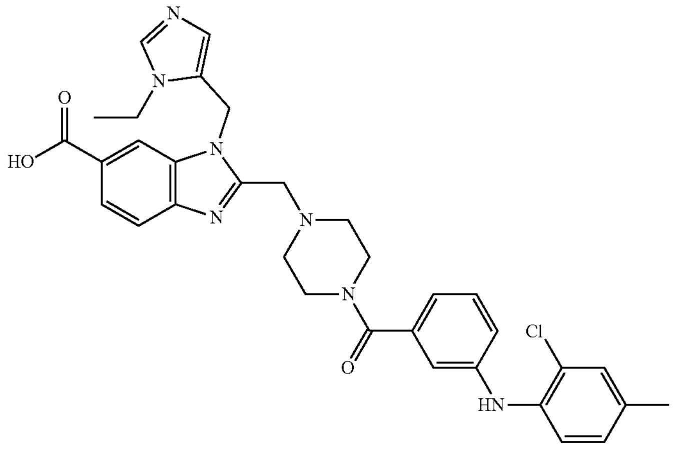 [SMILES: CCn1cncc1Cn1c(CN2CCN(C(=O)c3cccc(Nc4ccc(C)cc4Cl)c3)CC2)nc2ccc(C(=O)O)cc21] | 2-[(4-{3-[(2-chloro-4-methylphenyl)amino]benzoyl}piperazin-1-yl)methyl]-1-[(1-ethyl-1H-imidazol-5-yl)methyl]-1H-1,3-benzodiazole-6-carboxylic acid |
| 59 | 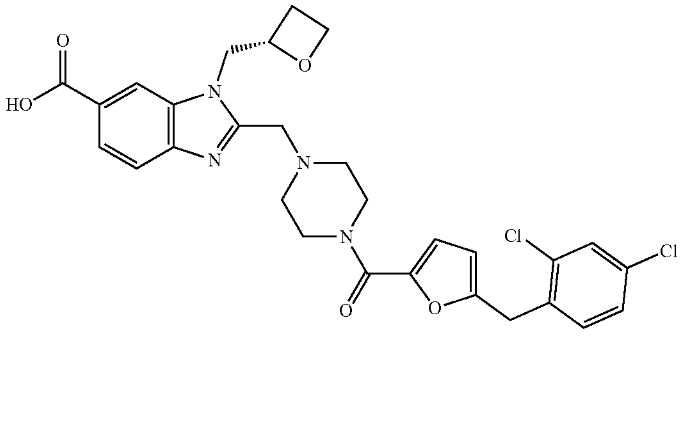 [SMILES: O=C(O)c1ccc2nc(CN3CCN(C(=O)c4ccc(Cc5ccc(Cl)cc5Cl)o4)CC3)n(C[C@@H]3CCO3)c2c1] | 2-[(4-{5-[(2,4-dichlorophenyl)methyl]furan-2-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
| --- | --- | --- |
| 60 | 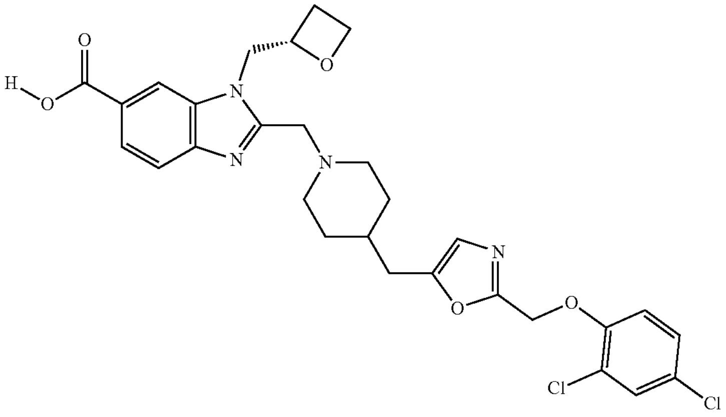 [SMILES: O=C(O)c1ccc2nc(CN3CCC(Cc4cnc(COc5ccc(Cl)cc5Cl)o4)CC3)n(C[C@@H]3CCO3)c2c1] | 2-{[4-({2-[(2,4-dichlorophenoxy)methyl]-1,3-oxazol-5-yl}methyl)piperidin-1-yl]methyl}-1-{[(2S)-oxetan-2-yl]methyl}-1H-1,3-benzodiazole-6-carboxylic acid |
| 61 | 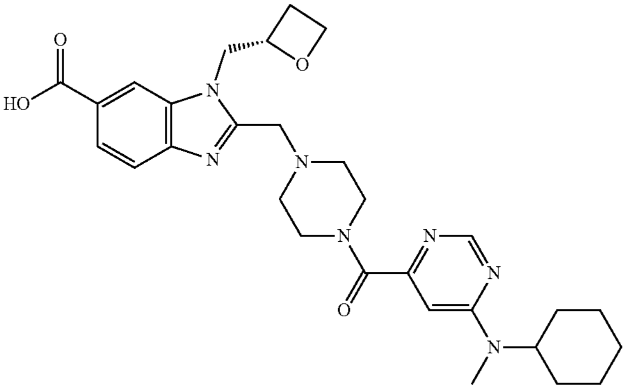 [SMILES: CN(c1cc(C(=O)N2CCN(Cc3nc4ccc(C(=O)O)cc4n3C[C@@H]3CCO3)CC2)ncn1)C1CCCCC1] | 2-[(4-{6-[cyclohexyl(methyl)amino]pyrimidine-4-carbonyl}piperazin-1-yl)methyl]-1-{[(2S)-oxetan-2-yl]methyl}-1H-1,3-benzodiazole-6-carboxylic acid |
| 62 | 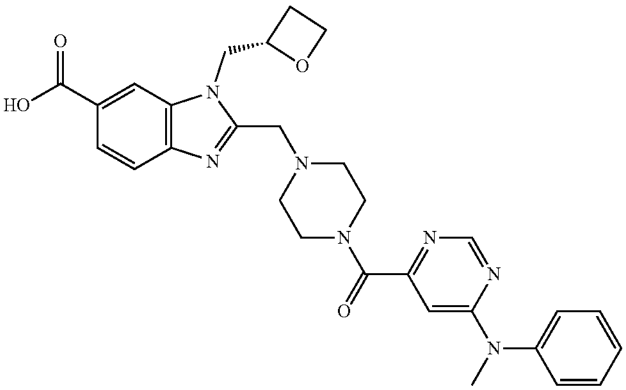 [SMILES: CN(c1ccccc1)c1cc(C(=O)N2CCN(Cc3nc4ccc(C(=O)O)cc4n3C[C@@H]3CCO3)CC2)ncn1] | 2-[(4-{6-[methyl(phenyl)amino]pyrimidine-4-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
| --- | --- | --- |
| 63 | 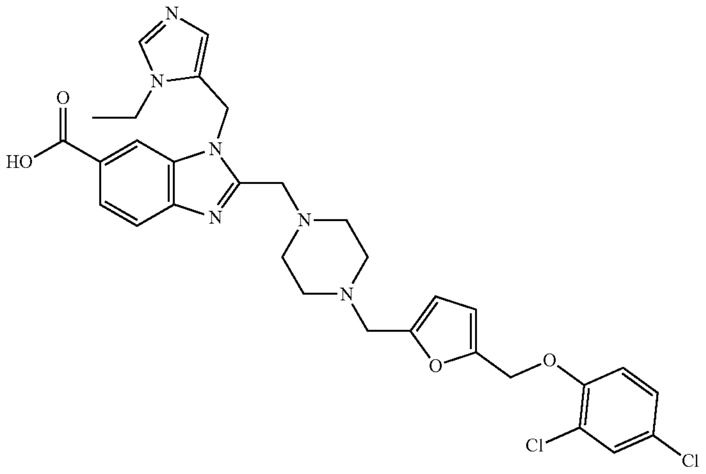 [SMILES: CCn1cncc1Cn1c(CN2CCN(Cc3ccc(COc4ccc(Cl)cc4Cl)o3)CC2)nc2ccc(C(=O)O)cc21] | 2-{[4-({5-[(2,4-dichlorophenoxy)methyl]furan-2-yl}methyl)piperazin-1-yl]methyl}-1-[(1-ethyl-1H-imidazol-5-yl)methyl]-1H-1,3-benzodiazole-6-carboxylic acid |
| 64 | 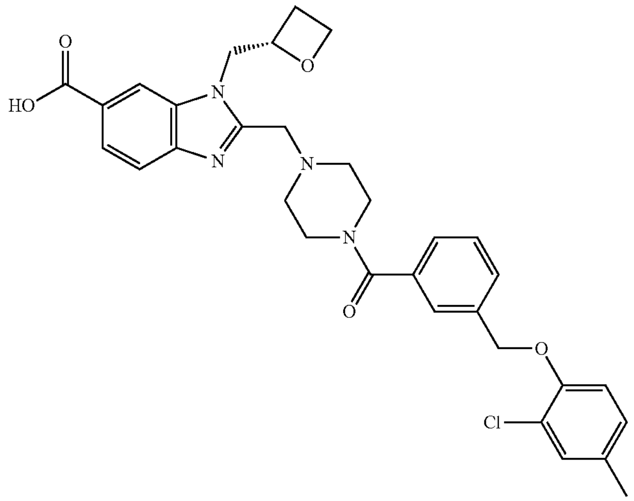 [SMILES: Cc1ccc(OCc2cccc(C(=O)N3CCN(Cc4nc5ccc(C(=O)O)cc5n4C[C@@H]4CCO4)CC3)c2)c(Cl)c1] | 2-[(4-{3-[(2-chloro-4-methylphenoxy)methyl]benzoyl}piperazin-1-yl)methyl]-1-{[(2S)-oxetan-2-yl]methyl}-1H-1,3-benzodiazole-6-carboxylic acid |
| 65 | 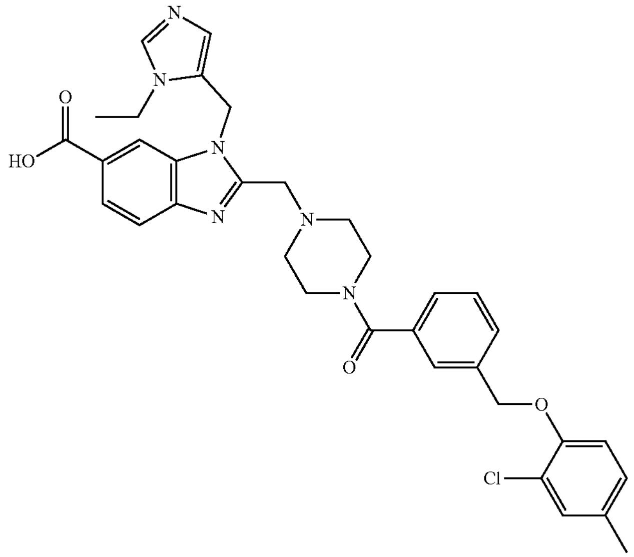 [SMILES: CCn1cncc1Cn1c(CN2CCN(C(=O)c3cccc(COc4ccc(C)cc4Cl)c3)CC2)nc2ccc(C(=O)O)cc21] | 2-[(4-{3-[(2-chloro-4-methylphenoxy)methyl]benzoyl}piperazin-1-yl)methyl]-1-[(1-ethyl-1H-imidazol-5-yl)methyl]-1H-1,3-benzodiazole-6-carboxylic acid |

-continued
| Compound | Structure | IUPAC |
|---|---|---|
| 66 | 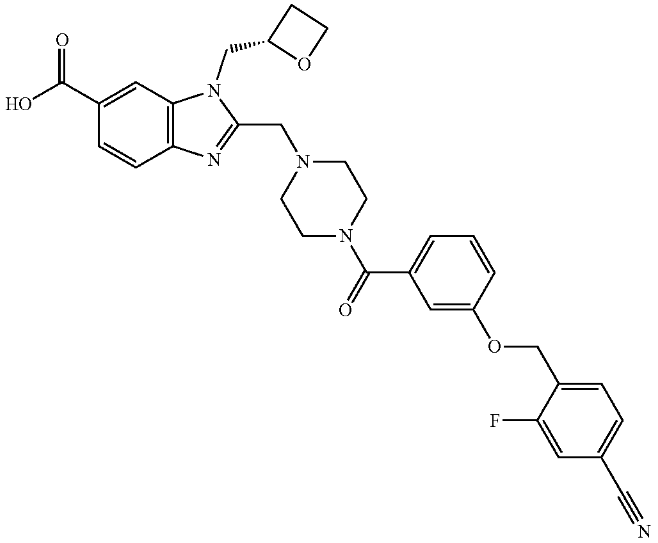 | 2-[(4-{3-[(4-cyano-2-fluorophenyl)methoxy]benzoyl}piperazin-1-yl)methyl]-1-{[(2S)-oxetan-2-yl]methyl}-1H-1,3-benzodiazole-6-carboxylic acid |
| 67 | 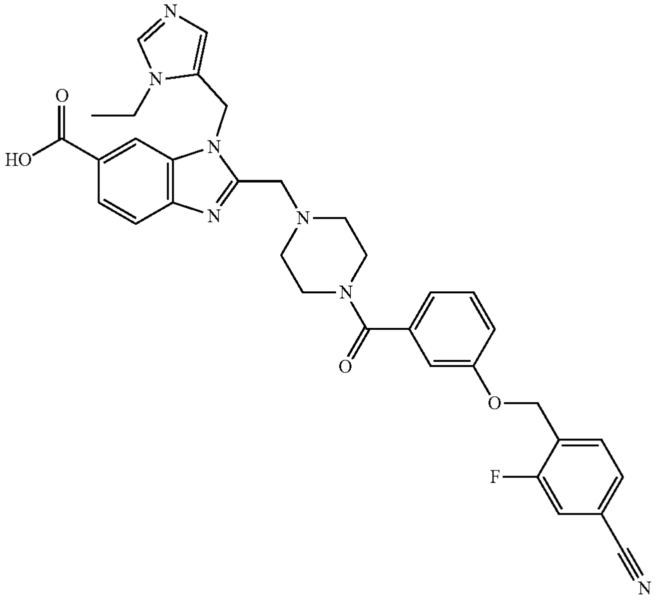 [SMILES: CCn1cncc1Cn1c(CN2CCN(C(=O)c3cccc(OCc4ccc(C#N)cc4F)c3)CC2)nc2ccc(C(=O)O)cc21] | 2-[(4-{3-[(4-cyano-2-fluorophenyl)methoxy]benzoyl}piperazin-1-yl)methyl]-1-[(1-ethyl-1H-imidazol-5-yl)methyl]-1H-1,3-benzodiazole-6-carboxylic acid |

-continued

| Compound | Structure | IUPAC |
|---|---|---|
| 68 | 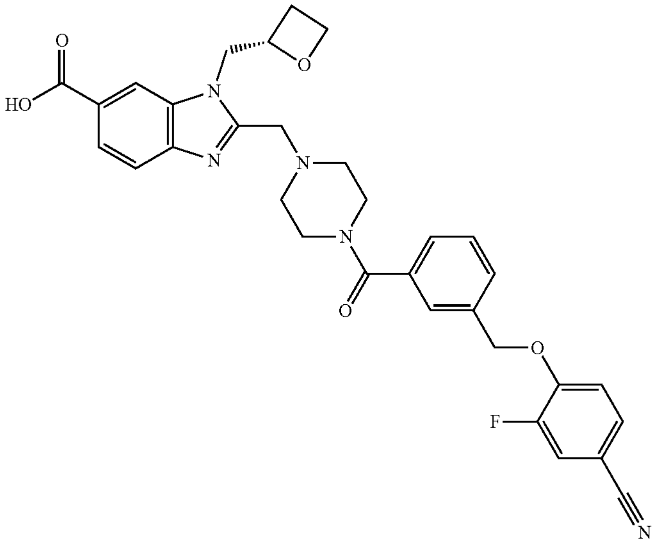 [SMILES: N#Cc1ccc(OCc2cccc(C(=O)N3CCN(Cc4nc5ccc(C(=O)O)cc5n4C[C@@H]4CCO4)CC3)c2)c(F)c1] | 2-[(4-{3-[(4-cyano-2-fluorophenoxy)methyl]benzoyl}piperazin-1-yl)methyl]-1-{[(2S)-oxetan-2-yl]methyl}-1H-1,3-benzodiazole-6-carboxylic acid |
| 69 | 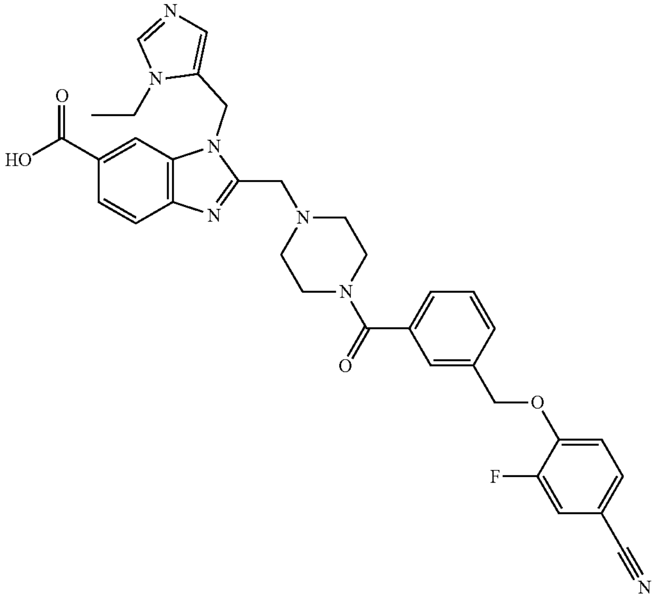 [SMILES: CCn1cncc1Cn1c(CN2CCN(C(=O)c3cccc(COc4ccc(C#N)cc4F)c3)CC2)nc2ccc(C(=O)O)cc21] | 2-[(4-{3-[(4-cyano-2-fluorophenoxy)methyl]benzoyl}piperazin-1-yl)methyl]-1-[(1-ethyl-1H-imidazol-5-yl)methyl]-1H-1,3-benzodiazole-6-carboxylic acid |
| 70 | 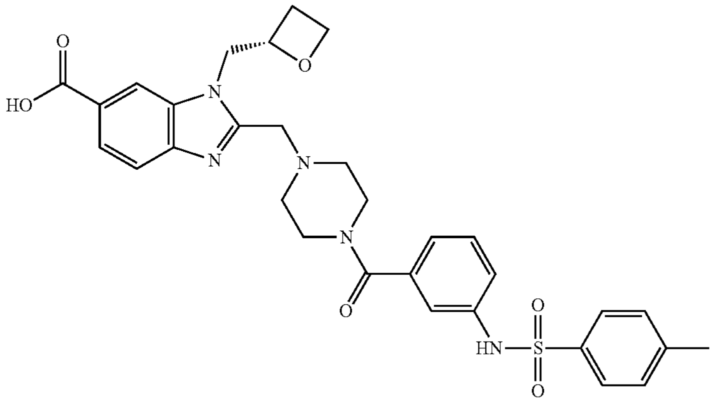 [SMILES: Cc1ccc(S(=O)(=O)Nc2cccc(C(=O)N3CCN(Cc4nc5ccc(C(=O)O)cc5n4C[C@@H]4CCO4)CC3)c2)cc1] | 2-({4-[3-(4-methyl-benzenesulfonamido)benzoyl]piperazin-1-yl}methyl)-1-{[(2S)-oxetan-2-yl]methyl}-1H-1,3-benzodiazole-6-carboxylic acid |

-continued

| Compound | Structure | IUPAC |
|---|---|---|
| 71 | 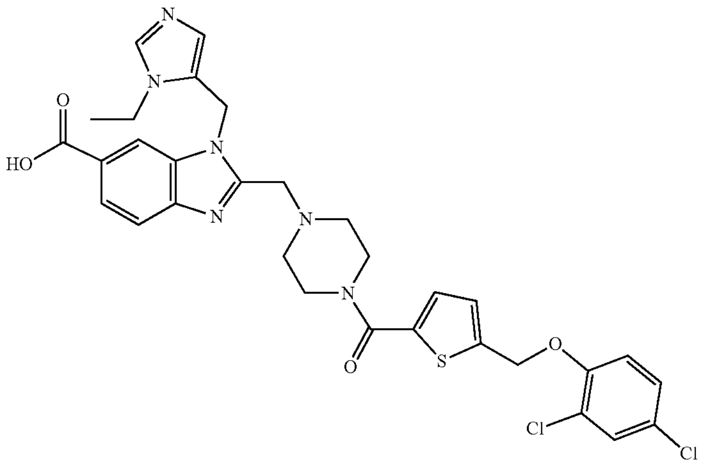 [SMILES: CCn1cncc1Cn1c(CN2CCN(C(=O)c3ccc(COc4ccc(Cl)cc4Cl)s3)CC2)nc2ccc(C(=O)O)cc21] | 2-[(4-{5-[(2,4-dichlorophenoxy) methyl]thiophene-2-carbonyl}piperazin-1-yl)methyl]-1-[(1-ethyl-1H-imidazol-5-yl)methyl]-1H-1,3-benzodiazole-6-carboxylic acid |
| 72 | 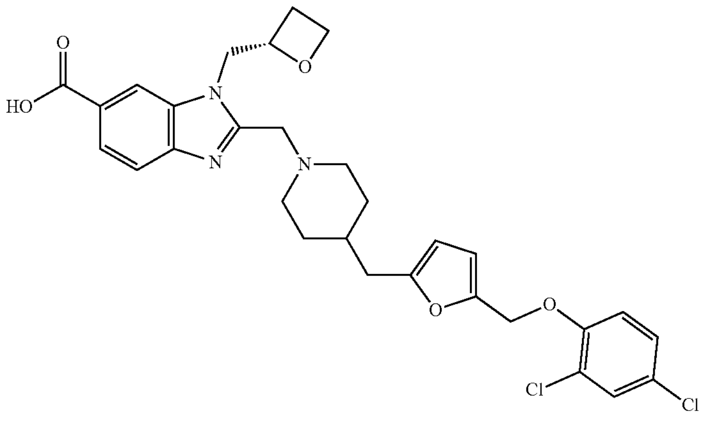 [SMILES: O=C(O)c1ccc2nc(CN3CCC(Cc4ccc(COc5ccc(Cl)cc5Cl)o4)CC3)n(C[C@@H]3CCO3)c2c1] | 2-{[4-({5-[(2,4-dichlorophenoxy) methyl]furan-2-yl}methyl) piperidin-1-yl]methyl}-1-{[(2S)-oxetan-2-yl]methyl}-1H-1,3-benzodiazole-6-carboxylic acid |
| 73 | 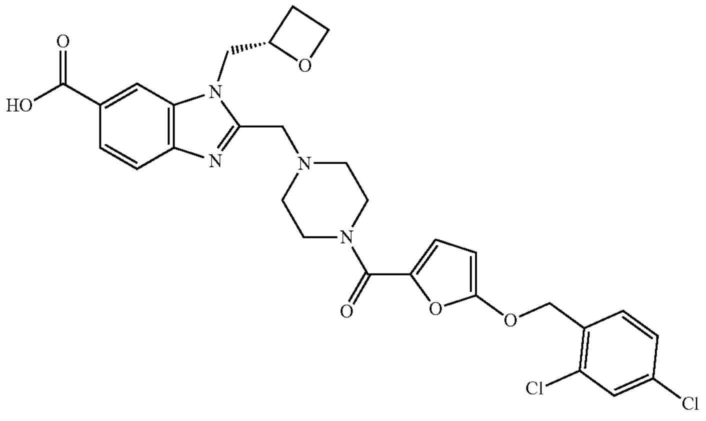 | 2-[(4-{5-[(2,4-dichlorophenyl)methoxy] furan-2-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
|---|---|---|
| 74 | 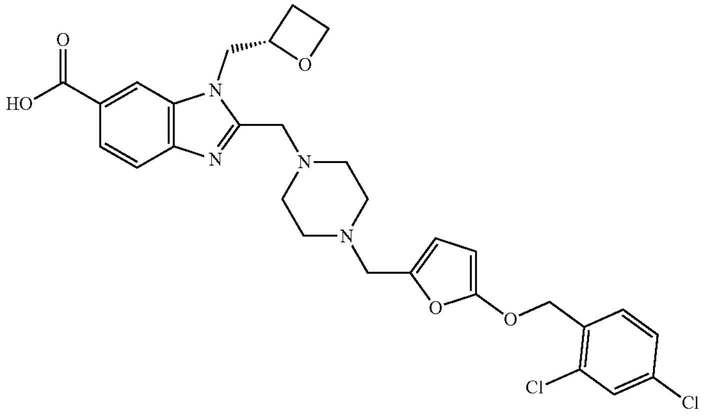 [SMILES: O=C(O)c1ccc2nc(CN3CCN(Cc4ccc(OCc5ccc(Cl)cc5Cl)o4)CC3)n(C[C@@H]3CCO3)c2c1] | 2-{[4-({5-[(2,4-dichlorophenyl)methoxy]furan-2-yl}methyl)piperazin-1-yl]methyl}-1-{[(2S)-oxetan-2-yl]methyl}-1H-1,3-benzodiazole-6-carboxylic acid |
| 75 | 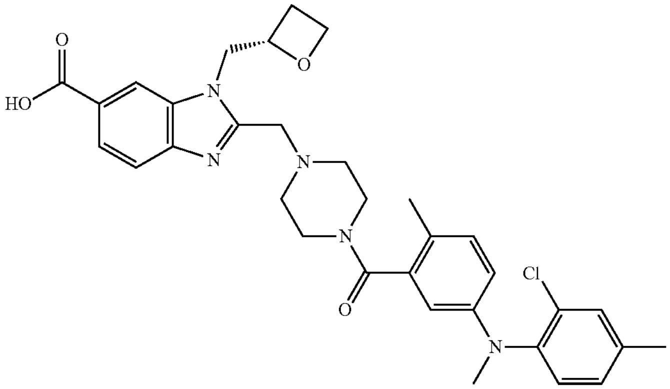 [SMILES: Cc1ccc(N(C)c2ccc(C)c(C(=O)N3CCN(Cc4nc5ccc(C(=O)O)cc5n4C[C@@H]4CCO4)CC3)c2)c(Cl)c1] | 2-[(4-{5-[(2-chloro-4-methylphenyl)(methyl)amino]-2-methylbenzoyl}piperazin-1-yl)methyl]-1-{[(2S)-oxetan-2-yl]methyl}-1H-1,3-benzodiazole-6-carboxylic acid |
| 76 | 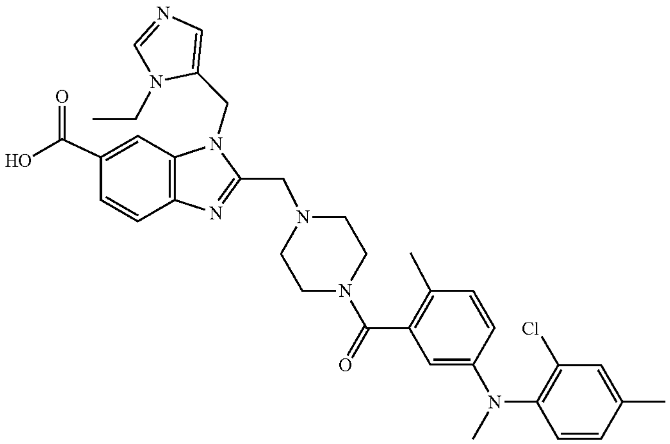 [SMILES: CCn1cncc1Cn1c(CN2CCN(C(=O)c3cc(N(C)c4ccc(C)cc4Cl)ccc3C)CC2)nc2ccc(C(=O)O)cc21] | 2-[(4-{5-[(2-chloro-4-methylphenyl)(methyl)amino]-2-methylbenzoyl}piperazin-1-yl)methyl]-1-[(1-ethyl-1H-imidazol-5-yl)methyl]-1H-1,3-benzodiazole-6-carboxylic acid |

-continued
| Compound | Structure | IUPAC |
|---|---|---|
| 77 | 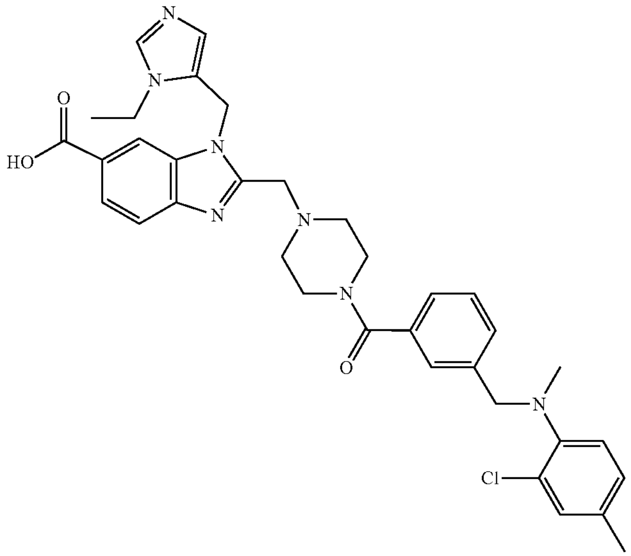 [SMILES: CCn1cncc1Cn1c(CN2CCN(C(=O)c3cccc(CN(C)c4ccc(C)cc4Cl)c3)CC2)nc2ccc(C(=O)O)cc21] | 2-{[4-(3-{[(2-chloro-4-methylphenyl)(methyl)amino]methyl}benzoyl)piperazin-1-yl]methyl}-1-[(1-ethyl-1H-imidazol-5-yl)methyl]-1H-1,3-benzodiazole-6-carboxylic acid |
| 78 | 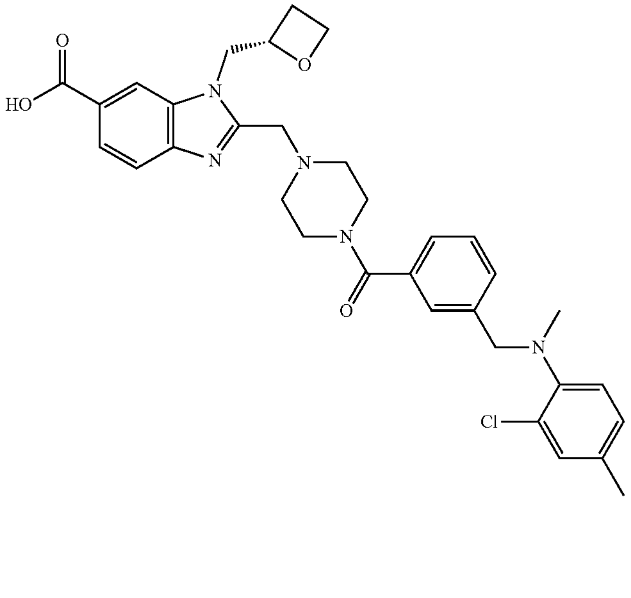 [SMILES: Cc1ccc(N(C)Cc2cccc(C(=O)N3CCN(Cc4nc5ccc(C(=O)O)cc5n4C[C@@H]4CCO4)CC3)c2)c(Cl)c1] | 2-{[4-(3-{[(2-chloro-4-methylphenyl)(methyl)amino]methyl}benzoyl)piperazin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 79 | 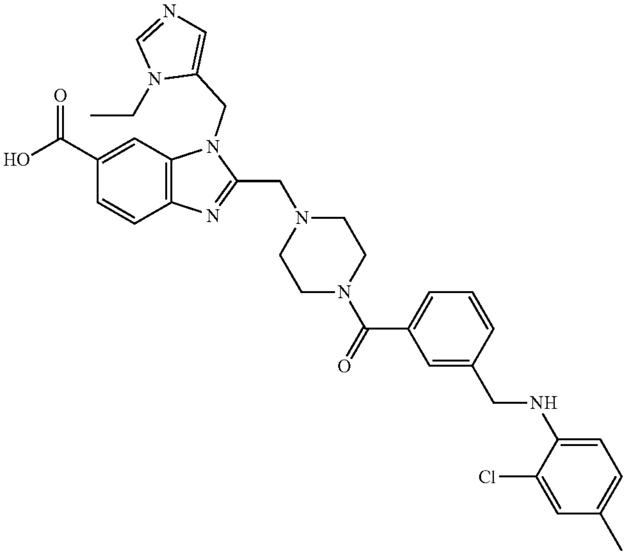 [SMILES: CCn1cncc1Cn1c(CN2CCN(C(=O)c3cccc(CNc4ccc(C)cc4Cl)c3)CC2)nc2ccc(C(=O)O)cc21] | 2-{[4-(3-{[(2-chloro-4-methylphenyl)amino]methyl}benzoyl)piperazin-1-yl]methyl}-1-[(1-ethyl-1H-imidazol-5-yl)methyl]-1H-1,3-benzodiazole-6-carboxylic acid |
| 80 | 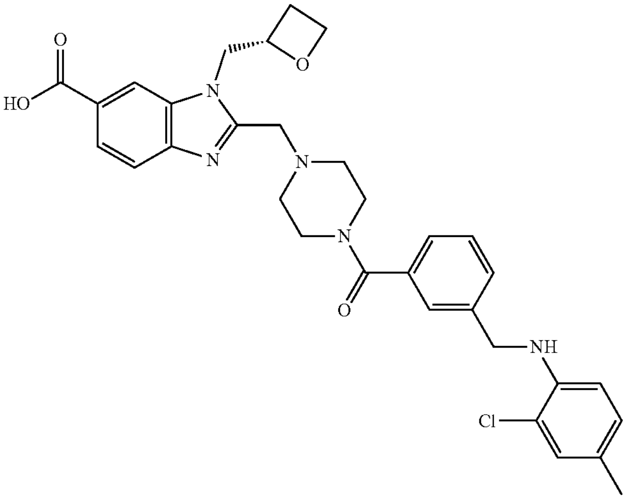 [SMILES: Cc1ccc(NCc2cccc(C(=O)N3CCN(Cc4nc5ccc(C(=O)O)cc5n4C[C@@H]4CCO4)CC3)c2)c(Cl)c1] | 2-{[4-(3-{[(2-chloro-4-methylphenyl)amino]methyl}benzoyl)piperazin-1-yl]methyl}-1-{[(2S)-oxetan-2-yl]methyl}-1H-1,3-benzodiazole-6-carboxylic acid |
| 81 | 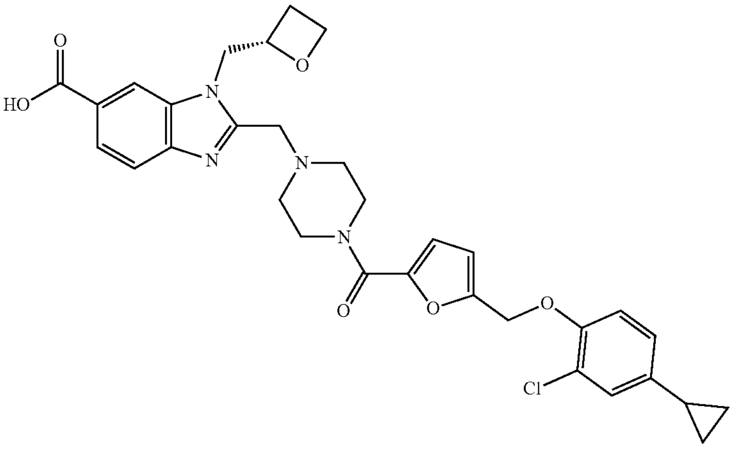 [SMILES: O=C(O)c1ccc2nc(CN3CCN(C(=O)c4ccc(COc5ccc(C6CC6)cc5Cl)o4)CC3)n(C[C@@H]3CCO3)c2c1] | 2-[(4-{5-[(2-chloro-4-cyclopropylphenoxy)methyl]furan-2-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
|---|---|---|
| 82 | 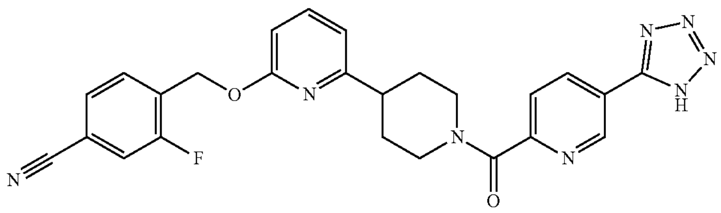 [SMILES: N#Cc1ccc(COc2cccc(C3CCN(C(=O)c4ccc(-c5nnn[nH]5)cn4)CC3)n2)c(F)c1] | 3-fluoro-4-{[(6-{1-[5-(1H-1,2,3,4-tetrazol-5-yl)pyridine-2-carbonyl]piperidin-4-yl}pyridin-2-yl)oxy]methyl}benzonitrile |
| 83 | 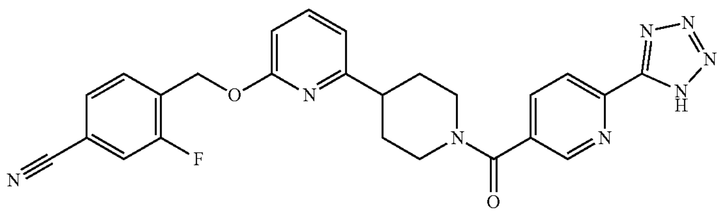 [SMILES: N#Cc1ccc(COc2cccc(C3CCN(C(=O)c4ccc(-c5nnn[nH]5)nc4)CC3)n2)c(F)c1] | 3-fluoro-4-{[(6-{1-[6-(1H-1,2,3,4-tetrazol-5-yl)pyridine-3-carbonyl]piperidin-4-yl}pyridin-2-yl)oxy]methyl}benzonitrile |
| 84 | 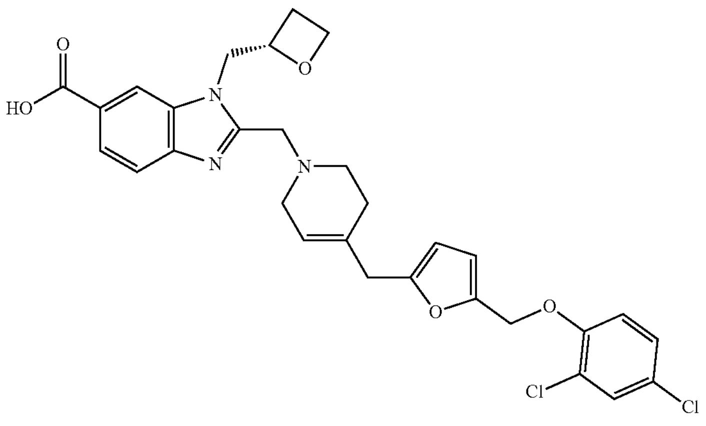 | 2-{[4-({5-[(2,4-dichlorophenoxy)methyl]furan-2-yl}methyl)-1,2,3,6-tetrahydropyridin-1-yl]methyl}-1-{[(2S)-oxetan-2-yl]methyl}-1H-1,3-benzodiazole-6-carboxylic acid |
| 85 | 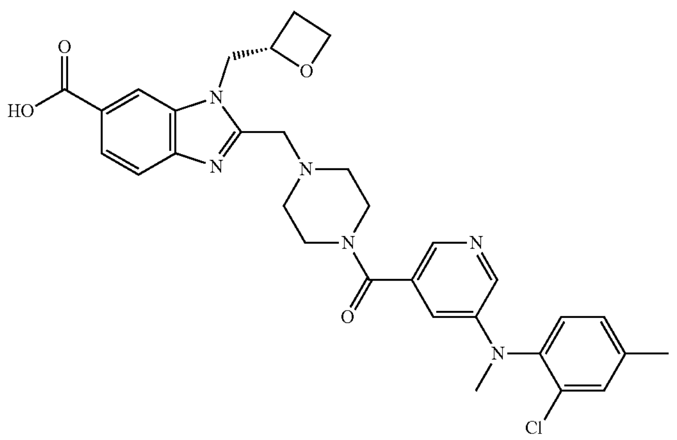 [SMILES: Cc1ccc(N(C)c2cncc(C(=O)N3CCN(Cc4nc5ccc(C(=O)O)cc5n4C[C@@H]4CCO4)CC3)c2)c(Cl)c1] | 2-[(4-{5-[(2-chloro-4-methylphenyl)(methyl)amino]pyridine-3-carbonyl}piperazin-1-yl)methyl]-1-{[(2S)-oxetan-2-yl]methyl}-1H-1,3-benzodiazole-6-carboxylic acid |

-continued

| Compound | Structure | IUPAC |
|---|---|---|
| 86 | 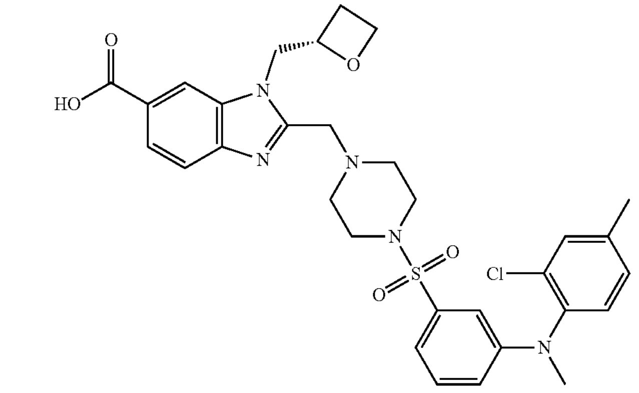 [SMILES: Cc1ccc(N(C)c2cccc(S(=O)(=O)N3CCN(Cc4nc5ccc(C(=O)O)cc5n4C[C@@H]4CCO4)CC3)c2)c(Cl)c1] | 2-[(4-{3-[(2-chloro-4-methylphenyl)(methyl)amino]benzenesulfonyl}piperazin-1-yl)methyl]-1-{[(2S)-oxetan-2-yl]methyl}-1H-1,3-benzodiazole-6-carboxylic acid |
| 87 | 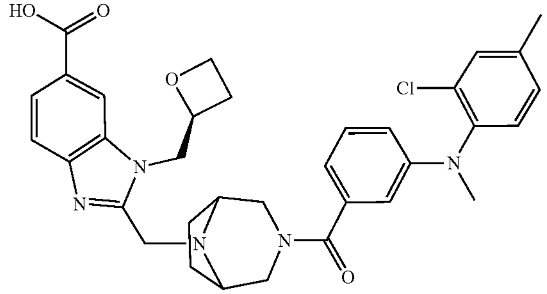 | 2-[(3-{3-[(2-chloro-4-methylphenyl)(methyl)amino]benzoyl}-3,8-diazabicyclo[3.2.1]octan-8-yl)methyl]-1-{[(2S)-oxetan-2-yl]methyl}-1H-1,3-benzodiazole-6-carboxylic acid |
| 88 | 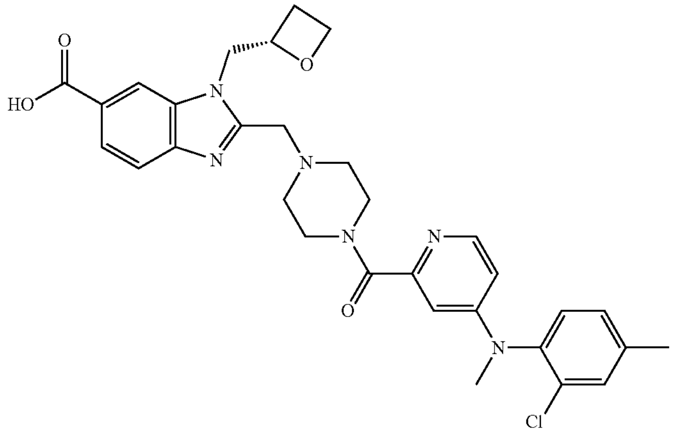 | 2-[(4-{4-[(2-chloro-4-methylphenyl)(methyl)amino]pyridine-2-carbonyl}piperazin-1-yl)methyl]-1-{[(2S)-oxetan-2-yl]methyl}-1H-1,3-benzodiazole-6-carboxylic acid |
| 89 | 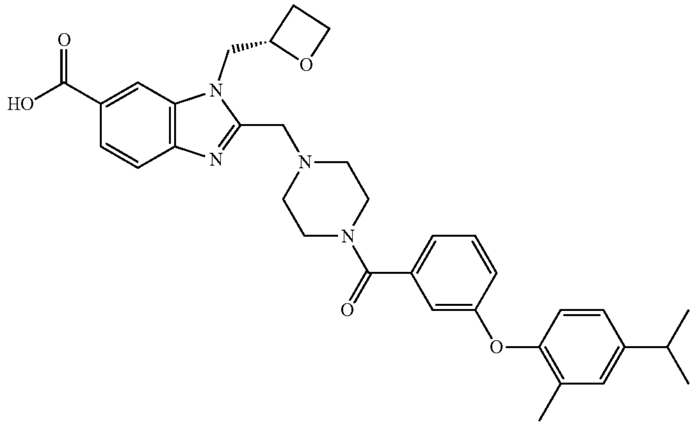 [SMILES: Cc1cc(C(C)C)ccc1Oc1cccc(C(=O)N2CCN(Cc3nc4ccc(C(=O)O)cc4n3C[C@@H]3CCO3)CC2)c1] | 2-[(4-{3-[2-methyl-4-(propan-2-yl)phenoxy]benzoyl}piperazin-1-yl)methyl]-1-{[(2S)-oxetan-2-yl]methyl}-1H-1,3-benzodiazole-6-carboxylic acid |

-continued

| Compound | Structure | IUPAC |
|---|---|---|
| 90 | 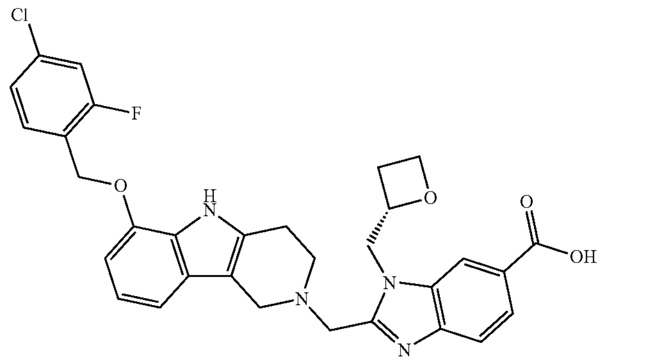 [SMILES: O=C(O)c1ccc2nc(CN3CCc4[nH]c5c(OCc6ccc(Cl)cc6F)cccc5c4C3)n(C[C@@H]3CCO3)c2c1] | 2-({6-[(4-chloro-2-fluorophenyl)methoxy]-1H,2H,3H,4H,5H-pyrido[4,3-b]indol-2-yl}methyl)-1-{[(2S)-oxetan-2-yl]methyl}-1H-1,3-benzodiazole-6-carboxylic acid |
| 91 | 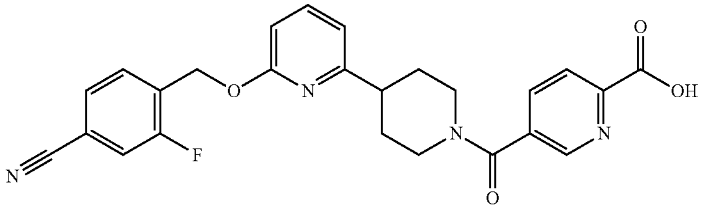 [SMILES: N#Cc1ccc(COc2cccc(C3CCN(C(=O)c4ccc(C(=O)O)nc4)CC3)n2)c(F)c1] | 5-(4-{6-[(4-cyano-2-fluorophenyl)methoxy]pyridin-2-yl}piperidine-1-carbonyl)pyridine-2-carboxylic acid |
| 92 | 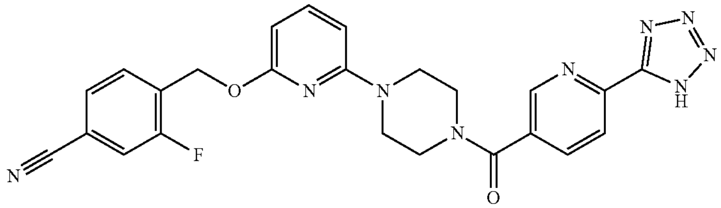 [SMILES: N#Cc1ccc(COc2cccc(N3CCN(C(=O)c4ccc(-c5nnn[nH]5)nc4)CC3)n2)c(F)c1] | 3-fluoro-4-{[(6-{4-[6-(1H-1,2,3,4-tetrazol-5-yl)pyridine-3-carbonyl]piperazin-1-yl}pyridin-2-yl)oxy]methyl}benzonitrile |
| 93 | 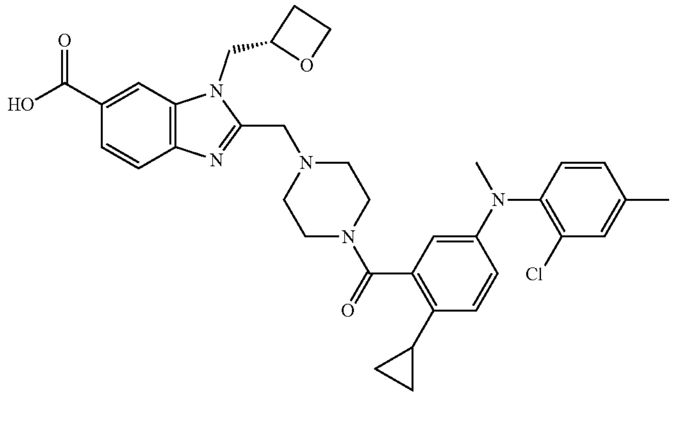 [SMILES: Cc1ccc(N(C)c2ccc(C3CC3)c(C(=O)N3CCN(Cc4nc5ccc(C(=O)O)cc5n4C[C@@H]4CCO4)CC3)c2)c(Cl)c1] | 2-[(4-{5-[(2-chloro-4-methylphenyl)(methyl)amino]-2-cyclopropylbenzoyl}piperazin-1-yl)methyl]-1-{[(2S)-oxetan-2-yl]methyl}-1H-1,3-benzodiazole-6-carboxylic acid |

-continued

| Compound | Structure | IUPAC |
| --- | --- | --- |
| 94 | 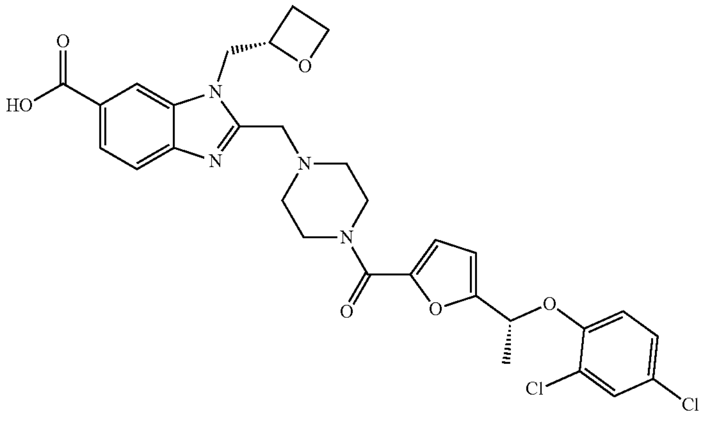 [SMILES: C[C@@H](Oc1ccc(Cl)cc1Cl)c1ccc(C(=O)N2CCN(Cc3nc4ccc(C(=O)O)cc4n3C[C@@H]3CCO3)CC2)o1] | 2-[(4-{5-[(1R*)-1-(2,4-dichlorophenoxy)ethyl]furan-2-carbonyl}piperazin-1-yl)methyl]-1-{[(2S)-oxetan-2-yl]methyl}-1H-1,3-benzodiazole-6-carboxylic acid |
| 95 | 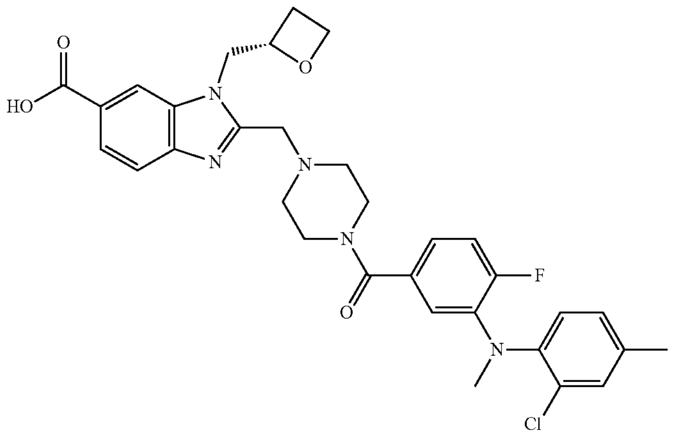 [SMILES: Cc1ccc(N(C)c2cc(C(=O)N3CCN(Cc4nc5ccc(C(=O)O)cc5n4C[C@@H]4CCO4)CC3)ccc2F)c(Cl)c1] | 2-[(4-{3-[(2-chloro-4-methylphenyl)(methyl)amino]-4-fluorobenzoyl}piperazin-1-yl)methyl]-1-{[(2S)-oxetan-2-yl]methyl}-1H-1,3-benzodiazole-6-carboxylic acid |
| 96 | 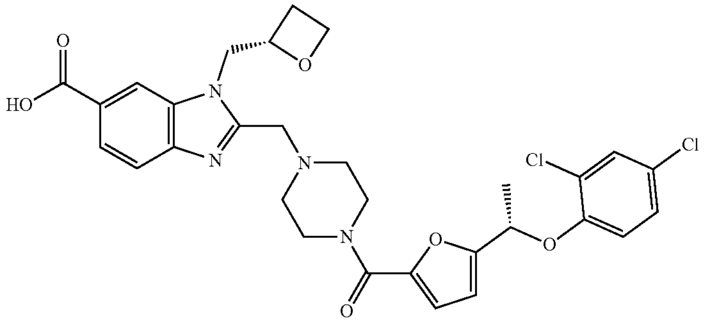 [SMILES: C[C@H](Oc1ccc(Cl)cc1Cl)c1ccc(C(=O)N2CCN(Cc3nc4ccc(C(=O)O)cc4n3C[C@@H]3CCO3)CC2)o1] | 2-[(4-{5-[(1S)-1-(2,4-dichlorophenoxy)ethyl]furan-2-carbonyl}piperazin-1-yl)methyl]-1-{[(2S)-oxetan-2-yl]methyl}-1H-1,3-benzodiazole-6-carboxylic acid |
| 97 | 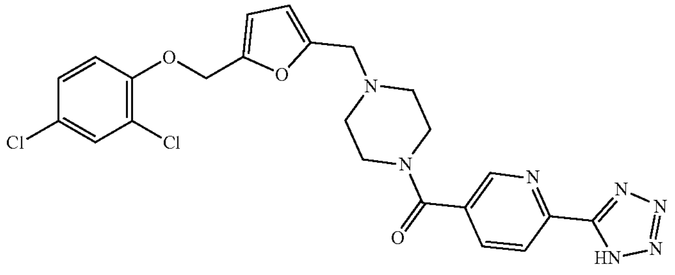 [SMILES: O=C(c1ccc(-c2nnn[nH]2)nc1)N1CCN(Cc2ccc(COc3ccc(Cl)cc3Cl)o2)CC1] | 1-({5-[(2,4-dichlorophenoxy)methyl]furan-2-yl}methyl)-4-[6-(1H-1,2,3,4-tetrazol-5-yl)pyridine-3-carbonyl]piperazine |

-continued

| Compound | Structure | IUPAC |
|---|---|---|
| 98 | 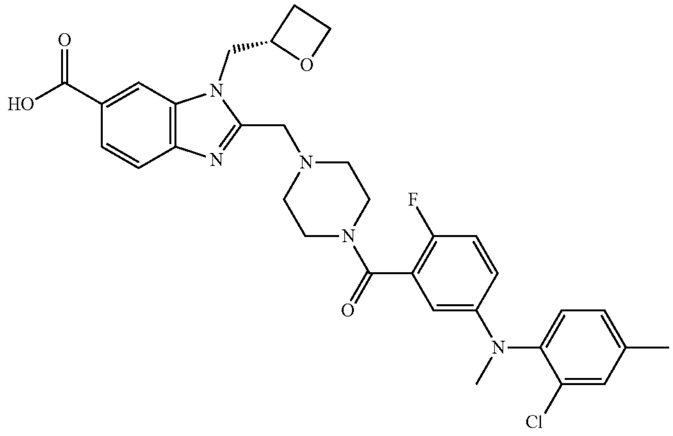 [SMILES: Cc1ccc(N(C)c2ccc(F)c(C(=O)N3CCN(Cc4nc5ccc(C(=O)O)cc5n4C[C@@H]4CCO4)CC3)c2)c(Cl)c1] | 2-[(4-{5-[(2-chloro-4-methylphenyl)(methyl)amino]-2-fluorobenzoyl}piperazin-1-yl)methyl]-1-{[(2S)-oxetan-2-yl]methyl}-1H-1,3-benzodiazole-6-carboxylic acid |
| 99 | 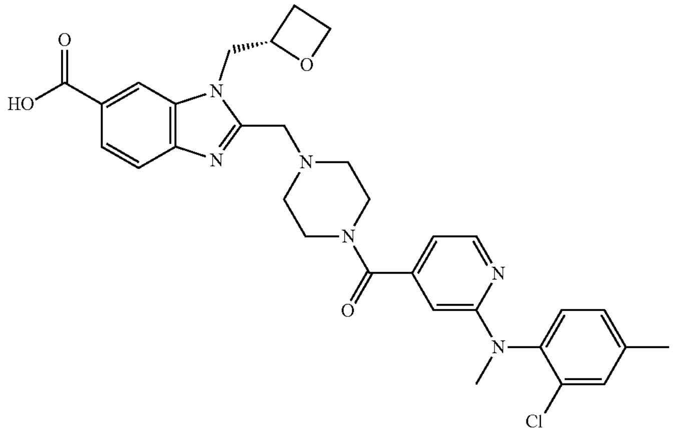 [SMILES: Cc1ccc(N(C)c2cc(C(=O)N3CCN(Cc4nc5ccc(C(=O)O)cc5n4C[C@@H]4CCO4)CC3)ccn2)c(Cl)c1] | 2-[(4-{2-[(2-chloro-4-methylphenyl)(methyl)amino]pyridine-4-carbonyl}piperazin-1-yl)methyl]-1-{[(2S)-oxetan-2-yl]methyl}-1H-1,3-benzodiazole-6-carboxylic acid |
| 100 | 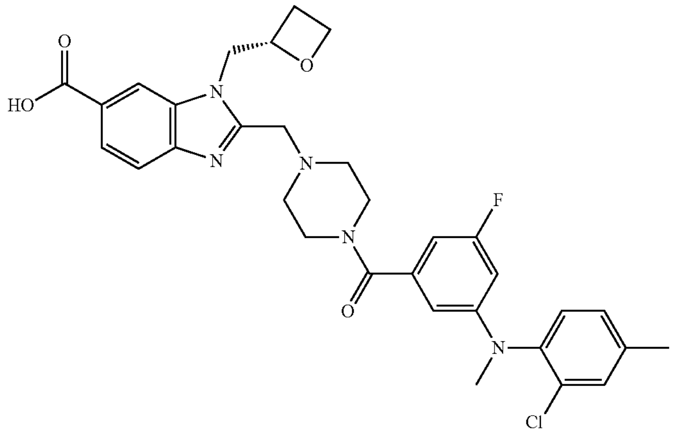 [SMILES: Cc1ccc(N(C)c2cc(F)cc(C(=O)N3CCN(Cc4nc5ccc(C(=O)O)cc5n4C[C@@H]4CCO4)CC3)c2)c(Cl)c1] | 2-[(4-{3-[(2-chloro-4-methylphenyl)(methyl)amino]-5-fluorobenzoyl}piperazin-1-yl)methyl]-1-{[(2S)-oxetan-2-yl]methyl}-1H-1,3-benzodiazole-6-carboxylic acid |

-continued

| Compound | Structure | IUPAC |
| --- | --- | --- |
| 101 | 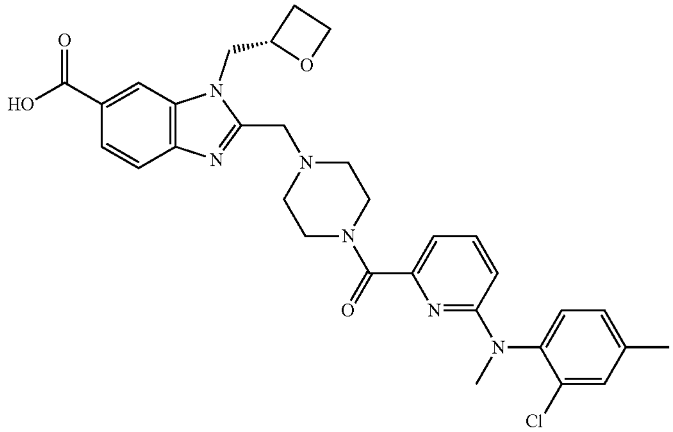 [SMILES: Cc1ccc(N(C)c2cccc(C(=O)N3CCN(Cc4nc5ccc(C(=O)O)cc5n4C[C@@H]4CCO4)CC3)n2)c(Cl)c1] | 2-[(4-{6-[(2-chloro-4-methylphenyl)(methyl)amino]pyridine-2-carbonyl}piperazin-1-yl)methyl]-1-{[(2S)-oxetan-2-yl]methyl}-1H-1,3-benzodiazole-6-carboxylic acid |
| 102 | 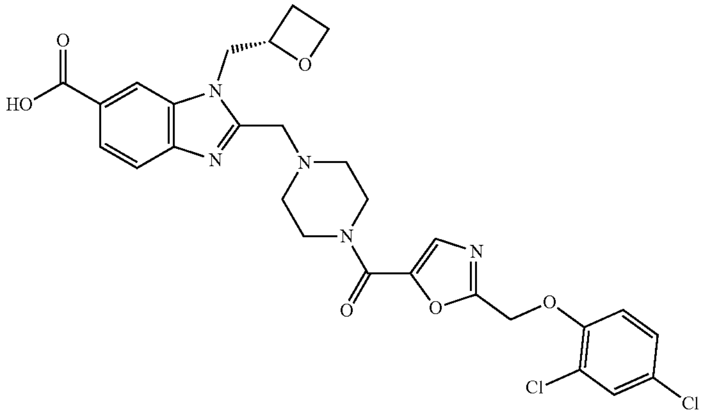 | 2-[(4-{2-[(2,4-dichlorophenoxy)methyl]-1,3-oxazole-5-carbonyl}piperazin-1-yl)methyl]-1-{[(2S)-oxetan-2-yl]methyl}-1H-1,3-benzodiazole-6-carboxylic acid |
| 103 | 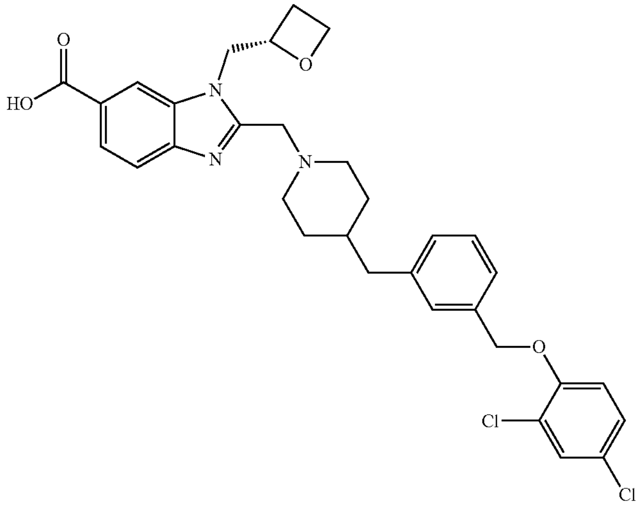 [SMILES: O=C(O)c1ccc2nc(CN3CCC(Cc4cccc(COc5ccc(Cl)cc5Cl)c4)CC3)n(C[C@@H]3CCO3)c2c1] | 2-{[4-({3-[(2,4-dichlorophenoxy)methyl]phenyl}methyl)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 104 | 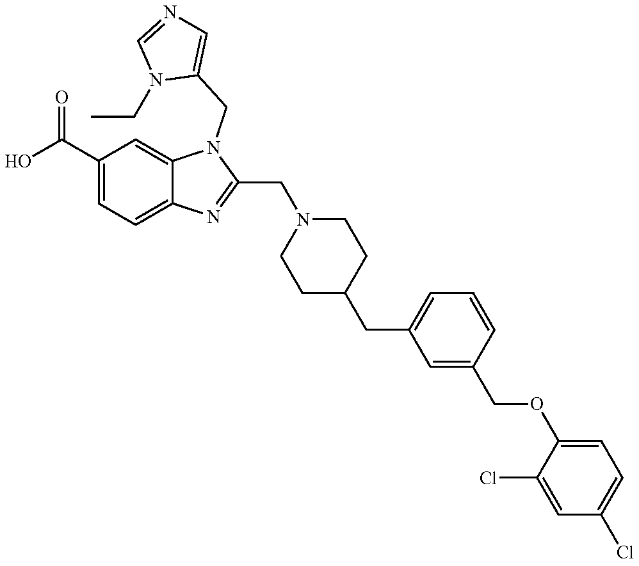 [SMILES: CCn1cncc1Cn1c(CN2CCC(Cc3cccc(COc4ccc(Cl)cc4Cl)c3)CC2)nc2ccc(C(=O)O)cc21] | 2-{[4-({3-[(2,4-dichlorophenoxy)methyl] phenyl}methyl) piperidin-1-yl]methyl}-1-[(1-ethyl-1H-imidazol-5-yl)methyl]-1H-1,3-benzodiazole-6-carboxylic acid |
| 105 | 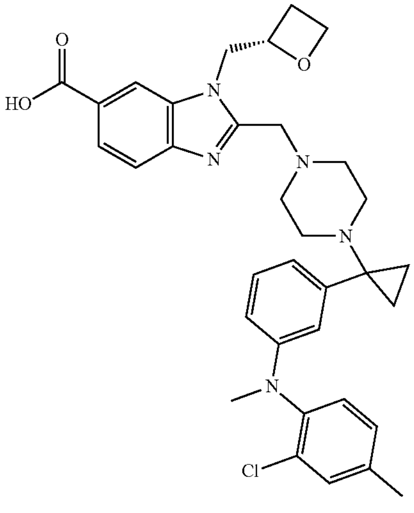 [SMILES: Cc1ccc(N(C)c2cccc(C3(N4CCN(Cc5nc6ccc(C(=O)O)cc6n5C[C@@H]5CCO5)CC4)CC3)c2)c(Cl)c1] | 2-{[4-(1-{3-[(2-chloro-4-methylphenyl)(methyl) amino]phenyl} cyclopropyl)piperazin-1-yl]methyl}-1-{[(2S)-oxetan-2-yl]methyl}-1H-1,3-benzodiazole-6-carboxylic acid |
| 106 | 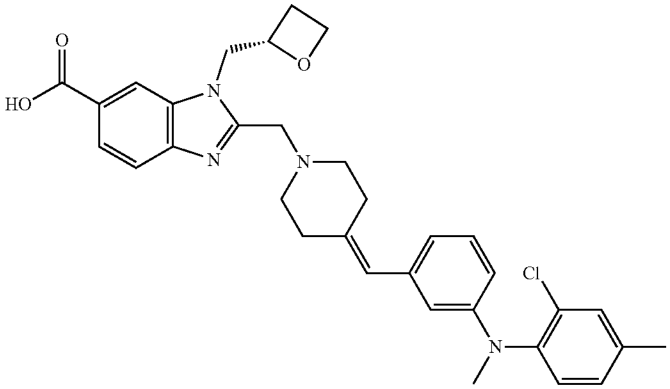 [SMILES: Cc1ccc(N(C)c2cccc(C=C3CCN(Cc4nc5ccc(C(=O)O)cc5n4C[C@@H]4CCO4)CC3)c2)c(Cl)c1] | 2-{[4-({3-[(2-chloro-4-methylphenyl)(methyl) amino]phenyl} methylidene)piperidin-1-yl]methyl}-1-{[(2S)-oxetan-2-yl]methyl}-1H-1,3-benzodiazole-6-carboxylic acid |

-continued

| Compound | Structure | IUPAC |
| --- | --- | --- |
| 107 | 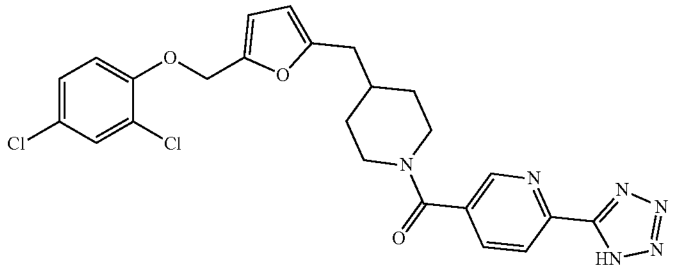 [SMILES: O=C(c1ccc(-c2nnn[nH]2)nc1)N1CCC(Cc2ccc(COc3ccc(Cl)cc3Cl)o2)CC1] | 5-[4-({5-[(2,4-dichlorophenoxy)methyl]furan-2-yl}methyl)piperidine-1-carbonyl]-2-(1H-1,2,3,4-tetrazol-5-yl)pyridine |
| 108 | 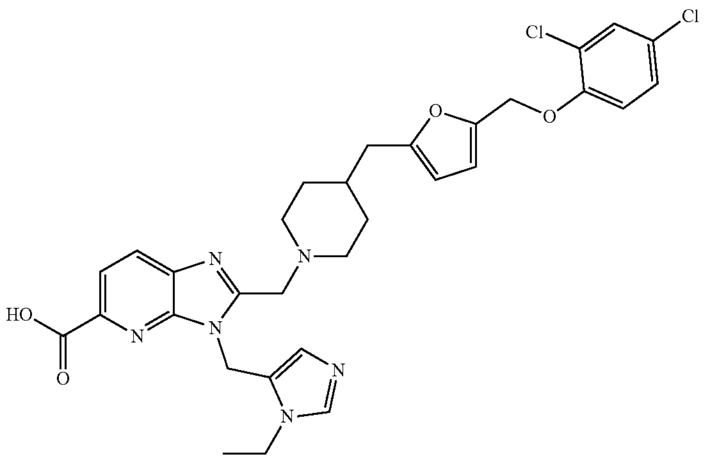 [SMILES: CCn1cncc1Cn1c(CN2CCC(Cc3ccc(COc4ccc(Cl)cc4Cl)o3)CC2)nc2ccc(C(=O)O)nc21] | 2-{[4-({5-[(2,4-dichlorophenoxy)methyl]furan-2-yl}methyl)piperidin-1-yl]methyl}-3-[(1-ethyl-1H-imidazol-5-yl)methyl]-3H-imidazo[4,5-b]pyridine-5-carboxylic acid |
| 109 | 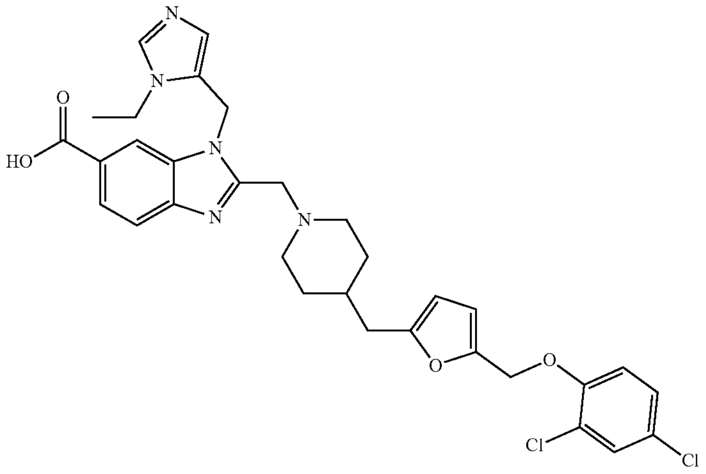 [SMILES: CCn1cncc1Cn1c(CN2CCC(Cc3ccc(COc4ccc(Cl)cc4Cl)o3)CC2)nc2ccc(C(=O)O)cc21] | 2-{[4-({5-[(2,4-dichlorophenoxy)methyl]furan-2-yl}methyl)piperidin-1-yl]methyl}-1-[(1-ethyl-1H-imidazol-5-yl)methyl]-1H-1,3-benzodiazole-6-carboxylic acid |
| 110 | 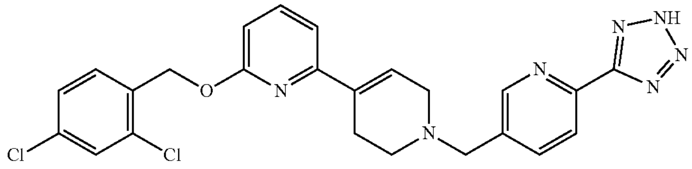 [SMILES: Clc1ccc(COc2cccc(C3=CCN(Cc4ccc(-c5nn[nH]n5)nc4)CC3)n2)c(Cl)c1] | 6-[(2,4-dichlorophenyl)methoxy]-1'-{[6-(2H-1,2,3,4-tetrazol-5-yl)pyridin-3-yl]methyl}-1',2',3',6'-tetrahydro-2,4'-bipyridine |

-continued

| Compound | Structure | IUPAC |
|---|---|---|
| 111 | 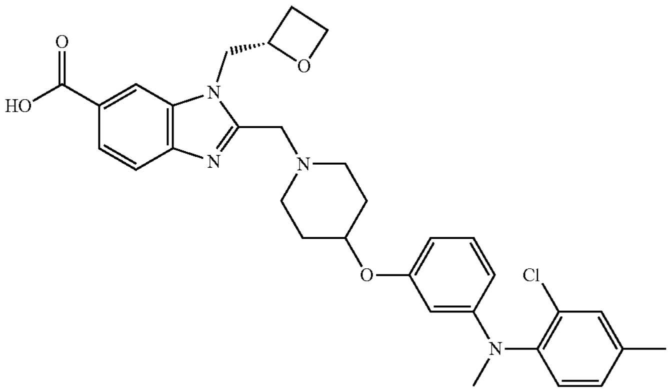 | 2-[(4-{3-[(2-chloro-4-methylphenyl)(methyl)amino]phenoxy}piperidin-1-yl)methyl]-1-{[(2S)-oxetan-2-yl]methyl}-1H-1,3-benzodiazole-6-carboxylic acid |
| 112 | 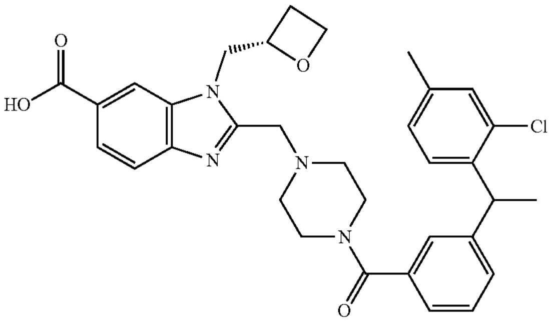 [SMILES: Cc1ccc(C(C)c2cccc(C(=O)N3CCN(Cc4nc5ccc(C(=O)O)cc5n4C[C@@H]4CCO4)CC3)c2)c(Cl)c1] | 2-[(4-{3-[1-(2-chloro-4-methylphenyl)ethyl]benzoyl}piperazin-1-yl)methyl]-1-{[(2S)-oxetan-2-yl]methyl}-1H-1,3-benzodiazole-6-carboxylic acid |
| 113 | 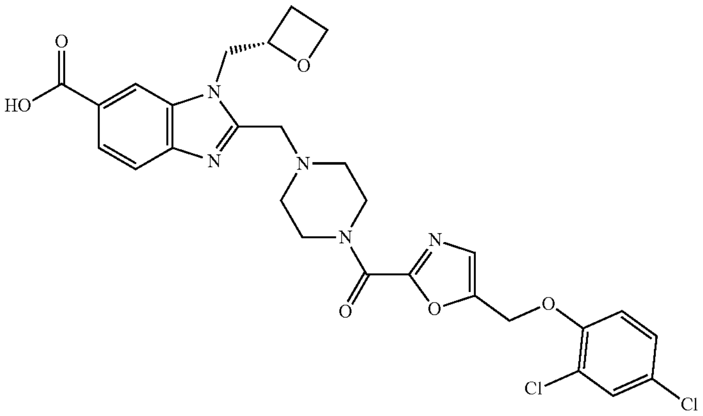 [SMILES: O=C(O)c1ccc2nc(CN3CCN(C(=O)c4ncc(COc5ccc(Cl)cc5Cl)o4)CC3)n(C[C@@H]3CCO3)c2c1] | 2-[(4-{5-[(2,4-dichlorophenoxy)methyl]-1,3-oxazole-2-carbonyl}piperazin-1-yl)methyl]-1-{[(2S)-oxetan-2-yl]methyl}-1H-1,3-benzodiazole-6-carboxylic acid |

-continued
| Compound | Structure | IUPAC |
| --- | --- | --- |
| 114 | 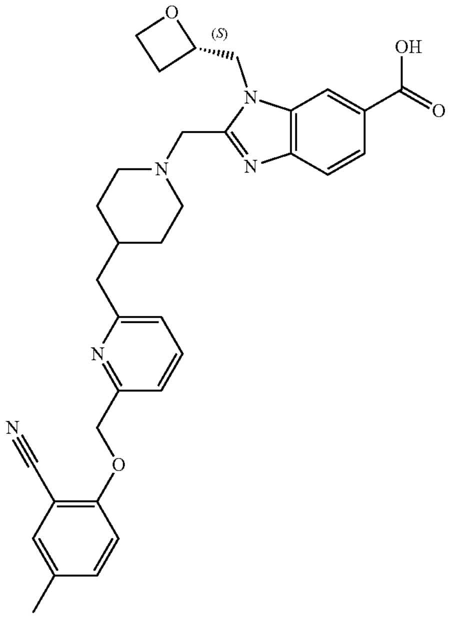 | 2-{[4-({6-[(2-cyano-4-methylphenoxy)methyl] pyridin-2-yl}methyl) piperidin-1-yl]methyl}-1-{[(2S)-oxetan-2-yl] methyl}-1H-1,3-benzodiazole-6-carboxylic acid |
| 115 | 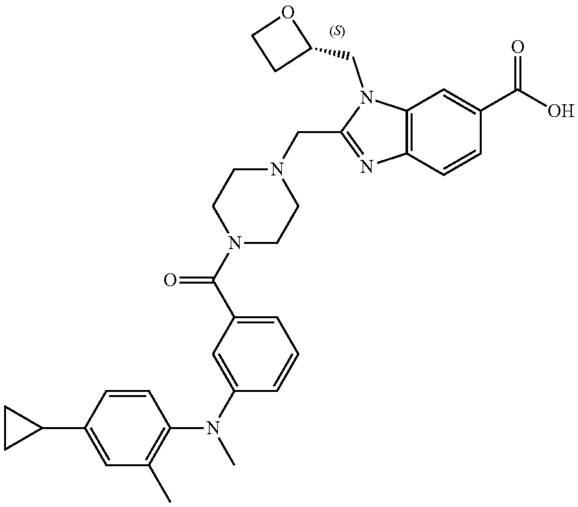 | 2-[(4-{3-[(4-cyclopropyl-2-methylphenyl)(methyl) amino]benzoyl} piperazin-1-yl)methyl]-1-{[(2S)-oxetan-2-yl]methyl}-1H-1,3-benzodiazole-6-carboxylic acid |

-continued
| Compound | Structure | IUPAC |
| --- | --- | --- |
| 116 | 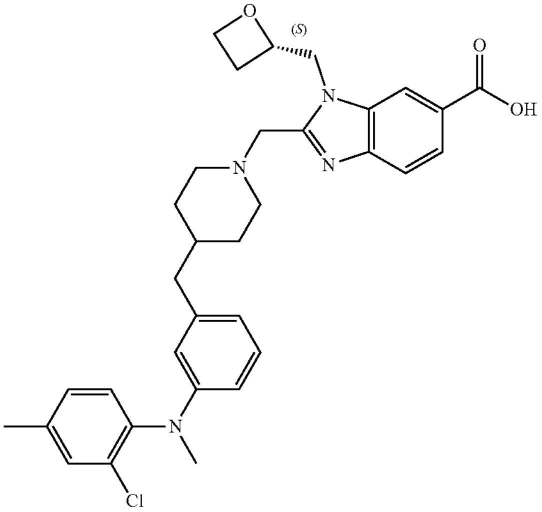 | 2-{[4-({3-[(2-chloro-4-methylphenyl)(methyl)amino]phenyl}methyl)piperidin-1-yl]methyl}-1-{[(2S)-oxetan-2-yl]methyl}-1H-1,3-benzodiazole-6-carboxylic acid |
| 117 | 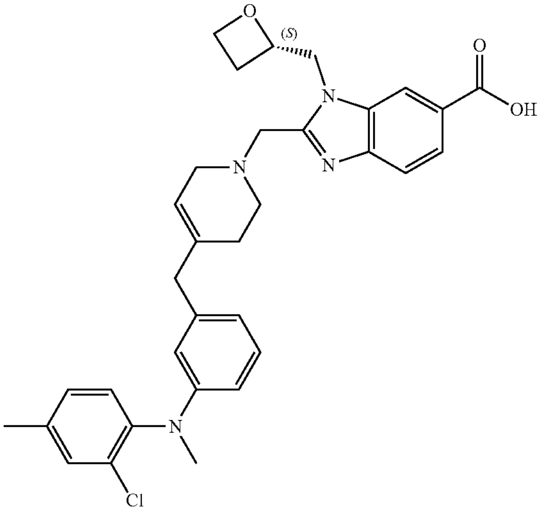 | 2-{[4-({3-[(2-chloro-4-methylphenyl)(methyl)amino]phenyl}methyl)-1,2,3,6-tetrahydropyridin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 118 | 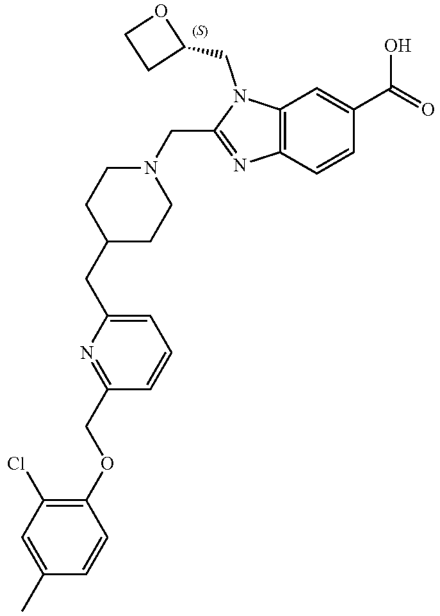 | 2-{[4-({6-[(2-chloro-4-methylphenoxy)methyl]pyridin-2-yl}methyl)piperidin-1-yl]methyl}-1-{[(2S)-oxetan-2-yl]methyl}-1H-1,3-benzodiazole-6-carboxylic acid |
| 120 | 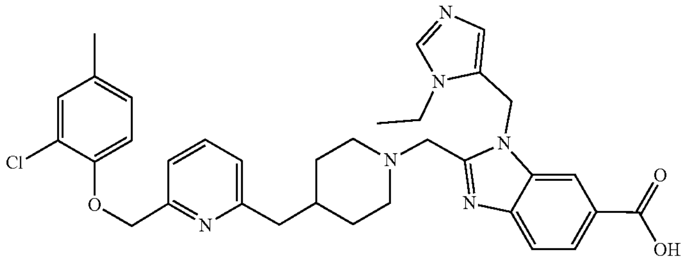 [SMILES: CCn1cncc1Cn1c(CN2CCC(Cc3cccc(COc4ccc(C)cc4Cl)n3)CC2)nc2ccc(C(=O)O)cc21] | 2-{[4-({6-[(2-chloro-4-methylphenoxy)methyl]pyridin-2-yl}methyl)piperidin-1-yl]methyl}-1-[(1-ethyl-1H-imidazol-5-yl)methyl]-1H-1,3-benzodiazole-6-carboxylic acid |
| 121 | 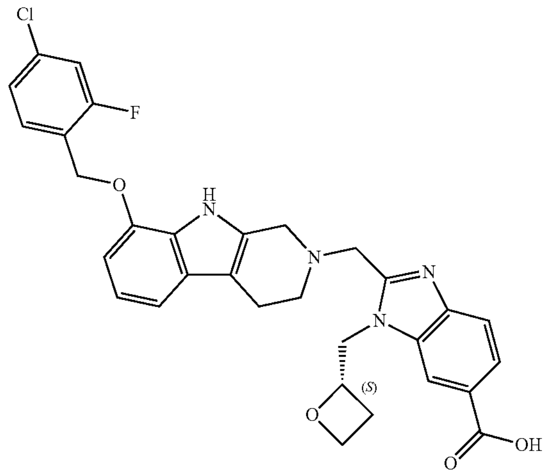 | 2-({8-[(4-chloro-2-fluorophenyl)methoxy]-1H,2H,3H,4H,9H-pyrido[3,4-b]indol-2-yl}methyl)-1-{[(2S)-oxetan-2-yl]methyl}-1H-1,3-benzodiazole-6-carboxylic acid |

-continued

| Compound | Structure | IUPAC |
|---|---|---|
| 122 | 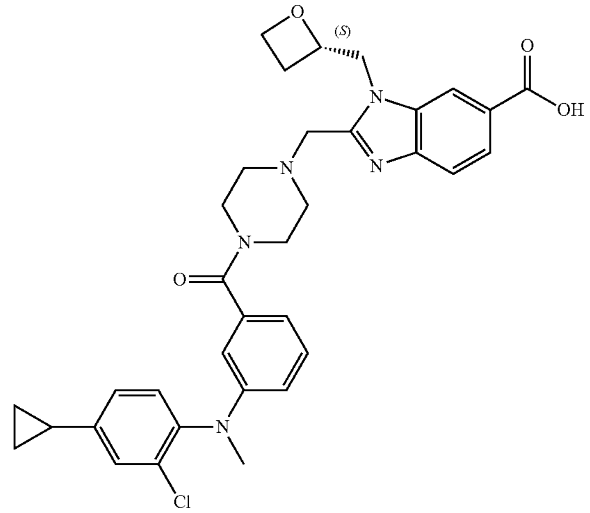 | 2-[(4-{3-[(2-chloro-4-cyclopropylphenyl)(methyl)amino]benzoyl}piperazin-1-yl)methyl]-1-{[(2S)-oxetan-2-yl]methyl}-1H-1,3-benzodiazole-6-carboxylic acid |
| 123 | 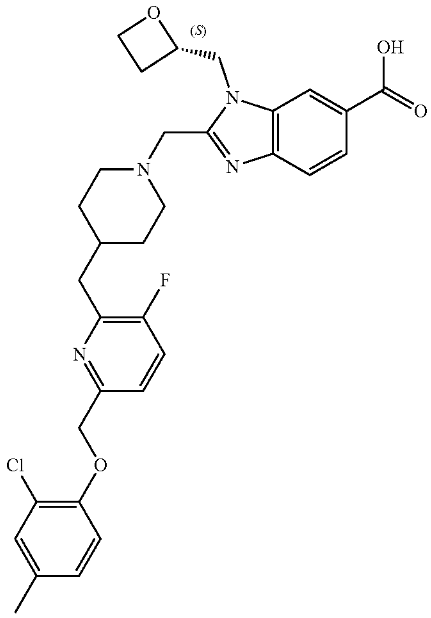 | 2-{[4-({6-[(2-chloro-4-methylphenoxy)methyl]-3-fluoropyridin-2-yl}methyl)piperidin-1-yl]methyl}-1-{[(2S)-oxetan-2-yl]methyl}-1H-1,3-benzodiazole-6-carboxylic acid |
| 124 | 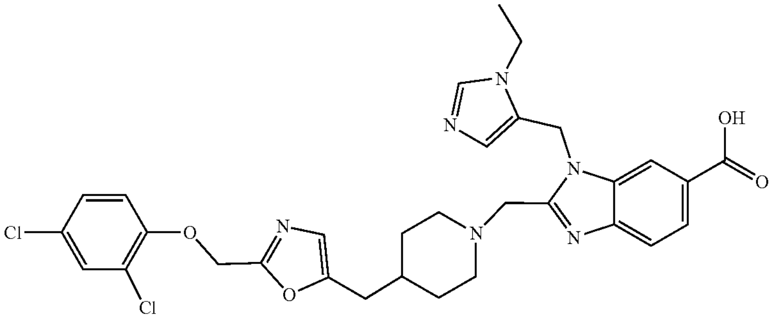 [SMILES: CCn1cncc1Cn1c(CN2CCC(Cc3cnc(COc4ccc(Cl)cc4Cl)o3)CC2)nc2ccc(C(=O)O)cc21] | 2-{[4-({2-[(2,4-dichlorophenoxy)methyl]-1,3-oxazol-5-yl}methyl)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 125 | 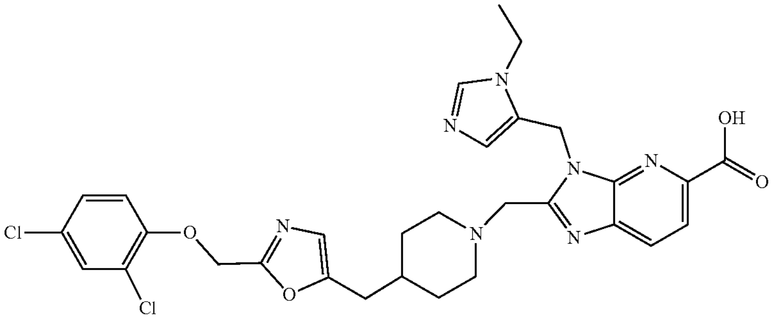 [SMILES: CCn1cncc1Cn1c(CN2CCC(Cc3cnc(COc4ccc(Cl)cc4Cl)o3)CC2)nc2ccc(C(=O)O)nc21] | 2-{[4-({2-[(2,4-dichlorophenoxy)methyl]-1,3-oxazol-5-yl}methyl)piperidin-1-yl]methyl}-3-[(1-ethyl-1H-imidazol-5-yl)methyl]-3H-imidazo[4,5-b]pyridine-5-carboxylic acid |
| 126 | 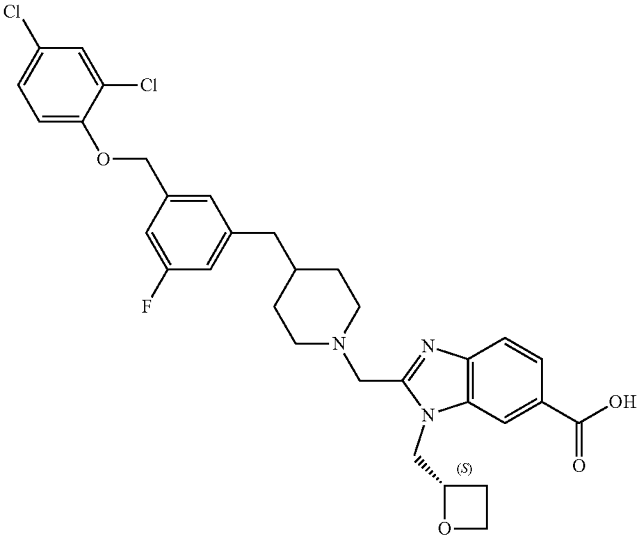 | 2-{[4-({3-[(2,4-dichlorophenoxy)methyl]-5-fluorophenyl}methyl)piperidin-1-yl]methyl}-1-{[(2S)-oxetan-2-yl]methyl}-1H-1,3-benzodiazole-6-carboxylic acid |
| 128 | 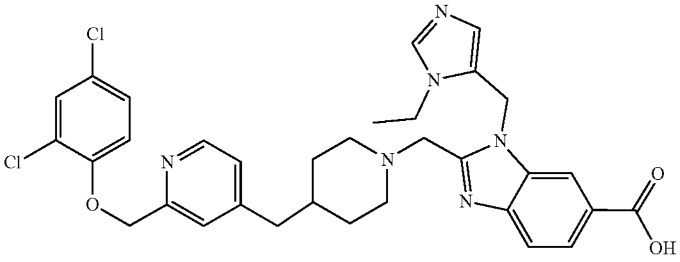 [SMILES: CCn1cncc1Cn1c(CN2CCC(Cc3ccnc(COc4ccc(Cl)cc4Cl)c3)CC2)nc2ccc(C(=O)O)cc21] | 2-{[4-({2-[(2,4-dichlorophenoxy)methyl]pyridin-4-yl}methyl)piperidin-1-yl]methyl}-1-[(1-ethyl-1H-imidazol-5-yl)methyl]-1H-1,3-benzodiazole-6-carboxylic acid |
| 129 | 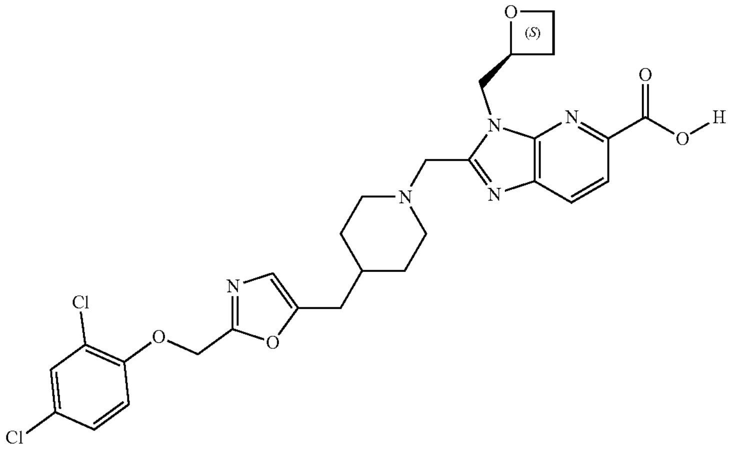 | 2-{[4-({2-[(2,4-dichlorophenoxy)methyl]-1,3-oxazol-5-yl}methyl)piperidin-1-yl]methyl}-3-{[(2S)-oxetan-2-yl]methyl}-3H-imidazo[4,5-b]pyridine-5-carboxylic acid |

-continued

| Compound | Structure | IUPAC |
|---|---|---|
| 130 | 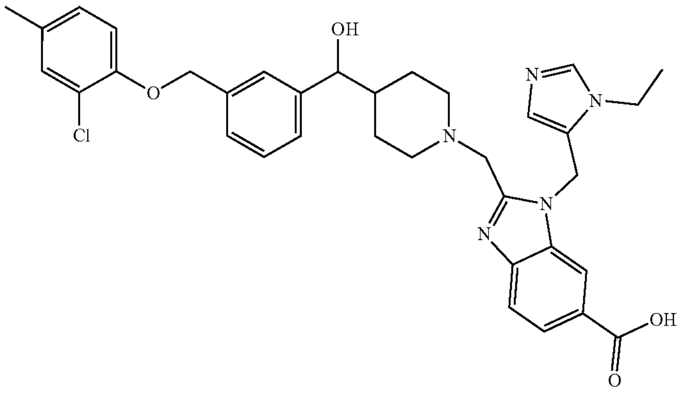 [SMILES: CCn1cncc1Cn1c(CN2CCC(C(O)c3cccc(COc4ccc(C)cc4Cl)c3)CC2)nc2ccc(C(=O)O)cc21] | 2-{[4-({3-[(2-chloro-4-methylphenoxy)methyl]phenyl}(hydroxy)methyl)piperidin-1-yl]methyl}-1-[(1-ethyl-1H-imidazol-5-yl)methyl]-1H-1,3-benzodiazole-6-carboxylic acid |
| 131 | 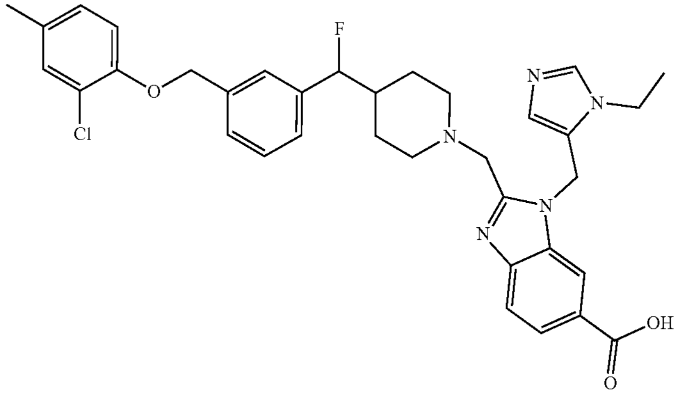 [SMILES: CCn1cncc1Cn1c(CN2CCC(C(F)c3cccc(COc4ccc(C)cc4Cl)c3)CC2)nc2ccc(C(=O)O)cc21] | 2-{[4-({3-[(2-chloro-4-methylphenoxy)methyl]phenyl}(fluoro)methyl)piperidin-1-yl]methyl}-1-[(1-ethyl-1H-imidazol-5-yl)methyl]-1H-1,3-benzodiazole-6-carboxylic acid |
| 132 | 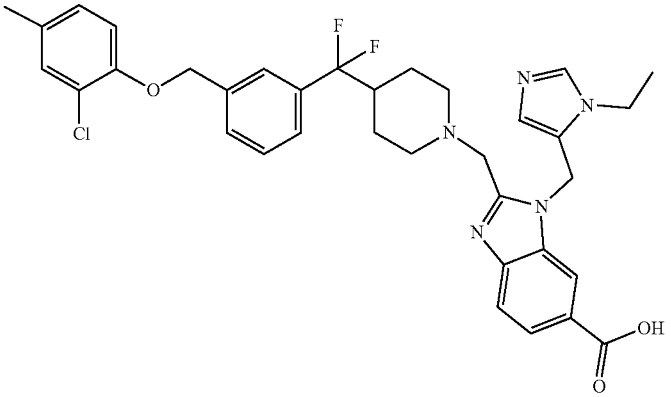 [SMILES: CCn1cncc1Cn1c(CN2CCC(C(F)(F)c3cccc(COc4ccc(C)cc4Cl)c3)CC2)nc2ccc(C(=O)O)cc21] | 2-{[4-({3-[(2-chloro-4-methylphenoxy)methyl]phenyl}difluoromethyl)piperidin-1-yl]methyl}-1-[(1-ethyl-1H-imidazol-5-yl)methyl]-1H-1,3-benzodiazole-6-carboxylic acid |
| 133 | 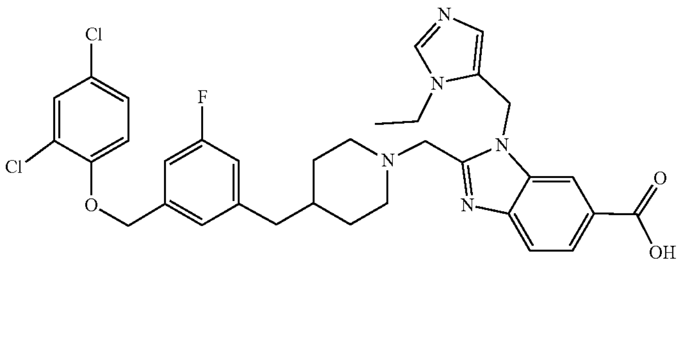 [SMILES: CCn1cncc1Cn1c(CN2CCC(Cc3cc(F)cc(COc4ccc(Cl)cc4Cl)c3)CC2)nc2ccc(C(=O)O)cc21] | 2-{[4-({3-[(2,4-dichlorophenoxy)methyl]-5-fluorophenyl}methyl)piperidin-1-yl]methyl}-1-[(1-ethyl-1H-imidazol-5-yl)methyl]-1H-1,3-benzodiazole-6-carboxylic acid |

-continued

| Com-pound | Structure | IUPAC |
|---|---|---|
| 135 | 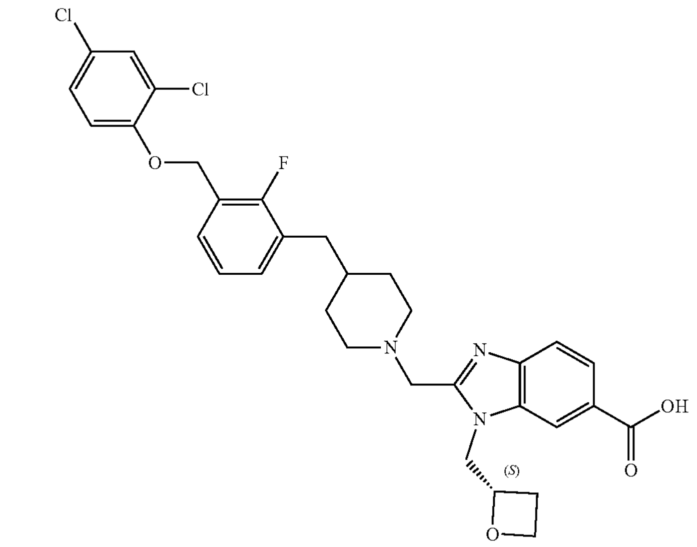 | 2-{[4-({3-[(2,4-dichlorophenoxy)methyl]-2-fluorophenyl}methyl) piperidin-1-yl]methyl}-1-{[(2S)-oxetan-2-yl]methyl}-1H-1,3-benzodiazole-6-carboxylic acid |
| 136 | 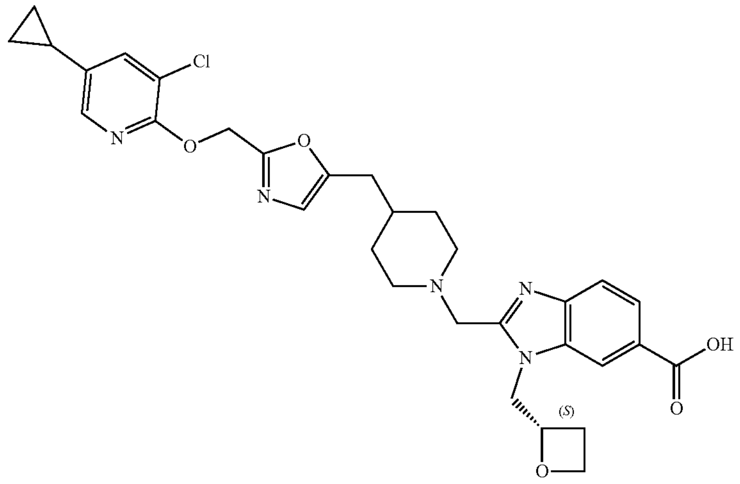 | 2-({4-[(2-{[(3-chloro-5-cyclopropylpyridin-2-yl)oxy]methyl}-1,3-oxazol-5-yl)methyl] piperidin-1-yl}methyl)-1-{[(2S)-oxetan-2-yl]methyl}-1H-1,3-benzodiazole-6-carboxylic acid |
| 137 | 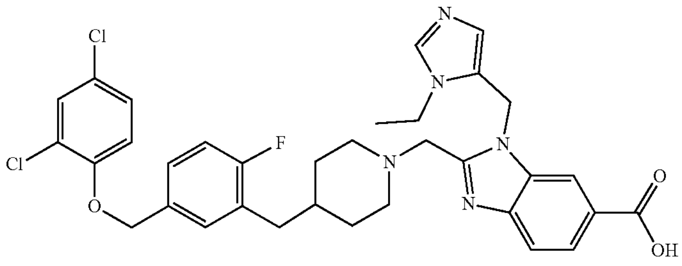 [SMILES: CCn1cncc1Cn1c(CN2CCC(Cc3cc(COc4ccc(Cl)cc4Cl)ccc3F)CC2)nc2ccc(C(=O)O)cc21] | 2-{[4-({5-[(2,4-dichlorophenoxy)methyl]-2-fluorophenyl}methyl) piperidin-1-yl]methyl}-1-[(1-ethyl-1H-imidazol-5-yl)methyl]-1H-1,3-benzodiazole-6-carboxylic acid |

-continued

| Compound | Structure | IUPAC |
| --- | --- | --- |
| 138 | 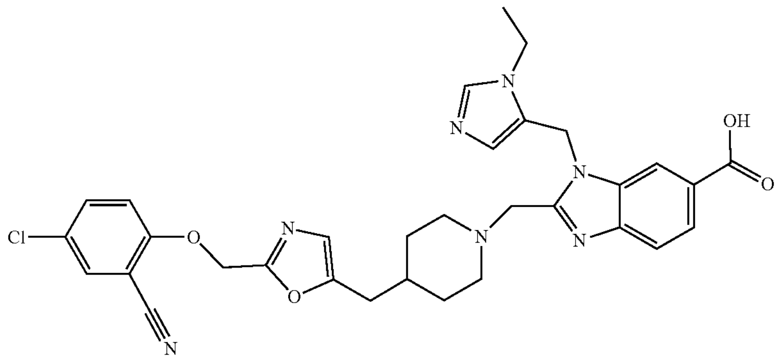 [SMILES: CCn1cncc1Cn1c(CN2CCC(Cc3cnc(COc4ccc(Cl)cc4C#N)o3)CC2)nc2ccc(C(=O)O)cc21] | 2-{[4-({2-[(4-chloro-2-cyanophenoxy)methyl]-1,3-oxazol-5-yl}methyl)piperidin-1-yl]methyl}-1-[(1-ethyl-1H-imidazol-5-yl)methyl]-1H-1,3-benzodiazole-6-carboxylic acid |
| 139 | 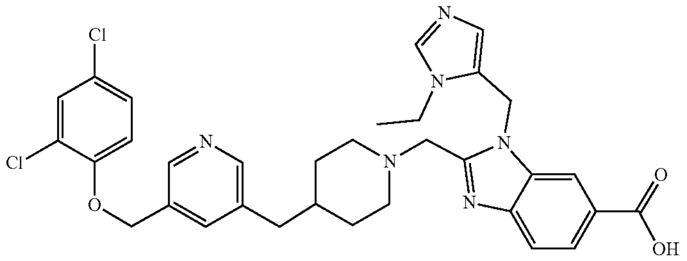 [SMILES: CCn1cncc1Cn1c(CN2CCC(Cc3cncc(COc4ccc(Cl)cc4Cl)c3)CC2)nc2ccc(C(=O)O)cc21] | 2-{[4-({5-[(2,4-dichlorophenoxy)methyl]pyridin-3-yl}methyl)piperidin-1-yl]methyl}-1-[(1-ethyl-1H-imidazol-5-yl)methyl]-1H-1,3-benzodiazole-6-carboxylic acid |
| 140 | 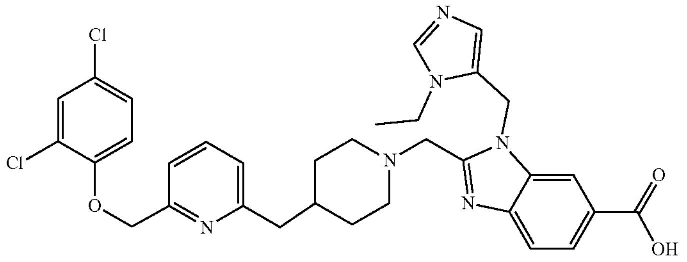 [SMILES: CCn1cncc1Cn1c(CN2CCC(Cc3cccc(COc4ccc(Cl)cc4Cl)n3)CC2)nc2ccc(C(=O)O)cc21] | 2-{[4-({6-[(2,4-dichlorophenoxy)methyl]pyridin-2-yl}methyl)piperidin-1-yl]methyl}-1-[(1-ethyl-1H-imidazol-5-yl)methyl]-1H-1,3-benzodiazole-6-carboxylic acid |
| 141 | 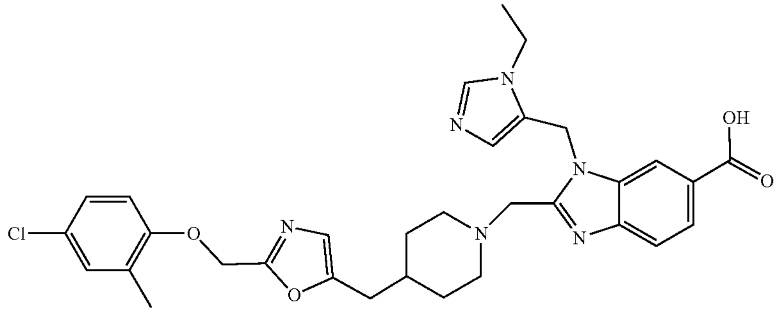 [SMILES: CCn1cncc1Cn1c(CN2CCC(Cc3cnc(COc4ccc(Cl)cc4C)o3)CC2)nc2ccc(C(=O)O)cc21] | 2-{[4-({2-[(4-chloro-2-methylphenoxy)methyl]-1,3-oxazol-5-yl}methyl)piperidin-1-yl]methyl}-1-[(1-ethyl-1H-imidazol-5-yl)methyl]-1H-1,3-benzodiazole-6-carboxylic acid |
| 142 | 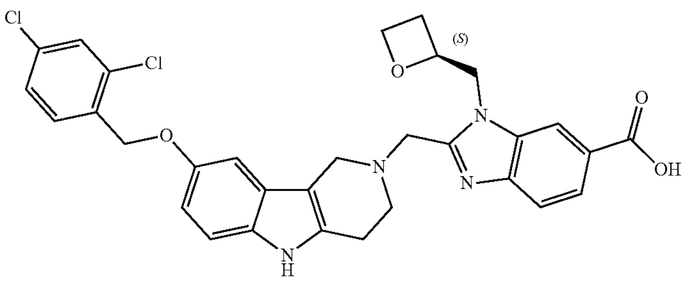 | 2-({8-[(2,4-dichlorophenyl)methoxy]-1H,2H,3H,4H,5H-pyrido[4,3-b]indol-2-yl}methyl)-1-{[(2S)-oxetan-2-yl]methyl}-1H-1,3-benzodiazole-6-carboxylic acid |

-continued

| Compound | Structure | IUPAC |
| --- | --- | --- |
| 143 | 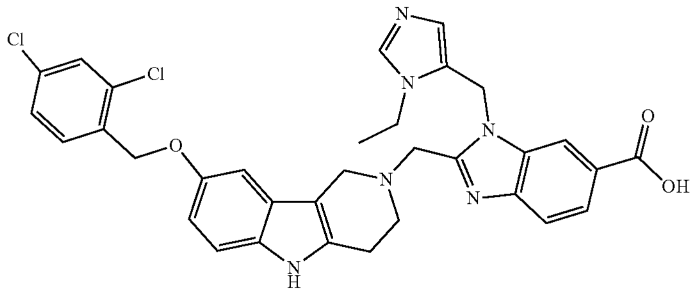 [SMILES: CCn1cncc1Cn1c(CN2CCc3[nH]c4ccc(OCc5ccc(Cl)cc5Cl)cc4c3C2)nc2ccc(C(=O)O)cc21] | 2-({8-[(2,4-dichlorophenyl)methoxy]-1H,2H,3H,4H,5H-pyrido[4,3-b]indol-2-yl}methyl)-1-[(1-ethyl-1H-imidazol-5-yl)methyl]-1H-1,3-benzodiazole-6-carboxylic acid |
| 144 | 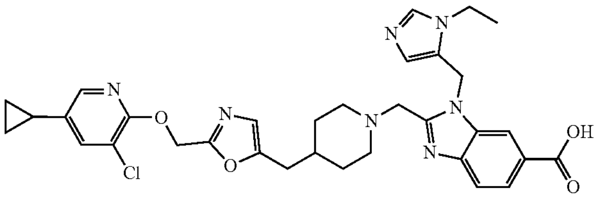 [SMILES: CCn1cncc1Cn1c(CN2CCC(Cc3cnc(COc4ncc(C5CC5)cc4Cl)o3)CC2)nc2ccc(C(=O)O)cc21] | 2-({4-[(2-{[(3-chloro-5-cyclopropylpyridin-2-yl)oxy]methyl}-1,3-oxazol-5-yl)methyl]piperidin-1-yl}methyl)-1-[(1-ethyl-1H-imidazol-5-yl)methyl]-1H-1,3-benzodiazole-6-carboxylic acid |
| 145 | 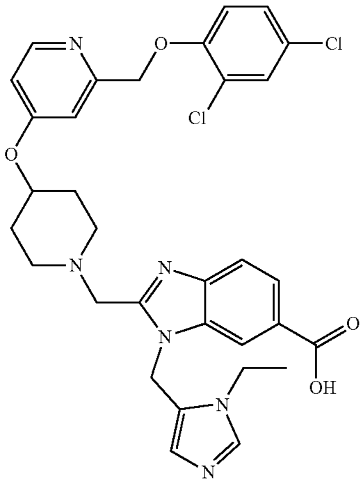 | 2-{[4-({2-[(2,4-dichlorophenoxy)methyl]pyridin-4-yl}oxy)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 146 | 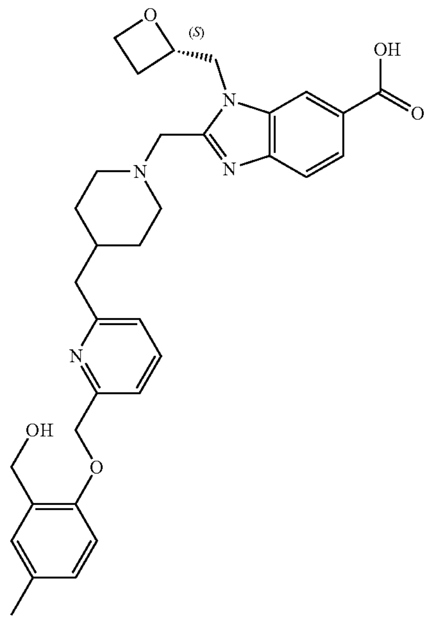 | 2-({4-[(6-{[2-(hydroxymethyl)-4-methylphenoxy]methyl}pyridin-2-yl)methyl]piperidin-1-yl}methyl)-1-{[(2S)-oxetan-2-yl]methyl}-1H-1,3-benzodiazole-6-carboxylic acid |
| 148 | 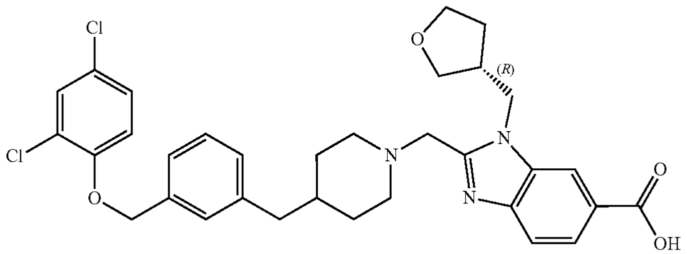 | 2-{[4-({3-[(2,4-dichlorophenoxy)methyl]phenyl}methyl)piperidin-1-yl]methyl}-1-{[(3R)-oxolan-3-yl]methyl}-1H-1,3-benzodiazole-6-carboxylic acid |
| 149 | 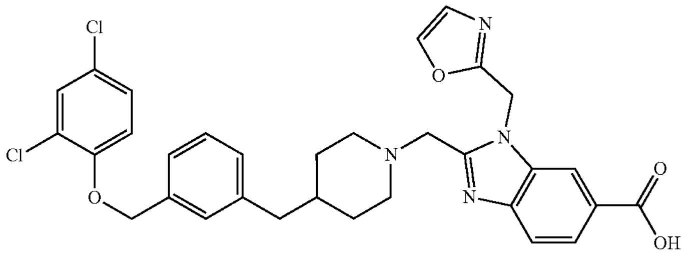 [SMILES: O=C(O)c1ccc2nc(CN3CCC(Cc4cccc(COc5ccc(Cl)cc5Cl)c4)CC3)n(Cc3ncco3)c2c1] | 2-{[4-({3-[(2,4-dichlorophenoxy)methyl]phenyl}methyl)piperidin-1-yl]methyl}-1-[(1,3-oxazol-2-yl)methyl]-1H-1,3-benzodiazole-6-carboxylic acid |
| 150 | 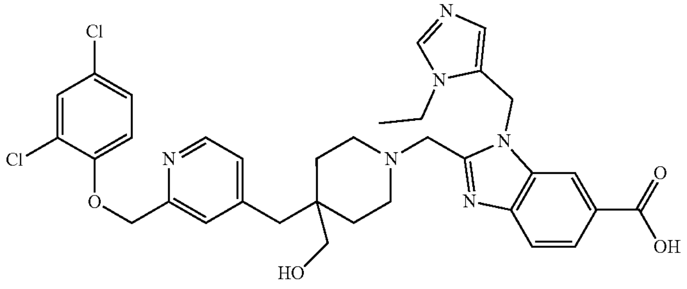 [SMILES: CCn1cncc1Cn1c(CN2CCC(CO)(Cc3ccnc(COc4ccc(Cl)cc4Cl)c3)CC2)nc2ccc(C(=O)O)cc21] | 2-{[4-({2-[(2,4-dichlorophenoxy)methyl]pyridin-4-yl}methyl)-4-(hydroxymethyl)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 151 | 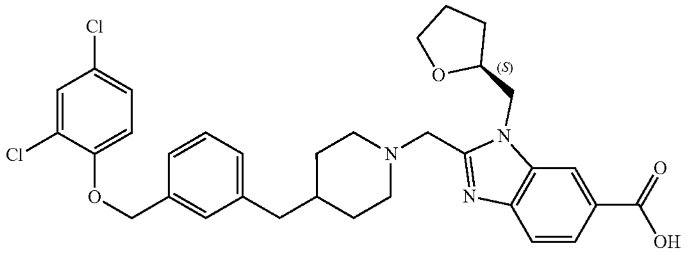 | 2-{[4-({3-[(2,4-dichlorophenoxy)methyl]phenyl}methyl)piperidin-1-yl]methyl}-1-{[(2S)-oxolan-2-yl]methyl}-1H-1,3-benzodiazole-6-carboxylic acid |
| 152 | 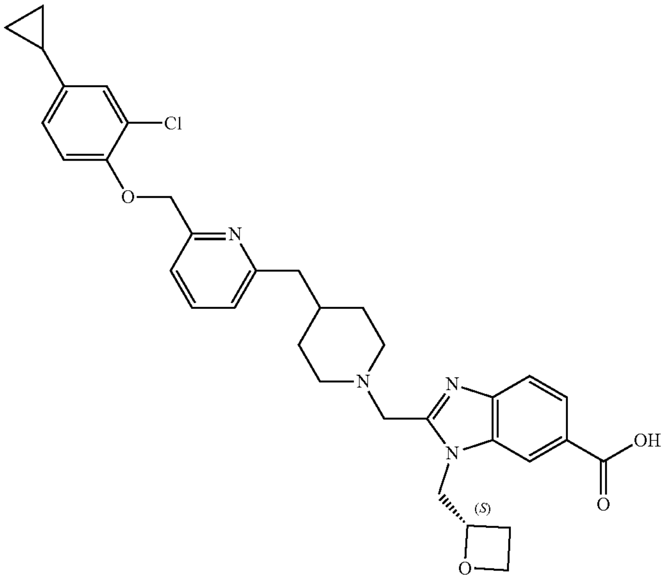 | 2-{[4-({6-[(2-chloro-4-cyclopropylphenoxy)methyl]pyridin-2-yl}methyl)piperidin-1-yl]methyl}-1-{[(2S)-oxetan-2-yl]methyl}-1H-1,3-benzodiazole-6-carboxylic acid |
| 153 | 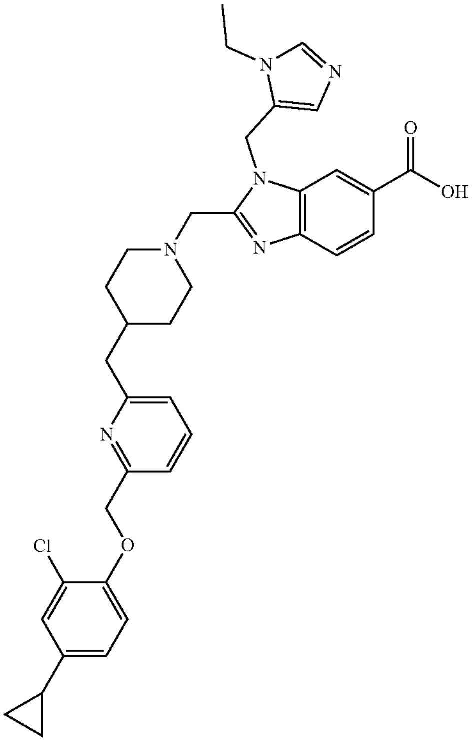 [SMILES: CCn1cncc1Cn1c(CN2CCC(Cc3cccc(COc4ccc(C5CC5)cc4Cl)n3)CC2)nc2ccc(C(=O)O)cc21] | 2-{[4-({6-[(2-chloro-4-cyclopropylphenoxy)methyl]pyridin-2-yl}methyl)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 154 | 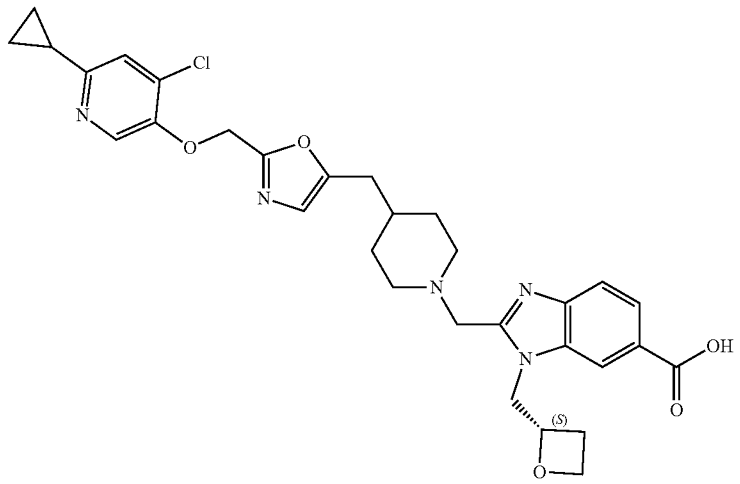 | 2-({4-[(2-{[(4-chloro-6-cyclopropylpyridin-3-yl)oxy]methyl}-1,3-oxazol-5-yl)methyl]piperidin-1-yl}methyl)-1-{[(2S)-oxetan-2-yl]methyl}-1H-1,3-benzodiazole-6-carboxylic acid |
| 155 | 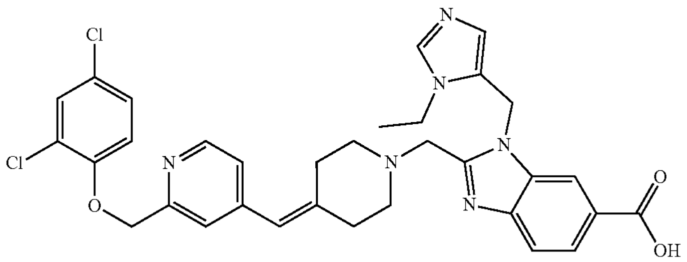 [SMILES: CCn1cncc1Cn1c(CN2CCC(=Cc3ccnc(COc4ccc(Cl)cc4Cl)c3)CC2)nc2ccc(C(=O)O)cc21] | 2-{[4-({2-[(2,4-dichlorophenoxy)methyl]pyridin-4-yl}methylidene)piperidin-1-yl]methyl}-1-[(1-ethyl-1H-imidazol-5-yl)methyl]-1H-1,3-benzodiazole-6-carboxylic acid |
| 156 | 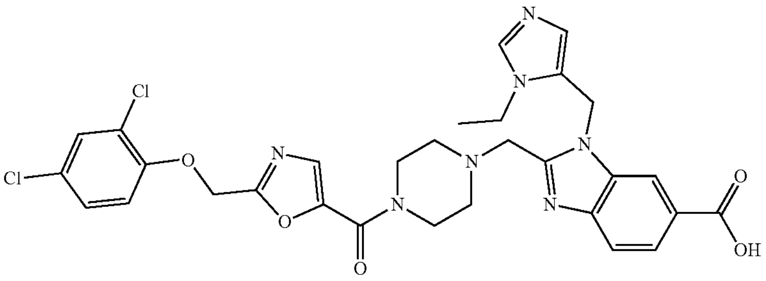 [SMILES: CCn1cncc1Cn1c(CN2CCN(C(=O)c3cnc(COc4ccc(Cl)cc4Cl)o3)CC2)nc2ccc(C(=O)O)cc21] | 2-[(4-{2-[(2,4-dichlorophenoxy)methyl]-1,3-oxazole-5-carbonyl}piperazin-1-yl)methyl]-1-[(1-ethyl-1H-imidazol-5-yl)methyl]-1H-1,3-benzodiazole-6-carboxylic acid |
| 157 | 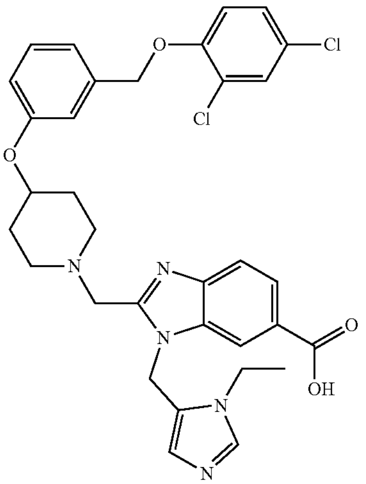 [SMILES: CCn1cncc1Cn1c(CN2CCC(Oc3cccc(COc4ccc(Cl)cc4Cl)c3)CC2)nc2ccc(C(=O)O)cc21] | 2-[(4-{3-[(2,4-dichlorophenoxy)methyl]phenoxy}piperidin-1-yl)methyl]-1-[(1-ethyl-1H-imidazol-5-yl)methyl]-1H-1,3-benzodiazole-6-carboxylic acid |

-continued

| Compound | Structure | IUPAC |
|---|---|---|
| 158 | 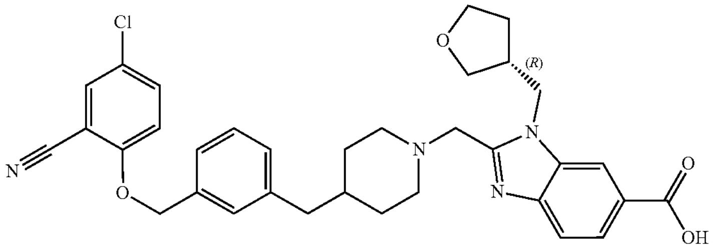 | 2-{[4-({3-[(4-chloro-2-cyanophenoxy)methyl]phenyl}methyl)piperidin-1-yl]methyl}-1-{[(3R)-oxolan-3-yl]methyl}-1H-1,3-benzodiazole-6-carboxylic acid |
| 159 | 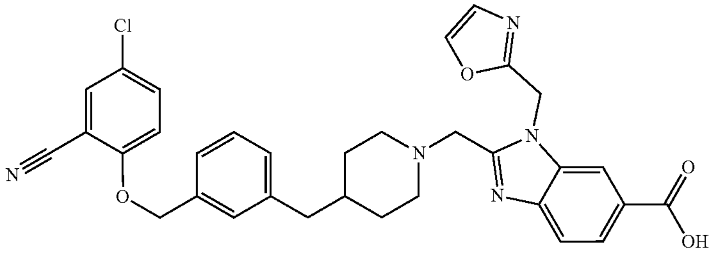 [SMILES: N#Cc1cc(Cl)ccc1OCc1cccc(CC2CCN(Cc3nc4ccc(C(=O)O)cc4n3Cc3ncco3)CC2)c1] | 2-{[4-({3-[(4-chloro-2-cyanophenoxy)methyl]phenyl}methyl)piperidin-1-yl]methyl}-1-[(1,3-oxazol-2-yl)methyl]-1H-1,3-benzodiazole-6-carboxylic acid |
| 160 | 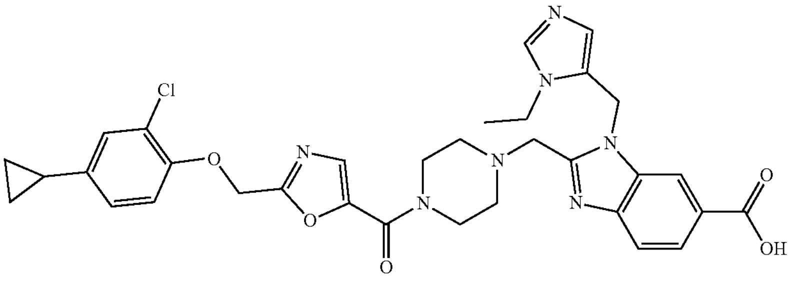 [SMILES: CCn1cncc1Cn1c(CN2CCN(C(=O)c3cnc(COc4ccc(C5CC5)cc4Cl)o3)CC2)nc2ccc(C(=O)O)cc21] | 2-[(4-{2-[(2-chloro-4-cyclopropylphenoxy)methyl]-1,3-oxazole-5-carbonyl}piperazin-1-yl)methyl]-1-[(1-ethyl-1H-imidazol-5-yl)methyl]-1H-1,3-benzodiazole-6-carboxylic acid |
| 161 | 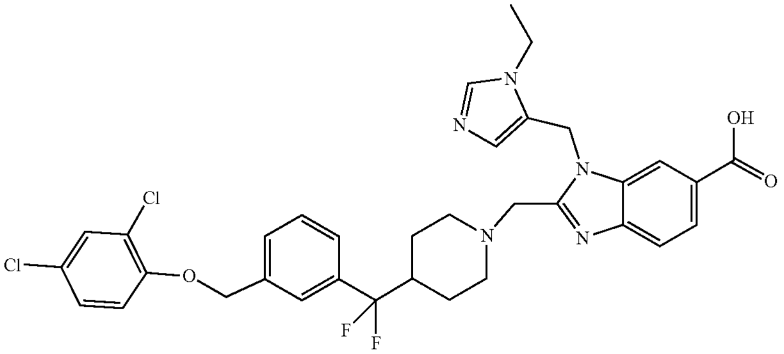 [SMILES: CCn1cncc1Cn1c(CN2CCC(C(F)(F)c3cccc(COc4ccc(Cl)cc4Cl)c3)CC2)nc2ccc(C(=O)O)cc21] | 2-{[4-({3-[(2,4-dichlorophenoxy)methyl]phenyl}difluoromethyl)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 162 | 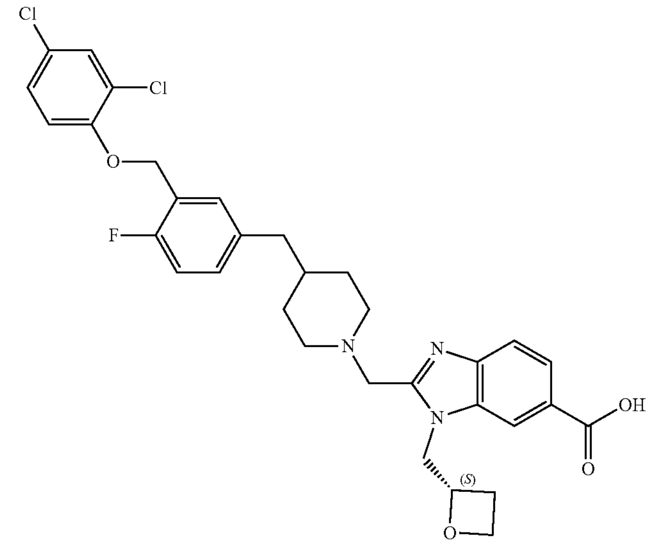 | 2-{[4-({3-[(2,4-dichlorophenoxy)methyl]-4-fluorophenyl}methyl) piperidin-1-yl]methyl}-1-{[(2S)-oxetan-2-yl]methyl}-1H-1,3-benzodiazole-6-carboxylic acid |
| 163 | 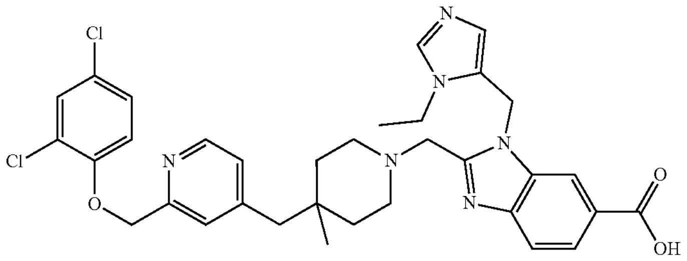 [SMILES: CCn1cncc1Cn1c(CN2CCC(C)(Cc3ccnc(COc4ccc(Cl)cc4Cl)c3)CC2)nc2ccc(C(=O)O)cc21] | 2-{[4-({2-[(2,4-dichlorophenoxy) methyl]pyridin-4-yl}methyl)-4-methylpiperidin-1-yl] methyl}-1-[(1-ethyl-1H-imidazol-5-yl)methyl]-1H-1,3-benzodiazole-6-carboxylic acid |
| 164 | 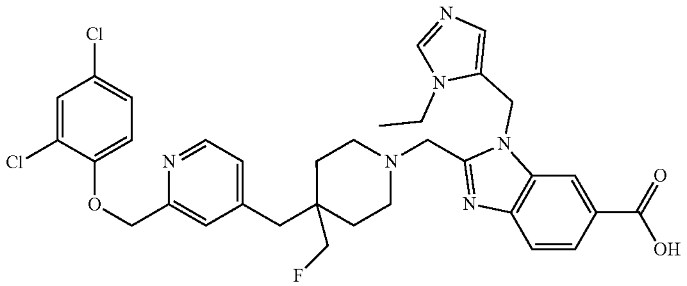 [SMILES: CCn1cncc1Cn1c(CN2CCC(CF)(Cc3ccnc(COc4ccc(Cl)cc4Cl)c3)CC2)nc2ccc(C(=O)O)cc21] | 2-{[4-({2-[(2,4-dichlorophenoxy) methyl]pyridin-4-yl}methyl)-4-(fluoromethyl)piperidin-1-yl]methyl}-1-[(1-ethyl-1H-imidazol-5-yl)methyl]-1H-1,3-benzodiazole-6-carboxylic acid |
| 165 | 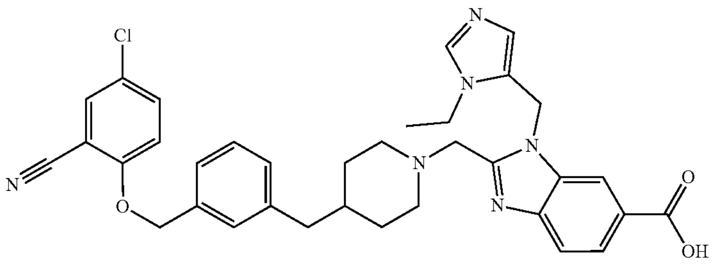 [SMILES: CCn1cncc1Cn1c(CN2CCC(Cc3cccc(COc4ccc(Cl)cc4C#N)c3)CC2)nc2ccc(C(=O)O)cc21] | 2-{[4-({3-[(4-chloro-2-cyanophenoxy)methyl] phenyl}methyl) piperidin-1-yl]methyl}-1-[(1-ethyl-1H-imidazol-5-yl)methyl]-1H-1,3-benzodiazole-6-carboxylic acid |

-continued

| Compound | Structure | IUPAC |
| --- | --- | --- |
| 166 | 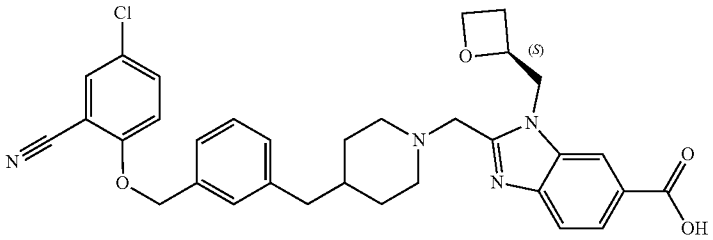 | 2-{[4-({3-[(4-chloro-2-cyanophenoxy)methyl] phenyl}methyl) piperidin-1-yl]methyl}-1-{[(2S)-oxetan-2-yl]methyl}-1H-1,3-benzodiazole-6-carboxylic acid |
| 168 | 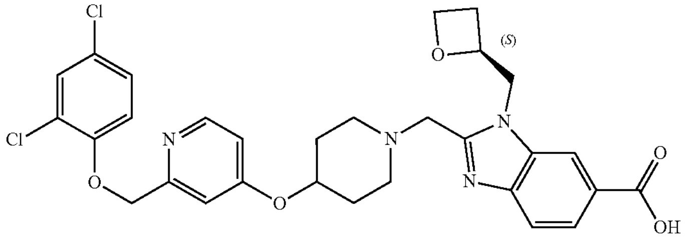 | 2-{[4-({2-[(2,4-dichlorophenoxy) methyl]pyridin-4-yl}oxy)piperidin-1-yl]methyl}-1-{[(2S)-oxetan-2-yl]methyl}-1H-1,3-benzodiazole-6-carboxylic acid |
| 169 | 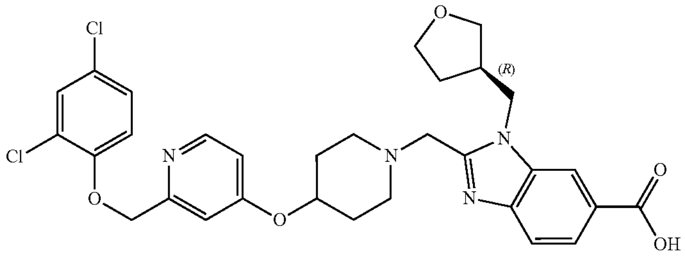 | 2-{[4-({2-[(2,4-dichlorophenoxy) methyl]pyridin-4-yl}oxy)piperidin-1-yl]methyl}-1-{[(3R)-oxolan-3-yl]methyl}-1H-1,3-benzodiazole-6-carboxylic acid |
| 170 | 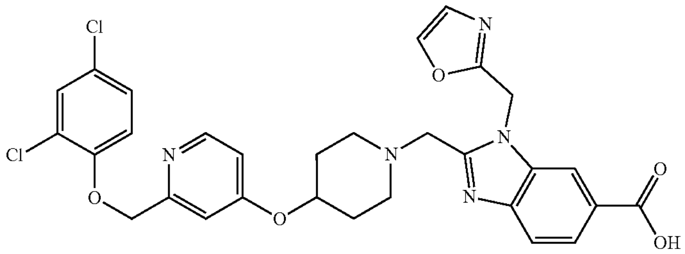 [SMILES: O=C(O)c1ccc2nc(CN3CCC(Oc4ccnc(COc5ccc(Cl)cc5Cl)c4)CC3)n(Cc3ncco3)c2c1] | 2-{[4-({2-[(2,4-dichlorophenoxy) methyl]pyridin-4-yl}oxy)piperidin-1-yl]methyl}-1-[(1,3-oxazol-2-yl)methyl]-1H-1,3-benzodiazole-6-carboxylic acid |
| 171 | 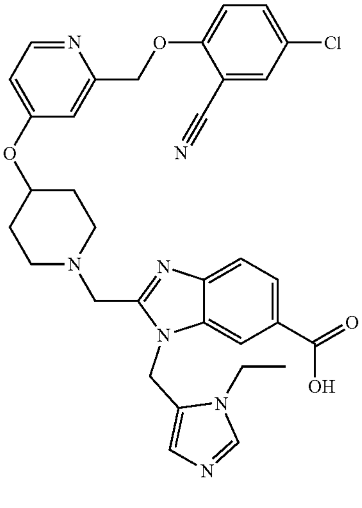 | 2-{[4-({2-[(4-chloro-2-cyanophenoxy)methyl] pyridin-4-yl}oxy)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
| --- | --- | --- |
| 174 | 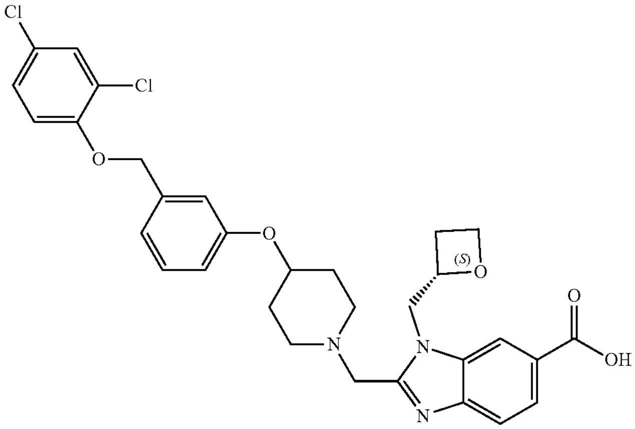 | 2-[(4-{3-[(2,4-dichlorophenoxy)methyl]phenoxy}piperidin-1-yl)methyl]-1-{[(2S)-oxetan-2-yl]methyl}-1H-1,3-benzodiazole-6-carboxylic acid |
| 178 | 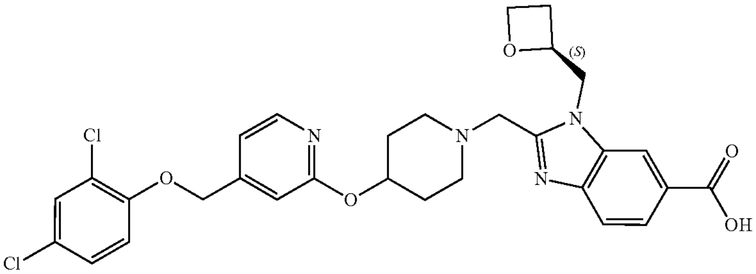 | 2-{[4-({4-[(2,4-dichlorophenoxy)methyl]pyridin-2-yl}oxy)piperidin-1-yl]methyl}-1-{[(2S)-oxetan-2-yl]methyl}-1H-1,3-benzodiazole-6-carboxylic acid |
| 179 | 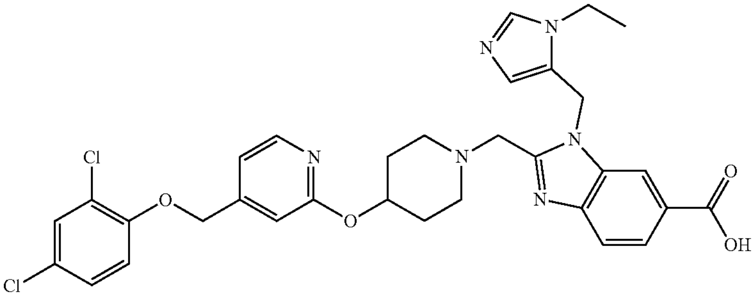 [SMILES: CCn1cncc1Cn1c(CN2CCC(Oc3cc(COc4ccc(Cl)cc4Cl)ccn3)CC2)nc2ccc(C(=O)O)cc21] | 2-{[4-({4-[(2,4-dichlorophenoxy)methyl]pyridin-2-yl}oxy)piperidin-1-yl]methyl}-1-[(1-ethyl-1H-imidazol-5-yl)methyl]-1H-1,3-benzodiazole-6-carboxylic acid |
| 182 | 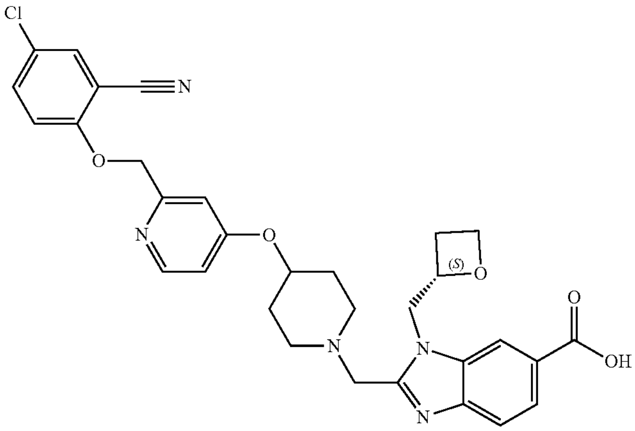 | 2-{[4-({2-[(4-chloro-2-cyanophenoxy)methyl]pyridin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 183 | 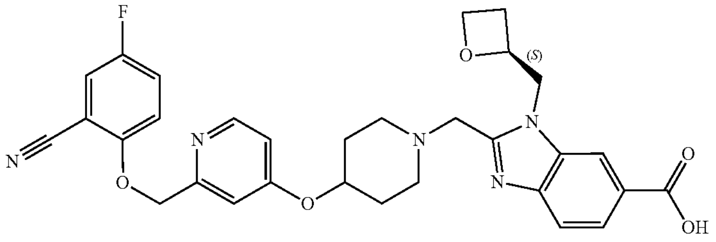 | 2-{[4-({2-[(2-cyano-4-fluorophenoxy)methyl] pyridin-4-yl}oxy)piperidin-1-yl]methyl}-1-{[(2S)-oxetan-2-yl]methyl}-1H-1,3-benzodiazole-6-carboxylic acid |
| 186 | 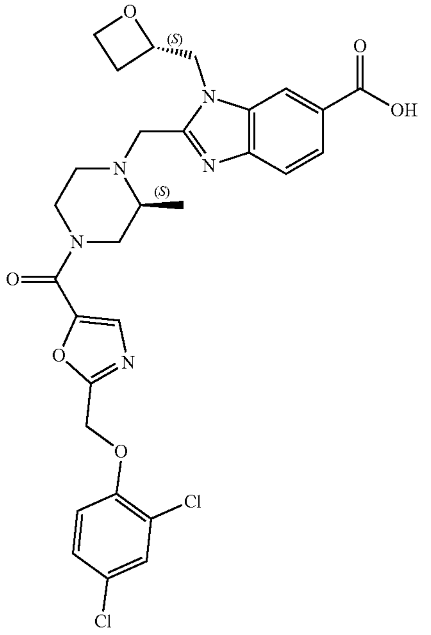 | 2-{[(2S)-4-{2-[(2,4-dichlorophenoxy) methyl]-1,3-oxazole-5-carbonyl}-2-methylpiperazin-1-yl]methyl}-1-{[(2S)-oxetan-2-yl]methyl}-1H-1,3-benzodiazole-6-carboxylic acid |
| 187 | 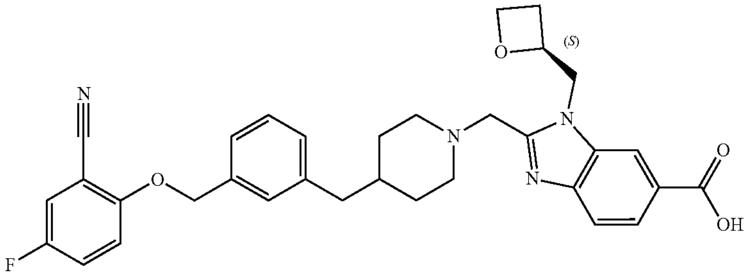 | 2-{[4-({3-[(2-cyano-4-fluorophenoxy)methyl] phenyl}methyl) piperidin-1-yl]methyl}-1-{[(2S)-oxetan-2-yl]methyl}-1H-1,3-benzodiazole-6-carboxylic acid |
| 188 | 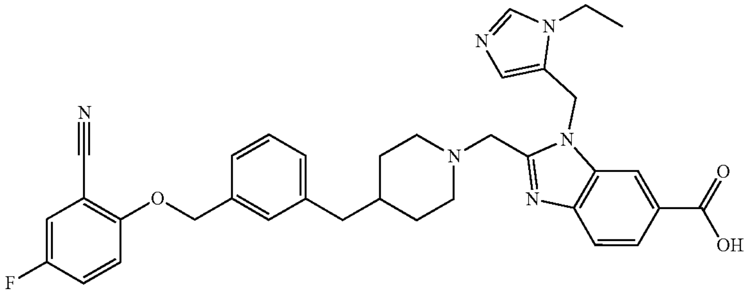 [SMILES: CCn1cncc1Cn1c(CN2CCC(Cc3cccc(COc4ccc(F)cc4C#N)c3)CC2)nc2ccc(C(=O)O)cc21] | 2-{[4-({3-[(2-cyano-4-fluorophenoxy)methyl] phenyl}methyl) piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 189 | 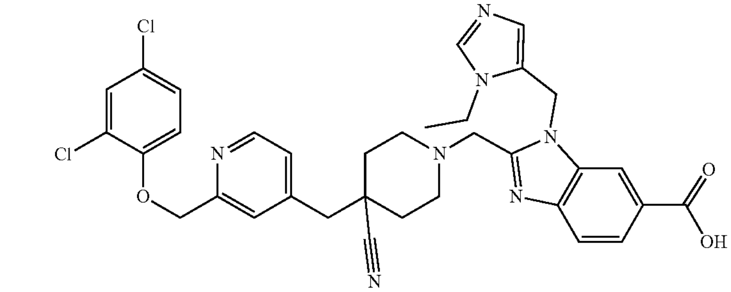 [SMILES: CCn1cncc1Cn1c(CN2CCC(C#N)(Cc3ccnc(COc4ccc(Cl)cc4Cl)c3)CC2)nc2ccc(C(=O)O)cc21] | 2-{[4-cyano-4-({2-[(2,4-dichlorophenoxy)methyl]pyridin-4-yl}methyl)piperidin-1-yl]methyl}-1-[(1-ethyl-1H-imidazol-5-yl)methyl]-1H-1,3-benzodiazole-6-carboxylic acid |
| 198 | 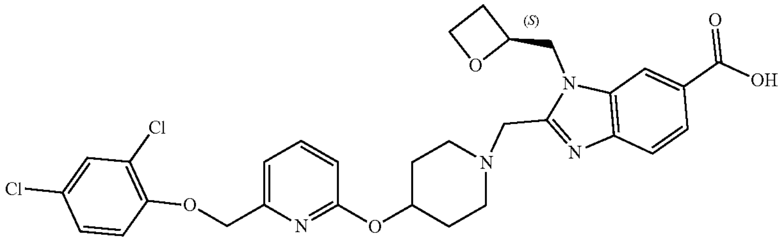 | (S)-2-((4-((6-((2,4-Dichlorophenoxy)methyl)pyridin-2-yl)oxy)piperidin-1-yl)methyl)-1-(oxetan-2-ylmethyl)-1H-benzo[d]imidazole-6-carboxylic acid |
| 199 | 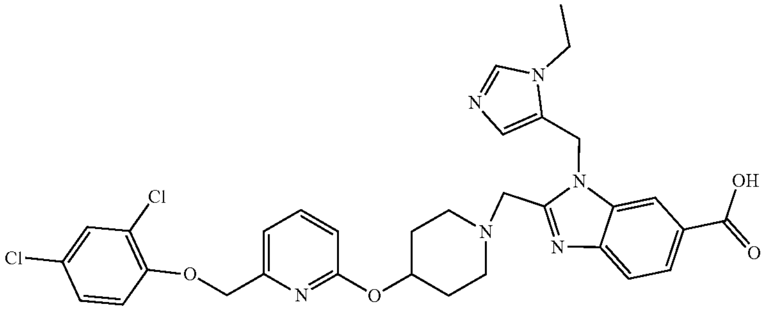 [SMILES: CCn1cncc1Cn1c(CN2CCC(Oc3cccc(COc4ccc(Cl)cc4Cl)n3)CC2)nc2ccc(C(=O)O)cc21] | 2-{[4-({6-[(2,4-dichlorophenoxy)methyl]pyridin-2-yl}oxy)piperidin-1-yl]methyl}-1-[(1-ethyl-1H-imidazol-5-yl)methyl]-1H-1,3-benzodiazole-6-carboxylic acid |
| 200 | 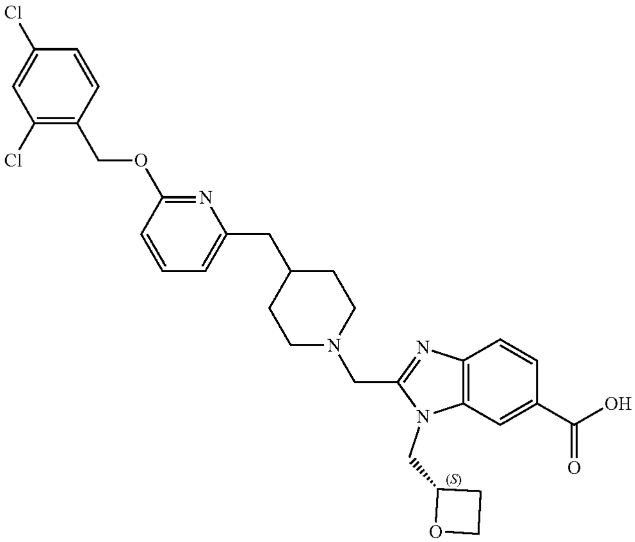 | 2-{[4-({6-[(2,4-dichlorophenyl)methoxy]pyridin-2-yl}methyl)piperidin-1-yl]methyl}-1-{[(2S)-oxetan-2-yl]methyl}-1H-1,3-benzodiazole-6-carboxylic acid |

-continued
| Compound | Structure | IUPAC |
| --- | --- | --- |
| 202 | 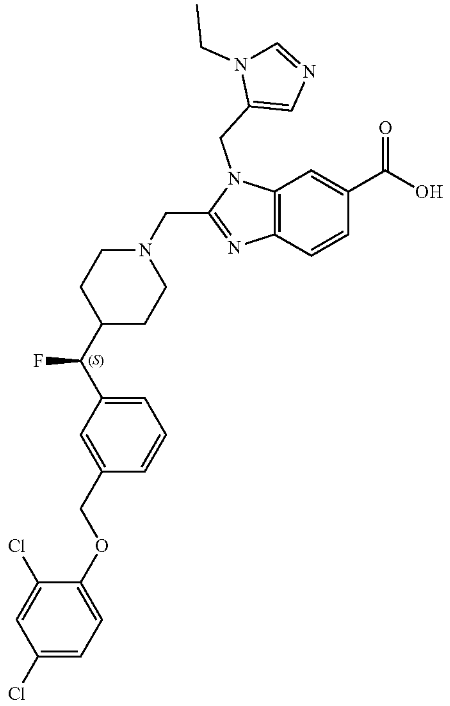 | 2-({4-[(S)-{3-[(2,4-dichlorophenoxy)methyl]phenyl}(fluoro)methyl]piperidin-1-yl}methyl)-1-[(1-ethyl-1H-imidazol-5-yl)methyl]-1H-1,3-benzodiazole-6-carboxylic acid |
| 203 | 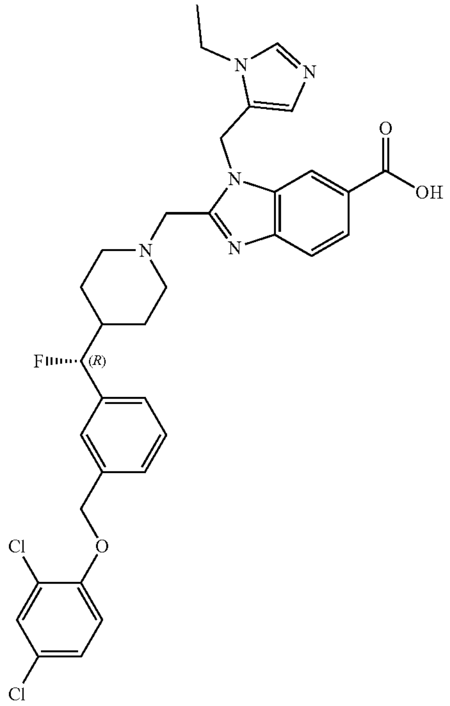 | 2-({4-[(R)-{3-[(2,4-dichlorophenoxy)methyl]phenyl}(fluoro)methyl]piperidin-1-yl}methyl)-1-[(1-ethyl-1H-imidazol-5-yl)methyl]-1H-1,3-benzodiazole-6-carboxylic acid |

-continued
| Compound | Structure | IUPAC |
|---|---|---|
| 204 | 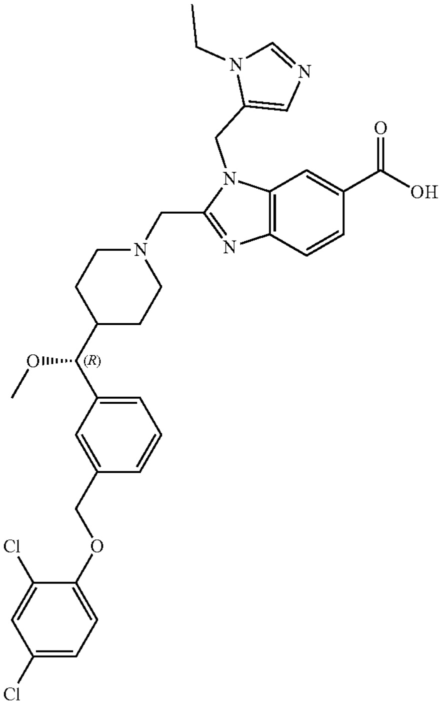 | (R)-2-((4-((3-((2,4-dichlorophenoxy)methyl) phenyl)(methoxy) methyl)piperidin-1-yl) methyl)-1-((1-ethyl-1H-imidazol-5-yl)methyl)-1H-benzo[d]imidazole-6-carboxylic acid |
| 205 | 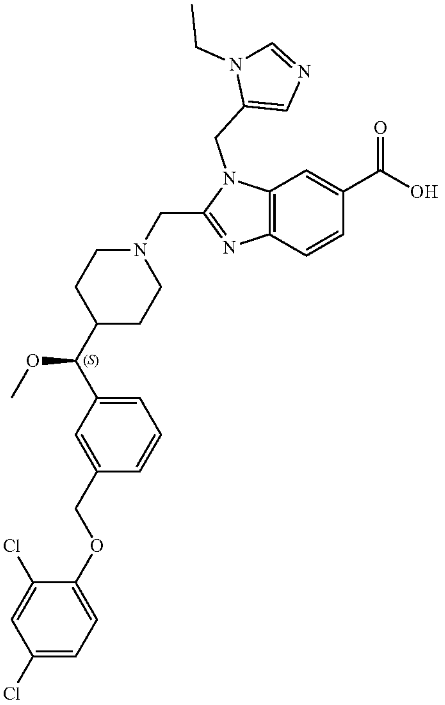 | (S)-2-((4-((3-((2,4-dichlorophenoxy)methyl) phenyl)(methoxy) methyl)piperidin-1-yl) methyl)-1-((1-ethyl-1H-imidazol-5-yl) methyl)-1H-benzo[d] imidazole-6-carboxylic acid |

-continued
| Compound | Structure | IUPAC |
| --- | --- | --- |
| 206 | 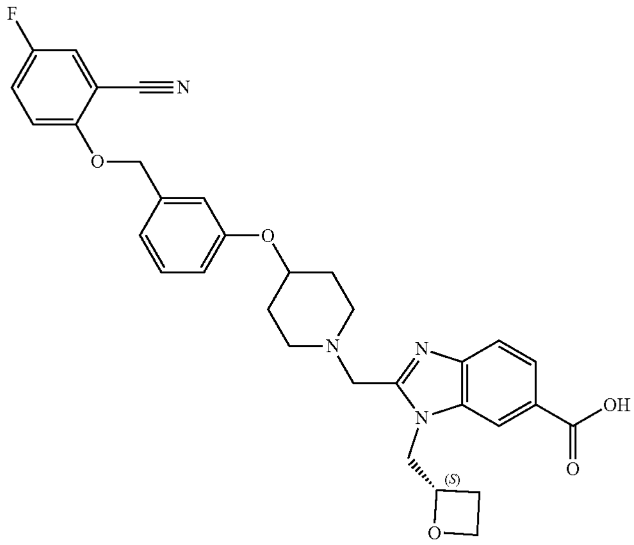 | (S)-2-((4-(3-((2-Cyano-4-fluorophenoxy)methyl) phenoxy)piperidin-1-yl)methyl)-1-(oxetan-2-ylmethyl)-1H-benzo[d]imidazole-6-carboxylic acid |
| 207 | 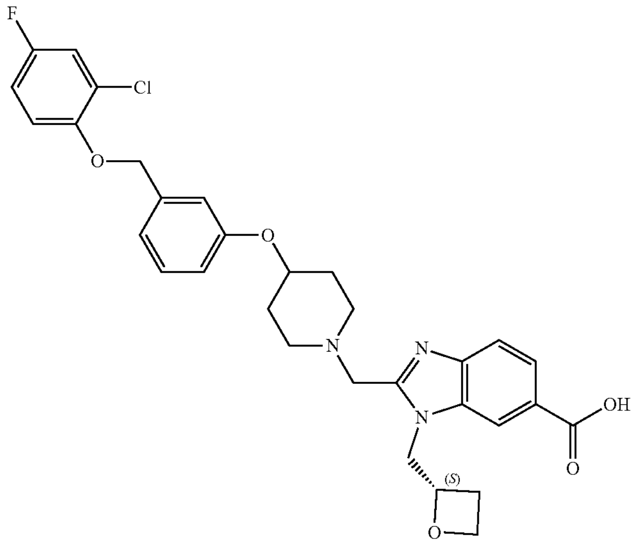 | 2-[(4-{3-[(2,4-dichlorophenoxy) methyl]phenoxy}piperidin-1-yl)methyl]-1-[(1,2-oxazol-5-yl)methyl]-1H-1,3-benzodiazole-6-carboxylic acid |

-continued

| Compound | Structure | IUPAC |
|---|---|---|
| 208 | 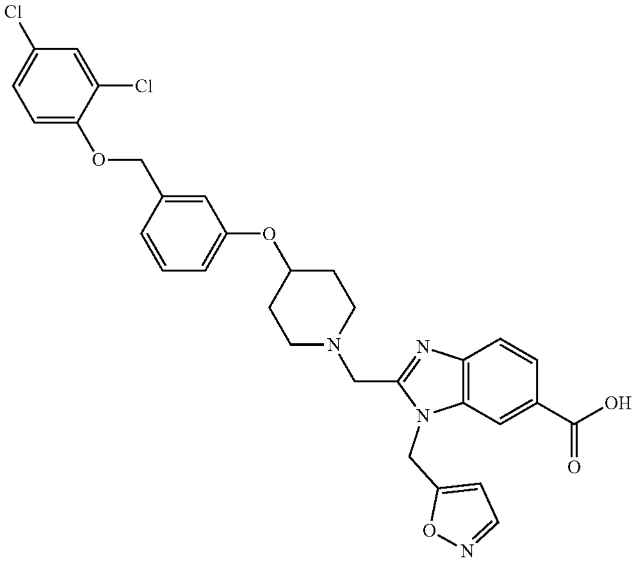 [SMILES: O=C(O)c1ccc2nc(CN3CCC(Oc4cccc(COc5ccc(Cl)cc5Cl)c4)CC3)n(Cc3ccno3)c2c1] | 2-((4-(3-((2,4-Dichlorophenoxy)methyl) phenoxy)piperidin-1-yl)methyl)-1-(isoxazol-5-ylmethyl)-1H-benzo[d]imidazole-6-carboxylic acid |
| 214 | 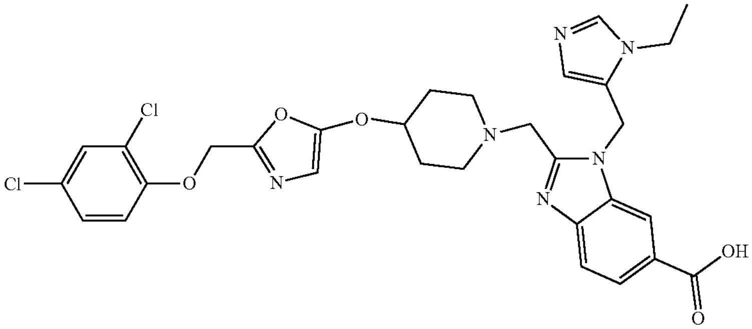 [SMILES: CCn1cncc1Cn1c(CN2CCC(Oc3cnc(COc4ccc(Cl)cc4Cl)o3)CC2)nc2ccc(C(=O)O)cc21] | 2-{[4-({2-[(2,4-dichlorophenoxy)methyl]-1,3-oxazol-5-yl}oxy) piperidin-1-yl]methyl}-1-[(1-ethyl-1H-imidazol-5-yl)methyl]-1H-1,3-benzodiazole-6-carboxylic acid |
| 215 | 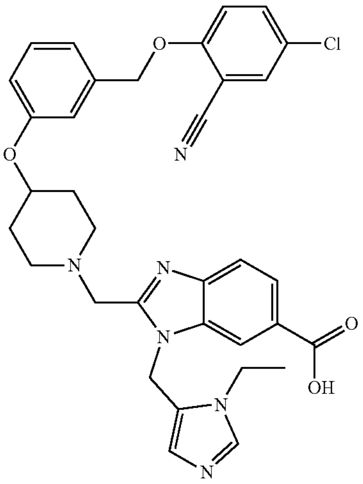 [SMILES: CCn1cncc1Cn1c(CN2CCC(Oc3cccc(COc4ccc(Cl)cc4C#N)c3)CC2)nc2ccc(C(=O)O)cc21] | 2-[(4-{3-[(4-chloro-2-cyanophenoxy) methylphenoxy}piperidin-1-yl)methyl]-1-[(1-ethyl-1H-imidazol-5-yl)methyl]-1H-1,3-benzodiazole-6-carboxylic acid |

-continued

| Compound | Structure | IUPAC |
|---|---|---|
| 216 | 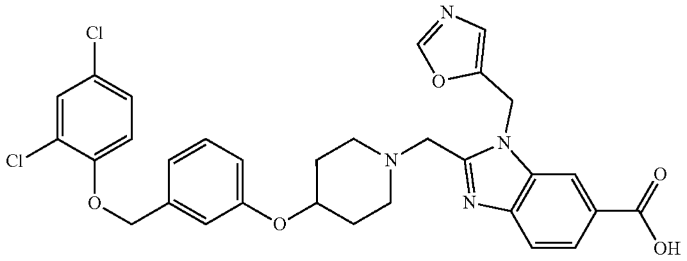 [SMILES: O=C(O)c1ccc2nc(CN3CCC(Oc4cccc(COc5ccc(Cl)cc5Cl)c4)CC3)n(Cc3cnco3)c2c1] | 2-((4-(3-((2,4-Dichlorophenoxy)methyl)phenoxy)piperidin-1-yl)methyl)-1-(oxazol-5-ylmethyl)-1H-benzo[d]imidazole-6-carboxylic acid |
| 217 | 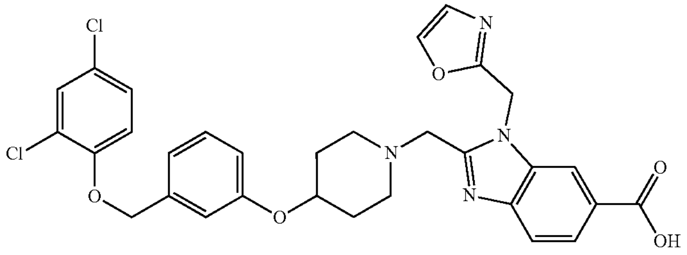 [SMILES: O=C(O)c1ccc2nc(CN3CCC(Oc4cccc(COc5ccc(Cl)cc5Cl)c4)CC3)n(Cc3ncco3)c2c1] | 2-[(4-{3-[(2,4-dichlorophenoxy)methyl]phenoxy}piperidin-1-yl)methyl]-1-[(1,3-oxazol-2-yl)methyl]-1H-1,3-benzodiazole-6-carboxylic acid |
| 220 | 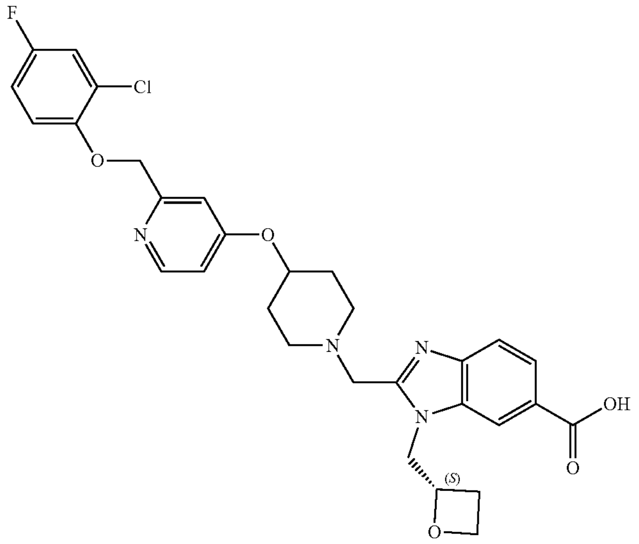 | (S)-2-((4-((2-((2-Chloro-4-fluorophenoxy)methyl)pyridin-4-yl)oxy)piperidin-1-yl)methyl)-1-(oxetan-2-ylmethyl)-1H-benzo[d]imidazole-6-carboxylic acid |

-continued

| Compound | Structure | IUPAC |
|---|---|---|
| 221 | 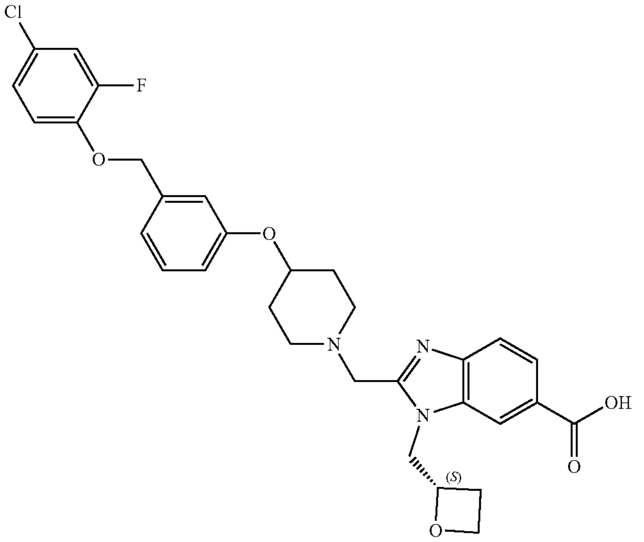 | 2-[(4-{3-[(4-chloro-2-fluorophenoxy)methyl]phenoxy}piperidin-1-yl)methyl]-1-{[(2S)-oxetan-2-yl]methyl}-1H-1,3-benzodiazole-6-carboxylic acid |
| 224 | 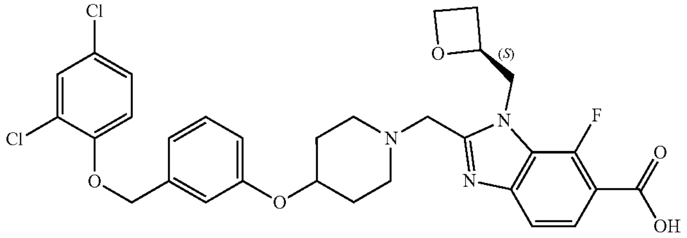 | 2-[(4-{3-[(2,4-dichlorophenoxy)methyl]phenoxy}piperidin-1-yl)methyl]-7-fluoro-1-{[(2S)-oxetan-2-yl]methyl}-1H-1,3-benzodiazole-6-carboxylic acid |
| 227 | 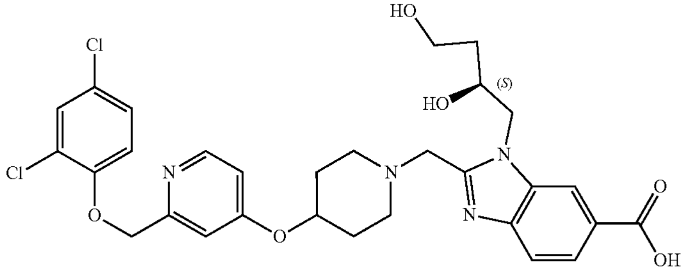 | 2-{[4-({2-[(2,4-dichlorophenoxy)methyl]pyridin-4-yl}oxy)piperidin-1-yl]methyl}-1-[(2S)-2,4-dihydroxybutyl]-1H-1,3-benzodiazole-6-carboxylic acid |
| 230 | 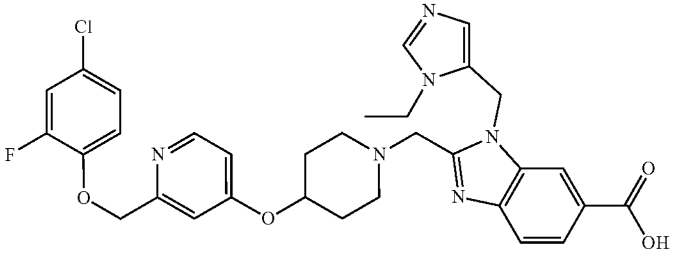 [SMILES: CCn1cncc1Cn1c(CN2CCC(Oc3ccnc(COc4ccc(Cl)cc4F)c3)CC2)nc2ccc(C(=O)O)cc21] | 2-((4-((2-((4-Chloro-2-fluorophenoxy)methyl)pyridin-4-yl)oxy)piperidin-1-yl)methyl)-1-((1-ethyl-1H-imidazol-5-yl)methyl)-1H-benzo[d]imidazole-6-carboxylic acid |
| 231 | 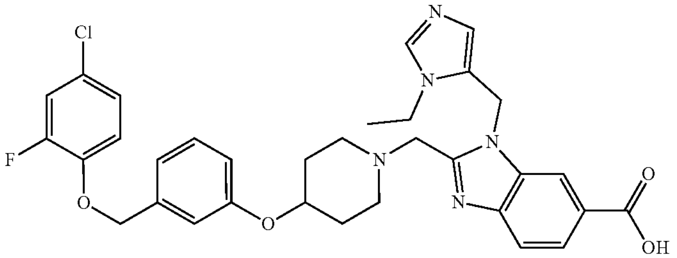 [SMILES: CCn1cncc1Cn1c(CN2CCC(Oc3cccc(COc4ccc(Cl)cc4F)c3)CC2)nc2ccc(C(=O)O)cc21] | 2-[(4-{3-[(4-chloro-2-fluorophenoxy)methyl]phenoxy}piperidin-1-yl)methyl]-1-[(1-ethyl-1H-imidazol-5-yl)methyl]-1H-1,3-benzodiazole-6-carboxylic acid |

-continued

| Compound | Structure | IUPAC |
|---|---|---|
| 232 | 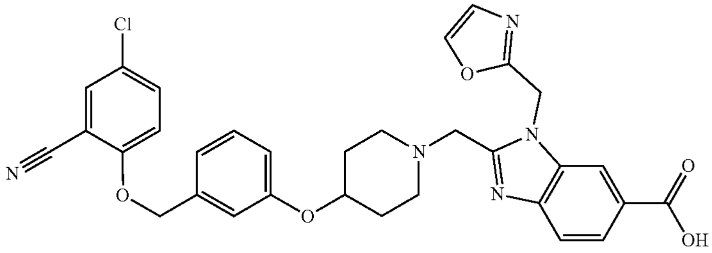 [SMILES: N#Cc1cc(Cl)ccc1OCc1cccc(OC2CCN(Cc3nc4ccc(C(=O)O)cc4n3Cc3ncco3)CC2)c1] | 2-[(4-{3-[(4-chloro-2-cyanophenoxy) methylphenoxy}piperidin-1-yl)methyl]-1-[(1,3-oxazol-2-yl)methyl]-1H-1,3-benzodiazole-6-carboxylic acid |
| 239 | 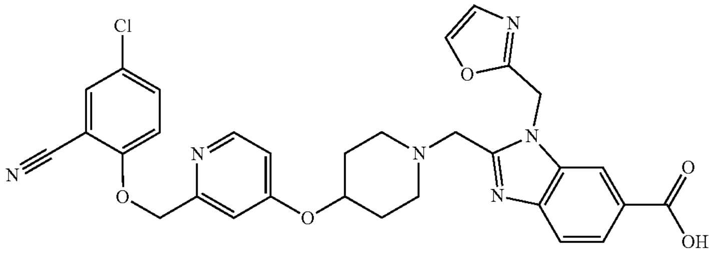 [SMILES: N#Cc1cc(Cl)ccc1OCc1cc(OC2CCN(Cc3nc4ccc(C(=O)O)cc4n3Cc3ncco3)CC2)ccn1] | 2-((4-((2-((4-Chloro-2-isocyanophenoxy) methyl)pyridin-4-yl)oxy)piperidin-1-yl)methyl)-1-(oxazol-2-ylmethyl)-1H-benzo[d]imidazole-6-carboxylic acid |
| 240 | 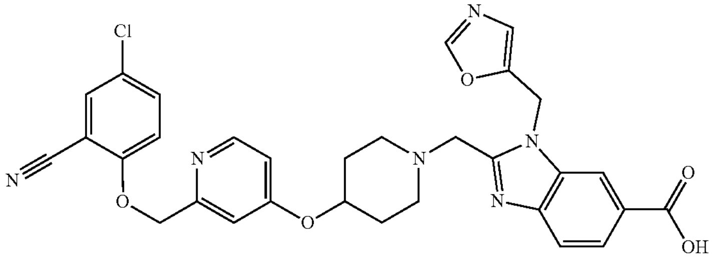 [SMILES: N#Cc1cc(Cl)ccc1OCc1cc(OC2CCN(Cc3nc4ccc(C(=O)O)cc4n3Cc3cnco3)CC2)ccn1] | 2-{[4-({2-[(4-chloro-2-cyanophenoxy)methyl] pyridin-4-yl}oxy)piperidin-1-yl]methyl}-1-[(1,3-oxazol-5-yl)methyl]-1H-1,3-benzodiazole-6-carboxylic acid |
| 241 | 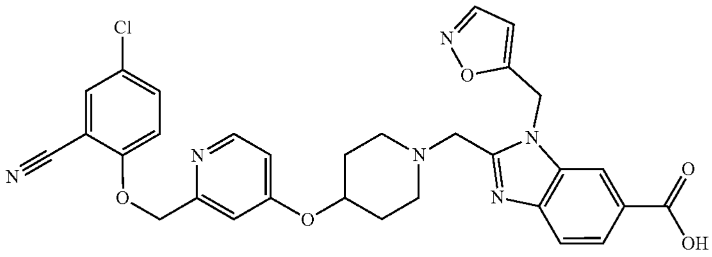 [SMILES: N#Cc1cc(Cl)ccc1OCc1cc(OC2CCN(Cc3nc4ccc(C(=O)O)cc4n3Cc3ccno3)CC2)ccn1] | 2-{[4-({2-[(4-chloro-2-cyanophenoxy) methyl]pyridin-4-yl}oxy)piperidin-1-yl]methyl}-1-[(1,2-oxazol-5-yl)methyl]-1H-1,3-benzodiazole-6-carboxylic acid |
| 242 | 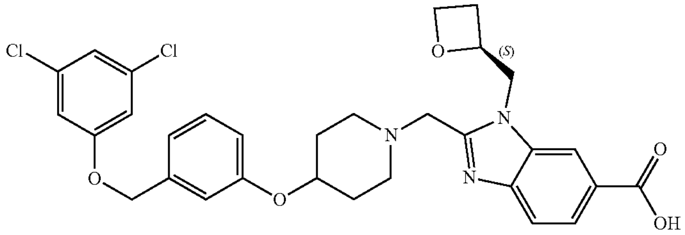 | 2-[(4-{3-[(3,5-dichlorophenoxy) methyl]phenoxy} piperidin-1-yl)methyl]-1-{[(2S)-oxetan-2-yl]methyl}-1H-1,3-benzodiazole-6-carboxylic acid |
| 243 | 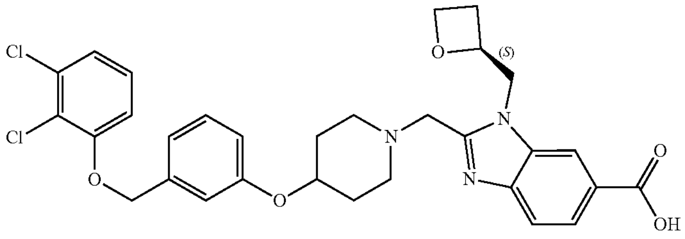 | 2-[(4-{3-[(2,3-dichlorophenoxy) methyl]phenoxy}piperidin-1-yl)methyl]-1-{[(2S)-oxetan-2-yl]methyl}-1H-1,3-benzodiazole-6-carboxylic acid |

-continued

| Compound | Structure | IUPAC |
|---|---|---|
| 246 | 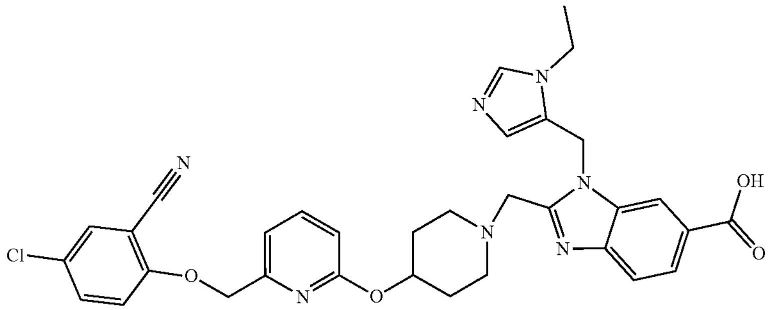 [SMILES: CCn1cncc1Cn1c(CN2CCC(Oc3cccc(COc4ccc(Cl)cc4C#N)n3)CC2)nc2ccc(C(=O)O)cc21] | 2-{[4-({6-[(4-chloro-2-cyanophenoxy)methyl]pyridin-2-yl}oxy)piperidin-1-yl]methyl}-1-[(1-ethyl-1H-imidazol-5-yl)methyl]-1H-1,3-benzodiazole-6-carboxylic acid |
| 247 | 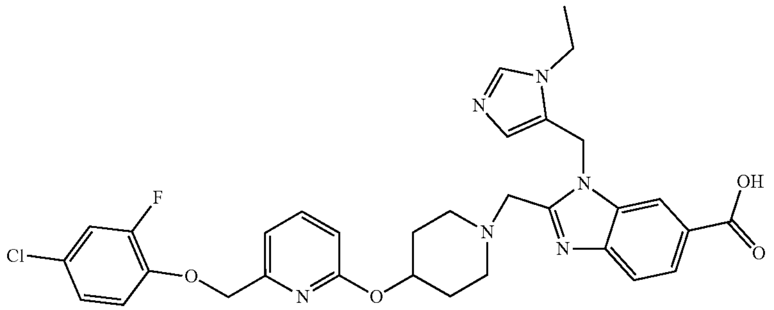 [SMILES: CCn1cncc1Cn1c(CN2CCC(Oc3cccc(COc4ccc(Cl)cc4F)n3)CC2)nc2ccc(C(=O)O)cc21] | 2-{[4-({6-[(4-chloro-2-fluorophenoxy)methyl]pyridin-2-yl}oxy)piperidin-1-yl]methyl}-1-[(1-ethyl-1H-imidazol-5-yl)methyl]-1H-1,3-benzodiazole-6-carboxylic acid |
| 248 | 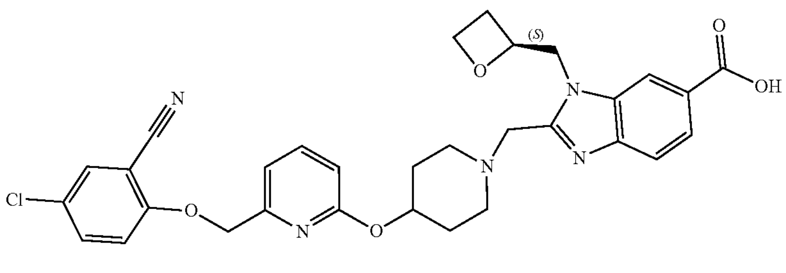 | 2-{[4-({6-[(4-chloro-2-cyanophenoxy)methyl]pyridin-2-yl}oxy)piperidin-1-yl]methyl}-1-{[(2S)-oxetan-2-yl]methyl}-1H-1,3-benzodiazole-6-carboxylic acid |
| 249 | 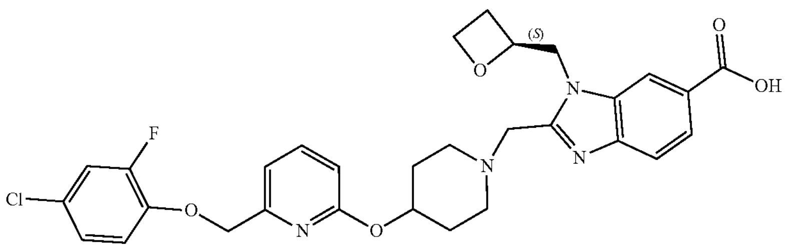 | 2-{[4-({6-[(4-chloro-2-fluorophenoxy)methyl]pyridin-2-yl}oxy)piperidin-1-yl]methyl}-1-{[(2S)-oxetan-2-yl]methyl}-1H-1,3-benzodiazole-6-carboxylic acid |
| 250 | 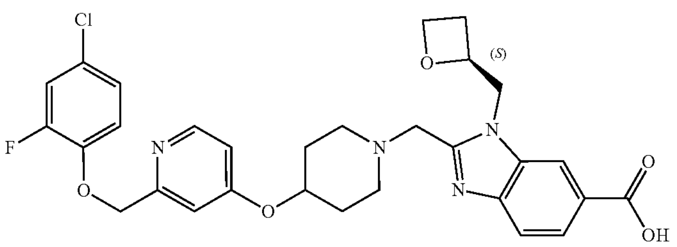 | 2-{[4-({2-[(4-chloro-2-fluorophenoxy)methyl]pyridin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 251 | 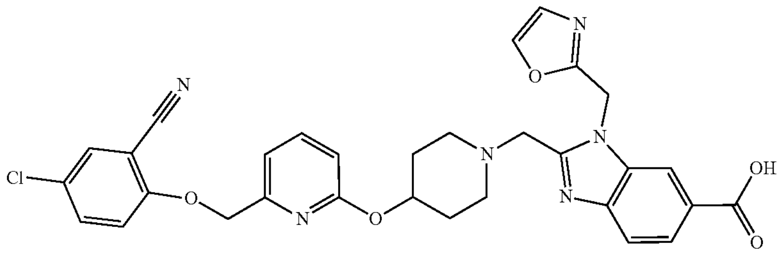 [SMILES: N#Cc1cc(Cl)ccc1OCc1cccc(OC2CCN(Cc3nc4ccc(C(=O)O)cc4n3Cc3ncco3)CC2)n1] | 2-{[4-({6-[(4-chloro-2-cyanophenoxy)methyl]pyridin-2-yl}oxy)piperidin-1-yl]methyl}-1-[(1,3-oxazol-2-yl)methyl]-1H-1,3-benzodiazole-6-carboxylic acid |
| 252 | 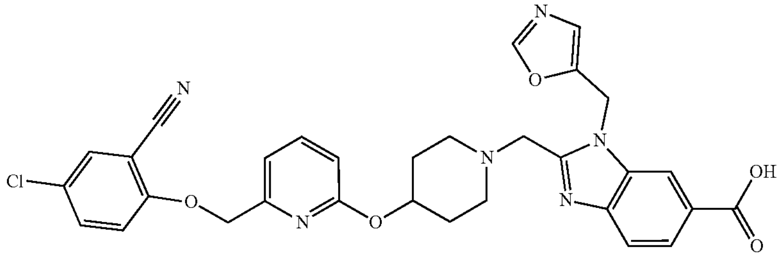 [SMILES: N#Cc1cc(Cl)ccc1OCc1cccc(OC2CCN(Cc3nc4ccc(C(=O)O)cc4n3Cc3cnco3)CC2)n1] | 2-{[4-({6-[(4-chloro-2-cyanophenoxy)methyl]pyridin-2-yl}oxy)piperidin-1-yl]methyl}-1-[(1,3-oxazol-5-yl)methyl]-1H-1,3-benzodiazole-6-carboxylic acid |
| 253 | 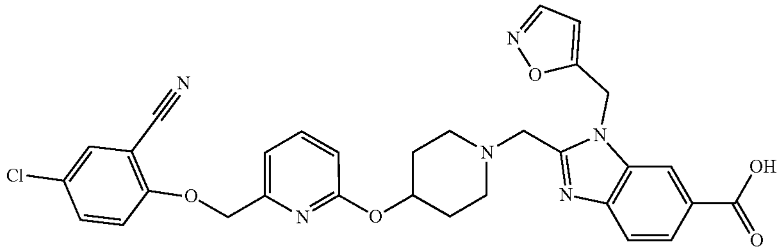 [SMILES: N#Cc1cc(Cl)ccc1OCc1cccc(OC2CCN(Cc3nc4ccc(C(=O)O)cc4n3Cc3ccno3)CC2)n1] | 2-{[4-({6-[(4-chloro-2-cyanophenoxy)methyl]pyridin-2-yl}oxy)piperidin-1-yl]methyl}-1-[(1,2-oxazol-5-yl)methyl]-1H-1,3-benzodiazole-6-carboxylic acid |
| 254 | 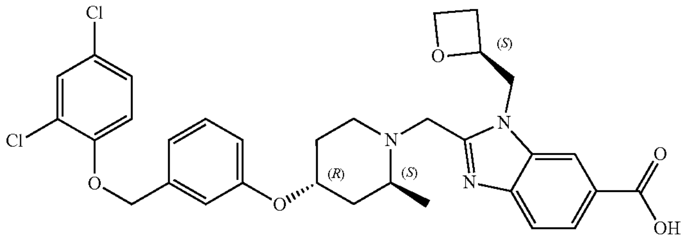 | 2-{[(2S,4R)-4-{3-[(2,4-dichlorophenoxy)methyl]phenoxy}-2-methylpiperidin-1-yl]methyl}-1-{[(2S)-oxetan-2-yl]methyl}-1H-1,3-benzodiazole-6-carboxylic acid |
| 255 | 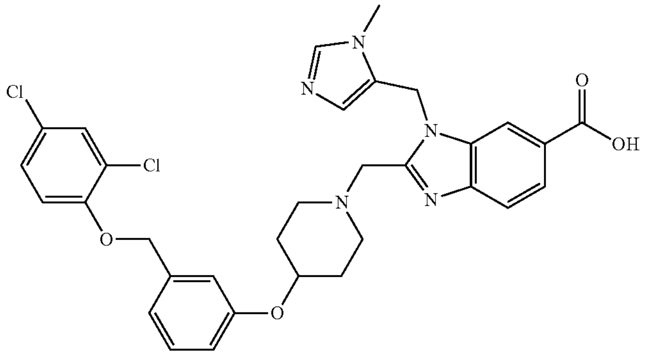 [SMILES: Cn1cncc1Cn1c(CN2CCC(Oc3cccc(COc4ccc(Cl)cc4Cl)c3)CC2)nc2ccc(C(=O)O)cc21] | 2-[(4-{3-[(2,4-dichlorophenoxy)methyl]phenoxy}piperidin-1-yl)methyl]-1-[(1-methyl-1H-imidazol-5-yl)methyl]-1H-1,3-benzodiazole-6-carboxylic acid |

-continued

| Compound | Structure | IUPAC |
|---|---|---|
| 256 | 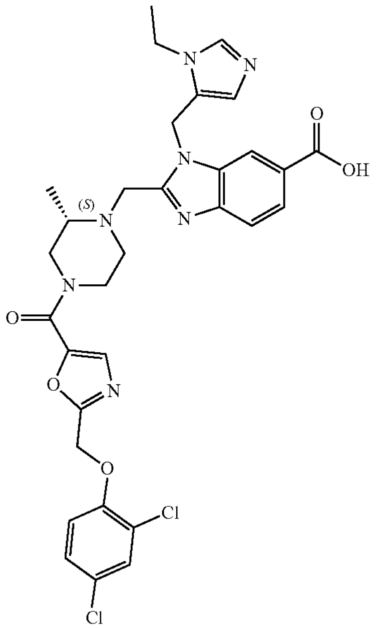 | 2-{[(2S)-4-{2-[(2,4-dichlorophenoxy)methyl]-1,3-oxazole-5-carbonyl}-2-methylpiperazin-1-yl]methyl}-1-[(1-ethyl-1H-imidazol-5-yl)methyl]-1H-1,3-benzodiazole-6-carboxylic acid |
| 257 | 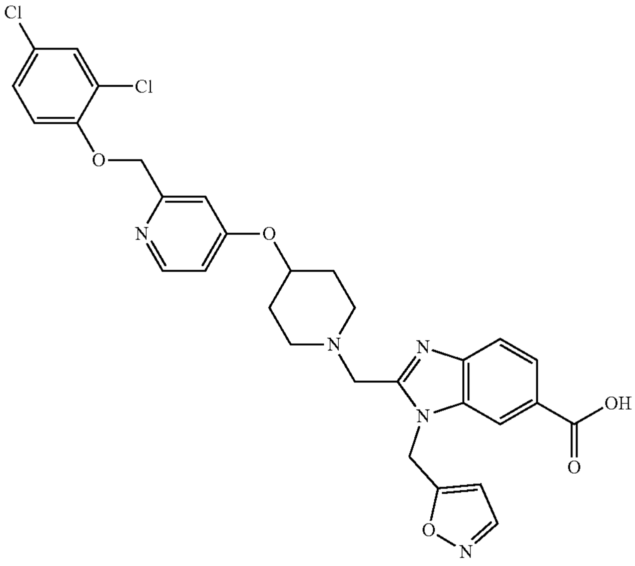 [SMILES: O=C(O)c1ccc2nc(CN3CCC(Oc4ccnc(COc5ccc(Cl)cc5Cl)c4)CC3)n(Cc3ccno3)c2c1] | 2-{[4-({2-[(2,4-dichlorophenoxy)methyl] pyridin-4-yl}oxy)piperidin-1-yl]methyl}-1-[(1,2-oxazol-5-yl)methyl]-1H-1,3-benzodiazole-6-carboxylic acid |
| 258 | 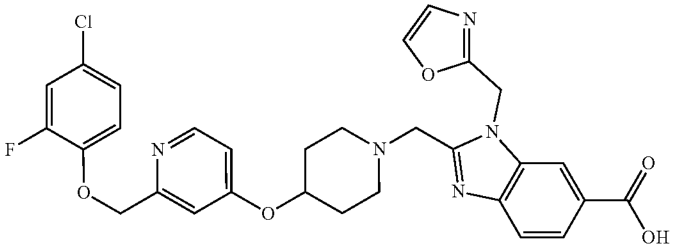 [SMILES: O=C(O)c1ccc2nc(CN3CCC(Oc4ccnc(COc5ccc(Cl)cc5F)c4)CC3)n(Cc3ncco3)c2c1] | 2-{[4-({2-[(4-chloro-2-fluorophenoxy)methyl] pyridin-4-yl}oxy)piperidin-1-yl]methyl}-1-[(1,3-oxazol-2-yl)methyl]-1H-1,3-benzodiazole-6-carboxylic acid |

-continued

| Compound | Structure | IUPAC |
|---|---|---|
| 259 | 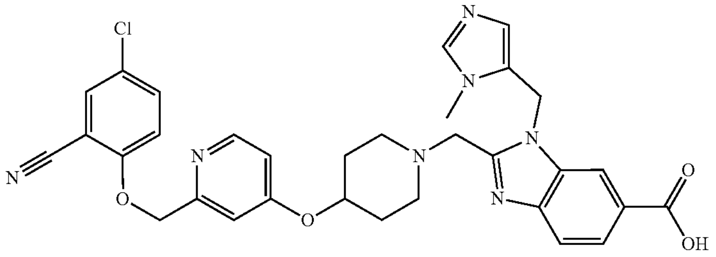 [SMILES: Cn1cncc1Cn1c(CN2CCC(Oc3ccnc(COc4ccc(Cl)cc4C#N)c3)CC2)nc2ccc(C(=O)O)cc21] | 2-{[4-({2-[(4-chloro-2-cyanophenoxy)methyl]pyridin-4-yl}oxy)piperidin-1-yl]methyl}-1-[(1-methyl-1H-imidazol-5-yl)methyl]-1H-1,3-benzodiazole-6-carboxylic acid |
| 260 | 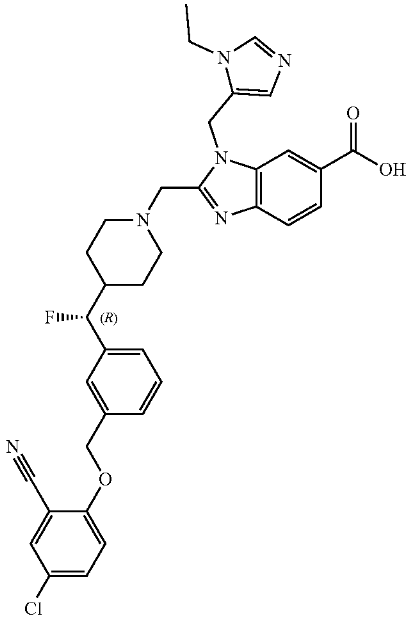 | )-2-((4-((3-((4-Chloro-2-cyanophenoxy)methyl)phenyl)fluoromethyl)piperidin-1-yl)methyl)-1-((1-ethyl-1H-imidazol-5-yl)methyl)-1H-benzo[d]imidazole-6-carboxylic acid |
| 261 | 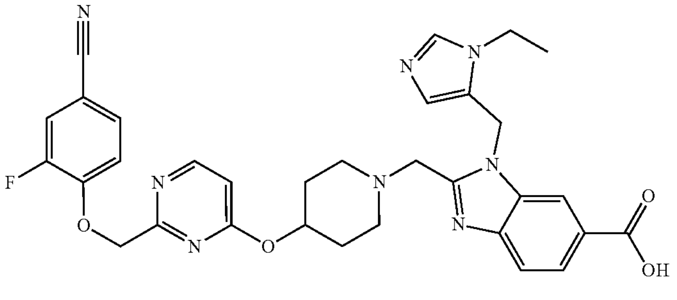 [SMILES: CCn1cncc1Cn1c(CN2CCC(Oc3ccnc(COc4ccc(C#N)cc4F)n3)CC2)nc2ccc(C(=O)O)cc21] | 2-((4-((2-((4-Cyano-2-fluorophenoxy)methyl)pyrimidin-4-yl)oxy)piperidin-1-yl)methyl)-1-((1-ethyl-1H-imidazol-5-yl)methyl)-1H-benzo[d]imidazole-6-carboxylic acid |
| 262 | 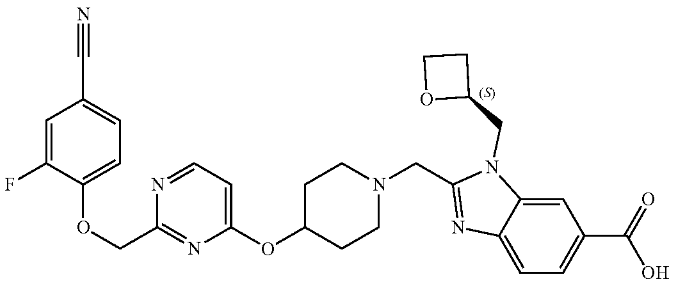 | (S)-2-((4-((2-((4-Cyano-2-fluorophenoxy)methyl)pyrimidin-4-yl)oxy)piperidin-1-yl)methyl)-1-(oxetan-2-ylmethyl)-1H-benzo[d]imidazole-6-carboxylic acid |

-continued

| Compound | Structure | IUPAC |
| --- | --- | --- |
| 263 | 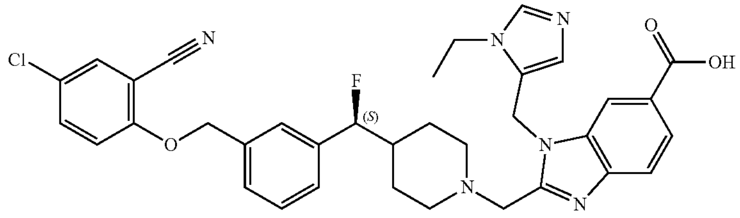 | (S)-2-((4-((3-((4-chloro-2-cyanophenoxy)methyl) phenyl)fluoromethyl)piperidin-1-yl)methyl)-1-((1-ethyl-1H-imidazol-5-yl)methyl)-1H-benzo[d]imidazole-6-carboxylic acid |
| 264 | 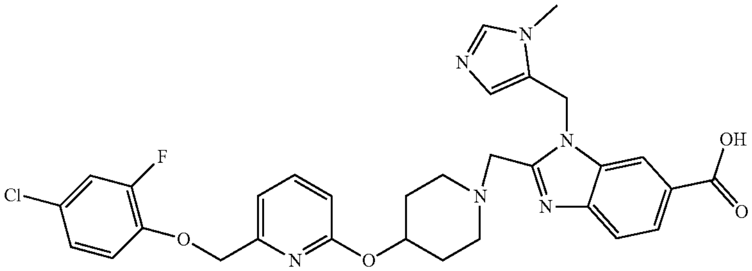 [SMILES: Cn1cncc1Cn1c(CN2CCC(Oc3cccc(COc4ccc(Cl)cc4F)n3)CC2)nc2ccc(C(=O)O)cc21] | 2-{[4-({6-[(4-chloro-2-fluorophenoxy) methyl]pyridin-2-yl}oxy)piperidin-1-yl]methyl}-1-[(1-methyl-1H-imidazol-5-yl)methyl]-1H-1,3-benzodiazole-6-carboxylic acid |
| 265 | 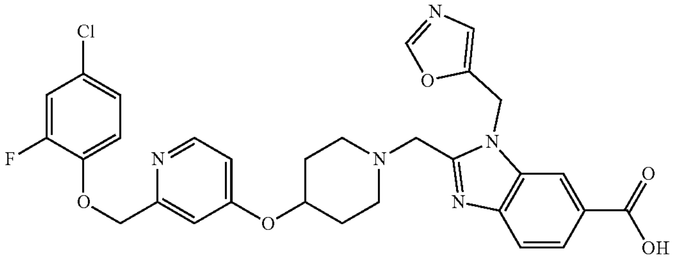 [SMILES: O=C(O)c1ccc2nc(CN3CCC(Oc4ccnc(COc5ccc(Cl)cc5F)c4)CC3)n(Cc3cnco3)c2c1] | 2-{[4-({2-[(4-chloro-2-fluorophenoxy)methyl] pyridin-4-yl}oxy)piperidin-1-yl]methyl}-1-[(1,3-oxazol-5-yl)methyl]-1H-1,3-benzodiazole-6-carboxylic acid |
| 266 | 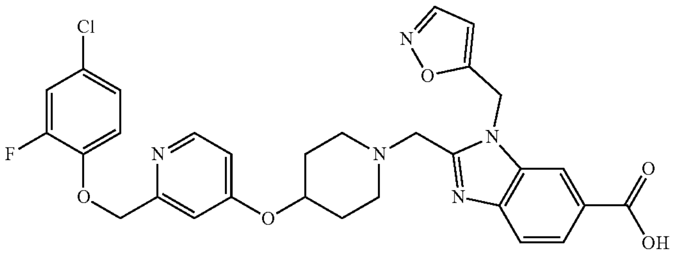 [SMILES: O=C(O)c1ccc2nc(CN3CCC(Oc4ccnc(COc5ccc(Cl)cc5F)c4)CC3)n(Cc3ccno3)c2c1] | 2-{[4-({2-[(4-chloro-2-fluorophenoxy)methyl] pyridin-4-yl}oxy)piperidin-1-yl]methyl}-1-[(1,2-oxazol-5-yl)methyl]-1H-1,3-benzodiazole-6-carboxylic acid |
| 267 | 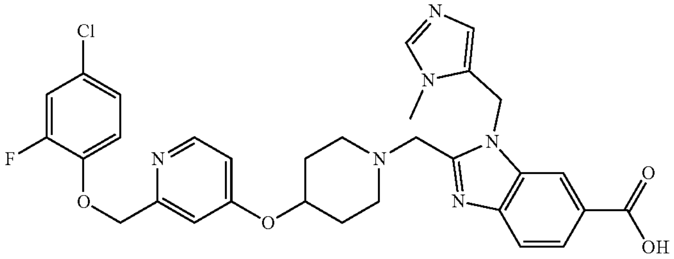 [SMILES: Cn1cncc1Cn1c(CN2CCC(Oc3ccnc(COc4ccc(Cl)cc4F)c3)CC2)nc2ccc(C(=O)O)cc21] | 2-{[4-({2-[(4-chloro-2-fluorophenoxy)methyl] pyridin-4-yl}oxy)piperidin-1-yl]methyl}-1-[(1-methyl-1H-imidazol-5-yl)methyl]-1H-1,3-benzodiazole-6-carboxylic acid |
| 268 | 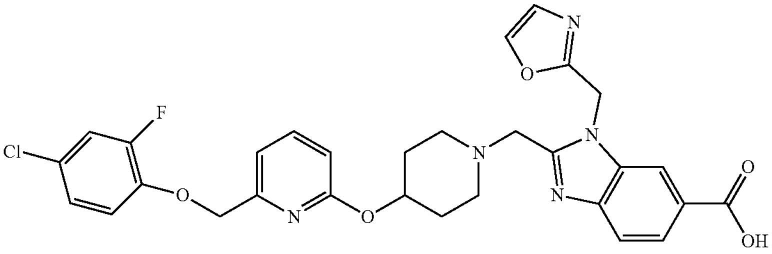 [SMILES: O=C(O)c1ccc2nc(CN3CCC(Oc4cccc(COc5ccc(Cl)cc5F)n4)CC3)n(Cc3ncco3)c2c1] | 2-{[4-({6-[(4-chloro-2-fluorophenoxy)methyl] pyridin-2-yl}oxy)piperidin-1-yl]methyl}-1-[(1,3-oxazol-2-yl)methyl]-1H-1,3-benzodiazole-6-carboxylic acid |

-continued

| Compound | Structure | IUPAC |
| --- | --- | --- |
| 269 | 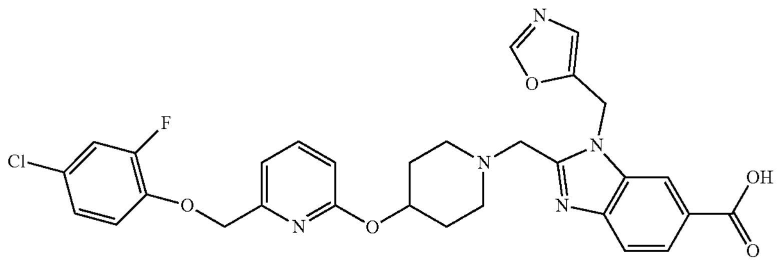 [SMILES: O=C(O)c1ccc2nc(CN3CCC(Oc4cccc(COc5ccc(Cl)cc5F)n4)CC3)n(Cc3cnco3)c2c1] | 2-{[4-({6-[(4-chloro-2-fluorophenoxy)methyl]pyridin-2-yl}oxy)piperidin-1-yl]methyl}-1-[(1,3-oxazol-5-yl)methyl]-1H-1,3-benzodiazole-6-carboxylic acid |
| 270 | 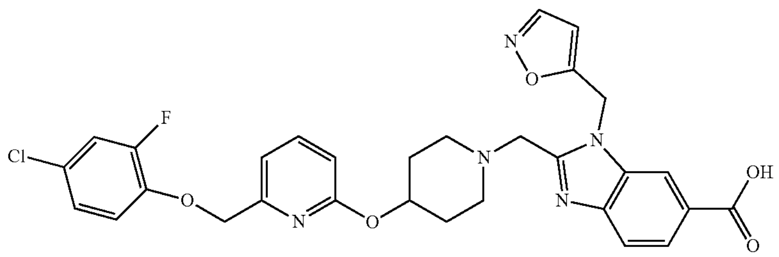 [SMILES: O=C(O)c1ccc2nc(CN3CCC(Oc4cccc(COc5ccc(Cl)cc5F)n4)CC3)n(Cc3ccno3)c2c1] | 2-{[4-({6-[(4-chloro-2-fluorophenoxy)methyl]pyridin-2-yl}oxy)piperidin-1-yl]methyl}-1-[(1,2-oxazol-5-yl)methyl]-1H-1,3-benzodiazole-6-carboxylic acid |
| 271 | 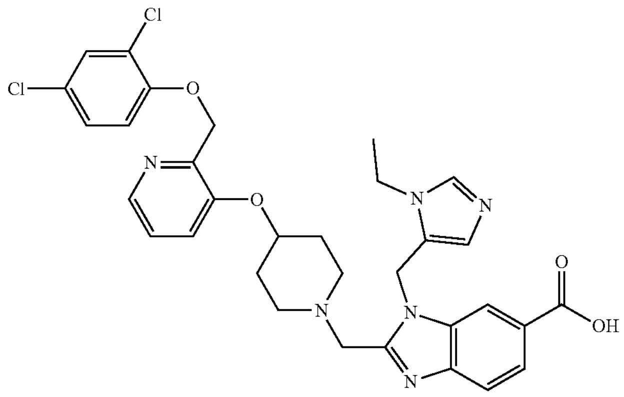 | 2-((4-((2-((2,4-Dichlorophenoxy)methyl)pyridin-3-yl)oxy)piperidin-1-yl)methyl)-1-((1-ethyl-1H-imidazol-5-yl)methyl)-1H-benzo[d]imidazole-6-carboxylic acid |
| 272 | 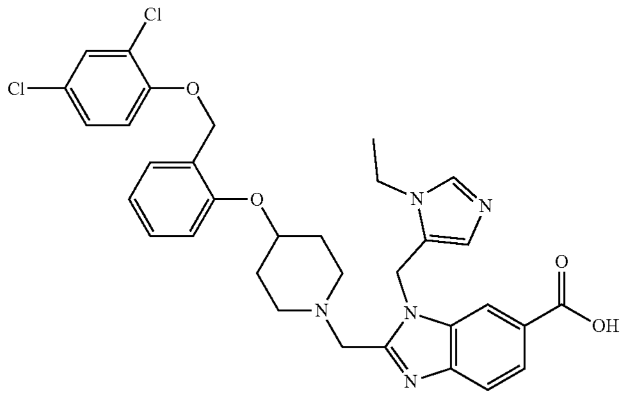 [SMILES: CCn1cncc1Cn1c(CN2CCC(Oc3cccnc3COc3ccc(Cl)cc3Cl)CC2)nc2ccc(C(=O)O)cc21] | 2-[(4-{2-[(2,4-dichlorophenoxy)methyl]phenoxy}piperidin-1-yl)methyl]-1-[(1-ethyl-1H-imidazol-5-yl)methyl]-1H-1,3-benzodiazole-6-carboxylic acid |

-continued
| Compound | Structure | IUPAC |
|---|---|---|
| 274 | 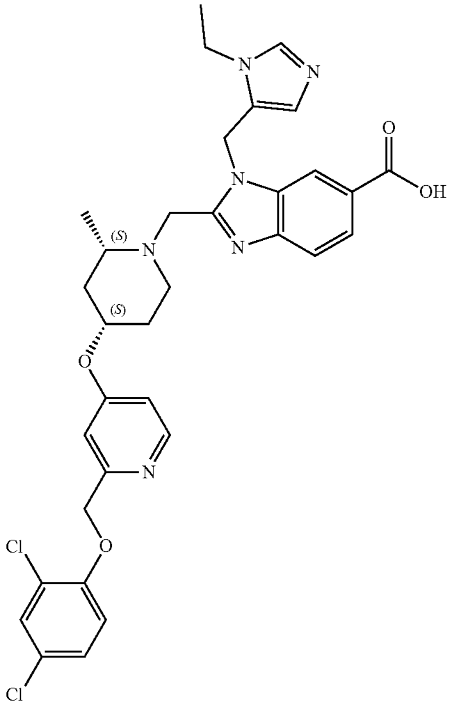 | 2-(((2S,4S)-4-((2-((2,4-Dichlorophenoxy)methyl) pyridin-4-yl)oxy)-2-methylpiperidin-1-yl)methyl)-1-((1-ethyl-1H-imidazol-5-yl)methyl)-1H-benzo[d]imidazole-6-carboxylic acid |
| 275 | 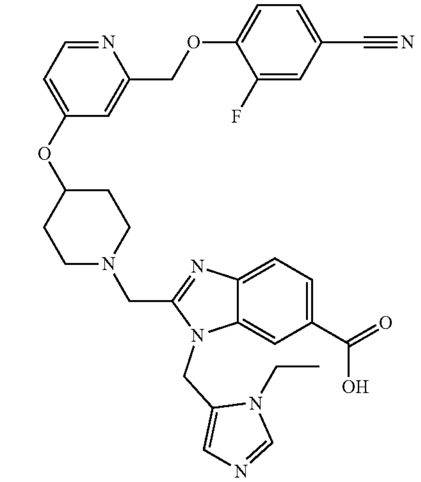 [SMILES: CCn1cncc1Cn1c(CN2CCC(Oc3ccnc(COc4ccc(C#N)cc4F)c3)CC2)nc2ccc(C(=O)O)cc21] | 2-{[4-({2-[(4-cyano-2-fluorophenoxy)methyl]pyridin-4-yl}oxy)piperidin-1-yl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 276 | 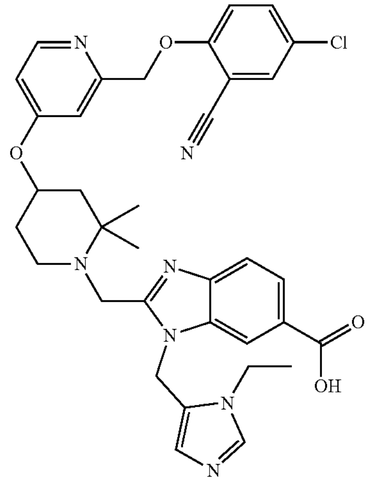 [SMILES: CCn1cncc1Cn1c(CN2CCC(Oc3ccnc(COc4ccc(Cl)cc4C#N)c3)CC2(C)C)nc2ccc(C(=O)O)cc21] | 2-((4-((2-((4-Chloro-2-cyanophenoxy)methyl) pyridin-4-yl)oxy)-2,2-dimethylpiperidin-1-yl)methyl)-1-((1-ethyl-1H-imidazol-5-yl)methyl)-1H-benzo[d]imidazole-6-carboxylic acid |
| 277 | 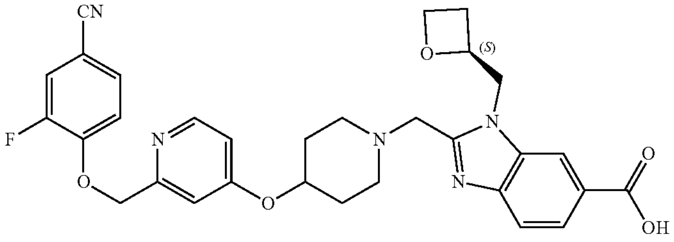 | 2-{[4-({2-[(4-cyano-2-fluorophenoxy)methyl] pyridin-4-yl}oxy)piperidin-1-yl]methyl}-1-{[(2S)-oxetan-2-yl]methyl}-1H-1,3-benzodiazole-6-carboxylic acid |
| 278 | 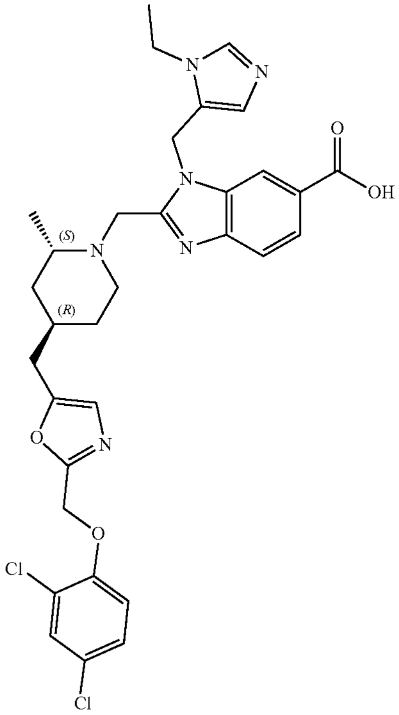 | 2-{[(2S,4R)-4-({2-[(2,4-dichlorophenoxy)methyl]-1,3-oxazol-5-yl}methyl)-2-methylpiperidin-1-yl] methyl}-1-[(1-ethyl-1H-imidazol-5-yl)methyl]-1H-1,3-benzodiazole-6-carboxylic acid |

-continued
| Compound | Structure | IUPAC |
|---|---|---|
| 279 | 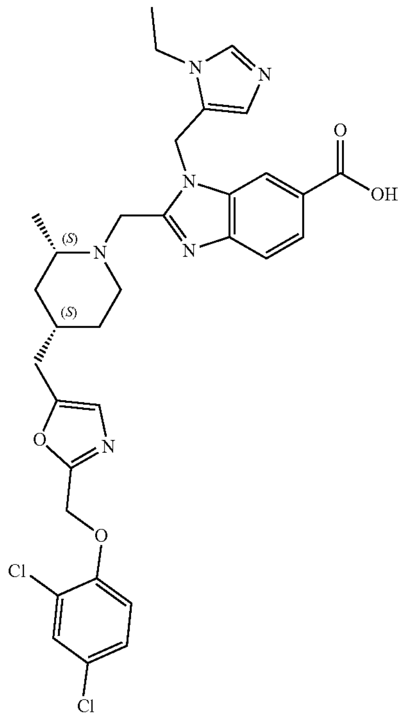 | 2-{[(2S,4S)-4-({2-[(2,4-dichlorophenoxy)methyl]-1,3-oxazol-5-yl}methyl)-2-methylpiperidin-1-yl]methyl}-1-[(1-ethyl-1H-imidazol-5-yl)methyl]-1H-1,3-benzodiazole-6-carboxylic acid |
| 280 | 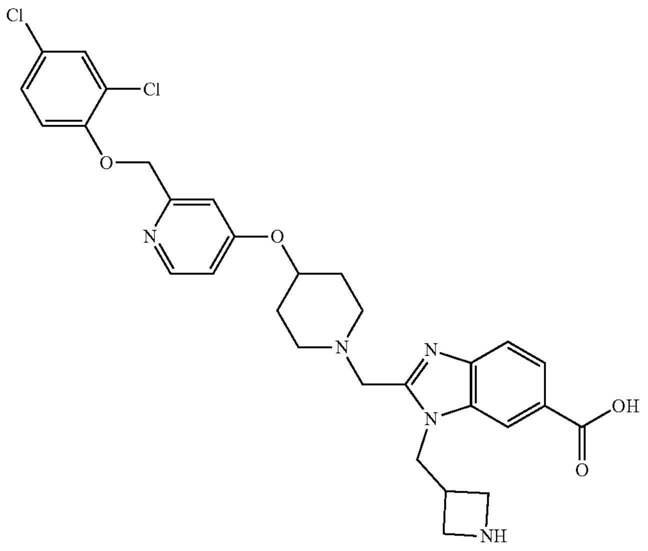 [SMILES: O=C(O)c1ccc2nc(CN3CCC(Oc4ccnc(COc5ccc(Cl)cc5Cl)c4)CC3)n(CC3CNC3)c2c1] | 1-[(azetidin-3-yl) methyl]-2-{[4-({2-[(2,4-dichlorophenoxy)methyl] pyridin-4-yl}oxy)piperidin-1-yl]methyl}-1H-1,3-benzodiazole-6-carboxylic acid |

-continued

| Compound | Structure | IUPAC |
|---|---|---|
| 283 | 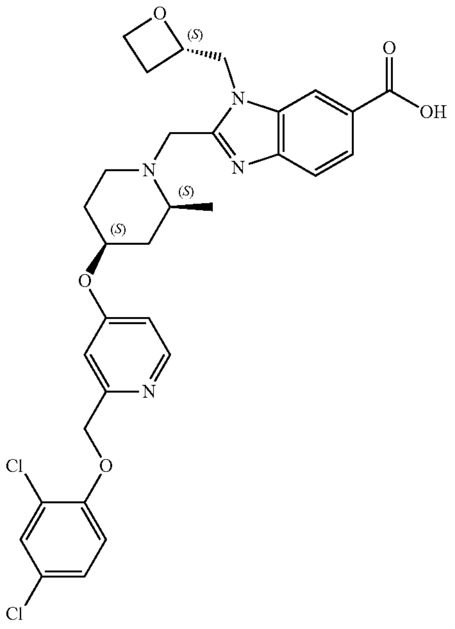 | 2-{[(2S,4S)-4-({2-[(2,4-dichlorophenoxy)methyl] pyridin-4-yl}oxy)-2-methylpiperidin-1-yl]methyl}-1-{[(2S)-oxetan-2-yl]methyl}-1H-1,3-benzodiazole-6-carboxylic acid |
| 284 | 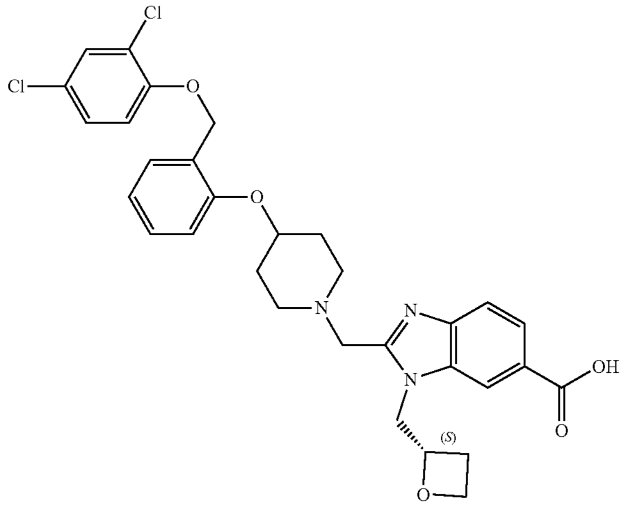 | 2-[(4-{2-[(2,4-dichlorophenoxy) methyl]phenoxy}piperidin-1-yl)methyl]-1-{[(2S)-oxetan-2-yl]methyl}-1H-1,3-benzodiazole-6-carboxylic acid |
| 285 | 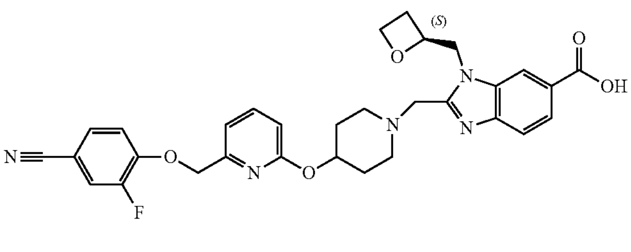 | (S)-2-((4-((6-((4-Cyano-2-fluorophenoxy)methyl) pyridin-2-yl)oxy)piperidin-1-yl)methyl)-1-(oxetan-2-ylmethyl)-1H-benzo[d]imidazole-6-carboxylic acid |

-continued
| Compound | Structure | IUPAC |
| --- | --- | --- |
| 286 | 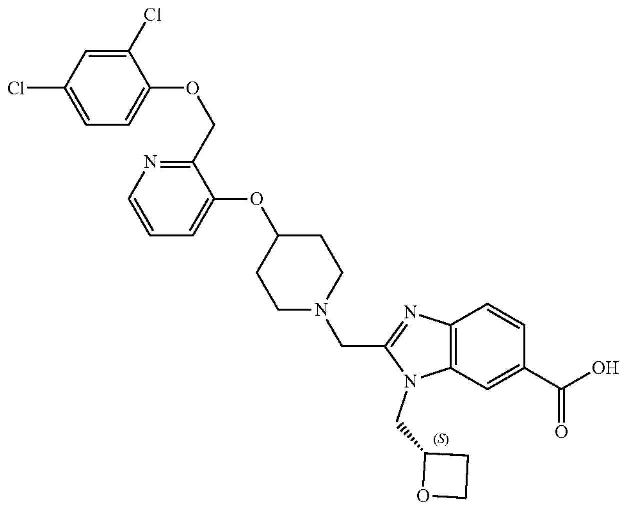 | 2-{[4-({2-[(2,4-dichlorophenoxy) methyl]pyridin-3-yl}oxy)piperidin-1-yl]methyl}-1-{[(2S)-oxetan-2-yl]methyl}-1H-1,3-benzodiazole-6-carboxylic acid |
| 287 | 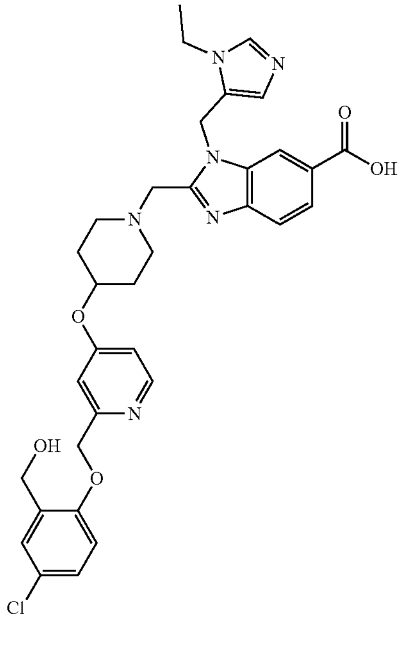 [SMILES: CCn1cncc1Cn1c(CN2CCC(Oc3ccnc(COc4ccc(Cl)cc4CO)c3)CC2)nc2ccc(C(=O)O)cc21] | 2-({4-[(2-{[4-chloro-2-(hydroxymethyl)phenoxy] methyl}pyridin-4-yl)oxy]piperidin-1-yl}methyl)-1-[(1-ethyl-1H-imidazol-5-yl)methyl]-1H-1,3-benzodiazole-6-carboxylic acid |

-continued
| Compound | Structure | IUPAC |
| --- | --- | --- |
| 288 | 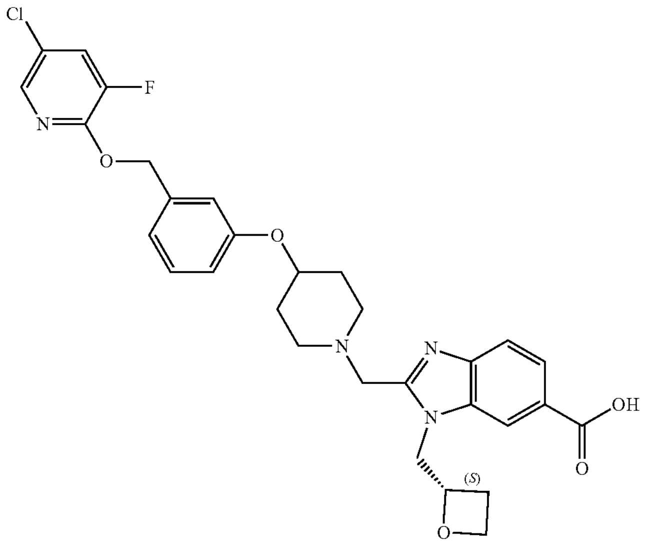 | 2-{[4-(3-{[(5-chloro-3-fluoropyridin-2-yl)oxy]methyl}phenoxy)piperidin-1-yl]methyl}-1-{[(2S)-oxetan-2-yl]methyl}-1H-1,3-benzodiazole-6-carboxylic acid |
| 290 | 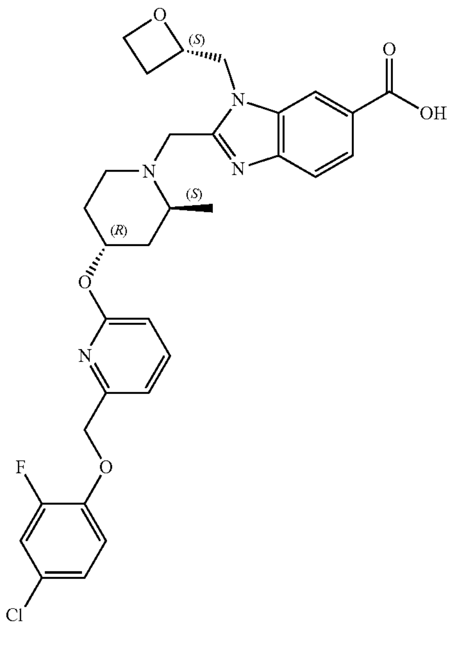 | 2-{[(2S,4R)-4-({6-[(4-chloro-2-fluorophenoxy)methyl]pyridin-2-yl}oxy)-2-methylpiperidin-1-yl]methyl}-1-{[(2S)-oxetan-2-yl]methyl}-1H-1,3-benzodiazole-6-carboxylic acid |

-continued
| Compound | Structure | IUPAC |
| --- | --- | --- |
| 291 | 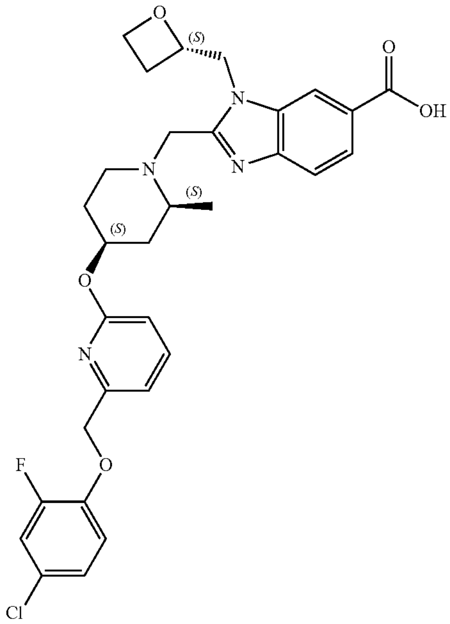 | 2-{[(2S,4S)-4-({6-[(4-chloro-2-fluorophenoxy)methyl]pyridin-2-yl}oxy)-2-methylpiperidin-1-yl]methyl}-1-{[(2S)-oxetan-2-yl]methyl}-1H-1,3-benzodiazole-6-carboxylic acid |
| 292 | 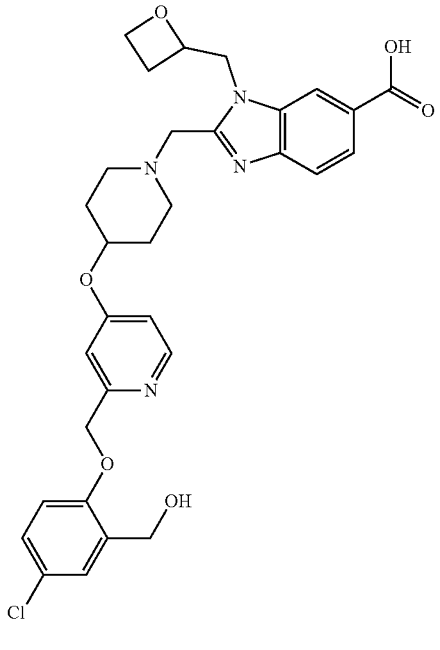 [SMILES: O=C(O)c1ccc2nc(CN3CCC(Oc4ccnc(COc5ccc(Cl)cc5CO)c4)CC3)n(CC3CCO3)c2c1] | 2-({4-[(2-{[4-chloro-2-(hydroxymethyl)phenoxy]methyl}pyridin-4-yl)oxy]piperidin-1-yl}methyl)-1-[(oxetan-2-yl)methyl]-1H-1,3-benzodiazole-6-carboxylic acid |

-continued

| Compound | Structure | IUPAC |
|---|---|---|
| 294 | 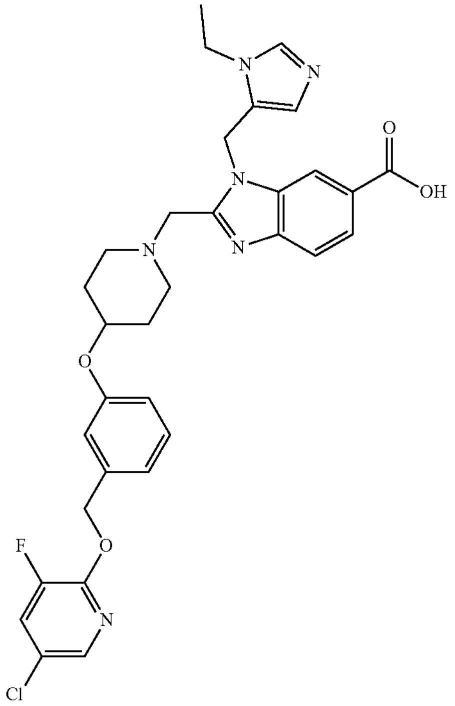 [SMILES: CCn1cncc1Cn1c(CN2CCC(Oc3cccc(COc4ncc(Cl)cc4F)c3)CC2)nc2ccc(C(=O)O)cc21] | 2-{[4-(3-{[(5-chloro-3-fluoropyridin-2-yl)oxy]methyl}phenoxy)piperidin-1-yl]methyl}-1-[(1-ethyl-1H-imidazol-5-yl)methyl]-1H-1,3-benzodiazole-6-carboxylic acid |
| 295 | 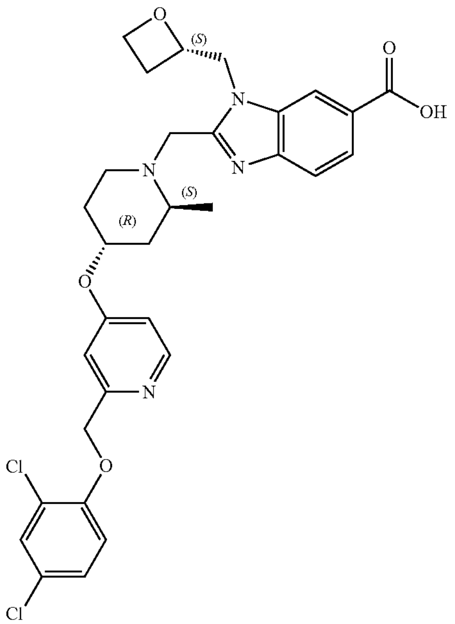 | 2-{[(2S,4R)-4-({2-[(2,4-dichlorophenoxy)methyl]pyridin-4-yl}oxy)-2-methylpiperidin-1-yl]methyl}-1-{[(2S)-oxetan-2-yl]methyl}-1H-1,3-benzodiazole-6-carboxylic acid |
| 296 | 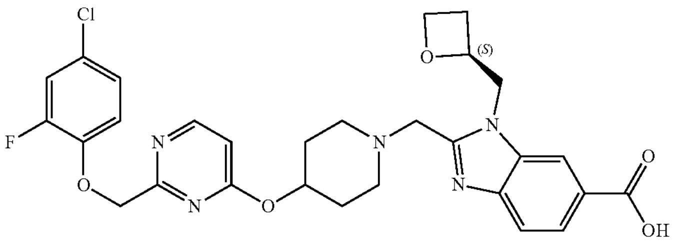 | 2-{[4-({2-[(4-chloro-2-fluorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
| --- | --- | --- |
| 297 | 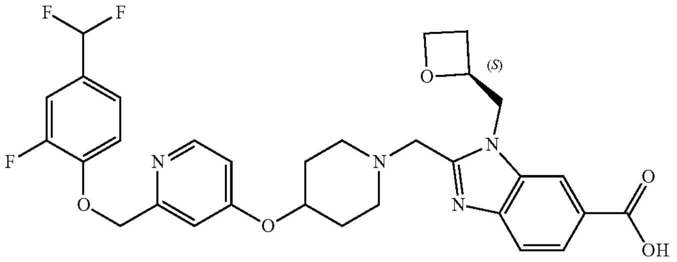 | (S)-2-((4-((2-((4-(Difluoromethyl)-2-fluorophenoxy)methyl)pyridin-4-yl)oxy)piperidin-1-yl)methyl)-1-(oxetan-2-ylmethyl)-1H-benzo[d]imidazole-6-carboxylic acid |
| 299 | 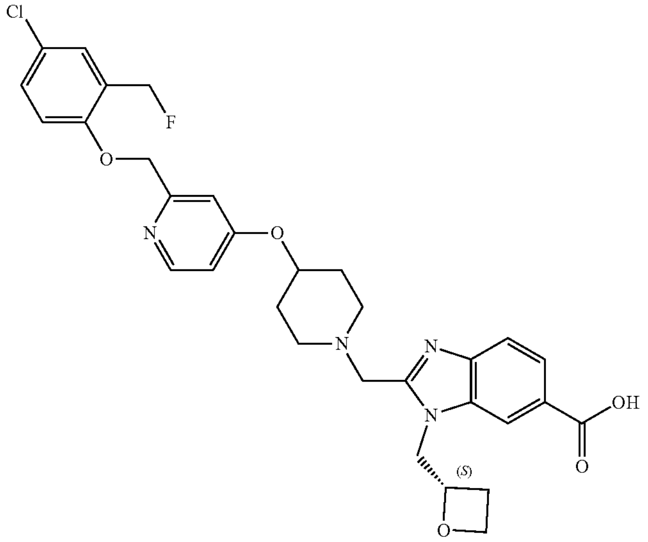 | (S)-2-((4-((2-((4-Chloro-2-(fluoromethyl)phenoxy)methyl)pyridin-4-yl)oxy)piperidin-1-yl)methyl)-1-(oxetan-2-ylmethyl)-1H-benzo[d]imidazole-6-carboxylic acid |
| 300 | 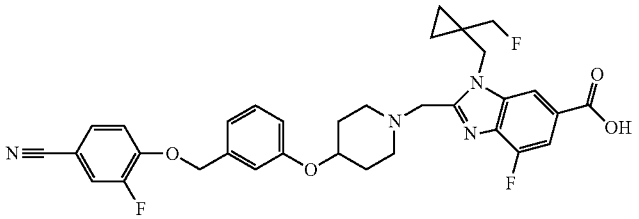 [SMILES: N#Cc1ccc(OCc2cccc(OC3CCN(Cc4nc5c(F)cc(C(=O)O)cc5n4CC4(CF)CC4)CC3)c2)c(F)c1] | 2-((4-(3-((4-Cyano-2-fluorophenoxy)methyl)phenoxy)piperidin-1-yl)methyl)-4-fluoro-1-((1-(fluoromethyl)cyclopropyl)methyl)-1H-benzo[d]imidazole-6-carboxylic acid |
| 301 | 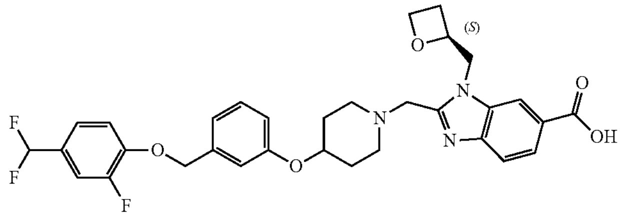 | 2-[(4-{3-[(4-cyano-2-fluorophenoxy)methyl]phenoxy}piperidin-1-yl)methyl]-4-fluoro-1-{[1-(fluoromethyl)cyclopropyl]methyl}-1H-1,3-benzodiazole-6-carboxylic acid |
| 302 | 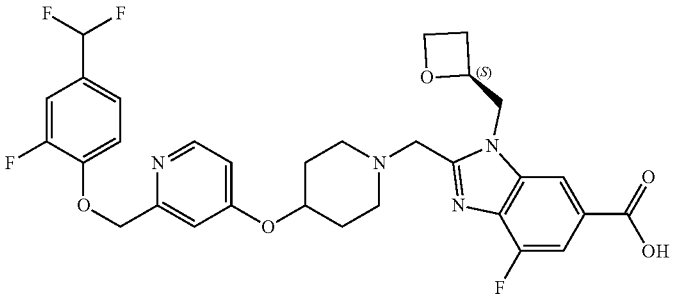 | 2-{[4-(3-{[4-(difluoromethyl)-2-fluorophenoxy]methyl}phenoxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 303 | 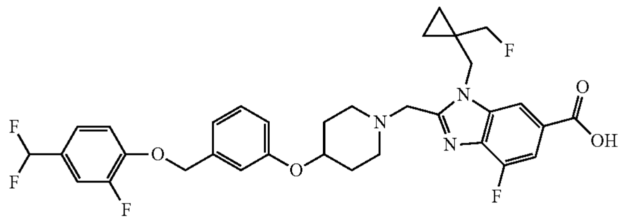 [SMILES: O=C(O)c1cc(F)c2nc(CN3CCC(Oc4cccc(COc5ccc(C(F)F)cc5F)c4)CC3)n(CC3(CF)CC3)c2c1] | 2-({4-[(2-{[4-(difluoromethyl)-2-fluorophenoxy]methyl}pyridin-4-yl)oxy]piperidin-1-yl}methyl)-4-fluoro-1-{[(2S)-oxetan-2-yl]methyl}-1H-1,3-benzodiazole-6-carboxylic acid |
| 304 | 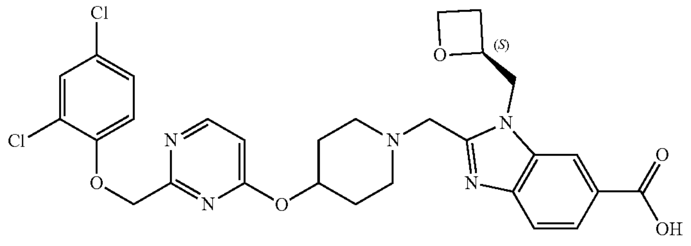 | (S)-2-((4-((2-((2,4-Dichlorophenoxy)methyl)pyrimidin-4-yl)oxy)piperidin-1-yl)methyl)-1-(oxetan-2-ylmethyl)-1H-benzo[d]imidazole-6-carboxylic acid |
| 305 | 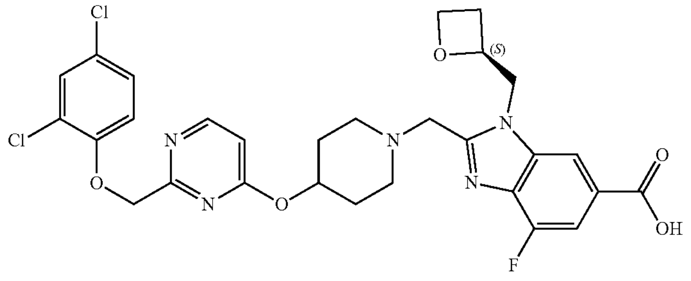 | 2-{[4-({2-[(2,4-dichlorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |
| 306 | 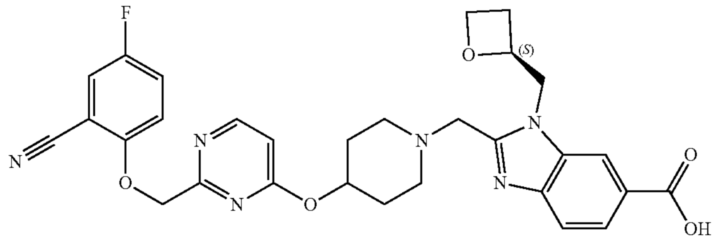 | 2-{[4-({2-[(2,4-dichlorophenoxy)methyl]pyrimidin-4-yl}oxy)piperidin-1-yl]methyl}-4-fluoro-1-{[(2S)-oxetan-2-yl]methyl}-1H-1,3-benzodiazole-6-carboxylic acid |
| 307 | 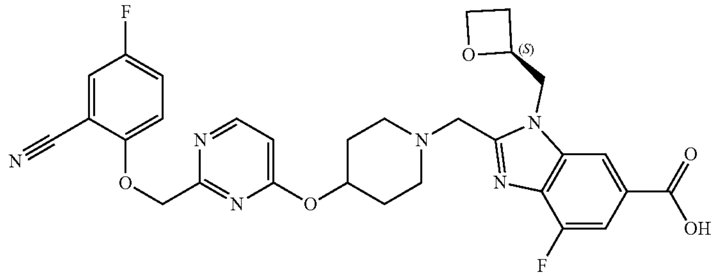 | 2-{[4-({2-[(2-cyano-4-fluorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 308 | 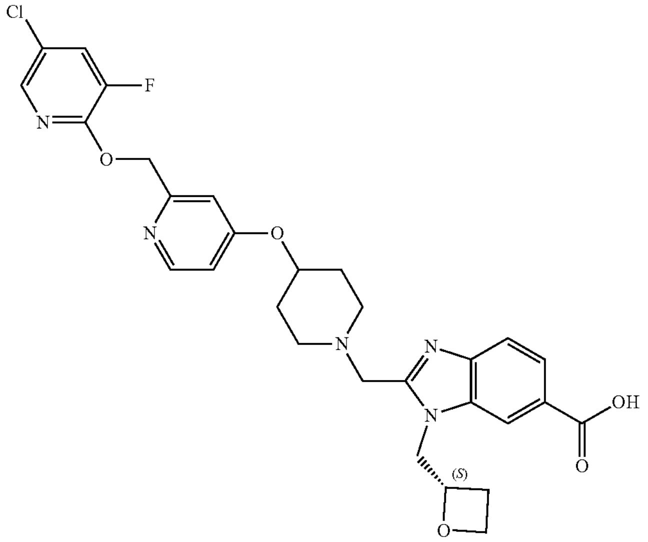 | 2-{[4-({2-[(2-cyano-4-fluorophenoxy)methyl]pyrimidin-4-yl}oxy)piperidin-1-yl]methyl}-4-fluoro-1-{[(2S)-oxetan-2-yl]methyl}-1H-1,3-benzodiazole-6-carboxylic acid |
| 309 | 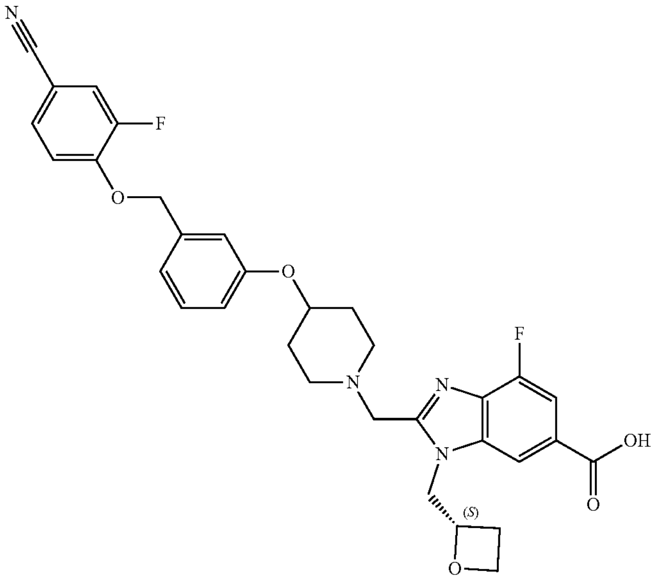 | 2-({4-[(2-{[(5-chloro-3-fluoropyridin-2-yl)oxy]methyl}pyridin-4-yl)oxy]piperidin-1-yl}methyl)-1-{[(2S)-oxetan-2-yl]methyl}-1H-1,3-benzodiazole-6-carboxylic acid |
| 310 | 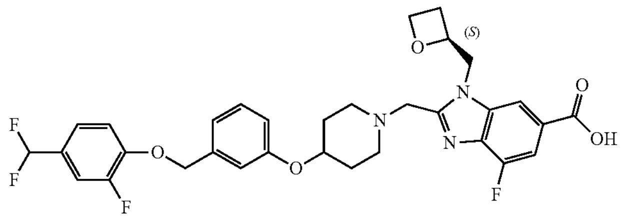 | 2-[(4-{3-[(4-cyano-2-fluorophenoxy)methyl]phenoxy}piperidin-1-yl)methyl]-4-fluoro-1-{[(2S)-oxetan-2-yl]methyl}-1H-1,3-benzodiazole-6-carboxylic acid |
| 311 | 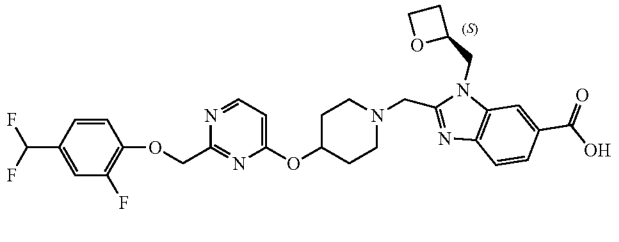 | 2-{[4-(3-{[4-(difluoromethyl)-2-fluorophenoxy]methyl}phenoxy)piperidin-1-yl]methyl}-4-fluoro-1-{[(2S)-oxetan-2-yl]methyl}-1H-1,3-benzodiazole-6-carboxylic acid |

-continued

| Compound | Structure | IUPAC |
|---|---|---|
| 312 | 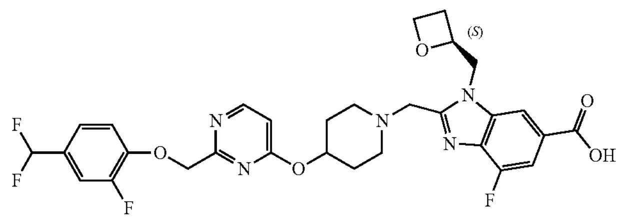 | 2-({4-[(2-{[4-(difluoromethyl)-2-fluorophenoxy]methyl}pyrimidin-4-yl)oxy]piperidin-1-yl}methyl)-1-{[(2S)-oxetan-2-yl]methyl}-1H-1,3-benzodiazole-6-carboxylic acid |
| 313 | 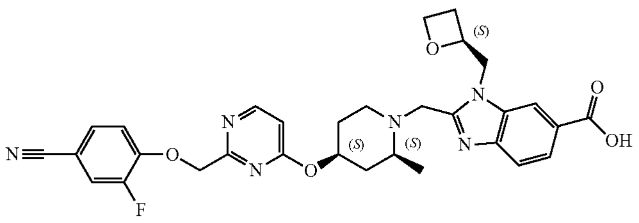 | 2-(((2S,4S)-4-((2-((4-Cyano-2-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid |
| 314 | 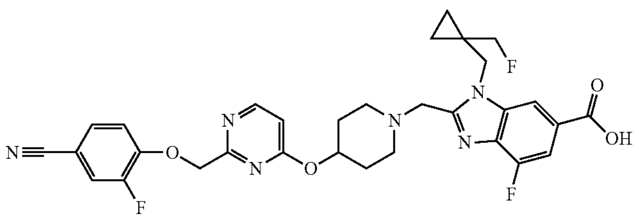 [SMILES: N#Cc1ccc(OCc2nccc(OC3CCN(Cc4nc5c(F)cc(C(=O)O)cc5n4CC4(CF)CC4)CC3)n2)c(F)c1] | 2-{[(2S,4S)-4-({2-[(4-cyano-2-fluorophenoxy)methyl]pyrimidin-4-yl}oxy)-2-methylpiperidin-1-yl]methyl}-1-{[(2S)-oxetan-2-yl]methyl}-1H-1,3-benzodiazole-6-carboxylic acid |
| 315 | 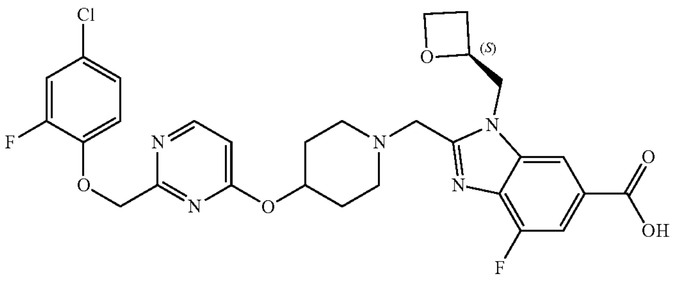 | 2-{[4-({2-[(4-cyano-2-fluorophenoxy)methyl]pyrimidin-4-yl}oxy)piperidin-1-yl]methyl}-4-fluoro-1-{[1-(fluoromethyl)cyclopropyl]methyl}-1H-1,3-benzodiazole-6-carboxylic acid |

-continued
| Compound | Structure | IUPAC |
|---|---|---|
| 316 | 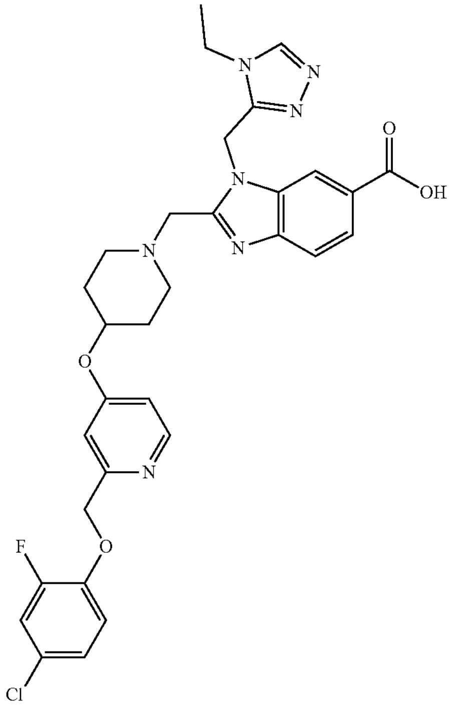 [SMILES: CCn1cnnc1Cn1c(CN2CCC(Oc3ccnc(COc4ccc(Cl)cc4F)c3)CC2)nc2ccc(C(=O)O)cc21] | 2-{[4-({2-[(4-chloro-2-fluorophenoxy)methyl]pyrimidin-4-yl}oxy)piperidin-1-yl]methyl}-4-fluoro-1-{[(2S)-oxetan-2-yl]methyl}-1H-1,3-benzodiazole-6-carboxylic acid |
| 317 | 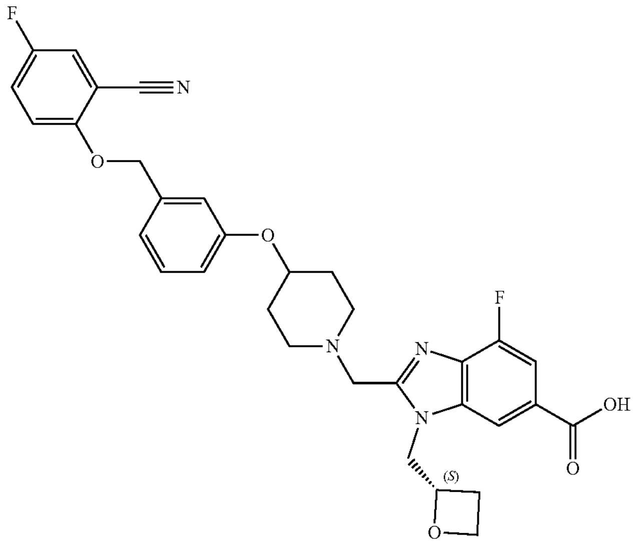 | 2-{[4-({2-[(4-chloro-2-fluorophenoxy)methyl]pyridin-4-yl}oxy)piperidin-1-yl]methyl}-1-[(4-ethyl-4H-1,2,4-triazol-3-yl)methyl]-1H-1,3-benzodiazole-6-carboxylic acid |

-continued

| Compound | Structure | IUPAC |
|---|---|---|
| 318 | 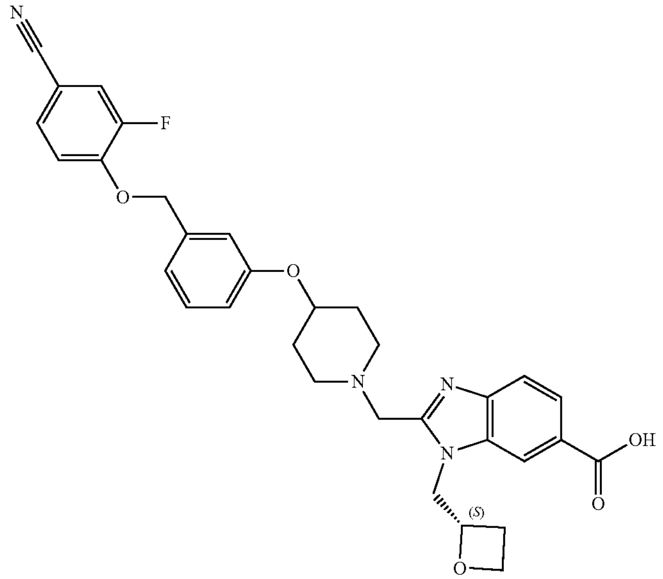 | 2-[(4-{3-[(2-cyano-4-fluorophenoxy)methyl] phenoxy}piperidin-1-yl)methyl]-4-fluoro-1-{[(2S)-oxetan-2-yl]methyl}-1H-1,3-benzodiazole-6-carboxylic acid |
| 319 | 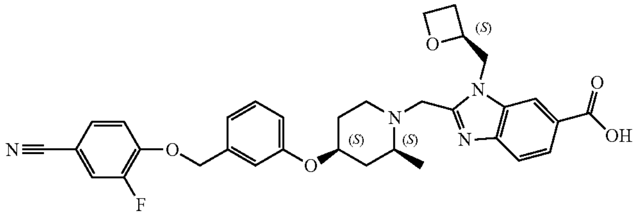 | 2-[(4-{3-[(4-cyano-2-fluorophenoxy)methyl] phenoxy}piperidin-1-yl)methyl]-1-{[(2S)-oxetan-2-yl]methyl}-1H-1,3-benzodiazole-6-carboxylic acid |
| 320 | 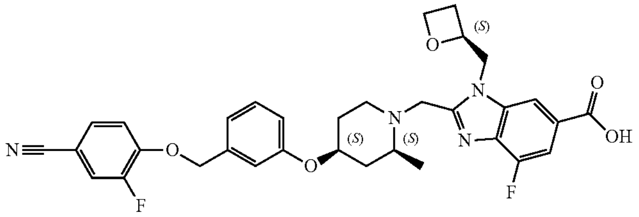 | 2-{[(2S,4S)-4-{3-[(4-cyano-2-fluorophenoxy) methyl]phenoxy}-2-methylpiperidin-1-yl]methyl}-1-{[(2S)-oxetan-2-yl]methyl}-1H-1,3-benzodiazole-6-carboxylic acid |
| 321 | 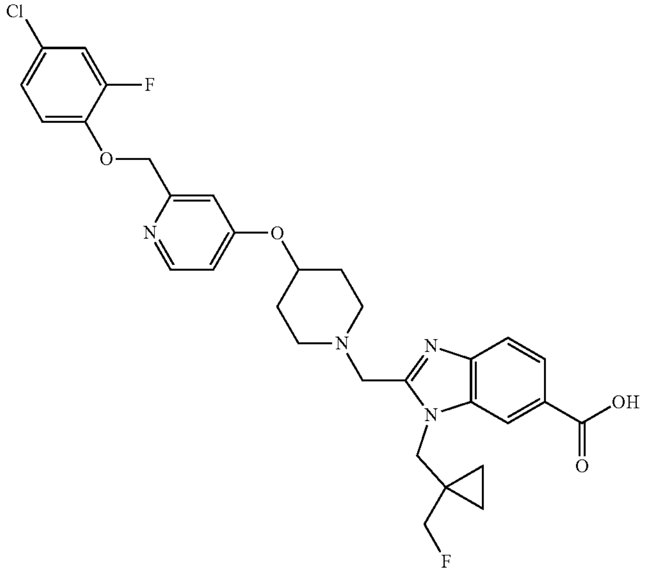 [SMILES: O=C(O)c1ccc2nc(CN3CCC(Oc4ccnc(COc5ccc(Cl)cc5F)c4)CC3)n(CC3(CF)CC3)c2c1] | 2-{[(2S,4S)-4-{3-[(4-cyano-2-fluorophenoxy) methyl]phenoxy}-2-methylpiperidin-1-yl]methyl}-4-fluoro-1-{[(2S)-oxetan-2-yl]methyl}-1H-1,3-benzodiazole-6-carboxylic acid |

-continued

| Compound | Structure | IUPAC |
|---|---|---|
| 322 | 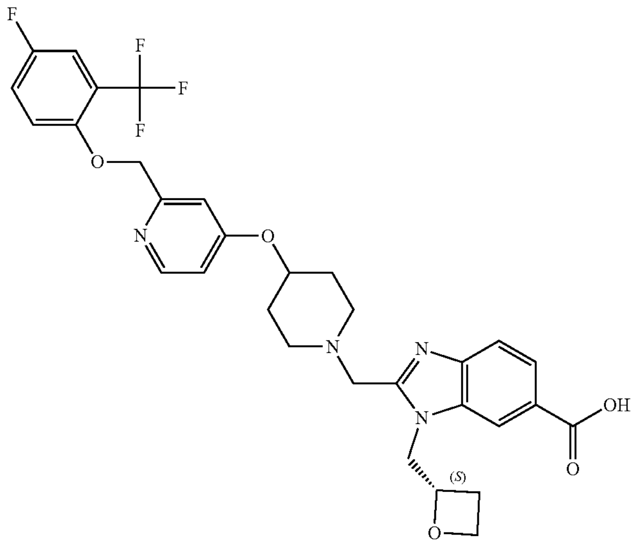 | 2-{[4-({2-[(4-chloro-2-fluorophenoxy)methyl] pyridin-4-yl}oxy)piperidin-1-yl]methyl}-1-{[1-(fluoromethyl)cyclopropyl] methyl}-1H-1,3-benzodiazole-6-carboxylic acid |
| 323 | 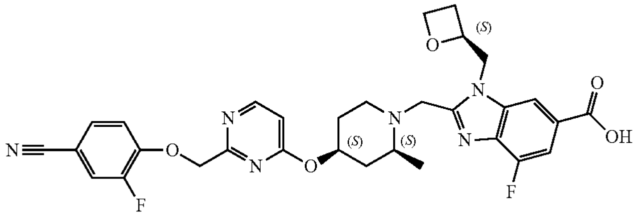 | 2-({4-[(2-{[4-fluoro-2-(trifluoromethyl)phenoxy] methyl}pyridin-4-yl)oxy] piperidin-1-yl}methyl)-1-{[(2S)-oxetan-2-yl] methyl}-1H-1,3-benzodiazole-6-carboxylic acid |
| 324 | 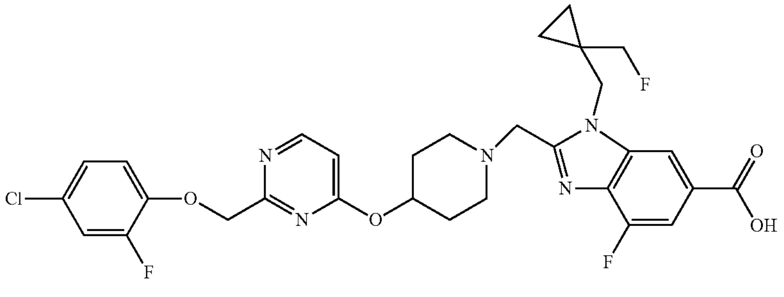 [SMILES: O=C(O)c1cc(F)c2nc(CN3CCC(Oc4ccnc(COc5ccc(Cl)cc5F)n4)CC3)n(CC3(CF)CC3)c2c1] | 2-{[(2S,4S)-4-({2-[(4-cyano-2-fluorophenoxy) methyl]pyrimidin-4-yl}oxy)-2-methylpiperidin-1-yl]methyl}-4-fluoro-1-{[(2S)-oxetan-2-yl]methyl}-1H-1,3-benzodiazole-6-carboxylic acid |
| 325 | 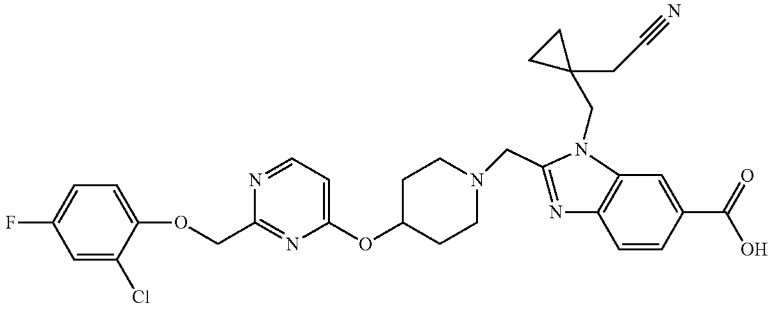 [SMILES: N#CCC1(Cn2c(CN3CCC(Oc4ccnc(COc5ccc(F)cc5Cl)n4)CC3)nc3ccc(C(=O)O)cc32)CC1] | 2-{[4-({2-[(4-chloro-2-fluorophenoxy) methyl]pyrimidin-4-yl}oxy)piperidin-1-yl]methyl}-4-fluoro-1-{[1-(fluoromethyl) cyclopropyl]methyl}-1H-1,3-benzodiazole-6-carboxylic acid |

-continued

| Compound | Structure | IUPAC |
|---|---|---|
| 326 | 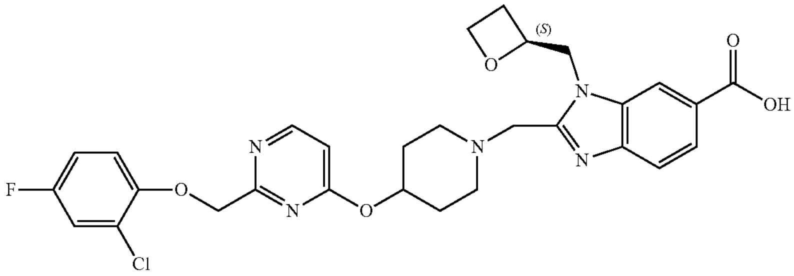 | 2-{[4-({2-[(2-chloro-4-fluorophenoxy)methyl] pyrimidin-4-yl}oxy)piperidin-1-yl]methyl}-1-{[1-(cyanomethyl)cyclopropyl] methyl}-1H-1,3-benzodiazole-6-carboxylic acid |
| 327 | 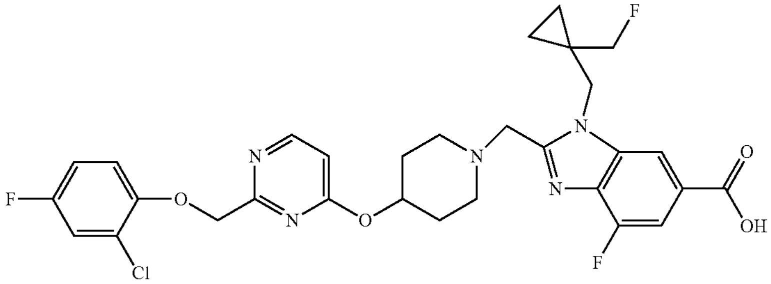 [SMILES: O=C(O)c1cc(F)c2nc(CN3CCC(Oc4ccnc(COc5ccc(F)cc5Cl)n4)CC3)n(CC3(CF)CC3)c2c1] | 2-{[4-({2-[(2-chloro-4-fluorophenoxy)methyl] pyrimidin-4-yl}oxy)piperidin-1-yl]methyl}-1-{[(2S)-oxetan-2-yl]methyl}-1H-1,3-benzodiazole-6-carboxylic acid |
| 328 | 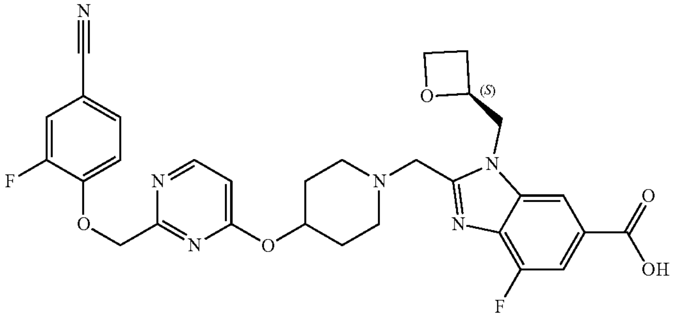 | 2-{[4-({2-[(2-chloro-4-fluorophenoxy)methyl] pyrimidin-4-yl}oxy)piperidin-1-yl]methyl}-4-fluoro-1-{[1-(fluoromethyl) cyclopropyl]methyl}-1H-1,3-benzodiazole-6-carboxylic acid |
| 329 | 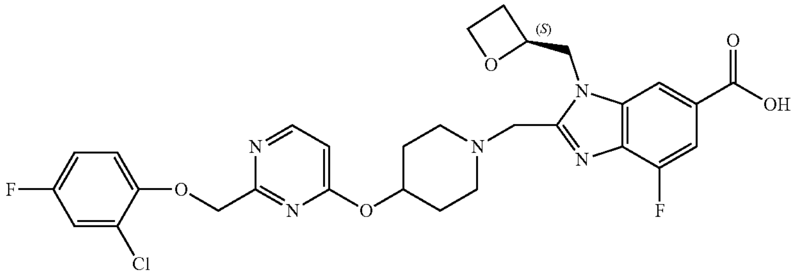 | 2-{[4-({2-[(4-cyano-2-fluorophenoxy)methyl] pyrimidin-4-yl}oxy)piperidin-1-yl]methyl}-4-fluoro-1-{[(2S)-oxetan-2-yl] methyl}-1H-1,3-benzodiazole-6-carboxylic acid |
| 330 | 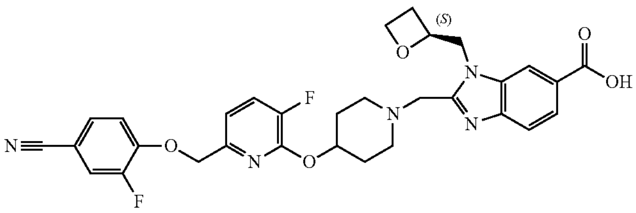 | (S)-2-((4-((6-((4-Cyano-2-fluorophenoxy)methyl)-3-fluoropyridin-2-yl)oxy)piperidin-1-yl) methyl)-1-(oxetan-2-ylmethyl)-1H-benzo [d]imidazole-6-carboxylic acid |

-continued

| Compound | Structure | IUPAC |
| --- | --- | --- |
| 331 | 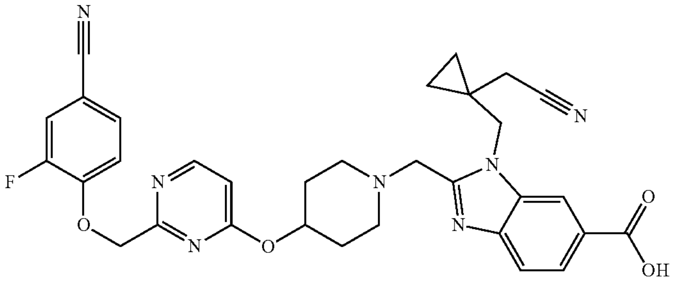 [SMILES: N#CCC1(Cn2c(CN3CCC(Oc4ccnc(COc5ccc(C#N)cc5F)n4)CC3)nc3ccc(C(=O)O)cc32)CC1] | 2-{[4-({6-[(4-cyano-2-fluorophenoxy)methyl]-3-fluoropyridin-2-yl}oxy)piperidin-1-yl]methyl}-1-{[(2S)-oxetan-2-yl]methyl}-1H-1,3-benzodiazole-6-carboxylic acid |
| 333 | 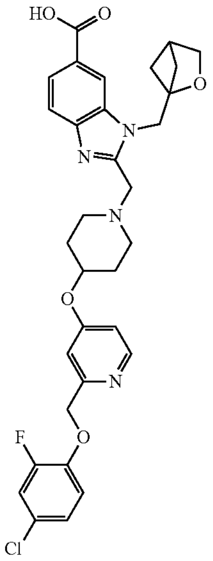 [SMILES: O=C(O)c1ccc2nc(CN3CCC(Oc4ccnc(COc5ccc(Cl)cc5F)c4)CC3)n(CC34CC(CO3)C4)c2c1] | 2-{[(3S)-3-{3-[(4-cyano-2-fluorophenoxy)methyl]phenoxy}pyrrolidin-1-yl]methyl}-4-fluoro-1-{[(2S)-oxetan-2-yl]methyl}-1H-1,3-benzodiazole-6-carboxylic acid |
| 335 | 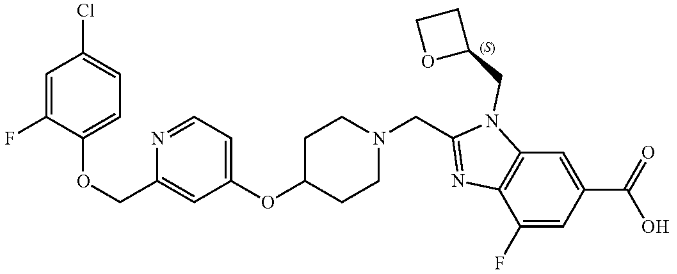 | 2-{[(3S)-3-{3-[(4-chloro-2-fluorophenoxy)methyl]phenoxy}pyrrolidin-1-yl]methyl}-1-{[(2S)-oxetan-2-yl]methyl}-1H-1,3-benzodiazole-6-carboxylic acid |
| 336 | 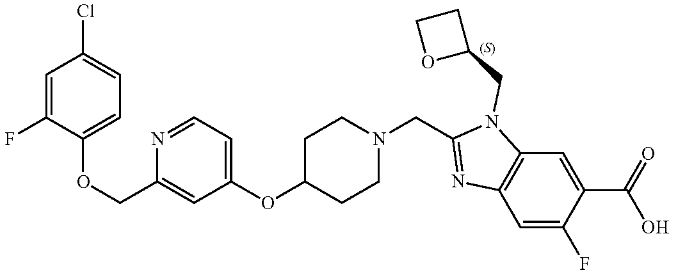 | 2-{[4-({2-[(4-chloro-2-fluorophenoxy)methyl]pyridin-4-yl}oxy)piperidin-1-yl]methyl}-4-fluoro-1-{[(2S)-oxetan-2-yl]methyl}-1H-1,3-benzodiazole-6-carboxylic acid |

-continued

| Compound | Structure | IUPAC |
|---|---|---|
| 337 | 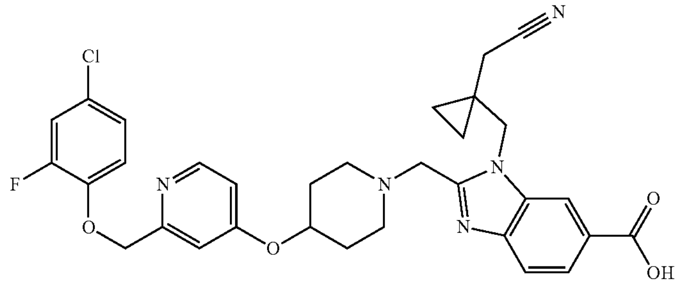 [SMILES: N#CCC1(Cn2c(CN3CCC(Oc4ccnc(COc5ccc(Cl)cc5F)c4)CC3)nc3ccc(C(=O)O)cc32)CC1] | 2-{[4-({2-[(4-chloro-2-fluorophenoxy)methyl]pyridin-4-yl}oxy)piperidin-1-yl]methyl}-5-fluoro-1-{[(2S)-oxetan-2-yl]methyl}-1H-1,3-benzodiazole-6-carboxylic acid |
| 338 | 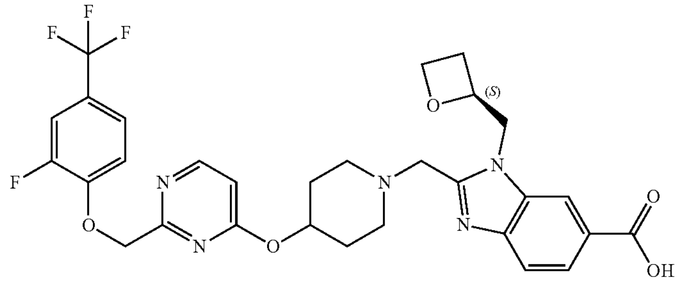 | 2-{[4-({2-[(4-chloro-2-fluorophenoxy)methyl]pyridin-4-yl}oxy)piperidin-1-yl]methyl}-1-{[1-(cyanomethyl)cyclopropyl]methyl}-1H-1,3-benzodiazole-6-carboxylic acid |
| 339 | 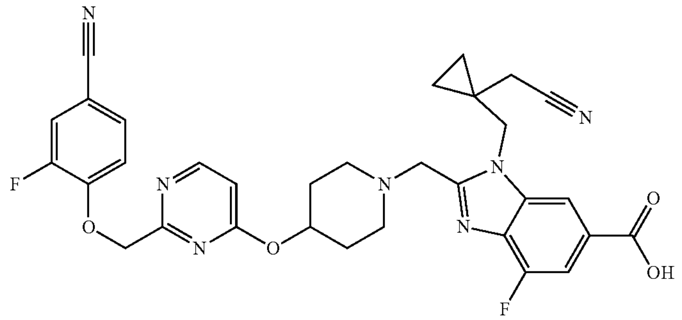 [SMILES: N#CCC1(Cn2c(CN3CCC(Oc4ccnc(COc5ccc(C#N)cc5F)n4)CC3)nc3c(F)cc(C(=O)O)cc32)CC1] | 2-({4-[(2-{[2-fluoro-4-(trifluoromethyl)phenoxy]methyl}pyrimidin-4-yl)oxy]piperidin-1-yl}methyl)-1-{[(2S)-oxetan-2-yl]methyl}-1H-1,3-benzodiazole-6-carboxylic acid |
| 340 | 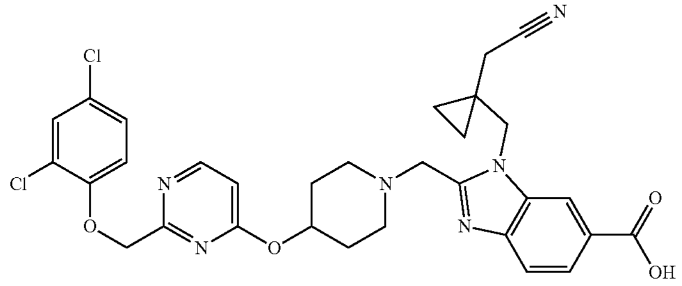 | 2-{[4-({2-[(4-cyano-2-fluorophenoxy)methyl]pyrimidin-4-yl}oxy)piperidin-1-yl]methyl}-1-{[1-(cyanomethyl)cyclopropyl]methyl}-4-fluoro-1H-1,3-benzodiazole-6-carboxylic acid |
| 341 | 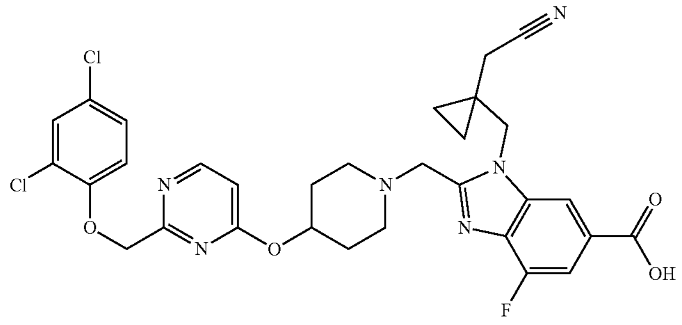 [SMILES: N#CCC1(Cn2c(CN3CCC(Oc4ccnc(COc5ccc(Cl)cc5Cl)n4)CC3)nc3c(F)cc(C(=O)O)cc32)CC1] | 1-{[1-(cyanomethyl)cyclopropyl]methyl}-2-{[4-({2-[(2,4-dichlorophenoxy)methyl]pyrimidin-4-yl}oxy)piperidin-1-yl]methyl}-1H-1,3-benzodiazole-6-carboxylic acid |

-continued

| Compound | Structure | IUPAC |
|---|---|---|
| 342 | 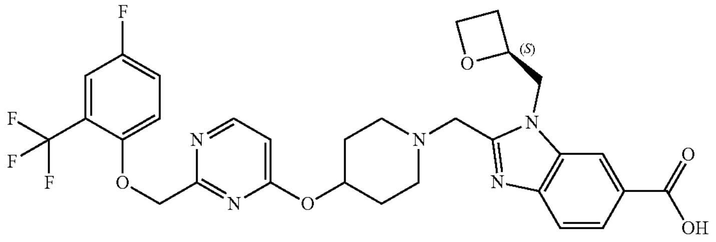 | 1-{[1-(cyanomethyl) cyclopropyl]methyl}-2-{[4-({2-[(2,4-dichlorophenoxy) methyl]pyrimidin-4-yl}oxy)piperidin-1-yl]methyl}-4-fluoro-1H-1,3-benzodiazole-6-carboxylic acid |
| 343 | 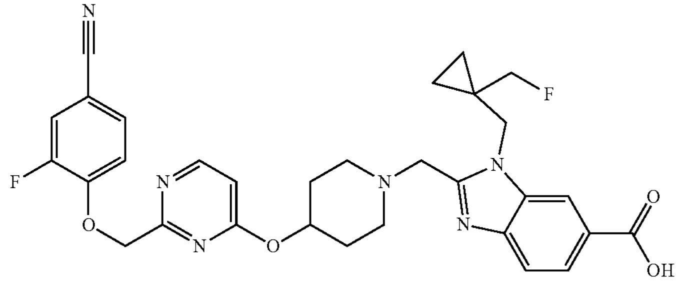 [SMILES: N#Cc1ccc(OCc2nccc(OC3CCN(Cc4nc5ccc(C(=O)O)cc5n4CC4(CF)CC4)CC3)n2)c(F)c1] | 2-({4-[(2-{[4-fluoro-2-(trifluoromethyl)phenoxy] methyl}pyrimidin-4-yl)oxy] piperidin-1-yl}methyl)-1-{[(2S)-oxetan-2-yl]methyl}-1H-1,3-benzodiazole-6-carboxylic acid |
| 344 | 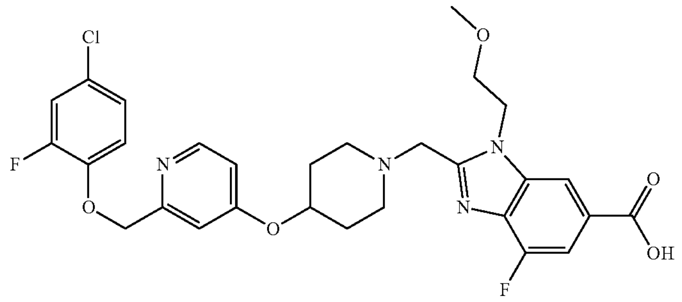 [SMILES: COCCn1c(CN2CCC(Oc3ccnc(COc4ccc(Cl)cc4F)c3)CC2)nc2c(F)cc(C(=O)O)cc21] | 2-{[4-({2-[(4-cyano-2-fluorophenoxy)methyl] pyrimidin-4-yl}oxy)piperidin-1-yl]methyl}-1-{[1-(fluoromethyl)cyclopropyl] methyl}-1H-1,3-benzodiazole-6-carboxylic acid |
| 345 | 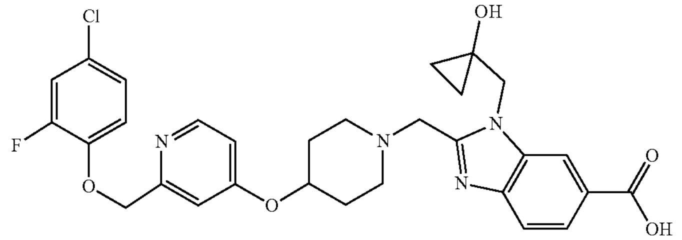 [SMILES: O=C(O)c1ccc2nc(CN3CCC(Oc4ccnc(COc5ccc(Cl)cc5F)c4)CC3)n(CC3(O)CC3)c2c1] | 2-{[4-({2-[(4-chloro-2-fluorophenoxy)methyl] pyridin-4-yl}oxy)piperidin-1-yl]methyl}-4-fluoro-1-(2-methoxyethyl)-1H-1,3-benzodiazole-6-carboxylic acid |
| 346 | 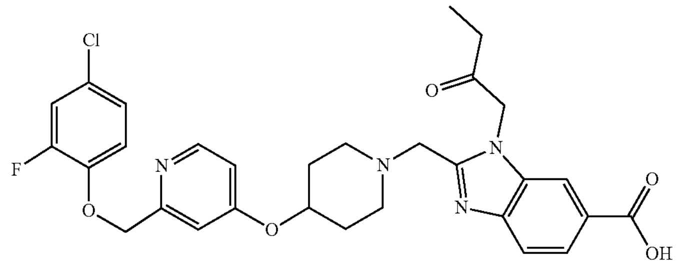 [SMILES: CCC(=O)Cn1c(CN2CCC(Oc3ccnc(COc4ccc(Cl)cc4F)c3)CC2)nc2ccc(C(=O)O)cc21] | 2-{[4-({2-[(4-chloro-2-fluorophenoxy)methyl] pyridin-4-yl}oxy)piperidin-1-yl]methyl}-1-[(1-hydroxycyclopropyl) methyl]-1H-1,3-benzodiazole-6-carboxylic acid |
| 347 | 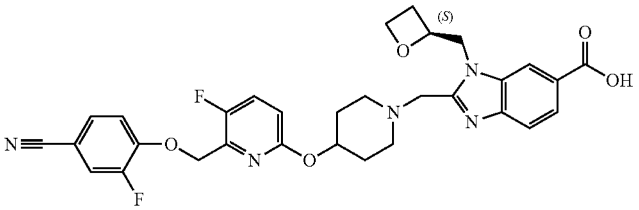 | 2-{[4-({2-[(4-chloro-2-fluorophenoxy)methyl] pyridin-4-yl}oxy)piperidin-1-yl]methyl}-1-(2-oxobutyl)-1H-1,3-benzodiazole-6-carboxylic acid |

-continued

| Compound | Structure | IUPAC |
|---|---|---|
| 348 | 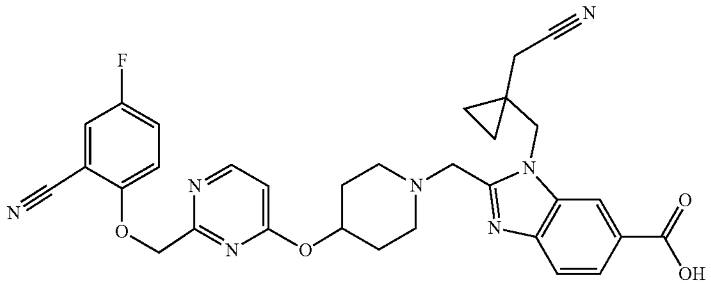 [SMILES: N#CCC1(Cn2c(CN3CCC(Oc4ccnc(COc5ccc(F)cc5C#N)n4)CC3)nc3ccc(C(=O)O)cc32)CC1] | 2-{[4-({6-[(4-cyano-2-fluorophenoxy)methyl]-5-fluoropyridin-2-yl}oxy)piperidin-1-yl]methyl}-1-{[(2S)-oxetan-2-yl]methyl}-1H-1,3-benzodiazole-6-carboxylic acid |
| 349 | 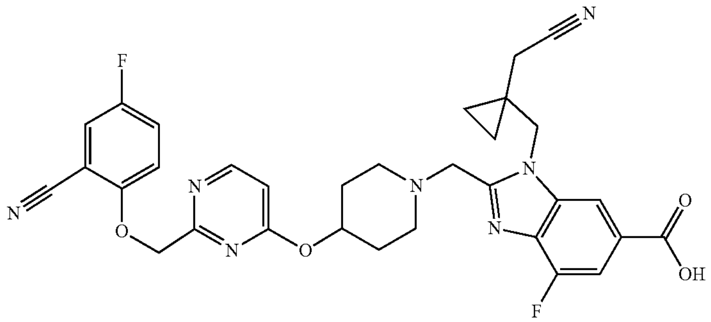 [SMILES: N#CCC1(Cn2c(CN3CCC(Oc4ccnc(COc5ccc(F)cc5C#N)n4)CC3)nc3c(F)cc(C(=O)O)cc32)CC1] | 2-{[4-({2-[(2-cyano-4-fluorophenoxy)methyl] pyrimidin-4-yl}oxy)piperidin-1-yl]methyl}-1-{[1-(cyanomethyl)cyclopropyl] methyl}-1H-1,3-benzodiazole-6-carboxylic acid |
| 352 | 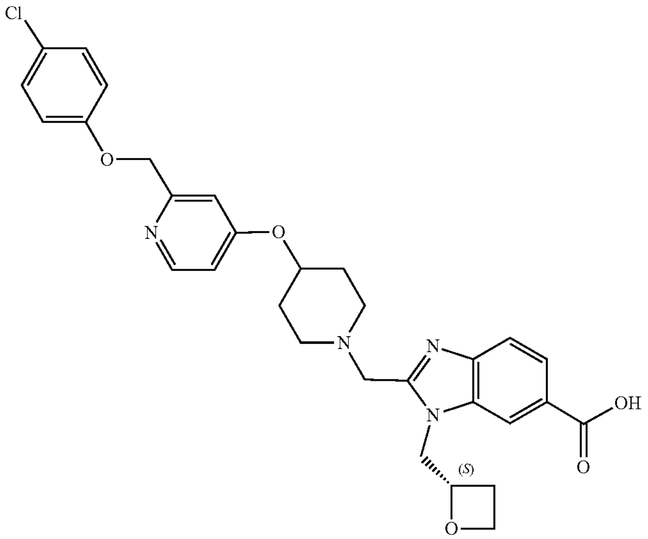 | 2-{[(3S)-3-{3-[(4-chloro-2-fluorophenoxy)methylphenoxy}pyrrolidin-1-yl]methyl}-4-fluoro-1-{[(2S)-oxetan-2-yl]methyl}-1H-1,3-benzodiazole-6-carboxylic acid |
| 353 | 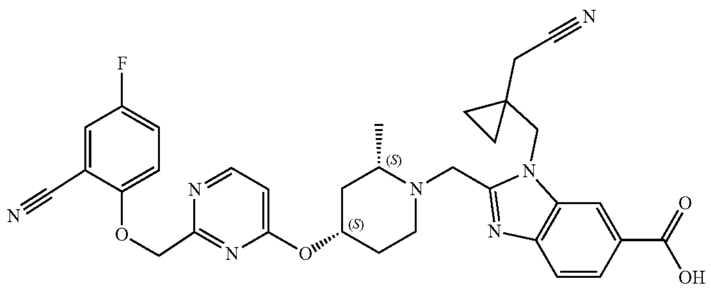 | 2-{[4-({2-[(4-chlorophenoxy)methyl] pyridin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
| --- | --- | --- |
| 354 | 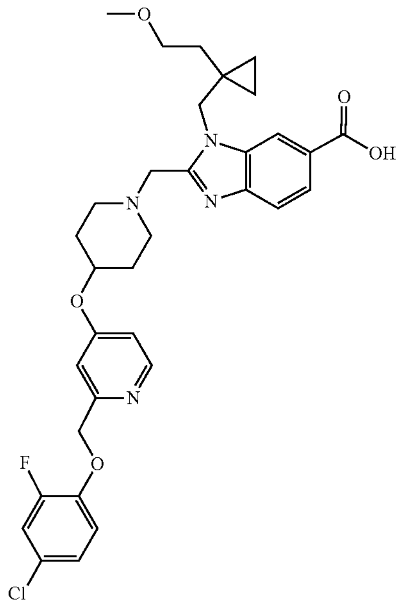 [SMILES: COCCC1(Cn2c(CN3CCC(Oc4ccnc(COc5ccc(Cl)cc5F)c4)CC3)nc3ccc(C(=O)O)cc32)CC1] | 2-{[(2S,4S)-4-({2-[(2-cyano-4-fluorophenoxy)methyl]pyrimidin-4-yl}oxy)-2-methylpiperidin-1-yl]methyl}-1-{[1-(cyanomethyl)cyclopropyl]methyl}-1H-1,3-benzodiazole-6-carboxylic acid |
| 355 | 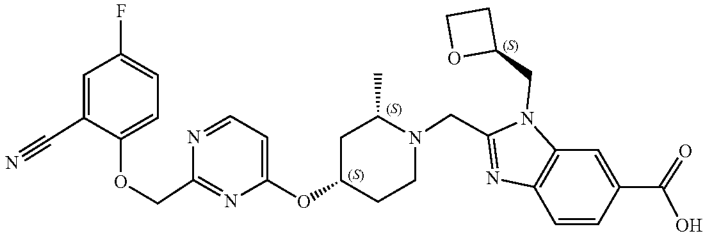 | 2-(((2S,4S)-4-((2-((2-cyano-4-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid |
| 356 | 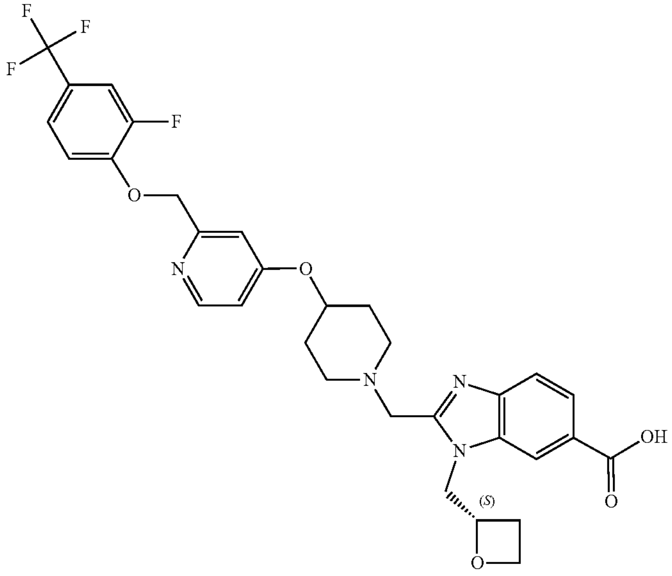 | 2-{[(2S,4S)-4-({2-[(2-cyano-4-fluorophenoxy)methyl]pyrimidin-4-yl}oxy)-2-methylpiperidin-1-yl]methyl}-1-{[(2S)-oxetan-2-yl]methyl}-1H-1,3-benzodiazole-6-carboxylic acid |

-continued
| Compound | Structure | IUPAC |
| --- | --- | --- |
| 357 | 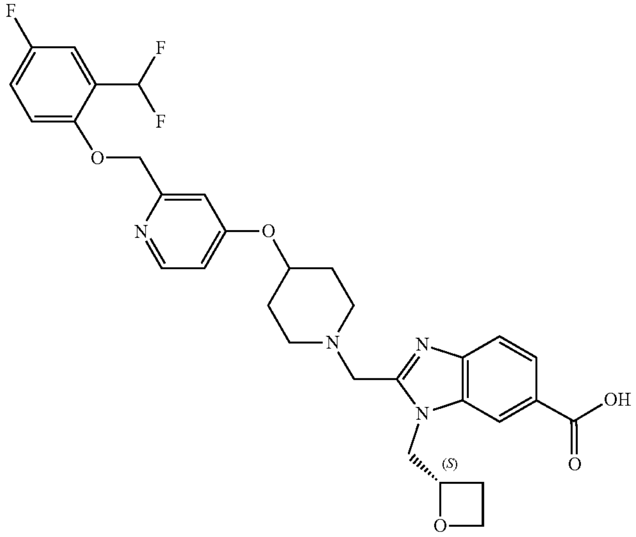 | 2-({4-[(2-{[2-fluoro-4-(trifluoromethyl)phenoxy]methyl}pyridin-4-yl)oxy]piperidin-1-yl}methyl)-1-{[(2S)-oxetan-2-yl]methyl}-1H-1,3-benzodiazole-6-carboxylic acid |
| 358 | 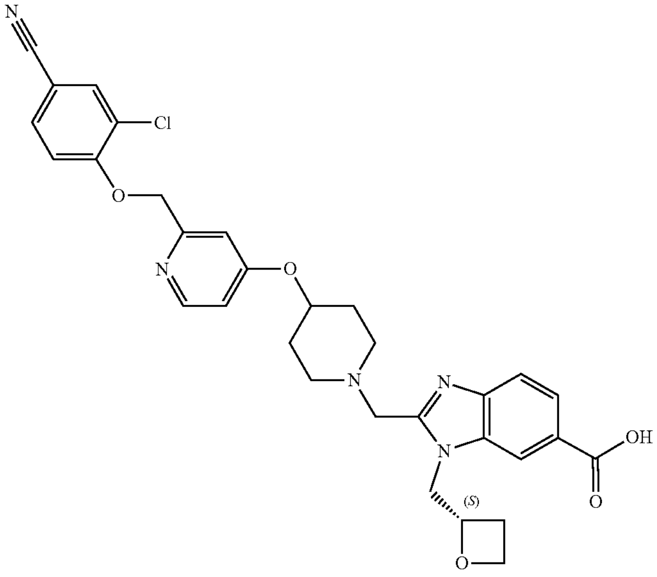 | 2-({4-[(2-{[2-(difluoromethyl)-4-fluorophenoxy]methyl}pyridin-4-yl)oxy]piperidin-1-yl}methyl)-1-{[(2S)-oxetan-2-yl]methyl}-1H-1,3-benzodiazole-6-carboxylic acid |

-continued

| Compound | Structure | IUPAC |
|---|---|---|
| 359 | 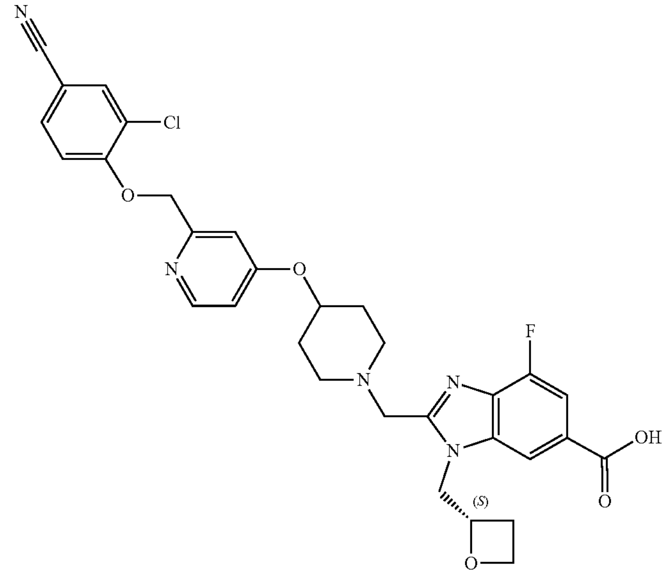 | 2-{[4-({2-[(2-chloro-4-cyanophenoxy) methyl]pyridin-4-yl}oxy)piperidin-1-yl]methyl}-1-{[(2S)-oxetan-2-yl]methyl}-1H-1,3-benzodiazole-6-carboxylic acid |
| 362 | 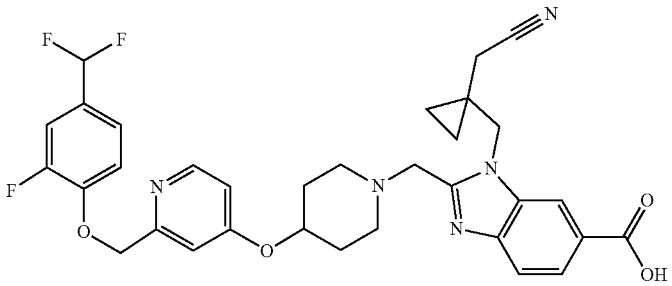 [SMILES: N#CCC1(Cn2c(CN3CCC(Oc4ccnc(COc5ccc(C(F)F)cc5F)c4)CC3)nc3ccc(C(=O)O)cc32)CC1] | 2-{[(3S)-3-({2-[(4-chloro-2-fluorophenoxy)methyl] pyrimidin-4-yl}oxy)pyrrolidin-1-yl]methyl}-4-fluoro-1-[(oxetan-2-yl)methyl]-1H-1,3-benzodiazole-6-carboxylic acid |
| 363 | 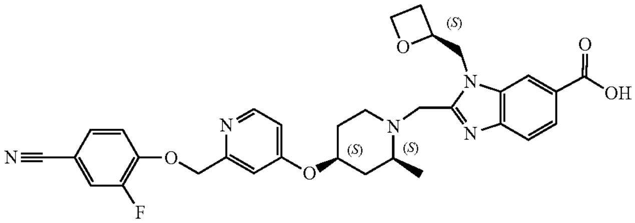 | 1-{[1-(cyanomethyl) cyclopropyl]methyl}-2-({4-[(2-{[4-(difluoromethyl)-2-fluorophenoxy]methyl} pyridin-4-yl)oxy]piperidin-1-yl}methyl)-1H-1,3-benzodiazole-6-carboxylic acid |
| 364 | 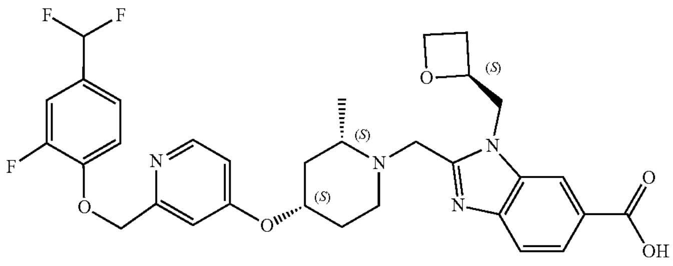 | 2-{[(2S,4S)-4-({2-[(4-cyano-2-fluorophenoxy)methyl] pyridin-4-yl}oxy)-2-methylpiperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 365 | 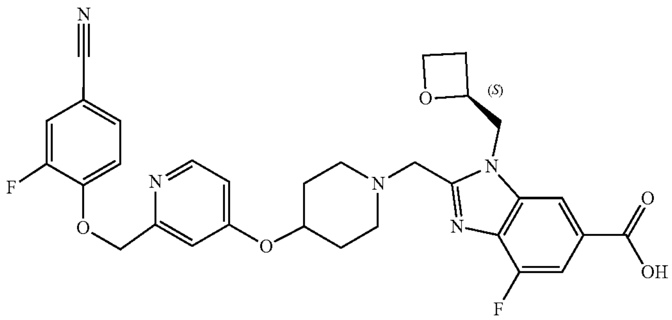 | 2-{[(2S,4S)-4-[(2-{[4-(difluoromethyl)-2-fluorophenoxy]methyl}pyridin-4-yl)oxy]-2-methylpiperidin-1-yl]methyl}-1-{[(2S)-oxetan-2-yl]methyl}-1H-1,3-benzodiazole-6-carboxylic acid |
| 366 | 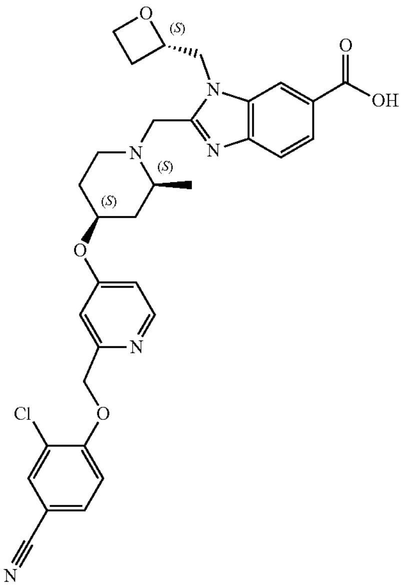 | 2-{[4-({2-[(4-cyano-2-fluorophenoxy)methyl]pyridin-4-yl}oxy)piperidin-1-yl]methyl}-4-fluoro-1-{[(2S)-oxetan-2-yl]methyl}-1H-1,3-benzodiazole-6-carboxylic acid |
| 367 | 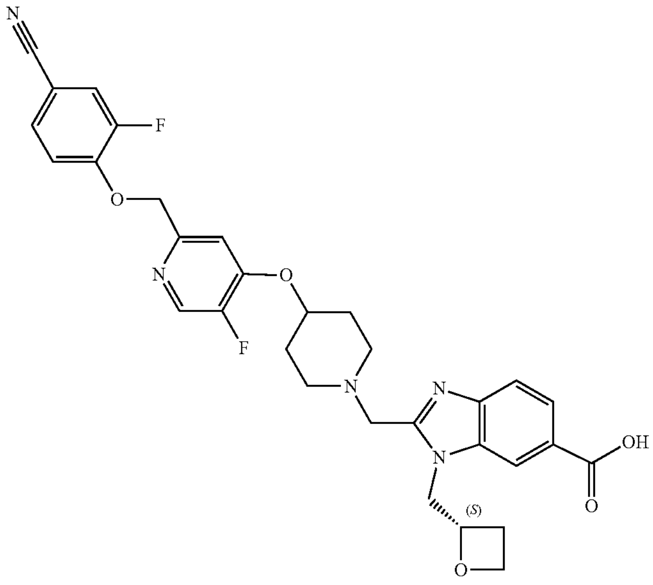 | (S)-2-((4-((2-((4-Cyano-2-fluorophenoxy)methyl)-5-fluoropyridin-4-yl)oxy)piperidin-1-yl)methyl)-1-(oxetan-2-ylmethyl)-1H-benzo[d]imidazole-6-carboxylic acid |

-continued

| Compound | Structure | IUPAC |
| --- | --- | --- |
| 368 | 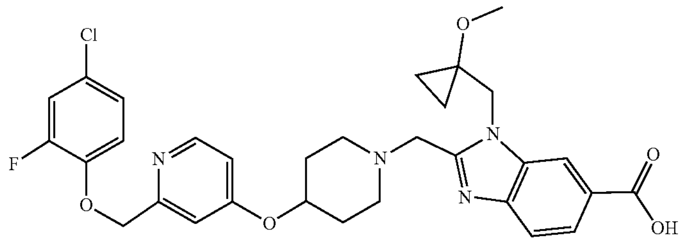 [SMILES: COC1(Cn2c(CN3CCC(Oc4ccnc(COc5ccc(Cl)cc5F)c4)CC3)nc3ccc(C(=O)O)cc32)CC1] | 2-((4-((2-((4-Chloro-2-fluorophenoxy) methyl)pyridin-4-yl)oxy)piperidin-1-yl)methyl)-1-((1-methoxycyclopropyl) methyl)-1H-benzo[d]imidazole-6-carboxylic acid |
| 369 | 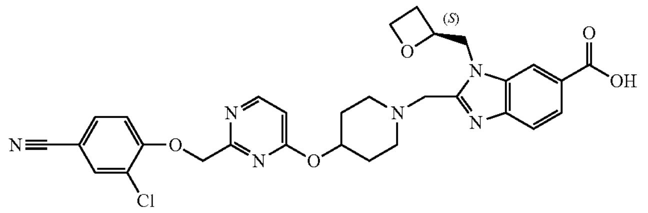 | 2-{[4-({2-[(4-chloro-2-fluorophenoxy) methyl]pyridin-4-yl}oxy)piperidin-1-yl]methyl}-1-[(1-methoxycyclopropyl) methyl]-1H-1,3-benzodiazole-6-carboxylic acid |
| 370 | 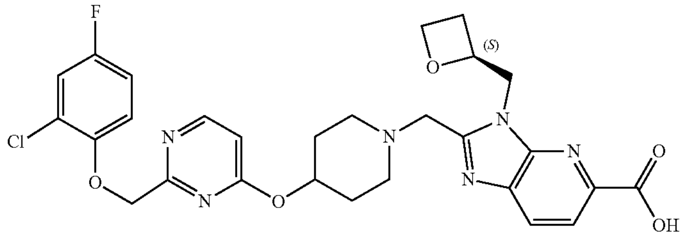 | 2-{[4-({2-[(2-chloro-4-cyanophenoxy)methyl] pyrimidin-4-yl}oxy)piperidin-1-yl]methyl}-1-{[(2S)-oxetan-2-yl]methyl}-1H-1,3-benzodiazole-6-carboxylic acid |
| 371 | 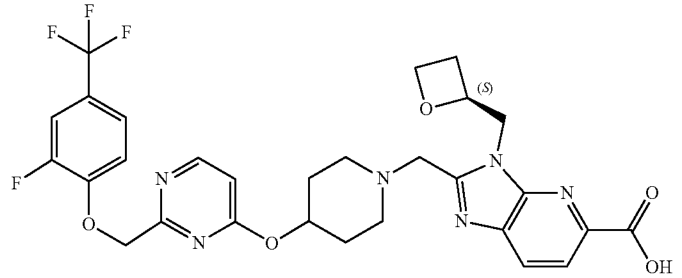 | 2-{[4-({2-[(2-chloro-4-fluorophenoxy)methyl] pyrimidin-4-yl}oxy)piperidin-1-yl] methyl}-3-{[(2S)-oxetan-2-yl]methyl}-3H-imidazo[4,5-b]pyridine-5-carboxylic acid |
| 372 | 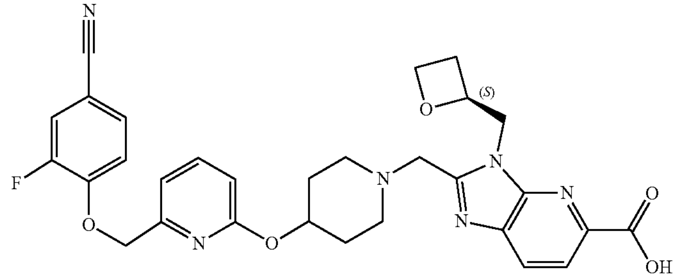 | (S)-2-((4-((6-((4-Cyano-2-fluorophenoxy) methyl)pyridin-2-yl)oxy)piperidin-1-yl) methyl)-3-(oxetan-2-ylmethyl)-3H-imidazo [4,5-b]pyridine-5-carboxylic acid |
| 373 | 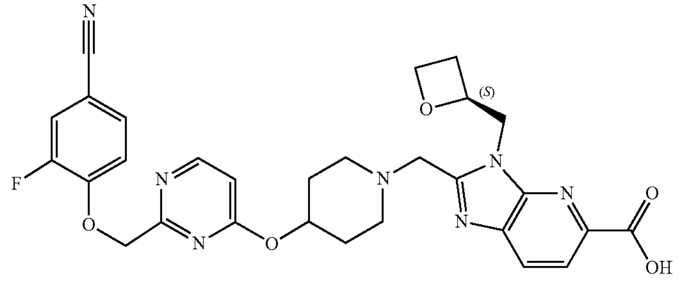 | 2-{[4-({6-[(4-cyano-2-fluorophenoxy)methyl] pyridin-2-yl}oxy)piperidin-1-yl]methyl}-3-{[(2S)-oxetan-2-yl]methyl}-3H-imidazo[4,5-b]pyridine-5-carboxylic acid |

-continued

| Compound | Structure | IUPAC |
|---|---|---|
| 374 | 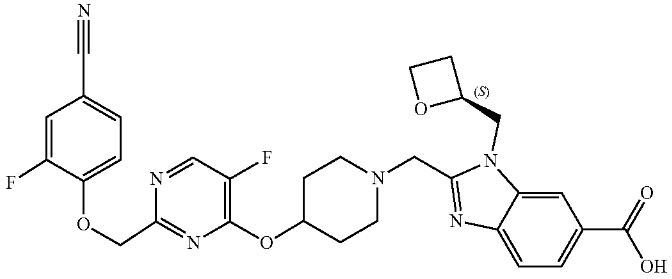 | 2-{[4-({2-[(4-cyano-2-fluorophenoxy)methyl] pyrimidin-4-yl}oxy)piperidin-1-yl]methyl}-3-{[(2S)-oxetan-2-yl]methyl}-3H-imidazo[4,5-b]pyridine-5-carboxylic acid |
| 375 | 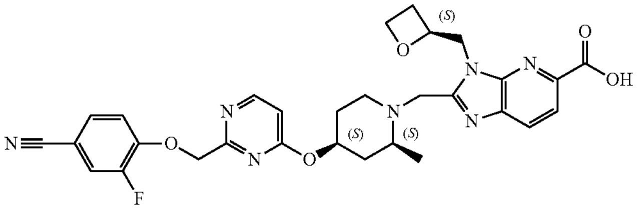 | 2-{[4-({2-[(4-cyano-2-fluorophenoxy)methyl]-5-fluoropyrimidin-4-yl}oxy)piperidin-1-yl]methyl}-1-{[(2S)-oxetan-2-yl]methyl}-1H-1,3-benzodiazole-6-carboxylic acid |
| 376 | 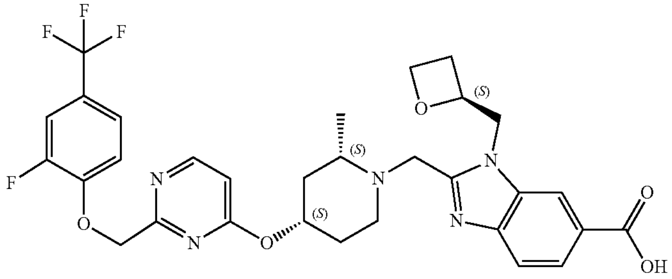 | 2-{[(2S,4S)-4-({2-[(4-cyano-2-fluorophenoxy)methyl] pyrimidin-4-yl}oxy)-2-methylpiperidin-1-yl]methyl}-3-{[(2S)-oxetan-2-yl] methyl}-3H-imidazo[4,5-b] pyridine-5-carboxylic acid |
| 377 | 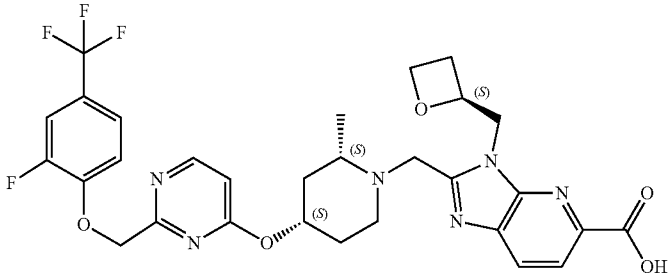 | 2-{[4-({2-[(4-cyano-2-fluorophenoxy)methyl] pyrimidin-4-yl}oxy)-2-fluorophenyl]methyl}-1-[(1-ethyl-1H-imidazol-5-yl)methyl]-1H-1,3-benzodiazole-6-carboxylic acid |
| 378 | 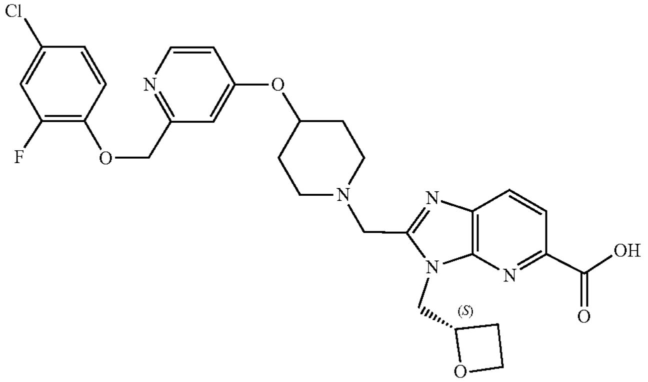 | 2-{[4-({6-[(4-cyano-2-fluorophenoxy)methyl] pyridin-2-yl}oxy)-2-fluorophenyl]methyl}-1-[(1-ethyl-1H-imidazol-5-yl)methyl]-1H-1,3-benzodiazole-6-carboxylic acid |

-continued

| Compound | Structure | IUPAC |
|---|---|---|
| 379 | 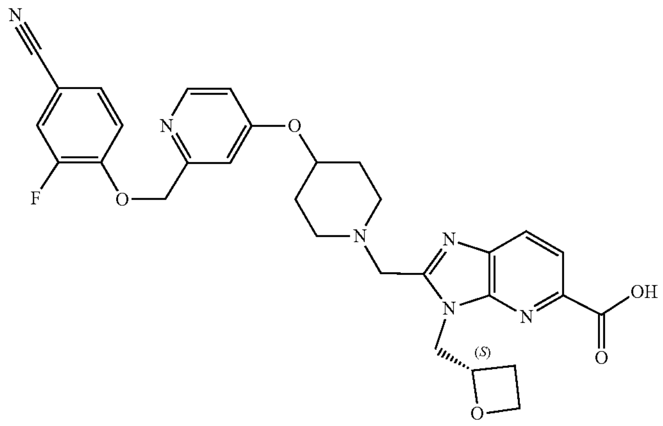 | 2-{[4-({2-[(4-chloro-2-fluorophenoxy)methyl]pyridin-4-yl}oxy)-2-fluorophenyl]methyl}-1-[(1-ethyl-1H-imidazol-5-yl)methyl]-1H-1,3-benzodiazole-6-carboxylic acid |
| 380 | 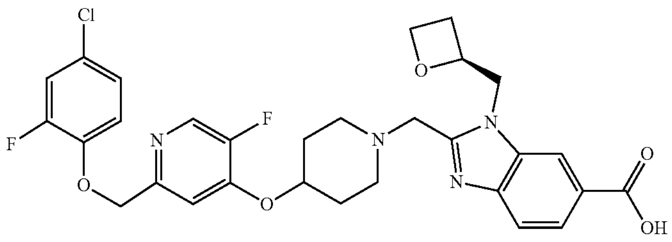 [SMILES: O=C(O)c1ccc2nc(CN3CCC(Oc4cc(COc5ccc(Cl)cc5F)ncc4F)CC3)n(C[C@@H]3CCO3)c2c1] | (S)-2-((4-((2-((4-chloro-2-fluorophenoxy)methyl)-5-fluoropyridin-4-yl)oxy)piperidin-1-yl)methyl)-1-(oxetan-2-ylmethyl)-1H-benzo[d]imidazole-6-carboxylic acid |
| 381 | 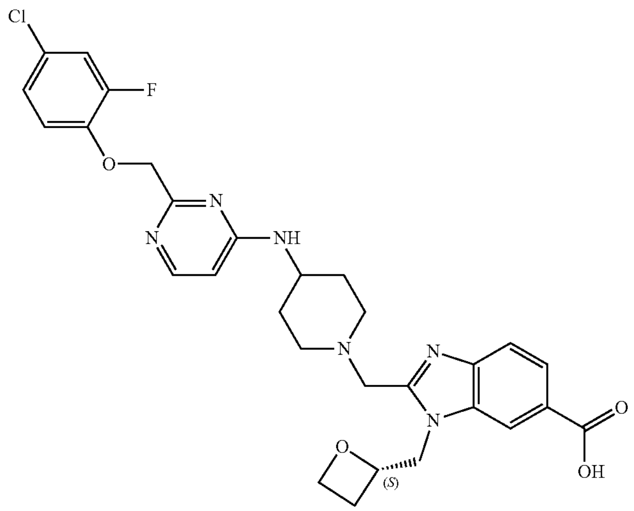 | 2-{[4-({2-[(4-chloro-2-fluorophenoxy)methyl]pyrimidin-4-yl}amino)piperidin-1-yl]methyl}-1-{[(2S)-oxetan-2-yl]methyl}-1H-1,3-benzodiazole-6-carboxylic acid |

-continued
| Compound | Structure | IUPAC |
|---|---|---|
| 382 | 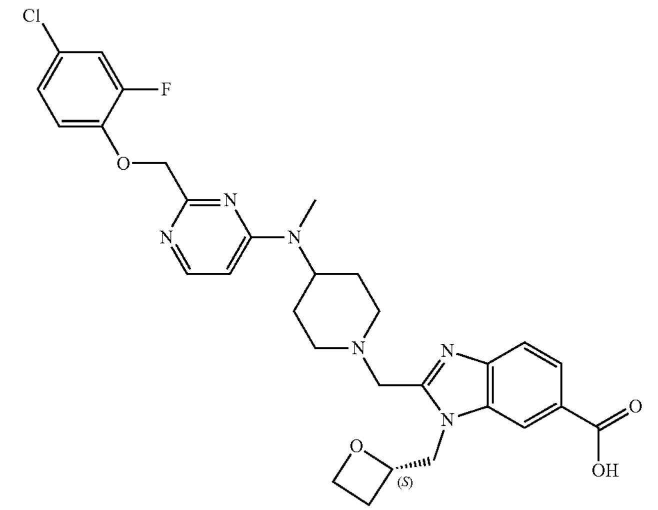 | 2-{[4-({2-[(4-chloro-2-fluorophenoxy)methyl] pyrimidin-4-yl}(methyl) amino)piperidin-1-yl] methyl}-1-{[(2S)-oxetan-2-yl]methyl}-1H-1,3-benzodiazole-6-carboxylic acid |
| 475 | 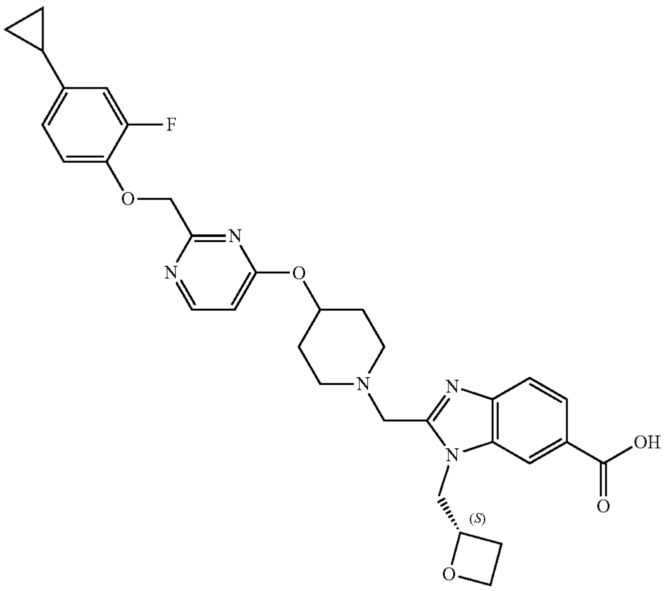 | 2-{[4-({2-[(4-cyclopropyl-2-fluorophenoxy) methyl]pyrimidin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 476 | 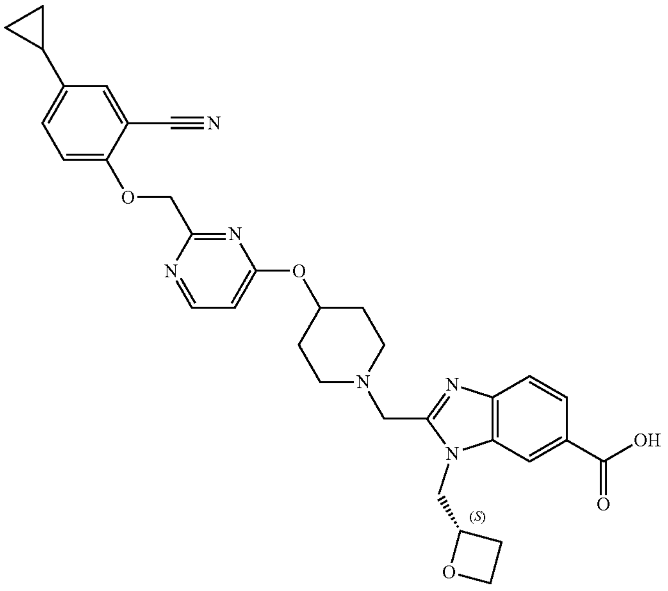 | 2-{[4-({2-[(2-cyano-4-cyclopropylphenoxy)methyl]pyrimidin-4-yl}oxy)piperidin-1-yl]methyl}-1-{[(2S)-oxetan-2-yl]methyl}-1H-1,3-benzodiazole-6-carboxylic acid |
| 477 | 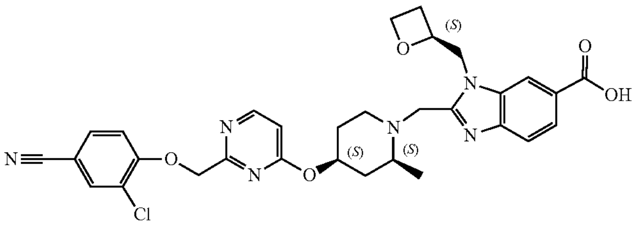 | 2-{[(2S,4S)-4-({2-[(2-chloro-4-cyanophenoxy)methyl]pyrimidin-4-yl}oxy)-2-methylpiperidin-1-yl]methyl}-1-{[(2S)-oxetan-2-yl]methyl}-1H-1,3-benzodiazole-6-carboxylic acid |
| 478 | 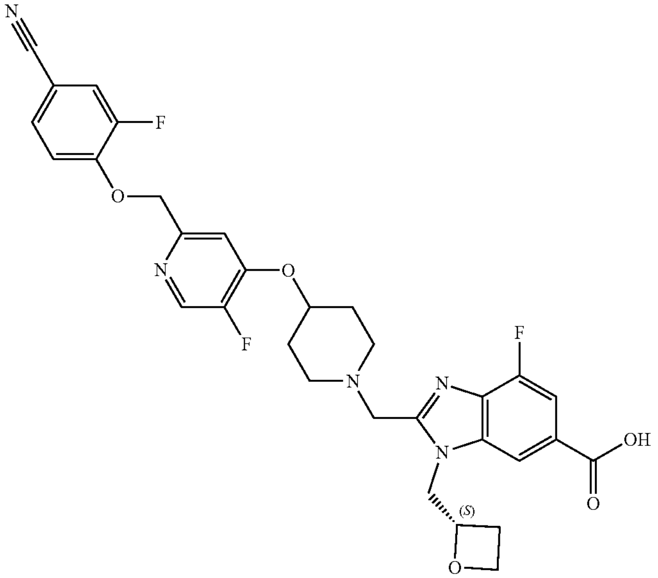 | 2-{[4-({2-[(4-cyano-2-fluorophenoxy)methyl]-5-fluoropyridin-4-yl}oxy)piperidin-1-yl]methyl}-4-fluoro-1-{[(2S)-oxetan-2-yl]methyl}-1H-1,3-benzodiazole-6-carboxylic acid |

-continued
| Compound | Structure | IUPAC |
|---|---|---|
| 479 | 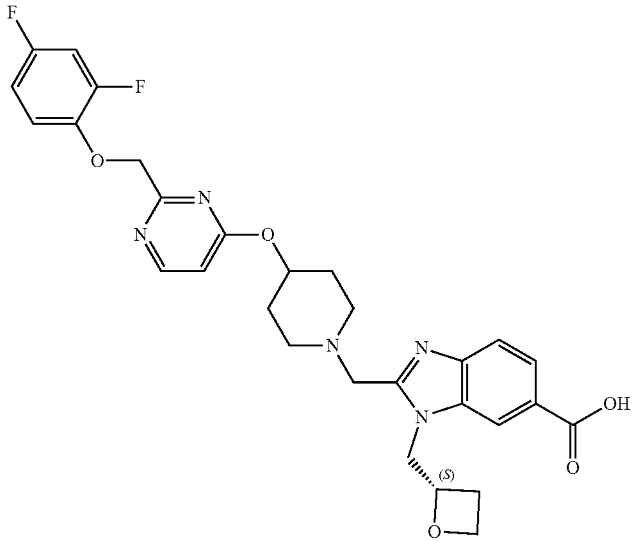 | 2-{[4-({2-[(2,4-difluorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |
| 480 | 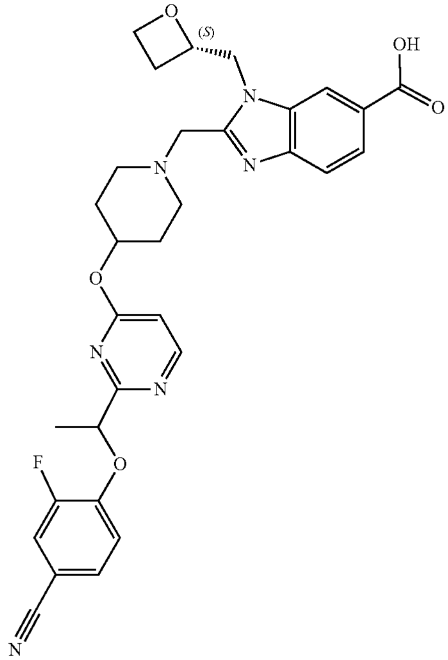 | 2-{[4-({2-[1-(4-cyano-2-fluorophenoxy)ethyl]pyrimidin-4-yl}oxy)piperidin-1-yl]methyl}-1-{[(2S)-oxetan-2-yl]methyl}-1H-1,3-benzodiazole-6-carboxylic acid |

-continued
| Compound | Structure | IUPAC |
|---|---|---|
| 481 | 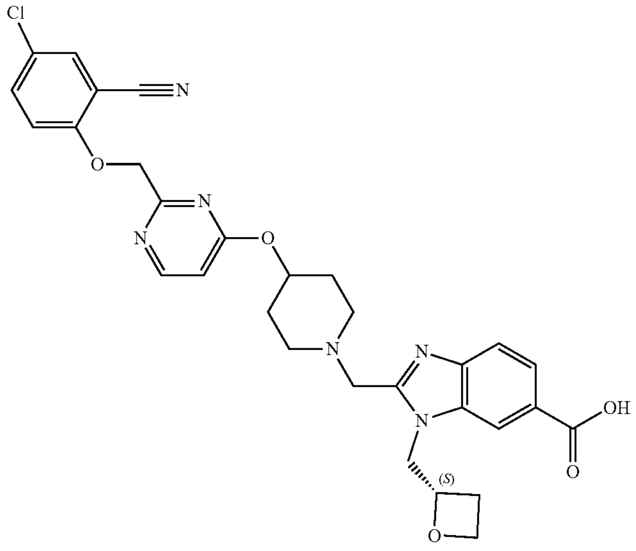 | 2-{[4-({2-[(4-chloro-2-cyanophenoxy)methyl]pyrimidin-4-yl}oxy)piperidin-1-yl]methyl}-1-{[(2S)-oxetan-2-yl]methyl}-1H-1,3-benzodiazole-6-carboxylic acid |
| 482 | 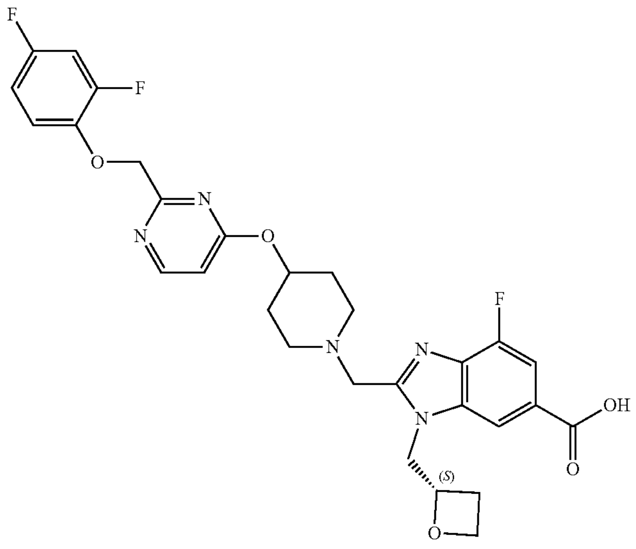 | 2-{[4-({2-[(2,4-difluorophenoxy)methyl]pyrimidin-4-yl}oxy)piperidin-1-yl]methyl}-4-fluoro-1-{[(2S)-oxetan-2-yl]methyl}-1H-1,3-benzodiazole-6-carboxylic acid |

-continued

| Compound | Structure | IUPAC |
|---|---|---|
| 483 | 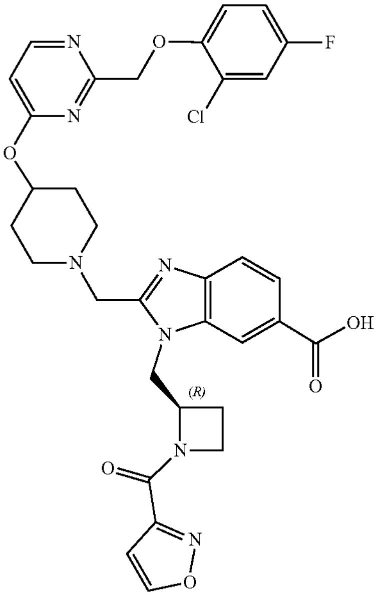 | 2-{[4-({2-[(2-chloro-4-fluorophenoxy)methyl]pyrimidin-4-yl}oxy)piperidin-1-yl]methyl}-1-{[(2R)-1-(1,2-oxazole-3-carbonyl)azetidin-2-yl]methyl}-1H-1,3-benzodiazole-6-carboxylic acid |
| 484 | 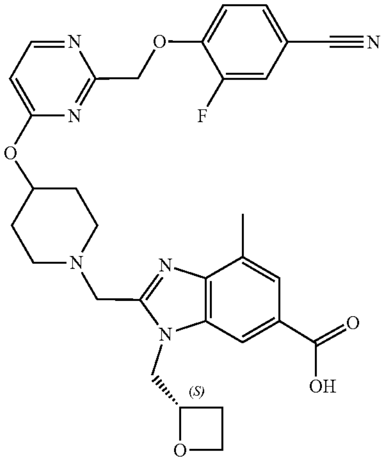 | 2-{[4-({2-[(4-cyano-2-fluorophenoxy)methyl]pyrimidin-4-yl}oxy)piperidin-1-yl]methyl}-4-methyl-1-{[(2S)-oxetan-2-yl]methyl}-1H-1,3-benzodiazole-6-carboxylic acid |
| 485 | 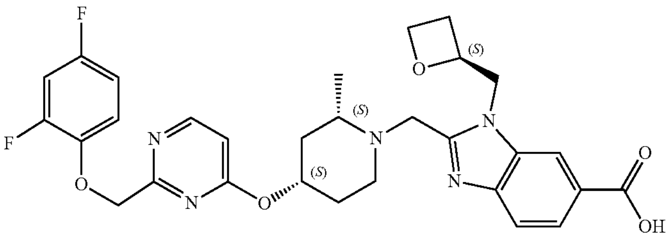 | 2-{[(2S,4S)-4-({2-[(2,4-difluorophenoxy)methyl]pyrimidin-4-yl}oxy)-2-methylpiperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 486 | 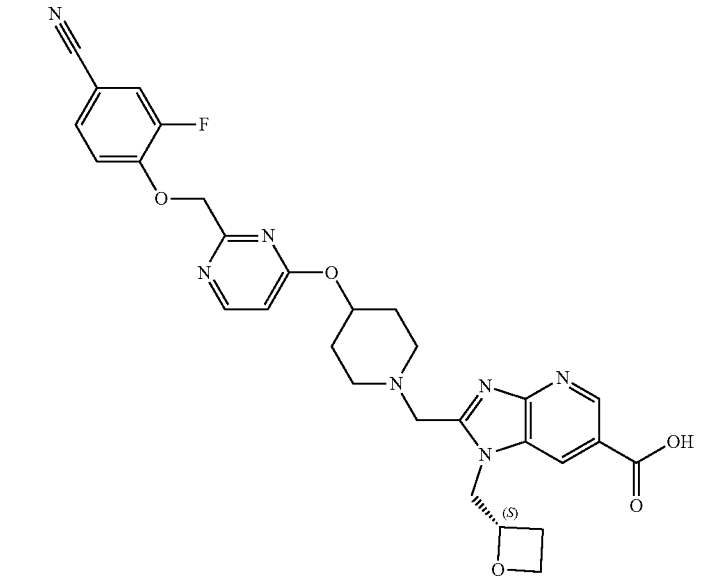 | 2-{[4-({2-[(4-cyano-2-fluorophenoxy)methyl]pyrimidin-4-yl}oxy)piperidin-1-yl]methyl}-1-{[(2S)-oxetan-2-yl]methyl}-1H-imidazo[4,5-b]pyridine-6-carboxylic acid |
| 487 | 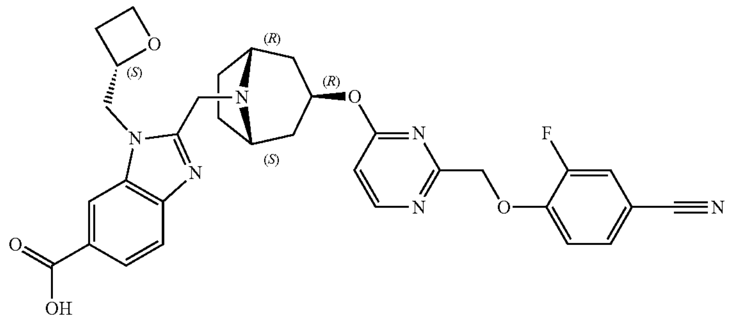 | 2-{[(1R,3S,5S)-3-({2-[(4-cyano-2-fluorophenoxy)methyl]pyrimidin-4-yl}oxy)-8-azabicyclo[3.2.1]octan-8-yl]methyl}-1-{[(2S)-oxetan-2-yl]methyl}-1H-1,3-benzodiazole-6-carboxylic acid |
| 488 | 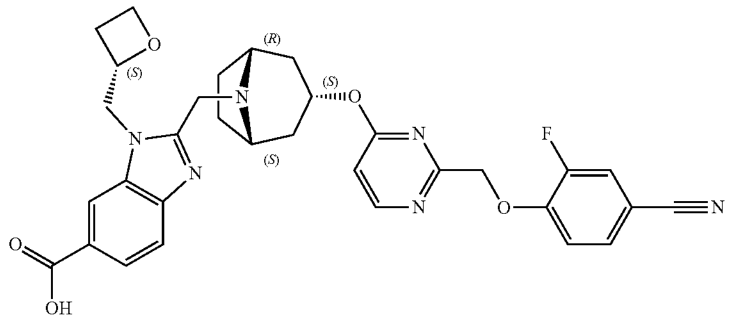 | 2-{[(1R,3R,5S)-3-({2-[(4-cyano-2-fluorophenoxy)methyl]pyrimidin-4-yl}oxy)-8-azabicyclo[3.2.1]octan-8-yl]methyl}-1-{[(2S)-oxetan-2-yl]methyl}-1H-1,3-benzodiazole-6-carboxylic acid |

-continued

| Compound | Structure | IUPAC |
|---|---|---|
| 489 | 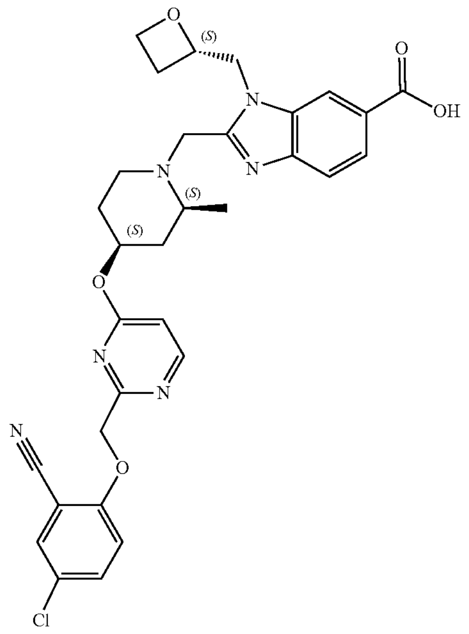 | 2-{[(2S,4S)-4-({2-[(4-chloro-2-cyanophenoxy)methyl]pyrimidin-4-yl}oxy)-2-methylpiperidin-1-yl]methyl}-1-{[(2S)-oxetan-2-yl]methyl}-1H-1,3-benzodiazole-6-carboxylic acid |
| 490 | 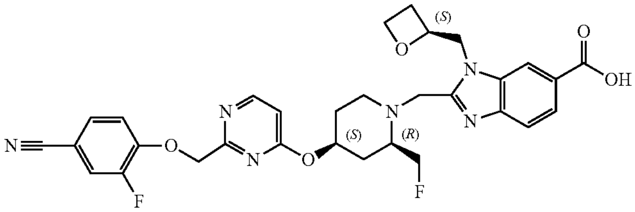 | 2-{[(2R,4S)-4-({2-[(4-cyano-2-fluorophenoxy)methyl]pyrimidin-4-yl}oxy)-2-(fluoromethyl)piperidin-1-yl]methyl}-1-{[(2S)-oxetan-2-yl]methyl}-1H-1,3-benzodiazole-6-carboxylic acid |
| 491 | 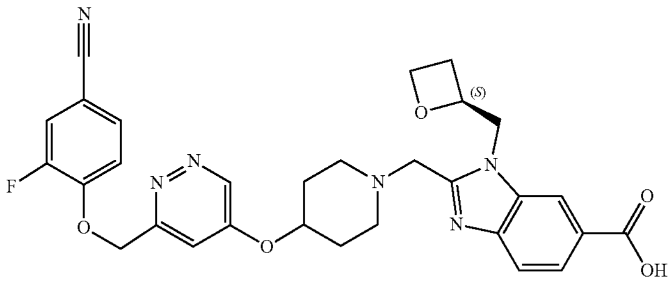 | 2-{[4-({6-[(4-cyano-2-fluorophenoxy)methyl]pyridazin-4-yl}oxy)piperidin-1-yl]methyl}-1-{[(2S)-oxetan-2-yl]methyl}-1H-1,3-benzodiazole-6-carboxylic acid |
| 492 | 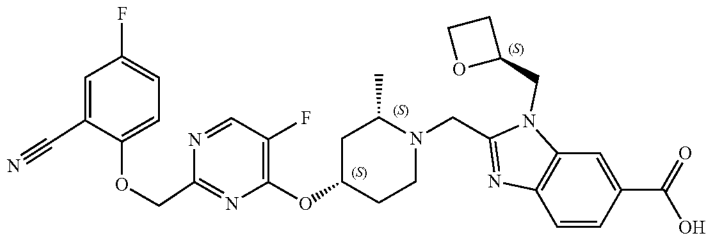 | 2-{[(2S,4S)-4-({2-[(2-cyano-4-fluorophenoxy)methyl]-5-fluoropyrimidin-4-yl}oxy)-2-methylpiperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 493 | 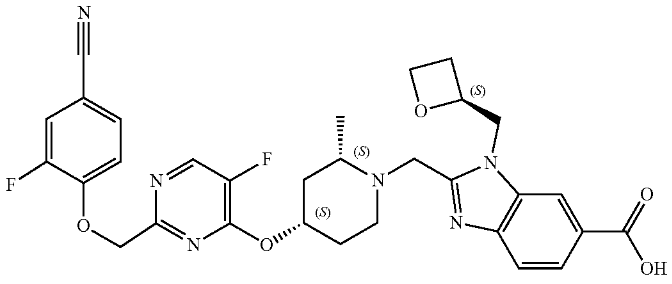 | 2-{[(2S,4S)-4-({2-[(4-cyano-2-fluorophenoxy)methyl]-5-fluoropyrimidin-4-yl}oxy)-2-methylpiperidin-1-yl]methyl}-1-{[(2S)-oxetan-2-yl]methyl}-1H-1,3-benzodiazole-6-carboxylic acid |
| 494 | 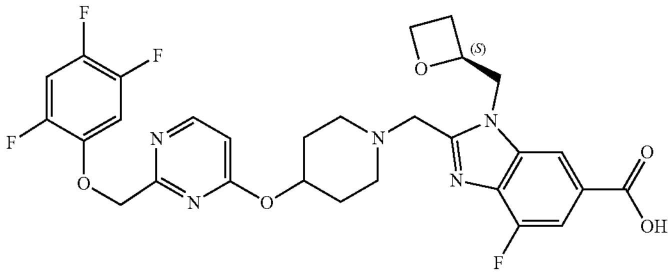 | 4-fluoro-1-{[(2S)-oxetan-2-yl]methyl}-2-{[4-({2-[(2,4,5-trifluorophenoxy)methyl]pyrimidin-4-yl}oxy)piperidin-1-yl]methyl}-1H-1,3-benzodiazole-6-carboxylic acid |
| 495 | 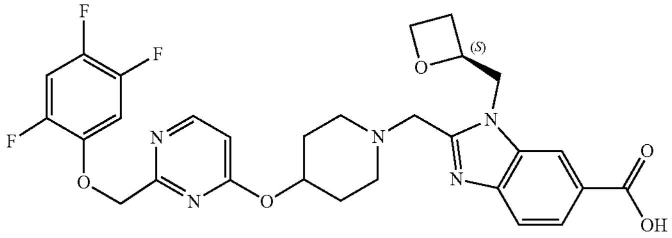 | 1-{[(2S)-oxetan-2-yl]methyl}-2-{[4-({2-[(2,4,5-trifluorophenoxy)methyl]pyrimidin-4-yl}oxy)piperidin-1-yl]methyl}-1H-1,3-benzodiazole-6-carboxylic acid |
| 496 | 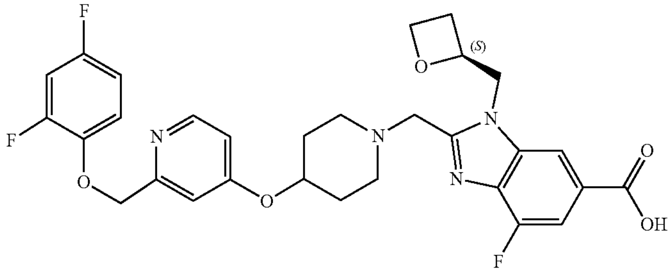 | 2-{[4-({2-[(2,4-difluorophenoxy)methyl]pyridin-4-yl}oxy)piperidin-1-yl]methyl}-4-fluoro-1-{[(2S)-oxetan-2-yl]methyl}-1H-1,3-benzodiazole-6-carboxylic acid |

-continued
| Compound | Structure | IUPAC |
|---|---|---|
| 497 | 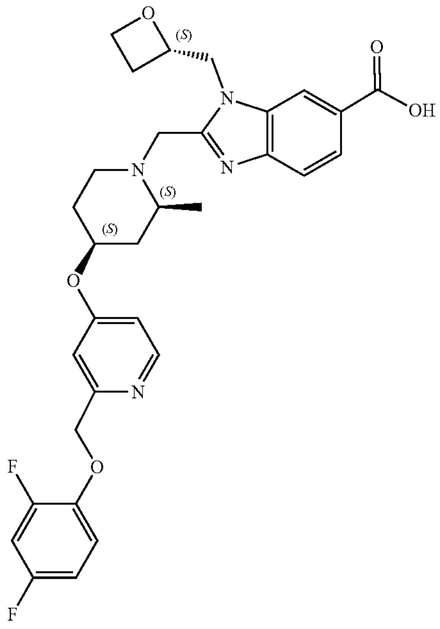 | 2-{[(2S,4S)-4-({2-[(2,4-difluorophenoxy)methyl]pyridin-4-yl}oxy)-2-methylpiperidin-1-yl]methyl}-1-{[(2S)-oxetan-2-yl]methyl}-1H-1,3-benzodiazole-6-carboxylic acid |
| 498 | 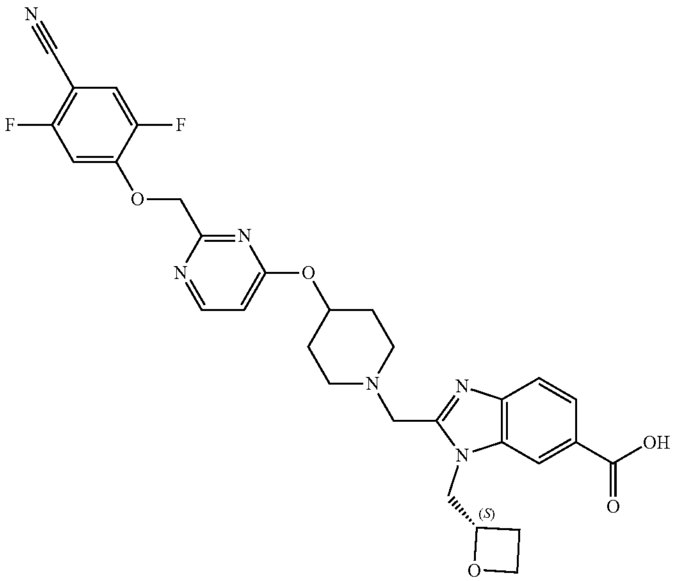 | 2-{[4-({2-[(4-cyano-2,5-difluorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 499 | 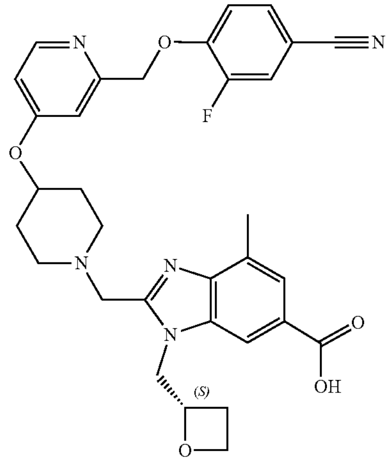 | 2-{[4-({2-[(4-cyano-2-fluorophenoxy)methyl]pyridin-4-yl}oxy)piperidin-1-yl]methyl}-4-methyl-1-{[(2S)-oxetan-2-yl]methyl}-1H-1,3-benzodiazole-6-carboxylic acid |
| 500 | 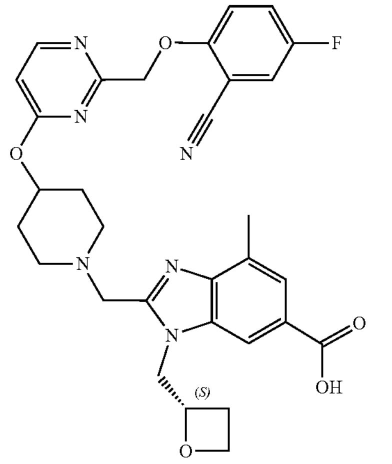 | 2-{[4-({2-[(2-cyano-4-fluorophenoxy)methyl]pyrimidin-4-yl}oxy)piperidin-1-yl]methyl}-4-methyl-1-{[(2S)-oxetan-2-yl]methyl}-1H-1,3-benzodiazole-6-carboxylic acid |
| 501 | 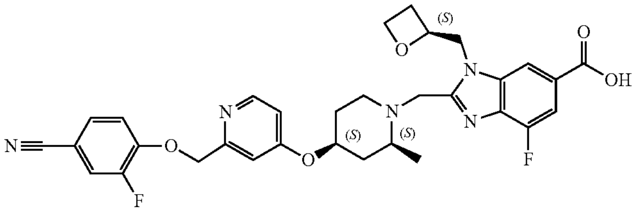 | 2-{[(2S,4S)-4-({2-[(4-cyano-2-fluorophenoxy)methyl]pyridin-4-yl}oxy)-2-methylpiperidin-1-yl]methyl}-4-fluoro-1-{[(2S)-oxetan-2-yl]methyl}-1H-1,3-benzodiazole-6-carboxylic acid |

-continued

| Compound | Structure | IUPAC |
|---|---|---|
| 502 | 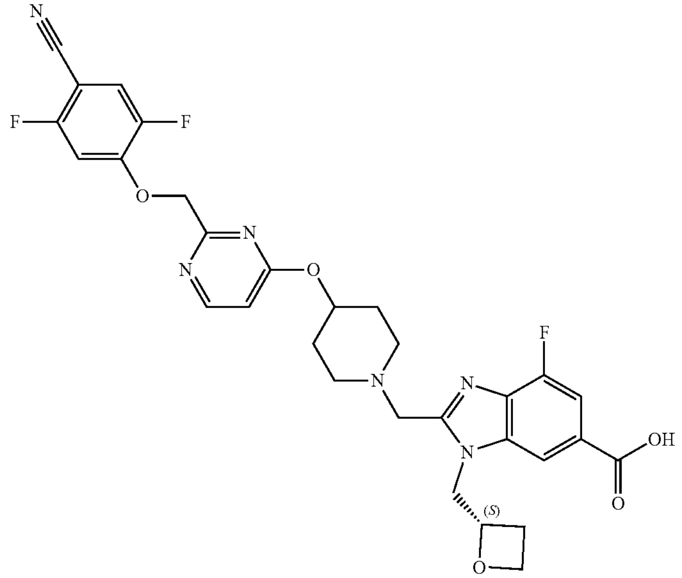 | 2-{[4-({2-[(4-cyano-2,5-difluorophenoxy)methyl]pyrimidin-4-yl}oxy)piperidin-1-yl]methyl}-4-fluoro-1-{[(2S)-oxetan-2-yl]methyl}-1H-1,3-benzodiazole-6-carboxylic acid |
| 503 | 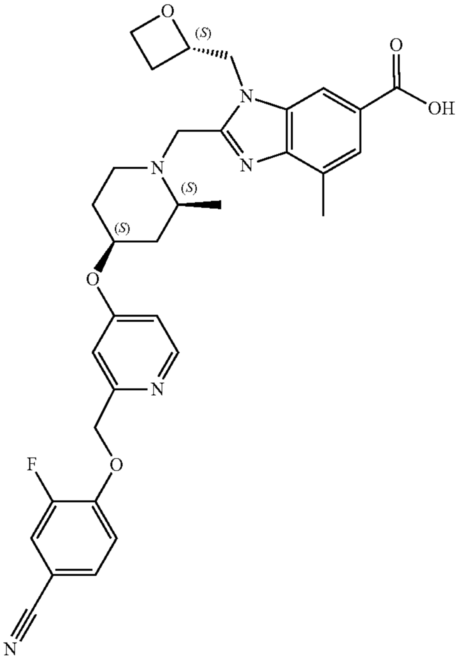 | 2-{[(2S,4S)-4-({2-[(4-cyano-2-fluorophenoxy)methyl]pyridin-4-yl}oxy)-2-methylpiperidin-1-yl]methyl}-4-methyl-1-{[(2S)-oxetan-2-yl]methyl}-1H-1,3-benzodiazole-6-carboxylic acid |
| 504 | 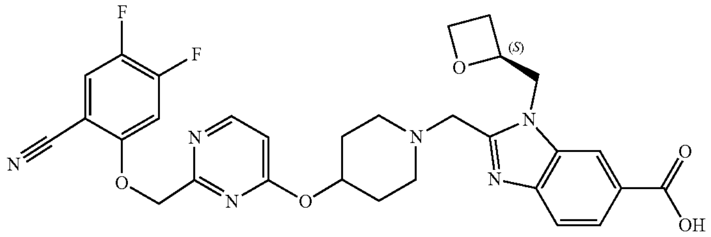 | 2-{[4-({2-[(2-cyano-4,5-difluorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 505 | 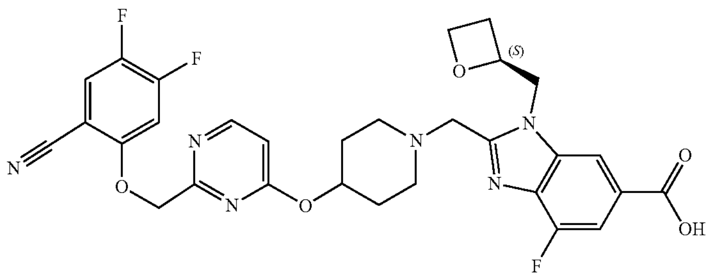 | 2-{[4-({2-[(2-cyano-4,5-difluorophenoxy)methyl] pyrimidin-4-yl}oxy) piperidin-1-yl]methyl}-4-fluoro-1-{[(2S)-oxetan-2-yl]methyl}-1H-1,3-benzodiazole-6-carboxylic acid |
| 506 | 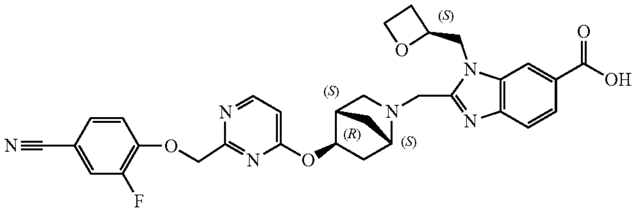 | 2-{[(1S,4S,5R)-5-({2-[(4-cyano-2-fluorophenoxy)methyl] pyrimidin-4-yl}oxy)-2-azabicyclo[2.2.1]heptan-2-yl]methyl}-1-{[(2S)-oxetan-2-yl]methyl}-1H-1,3-benzodiazole-6-carboxylic acid |
| 507 | 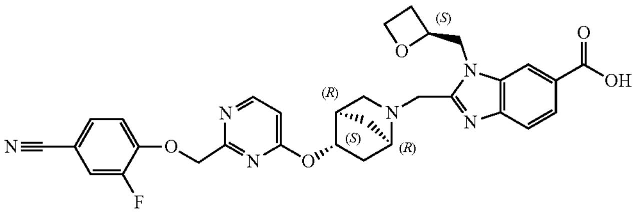 | 2-{[(1R,4R,5S)-5-({2-[(4-cyano-2-fluorophenoxy)methyl] pyrimidin-4-yl}oxy)-2-azabicyclo[2.2.1]heptan-2-yl]methyl}-1-{[(2S)-oxetan-2-yl]methyl}-1H-1,3-benzodiazole-6-carboxylic acid |
| 508 | 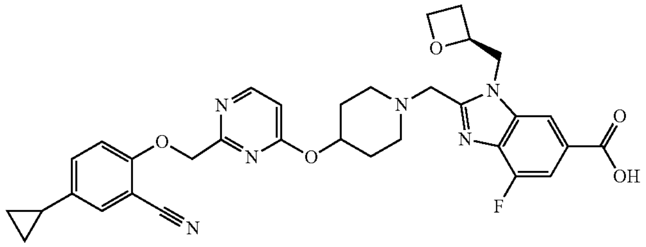 [SMILES: N#Cc1cc(C2CC2)ccc1OCc1nccc(OC2CCN(Cc3nc4c(F)cc(C(=O)O)cc4n3C[C@@H]3CCO3)CC2)n1] | (S)-2-((4-((2-((2-cyano-4-cyclopropylphenoxy) methyl)pyrimidin-4-yl)oxy)piperidin-1-yl)methyl)-4-fluoro-1-(oxetan-2-ylmethyl)-1H-benzo[d]imidazole-6-carboxylic acid |
| 509 | 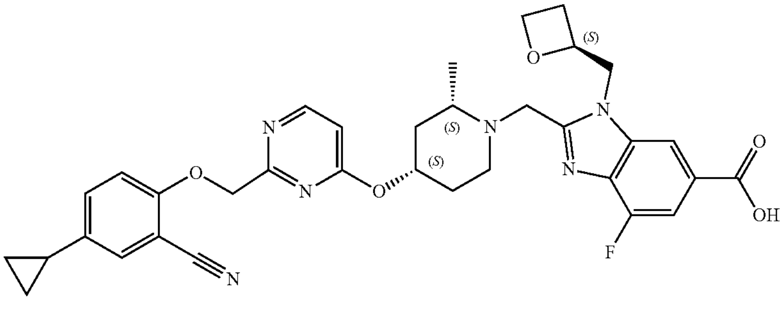 | 2-(((2S,4S)-4-((2-((2-cyano-4-cyclopropylphenoxy) methyl)pyrimidin-4-yl)oxy)-2-methylpiperidin-1-yl)methyl)-4-fluoro-1-(((S)-oxetan-2-yl)methyl)-1H-benzo[d]imidazole-6-carboxylic acid |
| 510 | 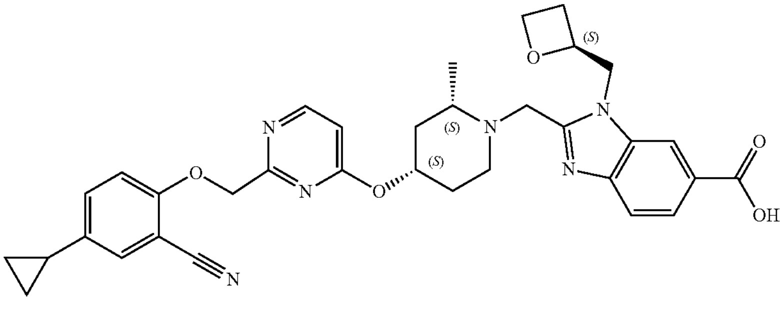 | 2-(((2S,4S)-4-((2-((2-cyano-4-cyclopropylphenoxy) methyl)pyrimidin-4-yl)oxy)-2-methylpiperidin-1-yl)-1-(((S)-oxetan-2-yl)methyl)-1H-benzo[d]imidazole-6-carboxylic acid |

-continued
| Compound | Structure | IUPAC |
|---|---|---|
| 511 | 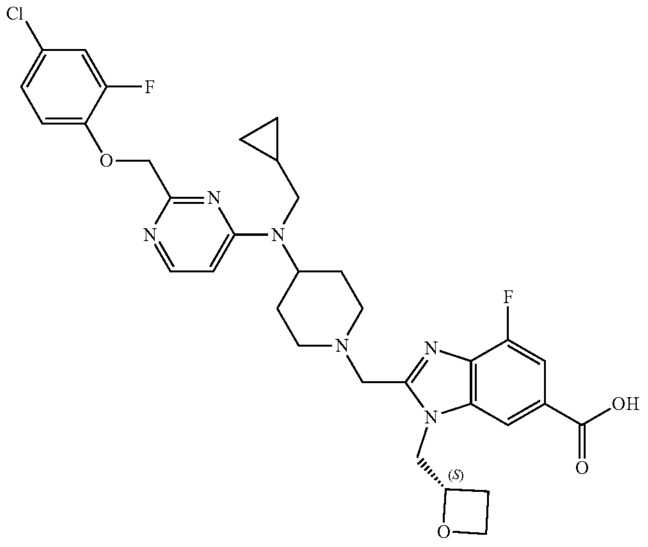 | 2-{[4-({2-[(4-chloro-2-fluorophenoxy)methyl]pyrimidin-4-yl}(cyclopropylmethyl)amino)piperidin-1-yl]methyl}-4-fluoro-1-{[(2S)-oxetan-2-yl]methyl}-1H-1,3-benzodiazole-6-carboxylic acid |
| 512 | 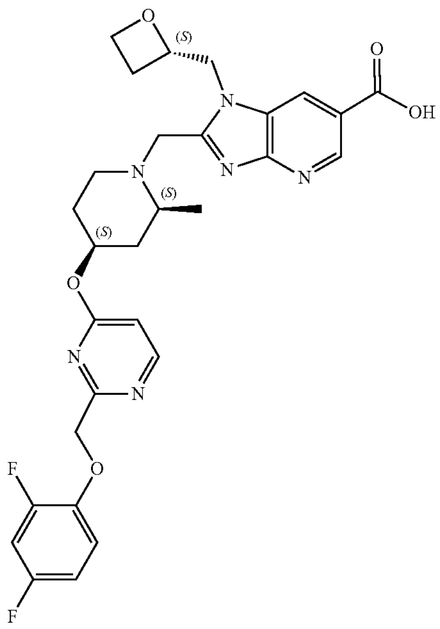 | 2-{[(2S,4S)-4-({2-[(2,4-difluorophenoxy)methyl]pyrimidin-4-yl}oxy)-2-methylpiperidin-1-yl]methyl}-1-{[(2S)-oxetan-2-yl]methyl}-1H-imidazo[4,5-b]pyridine-6-carboxylic acid |

-continued
| Compound | Structure | IUPAC |
|---|---|---|
| 513 | 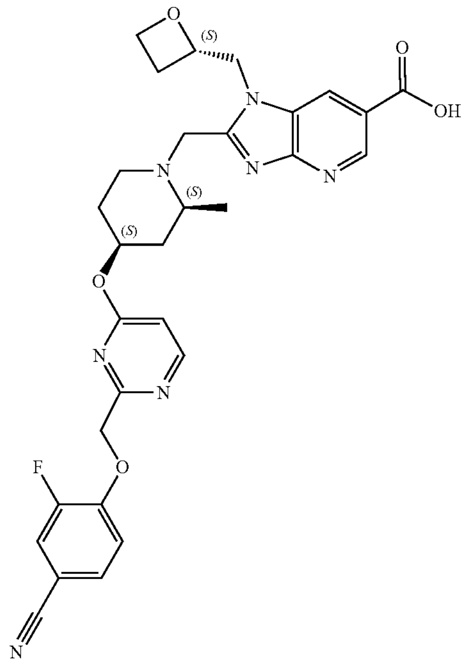 | 2-{[(2S,4S)-4-({2-[(4-cyano-2-fluorophenoxy)methyl]pyrimidin-4-yl}oxy)-2-methylpiperidin-1-yl]methyl}-1-{[(2S)-oxetan-2-yl]methyl}-1H-imidazo[4,5-b]pyridine-6-carboxylic acid |
| 514 | 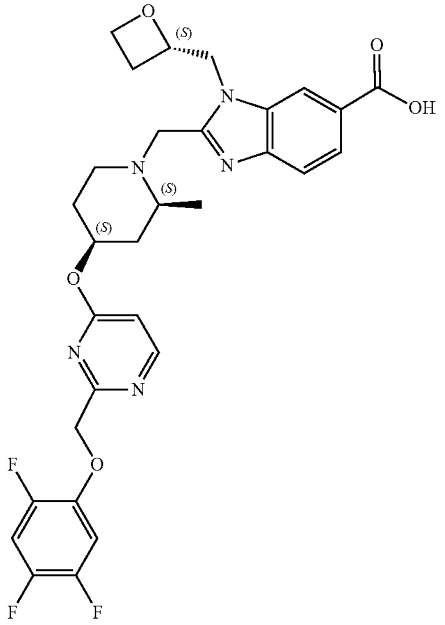 | 2-{[(2S,4S)-2-methyl-4-({2-[(2,4,5-trifluorophenoxy)methyl]pyrimidin-4-yl}oxy)piperidin-1-yl]methyl}-1-{[(2S)-oxetan-2-yl]methyl}-1H-1,3-benzodiazole-6-carboxylic acid |

-continued

| Compound | Structure | IUPAC |
|---|---|---|
| 515 | 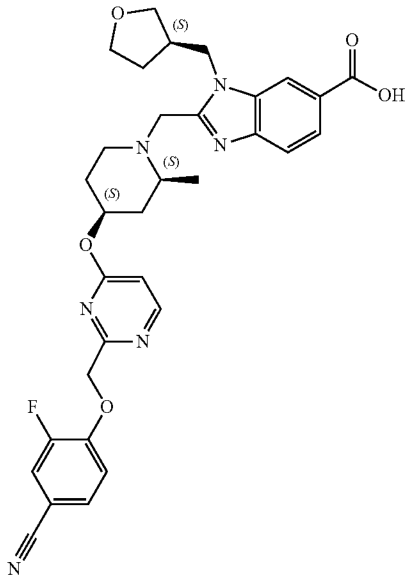 | 2-{[(2S,4S)-4-({2-[(4-cyano-2-fluorophenoxy)methyl]pyrimidin-4-yl}oxy)-2-methylpiperidin-1-yl]methyl}-1-{[(3R)-oxolan-3-yl]methyl}-1H-1,3-benzodiazole-6-carboxylic acid |

Optically Active Compounds

In certain embodiments, compounds provided herein may have several chiral centers and may exist in and be isolated in optically active and racemic forms. In certain embodiments, some compounds may exhibit polymorphism. A person of skill in the art will appreciate that compounds provided herein can exist in any racemic, optically-active, diastereomeric, polymorphic, or stereoisomeric form, and/or mixtures thereof. A person of skill in the art will also appreciate that such compounds described herein that possess the useful properties also described herein is within the scope of this disclosure. A person of skill in the art will further appreciate how to prepare optically active forms of the compounds described herein, for example, by resolution of racemic forms via recrystallization techniques, by synthesis from optically-active starting materials, by chiral synthesis, or by chromatographic separation using a chiral stationary phase. In addition, most amino acids are chiral (i.e., designated as L- or D-, wherein the L-enantiomer is the naturally occurring configuration) and can exist as separate enantiomers.

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist (i.e., the material is a conglomerate, and the crystals are visually distinct);

ii) simultaneous crystallization—a technique whereby the individual enantiomers are separately crystallized from a solution of the racemate, only if the latter is a conglomerate in the solid state;

iii) enzymatic resolutions—a technique wherein partial, or complete separation of a racemate is accomplished by virtue of different rates of reaction of the enantiomers in the presence of an enzyme;

iv) enzymatic asymmetric synthesis—a synthetic technique wherein at least one step of the synthesis uses an enzymatic reaction to obtain an enantiomerically pure, or enriched synthetic precursor of the desired enantiomer;

v) chemical asymmetric synthesis—a synthetic technique wherein the desired enantiomer is synthesized from an achiral precursor using chiral catalysts, or chiral auxiliaries to produce asymmetry (i.e., chirality) in the product;

vi) diastereomer separations—a technique wherein a racemic compound is treated with an enantiomerically pure reagent (a chiral auxiliary) that converts the individual enantiomers to diastereomers. The resulting diastereomers are then separated by chromatography, or crystallization by virtue of their now more distinct diastereomeric differences, and then the chiral auxiliary is removed to obtain each enantiomer;

vii) first- and second-order asymmetric transformations—a technique wherein diastereomers of the racemate equilibrate in solution to yield a preponderance of a diastereomer of the desired enantiomer, or where kinetic, or thermodynamic crystallization of the diastereomer of the desired enantiomer perturbs the equilibrium such that eventually in principle all the material is converted to the crystalline diastereomer of the desired enantiomer. The desired enantiomer is then derived from the diastereomer;

viii) kinetic resolutions—this technique refers to the achievement of partial or complete resolution of a racemate (or of a further resolution of a partially resolved compound) by virtue of unequal reaction rates of the enantiomers with a chiral, or non-racemic reagent, or catalyst under kinetic conditions;

ix) enantiospecific synthesis from non-racemic precursors—a synthetic technique wherein the desired enantiomer is obtained from chiral starting materials, and where the stereochemical integrity is not or is only minimally compromised over the course of the synthesis;

x) chiral liquid chromatography—a technique wherein the enantiomers of a racemate are separated in a liquid mobile phase by virtue of their different interactions with a stationary phase. The stationary phase can be made of chiral material, or the mobile phase can contain an additional chiral material to provoke the different interactions;

xi) chiral gas chromatography—a technique wherein the racemate is volatilized and enantiomers are separated by virtue of their different interactions in the gaseous mobile phase with a column containing a fixed non-racemic adsorbent phase;

xii) extraction with chiral solvents—a technique wherein the enantiomers are separated by virtue of kinetic or thermodynamic dissolution of one enantiomer into a particular chiral solvent;

xiii) transport across chiral membranes—a technique wherein a racemate is placed in contact with a thin membrane barrier. The barrier typically separates two miscible fluids, one containing the racemate, and a driving force such as a concentration, or pressure differential causes preferential transport across the membrane barrier. Separation occurs as a result of the non-racemic nature of the membrane which allows only one enantiomer of the racemate to pass through.

In some embodiments, provided herein are compositions of compounds of any of Formulas (I)-(XVIII), (XXV)-(XXVII), (XXX), (XXXI), (XXXIX), and (XL-XLVII), that are substantially free of a designated stereoisomer of that compound. In certain embodiments, in the methods and compounds of this disclosure, the compounds are substantially free of other stereoisomers. In some embodiments, the composition includes a compound that is at least 85%, 90%, 95%, 98%, or 99% to 100% by weight of the compound, the remainder comprising other chemical species, or enantiomers. In some embodiments, provided herein are compositions of compounds of any of Formulas (I)-(XVIII), (XXV)-(XXVII), (XXX), (XXXI), (XXXIX), and (XL-XLVII).

that are substantially free of a designated enantiomer of that compound. In certain embodiments, in the methods and compounds of this disclosure, the compounds are substantially free of other enantiomers. In some embodiments, the composition includes a compound that is at least 85%, 90%, 95%, 98%, or 99% to 100% by weight of the compound, the remainder comprising other chemical species or enantiomers.

Isotopically Enriched Compounds

Also provided herein are isotopically enriched compounds including, but not limited to, isotopically enriched compounds of any of Formulas (I)-(XVIII), (XXV)-(XXVII), (XXX), (XXXI), (XXXIX), and (XL-XLVII).

Isotopic enrichment (for example, deuteration) of pharmaceuticals to improve pharmacokinetics ("PK"), pharmacodynamics ("PD"), and/or toxicity profiles, has been previously demonstrated within some classes of drugs. See, for example, Lijinsky et al., Food Cosmet. Toxicol., 20:393 (1982); Lijinsky et al., J. Nat. Cancer Inst., 69:1127 (1982); Mangold et al., Mutation Res. 308:33 (1994); Gordon et al., Drug Metab. Dispos., 15:589 (1987); Zello et al., Metabolism, 43:487 (1994); Gately et al., J. Nucl. Med., 27:388 (1986); Wade D, Chem. Biol. Interact. 117:191 (1999).

Isotopic enrichment of a drug can be used, for example, to (1) reduce or eliminate unwanted metabolites; (2) increase the half-life of the parent drug; (3) decrease the number of doses needed to achieve a desired effect; (4) decrease the amount of a dose necessary to achieve a desired effect; (5) increase the formation of active metabolites if any are formed; and/or (6) decrease the production of deleterious metabolites in specific tissues. Isotopic enrichment of a drug can also be used to create a more effective and/or safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e., the step with the highest transition state energy), substitution of a (heavier) isotope for that reactive hydrogen will cause a decrease in the reaction rate. The Deuterium Kinetic Isotope Effect ("DKIE") is the most common form of KIE. (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen and the C-D bond is broken. The DKIE can range from about one (no isotope effect) to very large numbers, such as 50, or more, meaning that the reaction can be fifty, or more, times slower when deuterium has been substituted for hydrogen.

Substitution of tritium ("T") for hydrogen results in yet a stronger bond than deuterium and gives numerically larger isotope effects. Similarly, substitution of isotopes for other elements including, but not limited to, $^{13}C$, or $^{14}C$ for carbon; $^{33}S$, $^{34}S$, or $^{36}S$ for sulfur; $^{15}N$ for nitrogen; and $^{17}O$, or $^{18}O$ for oxygen may lead to a similar kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases to react with and convert these foreign substances to more polar intermediates, or metabolites for renal excretion. Some of the most common metabolic reactions of pharmaceutical compounds involve the oxidation of a carbon-hydrogen (C—H) bond to either a carbon-oxygen (C—O), or carbon-carbon (C═C) pi-bond. The resultant metabolites may be stable, or unstable under physiological conditions, and can have substantially different PK/PD, and acute, and long-term toxicity profiles relative to the parent compounds. For many drugs, such oxidations are rapid. Therefore, these drugs often require the administration of multiple or high daily doses.

Therefore, isotopic enrichment at certain positions of a compound provided herein will produce a detectable KIE that will affect the pharmacologic, PK, PD, and/or toxicological profiles of a compound provided herein in comparison with a similar compound having a natural isotopic composition.

Compositions and Uses

Pharmaceutical Compositions and Methods of Administration

The compounds provided herein can be formulated into pharmaceutical compositions using methods available in the art and those disclosed herein. Any of the compounds provided herein can be provided in the appropriate pharmaceutical composition and be administered by a suitable route of administration.

The methods provided herein encompass administering pharmaceutical compositions comprising at least one compound provided herein and one or more compatible and pharmaceutically acceptable carriers. In this context, the term "pharmaceutically acceptable" means approved by a regulatory agency of the Federal, or state government, or listed in the U.S. Pharmacopeia, or other generally recognized pharmacopeia for use in animals, and in certain embodiments in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils including petroleum, animal, vegetable, or oils of synthetic origin, such as peanut oil, soybean oil, mineral oil, sesame oil, and the like. Water can be used as a carrier when the pharmaceutical composition is administered intravenously. Saline solutions, and aqueous dextrose, and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions, or compounds provided herein may be administered by any route known in the art. Exemplary routes of administration include, but are not limited to, inhalation, intraarterial, intradermal, intramuscular, intraperitoneal, intravenous, nasal, parenteral, pulmonary, and subcutaneous routes. In some embodiments, a pharmaceutical composition or compound provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing, and stabilizing agents. Sterilization can be carried out in several ways, for example, using a bacteriological filter, via radiation, or via heating. Parenteral compositions can also be prepared in the form of sterile solid compositions which can be dissolved at the time of use in sterile water, or any other injectable sterile medium.

In some embodiments, a composition provided herein is a pharmaceutical composition, or a single unit dosage form. Pharmaceutical compositions, and single unit dosage forms provided herein comprise a prophylactically, or therapeutically effective amount of one, or more prophylactic, or therapeutic compounds.

The pharmaceutical composition may comprise one, or more pharmaceutical excipients. Any suitable pharmaceutical excipient may be used, wherein a person of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. Whether a particular excipient is suitable for incorporation into a pharmaceutical composition, or dosage form depends on a variety of factors well known in the art including, but not limited to, the way in which the dosage form will be administered to a subject and the specific compound in the dosage form. The composition, or single unit dosage form, if desired, can also contain minor amounts of wetting, or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference herein in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long-chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a co-solvent. Illustrative examples of co-solvents include, ethanol, poly(ethylene) glycol, butylene glycol, dimethylacetamide, glycerin, and propylene glycol.

In some embodiments, the pharmaceutical composition comprises a buffer. Illustrative examples of buffers include, acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier, or filler. Illustrative examples of carriers, or fillers include, lactose, maltodextrin, mannitol, sorbitol, chitosan, stearic acid, xanthan gum, and guar gum.

In some embodiments, the pharmaceutical composition comprises a surfactant. Illustrative examples of surfactants, include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene (glycol) succinate.

In some embodiments, the pharmaceutical composition comprises an anti-caking agent. Illustrative examples of anti-caking agents include, calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference herein in its entirety.

In some embodiments, the pharmaceutical composition comprises a solvent. In some aspects, the solvent is saline solution, such as a sterile isotonic saline solution, or dextrose solution. In some aspects, the solvent is water for injection.

In some embodiments, the pharmaceutical compositions are in a particulate form, such as a microparticle or a nanoparticle. Microparticles, and nanoparticles may be formed from any suitable material, such as a polymer, or a lipid. In some aspects, the microparticles, or nanoparticles are micelles, liposomes, or polymersomes.

Further provided herein are anhydrous pharmaceutical compositions, and dosage forms comprising a compound, since, in some embodiments, water can facilitate the degradation of some compounds.

Anhydrous pharmaceutical compositions, and dosage forms provided herein can be prepared using anhydrous, or low moisture containing ingredients, and low moisture, or low humidity conditions. Pharmaceutical compositions, and dosage forms that comprise lactose, and at least one active ingredient that comprises a primary, or secondary amine can be anhydrous if substantial contact with moisture, and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopeia (USP) SP (XXI)/NF (XVI). In general, lactose-free compositions comprise an active ingredient, a binder/filler, and a lubricant in pharmaceutically compatible, and pharmaceutically acceptable amounts. Exemplary lactose-free dosage forms comprise an active ingredient, microcrystalline cellulose, pre gelatinized starch, and magnesium stearate.

Also provided are pharmaceutical compositions, and dosage forms that comprise one, or more excipients that reduce the rate by which a compound will decompose. Such excipients, which are referred to herein as "stabilizers," include, but are not limited to, antioxidants such as ascorbic acid, pH buffers, or salt buffers.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically sterile, or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to Water for Injection USP; aqueous vehicles such as, but not limited to, Sodium Chloride Injection, Ringer's Injection, Dextrose Injection, Dextrose, and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one, or more of the antibodies disclosed herein can also be incorporated into the parenteral dosage forms.

Dosage and Unit Dosage Forms

In human therapeutics, the doctor will determine the posology which he considers most appropriate according to a preventive, or curative treatment, and according to the age, weight, condition, and other factors specific to the subject to be treated.

In certain embodiments, a composition provided herein is a pharmaceutical composition, or a single unit dosage form. Pharmaceutical compositions, and single unit dosage forms provided herein comprise a prophylactically, or therapeutically effective amount of one, or more prophylactic, or therapeutic antibodies, or antigen binding fragments thereof.

The amount of the compound, or composition which will be effective in the prevention, or treatment of a disorder, or one, or more symptoms thereof will vary with the nature, and severity of the disease, or condition, and the route by which the compound is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro, or animal model test systems.

In certain embodiments, exemplary doses of a composition include milligram, or microgram amounts of the compound per kilogram of subject, or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiments, the dosage of the compound provided herein, based on weight of the compound, administered to prevent, treat, manage, or ameliorate a disorder, or one, or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition, or a composition provided herein administered to prevent, treat, manage, or ameliorate a disorder, or one, or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or four times weekly. It may be necessary to use dosages of the compound outside the ranges disclosed herein in some cases, as will be apparent to those of ordinary skill in the art. Furthermore, it is noted that the clinician, or treating physician will know how, and when to interrupt, adjust, or terminate therapy in conjunction with subject response.

Different therapeutically effective amounts may be applicable for different diseases, and conditions, as will be readily known by those of ordinary skill in the art. Similarly, amounts sufficient to prevent, manage, treat, or ameliorate such disorders, but insufficient to cause, or sufficient to reduce, adverse effects associated with the antibodies, or antigen binding fragments thereof provided herein are also encompassed by the described dosage amounts, and dose frequency schedules herein. Further, when a subject is administered multiple dosages of a composition provided herein, not all of the dosages need be the same. For example, the dosage administered to the subject may be increased to improve the prophylactic, or therapeutic effect of the composition, or it may be decreased to reduce one, or more side effects that a particular subject is experiencing.

In certain embodiments, treatment, or prevention can be initiated with one, or more loading doses of a compound, or composition provided herein followed by one, or more maintenance doses.

In certain embodiments, a dose of a compound, or composition provided herein can be administered to achieve a steady-state concentration of the compound in blood, or serum of the subject. The steady-state concentration can be determined by measurement according to techniques available to those of skill or can be based on the physical characteristics of the subject such as height, weight, and age.

In certain embodiments, administration of the same composition may be repeated and the administrations may be separated by at least one day, two days, three days, five days, ten days, fifteen days, thirty days, forty-five days, two months, seventy-five days, three months, or six months. In other embodiments, administration of the same prophylactic, or therapeutic agent may be repeated, and the administration may be separated by at least one day, two days, three days, five days, ten days, fifteen days, thirty days, forty-five days, two months, seventy-five days, three months, or six months.

Therapeutic Applications

For therapeutic applications, the compounds are administered to a mammal, in certain embodiments, a human, in a pharmaceutically acceptable dosage suitable for administration form such as those known in the art, and those discussed herein, intravenously as a bolus or by continuous infusion over a period of time, by intramuscular, intraperitoneal, intra-cerebrospinal, subcutaneous, intra-articular, intrasynovial, intrathecal, or intratumoral routes. The compounds also are suitably administered by peritumoral, intralesional, or perilesional routes, to exert local as well as systemic therapeutic effects. In certain embodiments, the compounds are administered to a mammal, in certain embodiments, a human, in a pharmaceutically acceptable dosage suitable for oral administration form such as those known in the art, and those discussed herein. For example, the compounds of this disclosure may be administered orally to a human as a liquid, or solid form. Solid dosage forms include, capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The compounds provided herein may be useful for the treatment of any disease, or condition described herein (e.g., a metabolic disease or condition). In certain embodiments, the disease, or condition is any disease, or condition that benefits from modulation of GLP-1 receptor activity. In certain embodiments, the disease, or condition is any disease, or condition that benefits from agonizing GLP-1 receptor activity. In certain embodiments, the methods reduce blood glucose levels. In certain embodiments, the methods promote insulin synthesis, stimulate insulin secretion, increase the mass of β-cells, modulate gastric acid secretion, modulate gastric emptying, and/or decrease glucagon production. In certain embodiments, the disease, or condition is type 2 diabetes.

In certain embodiments, the disease, or condition is obesity, or one, or more diseases, or conditions associated with obesity. Non-limiting examples of obesity, and obesity related conditions include, symptomatic obesity, simple obesity, childhood obesity, morbid obesity, and abdominal obesity (central obesity characterized by abdominal adiposity). Non-limiting examples of symptomatic obesity include, endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

Examples of such diseases, and conditions associated with obesity include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone, or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, and metabolic syndrome. In certain embodiments, the compounds described herein can be used to treat subjects exhibiting symptoms of both obesity, and insulin deficiency.

In some embodiments, the disease, or condition is diabetes. Non-limiting examples of diabetes include, type 1 diabetes, type 2 diabetes (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes.

In some embodiments, the disease, or condition is associated with diabetes (e.g., a complication of diabetes). Non-limiting examples of disorders associated with diabetes include, obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors, (e.g., coronary artery disease, peripheral artery disease, cerebrovascular disease, hypertension, and risk factors related to unmanaged cholesterol, and/or lipid levels, and/or inflammation), NASH, bone fracture, and cognitive dysfunction Other non-limiting examples of diseases, or conditions related to diabetes include, pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the disease, or condition is diabetes, and obesity (diabesity). In certain embodiments, the compounds described herein are useful in improving the therapeutic effectiveness of metformin.

In some embodiments, the disease or condition is a disorder of a metabolically important tissue.

In some embodiments, the disease, or condition is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

Non-alcoholic fatty liver disease (NAFLD) represents a spectrum of disease occurring in the absence of alcohol abuse, and is typically characterized by the presence of steatosis (fat in the liver). NAFLDis believed to be linked to a variety of conditions, e.g., metabolic syndrome (including obesity, diabetes, and hypertriglyceridemia), and insulin resistance. It can cause liver disease in adults and children, and may ultimately lead to cirrhosis (Skelly et al., J Hepatol 2001; 35:195-9; Chitturi et al., Hepatology 2002; 35 (2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 SuppkS 186-90). In certain embodiments, the subject is a pediactric subject (e.g., 6-16 years old; or 6-12 years old; or 6-10 years old). In certain embodiments, the subject is an adult subject.

Other non-limiting examples of diseases, or conditions in metabolically important tissues include, joint disorders (e.g., osteoarthritis, secondary osteoarthritis), steatosis (e.g. in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease, and the altered bone metabolism caused by renal failure, or haemodialysis, bone fracture, bone surgery, aging, pregnancy, protection against bone fractures, and malnutritionpolycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute, or chronic diarrhea, testicular dysfunction, respiratory dysfunction, frailty, sexual dysfunction (e.g., erectile dysfunction), and geriatric syndrome. In certain embodiments, the chemical entities described herein can be used for treating surgical trauma by improving recovery after surgery, and/or by preventing the catabolic reaction caused by surgical trauma.

In some embodiments, the disease, or condition is a cardiovascular disease. Non-limiting examples of cardiovascular disease include, congestive heart failure, atherosclerosis, arteriosclerosis, coronary heart disease, or peripheral artery disease, stroke, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen, or plasminogen activator inhibitor in the blood).

In some embodiments, the disease, or condition is a neurological disorder (e.g., neurodegenerative disorder), or a psychiatric disorder. Non-limiting examples of neurological disorders include, brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), chronic wasting syndrome). See, e.g., US20060275288A1.

Non-limiting examples of psychiatric disorders include, drug dependence/addiction (narcotics, amphetamines, and attention deficit/hyperactivity disorder (ADHD). The chemical entities described herein can be useful in improving behavioral response to addictive drugs, decreasing drug dependence, prevention drug abuse relapse, and relieving anxiety caused by the absence of a given addictive substance. See, e.g., US20120021979A1.

In certain embodiments, the chemical entities described herein are useful in improving learning, and memory by enhancing neuronal plasticity, and facilitation of cellular differentiation, and also in preserving dopamine neurons, and motor function in Morbus Parkinson.

In some embodiments, the disease, or condition is impaired fasting glucose (IFG), impaired fasting glycemia (IFG), hyperglycemia, insulin resistance (impaired glucose homeostasis), hyperinsulinemia, elevated blood levels of fatty acids, or glycerol, a hypoglycemic condition, insulin resistant syndrome, paresthesia caused by hyperinsulinemia, hyperlipidemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In certain embodiments, the compounds described herein can reduce, or slow down the progression of borderline type, impaired fasting glucose, or impaired fasting glycemia into diabetes.

In some embodiments, the disease, or condition is an autoimmune disorder. Non-limiting examples of autoimmune disorders include, multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., US20120148586A1.

In some embodiments, the disease, or condition is a stomach, or intestine related disorder. Non-limiting examples of these disorders include, ulcers of any etiology (e.g. peptic ulcers, Zollinger-Ellison syndrome, drug-induced ulcers, ulcers related to infections, or other pathogens), digestion disorders, malabsorption, short bowel syndrome, cul-de-sac syndrome, inflammatory bowel diseases (Crohn's disease, and ulcerative colitis), celiac sprue, hypogammaglobulinemic sprue, chemotherapy, and/or radiation therapy-induced mucositis, and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, cachexia caused by acquired immunodeficiency syndrome).

In some embodiments, the compounds described herein can be used to reduce body weight (e.g., excess body weight), prevent body weight gain, induce weight loss, decrease body fat, or reduce food intake in a subject (e.g., a subject in need thereof). In certain embodiments, the weight increase in a subject may be attributed to excessive ingestion of food, or unbalanced diets, or may be weight increase derived from a concomitant drug (e.g., insulin sensitizers having a PPARγ agonist-like action, such as troglitazone, rosiglitazone, englitazone, ciglitazone, pioglitazone, and the like). Alternatively, the weight increase may be weight increase before reaching obesity, or may be weight increase in an obese subject. The weight increase may also be medication-induced weight gain, or weight gain subsequent to cessation of smoking.

In some embodiments, the condition, disease, or disorder is an eating disorder, such as hyperphagia, binge eating, bulimia, or compulsive eating.

In some embodiments, the disease, or condition is an inflammatory disorder. Non-limiting examples of inflammatory disorders include, chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney, and gut, and a proinflammatory state (e.g., elevated levels of proinflammatory cytokines or, markers of inflammation-like C-reactive protein in the blood).

In some embodiments, the disease, or condition is cancer. Suitable examples of cancer include, breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

In certain embodiments, provided herein are methods for the treatment that include, the administration of an effective amount of compounds provided herein, or a pharmaceutically acceptable salt thereof. In certain embodiments, the methods encompass the step of administering to the subject in need thereof an amount of a compound described herein effective for the treatment of disease, or condition in combination with a second agent effective for the treatment, or prevention of the disease, or condition. In certain embodiments, the compound is in the form of a pharmaceutical composition, or dosage form, as described elsewhere herein.

In certain embodiments, the subject is a treatment naïve subject. In further embodiments, the subject has previously received therapy. For instance, in certain embodiments, the subject has not responded to a single agent treatment regimen.

In certain embodiments, the subject is a subject that discontinued some other therapy because of one or more adverse events associated with the other therapy. In certain embodiments, the subject has received some other therapy and discontinued that therapy prior to administration of a method provided herein. In further embodiments, the subject has received therapy and continues to receive that therapy along with administration of a compound provided herein. The compounds described herein can be co-administered with other therapy for treatment of the disease or condition according to the judgment of one of skill in the art. In certain embodiments, the methods or compositions provided herein can be co-administered with a reduced dose of the other therapy for the treatment of the disease or condition.

Diagnostic Applications

In some embodiments, the compounds provided herein are used in diagnostic applications. These applications may be useful, for example, in making a diagnosis, and/or prognosis for a disease, or condition, such as a metabolic disease, or condition.

In some diagnostic and prognostic applications or embodiments, the compound may be labeled with a detectable moiety. Suitable detectable moieties include, but are not limited to, radioisotopes, fluorescent labels, and enzyme-substrate labels. In another embodiment, the compound need not be labeled, and the presence of the compound can be detected using a labeled antibody, or antigen binding fragment thereof which specifically binds to the compound.

Kits

In some embodiments, a compound provided herein is provided in the form of a kit (i.e., a packaged combination of reagents in predetermined amounts with instructions for performing a procedure). In some embodiments, the procedure is a diagnostic assay. In certain embodiments, the procedure is a therapeutic procedure.

In some embodiments, the kit further comprises a solvent for the reconstitution of the compound. In some embodiments, the compound is provided in the form of a pharmaceutical composition.

In some embodiments, the kits can include a compound, or composition provided herein, an optional second agent, or composition, and instructions providing information to a health care provider regarding usage for treating the disorder. Instructions may be provided in printed form, or in the form of an electronic medium such as a floppy disc, CD, or DVD, or in the form of a website address where such instructions may be obtained. A unit dose of a compound, or a composition provided herein, or a second agent, or composition, can include a dosage such that when administered to a subject, a therapeutically, or prophylactically effective plasma level of the compound, or composition can be maintained in the subject for at least one day. In some embodiments, a compound, or composition can be included as a sterile aqueous pharmaceutical composition, or dry powder (e.g., lyophilized) composition.

In some embodiments, suitable packaging is provided. As used herein, "packaging" includes a solid matrix, or material customarily used in a system, and capable of holding within fixed limits a compound provided herein, and/or a second agent suitable for administration to a subject. Such materials include, glass, and plastic (e.g., polyethylene, polypropylene, and polycarbonate) bottles, vials, paper, plastic, plastic-foil laminated envelopes, and the like. If e-beam sterilization techniques are employed, the packaging should have sufficiently low density to permit sterilization of the contents.

Preparation and Synthetic Procedures

In some embodiments, the compounds described herein are prepared as outlined in Schemes 1-7. The synthesis of the compounds in this application is not limited to these general reaction schemes illustrated here. For detailed synthesis of each individual compound, please check the Examples section.

Scheme 1

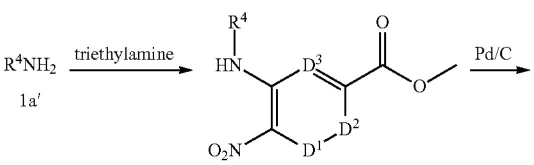

1a'

1b'

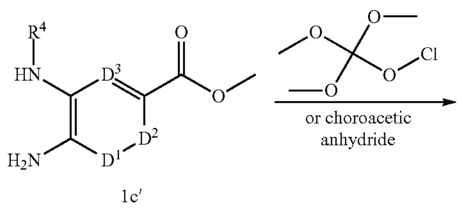

1c'

-continued

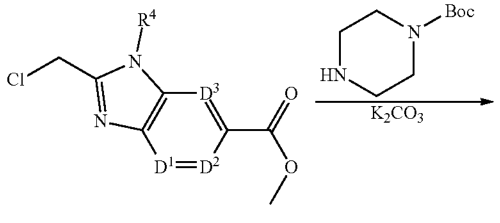

1d'

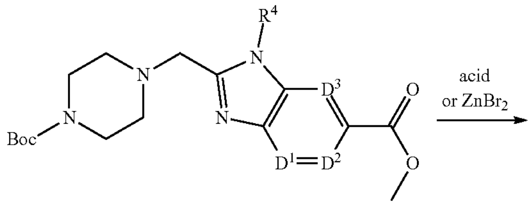

1e'

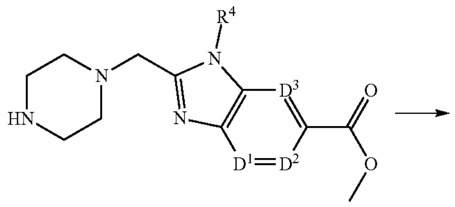

1f'

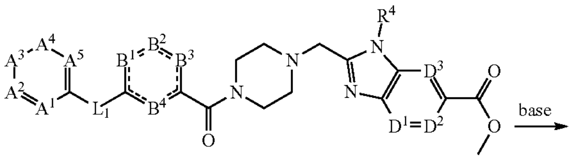

1g'

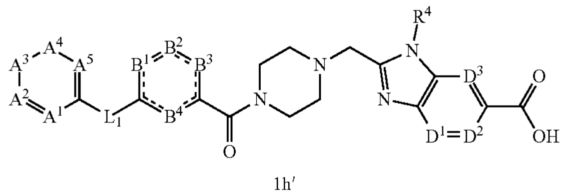

1h'

Scheme 1. Compound with a formula 1h' can be made as shown in Scheme 1. An amine can be reacted with fluoro, nitro-substituted aryl or heteroaryl compound through a SNAr reaction to provide 1b'. The nitro group in 1b' will be reduced to an amino group through hydrogenation. Reaction of 1c' with 2-chloro-1,1,1-trimethoxyethane or chloroacetic anhydride will form 1d'. Alkylation of 1d' with tert-butyl piperazine-1-carboxylate will provide 1e', in which the Boc protecting group can be removed by TFA or HCl. The resulting piperazine 1f' can be coupled with a carboxylic acid to form 1g', which can be deprotected to give 1h'.

Scheme 2

ArCOOH

2a'

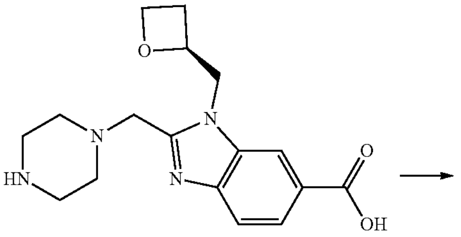

2b'

-continued

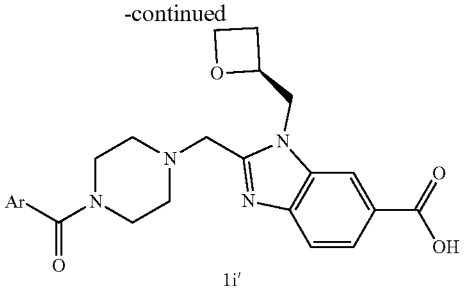

1i'

Scheme 2. Alternatively, compound 1i' (analog of 1h') can be synthesized though a direct coupling reaction of acid-containing piperazine 2b' with a carboxylic acid 2a'.

Scheme 3

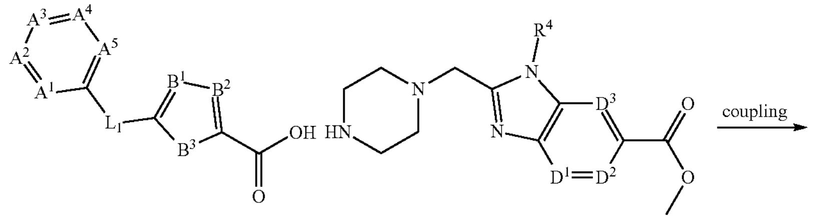

3a'

1f'

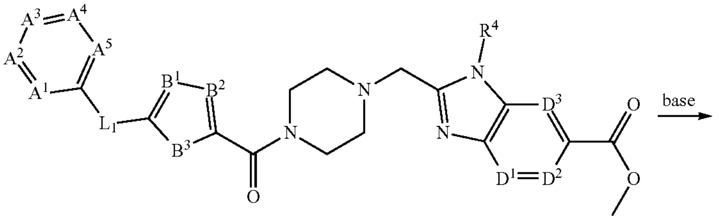

3b'

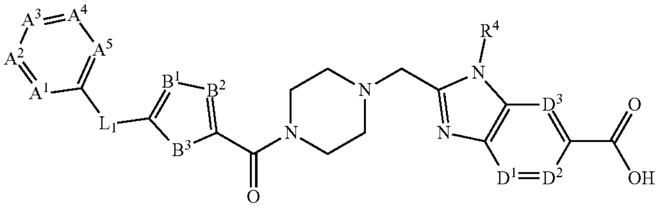

3c'

Scheme 3. Some of the alternative carboxylic acids 3a' contain 5-membered heteroaryl ring. They can be coupled with 1f' to provide compound 3b', which can be hydrolyzed to provide 3c'.

Scheme 4

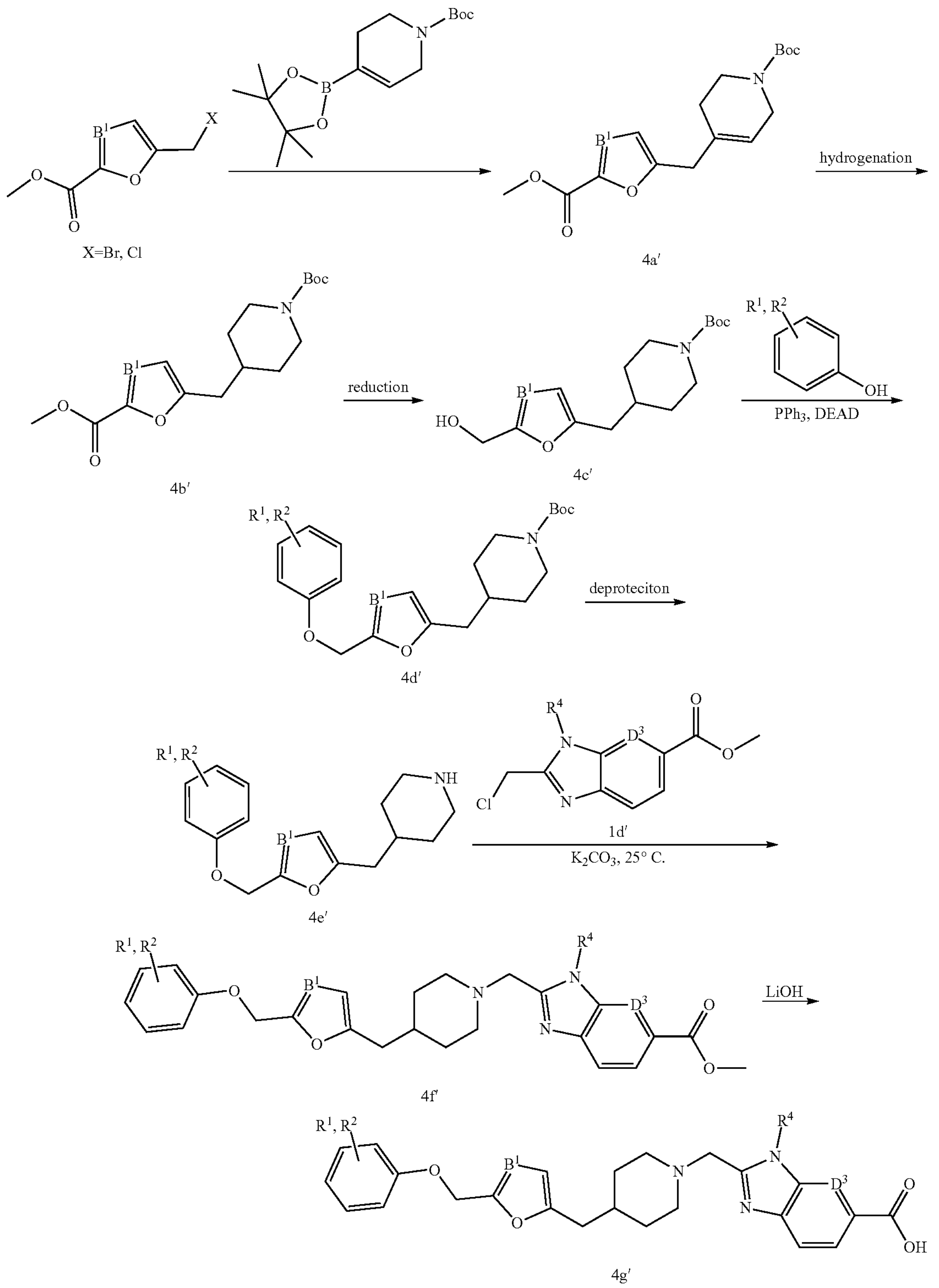

Scheme 4. Compound 4a' can be prepared from a halide and tert-butyl 4-(4,4,5,5-tetramethyl-1,3,2-dioxaborolan-2-yl)-3,6-dihydropyridine-1(2H)-carboxylate through a Suzuki reaction, which after hydrogenation would result in compound 4b'. Reduction of the ester group would form an alcohol 4c', which can be used to prepare compound 4d' through a Mitsunobu reaction. Alternatively, 4c' can be converted to a bromide and can be reacted with a phenol through an alkylation reaction to form 4d'. After deprotection of the Boc group, 4e' can be alkylated to give 4f', and hydrolyzed to provide 4g'.

Scheme 5

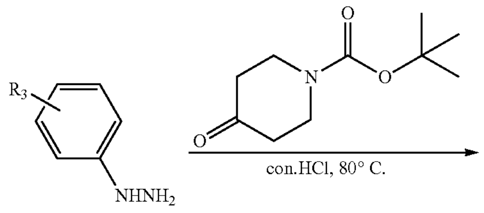

5a'

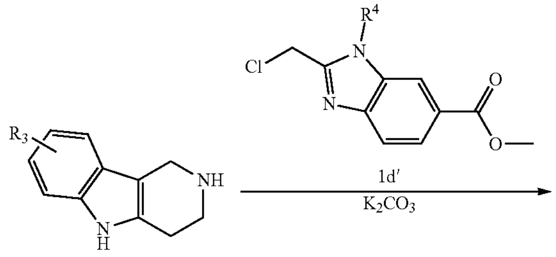

5b'

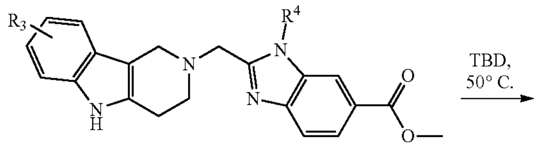

5c'

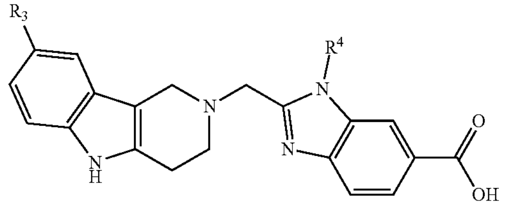

5d'

Scheme 5. Hydrazine 5a' can be reacted with tert-butyl 4-oxopiperidine-1-carboxylate through Fischer indole synthesis to form carboline 5b', which can be alkylated with 1d' to give 5c'. Compound 5d' can be prepared through hydrolysis of 5c'.

Scheme 6

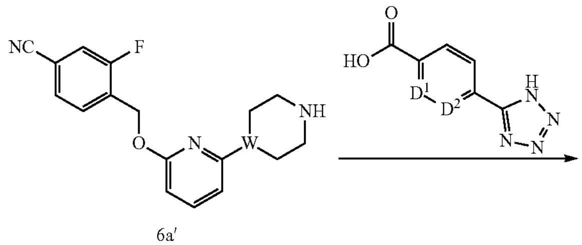

6a'

-continued

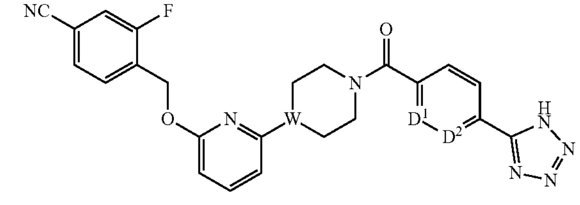

6b'

Scheme 7

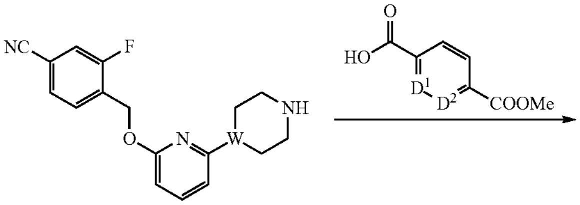

6a'

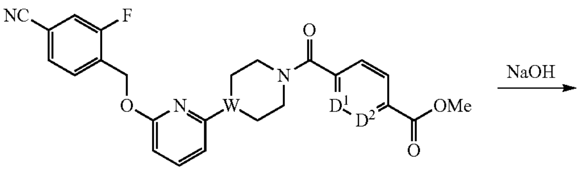

7a'

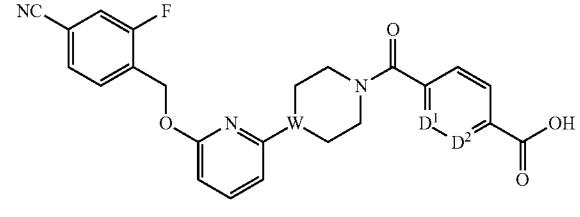

7b'

Schemes 6 and 7. Coupling of piperidine or piperazine 6a' with various carboxylic acid will lead to compound 6b', or 7b'.

Scheme 8

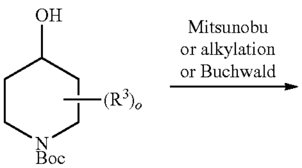

8a'

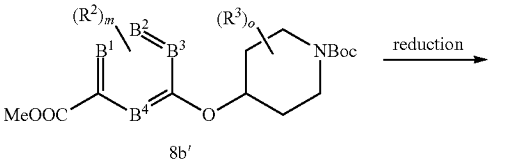

8b'

-continued

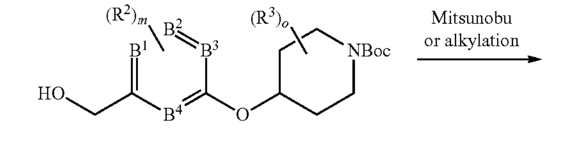

8c'

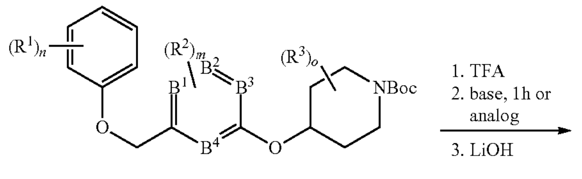

8d'

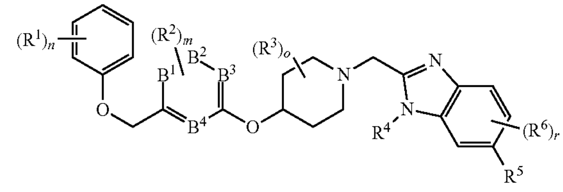

8e'

Scheme 8. (zero, one, or two of $B^1$, $B^2$, $B^3$, and $B^4$ are N, and the rest are CH). Alcohol 8a' can be used to synthesize 8b' through Mitsunobu reaction with an alcohol (e.g., phenol), or converted to a mesylate followed by alkylation with a phenol, or coupling with aryl halide through Buchwald reaction to form 8b'. Reduction of the ester group in 8b' can afford alcohol 8c'. Then through Mitsunobu reaction with a phenol or mesylate formation of 8c' followed by alkylation with a phenol can provide 8d'. Deprotection of the Boc group with TFA, followed by coupling with 1 h and hydrolysis can afford 8e'.

Scheme 9

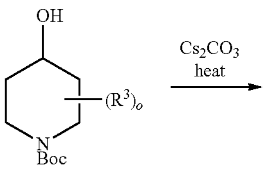

8a'

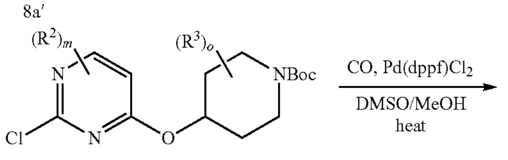

9a'

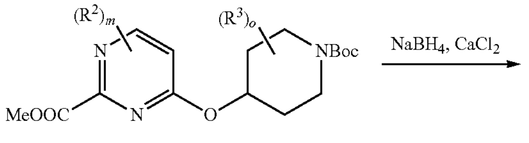

9b'

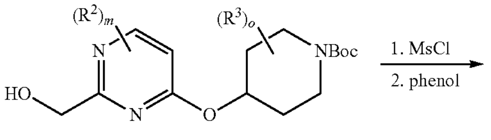

9c'

-continued

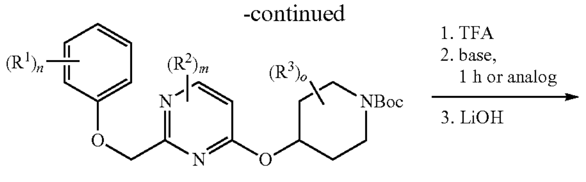

9d'

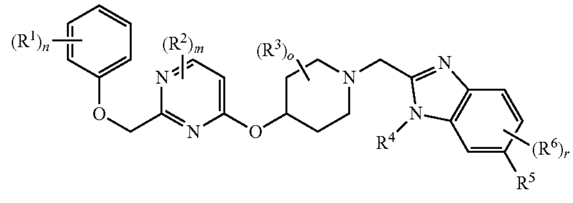

9e'

Scheme 9. 9a' can be synthesized from 8a' through alkylation. Palladium-catalyzed carbonylation would afford ester 9b', which can be reduced to provide alcohol 9c'. Mesylation formation of alcohol 9c' followed by alkylation with a phenol can provide 9d'. Deprotection of the Boc group with TFA, followed by coupling with 1 h and hydrolysis can afford 9e'.

EXAMPLES

Preparation of the Compounds

The compounds used in the reactions described herein are made according to organic synthesis techniques known to those skilled in this art, starting from commercially available chemicals, and/or from compounds described in the chemical literature. "Commercially available chemicals" are obtained from standard commercial sources such as Acros Organics (Pittsburgh, PA), Advanced ChemBlocks, Inc (Burlingame, CA), Aldrich Chemical (Milwaukee, WI, including Sigma Chemical and Fluka), AK Scientific (Union City, CA), AstaTech, Inc. (Bristol, PA), Aurum Pharmatech LLC (Franklin Park, NJ), Combi-Blocks, Inc. (San Diego, CA), Enamine (Monmouth Jct., NJ), Fisher Scientific Co. (Pittsburgh, PA), Frontier Scientific (Logan, UT), TCI America (Portland, OR), and VWR (Radnor, PA). Specific and analogous reactants are optionally identified through the indices of known chemicals prepared by the Chemical Abstract Service of the American Chemical Society, which are available in most public and university libraries, as well as through on-line databases.

Suitable reference books that detail the synthesis of reactants useful in the preparation of compounds described herein, or provide references to articles that describe their preparation, include for example, "Synthetic Organic Chemistry", John Wiley & Sons, Inc., New York; S. R. Sandler et al., "Organic Functional Group Preparations," 2nd Ed., Academic Press, New York, 1983; "T. L. Gilchrist, "Heterocyclic Chemistry", 2nd Ed., John Wiley & Sons, New York, 1992; and J. March, "Advanced Organic Chemistry: Reactions, Mechanisms and Structure", 4th Ed., Wiley-Interscience, New York, 1992; R. C. Larock "Comprehensive Organic Transformations: A Guide to Functional Group Preparations" 2nd Edition (1999) Wiley-VCH, ISBN: 0-471-19031-4; "Organic Reactions" (1942-2000) John Wiley & Sons, in over 55 volumes; and "Chemistry of Functional Groups" John Wiley & Sons, in 73 volumes. Some compounds require the application of protecting groups. The need for such protection is within the skill in the art. For a general description of protecting groups and their use, see T. W. Greene, P. G. M. Nuts, and Protective Groups in Organic Synthesis, John Wiley & Sons, New York, 1999.

Analytical Methods and Instrumentation

Proton nuclear magnetic resonance (NMR) spectra were obtained on either Bruker, or Varian spectrometers at 400, or 600 MHz. NMR spectra are reported relative to residual solvent signals as follows: chemical shift δ (ppm), multiplicity, coupling constant J (Hz), and integration. Tetramethylsilane (TMS) was used as an internal standard in some of the cases. Mass spectral data were measured using one of the two following systems: System A: Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI) (column: Acquity UPLC BEH C18 1.7 μι 2.1×50 mm). System B: Agilent LC/MS consisting of a 1200 series LC and 6140 Quadrupole MS detector (column: Agilent USGYL01131, HPH—C18 2.7 μM, 2.1×50 mm). Solvents used: acetonitrile/water, containing 0.1% formic acid; flow rate 0.7 mL/min. Preparatory HPLC purifications were conducted with a flow rate of 15 mL/min and detection by UV wavelength 214 nm and 254 nm (Column: Jupiter® 10 M Proteo 90 Å, 250×21.2 mm A, solvent: acetonitrile/water, containing modifier such as 0.1% trifluoroacetic acid, formic acid or acetic acid). Compound purity was checked on an analytical HPLC (Waters Acquity UPLC H-Class instrument), with a flow rate of 0.5 mL/min (Acquity BEH C18, 50×2.1 mm column).

Abbreviations Used in the Examples Include:

| Abbreviation | Name |
|---|---|
| $CH_3CN$ | acetonitrile |
| aq. | aqueous |
| atm | atmospheres |
| BINAP | (1,1'-binaphthalene-2,2'-diyl)bis(diphenylphosphine) |
| Boc | t-butoxycarbonyl |
| $CCl_4$ | carbon tetrachloride |
| $CDCl_3$ | deuterated chloroform |
| CO | carbon monoxide gas |
| $CO_2$ | carbon dioxide |
| $Cs_2CO_3$ | cesium carbonate |
| CuBr | copper(I) bromide |
| $Cu(OAc)_2$ | copper(II) acetate |
| DCM | dichloromethane |
| DEAD | diethyl azodicarboxylate |
| DIPEA | diisopropylethylamine |
| DMF | N,N-dimethylformamide |
| DMSO | dimethylsulfoxide |
| ESI | electrospray ionization |
| $Et_3N$ | triethylamine |
| EtOAc | ethyl acetate |
| EtOH | ethanol |
| h | hours |
| $H_2O$ | water |
| HATU | 1-[bis(dimethylamino)methylene]-1H-1,2,3-triazolo[4,5-b]pyridinium 3-oxid hexafluorophosphate |
| HCl | hydrochloric acid |
| HOAc | acetic acid |
| $K_2CO_3$ | potassium carbonate |
| KI | potassium iodide |
| KOH | potassium hydroxide |
| KOtBu | potassium tert-butoxide |
| $LiAlH_4$ | lithium aluminum hydride |
| LiOH | lithium hydroxide |
| MeOH | methanol |

-continued

| Abbreviation | Name |
|---|---|
| min | minutes |
| $N_2$ | nitrogen |
| $Na_2CO_3$ | sodium carbonate |
| $Na_2SO_4$ | sodium sulfate |
| NaH | sodium hydride |
| $NaHCO_3$ | sodium bicarbonate |
| $NaN_3$ | sodium azide |
| NaOH | sodium hydroxide |
| NBS | N-bromosuccinimide |
| $NH_4Cl$ | ammonium chloride |
| $NH_4HCO_3$ | ammonium bicarbonate |
| NMR | nuclear magnetic resonance |
| $Pd_2(dba)_3$ | tris(dibenzylideneacetone)dipalladium(0) |
| $Pd(dppf)Cl_2$ | [1,1'-bis(diphenylphosphino)ferrocene]dichloropalladium(II) |
| Pd/C | palladium on carbon |
| $Pd(OAc)_2$ | palladium(II) acetate |
| Prep-TLC | preparatory thin layer chromatography |
| RuPhos-Pd-G2 | chloro(2-dicyclohexylphosphino-2',6'-diisopropoxy-1,1'-biphenyl)[2-(2'-amino-1,1'-biphenyl)]palladium(II) |
| sat. | saturated |
| t-BuOH | tert-butanol |
| $T_3P$ | propylphosphonic anhydride |
| TBD | 1,5,7-triazabicyclo[4.4.0]dec-5-ene |
| TFA | trifluoracetic acid |
| THF | tetrahydrofuran |

Unless otherwise noted, reagents, and solvents were used as received from commercial suppliers. Anhydrous solvents and oven-dried glassware were used for synthetic transformations sensitive to moisture, and/or oxygen. Reaction times, and yields were not optimized. Example numbers and compound numbers are the same.

Example 1. (S)-2-((4-(6-(Dimethylamino)pyrimidine-4-carbonyl)piperazin-1-yl)methyl)-1-(oxetan-2-ylmethyl)-1H-benzo[d]imidazole-6-carboxylic acid (1)

1

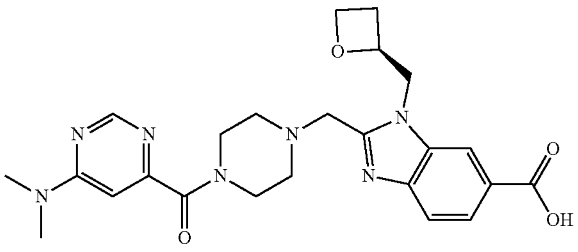

Step A. (S)-2-((Benzyloxy)methyl)oxetane (1a)

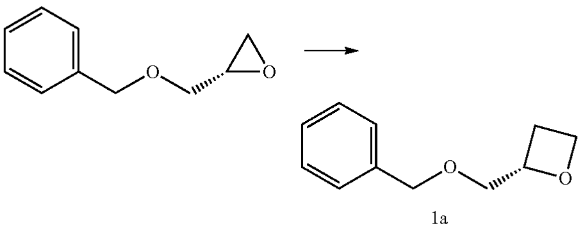

1a

To a solution of KO/Bu (2.97 g, 30.4 mmol) in/BuOH (50 mL) was added trimethylsulfoxonium (6.68 g, 30.4 mmol). The reaction mixture was stirred at 60° C. for 30 min, then (2S)-2-[(benzyloxy)methyl]oxirane (5 g, 30.4 mmol) was added. The mixture was heated at 80° C. for 2 h. After completion, the mixture was cooled to 25° C. and filtered through celite. The filtered cake was washed with petroleum ether (10 mL). The filtrate was added water (20 mL), and extracted with petroleum ether (10 mL×2). The combined organic layers were washed with saturated $NH_4Cl$ (10 mL), dried over magnesium sulfate, filtered, and concentrated in vacuo to provide a crude residue, which was purified by silica gel column chromatography (petroleum ether: EtOAc=1:1) to afford the title product (Ia) (2.5 g, 47%) as a yellow oil. m/z (ESI, +ve ion)=201.1 $[M+Na]^+$.

Step B. (S)-Oxetan-2-ylmethanol (1b)

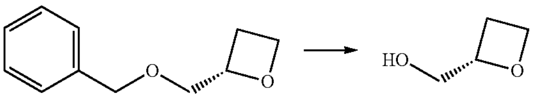

1a 1b

To a solution of 1a (7 g, 39.3 mmol) in THF (90 mL) was added $Pd(OH)_2$ (700 mg, 3.93 mmol). The reaction mixture was stirred at 45° C. under 0.4 Mpa $H_2$ for 48 h. After completion, the reaction was filtered through celite and the resulting crude mixture (1b) in THF was carried to the next step without further purification. m/z (ESI, +ve ion)=111.1 $[M+Na]^+$.

Step C. (S)-Oxetan-2-ylmethyl methanesulfonate (1c)

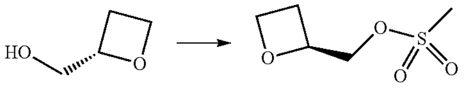

1b 1c

To a solution of 1b (6 g, 68 mmol) in THF (100 mL) was added methanesulfonic anhydride (17.1 g, 102 mmol), and triethylamine (TEA) (13.6 g, 136.5 mmol) at 0° C. The reaction mixture was stirred at 20° C. for 2 h. The reaction was quenched with water (30 mL), and extracted with EtOAc (30 mL×3). The combined organic layers were dried over anhydrous $Na_2SO_4$, filtered, and concentrated under reduced pressure. The residue was purified by silica gel column chromatography (petroleum:EtOAc=1:1) to afford the title product (1c) (6 g, 53.1%) as a yellow oil. m/z (ESI, +ve ion)=167.1 $[M+H]^+$.

Step D. (S)-2-(Azidomethyl)oxetane (1d)

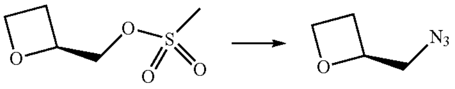

1c 1d

To a solution of 1c (6 g, 36.1 mmol) in DMF (100 mL) was added $NaN_3$ (7.02 g, 108 mmol). The reaction mixture was stirred at 80° C. for 16 h. The reaction was added water (20 mL), and extracted with EtOAc (20 mL×2). The organic layer was washed with $H_2O$ (10 mL), dried, and concentrated to provide a crude title product (1d) which was carried to the next step without further purification. m/z (ESI, +ve ion)=114.1 $[M+H]^+$.

Step E. (S)-Oxetan-2-ylmethanamine (1e)

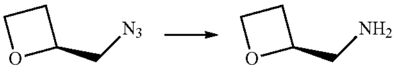

1d 1e

To a solution of 1d (900 mg, 7.96 mmol) in THF (30 mL) was added 10% Pd/C (10 mg). The reaction mixture was stirred at 20° C. for 2 h under hydrogen. After completion, the crude reaction mixture was filtered through celite. The filtrate (1e) was used in the next step without further purification. m/z (ESI, +ve ion)=88.2 $[M+H]^+$.

Step F. Methyl(S)-4-nitro-3-((oxetan-2-ylmethyl) amino)benzoate (1f)

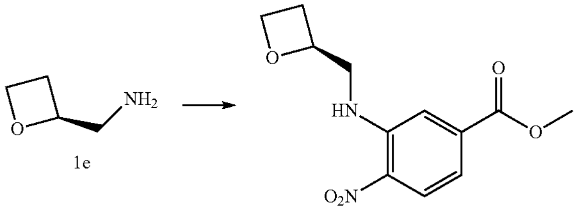

1e

1f

To a solution of 1e (700 mg, 10.5 mmol) in THF (3 mL) was added methyl 3-fluoro-4-nitrobenzoate (2.09 g, 10.5 mmol), and TEA (3.18 g, 31.5 mmol). The reaction mixture was stirred at 25° C. for 16 h, then added water (15 mL). The solution was extracted with EtOAc (10 mL×3). The combined organic layers were dried over anhydrous $Na_2SO_4$, filtered, and concentrated under reduced pressure. The crude residue was purified by silica gel column chromatography (petroleum ether:EtOAc=1:1) to afford the title product (1f) (1.2 g, 43.9%) as a yellow solid. m/z (ESI, +ve ion)=267.1 $[M+H]^+$.

Step G. Methyl(S)-4-amino-3-((oxetan-2-ylmethyl) amino)benzoate (1g)

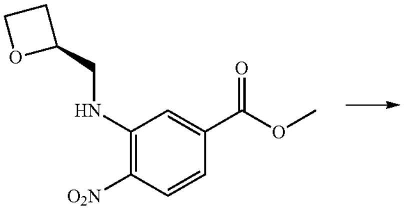

1f

-continued

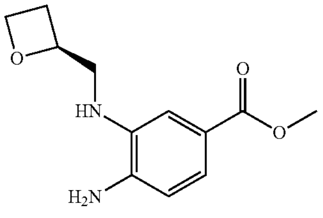

1g

To a solution of 1f (800 mg, 7.9 mmol) in THF (8 mL) was added 10% Pd/C (100 mg). The reaction mixture was stirred at 20° C. for 3 h under 50 psi $H_2$. After completion, the crude mixture was filtered through celite, and the filtrate was concentrated to give the title product (1g) (0.6 g, 43.9%) as a yellow solid. m/z (ESI, +ve ion)=237.2 $[M+H]^+$.

Step H. Methyl(S)-2-(chloromethyl)-1-(oxetan-2-ylmethyl)-1H-benzo[d]imidazole-6-carboxylate (1h)

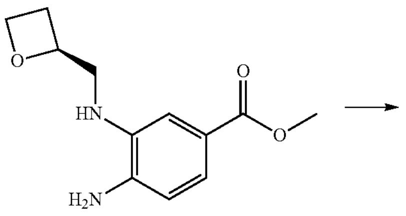

1g

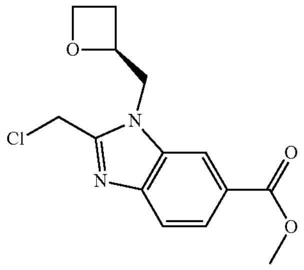

1h

To a solution of 1g (700 mg, 2.96 mmol) in $CH_3CN$ (10 mL) was added 2-chloro-1,1,1-trimethoxyethane (456 mg, 2.96 mmol), and 4-methyl-benzenesulfonic acid (25 mg, 0.14 mmol). The reaction mixture was stirred at 60° C. for 2 h. The residue was purified by silica gel column chromatography (petroleum ether:EtOAc=1:1) to afford the title product (1h) (0.6 g, 68.9%) as a yellow solid. m/z (ESI, +ve ion)=295.1 $[M+H]^+$.

Step I. Methyl(S)-2-((4-(tert-butoxycarbonyl)piperazin-1-yl)methyl)-1-(oxetan-2-ylmethyl)-1H-benzo[d]imidazole-6-carboxylate (1i)

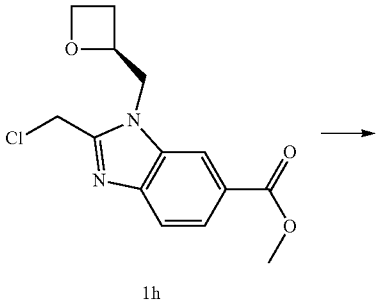

1h

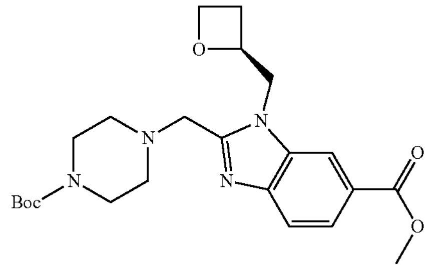

1i

To a solution of 1h (30 mg, 0.10 mmol) in DMF (2 mL) was added tert-butyl piperazine-1-carboxylate (18.9 mg, 0.10 mmol), and $K_2CO_3$ (22 mg, 0.15 mmol). The reaction mixture was stirred at 25° C. for 16 h. After completion, the mixture was quenched with water (20 mL), extracted with EtOAc (20 mL×3), and washed with water (10 mL). The organic phase was dried with anhydrous sodium sulfate, concentrated, and purified by silica gel column chromatography (gradient elution, 0-50% EtOAc in petroleum ether) to afford the title product (1i) (20 mg, 44.4%) as a yellow solid. m/z (ESI, +ve ion)=445.1 $[M+H]^+$.

Step J. Methyl(S)-1-(oxetan-2-ylmethyl)-2-(piperazin-1-ylmethyl)-1H-benzo[d]imidazole-6-carboxylate (1j)

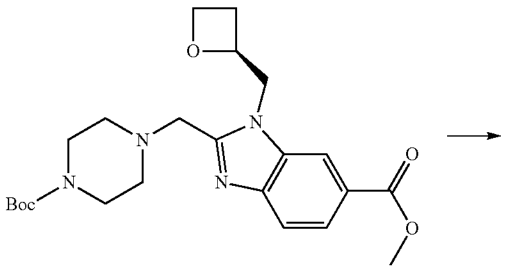

1i

-continued

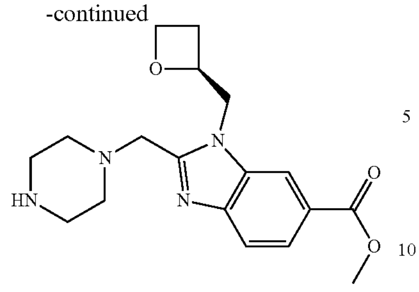

1j

To a solution of 1i (30 mg, 0.067 mmol) in DCM (2 mL) was added $ZnBr_2$ (60.8 mg, 0.27 mmol). The reaction mixture was stirred at 25° C. for 12 h. After completion, the residue was purified by reverse phase HPLC (gradient elution, 0-30% $CH_3CN$ in water with 0.1% TFA as a modifier) to afford the title product (1j) (15 mg, 65%) as a white solid. m/z (ESI, +ve ion)=345.3 $[M+H]^+$.

Step K. Methyl 6-(dimethylamino)pyrimidine-4-carboxylate (1k)

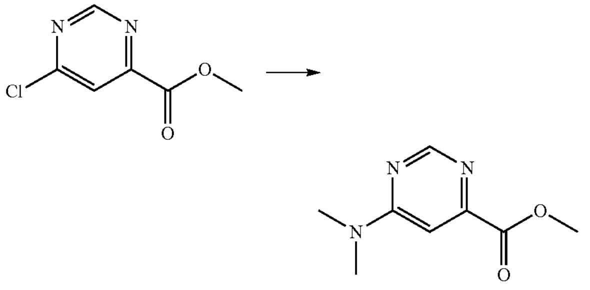

1k

A mixture of methyl 6-chloropyrimidine-4-carboxylate (500 mg, 2.28 mmol), dimethylamine (392 mg, 8.69 mmol), and N,N-diisopropylethylamine (1123 mg, 8.69 mmol) in THF (30 mL) was stirred at 25° C. for 2 h. The reaction was quenched with $H_2O$ (10 mL), saturated $NaHCO_3$ (10 mL) solution, and was then extracted with DCM (150 mL×3). The organic layers were combined, dried, and concentrated to afford the crude title product (1k) (1.06 g) as a yellow solid, which was used directly in the next step without further purification. m/z (ESI, +ve ion)=182.0 $[M+H]^+$.

Step L. 6-(Dimethylamino)pyrimidine-4-carboxylic acid (1l)

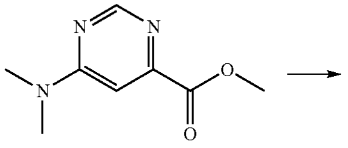

1k

-continued

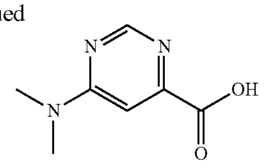

1l

A mixture of 1k (1.0 g, 5.51 mmol) and sodium hydroxide (1.1 g, 27.6 mmol) in MeOH:$H_2O$=10:1 (20 mL) was stirred at 25° C. for 2 h. The reaction was then extracted with EtOAc (150 mL×3). The organic layers were combined, dried over $Na_2SO_4$, and concentrated to afford a crude residue, which was purified by reverse phase HPLC to give the title product (1l) (346 mg, 37.5%) as a white solid. m/z (ESI, +ve ion)=168.0 $[M+H]^+$.

Step M. Methyl(S)-2-((4-(6-(dimethylamino)pyrimidine-4-carbonyl)piperazin-1-yl)methyl)-1-(oxetan-2-ylmethyl)-1H-benzo[d]imidazole-6-carboxylate (1m)

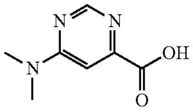

1l

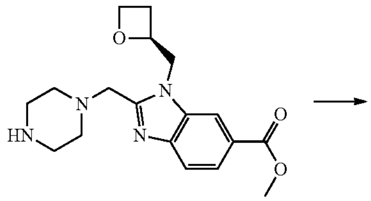

1j

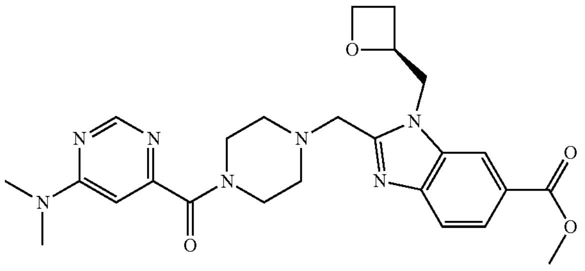

1m

A mixture of 1l (58 mg, 0.35 mmol), 1j (60 mg, 0.17 mmol), 1-hydroxybenzotriazole (30 mg, 0.23 mmol), N-(3-dimethylaminopropyl)-N'-ethylcarbodiimide hydrochloride (40 mg, 0.21 mmol), and N,N-diisopropylethylamine (112 mg, 0.87 mmol) were dissolved in DCM (10 mL) and stirred at 25° C. for 18 h. The reaction mixture was then diluted with DCM (50 mL), and washed with aqueous $NaHCO_3$ solution (100 mL×3). The organic layer was dried, filtered, and concentrated to give a crude residue, which was purified by Prep-TLC (silica gel, EtOAc:petroleum ether=1:4) to afford the title product (1m) (40 mg, 66.7%) as a yellow solid. m/z (ESI, +ve ion)=494.3 $[M+H]^+$.

Step N. (S)-2-((4-(6-(Dimethylamino)pyrimidine-4-carbonyl)piperazin-1-yl)methyl)-1-(oxetan-2-ylmethyl)-1H-benzo[d]imidazole-6-carboxylic acid (1)

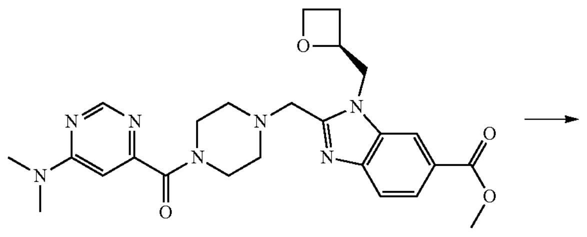

1m

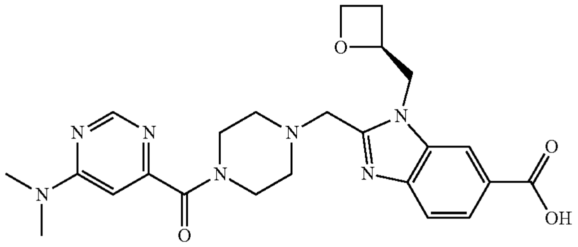

1

A mixture of 1m (35 mg, 0.07 mmol), and 1,5,7-triazabicyclo[4.4.0]dec-5-ene (TBD) (77 mg, 0.24 mmol) in $CH_3CN$:$H_2O$=1:1 (20 mL) was stirred at 50° C. for 2 h. The reaction mixture was then extracted with ethyl acetate (150 mL×3). The combined organic layers were dried over $Na_2SO_4$, filtered, and concentrated. The crude residue was purified by reverse phase HPLC to give the title product (1) (15 mg, 34.2%) as a white solid. $^1H$ NMR (400 MHZ, $CDCl_3$) δ ppm 8.57 (s, 1H), 8.20 (br s, 1H), 7.97-8.10 (m, 1H), 7.71-7.89 (m, 1H), 6.71 (s, 1H), 5.21 (br s, 1H), 4.47-4.74 (m, 3H), 4.24-4.46 (m, 1H), 4.03 (br d, J=6.14 Hz, 2H), 3.79 (br s, 2H), 3.58 (br s, 2H), 3.14 (br s, 6H), 2.59-2.73 (m, 2H), 2.57 (br s, 2H), 2.34-2.50 (m, 2H). m/z (ESI, +ve ion)=480.2 $[M+H]^+$.

Example 2. (S)-2-((4-(3-(2-Chloro-4-(trifluoromethyl)phenoxy)benzoyl)piperazin-1-yl)methyl)-1-(oxetan-2-ylmethyl)-1H-benzo[d]imidazole-6-carboxylic acid (2)

2

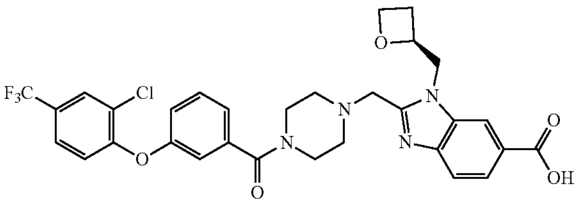

Step A. (S)-1-(Oxetan-2-ylmethyl)-2-(piperazin-1-ylmethyl)-1H-benzo[d]imidazole-6-carboxylic acid (2a)

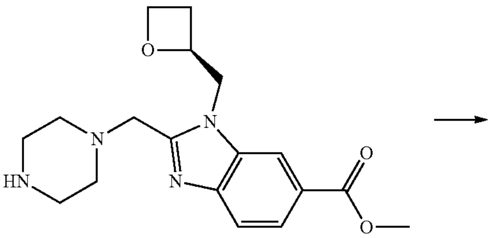

1j

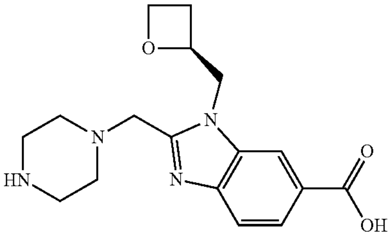

2a

To a solution of 1j (30 mg, 0.087 mmol) in $CH_3CN$ (1 mL) and $H_2O$ (1 mL) was added 1,5,7-triazabicyclo[4.4.0]dec-5-ene (24.4 mg, 0.17 mmol). The reaction mixture was stirred at 45° C. for 2 h. After completion, the reaction was adjusted to pH=2 by 10% citric acid. The mixture was concentrated and purified by reverse phase HPLC ($CH_3CN$ and $H_2O$, 0.5% formic acid as a modifier) to afford the title product (2a) (15 mg, 52%) as a white solid. m/z (ESI, +ve ion)=331.3 $[M+H]^+$.

Step B. (S)-2-((4-(3-(2-Chloro-4-(trifluoromethyl)phenoxy)benzoyl)piperazin-1-yl)methyl)-1-(oxetan-2-ylmethyl)-1H-benzo[d]imidazole-6-carboxylic acid (2)

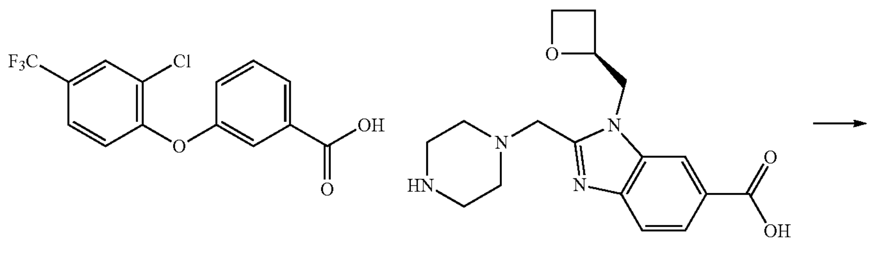

2a

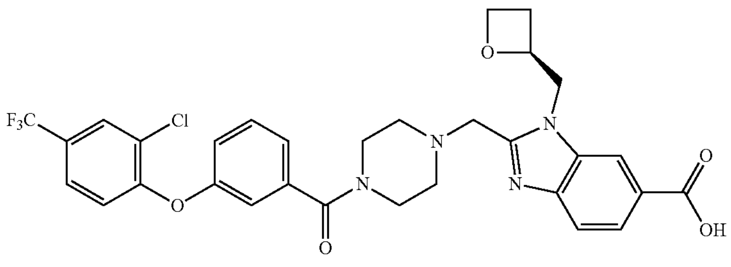

2

3-(2-Chloro-4-trifluoromethylphenoxy)benzoic acid (4.7 mg, 0.015 mmol) was mixed with HATU (4.6 mg, 0.012 mmol), and DIPEA (2.0 mg, 0.02 mmol) in DMF (0.3 mL) for 10 min at room temperature. Then 2a (3.3 mg, 0.01 mmol) was added into the mixture and the reaction was stirred for 5 min. The crude mixture was purified by reverse phase HPLC ($CH_3CN$ and water with 0.1% HOAc as a modifier) to give the title product (2) (1.2 mg, 17.4%) as a white powder. $^1H$ NMR (600 MHZ, $CD_3OD$) δ ppm 8.31 (s, 1H), 7.96 (dd, J=8.44, 1.47 Hz, 1H), 7.87 (br d, J=2.20 Hz, 1H), 7.66 (d, J=8.80 Hz, 1H), 7.62 (br dd, J=8.44, 1.83 Hz, 1H), 7.52 (br t, J=7.89 Hz, 1H), 7.26 (br d, J=7.70 Hz, 1H), 7.18 (d, J=8.44 Hz, 1H), 7.14 (dd, J=8.07, 1.83 Hz, 1H), 7.06-7.09 (m, 1H), 5.25 (qd, J=7.34, 2.57 Hz, 1H), 4.86-4.87 (m, 1H), 4.68-4.73 (m, 1H), 4.63 (td, J=7.89, 5.87 Hz, 1H), 4.44 (dt, J=9.17, 5.87 Hz, 1H), 4.03 (br d, J=13.57 Hz, 1H), 3.94 (br d, J=13.94 Hz, 1H), 3.78 (br s, 2H), 3.44-3.53 (m, 2H), 2.77-2.83 (m, 1H), 2.58-2.70 (m, 2H), 2.46-2.55 (m, 3H). m/z (ESI, +ve ion)=629.3 $[M+H]^+$.

Example compounds 3-7, 13, 21, 22, and 70 were synthesized as described in Example 2.

Example 10. (S)-2-((4-(3-(4-Cyano-2-fluorophenoxy)benzoyl)piperazin-1-yl)methyl)-1-(oxetan-2-ylmethyl)-1H-benzo[d]imidazole-6-carboxylic acid (10)

10

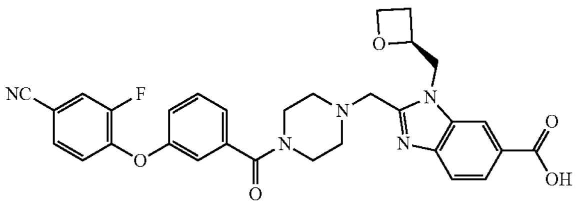

Step A. Methyl 3-(4-cyano-2-fluorophenoxy)benzoate (10a)

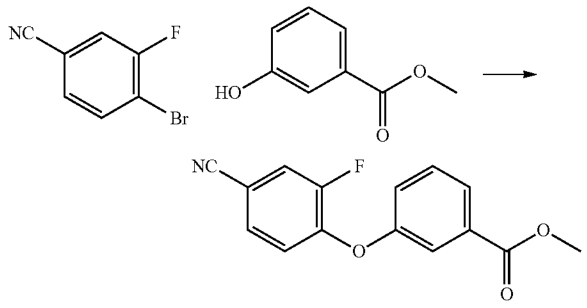

10a

A flask was charged with methyl 3-hydroxybenzoate (17 mg, 0.11 mmol), and DMF (1 mL) was added followed by sodium hydride (60% in mineral oil, 4.4 mg, 0.11 mmol). The reaction was stirred for 30 min at room temperature. Then 4-bromo-3-fluorobenzonitrile (20 mg, 0.1 mmol), and CuBr (2.2 mg, 0.01 mmol) were added and the resulting mixture was heated up to 100° C. overnight. The crude mixture was purified by reverse phase HPLC ($CH_3CN$ and water with 0.1% TFA as a modifier) to give the title product (10a) (1.6 mg, 5.9%) as a white solid. m/z (ESI, +ve ion)=272.1 $[M+H]^+$.

Step B. 3-(4-Cyano-2-fluorophenoxy)benzoic acid (10b)

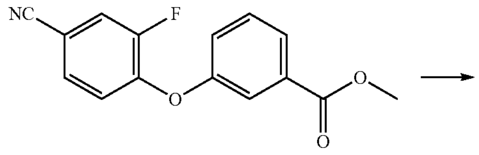

10a

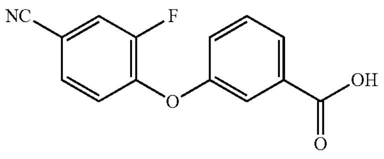

10b

LiOH (2.9 mg, 0.12 mmol) was added to a THF:water (5:1) solution (1.2 mL) of 10a (1.6 mg, 0.006 mmol), and stirred at room temperature for 5.5 h. The crude mixture was purified by reverse phase HPLC ($CH_3CN$ and water with 0.1% TFA as a modifier) to give the title product (10b) (0.8 mg, 53.3%) as a white solid. m/z (ESI, +ve ion)=258.2 $[M+H]^+$.

Step C. (S)-2-((4-(3-(4-Cyano-2-fluorophenoxy) benzoyl)piperazin-1-yl)methyl)-1-(oxetan-2-ylmethyl)-1H-benzo[d]imidazole-6-carboxylic acid (10)

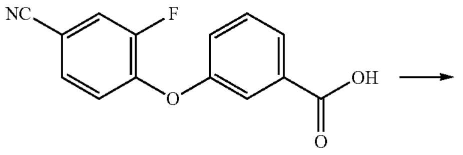

10b

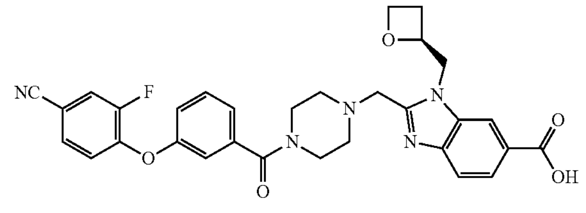

10

The title compound was prepared from 10b by procedures similar to those described in Example 2, Step B. m/z (ESI, +ve ion)=570.2 $[M+H]^+$.

Example compounds 11, and 12 were synthesized as described in Example 10.

Example 14. (S)-1-(Oxetan-2-ylmethyl)-2-((4-(3-(o-tolyloxy)benzoyl)piperazin-1-yl)methyl)-1H-benzo[d]imidazole-6-carboxylic acid (14)

14

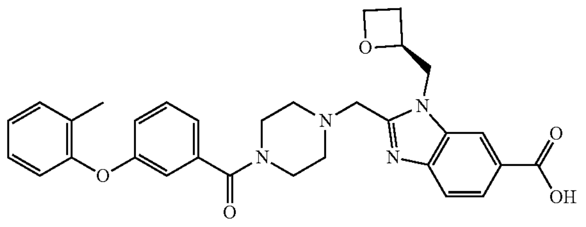

Step A. Methyl 3-(o-tolyloxy)benzoate (14a)

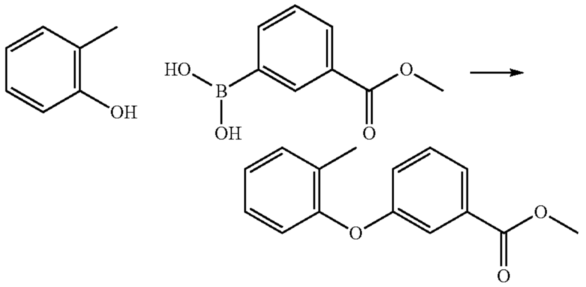

14a o-Cresol (10.8 mg, 0.1 mmol), (3-(methoxycarbonyl) phenyl)boronic acid (36 mg, 0.2 mmol), $Cu(OAc)_2$ (36.3 mg, 0.2 mmol), and molecular sieves were mixed in dry DCM (4 mL). $Et_3N$ (20.2 mg, 0.2 mmol) was added, and the mixture was stirred overnight. Then the solvent was removed in vacuo, and the residue was purified by reverse phase HPLC ($CH_3CN$ and water with 0.1% TFA as a modifier) to provide the title product (14a). m/z (ESI, +ve ion)=243.1 $[M+H]^+$.

Step B. 3-(o-Tolyloxy)benzoic acid (14b)

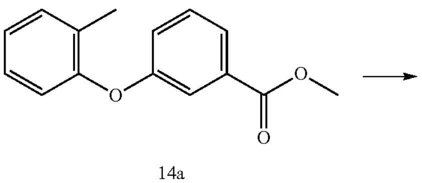

14a

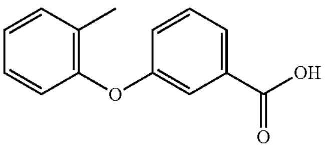

14b

The title compound 14b was prepared from 14a by procedures similar to those described in Example 10, Step B.

Step C. (S)-1-(Oxetan-2-ylmethyl)-2-((4-(3-(o-tolyloxy)benzoyl)piperazin-1-yl)methyl)-1H-benzo[d]imidazole-6-carboxylic acid (14)

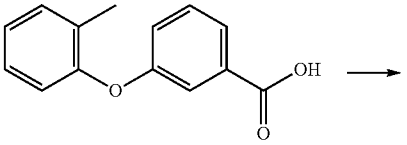

14b

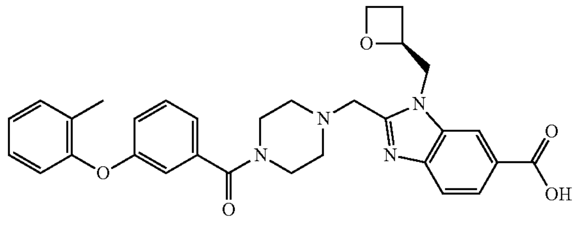

14

The title compound was prepared from 14b by procedures similar to those described in Example 2, Step B. $^1H$ NMR (600 MHZ, $CD_3OD$) δ ppm 8.30 (s, 1H), 7.96 (br d, J=8.44 Hz, 1H), 7.65 (d, J=8.80 Hz, 1H), 7.40 (t, J=7.89 Hz, 1H), 7.30 (br d, J=7.34 Hz, 1H), 7.21 (br t, J=7.52 Hz, 1H), 7.10-7.16 (m, 1H), 7.08 (d, J=7.34 Hz, 1H), 6.95-7.00 (m, 1H), 6.93 (d, J=8.07 Hz, 1H), 6.81-6.88 (m, 1H), 5.24 (qd, J=7.15, 2.75 Hz, 1H), 4.86-4.87 (m, 1H), 4.67-4.73 (m, 1H), 4.59-4.67 (m, 1H), 4.44 (dt, J=8.99, 6.14 Hz, 1H), 4.02 (d, J=13.94 Hz, 1H), 3.94 (d, J=13.57 Hz, 1H), 3.76 (br s, 2H), 3.38-3.49 (m, 2H), 2.76-2.83 (m, 1H), 2.57-2.65 (m, 2H), 2.44-2.57 (m, 3H), 2.18 (s, 3H). m/z (ESI, +ve ion)=541.4 $[M+H]^+$.

Example compounds 15, 16, 17, 18, 23, and 57 were synthesized as described in Example 14.

Example 19. (S)-2-((4-(5-((3-Chloro-2-methylphenoxy)methyl)furan-2-carbonyl)piperazin-1-yl)methyl)-1-(oxetan-2-ylmethyl)-1H-benzo[d]imidazole-6-carboxylic acid (19)

19

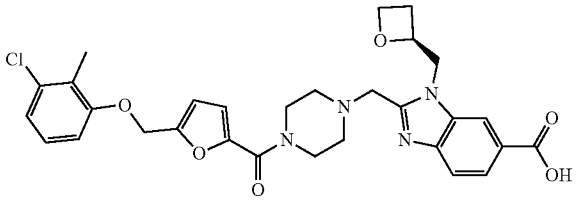

Step A. Ethyl 5-((3-chloro-2-methylphenoxy)methyl)furan-2-carboxylate (19a)

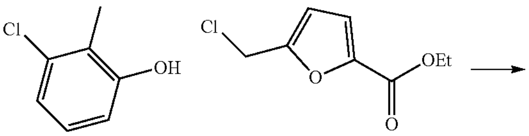

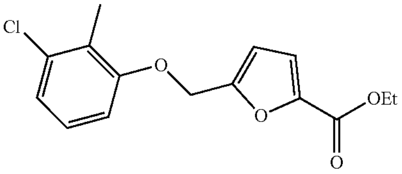

19a

A flask was charged with ethyl 5-(chloromethyl)furan-2-carboxylate (18 mg, 0.1 mmol), ethyl 5-(chloromethyl)furan-2-carboxylate (16 mg, 0.12 mmol), $K_2CO_3$ (32 mg, 0.24 mmol), and DMF (1 mL). The suspension was stirred overnight and purified by reverse phase HPLC ($CH_3CN$ and water with 0.1% HOAc as a modifier) to provide the title product (19a) (28 mg, 98%) as a white solid. m/z (ESI, +ve ion)=295.0 $[M+H]^+$.

Step B. 5-((3-Chloro-2-methylphenoxy)methyl)furan-2-carboxylic acid (19b)

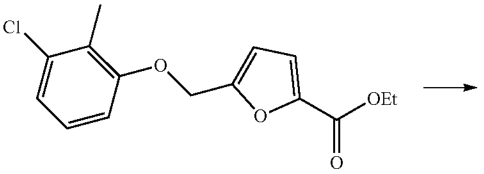

19a

-continued

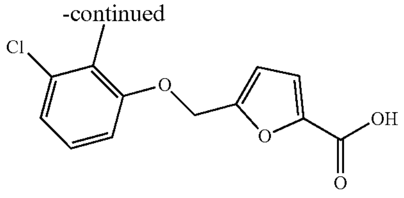

19b

The title compound was prepared from 19a by procedures similar to those described in Example 59, Step C.

Step C. (S)-2-((4-(5-((3-Chloro-2-methylphenoxy)methyl)furan-2-carbonyl)piperazin-1-yl)methyl)-1-(oxetan-2-ylmethyl)-1H-benzo[d]imidazole-6-carboxylic acid (19)

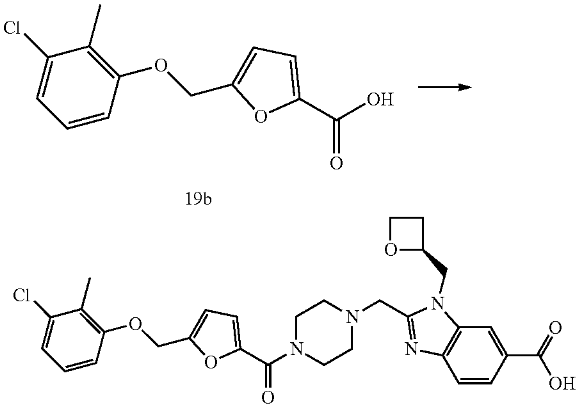

19b

19

The title compound was prepared from 19b by procedures similar to those described in Example 2, Step B. $^1$H NMR (600 MHZ, $CD_3OD$) δ ppm 8.26 (s, 1H), 7.97 (dd, J=8.44, 1.10 Hz, 1H), 7.64 (d, J=8.44 Hz, 1H), 7.08-7.13 (m, 1H), 6.97-7.04 (m, 2H), 6.94 (d, J=8.07 Hz, 1H), 6.62 (d, J=3.30 Hz, 1H), 5.26 (qd, J=7.15, 2.75 Hz, 1H), 5.14 (s, 2H), 4.86-4.89 (m, 1H), 4.69-4.75 (m, 1H), 4.63 (td, J=7.89, 5.87 Hz, 1H), 4.45 (dt, J=9.17, 5.87 Hz, 1H), 4.03 (d, J=13.57 Hz, 1H), 3.95 (d, J=13.57 Hz, 1H), 3.76 (br s, 4H), 2.77-2.83 (m, 1H), 2.48-2.64 (m, 5H), 2.20 (s, 3H). m/z (ESI, +ve ion)=579.2 [M+H]$^+$.

Example compounds 24, 26, 30, 31, 41, 42, 43, 47, 49, 55, 64-69, 71, and 81 were synthesized similar to as described in Example 19.

Example 20. (S)-1-(Oxetan-2-ylmethyl)-2-((4-((5-(phenoxymethyl)furan-2-yl)methyl)piperazin-1-yl)methyl)-1H-benzo[d]imidazole-6-carboxylic acid (20)

20

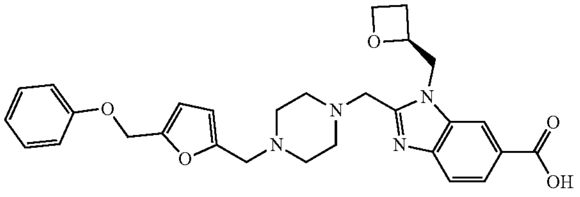

Step A. 5-(Phenoxymethyl)furan-2-carbaldehyde (20a)

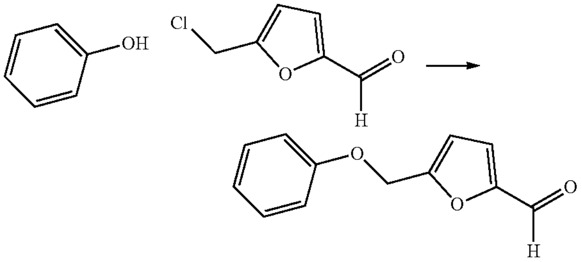

20a

The title compound was made from phenol and 5-(chloromethyl)furan-2-carbaldehyde by procedures similar to those described in Example 19, Step A.

Step B. (S)-1-(Oxetan-2-ylmethyl)-2-((4-((5-(phenoxymethyl)furan-2-yl)methyl)piperazin-1-yl)methyl)-1H-benzo[d]imidazole-6-carboxylic acid (20)

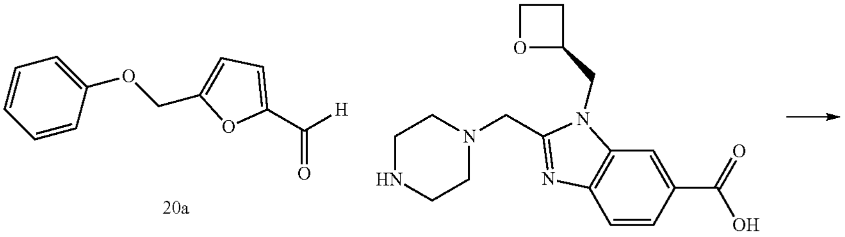

20a

2a

-continued

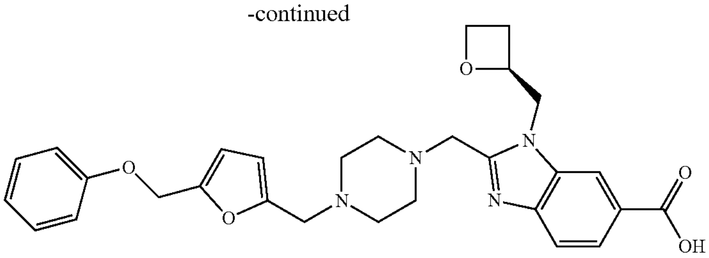

20

To a methoxyethanol (1 mL) solution of 5-(phenoxymethyl)furan-2-carbaldehyde (2.0 mg, 0.01 mmol), and 2a (1.7 mg, 0.005 mmol) was added 5-ethyl-2-methylpyridine borane (1.1 μL, 0.0075 mmol), and HOAc (0.4 μL, 0.0075 mmol). The mixture was stirred at 60° C. overnight, and subsequently cooled down. The crude reaction mixture was purified by reverse phase HPLC ($CH_3CN$ and water with 0.1% HOAc as a modifier) to provide the title product (20) (2.4 mg, 75%) as a white solid. $^1H$ NMR (600 MHZ, $CD_3OD$) δ ppm 8.27-8.35 (m, 1H), 7.96 (dd, J=8.44, 1.47 Hz, 1H), 7.66 (d, J=8.44 Hz, 1H), 7.20-7.26 (m, 2H), 6.93-6.98 (m, 2H), 6.87-6.91 (m, 1H), 6.45 (br d, J=2.93 Hz, 1H), 6.36 (br s, 1H), 5.21 (qd, J=7.21, 2.57 Hz, 1H), 5.01 (s, 1H), 4.78-4.82 (m, 2H), 4.66 (br dd, J=15.41, 2.57 Hz, 1H), 4.61 (td, J=7.89, 5.87 Hz, 1H), 4.43 (dt, J=9.17, 6.05 Hz, 1H), 4.01 (d, J=13.94 Hz, 1H), 3.91 (br d, J=13.94 Hz, 1H), 3.72-3.78 (m, 2H), 2.76 (dtd, J=11.32, 8.09, 8.09, 6.24 Hz, 1H), 2.54-2.72 (m, 8H), 2.44-2.52 (m, 1H). m/z (ESI, +ve ion)=517.2 $[M+H]^+$.

Example compounds 8, 9, 35, and 63 were synthesized as described in Example 20.

Example 27. (S)-2-((4-((6-(2,4-Dichlorophenyl)benzofuran-2-yl)methyl)piperazin-1-yl)methyl)-1-(oxetan-2-ylmethyl)-1H-benzo[d]imidazole-6-carboxylic acid (27)

27

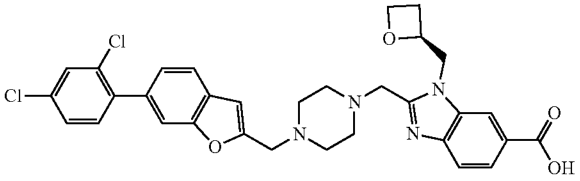

Step A. Ethyl 6-(2,4-dichlorophenyl)benzofuran-2-carboxylate (27a)

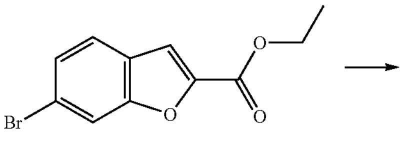

-continued

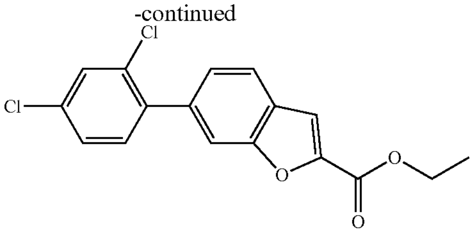

27a

Under a nitrogen atmosphere, [1,1'-Bis(diphenylphosphino)ferrocene]palladium(II) chloride complex with dichloromethane (1:1) (1.52 g, 1.8 mmol), (2,4-dichlorophenyl)boronic acid (2.13 g, 11.1 mmol), and ethyl 6-bromo-1-benzofuran-2-carboxylate (2.5 g, 9.3 mmol) were added to a mixture of 1,4-dioxane (24 mL), $K_2CO_3$ (3.86 g, 27.8 mmol), and water (12 mL). The reaction was heated to 80° C., stirred for one hour, and quenched with water (50 mL). The mixture was extracted with dichloromethane (50 mL, ×2). The combined organic layers were dried over $Na_2SO_4$, filtered, and concentrated. The crude residue was purified by silica gel column chromatography (n-pentane:EtOAc=95:5) to afford the title product (27a) as a white solid (1.5 g, 43%). m/z (ESI, +ve ion)=357.0 $[M+Na]^+$.

Step B. (6-(2,4-Dichlorophenyl)benzofuran-2-yl)methanol (27b)

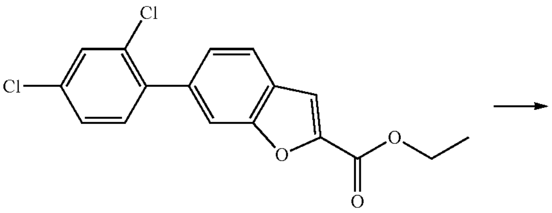

27a

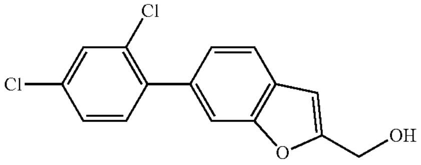

27b

A flask was charged with $LiAlH_4$ (0.2 g, 5.1 mmol), and THF (30 mL). Then 27a (1.5 g, 4.7 mmol) in 10 mL THF was added dropwise at 20° C. The reaction mixture was stirred at 70° C. for 3 h, then quenched by adding ethyl acetate (5 mL) slowly at 0° C. After removing the solvents, the crude residue was diluted with water (40 mL), and extracted with ethyl acetate (40 mL×3). The organic phase was washed with water (20 mL), brine (20 mL), dried with anhydrous sodium sulfate, filtered, concentrated, and purified by silica gel column chromatography (gradient elution, EtOAc in petroleum ether 0-20%) to afford the title product (27b) as a white solid (386.1 mg, 27.8%). m/z (ESI, +ve ion)=275.0 [M-OH]$^+$.

Step C. 2-(Bromomethyl)-6-(2,4-dichlorophenyl)benzofuran (27c)

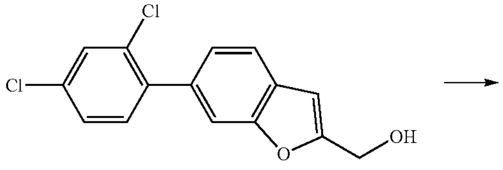

27b

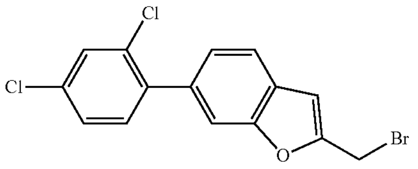

27c

To a stirred solution of 27b (50 mg, 0.15 mmol) in dichloromethane (1.5 mL) was added phosphorus tribromide (73 mg, 0.27 mmol). The mixture was stirred at 0° C. for one hour and diluted with sat. aq. $NaHCO_3$ (2 mL). The reaction mixture was then extracted with DCM (3 mL×3), and washed with brine (3 mL). The organic phase was dried with anhydrous sodium sulfate, filtered, and concentrated. The crude residue was purified by silica gel column chromatography (gradient elution, EtOAc in petroleum ether 0-10%) to afford the title product (27c) (53 mg, 81.6%) as a yellow oil.

Step D. Methyl(S)-2-((4-((6-(2,4-dichlorophenyl)benzofuran-2-yl)methyl)piperazin-1-yl)methyl)-1-(oxetan-2-ylmethyl)-1H-benzo[d]imidazole-6-carboxylate (27d)

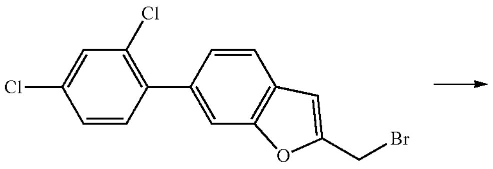

27c

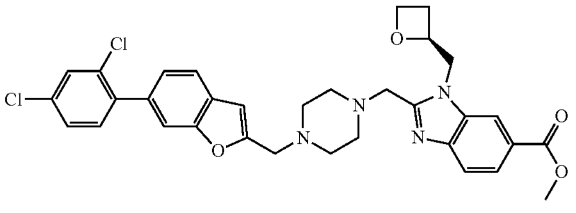

27d 27c (20 mg, 0.056 mmol) was added to a solution of 1j (19 mg, 0.056 mmol), and potassium carbonate (31 mg, 0.225 mmol,) in DMF (0.5 ml), and stirred for 24 h. The reaction was then diluted with water (2 mL), and extracted with EtOAc (2 mL×2). The organic phase was washed with saturated sodium bicarbonate solution (2 mL), dried over magnesium sulfate, filtered, and concentrated under reduced pressure. The crude mixture was purified by silica gel column chromatography (gradient elution, MeOH in dichloromethane 0-20%) to afford the title product (27d) (17 mg, 44.0%) as a yellow oil. m/z (ESI, +ve ion)=619.2 [M+H]$^+$.

Step E. (S)-2-((4-((6-(2,4-Dichlorophenyl)benzofuran-2-yl)methyl)piperazin-1-yl)methyl)-1-(oxetan-2-ylmethyl)-1H-benzo[d]imidazole-6-carboxylic acid (27)

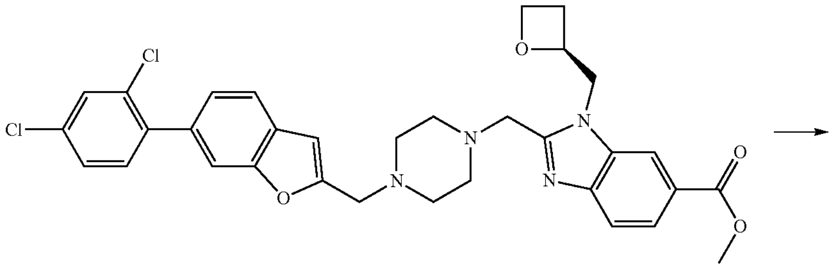

27d

-continued

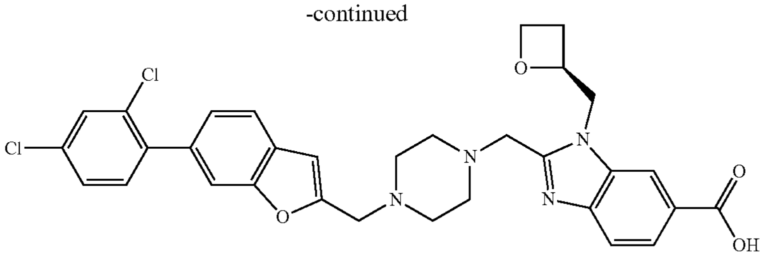

27

To a mixture of 27d (17 mg, 0.028 mmol) in acetonitrile (0.5 mL) and water (0.5 mL) was added 1,3,4,6,7,8-hexahydro-2H-pyrimido[1,2-a]pyrimidine (8 mg, 0.056 mmol). The reaction was stirred at 20° C. for 16 h. The mixture was concentrated and purified by reverse phase HPLC ($CH_3CN$ and $H_2O$ with 0.05% $NH_4HCO_3$ as modifier, gradient elution 0-80%) to afford the title product 27 (3.3 mg, 18.6%) as a white solid. $^1$H NMR (400 MHZ, $CDCl_3$) δ ppm 8.18 (s, 1H), 8.01 (d, J=8.5 Hz, 1H), 7.78 (d, J=8.4 Hz, 1H), 7.56 (d, J=8.0 Hz, 1H), 7.51 (d, J=5.5 Hz, 2H), 7.31 (s, 2H), 7.25 (s, 1H), 6.64 (s, 1H), 5.23-5.16 (m, 1H), 4.72-4.57 (m, 3H), 4.39-4.34 (m, 1H), 3.98 (s, 2H), 3.75 (s, 2H), 2.78-2.58 (m, 8H), 2.48-2.37 (m, 2H). m/z (ESI, +ve ion)=605.1 $[M+H]^+$.

Example compound 28 was synthesized as described in Example 27.

Example 32. (S)-2-((4-(3-(2-Chloro-4-methylbenzyl)benzoyl)piperazin-1-yl)methyl)-1-(oxetan-2-ylmethyl)-1H-benzo[d]imidazole-6-carboxylic acid (32)

32

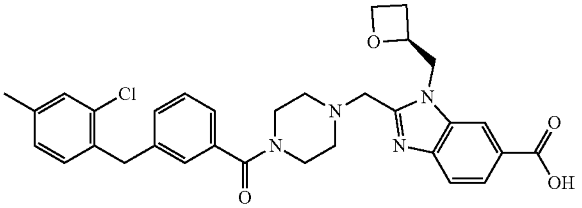

The title compound was made from methyl 3-(bromomethyl)benzoate and (2-chloro-4-methylphenyl)boronic acid by procedures similar to those described in Example 59, Steps B, and C, followed by procedures similar to those described in Example 2, Step B. 1H NMR (600 MHz, $CD_3OD$) δ ppm 8.29-8.33 (m, 1H), 7.94-8.00 (m, 1H), 7.63-7.69 (m, 1H), 7.34-7.40 (m, 1H), 7.28-7.33 (m, 1H), 7.20-7.26 (m, 2H), 7.14-7.20 (m, 2H), 7.05-7.10 (m, 1H), 5.24 (qd, J=7.34, 2.57 Hz, 1H), 4.86-4.87 (m, 1H), 4.67-4.74 (m, 1H), 4.63 (td, J=7.89, 5.87 Hz, 1H), 4.44 (dt, J=9.26, 6.01 Hz, 1H), 4.10 (s, 2H), 4.03 (br d, J=13.94 Hz, 1H), 3.94 (br d, J=13.94 Hz, 1H), 3.70-3.82 (m, 2H), 3.36-3.45 (m, 2H), 2.80 (dtd, J=11.23, 8.14, 8.14, 6.24 Hz, 1H), 2.57-2.68 (m, 2H), 2.41-2.57 (m, 3H), 2.26-2.30 (s, 3H). m/z (ESI, +ve ion)=573.2 $[M+H]^+$.

Example compounds 33, 48, and 56 were synthesized as described in Example 32.

Example 34. (S)-1-(Oxetan-2-ylmethyl)-2-((4-(6-(p-tolyloxy)pyrimidine-4-carbonyl)piperazin-1-yl)methyl)-1H-benzo[d]imidazole-6-carboxylic acid (34)

34

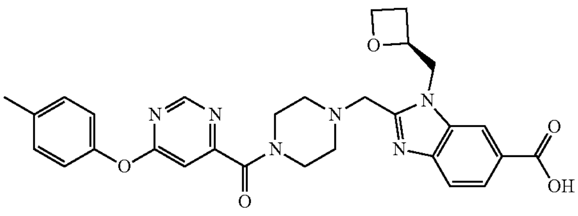

Step A. Methyl 6-(p-tolyloxy)pyrimidine-4-carboxylate (34a)

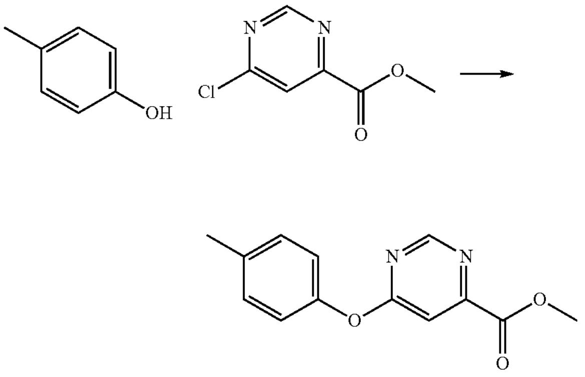

34a

Methyl 6-chloropyrimidine-4-carboxylate (1 g, 5.81 mmol), p-cresol (0.94 g, 8.71 mmol), and $Cs_2CO_3$ (1.94 g, 8.71 mmol) were added successively to DMSO (20 mL). The reaction mixture was stirred at 25° C. for 3 h. After completion, the mixture was quenched by water (20 mL), and extracted with EtOAc (20 mL×3). The organic layers were combined, dried, filtered, and concentrated to afford a crude residue, which was purified by silica gel column chromatography (petroleum ether:EtOAc=1:1) to give the title product (34a) (0.76 g, 53%) as a white solid. m/z (ESI, +ve ion)=245.1 $[M+H]^+$.

Step B. 6-(p-Tolyloxy)pyrimidine-4-carboxylic acid (34b)

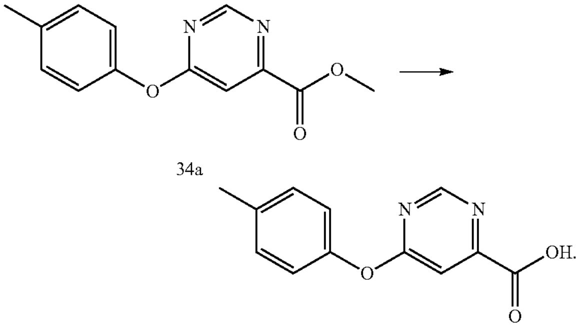

34a

34b 34a (1.1 g, 4.5 mmol) was dissolved in a mixed solvent of MeOH:$H_2O$ (20 mL:7 mL). Sodium hydroxide (1.8 g, 45 mmol) was added, and the reaction was stirred at 25° C. for 6 h. After completion, the reaction was quenched by water (20 mL), and the mixture was adjusted to pH=6.0 by 10% citric acid, and extracted with EtOAc (20 mL×3). The organic layer was dried, filtered, and concentrated to afford a crude residue, which was purified by silica gel column chromatography (petroleum:EtOAc=1:2) to give the title product 34b (830 mg, 80%) as a white solid. m/z (ESI, +ve ion)=231.1 $[M+H]^+$.

Step C. (S)-1-(Oxetan-2-ylmethyl)-2-((4-(6-(p-tolyloxy)pyrimidine-4-carbonyl)piperazin-1-yl)methyl)-1H-benzo[d]imidazole-6-carboxylic acid (34)

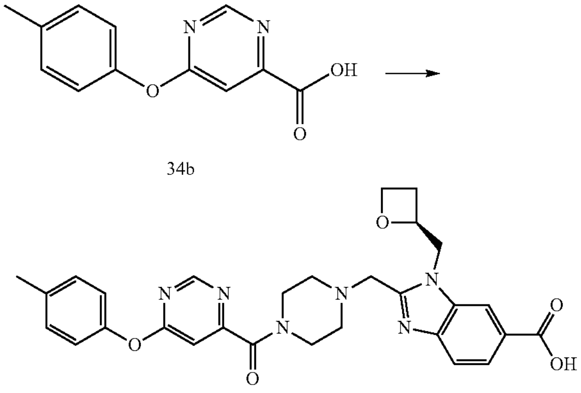

34b

34

The title compound was prepared from 34b by procedures similar to those described in Example 2, Step B. $^1H$ NMR (600 MHZ, $CD_3OD$) δ ppm 8.71 (d, J=0.73 Hz, 1H), 8.30-8.34 (m, 1H), 7.96 (dd, J=8.44, 1.47 Hz, 1H), 7.66 (d, J=8.44 Hz, 1H), 7.27 (d, J=8.44 Hz, 2H), 7.09-7.14 (m, 1H), 7.03-7.09 (m, 2H), 5.25 (qd, J=7.21, 2.57 Hz, 1H), 4.85-4.89 (m, 1H), 4.68-4.75 (m, 1H), 4.63 (td, J=7.89, 5.87 Hz, 1H), 4.44 (dt, J=9.17, 5.87 Hz, 1H), 4.04 (br d, J=13.57 Hz, 1H), 3.96 (br d, J=13.94 Hz, 1H), 3.75-3.83 (m, 2H), 3.50 (br dd, J=6.05, 3.85 Hz, 2H), 2.76-2.84 (m, 1H), 2.61-2.71 (m, 2H), 2.53-2.60 (m, 2H), 2.45-2.53 (m, 1H), 2.37 (s, 3H). m/z (ESI, +ve ion)=543.3 $[M+H]^+$.

Example 36. (S)-2-((4-(5-((4-Chloro-2-fluorophenoxy)methyl)furan-2-carbonyl)-piperazin-1-yl)methyl)-1-(oxetan-2-ylmethyl)-1H-benzo[d]imidazole-6-carboxylic acid (36)

36

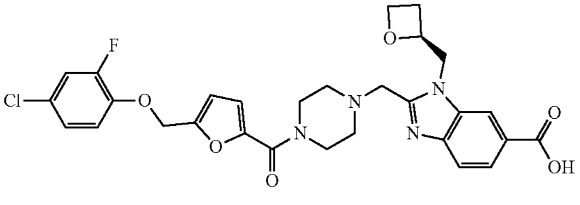

Step A. (S)-2-((4-(5-(Chloromethyl)furan-2-carbonyl)piperazin-1-yl)methyl)-1-(oxetan-2-ylmethyl)-1H-benzo[d]imidazole-6-carboxylic acid (36a)

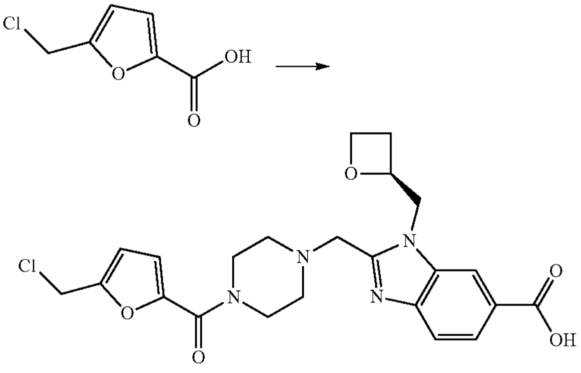

36a

The title compound was prepared from 5-(chloromethyl) furan-2-carboxylic acid and 2a by procedures similar to those described in Example 2, Step B.

Step B. (S)-2-((4-(5-((4-chloro-2-fluorophenoxy) methyl)furan-2-carbonyl)piperazin-1-yl)methyl)-1-(oxetan-2-ylmethyl)-1H-benzo[d]imidazole-6-carboxylic acid (36)

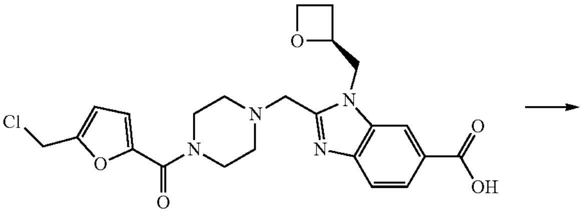

36a

-continued

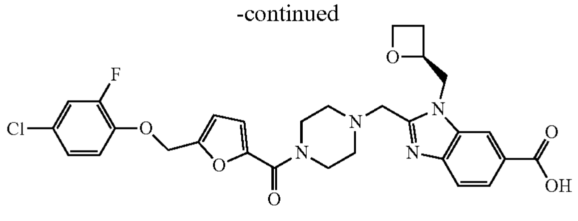

36

4-Chloro-2-fluorophenol (1.1 mg, 0.008 mmol), and 36a (3.2 mg, 0.007 mmol) were treated with $K_2CO_3$ (2.2 mg, 0.016 mmol) in DMF (0.5 mL). The reaction was stirred for 4 h at room temperature. The crude mixture was purified by reverse phase HPLC ($CH_3CN$ and water with 0.1% HOAc as a modifier) to provide the title product (36) (0.4 mg, 8.9%) as a white solid. $^1H$ NMR (600 MHZ, $CD_3OD$) δ ppm 8.35 (s, 1H), 7.98 (br d, J=8.44 Hz, 1H), 7.69 (d, J=8.44 Hz, 1H), 7.13-7.22 (m, 2H), 7.09 (ddd, J=8.80, 2.57, 1.47 Hz, 1H), 6.98-7.02 (m, 1H), 6.64 (d, J=3.30 Hz, 1H), 5.26 (qd, J=7.21, 2.57 Hz, 1H), 5.17 (s, 2H), 4.86-4.90 (m, 1H), 4.73 (br dd, J=15.41, 2.57 Hz, 1H), 4.60-4.69 (m, 1H), 4.46 (dt, J=9.17, 5.87 Hz, 1H), 4.06 (br d, J=13.94 Hz, 1H), 3.97 (br d, J=13.94 Hz, 1H), 3.76 (br s, 4H), 2.81 (m, 1H), 2.53-2.68 (br s, 4H), 2.52 (m, 1H). m/z (ESI, +ve ion)=583.2 $[M+H]^+$.

Example compounds 37, 38, 39, and 40 were synthesized as described in Example 36.

Example 44. (S)-2-((4-(7-Methyl-9-oxo-9H-xanthene-3-carbonyl)piperazin-1-yl)methyl)-1-(oxetan-2-ylmethyl)-1H-benzo[d]imidazole-6-carboxylic acid (44)

44

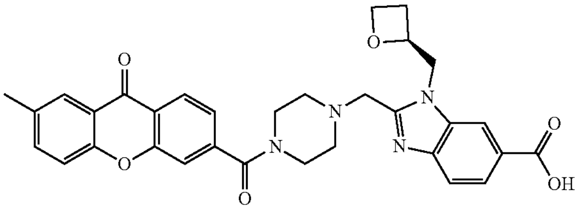

Step A. Dimethyl 2-fluoroterephthalate (44a)

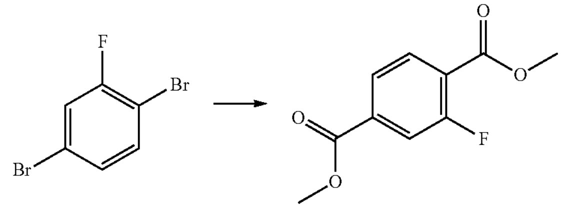

44a

To a mixture of 1,4-dibromo-2-fluorobenzene (1.0 g, 3.9 mmol) in MeOH:DMSO (20 mL, 1:1) was added $Pd(OAc)_2$ (253 mg, 0.78 mmol), DPPP (321 mg, 0.78 mmol), and TEA (5.4 mL, 39 mmol). The mixture was stirred at 85° C. for 16 h under a CO balloon. After completion, the reaction was quenched with water (100 mL), and extracted with EtOAc (50 mL×3). The organic layers were combined, dried, filtered, and concentrated to afford a crude residue, which was purified by silica gel column chromatography (petroleum ether:EtOAc=5:1) to give the title product (44a) (500 mg, 58%) as a brown solid. $^1H$ NMR (400 MHZ, $CDCl_3$) δ ppm 8.00-7.96 (m, 1H), 7.85 (dd, J=8.1, 1.5 Hz, 1H), 7.78 (dd, J=11.0, 1.5 Hz, 1H), 3.94 (s, 3H), 3.93 (s, 3H).

Step B. Dimethyl 2-(p-tolyloxy) terephthalate (44b)

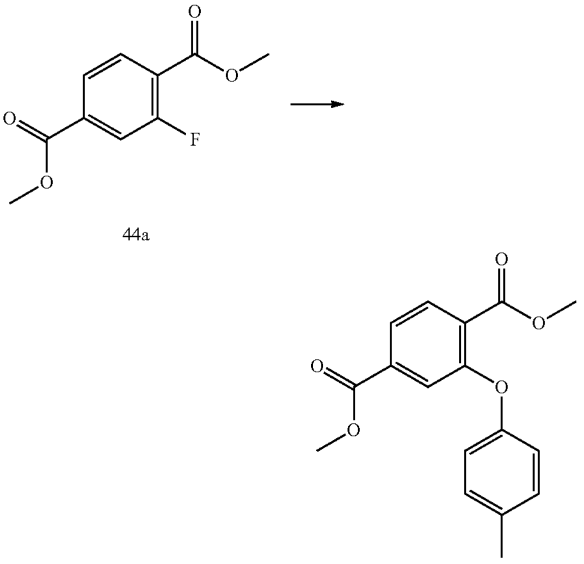

44a

44b

To a mixture of 44a (600 mg, 2.8 mmol) in DMF (30 mL) was added p-cresol (458 mg, 4.2 mmol), and $K_2CO_3$ (1.1 g, 8.4 mmol). The mixture was stirred at 85° C. for 2 h. After completion, the reaction was quenched with water (50 mL), and extracted with EtOAc (50 mL×3). The organic layers were combined, dried, filtered, and concentrated to afford a crude residue, which was purified by silica gel column chromatography (petroleum ether:EtOAc=5:1) to provide the title product (44b) (400 mg, 47%) as a white solid. m/z (ESI, +ve ion)=301.1 $[M+H]^+$.

Step C. Methyl 7-methyl-9-oxo-9H-xanthene-3-carboxylate (44c)

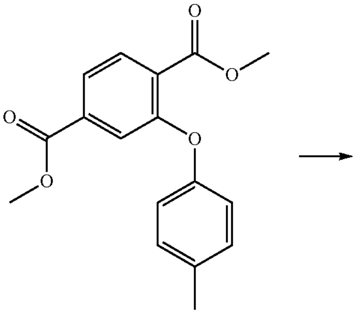

44b

-continued

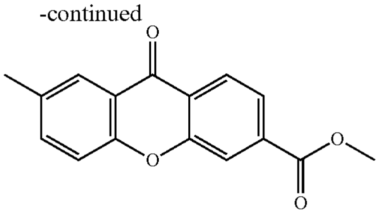

44c

A mixture of 44b (0.5 g, 1.665 mmol) in PPA (30 mL) was stirred at 125° C. for 2 h. After completion, the reaction was quenched with water (30 mL), washed with sat. aq. $Na_2CO_3$ solution, and extracted with EtOAc (20 mL×3). The organic layers were combined, dried, filtered, and concentrated to afford the crude title product (44c) (205 mg) as a white solid. m/z (ESI, +ve ion)=269.1 $[M+H]^+$.

Step D. 7-Methyl-9-oxo-9H-xanthene-3-carboxylic acid (44d)

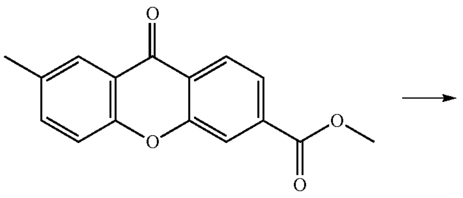

44c

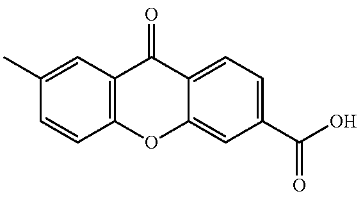

44d

To a mixture of 44c (250 mg, 0.93 mmol) in MeOH:$H_2O$ (6 mL:2 mL) was added NaOH (373 mg, 9.31 mmol). The mixture was stirred at 20° C. for 5 h. After completion, the reaction was quenched with water (30 mL). Then the mixture was adjusted to pH=6 with 10% citric acid, and extracted with EtOAc (30 mL×3). The organic layers were combined, dried, filtered, and concentrated to afford a crude residue, which was purified by silica gel column chromatography (petroleum ether:EtOAc=1:2) to afford the title product (44d) (180 mg, 76%) as a white solid. m/z (ESI, +ve ion)=255.0 $[M+H]^+$.

Step E. (S)-2-((4-(7-Methyl-9-oxo-9H-xanthene-3-carbonyl)piperazin-1-yl)methyl)-1-(oxetan-2-ylmethyl)-1H-benzo[d]imidazole-6-carboxylic acid (44)

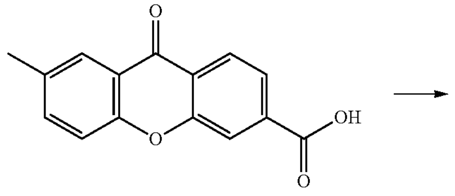

44d

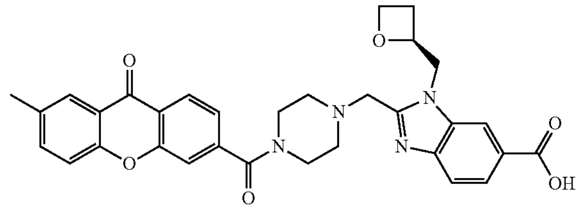

44

The title compound was prepared from 44d, and 2a by procedures similar to those described in Example 2, Step B. $^1H$ NMR (600 MHZ, $CD_3OD$) δ ppm 8.35 (d, J=8.07 Hz, 1H), 8.30 (s, 1H), 8.06-8.09 (m, 1H), 7.93-7.97 (m, 1H), 7.70 (br dd, J=8.44, 2.20 Hz, 1H), 7.64 (br d, J=8.44 Hz, 2H), 7.54 (d, J=8.44 Hz, 1H), 7.44-7.47 (m, 1H), 5.25 (qd, J=7.34, 2.57 Hz, 1H), 4.84-4.90 (m, 1H), 4.68-4.76 (m, 1H), 4.63 (td, J=7.89, 5.87 Hz, 1H), 4.45 (dt, J=9.17, 5.87 Hz, 1H), 4.06 (br d, J=13.57 Hz, 1H), 3.98 (br d, J=13.94 Hz, 1H), 3.85 (br s, 2H), 3.48 (br s, 2H), 2.77-2.84 (m, 1H), 2.62-2.74 (m, 2H), 2.51-2.57 (m, 3H), 2.49 (s, 3H). m/z (ESI, +ve ion)=567.2 $[M+H]^+$.

Example 46. 1-((1-Ethyl-1H-imidazol-5-yl)methyl)-2-((4-(3-(methyl(p-tolyl)amino)benzoyl)piperazin-1-yl)methyl)-1H-benzo[d]imidazole-6-carboxylic acid (46)

46

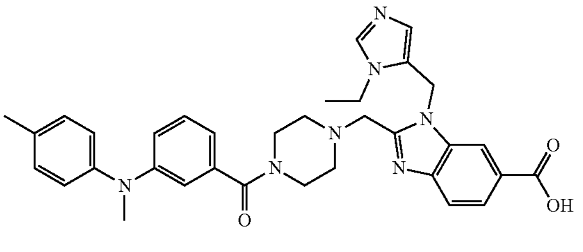

Step A. Methyl 3-(p-tolylamino)benzoate (46a)

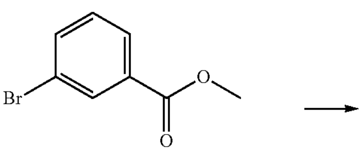

-continued

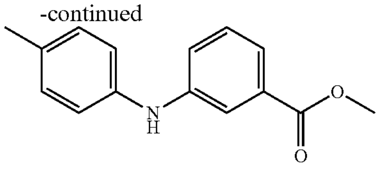

46a

To a mixture of methyl 3-bromobenzoate (3 g, 13.9 mmol), 4-methylaniline (2.2 g, 20.85 mmol), palladium diacetate (0.62 g, 2.78 mmol), BINAP (1.73 g, 2.78 mmol), and $Cs_2CO_3$ (9 g, 27.8 mmol) was added toluene (50 mL). The reaction mixture was stirred at 100° C. for 3 h. After completion, the mixture was quenched with water (50 mL), and extracted with EtOAc (50 mL×3). The organic layer was dried, filtered, and concentrated to afford a crude residue, which was purified by silica gel column chromatography (petroleum ether:EtOAc=20:1) to provide the title product (46a) (2.5 g, 80%) as a yellow solid. m/z (ESI, +ve ion)=242.1 $[M+H]^+$.

Step B. Methyl 3-(methyl (p-tolyl)amino)benzoate (46b)

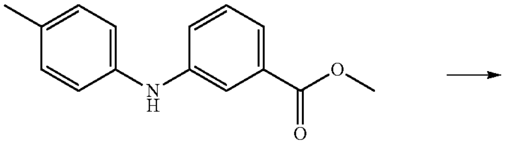

46a

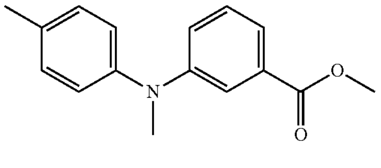

46b 46a (180 mg, 0.75 mmol) was dissolved in THF (3 mL), and cooled down in an ice bath. NaH (60% in mineral oil, 60 mg, 1.49 mmol) was added to the reaction mixture, and was stirred at 0° C. for 0.5 h. Then MeI (210 mg, 1.49 mmol) was added. The reaction temperature was raised to room temperature and stirred for 3 h. After completion, the mixture was quenched with water (3 mL), and extracted with EtOAc (3 mL×3). The organic layer was dried, filtered, and concentrated to afford a crude residue, which was purified by silica gel column chromatography (petroleum ether) to give the title product (46b) (158 mg, 85%) as a white solid. m/z (ESI, +ve ion)=256.0 $[M+H]^+$.

Step C. 3-(Methyl(p-tolyl)amino)benzoic acid (46c)

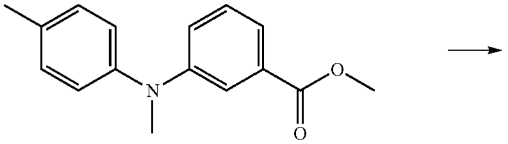

46b

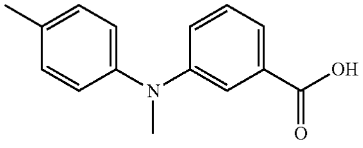

46c

To a mixture of 46b (500 mg, 1.9 mmol), and sodium hydroxide (2 g, 50 mmol) were added MeOH:$H_2O$ (10 mL:5 mL). The reaction mixture was stirred at room temperature for 5 h. After completion, the mixture was quenched with water (5 mL), and extracted with EtOAc (5 mL×3). The organic layers were combined, dried, filtered, and concentrated to afford a crude product, which was purified by silica gel column chromatography (petroleum ether:EtOAc=2:1) to provide the title product (46c) (366 mg, 80%) as a white solid. m/z (ESI, +ve ion)=242.2 $[M+H]^+$.

Step D. 1-((1-Ethyl-1H-imidazol-5-yl)methyl)-2-((4-(3-(methyl(p-tolyl)amino)benzoyl)piperazin-1-yl)methyl)-1H-benzo[d]imidazole-6-carboxylic acid (46)

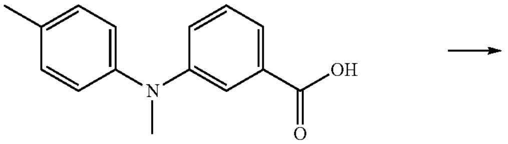

46c

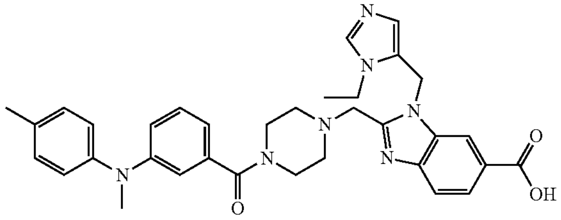

46

The title compound was prepared from 46c, and 57i by procedures similar to those described in Example 2, Step B. $^1H$ NMR (600 MHZ, $CD_3OD$) δ ppm 8.16 (d, J=0.73 Hz, 1H), 8.01 (br dd, J=8.44, 1.47 Hz, 1H), 7.79 (s, 1H), 7.72 (br d, J=8.44 Hz, 1H), 7.25 (br t, J=8.07 Hz, 1H), 7.20 (br d, J=8.07 Hz, 2H), 7.03-7.07 (m, 2H), 6.88-6.93 (m, 1H), 6.73-6.77 (m, 2H), 6.57 (s, 1H), 5.78 (s, 2H), 4.09 (q, J=7.34 Hz, 2H), 3.87-3.89 (m, 2H), 3.60 (br s, 2H), 3.31-3.35 (m, 2H), 3.28 (s, 3H), 2.56 (br s, 2H), 2.39 (br s, 2H), 2.28-2.33 (m, 3H), 1.27-1.34 (m, 3H). m/z (ESI, +ve ion)=592.4 $[M+H]^+$.

Example compounds 25, 29, 45, 50, 51, 52, 54, 58, 75, 76, 85, and 87 (last 2 steps follow Example 102, Step D, and C), and 88 were synthesized similar to as described in Example 46.

Example 57. 2-((4-(3-(2-Chloro-4-methylphenoxy) benzoyl)piperazin-1-yl)methyl)-1-((1-ethyl-1H-imidazol-5-yl)methyl)-1H-benzo[d]imidazole-6-carboxylic acid (57)

57

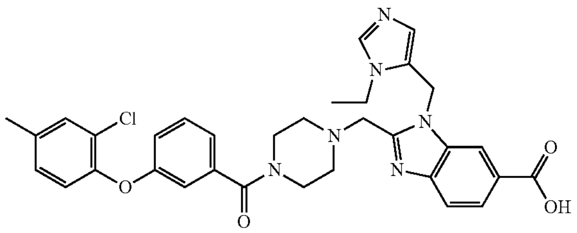

Step A. Ethyl 1-ethyl-1H-imidazole-5-carboxylate (57a)

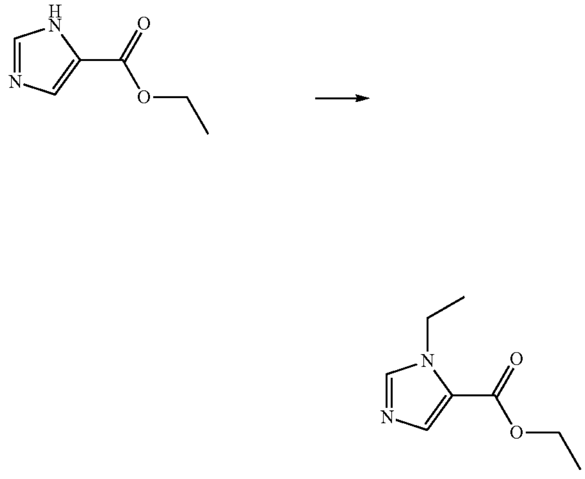

57a

To a solution of ethyl 1H-imidazole-5-carboxylate (2.8 g, 20.0 mmol) in DMF (10 mL) was added NaH (60% in mineral oil, 1.2 g, 30.0 mmol) at 0° C. After stirring at the same temperature for 0.5 h, iodoethane was added (3.12 g, 20.0 mmol), and the resulting mixture was stirred at 0° C. for another 0.5 h. After completion, the mixture was quenched with $H_2O$ (30 mL), and extracted with EtOAc (30 mL×3). The organic layer was washed with $H_2O$ (30 mL), brine (30 mL), dried over anhydrous $Na_2SO_4$, filtered, and concentrated in vacuo to give a crude residue. The residue was purified by silica gel column chromatography (petroleum ether:EtOAc=5:1) to afford the title product (57a) (850 mg, 25%) as a white solid. m/z (ESI, +ve ion)=169.1 $[M+H]^+$.

Step B. 1-Ethyl-1H-imidazole-5-carboxamide (57b)

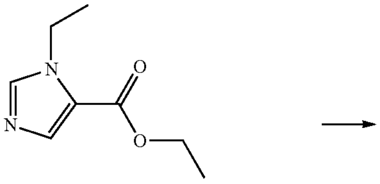

57a

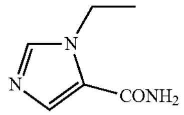

57b

A solution of 57a (3.6 g, 21.4 mmol) in 7 N $NH_3$ solution in MeOH (50 mL) was stirred at 80° C. for 36 h in a sealed reactor. After completion, the mixture was concentrated in vacuo to give a crude residue. The crude residue was purified by silica gel column chromatography (DCM:MeOH=10:1) to afford the title product (57b) (1.9 g, 64%) as a white solid. m/z (ESI, +ve ion)=140.1 $[M+H]^+$.

Step C. (1-Ethyl-1H-imidazol-5-yl) methanamine (57c)

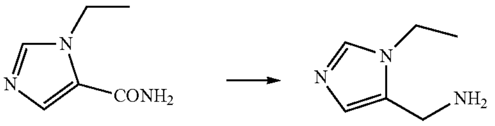

57b 57c

To a solution of 57b (1.9 g, 13.6 mmol) in THF (20 mL) was added $LiAlH_4$ (1.1 g, 27.2 mmol) at 0° C. The mixture was stirred at 60° C. for 16 h under $N_2$. After completion, the mixture was quenched with $Na_2SO_4 \cdot 10H_2O$, and filtered. The filtrate was extracted by DCM (100 mL). The organic layer was concentrated in vacuo to afford the crude title product (57c) (1.4 g) as a colorless oil, which was used in the next step without further purification. m/z (ESI, +ve ion)=126.2 $[M+H]^+$.

Step D. Methyl 3-(((1-ethyl-1H-imidazol-5-yl) methyl)amino)-4-nitrobenzoate (57d)

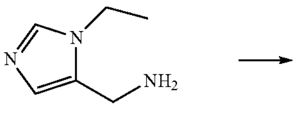

57c

-continued

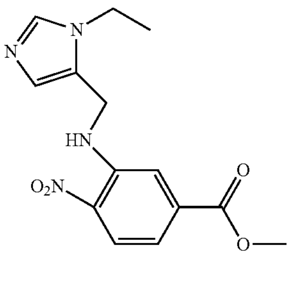

57d

A mixture of 57c (1.4 g, 11.1 mmol), methyl 3-fluoro-4-nitrobenzoate (2.4 g, 12.2 mmol), and TEA (3.3 g, 33.3 mmol) in THF (20 mL) was stirred at 25° C. for 16 h. After completion, the mixture was diluted with $H_2O$ (50 mL), and extracted with DCM (50 mL×3). The organic layer was dried over anhydrous $Na_2SO_4$, filtered, and concentrated in vacuo to give a crude residue. The residue was purified by silica gel column chromatography (DCM:MeOH=10:1) to afford the title product (57d) (1.6 g, 47%) as a white solid. m/z (ESI, +ve ion)=305.2 $[M+H]^+$.

Step E. Methyl 4-amino-3-(((1-ethyl-1H-imidazol-5-yl)methyl)amino)benzoate (57e)

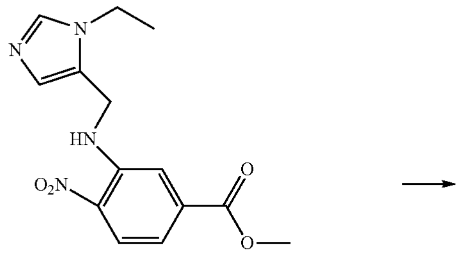

57d

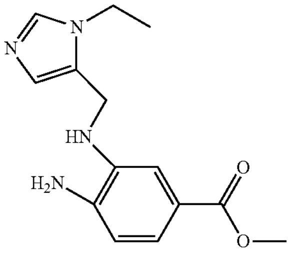

57e

A mixture of 57d (1.6 g, 5.26 mmol), and 10% Pd/C (200 mg) in MeOH (10 mL) was stirred at 25° C. for 2 h under $H_2$. After completion, the mixture was filtered through a pad of celite, which was rinsed with additional MeOH (100 mL). The organic layers were combined, and concentrated in vacuo to give a crude residue. The residue was purified by silica gel column chromatography (DCM:MeOH=10:1) to afford the title product (57e) (1.3 g, 90%) as a brown solid. m/z (ESI, +ve ion)=275.2 $[M+H]^+$.

Step F. Methyl 2-(chloromethyl)-1-((1-ethyl-1H-imidazol-5-yl)methyl)-1H-benzo[d]imidazole-6-carboxylate (57f)

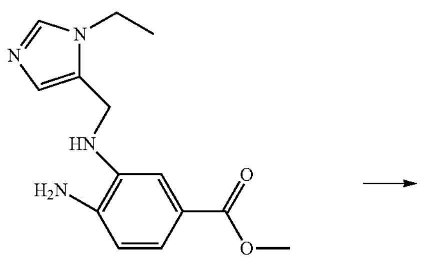

57e

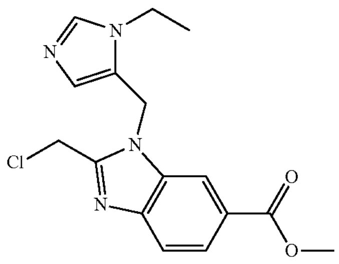

57f

To a solution of 57e (100 mg, 0.36 mmol) in $CH_3CN$ (3 mL) was added 2-chloro-1,1,1-trimethoxyethane (67.7 mg, 0.44 mmol), and p-toluenesulfonic acid monohydrate (3.4 mg, 0.018 mmol) at room temperature. The mixture was heated to 60° C., and stirred overnight. The crude reaction mixture was purified by reverse phase HPLC ($CH_3CN$ and water with 0.1% HOAc as a modifier) to give the title product (57f) (46.6 mg, 39.0%) as a white solid. m/z (ESI, +ve ion)=333.1 $[M+H]^+$.

Step G. Methyl 2-((4-(tert-butoxycarbonyl)piperazin-1-yl)methyl)-1-((1-ethyl-1H-imidazol-5-yl)methyl)-1H-benzo[d]imidazole-6-carboxylate (57g)

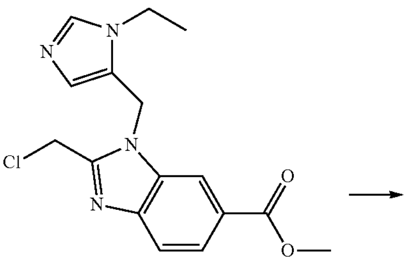

57f

-continued

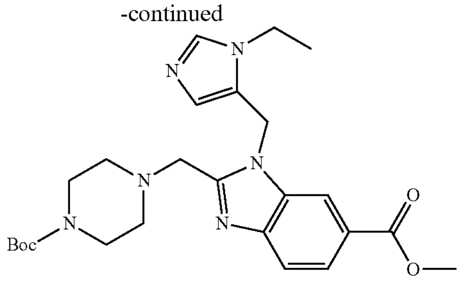

57g

A mixture of tert-butyl piperazine-1-carboxylate (11 mg, 0.06 mmol), 57f (20 mg, 0.06 mmol), and $K_2CO_3$ (18 mg, 0.13 mmol) was stirred in DMF (1 mL) overnight. The crude mixture was purified by reverse phase HPLC ($CH_3CN$ and water with 0.1% HOAc as a modifier) to provide the title product (57g) (23 mg, 79%). m/z (ESI, +ve ion)=483.3 $[M+H]^+$.

Step H. Methyl 1-((1-ethyl-1H-imidazol-5-yl) methyl)-2-(piperazin-1-ylmethyl)-1H-benzo[d]imidazole-6-carboxylate (57h)

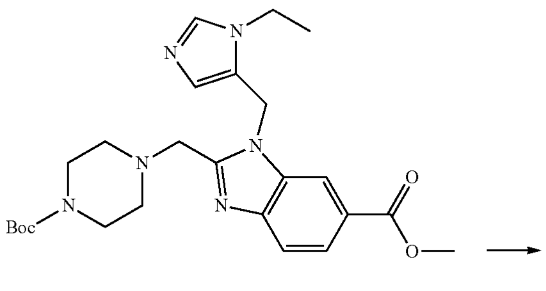

57g

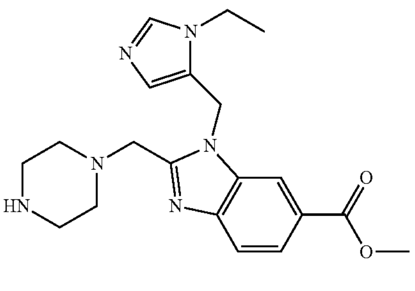

57h 57g (23 mg, 0.06 mmol) was dissolved in DCM (2 mL), and treated with trifluoroacetic acid (TFA, 2 mL) at room temperature for 10 min. The solvent and TFA were removed in vacuo to provide the title product (57h) as a crude residue, which was used in the next step without further purification. m/z (ESI, +ve ion)=383.2 $[M+H]^+$.

Step I. 1-((1-Ethyl-1H-imidazol-5-yl)methyl)-2-(piperazin-1-ylmethyl)-1H-benzo[d]imidazole-6-carboxylic acid (57i)

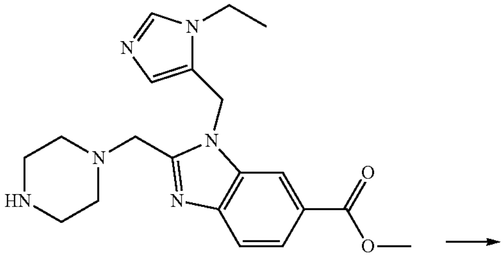

57h

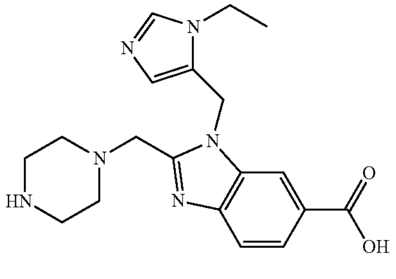

57i

Crude 57h was dissolved in $CH_3CN$ (1 mL), and LiOH (15 mg, 0.6 mmol) in $H_2O$ (0.5 mL) was added at room temperature. The reaction mixture was stirred overnight and purified by reverse phase HPLC ($CH_3CN$ and water with 0.1% HOAc as a modifier) to provide the title product (57i) (8.9 mg, 24.9%). m/z (ESI, +ve ion)=369.3 $[M+H]^+$.

Step J. 2-((4-(3-(2-Chloro-4-methylphenoxy)benzoyl)piperazin-1-yl)methyl)-1-((1-ethyl-1H-imidazol-5-yl)methyl)-1H-benzo[d]imidazole-6-carboxylic acid (57)

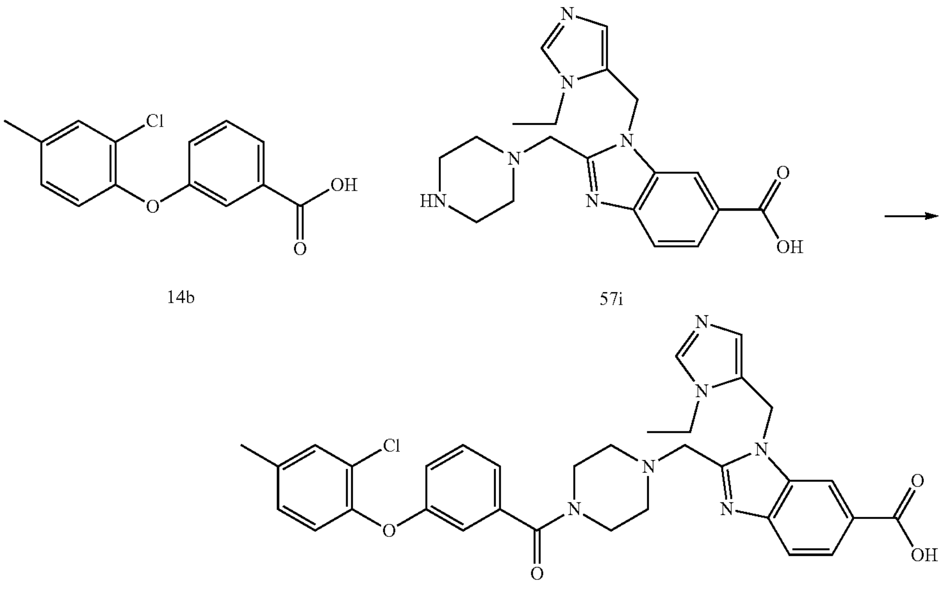

14b 57i

57

The title compound was prepared from 3-(2-chloro-4-methylphenoxy)benzoic acid (similarly prepared as 14b), and 57i by procedures similar to those described in Example 2, Step B. $^1$H NMR (600 MHZ, $CD_3OD$) δ ppm 8.15 (s, 1H), 7.99 (br dd, J=8.62, 1.28 Hz, 1H), 7.77 (s, 1H), 7.70 (d, J=8.44 Hz, 1H), 7.40 (t, J=8.07 Hz, 1H), 7.35 (d, J=1.83 Hz, 1H), 7.16 (br dd, J=8.25, 2.02 Hz, 1H), 7.07 (br d, J=7.34 Hz, 1H), 7.02 (d, J=8.44 Hz, 1H), 6.97 (br dd, J=8.07, 2.57 Hz, 1H), 6.80-6.84 (m, 1H), 6.56 (s, 1H), 5.76 (s, 2H), 4.07 (q, J=7.34 Hz, 2H), 3.88 (s, 2H), 3.59 (br s, 2H), 3.24-3.30 (m, 2H), 2.55 (br s, 2H), 2.40 (br s, 2H), 2.36 (s, 3H), 1.29 (t, J=7.34 Hz, 3H). m/z (ESI, +ve ion)=613.3 $[M+H]^+$.

Example 59. (S)-2-((4-(5-(2,4-Dichlorobenzyl)furan-2-carbonyl)piperazin-1-yl)methyl)-1-(oxetan-2-ylmethyl)-1H-benzo[d]imidazole-6-carboxylic acid (59)

59

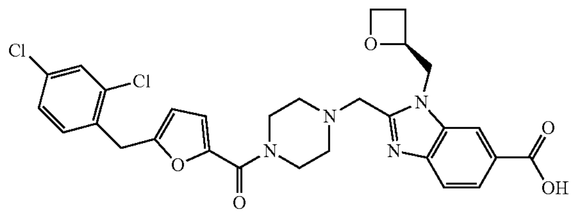

Step A. 1-(Bromomethyl)-2,4-dichlorobenzene (59a)

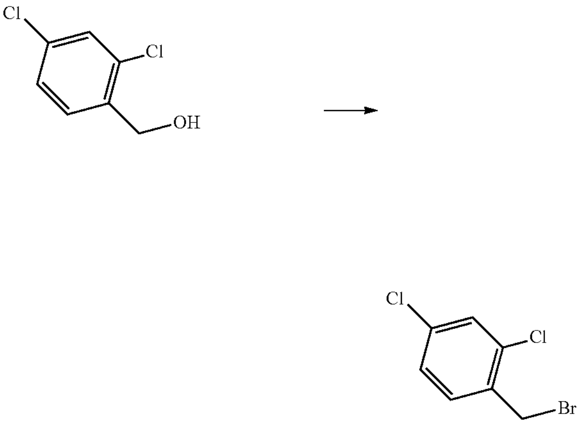

59a

To a solution of (2,4-dichlorophenyl)methanol (1.0 g, 5.6 mmol) in DCM (15 mL) under $N_2$ was added $PBr_3$ (760 mg, 2.8 mmol) at 0° C. After 0.5 h, the mixture was warmed to 25° C., and stirred for 1.5 h. After completion of the reaction, the mixture was quenched with $H_2O$ (10 mL), and adjusted to pH 7-8 by 7% aqueous $NaHCO_3$. The reaction mixture was extracted with DCM (20 mL×2). The organic layer was dried over anhydrous $Na_2SO_4$, filtered, and concentrated in vacuo to provide the title product (59a) (1.0 g), which was used in the next step without further purification.

Step B. Methyl 5-(2,4-dichlorobenzyl)furan-2-carboxylate (59b)

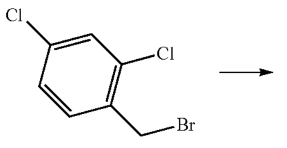

59a

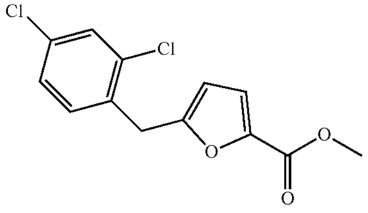

59b

To a mixture of 59a (0.9 g, 3.8 mmol), and (5-(methoxycarbonyl)furan-2-yl)boronic acid (0.65 g, 3.8 mmol) in dioxane (30 mL) and $H_2O$ (4 mL) were added sodium carbonate (1.21 g, 11.4 mmol) and Pd(dppf)$Cl_2$ (0.44 g, 0.3 mmol) at 20° C. The mixture was stirred at 80° C. for 12 h under $N_2$. After completion, the mixture was quenched with $H_2O$ (50 mL), and extracted with EtOAc (50 mL×3). The organic layer was washed with $H_2O$ (30 mL), brine (30 mL), dried over anhydrous $Na_2SO_4$, filtered, and concentrated in vacuo to provide a crude residue, which was purified by silica gel column chromatography (petroleum ether: EtOAc=20:1) to afford the title product (59b) (1.0 g, 86.8%) as a colorless oil. m/z (ESI, +ve ion)=285.0. $[M+H]^+$.

Step C. 5-[(2,4-Dichlorophenyl)methyl]furan-2-carboxylic acid (59c)

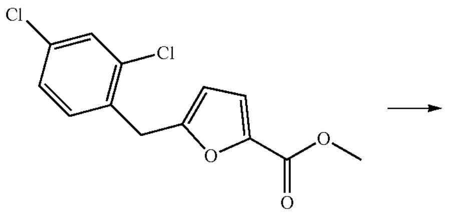

59b

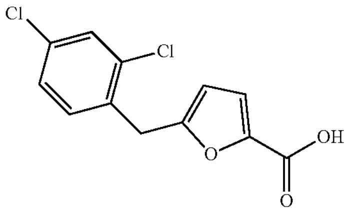

59c

To a mixture of 59b (1.0 g, 0.0035 mol) in THF (30 mL) and $H_2O$ (10 mL) was added LiOH (0.25 g, 0.0105 mol) at 25° C. The mixture was stirred for 12 h under $N_2$. After reaction completion, the mixture was adjusted to pH=7 with 1 N HCl, and extracted with EtOAc (10 mL×3). The organic layer was washed with $H_2O$ (30 mL), brine (30 mL), dried over anhydrous $Na_2SO_4$, filtered, and concentrated in vacuo to afford the title product (59c) (700 mg, 73.8%) as a white solid, which was used in the next step without further purification. m/z (ESI, +ve ion)=270.9 $[M+H]^+$.

Step D. Methyl(S)-2-((4-(5-(2,4-dichlorobenzyl)furan-2-carbonyl)piperazin-1-yl)methyl)-1-(oxetan-2-ylmethyl)-1H-benzo[d]imidazole-6-carboxylate (59d)

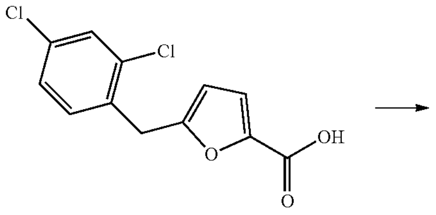

59c

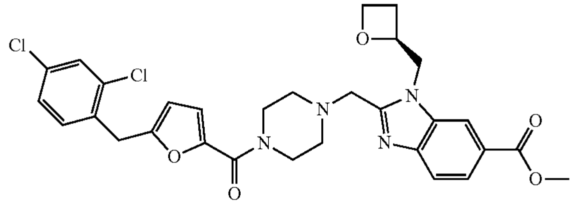

59d

To a solution of 59c (100 mg, 0.37 mmol) in DCM (10 mL) was added N,N-diisopropylethylamine (238 mg, 1.8 mmol), 1-hydroxybenzotriazole (68 mg, 0.48 mmol), N-(3-dimethylaminopropyl)-N'-ethylcarbodiimide hydrochloride (85 mg, 0.44 mmol) and 1j (127 mg, 0.37 mmol) at 25° C. The reaction was stirred at 25° C. for 16 h under $N_2$. After completion, the reaction was filtered, and concentrated in vacuo to give a crude residue, which was purified by silica gel column chromatography (petroleum ether:EtOAc=5:1) to afford the title product (59d) (160 mg, 50.8%) as a white solid. m/z (ESI, +ve ion)=597.1 $[M+H]^+$.

Step E. (S)-2-((4-(5-(2,4-Dichlorobenzyl)furan-2-carbonyl)piperazin-1-yl)methyl)-1-(oxetan-2-ylmethyl)-1H-benzo[d]imidazole-6-carboxylic acid (59)

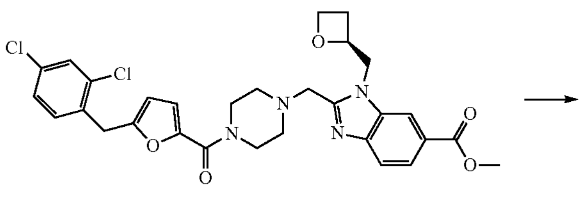

59d

-continued

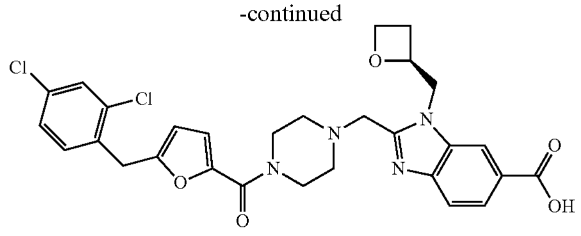

59

To a mixture of 59d (40 mg, 0.067 mmol) in $CH_3CN$:$H_2O$=1:1 (10 mL) was added TBD (56 mg, 0.40 mmol) at 25° C. The mixture was stirred at 50° C. for 2 h under $N_2$. After completion, the reaction mixture was adjusted to pH=7 with 1 N HCl, and extracted with EtOAc (10 mL×3). The organic layer was washed with water (10 mL), brine (10 mL), dried over $Na_2SO_4$, filtered, and concentrated in vacuo to provide a crude residue. The residue was purified by reverse phase HPLC($H_2O$:$CH_3CN$=1:1) to provide the title compound (59) (30 mg, 75.3%) as a white solid. $^1H$ NMR (400 MHZ, $CD_3OD$) δ ppm 8.35 (s, 1H), 7.98 (dd, J=8.33, 1.32 Hz, 1H), 7.69 (d, J=8.33 Hz, 1H), 7.46 (d, J=1.75 Hz, 1H), 7.21-7.40 (m, 2H), 6.96 (d, J=3.51 Hz, 1H), 6.25 (d, J=3.51 Hz, 1H), 5.25 (qd, J=7.16, 2.63 Hz, 1H), 4.90-4.84 (m, 1H), 4.72 (dd, J=15.57, 2.41 Hz, 1H), 4.64 (td, J=7.89, 6.14 Hz, 1H), 4.45 (dt, J=9.10, 5.97 Hz, 1H), 4.16 (s, 2H), 4.05 (br d, J=14.03 Hz, 1H), 3.95 (br d, J=14.03 Hz, 1H), 3.75 (br s, 4H), 2.75-2.87 (m, 1H), 2.57 (br s, 4H), 2.46-2.54 (m, 1H). m/z (ESI, +ve ion)=583.2 $[M+H]^+$.

Example 60. (S)-2-((4-((2-((2,4-Dichlorophenoxy)methyl)oxazol-5-yl)methyl)piperidin-1-yl)methyl)-1-(oxetan-2-ylmethyl)-1H-benzo[d]imidazole-6-carboxylic acid (60)

60

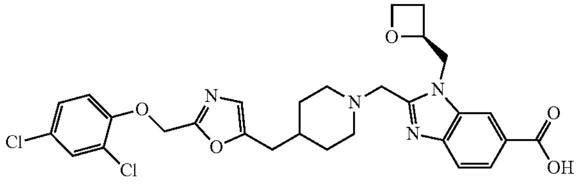

Step A. Methyl 5-(bromomethyl)oxazole-2-carboxylate (60a)

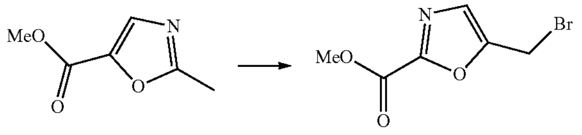

60a

NBS (1034 mg, 5.81 mmol), and AIBN (93 mg, 0.58 mmol) were added to methyl 5-methyl-1,3-oxazole-2-carboxylate (800 mg, 5.81 mmol) in anhydrous $CCl_4$ (58 mL) at room temperature, and the reaction was heated to 70° C. for one hour. The reaction was quenched with sat. aq. $NaHCO_3$, and extracted with DCM (20 mL×3). The organic layer was washed with brine, dried ($Na_2SO_4$), filtered, concentrated, and purified by silica gel column chromatography (gradient elution, EtOAc in hexanes 0-40%,) to provide the title product (60a) (1000 mg, 78%) as a colorless oil. m/z (ESI, +ve ion)=222.0 $[M+H]^+$.

Step B. Methyl 5-((1-(tert-butoxycarbonyl)-1,2,3,6-tetrahydropyridin-4-yl)methyl)oxazole-2-carboxylate (60b)

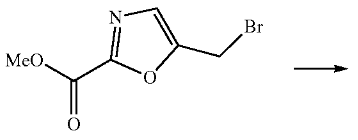

60a

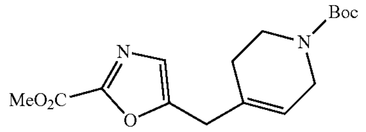

60b (1,1'-Bis(diphenylphosphino)ferrocene) palladium(II) dichloride (332 mg, 0.45 mmol), $K_2CO_3$ (1258 mg, 9.1 mmol), and tert-butyl 4-(4,4,5,5-tetramethyl-1,3,2-dioxaborolan-2-yl)-1,2,3,6-tetrahydropyridine-1-carboxylate (1406 mg, 4.55 mmol) were added to 60a (1000 mg, 4.55 mmol) in 1,4-dioxane:$H_2O$ (3:1, 46 mL) at room temperature. The mixture was degassed with argon for 10 min, then heated to 50° C. for 2 h. The reaction mixture was partitioned between EtOAc and sat. aq. $NaHCO_3$. The organic layer was washed with brine, dried ($Na_2SO_4$), filtered, concentrated, and purified by silica gel chromatography (gradient elution, EtOAc in hexanes 0-50%) to provide the title product (60b) (584 mg, 40%) as an amber oil. m/z (ESI, +ve ion)=345.1 $[M+Na]^+$ Step C. tert-Butyl 4-((2-(hydroxymethyl)oxazol-5-yl)methyl)piperidine-1-carboxylate (60c)

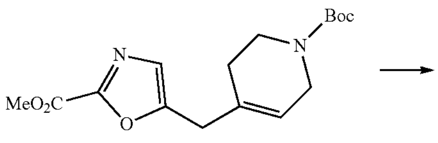

60b

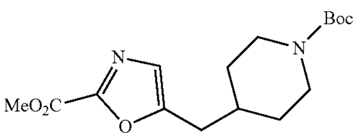

60c

10% Pd/C (96 mg, 0.09 mmol) was added to 60b (584 mg, 1.81 mmol) in EtOH (18 mL) at room temperature. The reaction was degassed with hydrogen for 10 min, then stirred under a $H_2$ balloon for 16 h. The mixture was filtered through a pad of celite, rinsed with EtOAc, and concentrated to give the title product (60c) (586 mg, 99%) as a light brown oil, which was used in the next step without further purification. m/z (ESI, +ve ion)=347.3 $[M+Na]^+$.

Step D. tert-Butyl 4-((2-(hydroxymethyl)oxazol-5-yl)methyl)piperidine-1-carboxylate (60d)

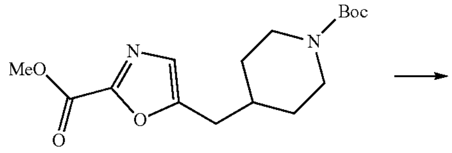

60c

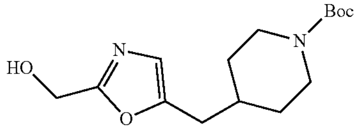

60d $LiAlH_4$ (1 M in THF) (3.6 mL, 3.6 mmol) was added to 60c (586 mg, 1.81 mmol) in anhydrous THF (18 mL) at −78° C., and stirred at 0° C. for 30 min. The reaction was quenched by adding $H_2O$ dropwise, followed by 15% NaOH, and extraction with EtOAc (20 mL×3). The organic layer was washed with brine, dried ($Na_2SO_4$), filtered, concentrated, and purified by silica gel column chromatography (gradient elution, MeOH in $CH_2Cl_2$ 0-10%) to provide the title product (60d) (57 mg, 11%) as a light yellow oil. m/z (ESI, +ve ion)=319.2 $[M+Na]^+$.

Step E. tert-Butyl 4-((2-((2,4-dichlorophenoxy)methyl)oxazol-5-yl)methyl)piperidine-1-carboxylate (60e)

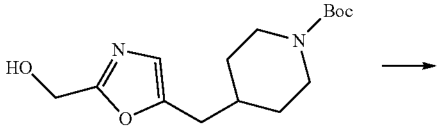

60d

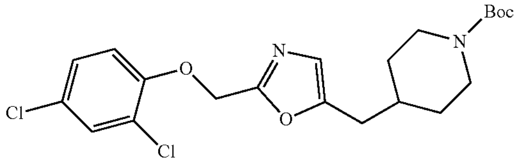

60e

DIAD (58 mg, 0.29 mmol), $PPh_3$ (76 mg, 0.29 mmol), and 2,4-dichlorophenol (31 mg, 0.19 mmol) were added to 60d (57 mg, 0.19 mmol) in anhydrous THF (1.9 mL) at 0° C. After 1.5 h, the reaction was partitioned between EtOAc and $H_2O$. The organic layer was washed with brine, dried ($Na_2SO_4$), filtered, concentrated, and purified by silica gel column chromatography (gradient elution, EtOAc in hexanes 0-90%) to provide the title product (60e) (65 mg, 76%) as a colorless oil. m/z (ESI, +ve ion)=385.0 $[M-tBu+H]^+$.

Step F. Methyl(S)-2-((4-((2-((2,4-dichlorophenoxy)methyl)oxazol-5-yl)methyl)piperidin-1-yl)methyl)-1-(oxetan-2-ylmethyl)-1H-benzo[d]imidazole-6-carboxylate (60f)

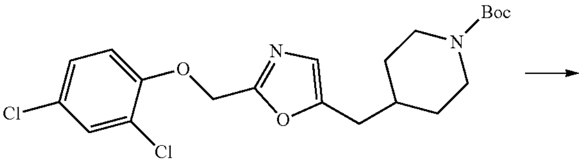

60e

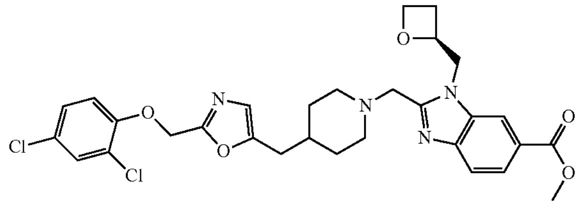

60f

TFA (0.03 mL, 0.41 mmol) was added to 60e (9 mg, 0.02 mmol) in DCM (0.2 mL) at room temperature. The reaction was stirred for 3 h, concentrated, and co-evaporated with DCM (2 mL×3) in vacuo to give a crude amine (7 mg). m/z (ESI, +ve ion)=341.1 $[M+H]^+$. The crude amine was redissolved in DCM (0.2 mL). DIPEA (0.07 mL, 0.04 mmol) and 1h (4 mg, 0.014 mmol) were added consecutively. The reaction was heated at 40° C. for 16 h, concentrated, and purified by silica gel column chromatography (gradient elution, MeOH in DCM 0-10%) to provide the title compound (60f) (9 mg, 75%). m/z (ESI, +ve ion)=599.3 $[M+H]^+$.

Step G. (S)-2-((4-((2-((2,4-Dichlorophenoxy)methyl)oxazol-5-yl)methyl)piperidin-1-yl)methyl)-1-(oxetan-2-ylmethyl)-1H-benzo[d]imidazole-6-carboxylic acid (60)

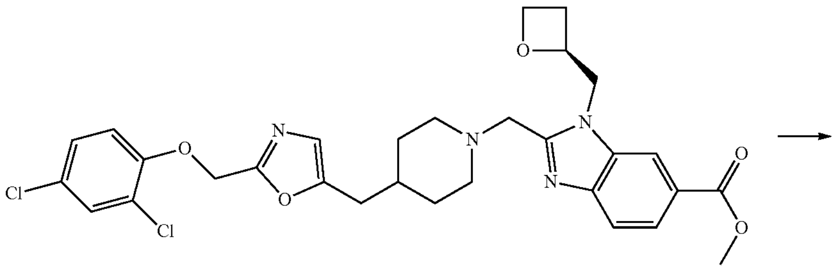

60f

-continued

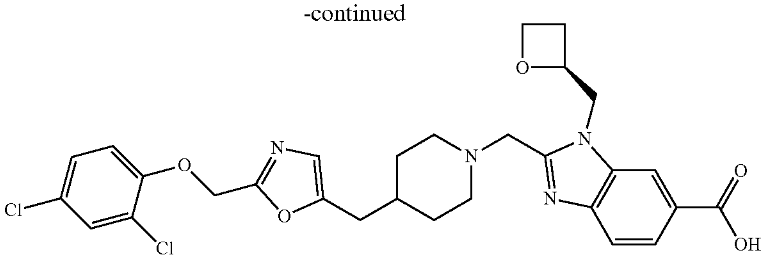

60

LiOH·$H_2O$ (0.6 mg, 0.015 mmol) was added to 60f (9 mg, 0.015 mmol) in THF:$H_2O$ (1:1, 0.3 mL), and stirred at room temperature. After 12 h, additional LiOH·$H_2O$ (0.3 mg, 0.007 mmol) was added, and the reaction was stirred for another 3 h. The reaction was acidified with 1 N HCl to pH=7 and partitioned between EtOAc and sat. aq. $NaHCO_3$. The organic layer was washed with brine, dried ($Na_2SO_4$), filtered, concentrated, and purified by silica gel column chromatography (gradient elution, MeOH in DCM 0-15%) to give the title compound (60) (8 mg, 91%) as a white solid. m/z (ESI, +ve ion)=585.3 $[M+H]^+$. $^1H$ NMR (600 MHz, $CD_3OD$) δ ppm 8.31 (s, 1H), 7.97 (br dd, J=8.44, 1.47 Hz, 1H), 7.65 (d, J=8.44 Hz, 1H), 7.40 (d, J=2.57 Hz, 1H), 7.25 (br dd, J=8.80, 2.57 Hz, 1H), 7.22-7.16 (m, 1H), 6.87 (s, 1H), 5.21-5.25 (m, 3H), 4.81-4.85 (m, 1H), 4.70-4.61 (m, 2H), 4.45 (dt, J=9.17, 5.87 Hz, 1H), 4.01 (d, J=13.9 Hz, 1H), 3.90 (d, J=13.9 Hz, 1H), 3.00-2.83 (m, 2H), 2.82-2.73 (m, 1H), 2.66 (br d, J=6.60 Hz, 1H), 2.50 (ddt, J=11.23, 9.03, 7.29, 7.29 Hz, 1H), 2.11-2.30 (m, 2H), 1.59-1.72 (m, 2H), 1.21-1.40 (m, 2H), 0.81-0.96 (m, 2H).

Example 61. (S)-2-((4-(6-(Cyclohexyl(methyl)amino)pyrimidine-4-carbonyl)piperazin-1-yl)methyl)-1-(oxetan-2-ylmethyl)-1H-benzo[d]imidazole-6-carboxylic acid (61)

61

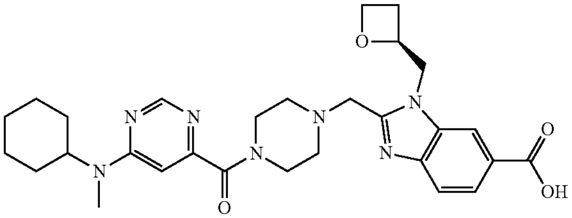

Step A. Methyl 6-(cyclohexyl(methyl)amino)pyrimidine-4-carboxylate (61a)

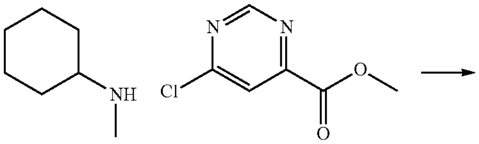

-continued

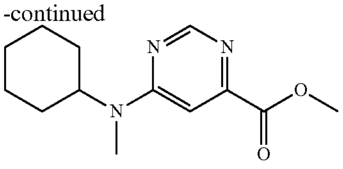

61a

A mixture of methyl 6-chloropyrimidine-4-carboxylate (500 mg, 2.89 mmol), N-methylcyclohexanamine (655 mg, 5.8 mmol), and N,N-diisopropylethylamine (748 mg, 5.79 mmol) in THF (50 mL) was heated to 65° C. for 24 h. The reaction was quenched with $H_2O$ (10 ml), $NaHCO_3$ (10 mL), and extracted with DCM (15 mL×3). The organic layers were combined, dried, filtered, and concentrated to afford the crude title product (61a) (600 mg), which was used in the next step without further purification. m/z (ESI, +ve ion)=250.2 $[M+H]^+$.

Step B. 6-(Cyclohexyl(methyl)amino)pyrimidine-4-carboxylic acid (61b)

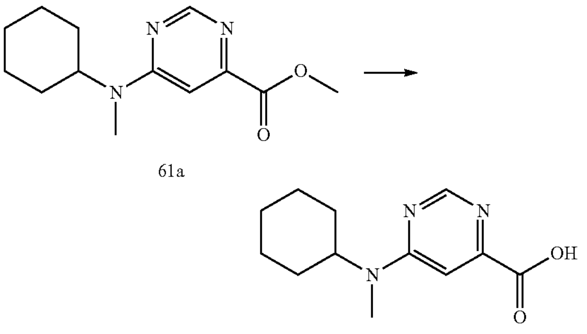

61a

61b

A mixture of 61a (500 mg, 2.00 mmol), and sodium hydroxide (401 mg, 10 mmol) in MeOH:$H_2O$=10:1 (20 mL) was stirred at 25° C. for 2 h. The reaction mixture was then extracted with EtOAc (50 mL×3). The combined organic layers were dried over anhydrous $Na_2SO_4$, filtered, and concentrated in vacuo. The crude residue was purified by reverse phase HPLC ($CH_3CN$:$H_2O$=1:3) to afford the title product (61b) (430 mg, 82.0%) as a white solid. m/z (ESI, +ve ion)=236.0 $[M+H]^+$.

Steps C and D. (S)-2-((4-(6-(Cyclohexyl(methyl)amino)pyrimidine-4-carbonyl)piperazin-1-yl)methyl)-1-(oxetan-2-ylmethyl)-1H-benzo[d]imidazole-6-carboxylic acid (61)

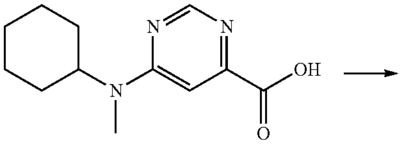

61b

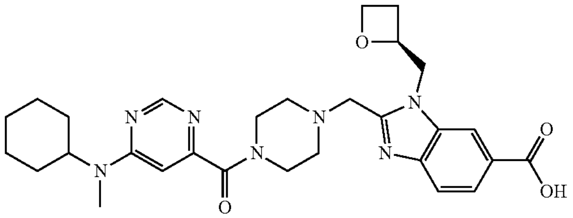

61

The title compound was prepared from 61b by procedures similar to those described in Example 61, Steps B, and C. $^1H$ NMR (400 MHZ, $CDCl_3$) δ ppm 8.55 (s, 1H), 8.20 (brs, 1H), 8.04 (d, J=7.89 Hz, 1H), 7.79 (d, J=8.33 Hz., 1H), 6.68 (br s, 1H), 5.14-5.28 (m, 1H), 4.53-4.68 (m, 4H), 4.35 (br d, J=8.33 Hz, 1H), 3.96-4.12 (m, 2H), 3.80 (br s, 2H), 3.59 (br s, 2H), 2.93 (br s, 3H), 2.62-2.75 (m, 2H), 2.57 (br s, 2H), 2.35-2.52 (m, 2H), 1.86 (br d, J=10.52 Hz, 2H), 1.71 (br d, J=10.96 Hz, 3H), 1.10-1.58 (m, 5H). m/z (ESI, +ve ion)= 274.7 $[M+H]^+$.

Example 62. (S)-2-((4-(6-(Methyl(phenyl)amino)pyrimidine-4-carbonyl)piperazin-1-yl)methyl)-1-(oxetan-2-ylmethyl)-1H-benzo[d]imidazole-6-carboxylic acid (62)

62

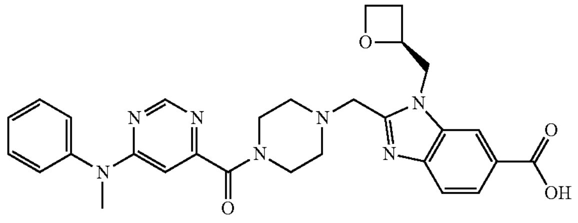

Step A. 6-(Methyl(phenyl)amino)pyrimidine-4-carboxylic acid (62a)

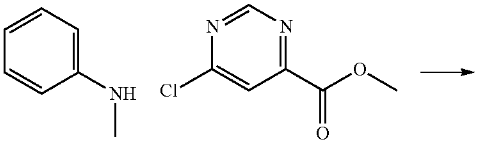

-continued

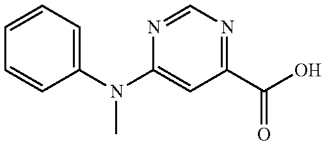

62a

A flask was charged with N-methylaniline (0.5 g, 2.9 mmol), and dioxane (15 mL). Methyl 6-chloropyrimidine-4-carboxylate (466 mg, 4.3 mmol), 4-methylbenzenesulfonic acid (1.47 g, 8.7 mmol), and $H_2O$ (62 mg, 3.5 mmol) were added. The resulting mixture was heated to 120° C. and stirred for 8 h. After completion, the mixture was quenched with $H_2O$ (10 mL), and extracted with DCM (20 mL×2). The aqueous phase was separated, lyophilized, and purified by silica gel column chromatography to provide the title product (62a) (0.41 g, 61.7%). $^1H$ NMR (400 MHZ, DMSO-$d_6$) δ 8.72 (s, 1H), 7.55 (t, J=7.7 Hz, 2H), 7.44-7.39 (m, 3H), 6.83 (s, 1H), 3.47 (s, 3H).

Step B. Methyl(S)-2-((4-(6-(methyl(phenyl)amino)pyrimidine-4-carbonyl)piperazin-1-yl)methyl)-1-(oxetan-2-ylmethyl)-1H-benzo[d]imidazole-6-carboxylate (62b)

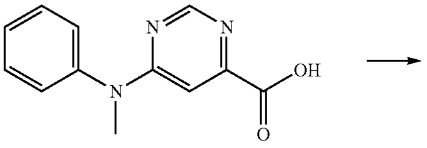

62a

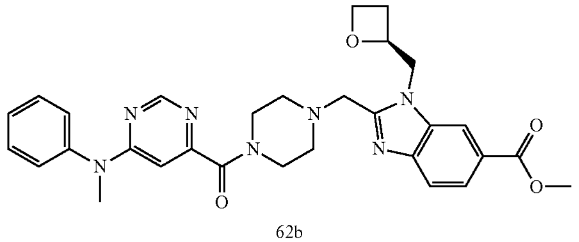

62b

The title compound was prepared from 62a and 1j by procedures similar to those described in Example 1, Step M. m/z (ESI, +ve ion)=556.3 $[M+H]^+$.

Step C. (S)-2-((4-(6-(Methyl(phenyl)amino)pyrimidine-4-carbonyl)piperazin-1-yl)methyl)-1-(oxetan-2-ylmethyl)-1H-benzo[d]imidazole-6-carboxylic acid (62)

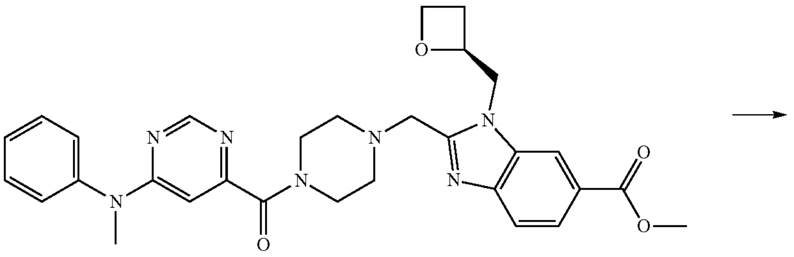

62b

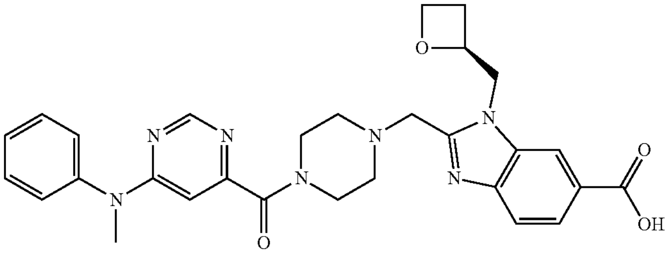

62

The title compound was prepared from 62b by procedures similar to those described in Example 1, Step N. $^1H$ NMR (400 MHZ, DMSO-$d_6$) δ ppm 8.60 (d, J=0.98 Hz, 1H), 8.47 (br s, 1H), 8.18 (s, 1H), 7.83 (br d, J=8.31 Hz, 1H), 7.45-7.58 (m, 2H), 7.30-7.45 (m, 3H), 6.33-6.46 (m, 1H), 5.07 (m, 1H), 4.70 (br dd, J=14.92, 6.85 Hz, 1H), 4.57 (br d, J=13.45 Hz, 1H), 4.41-4.52 (m, 1H), 4.34 (dt, J=8.86, 5.84 Hz, 1H), 3.91 (br d, J=13.69 Hz, 1H), 3.77 (br d, J=13.45 Hz, 1H), 3.47-3.62 (m, 2H), 3.43 (s, 3H), 3.12-3.26 (m, 2H), 2.60-2.76 (m, 1H), 2.34-2.49 (m, 4H), 2.30-2.33 (m, 1H). m/z (ESI, +ve ion)=542.3 $[M+H]^+$.

Example 72. (S)-2-((4-((5-((2,4-Dichlorophenoxy)methyl)furan-2-yl)methyl)piperidin-1-yl)methyl)-1-(oxetan-2-ylmethyl)-1H-benzo[d]imidazole-6-carboxylic acid (72)

72

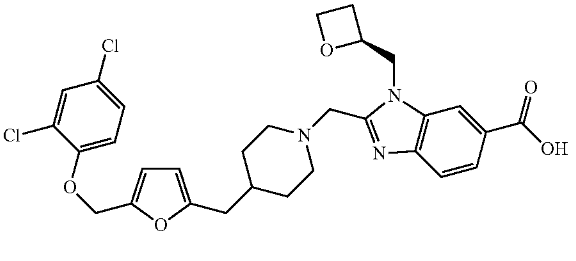

Step A. tert-Butyl 4-((5-(methoxycarbonyl)furan-2-yl)methyl)-3,6-dihydropyridine-1(2H)-carboxylate (72a)

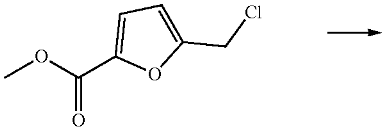

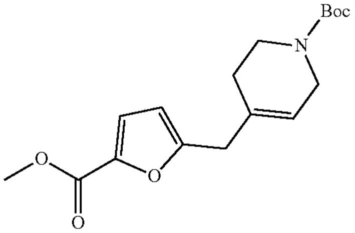

72a

To a mixture of methyl 5-(chloromethyl)furan-2-carboxylate (3.0 g, 0.017 mol), tert-butyl-4-(4,4,5,5-tetramethyl-1,3,2-dioxaborolan-2-yl)-3,6-dihydropyridine-1(2H)-carboxylate (6.4 g, 0.021 mmol), and sodium carbonate (3.7 g, 0.034 mol) in dioxane:$H_2O$=8:1 (80 mL) was added Pd(dppf)$Cl_2$·DCM (1.4 g, 0.0017 mol) at 25° C. The mixture was stirred at 90° C. for 18 h under $N_2$. After completion, the mixture was quenched with $H_2O$ (80 mL), and extracted with EtOAc (80 mL×3). The organic layer was washed with $H_2O$ (80 mL), brine (80 mL), dried over anhydrous $Na_2SO_4$, filtered, and concentrated in vacuo to give a crude residue, which was purified by silica gel column chromatography (petroleum ether:EtOAc=20:1) to give the title product (72a) (4.2 g, 68%) as a yellow oil. m/z (ESI, +ve ion)=344.2 $[M+Na]^+$.

Step B. tert-Butyl 4-((5-(methoxycarbonyl)furan-2-yl)methyl)piperidine-1-carboxylate (72b)

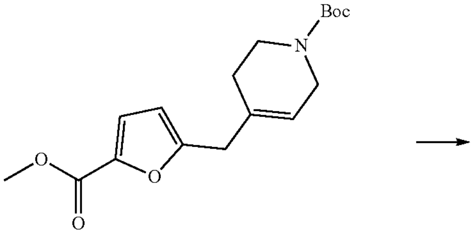

72a

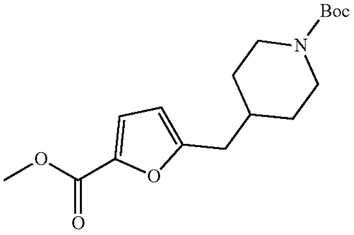

72b

A flask was charged with 72a (2.0 g, 0.0062 mol). MeOH (30 mL) and Raney-Ni (1.0 g) were added at 25° C. The mixture was stirred at 25° C. for 36 h under $H_2$. After reaction completion, the mixture was filtered through a pad of celite, and the filtrate was concentrated in vacuo to afford crude 72b (2.0 g) as a colorless oil, which was used in the next step without purification. m/z (ESI, +ve ion)=346.2 $[M+Na]^+$.

Step C. tert-Butyl 4-((5-(hydroxymethyl)furan-2-yl)methyl)piperidine-1-carboxylate (72c)

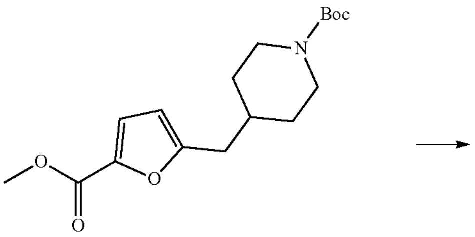

72b

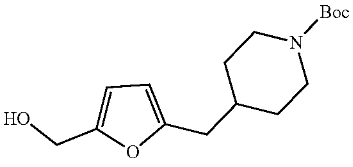

72c

To a mixture of 72b (1.5 g, 0.0046 mol) in THF (30 mL) was added diisobutylaluminum hydride (1.0 M solution in hexanes, 14 mL, 0.014 mol) at −40° C. The mixture was stirred at −40° C. for 3 h under $N_2$. After completion, the reaction was quenched with ice-cold aq. NaOH (2 N) and extracted with EtOAc. The organic layer was washed with water, brine, dried over $Na_2SO_4$, filtered, and concentrated in vacuo to give a crude residue, which was purified by silica gel column chromatography (petroleum ether:EtOAc=10:1) to afford the title product (72c) (1.3 g, 87%) as a yellow oil. m/z (ESI, +ve ion)=318.2 $[M+Na]^+$.

Step D. tert-Butyl 4-((5-((2,4-dichlorophenoxy)methyl)furan-2-yl)methyl)piperidine-1-carboxylate (72d)

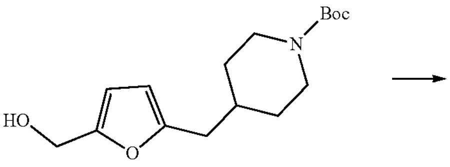

72c

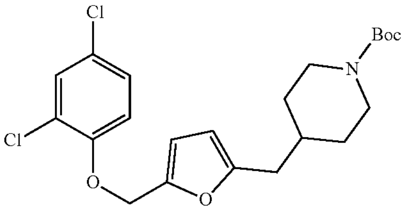

72d

To a mixture of 72c (1.3 g, 0.0044 mol), 2,4-dichlorophenol (0.79 g, 0.0048 mol), and triphenylphosphine (1.27 g, 0.0048 mol) in THF (30 mL) was added DEAD (0.84 g, 0.0048 mol) at 0° C. The mixture was warmed to room temperature and stirred for 16 h under $N_2$. After completion, the mixture was concentrated in vacuo to give a crude residue, which was purified by silica gel column chromatography (petroleum ether:EtOAc=10:1) to afford the title product (72d) (800 mg, 37%) as a colorless oil. m/z (ESI, +ve ion)=462.1 $[M+Na]^+$.

Step E. 4-((5-((2,4-Dichlorophenoxy)methyl)furan-2-yl)methyl)piperidine (72e)

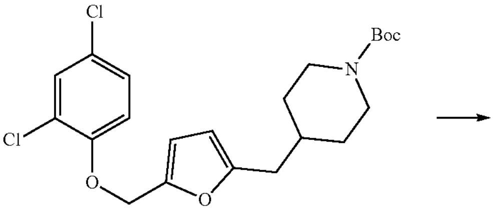

72d

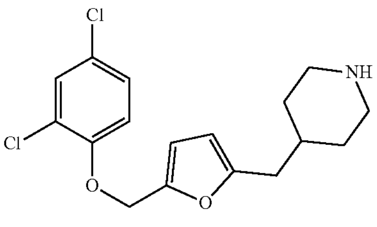

72e

To a mixture of 72d (500 mg, 1.1 mmol) in DCM (20 mL) was added 2,6-lutidine (3.7 g, 34 mmol), and TMSOTf (3.8 g, 17 mmol) at 0° C. The reaction was stirred at 0° C. for one hour under $N_2$. After completion, the mixture was quenched with $NH_4Cl$ (10 mL), and extracted with EtOAc (20 mL×3). The organic layer was washed with $H_2O$ (20 mL), brine (20 mL), dried over anhydrous $Na_2SO_4$, filtered, and concentrated in vacuo to afford a crude title product (72e) (400 mg) as a colorless oil, which was used in next step without further purification. m/z (ESI, +ve ion)=340.1 $[M+H]^+$.

Step F. Methyl(S)-2-((4-((5-((2,4-dichlorophenoxy)methyl)furan-2-yl)methyl)piperidin-1-yl)methyl)-1-(oxetan-2-ylmethyl)-1H-benzo[d]imidazole-6-carboxylate (72f)

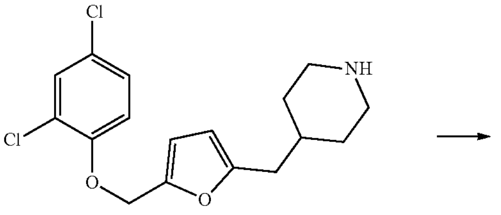

72e

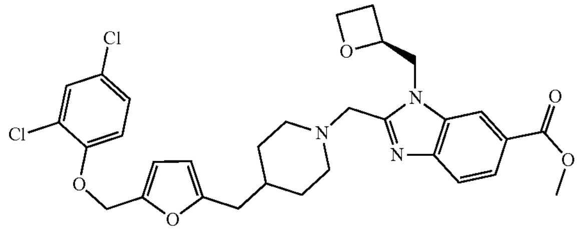

72f

To a mixture of 72e (400 mg, 1.2 mmol), and $K_2CO_3$ (325 mg, 2.4 mmol) in DMF (30 mL) was added 1h (346 mg, 1.2 mmol) at 25° C. The mixture was stirred at 25° C. for 16 h under $N_2$. After completion, the mixture was quenched with $H_2O$ (30 mL), and extracted with DCM (30 mL×3). The organic layer was washed with $H_2O$ (30 mL×3), brine (30 mL), dried over anhydrous $Na_2SO_4$, filtered, and concentrated in vacuo to give a crude residue, which was purified by silica gel column chromatography (petroleum ether: EtOAc=1:1) to afford the title product (72f) (520 mg, 67%) as a yellow oil. m/z (ESI, +ve ion)=598.2 $[M+H]^+$.

Step G. (S)-2-((4-((5-((2,4-Dichlorophenoxy)methyl)furan-2-yl)methyl)piperidin-1-yl)methyl)-1-(oxetan-2-ylmethyl)-1H-benzo[d]imidazole-6-carboxylic acid (72)

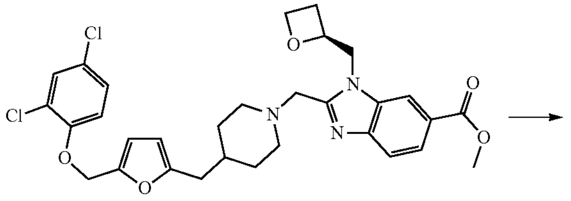

72f

-continued

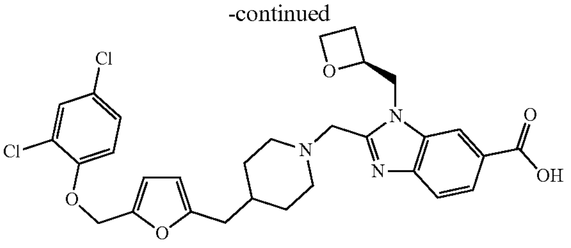

72

To a mixture of 72f (50 mg, 0.084 mmol) in THF (6 mL) and $H_2O$ (2 mL) was added lithium hydroxide (20 mg, 0.84 mmol), and the reaction was heated to 50° C. After stirring at 50° C. for 24 h under $N_2$, the mixture was adjusted to pH=7 with 1 N HCl, diluted with $H_2O$ (5 mL), and extracted with EtOAc (10 mL×3). The organic layer was washed with $H_2O$ (10 mL), brine (10 mL), dried over anhydrous $Na_2SO_4$, filtered, and concentrated in vacuo to give a crude residue, which was purified by reverse phase HPLC (55% $CH_3CN$ in $H_2O$ with formic acid as a modifier) to afford the title compound (72) (30 mg, 58%) as a white solid. 1H NMR (400 MHZ, $CD_3OD$) δ ppm 8.27 (d, J=0.88 Hz, 1H), 7.96 (dd, J=8.33, 1.32 Hz, 1H), 7.63 (d, J=8.33 Hz, 1H), 7.35 (d, J=2.63 Hz, 1H), 7.20-7.24 (m, 1H), 7.15-7.19 (m, 1H), 6.37 (d, J=3.07 Hz, 1H), 6.02 (d, J=3.07 Hz, 1H), 5.22 (qd, J=7.16, 2.63 Hz, 1H), 5.05 (s, 2H), 4.81-4.87 (m, 1H), 4.55-4.74 (m, 2H), 4.44 (dt, J=8.99, 6.03 Hz, 1H), 4.00 (d, J=14.03 Hz, 1H), 3.89 (d, J=14.03 Hz, 1H), 2.96 (br d, J=10.96 Hz, 1H), 2.86 (br d, J=10.96 Hz, 1H), 2.71-2.82 (m, 1H), 2.56 (d, J=6.58 Hz, 2H), 2.42-2.55 (m, 1H), 2.12-2.27 (m, 2H), 1.58-1.72 (m, 2H), 1.18-1.37 (m, 3H). m/z (ESI, +ve ion)=584.2 $[M+H]^+$.

Example compounds 84, 103, 104 (tert-butyl ester was used in the case of 104 and was deprotected using TFA in DCM), 108, and 109 were synthesized as described in Example 72.

Example 73. (S)-2-((4-(5-((2,4-Dichlorobenzyl)oxy)furan-2-carbonyl)piperazin-1-yl)methyl)-1-(oxetan-2-ylmethyl)-1H-benzo[d]imidazole-6-carboxylic acid (73)

73

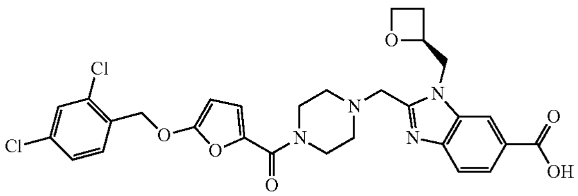

Step A. Methyl 5-((2,4-dichlorobenzyl)oxy)furan-2-carboxylate (73a)

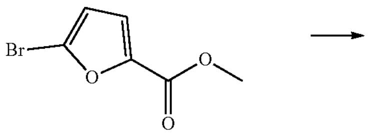

-continued

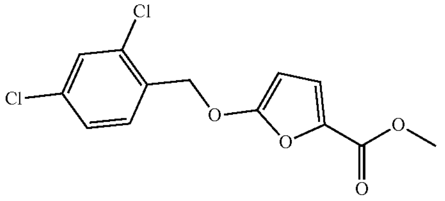

73a

To a mixture of methyl 5-bromofuran-2-carboxylate (1.0 g, 0.0049 mol), (2,4-dichlorophenyl)methanol (0.87 g, 0.0049 mol), 3,4,7,8-tetramethyl-1,10-phenanthroline (0.23 g, 0.00098 mol), and CuI (0.09 g, 0.0004 mol) in toluene (15 mL) was added $Cs_2CO_3$ (2.4 g, 0.0074 mol), and the reaction mixture was heated to 80° C. under $N_2$ for 18 h. After completion, the mixture was quenched with $H_2O$ (20 mL), and extracted with EtOAc (20 mL×3). The organic layer was washed with $H_2O$ (20 mL), brine (20 mL), dried over anhydrous $Na_2SO_4$, filtered, and concentrated in vacuo to give a crude residue, which was purified by silica gel column chromatography (petroleum ether:EtOAc=50:1) to afford the title product (73a) (220 mg, 13%) as a white solid. m/z (ESI, +ve ion)=301.0 [M+H]$^+$.

Step B. 5-((2,4-Dichlorobenzyl)oxy)furan-2-carboxylic acid (73b)

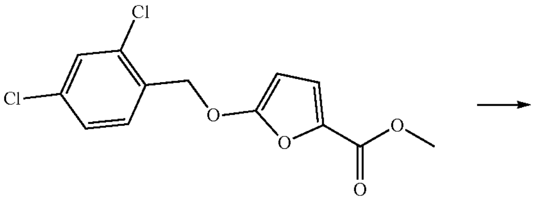

73a

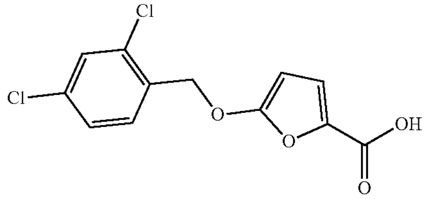

73b

The title compound was prepared from 73a by procedures similar to those described in Example 59, Step C. m/z (ESI, +ve ion)=287.0 [M+H]$^+$.

Step C. Methyl(S)-2-((4-(5-((2,4-dichlorobenzyl)oxy)furan-2-carbonyl)piperazin-1-yl)methyl)-1-(oxetan-2-ylmethyl)-1H-benzo[d]imidazole-6-carboxylate (73c)

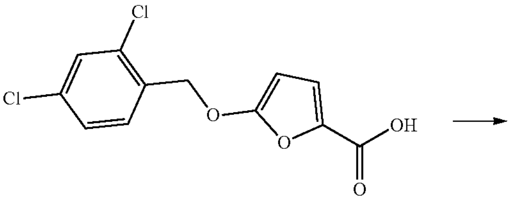

73b

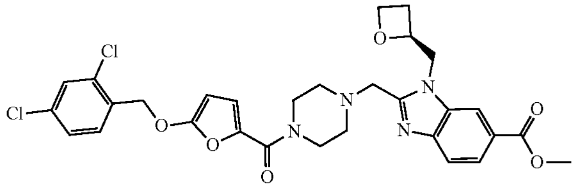

73c

The title compound was prepared from 73b, and 1j by procedures similar to those described in Example 59, Step D. m/z (ESI, +ve ion)=613.2 [M+H]$^+$.

Step D. (S)-2-((4-(5-((2,4-Dichlorobenzyl)oxy)furan-2-carbonyl)piperazin-1-yl)methyl)-1-(oxetan-2-ylmethyl)-1H-benzo[d]imidazole-6-carboxylic acid (73)

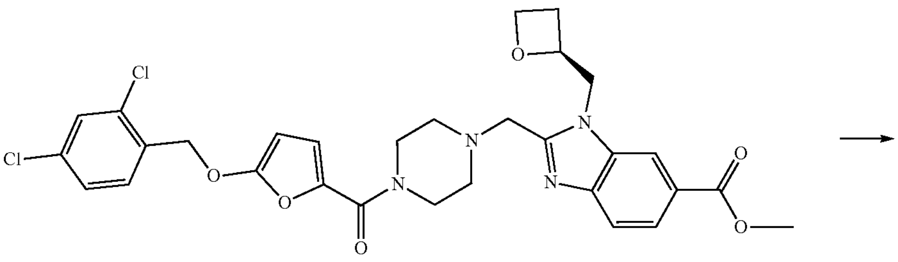

73c

-continued

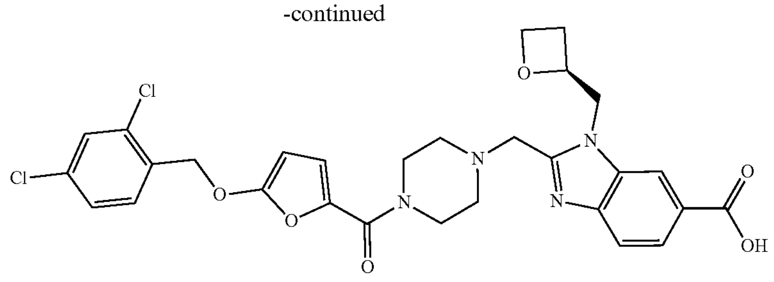

73

To a mixture of 73c (50 mg, 0.082 mmol) in THF: $H_2O$=3:1 (15 mL) was added lithium hydroxide (20 mg, 0.82 mmol), and the reaction mixture was heated to 50° C. After stirring at 50° C. for 16 h under $N_2$, the reaction was cooled down, and adjusted to pH=7 with 1 N HCl. Water (10 mL) was added, and the mixture was extracted with EtOAc (10 mL×3). The organic layer was washed with $H_2O$ (10 mL), brine (10 mL), dried over anhydrous $Na_2SO_4$, filtered, and concentrated in vacuo to give a crude residue, which was purified by reverse phase HPLC (45% $CH_3CN$ in $H_2O$ with 0.05% $NH_4HCO_4$ as a modifier) to afford the title compound (73) (30 mg, 60%) as a white solid. $^1H$ NMR (400 MHZ, $CD_3OD$) δ ppm 8.31 (d, J=0.9 Hz, 1H), 7.96 (dd, J=8.5, 1.4 Hz, 1H), 7.65 (d, J=8.5 Hz, 1H), 7.53 (dd, J=6.6, 5.3 Hz, 2H), 7.37 (dd, J=8.3, 2.1 Hz, 1H), 7.01 (d, J=3.6 Hz, 1H), 5.59 (d, J=3.6 Hz, 1H), 5.30-5.21 (m, 3H), 4.88-4.84 (m, 1H), 4.71 (dd, J=15.4, 2.6 Hz, 1H), 4.63 (dt, J=14.0, 7.1 Hz, 1H), 4.45 (dt, J=9.1, 5.9 Hz, 1H), 4.03 (d, J=13.8 Hz, 1H), 3.93 (d, J=13.8 Hz, 1H), 3.78 (s, 4H), 2.79 (ddd, J=16.2, 8.7, 5.7 Hz, 1H), 2.63-2.47 (m, 5H). m/z (ESI, +ve ion)=599.1 $[M+H]^+$.

Example 74. (S)-2-((4-((5-((2,4-Dichlorobenzyl)oxy)furan-2-yl)methyl)piperazin-1-yl)methyl)-1-(oxetan-2-ylmethyl)-1H-benzo[d]imidazole-6-carboxylic acid (74)

74

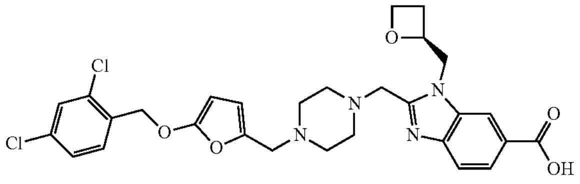

Step A. Methyl 5-((2,4-dichlorobenzyl)oxy)furan-2-carboxylate (74a)

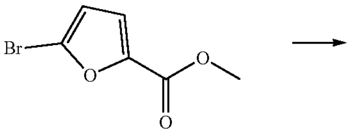

-continued

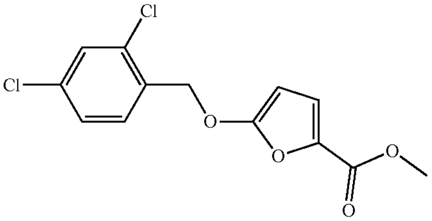

74a

To a mixture of methyl 5-bromofuran-2-carboxylate (1 g, 4.9 mmol), (2,4-dichlorophenyl)methanol (0.95 g, 5.3 mmol), 3,4,7,8-tetramethyl-1,10-phenanthroline (0.23 g, 0.9 mmol), and CuI (0.09 g, 0.4 mmol) in toluene (12 mL) was added $Cs_2CO_3$ (2.39 g, 7.3 mmol), and the reaction was heated to 80° C. for 18 h under $N_2$. The mixture was then filtered and concentrated in vacuo to give a crude residue, which was purified by silica gel column chromatography (EtOAc in petroleum ether, 20-30%) to provide the title product (74a) (0.35 g, 23.9%) as a yellow solid. m/z (ESI, +ve ion)=301.0 $[M+H]^+$.

Step B. (5-((2,4-Dichlorobenzyl)oxy)furan-2-yl)methanol (74b)

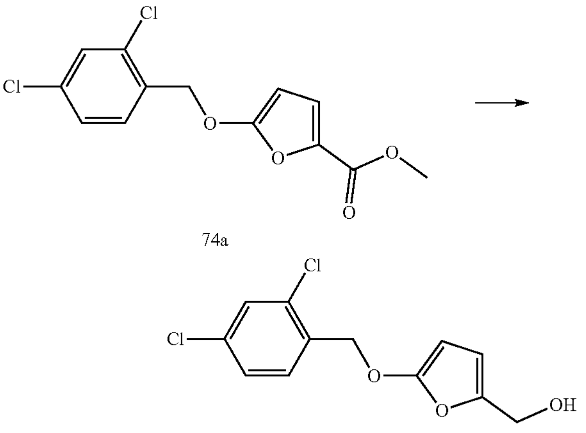

74a

74b

A mixture of 74a (350 mg, 1.16 mmol) in anhydrous THF (15 mL) was added DIBAL-H (3.5 mL, 3.5 mmol) at −45° C. under $N_2$ and the reaction was stirred for one hour at −45° C. The reaction was quenched with ice-cold aq. NaOH (2 N) and extracted with EtOAc (30 mL×3). The organic layer was washed with water (20 mL), brine (20 mL), dried over $Na_2SO_4$, filtered, and concentrated in vacuo. The crude residue was purified by Prep-TLC (40% EtOAc in petroleum ether) to afford the title product (74b) (181 mg, 51%) as a colorless oil. m/z (ESI, +ve ion)=294.9 $[M+Na]^+$.

Step C. 5-((2,4-Dichlorobenzyl)oxy)furan-2-carbaldehyde (74c)

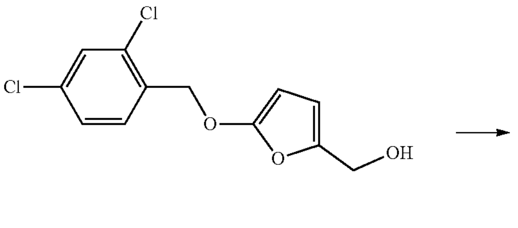

74b

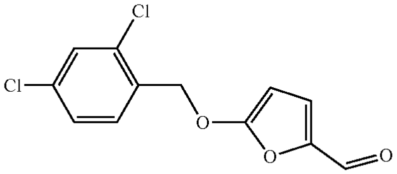

74c

To a mixture of 74b (30 mg, 0.11 mmol) in $CCl_4$ (3 mL) was added $MnO_2$ (47 mg, 0.55 mmol), and the reaction was stirred at 25° C. for 18 h. The mixture was then filtered and concentrated in vacuo to afford the title product (74c) (15 mg, 25%) as a colorless oil, which was used in the next step without further purification. m/z (ESI, +ve ion)=293.0 $[M+Na]^+$.

Step D. Methyl(S)-2-((4-((5-((2,4-dichlorobenzyl)oxy)furan-2-yl)methyl)piperazin-1-yl)methyl)-1-(oxetan-2-ylmethyl)-1H-benzo[d]imidazole-6-carboxylate (74d)

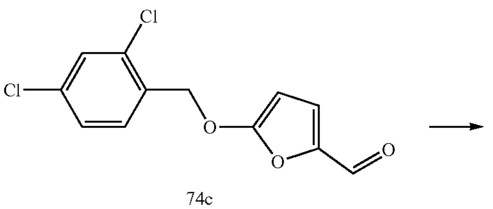

74c

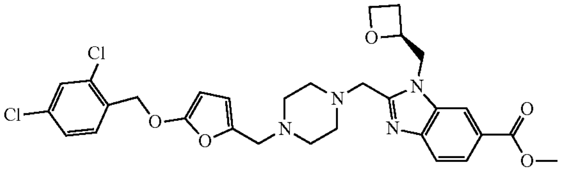

74d

To a mixture of 74c (118 mg, 0.435 mmol), and 1j (25 mg, 0.07 mmol) in $CH_3OH$ (5 mL) was added $NaBH_3CN$ (9 mg, 0.145 mmol). The reaction was stirred at 25° C. for 36 h. The mixture was quenched with ice-water (5 mL), and extracted with EtOAc (15 mL×3). The organic layer was washed with water (5 mL), brine (5 mL), dried, filtered, and concentrated to give a crude residue, which was purified by reverse phase HPLC (35% $CH_3CN$ in $H_2O$ with formic acid as a modifier) to afford the title product (74d) (13 mg, 3.6%) as a white solid. m/z (ESI, +ve ion)=599.2 $[M+H]^+$.

Step E. (S)-2-((4-((5-((2,4-Dichlorobenzyl)oxy)furan-2-yl)methyl)piperazin-1-yl)methyl)-1-(oxetan-2-ylmethyl)-1H-benzo[d]imidazole-6-carboxylic acid (74)

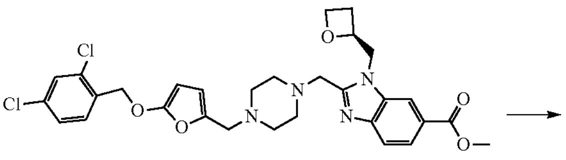

74d

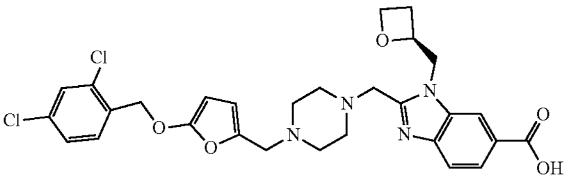

74

To a mixture of 74d (13 mg, 0.0217 mmol) in $CH_3OH:H_2O$ (6:1, 3.5 mL) was added LiOH (8 mg, 0.33 mmol), and the reaction was stirred at 25° C. for 18 h. The mixture was adjusted to pH=7 with 1 N HCl, and extracted with DCM:$CH_3OH$ (10:1) (10 mL×2). The organic layer was concentrated in vacuo to give a crude residue which was purified by reverse phase HPLC (56% $CH_3CN$ in $H_2O$ with $NH_4HCO_3$ as a modifier) to afford the title product (74) (4.4 mg, 31%) as a white solid. $^1H$ NMR (400 MHZ, $CD_3OD$) δ ppm 8.16 (s, 1H), 7.93 (dd, J=8.33, 1.32 Hz, 1H), 7.49-7.59 (m, 3H), 7.36 (br dd, J=8.11, 1.97 Hz, 1H), 6.16 (d, J=3.07 Hz, 1H), 5.29 (d, J=3.07 Hz, 1H), 5.24 (m, 1H), 5.16 (s, 2H), 4.76-4.86 (m, 1H), 4.54-4.72 (m, 2H), 4.41-4.48 (m, 1H), 3.98 (br d, J=13.59 Hz, 1H), 3.89 (br d, J=13.59 Hz, 1H), 3.46 (s, 2H), 2.70-2.81 (m, 1H), 2.39-2.67 (m, 9H). m/z (ESI, +ve ion)=585.2 $[M+H]^+$.

Example 78. (S)-2-((4-(3-(((2-Chloro-4-methylphenyl)(methyl)amino)methyl)benzoyl)piperazin-1-yl)methyl)-1-(oxetan-2-ylmethyl)-1H-benzo[d]imidazole-6-carboxylic acid (78)

78

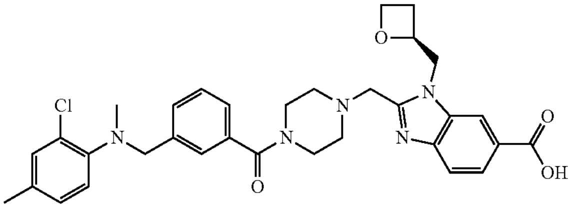

Step A. Methyl 3-(((2-chloro-4-methylphenyl) amino)methyl)benzoate (78a)

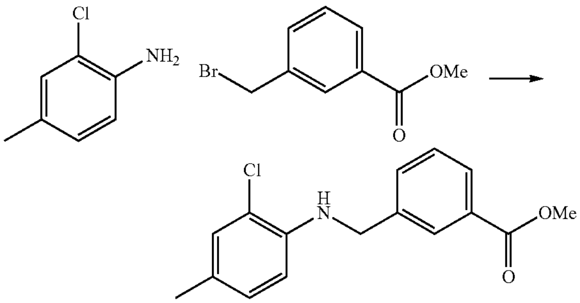

78a

2-Chloro-4-methylaniline (14.2 mg, 0.1 mmol), methyl 3-(bromomethyl)benzoate (27.5 mg, 0.12 mmol), and $K_2CO_3$ (17.3 mg, 0.125 mmol) were suspended in DMF (1 mL). The reaction mixture was stirred at 100° C. for 1.5 hours. After being cooled to room temperature, the crude residue was purified by reverse phase HPLC ($CH_3CN$ and water with 0.1% TFA as a modifier) to provide the title product (78a) (21 mg, 72.7%) as a light brown solid. m/z (ESI, +ve ion)=290.1 $[M+H]^+$.

Step B. (S)-2-((4-(3-(((2-Chloro-4-methylphenyl) (methyl)amino)methyl)benzoyl)piperazin-1-yl) methyl)-1-(oxetan-2-ylmethyl)-1H-benzo[d]imidazole-6-carboxylic acid (78)

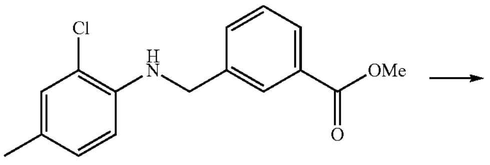

78a

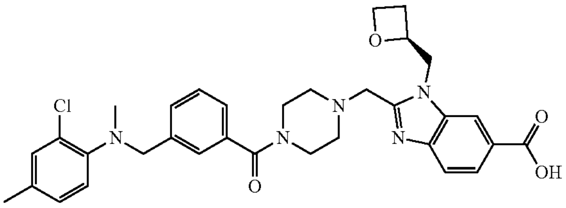

78

The title compound was prepared from 78a, and 2a by procedures similar to those described in Example 46, Steps B to D. $^1$H NMR (600 MHZ, $CD_3OD$) δ ppm 8.33 (s, 1H), 7.97 (dd, J=8.44, 1.47 Hz, 1H), 7.66 (d, J=8.44 Hz, 1H), 7.47 (br d, J=7.70 Hz, 1H), 7.34-7.43 (m, 2H), 7.28 (br d, J=7.70 Hz, 1H), 7.16 (s, 1H), 6.94-6.99 (m, 2H), 5.25 (qd, J=7.15, 2.75 Hz, 1H), 4.85-4.92 (m, 1H), 4.69-4.75 (m, 1H), 4.61-4.68 (m, 1H), 4.46 (dt, J=9.17, 5.87 Hz, 1H), 4.21 (s, 2H), 4.04 (d, J=13.57 Hz, 1H), 3.94 (d, J=13.94 Hz, 1H), 3.78-3.85 (m, 1H), 3.71-3.78 (m, 1H), 3.27-3.29 (m, 2H), 2.73-2.89 (m, 1H), 2.68 (s, 3H), 2.60-2.67 (m, 2H), 2.46-2.58 (m, 1H), 2.40 (br s, 2H), 1.88-2.01 (s, 3H). m/z (ESI, +ve ion)=602.4 $[M+H]^+$.

Example compounds 77, 79, and 80 were synthesized as described in Example 78.

Example 83. 4-(((6-(1-(6-(1H-Tetrazol-5-yl)nicotinoyl)piperidin-4-yl)pyridin-2-yl)oxy)methyl)-3-fluorobenzonitrile (83)

83

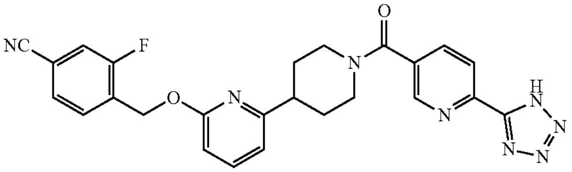

Step A. tert-Butyl 6-fluoro-3',6'-dihydro-[2,4'-bipyridine]-1'(2'H)-carboxylate (83a)

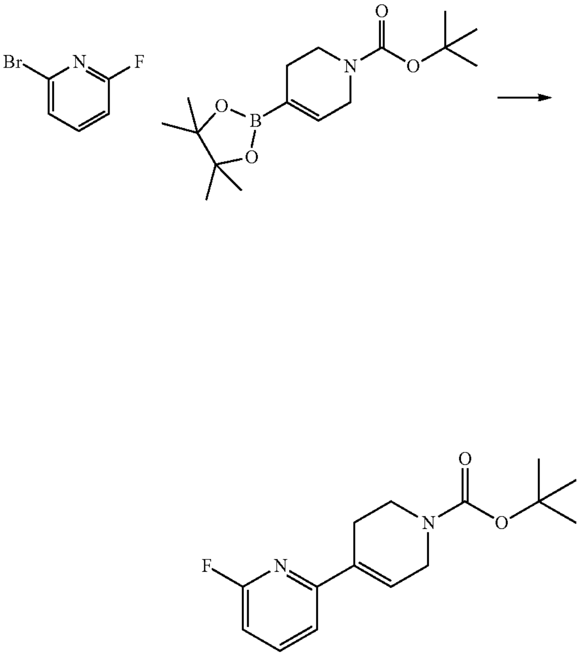

83a

A solution of 2-bromo-6-fluoropyridine (2 g, 11.36 mmol), tert-butyl 4-(4,4,5,5-tetramethyl-1,3,2-dioxaborolan-2-yl)-3,6-dihydro-2H-pyridine-1-carboxylate (3.86 g, 12.5 mmol), sodium carbonate (4.71 g, 34.08 mmol), and $Pd(dppf)Cl_2$ (831 mg, 1.14 mmol) in a mixture of DMF (50 mL), and water (10 mL) was stirred at 80° C. for 3 h under nitrogen. After completion, the reaction mixture was extracted with EtOAc (50 mL×2). The organic layer was washed with brine (50 mL), dried (sodium sulfate), filtered, and concentrated to give a crude residue, which was purified by silica gel column chromatography (gradient elution, EtOAc in hexanes 0-10%) to afford the title product (83a) (3.1 g, 97%) as a yellow oil. m/z (ESI, +ve ion)=301.2 $[M+Na]^+$.

Step B. tert-Butyl 4-(6-fluoropyridin-2-yl)piperidine-1-carboxylate (83b)

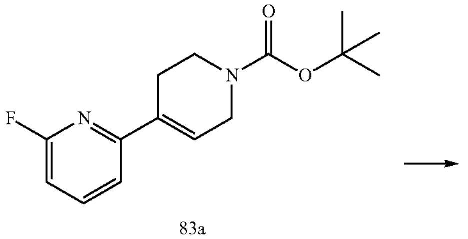

83a

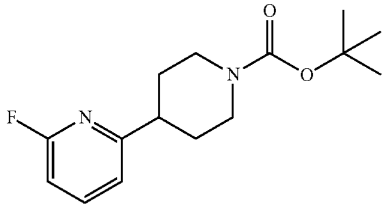

83b

To a solution of 83a (5 g, 17.96 mmol) in methanol (70 mL) was added 10% Pd/C (0.5 g). The mixture was stirred under a hydrogen atmosphere (1 atm) at 20° C. for one hour. The reaction mixture was filtered through a pad of celite, and the filtrate was concentrated under reduced pressure to afford the title product (83b) (3.9 g) as a yellow oil, which was used in the next step without further purification. m/z (ESI, +ve ion)=303.2 $[M+Na]^+$.

Step C. tert-Butyl 4-(6-((4-cyano-2-fluorobenzyl)oxy)pyridin-2-yl)piperidine-1-carboxylate (83c)

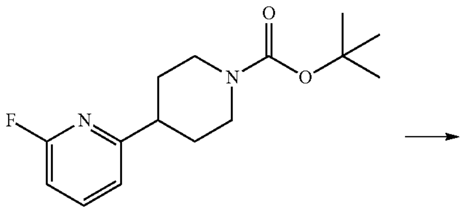

83b

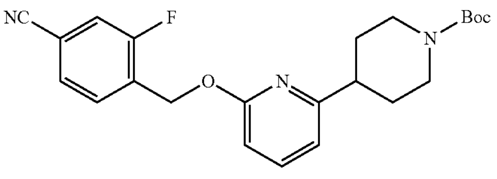

83c

To a solution of 83b (391 mg, 1.39 mmol), and 3-fluoro-4-(hydroxymethyl)benzonitrile (210 mg, 1.39 mmol) in dry 1,4-dioxane (2.5 mL) under nitrogen at 0° C. was added potassium tert-butoxide (156 mg, 1.39 mmol) in portions over 5 min. The mixture was heated to 110° C. for 4 h. After completion, the organic solvent was removed under reduced pressure. The crude residue was partitioned between EtOAc (5 mL) and water (5 mL). The organic phase was washed with water (5 mL), dried over anhydrous sodium sulfate, filtered, concentrated, and purified by reverse phase HPLC (gradient elution, $CH_3CN$ in $H_2O$ 0-90% with 0.1% $NH_3{\cdot}H_2O$ as a modifier) to afford the title product (83c) (305 mg, 74.2%) as a yellow oil. m/z (ESI, +ve ion)=434.2 $[M+Na]^+$.

Step D. 3-Fluoro-4-(((6-(piperidin-4-yl)pyridin-2-yl)oxy)methyl)benzonitrile (83d)

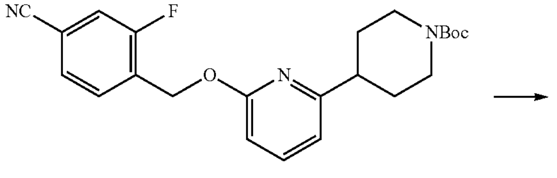

83c

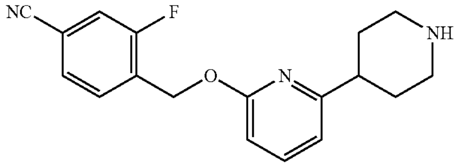

83d

A solution of 83c (305 mg, 0.74 mmol) in 2 N HCl:EtOAc (4 mL) was stirred at 20° C. for 0.5 h. After completion, the reaction mixture was concentrated and purified by silica gel column chromatography (gradient elution, MeOH in DCM 5-10%) to afford the title product (83d) (179 mg, 74.2%) as a yellow solid. m/z (ESI, +ve ion)=312.2 $[M+H]^+$.

Step E. 4-(((6-(1-(6-(1H-Tetrazol-5-yl)nicotinoyl)piperidin-4-yl)pyridin-2-yl)oxy)methyl)-3-fluorobenzonitrile (83)

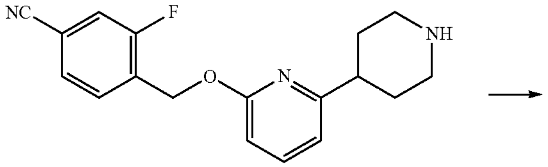

83d

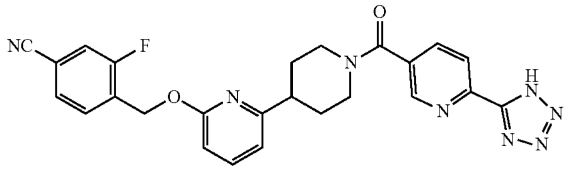

83

A flask was charged with 83d (6.8 mg, 0.022 mmol), 6-(1H-tetrazol-5-yl) nicotinic acid (3.8 mg, 0.02 mmol), and HATU (11.4 mg, 0.03 mmol). DMF (1 mL) was added, followed by DIPEA (0.014 mL, 0.08 mmol). The reaction was stirred for 10 min and then directly purified by reverse phase HPLC ($CH_3CN$ and water with 0.1% HOAc as a modifier) to give the title compound (83) (2.5 mg, 25.8%) as a white solid. $^1H$ NMR (600 MHZ, $CD_3OD$) δ ppm 8.83 (d, J=2.20 Hz, 1H), 8.35 (d, J=8.07 Hz, 1H), 8.10 (dd, J=8.07, 1.83 Hz, 1H), 7.57-7.68 (m, 3H), 7.51-7.57 (m, 1H), 6.88 (d, J=7.34 Hz, 1H), 6.72 (d, J=8.44 Hz, 1H), 5.46-5.59 (m, 2H), 4.69-4.76 (m, 1H), 3.80 (br d, J=12.84 Hz, 1H), 3.35 (br d, J=12.84 Hz, 1H), 3.05 (br d, J=12.47 Hz, 1H), 2.93-2.99 (m, 1H), 1.95 (br d, J=10.64 Hz, 1H), 1.71-1.87 (m, 3H). m/z (ESI, +ve ion)=485.2 $[M+H]^+$.

Example compounds 82, 97 (starting from 74c), and 107 (from 72e) were synthesized as described in Example 83.

Example 89. (S)-2-((4-(3-(4-Isopropyl-2-methylphenoxy)benzoyl)piperazin-1-yl)methyl)-1-(oxetan-2-ylmethyl)-1H-benzo[d]imidazole-6-carboxylic acid (89)

89

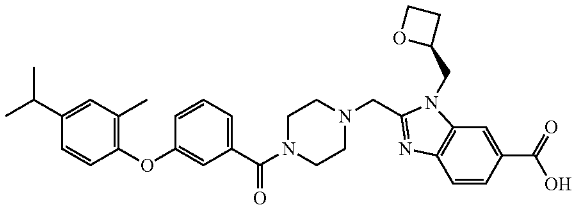

Step A. Methyl 3-(4-isopropyl-2-methylphenoxy)-4-nitrobenzoate (89a)

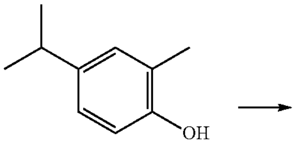

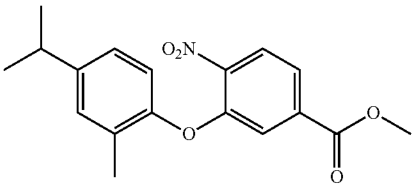

89a

To a mixture of methyl 3-fluoro-4-nitrobenzoate (2.65 g, 13.3 mmol) in DMF (50 mL) was added 4-isopropyl-2-methylphenol (2 g, 13.3 mmol), and $K_2CO_3$ (5.5 g, 39.9 mmol). The mixture was stirred at 25° C. for one hour. After reaction completion, the reaction was quenched with water (50 mL), and extracted with EtOAc (50 mL×3). The combined organic layers were dried over anhydrous $Na_2SO_4$, filtered, and concentrated to afford a crude residue, which was purified by silica gel column chromatography (petroleum:EtOAc=5:1) to afford the title product (89a) (1.45 g, 56%) as a white solid. m/z (ESI, +ve ion)=330.0 $[M+H]^+$.

Step B. Methyl 4-amino-3-(4-isopropyl-2-methylphenoxy)benzoate (89b)

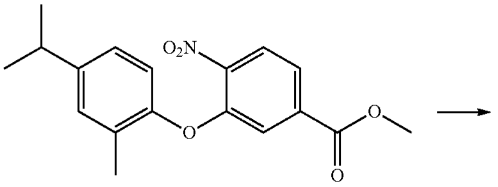

89a

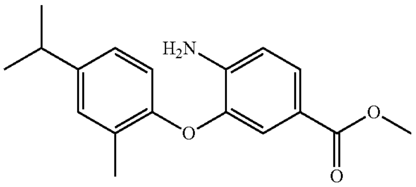

89b

To a mixture of 89a (3 g, 9.1 mmol) in MeOH (50 mL) was added 10% Pd/C (200 mg, 1.9 mmol). The mixture was stirred at 20° C. for 12 h under a $H_2$ atmosphere. After reaction completion, the mixture was filtered and concentrated under reduced pressure. The residue was purified by silica gel column chromatography (petroleum ether: EtOAc=3:1) to afford the title product (89b) (2.52 g, 92%) as a white solid. m/z (ESI, +ve ion)=300.1 $[M+H]^+$.

Step C. Methyl 3-(4-isopropyl-2-methylphenoxy)benzoate (89c)

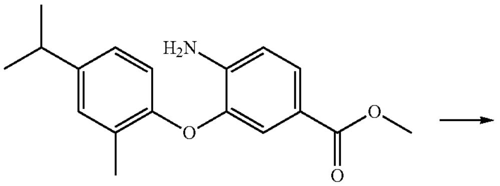

89b

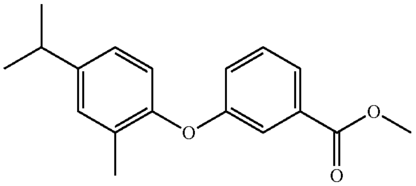

89c

A mixture of isobutyl nitrite (1.4 g, 13.2 mmol) in DMF (20 mL) was stirred at 70° C. for 10 min. Then, 89b (1.6 g, 5.3 mmol) was added to the above mixture. The reaction mixture was stirred at 70° C. for one hour. After completion, the reaction was quenched with $H_2O$ (20 mL), and extracted with EtOAc (20 mL×3). The organic layer was dried, filtered, and concentrated to afford a crude residue, which was purified by silica gel column chromatography (petroleum ether:EtOAc=20:1) to afford the title product (89c) (0.7 g, 45%) as a white solid.

Step D. 3-(4-Isopropyl-2-methylphenoxy)benzoic acid (89d)

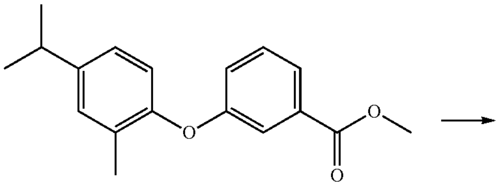

89c

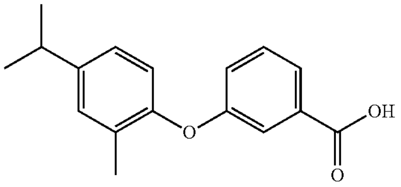

89d

The title compound was prepared from 89c by procedures similar to those described in Example 78, Step D. m/z (ESI, +ve ion)=271.1 [M+H]+.

Step E. Methyl(S)-2-((4-(3-(4-isopropyl-2-methylphenoxy)benzoyl)piperazin-1-yl)methyl)-1-(oxetan-2-ylmethyl)-1H-benzo[d]imidazole-6-carboxylate (89e)

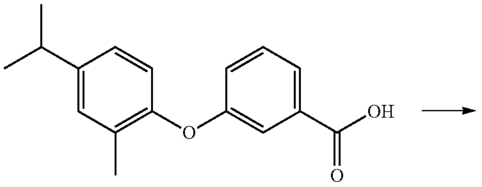

89d

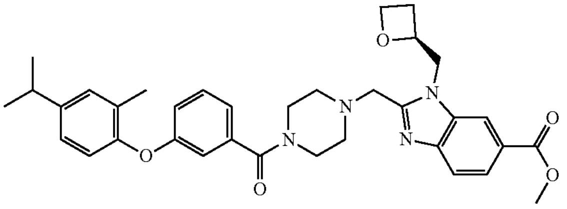

89e

The title compound was prepared from 89d by procedures similar to those described in Example 59, Step D. m/z (ESI, +ve ion)=597.3 [M+H]+.

Step F. (S)-2-((4-(3-(4-Isopropyl-2-methylphenoxy)benzoyl)piperazin-1-yl)methyl)-1-(oxetan-2-ylmethyl)-1H-benzo[d]imidazole-6-carboxylic acid (89)

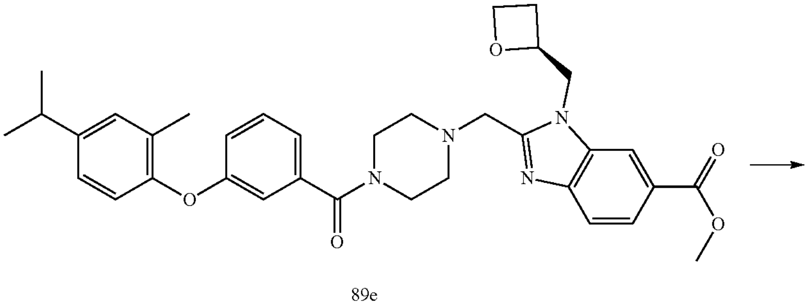

89e

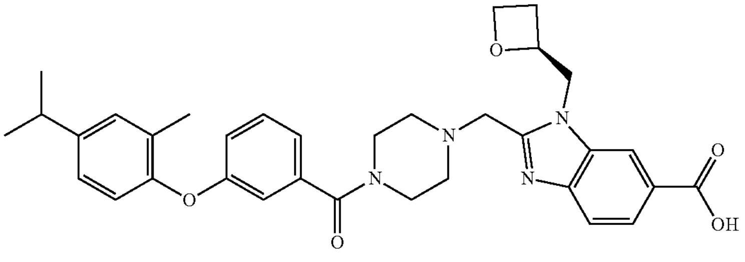

89

To a mixture of 89e (80 mg, 0.13 mmol) in MeOH:$H_2O$ (6 mL:2 mL) was added LiOH (64 mg, 2.68 mmol). The mixture was stirred at 20° C. for 5 h. After completion, the reaction was quenched with water (10 mL), adjusted to pH=6 by 10% citric acid, and extracted with EtOAc (10 mL×3). The organic layers were combined, dried, filtered, and concentrated to afford a crude residue, which was purified by reverse phase HPLC ($CH_3CN$:water with formic acid as a modifier) to give the title product (89) (20 mg, 26%) as a white solid. $^1H$ NMR (400 MHZ, $CD_3OD$) δ ppm 8.46 (d, J=0.9 Hz, 1H), 8.10-8.14 (m, 1H), 7.79 (d, J=8.3 Hz, 1H), 7.36-743 (m, 1H), 7.17 (d, J=1.8 Hz, 1H), 7.04-7.12 (m, 2H), 6.97 (ddd, J=8.3, 2.6, 0.9 Hz, 1H), 6.84-6.89 (m, 2H), 5.28-5.17 (m, 1H), 4.92-4.87 (m, 1H), 4.73 (dd, J=15.3, 2.6 Hz, 1H), 4.65 (td, J=7.9, 5.7 Hz, 1H), 4.46 (dt, J=9.2, 5.9 Hz, 1H), 4.30-4.39 (m, 2H), 3.85 (br s, 2H), 3.62 (br s, 2H), 2.97-2.79 (m, 6H), 2.48-2.55 (m, 1H), 2.15 (s, 3H), 1.25 (d, J=8.0 Hz, 6H). m/z (ESI, +ve ion)=583.3 $[M+H]^+$.

Example 90. (S)-2-((6-((4-Chloro-2-fluorobenzyl)oxy)-1,3,4,5-tetrahydro-2H-pyrido[4,3-b]indol-2-yl)methyl)-1-(oxetan-2-ylmethyl)-1H-benzo[d]imidazole-6-carboxylic acid (90)

90

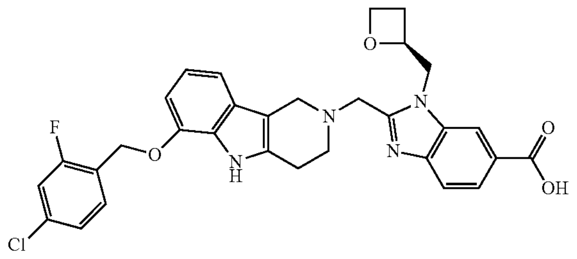

Step A. 1-(Bromomethyl)-4-chloro-2-fluorobenzene (90a)

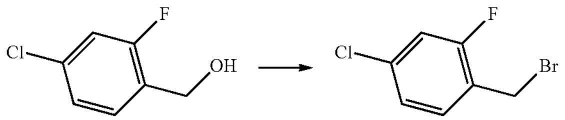

90a

To a solution of (4-chloro-2-fluorophenyl)methanol (1 g, 6.2 mmol) in DCM (10 mL) was added $PBr_3$ (0.84 g, 3.1 mmol) at 0° C., and the reaction was stirred at the same temperature for one hour. The mixture was diluted with DCM (50 mL), washed with sat. aq. $NaHCO_3$ (10 mL), $H_2O$ (10 mL), dried over $Na_2SO_4$, filtered, and concentrated in vacuo to give the title product (90a) (1.05 g, 73%) as a yellow oil, which was used in the next step without further purification.

Step B. 4-Chloro-2-fluoro-1-((2-iodophenoxy)methyl)benzene (90b)

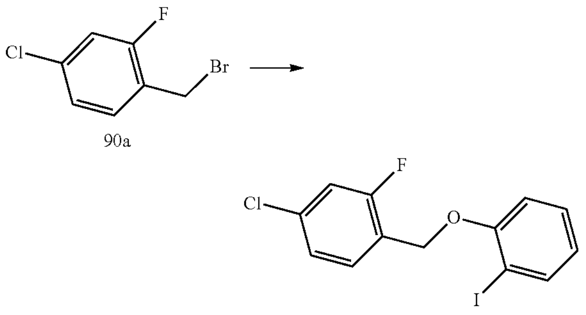

90a

90b

A mixture of 90a (1.0 g, 4.5 mmol), 2-iodophenol (1.0 g, 4.5 mmol), and potassium carbonate (1.87 g, 13.4 mmol) in $CH_3CN$ (20 mL) was stirred at 70° C. for 2 h. The mixture was diluted with EtOAc (100 mL), and washed with water (30 mL×2). The organic layer was dried over $Na_2SO_4$, filtered, and concentrated in vacuo to give a crude residue. The residue was purified by silica gel column chromatography (EtOAc in petroleum ether 5-10%) to afford the title product (90b) (1.5 g, 82%) as a white solid. $^1H$ NMR (400 MHz, DMSO-$d_6$) δ ppm 7.79 (dd, J=7.7, 1.2 Hz, 1H), 7.66 (t, J=8.1 Hz, 1H), 7.52 (dd, J=10.0, 1.8 Hz, 1H), 7.42-7.34 (m, 2H), 7.15 (d, J=8.2 Hz, 1H), 6.79 (t, J=7.5 Hz, 1H), 5.21 (s, 2H).

Step C. tert-Butyl 2-(2-((4-chloro-2-fluorobenzyl)oxy)phenyl) hydrazine-1-carboxylate (90c)

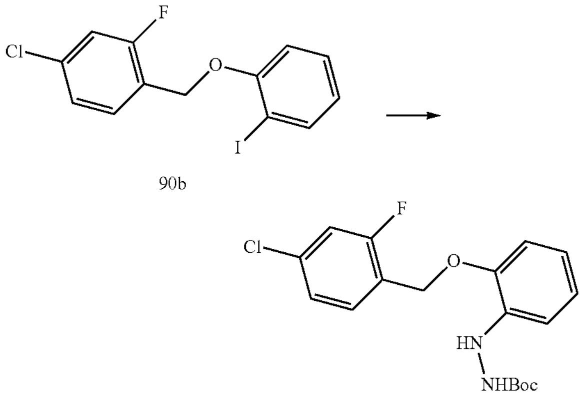

90b

90c

A mixture of 90b (1.5 g, 4.1 mmol), tert-butyl carbazate (700 mg, 5.3 mmol), $Cs_2CO_3$ (2.0 g, 6.1 mmol), copper(I) iodide (80 mg, 0.4 mmol), and 3,4,7,8-tetramethyl-1,10-phenanthroline (0.1 g, 0.4 mmol) in DMF (30 mL) was stirred at 80° C. under $N_2$ for 28 h. The mixture was diluted with EtOAc (250 mL), washed with $H_2O$ (100 mL), and then brine (100 mL). The organic layer was dried over $Na_2SO_4$, filtered, and concentrated in vacuo to give a crude residue, which was purified by silica gel column chromatography (EtOAc in petroleum ether 20-30%) to afford the title product (90c) (0.32 g, 17%) as a light-yellow oil. m/z (ESI, +ve ion)=389.2 $[M+Na]^+$.

Step D. (2-((4-Chloro-2-fluorobenzyl)oxy)phenyl) hydrazine (90d)

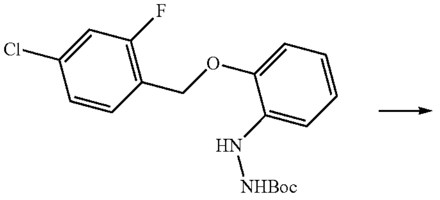

90c

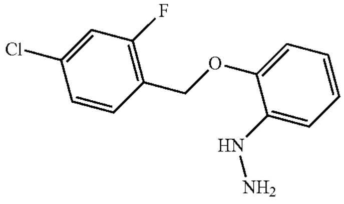

90d

To a solution of 90c (330 mg, 0.9 mmol) in DCM (3 mL) was added 4 N HCl in dioxane (5 mL). The mixture was stirred at 20° C. for 6 h and then concentrated to give the title product (90d) (220 mg) as a brown solid, which was used in next step without further purification. m/z (ESI, +ve ion)= 250.1 $[M-NH_2]^+$.

Step E. 6-((4-Chloro-2-fluorobenzyl)oxy)-2,3,4,5-tetrahydro-1H-pyrido[4,3-b]indole (90e)

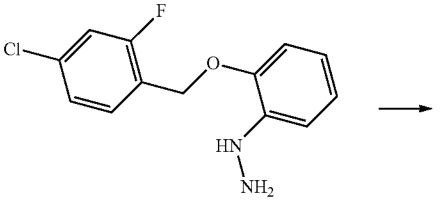

90d

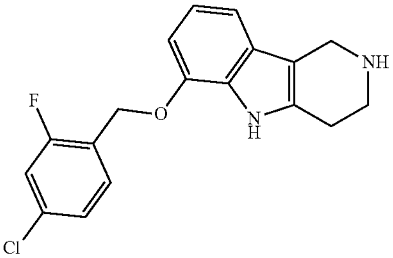

90e

A mixture of 90d (200 mg, 0.66 mmol) and tert-butyl 4-oxopiperidine-1-carboxylate (145 mg, 0.73 mmol) in EtOH (15 mL) and conc. HCl (3 mL) was stirred at 80° C. for 4 h. The mixture was concentrated in vacuo to give a crude residue, which was purified by reverse phase HPLC (37% $CH_3CN$ in $H_2O$, 0.5% formic acid as a modifier) to give the title product (90e) (160 mg, 66%) as a brown solid. m/z (ESI, +ve ion)=331.1 $[M+H]^+$.

Step F. Methyl(S)-2-((6-((4-chloro-2-fluorobenzyl) oxy)-1,3,4,5-tetrahydro-2H-pyrido[4,3-b]indol-2-yl) methyl)-1-(oxetan-2-ylmethyl)-1H-benzo[d]imidazole-6-carboxylate (90f)

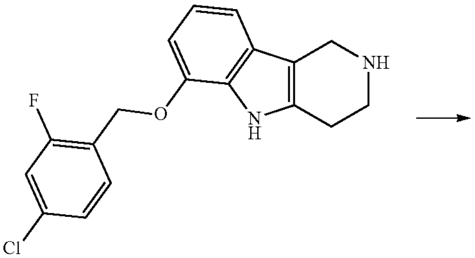

90e

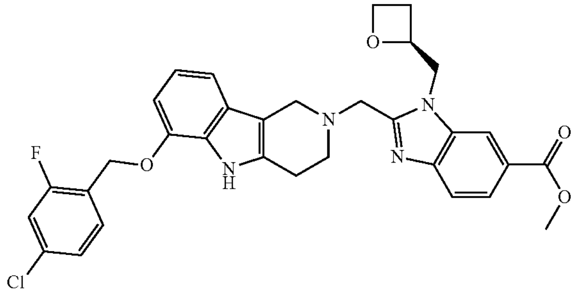

90f

To a mixture of 90e (61 mg, 0.186 mmol), and $K_2CO_3$ (70 mg, 0.51 mmol) in DMF (5 mL) was added 1h (50 mg, 0.17 mmol), and KI (14 mg, 0.08 mmol) in DMF (5 mL). The resulting mixture was stirred at 22° C. for 5 h. The mixture was poured into water (20 mL), and extracted with EtOAc (20 mL×2). The organic layer was washed with $H_2O$ (10 mL), brine (10 mL), dried over $Na_2SO_4$, filtered, and concentrated in vacuo to give a crude residue, which was purified by Prep-TLC (silica gel, DCM:$CH_3OH$=10:1) to give the title product (90f) (32 mg, 20%) as a yellow oil. m/z (ESI, +ve ion)=589.2 $[M+H]^+$.

Step G. (S)-2-((6-((4-Chloro-2-fluorobenzyl)oxy)-1,3,4,5-tetrahydro-2H-pyrido[4,3-b]indol-2-yl) methyl)-1-(oxetan-2-ylmethyl)-1H-benzo[d]imidazole-6-carboxylic acid (90)

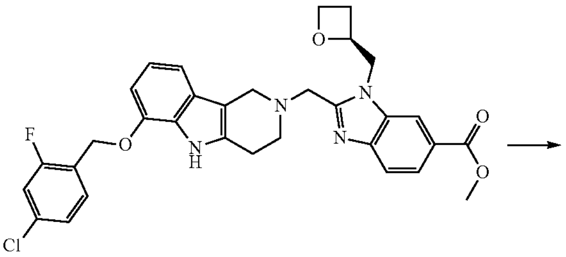

90f

-continued

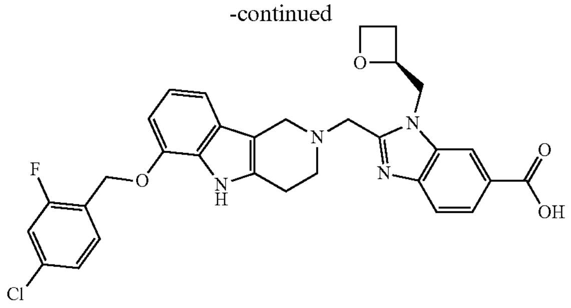

90

A mixture of 90f (32 mg, 0.056 mmol), and lithium hydroxide (27 mg, 1.12 mmol) in $CH_3OH:H_2O=10:1$ (6 mL) was stirred at 20° C. for 5 h. The mixture was adjusted to pH=7 with 1 N HCl. The solvent was removed, and the residue was purified by reverse phase HPLC (27% $CH_3CN$ in $H_2O$ with 0.5% TFA as a modifier) to afford the title compound (90) (9.7 mg, 23.9%) as a white solid. $^1$H NMR (400 MHZ, DMSO-$d_6$) δ ppm 10.87 (s, 1H), 8.08 (s, 1H), 7.80 (dd, J=8.6, 1.1 Hz, 1H), 7.76 (t, J=8.1 Hz, 1H), 7.56-7.41 (m, 2H), 7.35 (dd, J=8.1, 2.0 Hz, 1H), 6.91 (d, J=7.9 Hz, 1H), 6.83 (t, J=7.8 Hz, 1H), 6.70 (d, J=7.7 Hz, 1H), 5.25 (s, 2H), 5.01-5.13 (m, 1H), 4.73 (dd, J=14.9, 6.9 Hz, 1H), 4.56-4.65 (m, 1H), 4.45 (dd, J=13.6, 8.3 Hz, 1H), 4.38-4.30 (m, 1H), 4.15 (d, J=13.6 Hz, 1H), 4.03 (d, J=13.2 Hz, 1H), 3.62-3.74 (m, 2H), 2.83-2.90 (m, 2H), 2.73-2.80 (m, 1H), 2.65-269 (m, 1H), 2.53-2.58 (m, 1H), 2.30-2.35 (m, 1H). m/z (ESI, +ve ion)=575.1 $[M+H]^+$.

Example compound 53 was synthesized as described in Example 90.

Example 91. 5-(4-(6-((4-Cyano-2-fluorobenzyl)oxy)pyridin-2-yl)piperidine-1-carbonyl) picolinic acid (91)

91

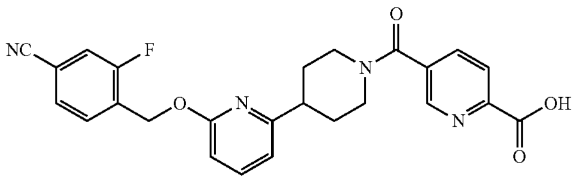

Step A. Methyl 5-(4-(6-((4-cyano-2-fluorobenzyl)oxy)pyridin-2-yl)piperidine-1-carbonyl)picolinate (91a)

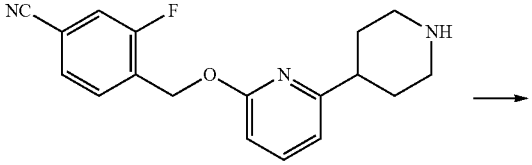

83d

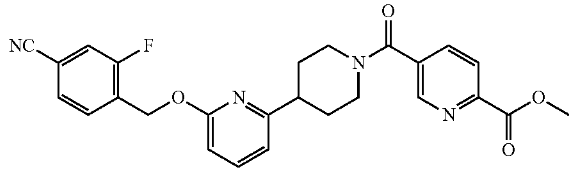

91a

To a flask charged with 83d (15 mg, 0.05 mmol), 6-(methoxycarbonyl)pyridine-3-carboxylic acid (14.5 mg, 0.08 mmol), and HATU (36.6 mg, 0.096 mmol) was added DMF (1 mL), followed by DIPEA (0.028 mL, 0.16 mmol). The reaction was stirred for 10 min and then was directly purified by reverse phase HPLC ($CH_3CN$ and water with 0.1% TFA as a modifier) to give the title product (91a) (23 mg, 60.1%) as a white solid. m/z (ESI, +ve ion)=475.2 $[M+H]^+$.

Step B. 5-(4-(6-((4-Cyano-2-fluorobenzyl)oxy)pyridin-2-yl)piperidine-1-carbonyl) picolinic acid (91)

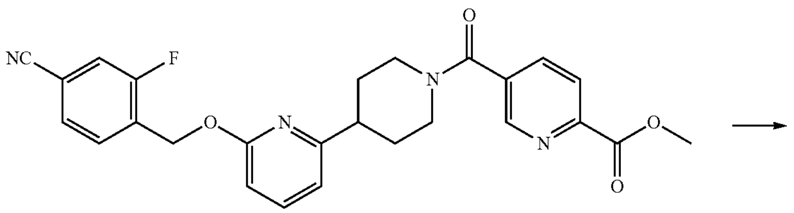

91a

-continued

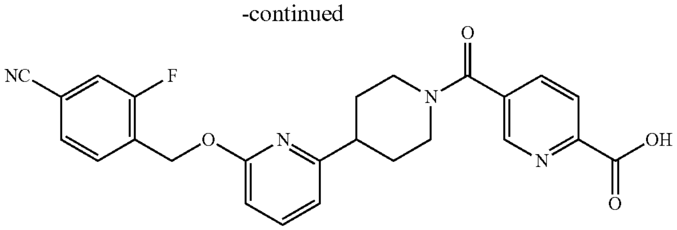

91

91a (23.0 mg, 0.049 mmol) was dissolved in $CH_3CN$ (0.5 mL), followed by the addition of 2 N NaOH aqueous solution (0.5 mL). The mixture was stirred at room temperature overnight and purified by reverse phase HPLC ($CH_3CN$ and water with 0.1% HOAc as a modifier) to give the title compound (91) as a white solid (13.6 mg, 60.9%). $^1$H NMR (600 MHz, $CD_3OD$) δ ppm 8.74 (s, 1H), 8.25 (d, J=8.07 Hz, 1H), 8.03-8.09 (m, 1H), 7.67 (t, J=7.52 Hz, 1H), 7.57-7.64 (m, 2H), 7.51-7.57 (m, 1H), 6.87 (d, J=7.34 Hz, 1H), 6.71 (d, J=8.07 Hz, 1H), 5.46-5.59 (m, 2H), 4.66-4.77 (m, 1H), 3.72 (br d, J=12.10 Hz, 1H), 3.30-3.39 (m, 1H), 2.98-3.06 (m, 1H), 2.94 (ddd, J=11.55, 7.70, 3.85 Hz, 1H), 1.91-1.97 (m, 1H), 1.72-1.88 (m, 3H). m/z (ESI, +ve ion)=461.2 [M+H]$^+$.

Example 92. 4-(((6-(4-(6-(1H-Tetrazol-5-yl) nicotinoyl)piperazin-1-yl)pyridin-2-yl)oxy)methyl)-3-fluorobenzonitrile (92)

92

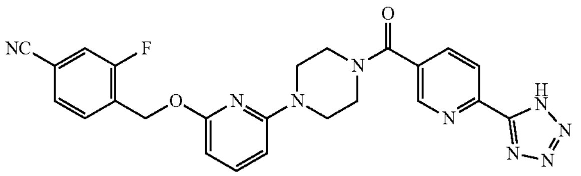

Step A. 4-(((6-Chloropyridin-2-yl)oxy)methyl)-3-fluorobenzonitrile (92a)

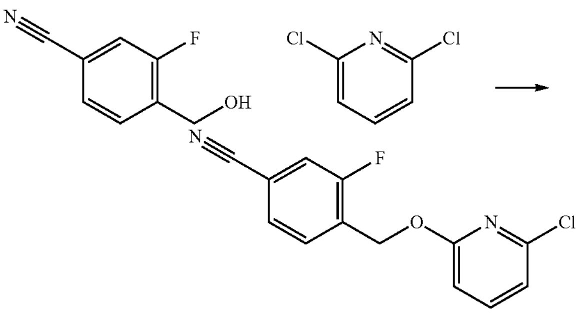

92a

A solution of 3-fluoro-4-(hydroxymethyl)benzonitrile (151 mg, 1.0 mmol) in THF (2 mL) was cooled to 0° C. KOtBu (168 mg, 1.5 mmol) was added portion wise. The resulting mixture was stirred at 0° C. for 5 min, followed by addition of 2,6-dichloropyridine (123 mg, 0.83 mmol). The reaction was slowly warmed up to room temperature, and stirred overnight. After completion, the reaction was quenched with sat. aq. $NH_4Cl$ solution (5 mL), and extracted with ethyl acetate (5 mL×3). The combined organic phase was washed with brine, dried with $Na_2SO_4$, filtered, then purified by silica gel column chromatography (hexanes: EtOAc=5:1). Fractions containing the desired product was concentrated to give the title product (92a) (79.4 mg, 36.4%) m/z (ESI, +ve ion)=263.2 [M+H]$^+$.

Step B. tert-Butyl 4-(6-((4-cyano-2-fluorobenzyl) oxy)pyridin-2-yl)piperazine-1-carboxylate (92b)

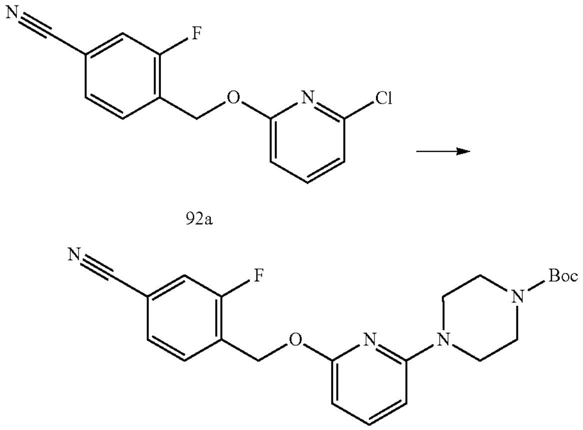

92a

92b

To a mixture of 92a (79.4 mg, 0.3 mmol), tert-butyl piperazine-1-carboxylate (61.5 mg, 0.33 mmol), $Pd_2(dba)_3$ (13.7 mg, 0.015 mmol), BINAP (18.7 mg, 0.3 mmol), and $Cs_2CO_3$ (195 mg, 0.6 mmol) was added toluene (5 mL). The reaction mixture was stirred at 110° C. overnight. After completion, the reaction mixture was quenched by water (50 mL), and extracted with EtOAc (50 mL×3). The combined organic layers were washed with brine, dried with $Na_2SO_4$, filtered, and concentrated. The crude residue was purified by reverse phase HPLC ($CH_3CN$ and water with 0.1% TFA as a modifier) to give the title product (92b) (20.7 mg, 17%) as a light brown solid. $^1$H NMR (400 MHZ, DMSO-$d_6$) δ ppm 7.24 (d, J=3.5 Hz, 1H), 6.46 (dd, J=3.5, 0.5 Hz, 1H), 5.54 (d, J=5.4 Hz, 1H), 4.78-4.68 (m, 1H), 3.79 (s, 3H), 1.38 (d, J=6.6 Hz, 3H).

Step 3. 3-Fluoro-4-(((6-(piperazin-1-yl)pyridin-2-yl) oxy)methyl)benzonitrile (92c)

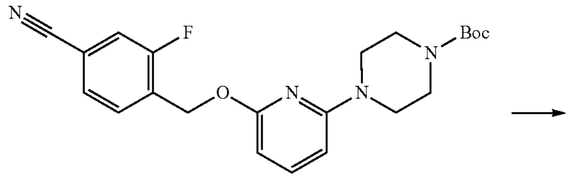

92b

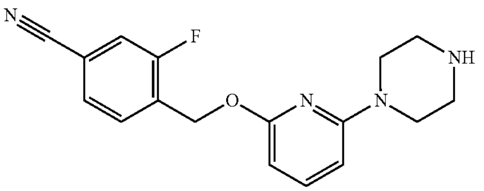

92c

To a mixture of 92b (20.7 mg, 0.05 mmol) in ethyl acetate (0.2 mL) was added 2 N HCl (1.2 mL). The reaction was stirred for 3 h, and the crude product was lyophilized to give the title product (92c) as a white solid (14.2 mg, 80%). m/z (ESI, +ve ion)=313.4 $[M+H]^+$.

Step D. 4-(((6-(4-(6-(1H-tetrazol-5-yl) nicotinoyl) piperazin-1-yl)pyridin-2-yl)oxy)methyl)-3-fluorobenzonitrile (92)

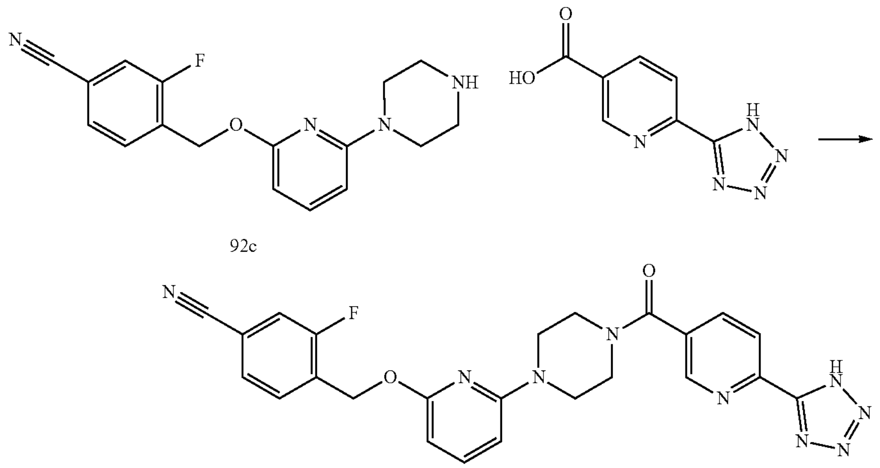

92c

92

To a flask charged with 92c (4 mg, 0.009 mmol), 6-(1H-tetrazol-5-yl) nicotinic acid (2.0 mg, 0.01 mmol), and HATU (4.3 mg, 0.011 mmol) was added DMF (1 mL), followed by DIPEA (0.005 mL, 0.028 mmol). The reaction was stirred for 10 min, and directly purified by reverse phase HPLC ($CH_3CN$ and water with 0.1% HOAc as a modifier) to give the title compound (92) (1.1 mg, 24.1%) as a white solid. $^1H$ NMR (600 MHZ, $CD_3OD$) δ ppm 8.22-8.41 (m, 2H), 8.08 (br d, J=7.70 Hz, 1H), 7.65 (br t, J=7.52 Hz, 1H), 7.56 (dd, J=12.10, 8.80 Hz, 2H), 7.50 (t, J=8.07 Hz, 1H), 6.36 (d, J=8.07 Hz, 1H), 6.20 (d, J=7.70 Hz, 1H), 5.46 (s, 2H), 3.84 (br s, 2H), 3.65 (br s, 2H), 3.56 (br s, 4H). m/z (ESI, +ve ion)=486.3 $[M+H]^+$.

Examples 94 and 96. 2-((4-(5-((R)-1-(2,4-dichlorophenoxy)ethyl)furan-2-carbonyl)piperazin-1-yl) methyl)-1-(((S)-oxetan-2-yl)methyl)-1H-benzo[d] imidazole-6-carboxylic acid (94) and 2-((4-(5-((S)-1-(2,4-dichlorophenoxy)ethyl)furan-2-carbonyl) piperazin-1-yl)methyl)-1-(((S)-oxetan-2-yl)methyl)-1H-benzo[d]imidazole-6-carboxylic acid (96)

94

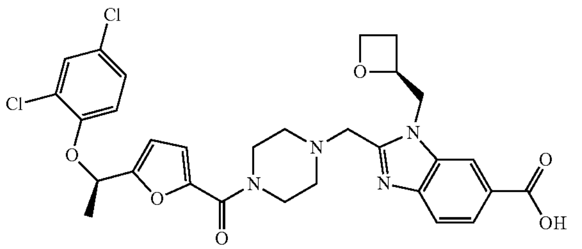

-continued

96

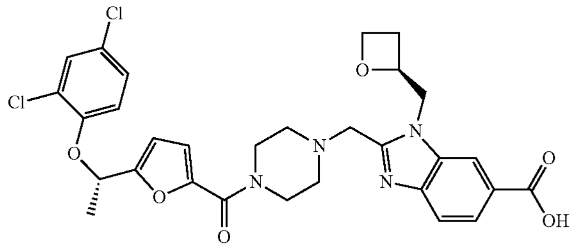

Step A. Methyl 5-acetylfuran-2-carboxylate (94a)

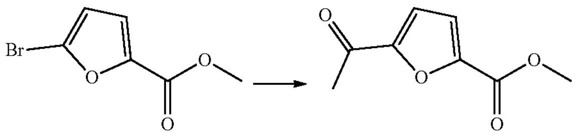

94a

A solution of methyl 5-bromofuran-2-carboxylate (50 mg, 0.24 mmol) in anhydrous DMF (1.2 mL) was treated with tributyl-(1-ethoxyvinyl)stannane (106 mg, 0.29 mmol), and bis(triphenylphosphine) palladium(II) chloride (17 mg, 0.024 mmol) under nitrogen. The reaction was heated to 115° C., and stirred for 18 h, cooled down, treated with 1 N HCl (5 mL), and stirred at 20° C. for 30 min. The reaction was then diluted with water (2 mL), and extracted with EtOAc (2 mL×3). The organic layer was washed with water (2 mL), brine (2 mL), dried with anhydrous sodium sulfate, filtered, concentrated, and purified by silica gel column chromatography (EtOAc in petroleum ether 0-11%) to afford the title product (94a) (33 mg, 74.1%) as a yellow oil. m/z (ESI, +ve ion)=169.1 $[M+H]^+$.

Step B. Methyl 5-(1-hydroxyethyl)furan-2-carboxylate (94b)

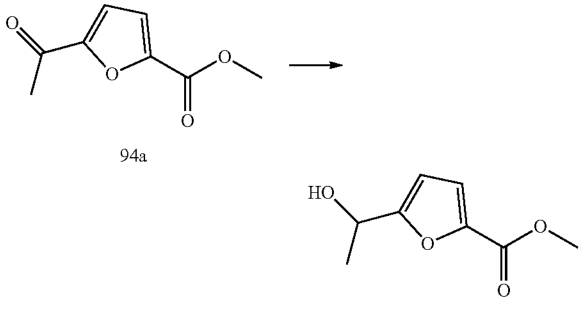

94a

94b

To a solution of 94a (1.3 g, 7.7 mmol) in anhydrous MeOH (20 mL) at 0° C. was added $NaBH_4$ (0.15 g, 3.85 mmol) in portions. The reaction mixture was stirred for 2 h at 25° C., and quenched with $H_2O$ (3 mL). The organic solvent was removed under reduced pressure, and the residue was extracted with EtOAc (3 mL×3). The combined organic extracts were washed with brine (5 mL), dried with $Na_2SO_4$, filtered, and concentrated. The resulting crude residue was purified by silica gel column chromatography (EtOAc in petroleum ether 0-20%) to afford the title product (94b) (1.2 g, 67.0%) as a yellow oil. m/z (ESI, +ve ion)=240.1 $[M+H]^+$.

Step C. Methyl 5-(1-(2,4-dichlorophenoxy)ethyl) furan-2-carboxylate (94c)

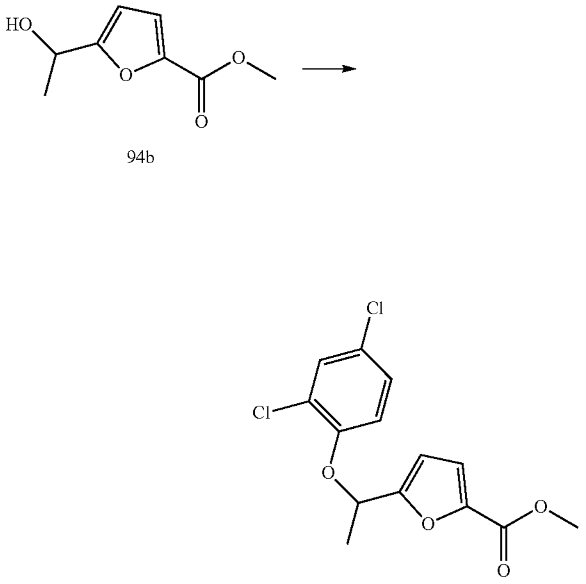

94b

94c

To a mixture of 94b (50 mg, 0.29 mmol), 2,4-dichlorophenol (53 mg, 0.32 mmol), and triphenylphosphine (85 mg, 0.32 mmol) in THF (2.5 mL) was added diethyl azodicarboxylate (56 mg, 0.32 mmol) at 0° C. The mixture was stirred at 25° C. for 16 h under $N_2$, and concentrated. The crude residue was purified by silica gel column chromatography (EtOAc in petroleum ether 0-10%) to afford the title product (94c) (31 mg, 30.1%) as a yellow oil. m/z (ESI, +ve ion)=337.0 $[M+Na]^+$.

Step D. 5-(1-(2,4-Dichlorophenoxy)ethyl)furan-2-carboxylic acid (94d)

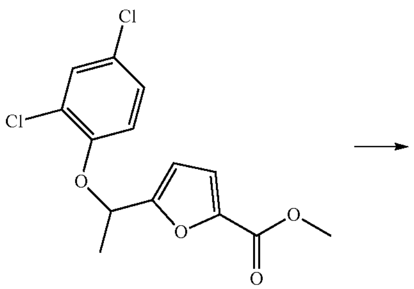

94c

-continued

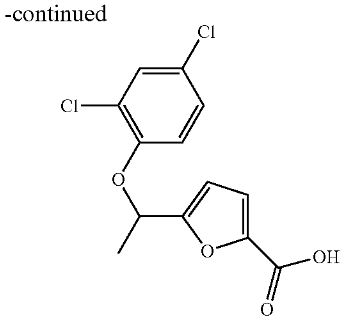

94d

A solution of 94c (15 mg, 0.05 mmol) in acetonitrile (0.5 mL) was treated with lithium hydroxide (6 mg, 0.24 mmol) in water (0.5 mL) at 0° C., and stirred at 25° C. for 2 h. The mixture was concentrated, acidified to pH=2 by 1 N HCl, and extracted with EtOAc (2 mL×3). The organic phase was washed with brine (2 mL), dried with anhydrous sodium sulfate, and concentrated to afford the title product (94d) (11 mg) as a yellow oil, which was used directly in the next step without further purification. m/z (ESI, −ve ion)=299.0 $[M-H]^-$.

Step E. Methyl 2-((4-(5-(1-(2,4-dichlorophenoxy)ethyl)furan-2-carbonyl)piperazin-1-yl)methyl)-1-(((S)-oxetan-2-yl)methyl)-1H-benzo[d]imidazole-6-carboxylate (94e)

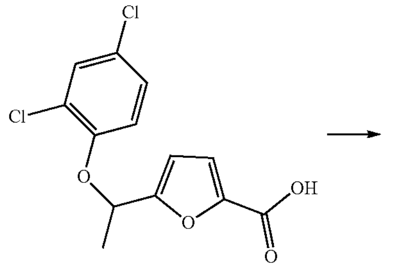

94d

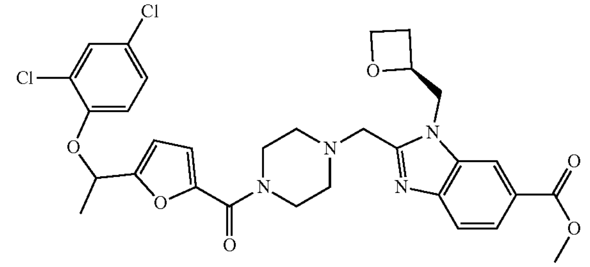

94e 1j (213 mg, 0.62 mmol), and 94d (186 mg, 0.62 mmol) were dissolved in DMF (3 mL). Diisopropylethylamine (319 mg, 2.47 mmol), and HATU (352 mg, 0.93 mmol) were added under a $N_2$ atmosphere, and the mixture was stirred at 20° C. for 2 h. The reaction was quenched with water (10 mL), and extracted with EtOAc (10 mL×3). The combined organic phase was washed with water (5 mL), brine (5 mL), dried with anhydrous sodium sulfate, filtered, and concentrated. The crude residue was purified by silica gel column chromatography (MeOH in DCM 5-10% with 0.5% formic acid) to afford the title product (94e) (180 mg, 42.5%) as a yellow oil. m/z (ESI, +ve ion)=627.2 $[M+H]^+$.

Step F. 2-((4-(5-((R)-1-(2,4-Dichlorophenoxy)ethyl)furan-2-carbonyl)piperazin-1-yl)methyl)-1-(((S)-oxetan-2-yl)methyl)-1H-benzo[d]imidazole-6-carboxylic acid (94) and 2-((4-(5-((S)-1-(2,4-dichlorophenoxy)ethyl)furan-2-carbonyl)piperazin-1-yl)methyl)-1-(((S)-oxetan-2-yl)methyl)-1H-benzo[d]imidazole-6-carboxylic acid (96)

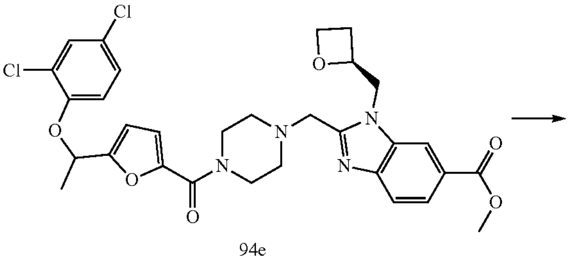

94e

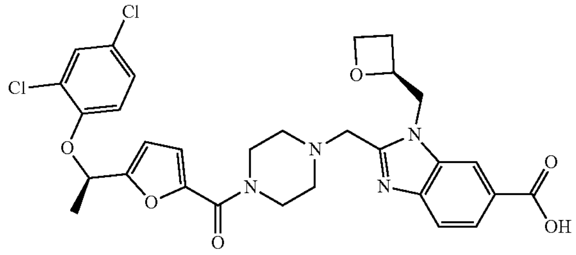

94

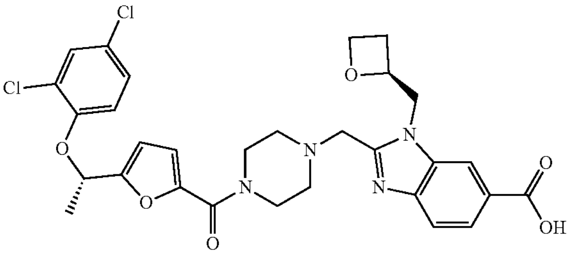

96

A solution of 94e (50 mg, 0.08 mmol) in MeOH (1 mL) was treated with sodium hydroxide (13 mg, 0.21 mmol) in water (1 mL) at 0° C., and the reaction mixture was stirred at 20° C. for 4 h. The mixture was concentrated, and then diluted with water (5 mL), adjusted to pH=5 with 0.1 N HCl, and extracted with EtOAc (5 mL×3). The organic phase was washed with water (2 mL), brine (2 mL), dried with anhydrous sodium sulfate, filtered, and concentrated. The mixture was purified by silica gel column chromatography (MeOH in DCM 5-10%, 0.5% formic acid), and further separated using a chiral column (ChiralPak OJ, 4.6*150 mm, 3 μm) with $CO_2$/MeOH 75:25 as the mobile phase, and a flow rate of 2.0 mL/min to afford the title compounds (94, $1^{st}$ eluting peak) (4.1 mg, 8.03%) and (96, $2^{nd}$ eluting peak) (5 mg, 9.3%) as white solids. Data for 94: $^1$H NMR (400 MHZ, $CD_3OD$) δ ppm 8.34 (s, 1H), 7.98 (br d, J=8.56 Hz, 1H), 7.68 (br d, J=8.56 Hz, 1H), 7.34 (br d, J=2.45 Hz, 1H), 7.18 (br dd, J=8.80, 2.45 Hz, 1H), 7.12 (br d, J=8.80 Hz, 1H), 6.97 (d, J=3.42 Hz, 1H), 6.54 (d, J=3.67 Hz, 1H), 5.54 (q, J=6.36 Hz, 1H), 5.21-5.29 (m, 1H), 4.72 (br dd, J=15.28, 2.57 Hz, 1H), 4.60-4.68 (m, 2H), 4.46 (dt, J=9.11, 5.96 Hz, 1H), 4.04 (br d, J=13.94 Hz, 1H), 3.94 (br d, J=13.94 Hz, 1H), 3.67-3.75 (m, 4H), 2.75-2.85 (m, 1H), 2.44-2.63 (m, 5H), 1.73 (d, J=6.36 Hz, 3H). m/z (ESI, +ve ion)=613.2 $[M+H]^+$. Data for 96: $^1$H NMR (400 MHZ, $CD_3OD$) δ ppm 8.31 (s, 1H), 7.97 (br d, J=8.56 Hz, 1H), 7.67 (br d, J=8.31 Hz, 1H), 7.27-7.35 (m, 1H), 7.19 (dd, J=8.80, 2.69 Hz, 1H), 7.12 (d, J=9.05 Hz, 1H), 6.97 (d, J=3.42 Hz, 1H), 6.54 (d, J=3.42 Hz, 1H), 5.54 (q, J=6.36 Hz, 1H), 5.26 (qd, J=7.17, 2.69 Hz, 1H), 4.72 (br dd, J=15.41, 2.69 Hz, 1H), 4.56-4.68 (m, 2H), 4.45 (dt, J=9.23, 5.90 Hz, 1H), 4.03 (br d, J=13.69 Hz, 1H), 3.94 (br d, J=13.69 Hz, 1H), 3.71 (br s, 4H), 2.80 (ddd, J=10.76, 5.75, 2.57 Hz, 1H), 2.40-2.67 (m, 5H), 1.73 (d, J=6.60 Hz, 3H). m/z (ESI, +ve ion)=613.2 $[M+H]^+$. The stereochemistries of 94, and 96 are assigned arbitrarily.

Example 95. (S)-2-((4-(3-((2-Chloro-4-methylphenyl)(methyl)amino)-4-fluorobenzoyl)piperazin-1-yl)methyl)-1-(oxetan-2-ylmethyl)-1H-benzo[d]imidazole-6-carboxylic acid (95)

95

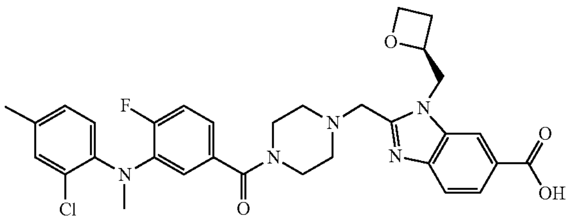

Step A. Methyl(S)-2-((4-(3-((2-chloro-4-methylphenyl)(methyl)amino)-4-fluorobenzoyl)piperazin-1-yl)methyl)-1-(oxetan-2-ylmethyl)-1H-benzo[d]imidazole-6-carboxylate (95a)

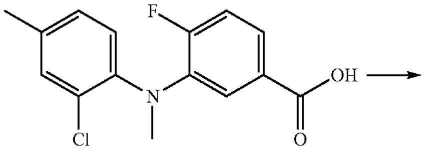

1j

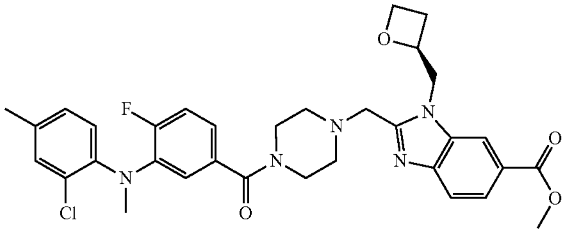

95a 1j (80 mg, 0.23 mmol), and 3-((2-chloro-4-methylphenyl)(methyl)amino)-4-fluorobenzoic acid (68 mg, 0.23 mmol, prepared by procedures similar to those described in Example 46, Steps A to C) were dissolved in DCM (2 mL). DIPEA (0.16 mL, 0.93 mmol), and propylphosphonic anhydride solution (50 wt. % in ethyl acetate, 442 mg, 0.69 mmol) was added. The solution was stirred at 20° C. for one hour and concentrated. The mixture was purified by silica gel column chromatography (MeOH in DCM 5-10%) to afford the title product (95a) (61 mg, 43.9%) as a yellow solid. m/z (ESI, +ve ion)=620.2 $[M+H]^+$.

Step B. (S)-2-((4-(3-((2-Chloro-4-methylphenyl)(methyl)amino)-4-fluorobenzoyl)piperazin-1-yl)methyl)-1-(oxetan-2-ylmethyl)-1H-benzo[d]imidazole-6-carboxylic acid (95)

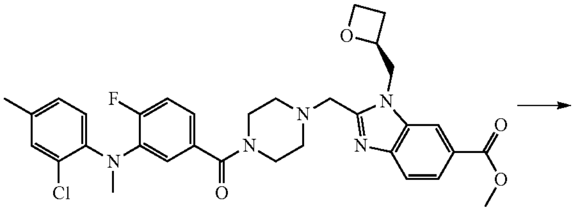

95a

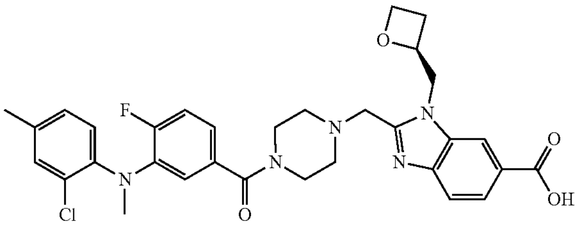

95

To a solution of 95a (65 mg, 0.1 mmol) in MeOH: $H_2O$=5:1 (1.2 mL) was added sodium hydroxide (21 mg, 0.5 mmol) at 0° C. The reaction mixture was then warmed to room temperature and stirred for 5 h. The mixture then was concentrated, diluted with water (5 mL), adjusted to pH=4 with 0.1 N HCl, and extracted with EtOAc (5 mL×3). The organic phase was washed with water (5 mL), brine (5 mL), dried with anhydrous sodium sulfate, filtered, and concentrated. The crude mixture was purified by silica gel column chromatography (MeOH in DCM 5-10%, gradient elution) to afford the title product (95) (10.4 mg, 16.0%) as a white solid. $^1$H NMR (400 MHZ, $CD_3OD$) δ ppm 8.34 (d, J=0.98 Hz, 1H), 7.97 (dd, J=8.56, 1.47 Hz, 1H), 7.68 (d, J=8.56 Hz, 1H), 7.25 (s, 1H), 7.02-7.18 (m, 3H), 6.96 (ddd, J=8.31, 4.16, 1.96 Hz, 1H), 6.85 (dd, J=8.44, 2.08 Hz, 1H), 5.24 (qd, J=7.21, 2.32 Hz, 1H), 4.78-4.85 (m, 1H), 4.71 (br dd, J=15.41, 2.69 Hz, 1H), 4.63 (td, J=7.82, 6.11 Hz, 1H), 4.44 (dt, J=9.05, 5.87 Hz, 1H), 3.99-4.06 (m, 1H), 3.90-3.96 (m, 1H), 3.72 (br s, 2H), 3.48 (br s, 2H), 3.25 (s, 3H), 2.74-2.86 (m, 1H), 2.39-2.69 (m, 5H), 2.32 (s, 3H). m/z (ESI, +ve ion)=606.2 $[M+H]^+$.

Example compounds 98, and 100 were synthesized as described in Example 95.

Example 99. (S)-2-((4-(2-((2-Chloro-4-methylphenyl)(methyl)amino)isonicotinoyl)piperazin-1-yl)methyl)-1-(oxetan-2-ylmethyl)-1H-benzo[d]imidazole-6-carboxylic acid (99)

99

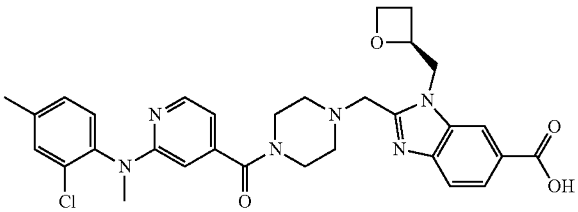

Step A. tert-Butyl 4-(2-bromoisonicotinoyl)piperazine-1-carboxylate (99a)

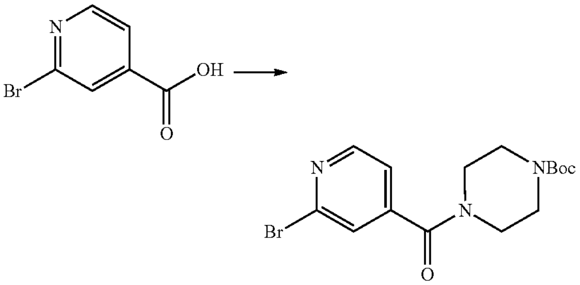

99a

A solution of 2-bromopyridine-4-carboxylic acid (1.0 g, 0.005 mol), tert-butyl piperazine-1-carboxylate (0.93 g, 0.005 mol), DIPEA (3.5 mL, 0.02 mol), and propylphosphonic anhydride ($T_3P$) (6.36 g, 0.02 mol) in DCM (10 mL) was stirred at 20° C. for 3 h. After completion, the reaction was diluted with $H_2O$ (50 mL), and extracted with EtOAc (50 mL×3). The organic layer was dried, concentrated and purified by silica gel column chromatography (petroleum ether:EtOAc=1:2) to afford the title product (99a) (1.85 g, 94%) as yellow solid. m/z (ESI, +ve ion)=370.1 $[M+H]^+$.

Step B. tert-Butyl 4-(2-((2-chloro-4-methylphenyl)amino)isonicotinoyl)piperazine-1-carboxylate (99b)

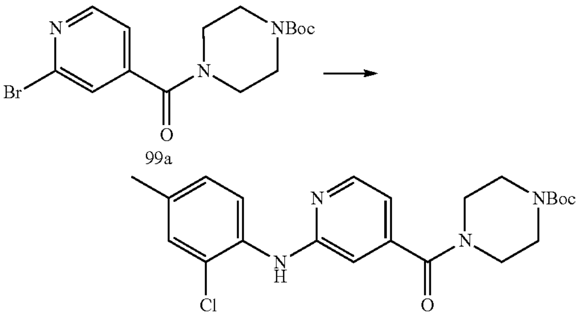

99a

99b

A solution of 99a (1.27 g, 3.4 mmol), 2-chloro-4-methylaniline (0.48 g, 3.4 mmol), chloro(2-dicyclohexylphosphino-2',6'-diisopropoxy-1,1'-biphenyl) [2-(2'-amino-1,1'-biphenyl)]palladium(II) (0.53 g, 0.6 mmol), and $Cs_2CO_3$ (2.82 g, 10.0 mmol) in dioxane (12 mL) was stirred at 95° C. for 12 h. After completion, the reaction was diluted with $H_2O$ (50 mL), and extracted with EtOAc (50 mL×3). The organic layer was dried, filtered, concentrated, and purified by silica gel column chromatography ($CH_2Cl_2$:MeOH=50:1) to afford the title product (99b) (0.85 g, 56%) as a yellow oil. m/z (ESI, +ve ion)=431.2 $[M+H]^+$.

Step C. tert-Butyl 4-(2-((2-chloro-4-methylphenyl)(methyl)amino)isonicotinoyl)piperazine-1-carboxylate (99c)

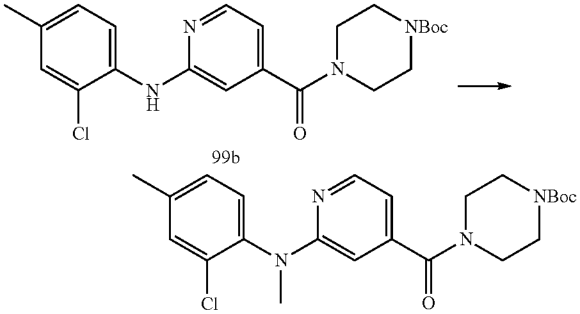

99b

99c

A solution of 99b (652 mg, 1.51 mmol), and NaH (60% in mineral oil, 72 mg, 3.03 mmol) in DMF (8 mL) was stirred at 0° C. for 0.5 h. Then MeI (258 mg, 1.81 mmol) was added. The resulting mixture was stirred at 0° C. for 1.5 h. After completion, the reaction was quenched with $H_2O$ (1 mL), and extracted with EtOAc (10 mL×3). The organic layer was dried, filtered, concentrated, and purified by silica gel column chromatography (DCM:MeOH=50:1) to afford the title product (99c) (575 mg, 81%) as a yellow solid. m/z (ESI, +ve ion)=445.2 $[M+H]^+$.

Step D. (2-((2-Chloro-4-methylphenyl)(methyl)amino)pyridin-4-yl) (piperazin-1-yl)methanone (99d)

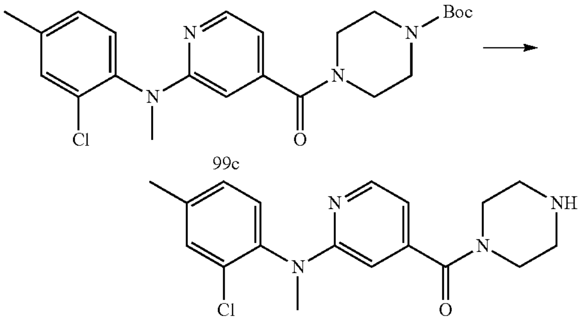

99c

99d

A solution of 99c (295 mg, 0.66 mmol), and 2 N HCl in EtOAc solution (5 mL) was stirred at 20° C. for 3 h. After completion, the reaction was cooled down in an ice bath.

Sat. aq. $NaHCO_3$ solution was added to the mixture to adjust to pH=7. The reaction was diluted with $H_2O$ (10 mL), and extracted with EtOAc (20 mL×3). The organic layer was dried, concentrated and purified by reversed phase HPLC (30% $CH_3CN$ in $H_2O$ with 0.05% formic acid as a modifier) to afford the title product (99d) (129 mg, 52%) as a yellow solid. m/z (ESI, +ve ion)=345.1 $[M+H]^+$.

Step E. Methyl(S)-2-((4-(2-((2-chloro-4-methylphenyl)(methyl)amino)isonicotinoyl)piperazin-1-yl)methyl)-1-(oxetan-2-ylmethyl)-1H-benzo[d]imidazole-6-carboxylate (99e)

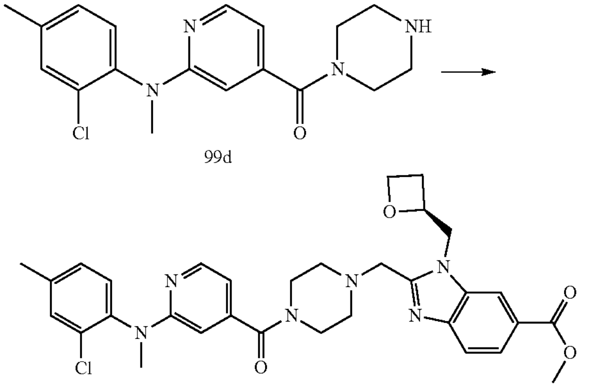

99d

99e

A solution of 99d (84 mg, 0.24 mmol), 1h (72 mg, 0.24 mmol), and $K_2CO_3$ (67 mg, 0.49 mmol) in DMF (2 mL) was stirred at 20° C. for 5 h. After completion, the reaction was diluted with $H_2O$ (20 mL), and extracted with EtOAc (20 mL×3). The organic layer was dried, filtered, concentrated, and purified by silica gel column chromatography (DCM: MeOH=50:1) to afford the title product (99e) (45 mg, 29%) as a white solid. m/z (ESI, +ve ion)=603.2 $[M+H]^+$.

Step F. (S)-2-((4-(2-((2-Chloro-4-methylphenyl)(methyl)amino)isonicotinoyl)piperazin-1-yl)methyl)-1-(oxetan-2-ylmethyl)-1H-benzo[d]imidazole-6-carboxylic acid (99)

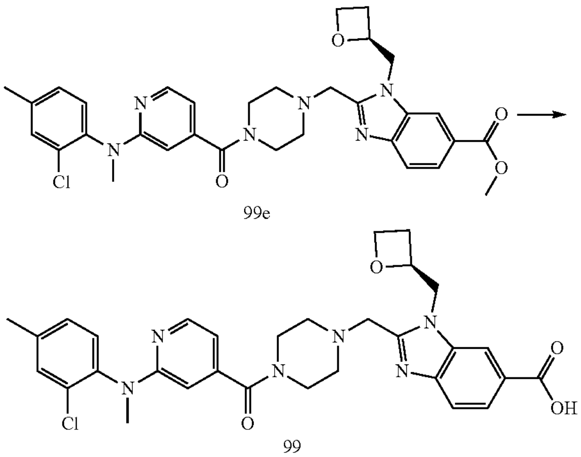 [SMILES: COC(=O)c1ccc2nc(CN3CCN(C(=O)c4ccnc(N(C)c5ccc(C)cc5Cl)c4)CC3)n(C[C@@H]3CCO3)c2c1 ; Cc1ccc(N(C)c2cc(C(=O)N3CCN(Cc4nc5ccc(C(=O)O)cc5n4C[C@@H]4CCO4)CC3)ccn2)c(Cl)c1]

99e

99

A solution of 99e (46 mg, 0.076 mmol), and LiOH (9 mg, 0.38 mmol) in THF:$H_2O$=1:1 (1 mL) was stirred at 20° C. for 3 h. After completion, the reaction was cooled down in an ice bath, and 1 N HCl was added to the mixture to adjust to pH=5, and the reaction was extracted with EtOAc (50 mL×3). The organic layer was dried, filtered, concentrated, and purified by reverse phase HPLC (25% $CH_3CN$ in $H_2O$ with 0.05% formic acid as a modifier) to afford the title product (99) (9.8 mg, 21.4%) as a white solid. $^1H$ NMR (400 MHZ, $CD_3OD$) δ ppm 8.32 (s, 1H), 8.18 (d, J=5.14 Hz, 1H), 7.97 (br d, J=8.31 Hz, 1H), 7.67 (d, J=8.31 Hz, 1H), 7.42 (s, 1H), 7.26 (d, J=0.98 Hz, 2H), 6.63 (dd, J=5.14, 1.22 Hz, 1H), 6.07 (s, 1H), 5.23 (qd, J=6.89, 2.08 Hz, 1H), 4.81-4.85 (m, 1H), 4.69 (br dd, J=15.41, 2.45 Hz, 1H), 4.56-4.66 (m, 1H), 4.43 (dt, J=9.05, 5.87 Hz, 1H), 4.01 (d, J=13.69 Hz, 1H), 3.91 (d, J=13.94 Hz, 1H), 3.69 (br s, 2H), 3.33-3.44 (m, 5H), 2.68-2.89 (m, 1H), 2.41-2.64 (m, 5H), 2.40 (s, 3H). m/z (ESI, +ve ion)=589.2 $[M+H]^+$.

Example compounds 86, 93, and 101 were synthesized as described in Example 99.

Example 102. (S)-2-((4-(2-((2,4-Dichlorophenoxy)methyl)oxazole-5-carbonyl)piperazin-1-yl)methyl)-1-(oxetan-2-ylmethyl)-1H-benzo[d]imidazole-6-carboxylic acid (102)

102

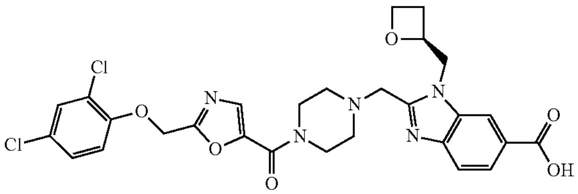

Step A. Methyl 2-(bromomethyl)oxazole-5-carboxylate (102a)

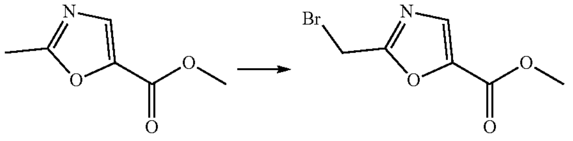

102a

To a stirred solution of NBS (1 g, 7.1 mmol), and AIBN (0.47 g, 2.8 mmol) in $CCl_4$ (20 mL) at 80° C. was added methyl 2-methyl-1,3-oxazole-5-carboxylate (1.9 g, 10.6 mmol). The reaction mixture was stirred at 80° C. for 16 h. After completion, the reaction was diluted with $H_2O$ (15 mL), and extracted with EtOAc (20 mL×3). The combined organic layers were dried, filtered, and concentrated to give a crude residue, which was purified by silica gel column chromatography (EtOAc:petroleum ether=1:10) to afford the title product (102a) (0.8 g, 49%) as a yellow oil. m/z (ESI, +ve ion)=220.1 $[M+H]^+$.

Step B. Methyl 2-((2,4-dichlorophenoxy)methyl) oxazole-5-carboxylate (102b)

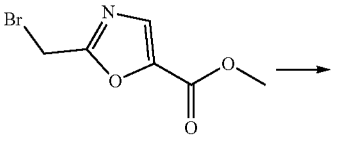

102a

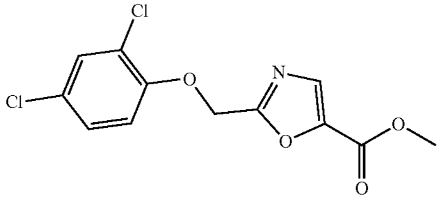

102b

To a solution of 102a (300 mg, 1.36 mmol), and 2,4-dichlorophenol (333 mg, 2.0 mmol) in $CH_3CN$ (10 mL) was added $K_2CO_3$ (565 mg, 4.1 mmol). The reaction mixture was stirred at 20° C. for 2 h. After completion, the reaction solution was diluted with $H_2O$ (10 mL), and extracted with EtOAc (20 mL×3). The combined organic layers were dried, filtered, and concentrated to give a crude residue, which was purified by silica gel column chromatography (EtOAc:petroleum ether=1:10) to afford the title product (102b) (267 mg, 62%) as a white solid. m/z (ESI, +ve ion)=302.2 $[M+H]^+$.

Step C. 2-((2,4-Dichlorophenoxy)methyl)oxazole-5-carboxylic acid (102c)

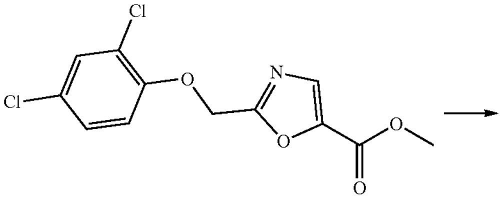

102b

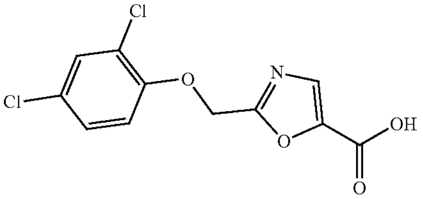

102c

To a stirred solution of 102b (300 mg, 0.99 mmol) in MeOH (5 mL) was added a solution of NaOH (198 mg, 4.97 mmol) in $H_2O$ (1 mL). The reaction mixture was stirred at 20° C. for 2 h, and cooled down in an ice bath. 1 N HCl (2.0 mL) was added to adjust to pH=5. The reaction mixture was then extracted with EtOAc (5 mL×3). The combined organic layers were dried, filtered, and concentrated to give a crude residue, which was purified by silica gel column chromatography (EtOAc in petroleum ether 20-30%) to afford the title product (102c) (210 mg, 70%) as a white solid. m/z (ESI, +ve ion)=288.0 $[M+H]^+$.

Step D. Methyl(S)-2-((4-(2-((2,4-dichlorophenoxy) methyl)oxazole-5-carbonyl)piperazin-1-yl)methyl)-1-(oxetan-2-ylmethyl)-1H-benzo[d]imidazole-6-carboxylate (102d)

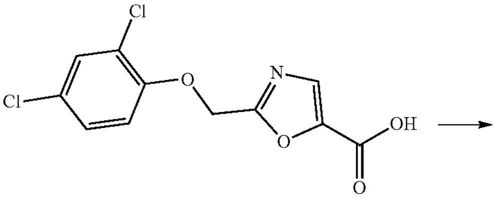

102c

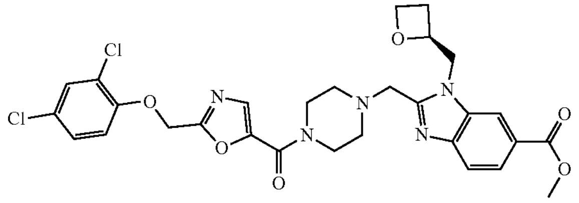

102d

To a stirred solution of 102c (100 mg, 0.35 mmol), 1j (143 mg, 0.42 mmol), and DIPEA (0.18 mL, 1.04 mmol) in DCM (3 mL) was added $T_3P$ (221 mg, 0.694 mmol, 2 equiv) at 20° C. The reaction mixture was stirred at 20° C. for 2 h. After completion, the reaction solution was diluted with $H_2O$ (5 mL), and extracted with EtOAc (20 mL×3). The combined organic layers were dried, filtered, and concentrated to give a crude residue which was purified by silica gel column chromatography (EtOAc:petroleum ether=1:5) to afford the title product (102d) (90 mg, 40%) as a white solid. m/z (ESI, +ve ion)=614.1 $[M+H]^+$.

Step E. (S)-2-((4-(2-((2,4-Dichlorophenoxy)methyl) oxazole-5-carbonyl)piperazin-1-yl)methyl)-1-(oxetan-2-ylmethyl)-1H-benzo[d]imidazole-6-carboxylic acid (102)

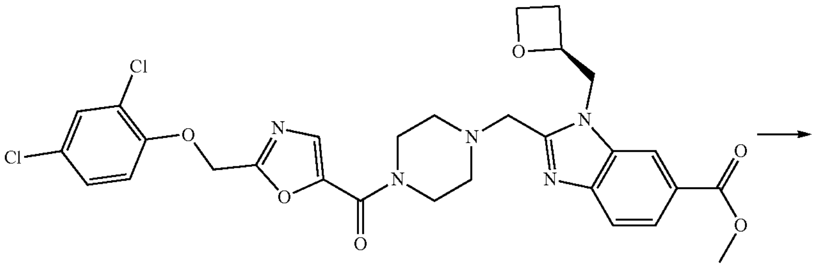

102d

-continued

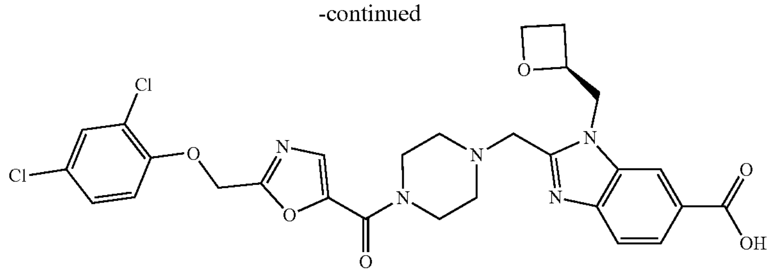

102

To a stirred solution of 102d (10 mg, 0.016 mmol) in $CH_3CN:H_2O$=1:1 (2 mL) was added TBD (5 mg, 0.033 mmol) at 20° C. The reaction mixture was stirred for 2 h, and cooled down in an ice bath. 1 N HCl (0.1 mL) was added to adjust to pH=5. The reaction mixture was then extracted with EtOAc (5 mL×3). The combined organic layers were dried, filtered, and concentrated to give a crude residue, which was purified by silica gel column chromatography (EtOAc in petroleum ether 20-30%) to afford the title product (102) (3.2 mg, 30%) as a white solid. $^1$H NMR (400 MHZ, $CD_3OD$) δ ppm 8.30 (s, 1H), 7.97 (br d, J=8.77 Hz, 1H), 7.62-7.68 (m, 2H), 7.41 (d, J=2.63 Hz, 1H), 7.24-7.30 (m, 1H), 7.21 (d, J=8.77 Hz, 1H), 5.34 (s, 2H), 5.26 (qd, J=7.24, 2.85 Hz, 1H), 4.89-4.92 (m, 1H), 4.71 (br dd, J=15.57, 2.85 Hz, 1H), 4.60-4.67 (m, 1H), 4.41-4.49 (m, 1H), 4.00-4.07 (m, 1H), 3.92-3.99 (m, 1H), 3.69-3.80 (m, 4H), 2.79 (br d, J=5.70 Hz, 1H), 2.46-2.64 (m, 5H). m/z (ESI, +ve ion)=600.1 [M+H]$^+$.

Example compound 113 was synthesized as described in Example 102.

Example 105. (S)-2-((4-(1-(3-((2-chloro-4-methylphenyl)(methyl)amino)phenyl)cyclopropyl)piperazin-1-yl)methyl)-1-(oxetan-2-ylmethyl)-1H-benzo[d]imidazole-6-carboxylic acid (105)

105

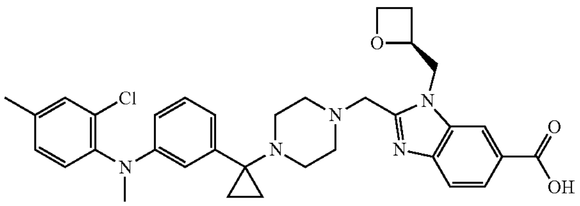

Step A. 1-(1-(3-Bromophenyl)cyclopropyl)-4-tosylpiperazine (105a)

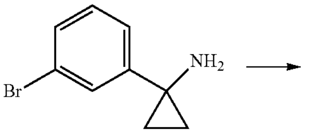

-continued

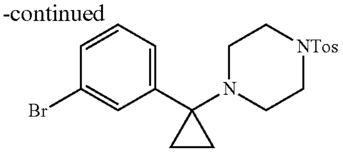

105a

A flask was charged with 1-(3-bromophenyl)cyclopropan-1-amine (50 mg, 0.24 mmol). DIPEA (1 mL), and N,N-bis(2-chloroethyl)-4-methylbenzenesulfonamide (77 mg, 0.26 mmol) were added. The reaction mixture was stirred at 120° C. for 40 h. The reaction was diluted with water (10 mL) and extracted with EtOAc (10 mL×3). The organic phase was washed with water (5 mL), brine (5 mL), dried with anhydrous sodium sulfate, filtered, and concentrated. The crude residue was purified by silica gel column chromatography (EtOAc in petroleum ether 0-20%) to afford the title product (105a) (53 mg, 46%) as a yellow solid. m/z (ESI, +ve ion)=435.1 [M+H]$^+$.

Step B. 2-Chloro-4-methyl-N-(3-(1-(4-tosylpiperazin-1-yl)cyclopropyl)phenyl)aniline (105b)

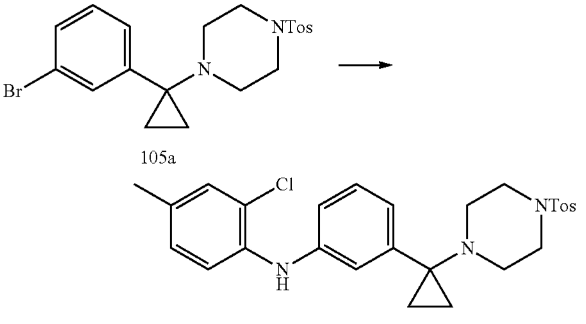

105a

105b

To a solution of 105a (18 mg, 0.04 mmol), cesium carbonate (27 mg, 0.08 mmol), palladium diacetate (1 mg, 0.004 mmol), and racemic-2,2'-bis(diphenylphosphino)-1,1'-binaphthyl (3 mg, 0.04 mmol) in toluene (0.5 mL) was added 2-chloro-4-methylaniline (6 mg, 0.04 mmol). The reaction was stirred at 100° C. for 2 h. After completion, the mixture was concentrated. The reaction was diluted with water (5 mL), and extracted with EtOAc (5 mL×3). The organic phase was washed with water (5 mL), brine (5 mL), dried with anhydrous sodium sulfate, filtered, and concentrated to give a crude residue, which was purified by silica gel column chromatography (EtOAc in petroleum ether 0-20%) to afford the title product (105b) (12 mg, 53%) as a yellow solid. m/z (ESI, +ve ion)=496.2 $[M+H]^+$.

Step C. 2-Chloro-N,4-dimethyl-N-(3-(1-(4-tosylpiperazin-1-yl)cyclopropyl)phenyl)aniline (105c)

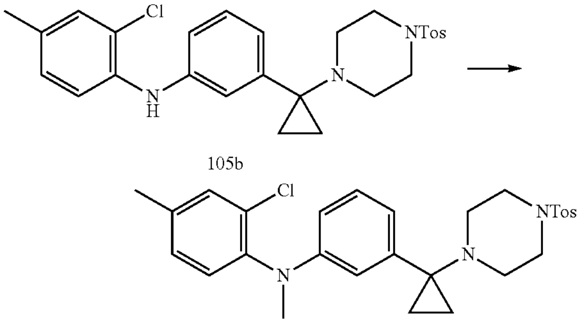

105b

105c

NaH (60% in mineral oil, 72 mg, 1.8 mmol) was added in successive portions to a solution of 105b (446 mg, 0.9 mmol) in anhydrous DMF (5 mL) under a nitrogen atmosphere at 0° C., followed by dropwise addition of iodomethane (255 mg, 1.8 mmol). The reaction mixture was stirred at 20° C. for one hour and quenched with water (20 mL) at 0° C. The mixture was extracted with EtOAc (20 mL×3), and the organic phase was washed with water (10 mL), brine (10 mL), dried with anhydrous sodium sulfate, filtered, and concentrated. The crude residue was purified by silica gel column chromatography (EtOAc in petroleum ether 0-20%) to afford the title product (105c) (12 mg, 58%) as a yellow oil. m/z (ESI, +ve ion)=510.2 $[M+H]^+$.

Step D. 2-Chloro-N,4-dimethyl-N-(3-(1-(piperazin-1-yl)cyclopropyl)phenyl)aniline (105d)

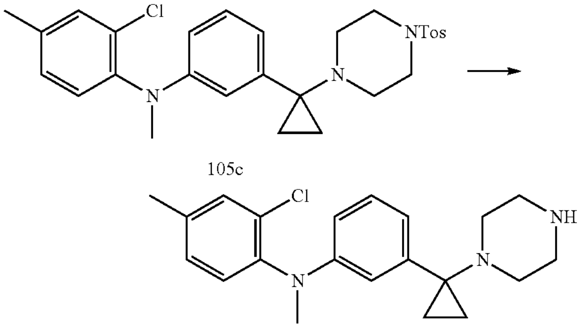

105c

105d

To a solution of 105c (240 mg, 0.47 mmol) in trifluoroacetic acid (4 mL) was added conc. $H_2SO_4$ (455 mg, 3.29 mmol). The mixture was heated at 75° C., and stirred for 3 h. After completion, the reaction was diluted with water (10 mL), and adjusted to pH=11 with $NH_3 \cdot H_2O$. The mixture was extracted with EtOAc (20 mL×3), and the organic phase was washed with water (10 mL), brine (10 mL), dried with anhydrous sodium sulfate, filtered, and concentrated. The crude was purified by silica gel column chromatography (MeOH in dichloromethane 5-10%, 0.5% $NH_3 \cdot H_2O$ as a modifier) to afford the title product (105d) (139 mg) as a white solid that was impure. m/z (ESI, +ve ion)=356.2 $[M+H]^+$.

Step E. Methyl(S)-2-((4-(1-(3-((2-chloro-4-methylphenyl)(methyl)amino)phenyl)cyclopropyl)piperazin-1-yl)methyl)-1-(oxetan-2-ylmethyl)-1H-benzo[d]imidazole-6-carboxylate (105e)

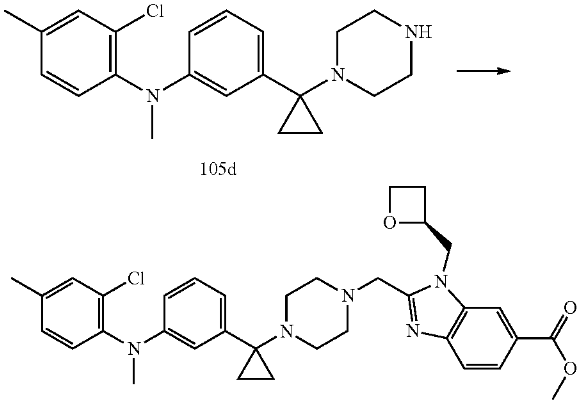

105d

105e

To a solution of 105d (139 mg, 0.39 mmol) in DMF (3 mL) was added 1h (127 mg, 0.43 mmol), and potassium carbonate (162 mg, 1.17 mmol). The reaction was stirred at 20° C. for 3 h. The reaction was diluted with water (10 mL), and extracted with EtOAc (20 mL×3). The organic phase was washed with water (10 mL), brine (10 mL), dried with anhydrous sodium sulfate, filtered, and concentrated. The crude residue was purified by silica gel column chromatography (MeOH in DCM 0-5%, gradient elution) to afford the title product (105e) (147 mg) as a white solid with 81% purity. m/z (ESI, +ve ion)=614.2 $[M+H]^+$.

Step F. (S)-2-((4-(1-(3-((2-chloro-4-methylphenyl)(methyl)amino)phenyl)cyclopropyl)piperazin-1-yl)methyl)-1-(oxetan-2-ylmethyl)-1H-benzo[d]imidazole-6-carboxylic acid (105)

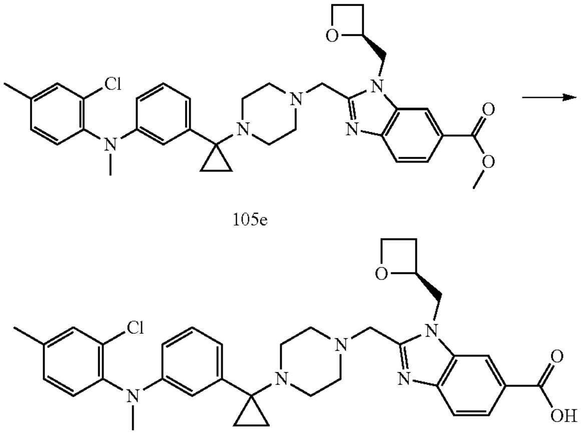

105e

105

To a solution of 105e (80 mg, 0.13 mmol) in THF:$H_2O$ (1:1, 2 mL) was added lithium hydroxide (6 mg, 0.26 mmol) at 0° C. The reaction mixture was stirred at 20° C. for 16 h. After completion, THF was removed in vacuo. The resulting mixture was adjusted to pH=7 with 1 N HCl, and extracted with DCM (5 mL×2). The combined organic phase was washed with water (2 mL), brine (2 mL), dried over magnesium sulfate, filtered, and concentrated to give a crude residue, which was purified by reverse phase HPLC (gradient 35-45% $CH_3CN$ in $H_2O$, 0.1% TFA as a modifier) to afford the title compound (105) (14.5 mg, 18%) as a white solid. $^1H$ NMR (400 MHZ, $CD_3OD$) δ ppm 8.39 (br s, 1H), 8.04-8.12 (m, 1H), 7.75 (br d, J=8.56 Hz, 1H), 7.35 (s, 1H), 7.15-7.29 (m, 3H), 6.86 (br d, J=7.58 Hz, 1H), 6.59-6.67 (m, 2H), 5.13 (qd, J=7.16, 2.63 Hz, 1H), 4.68-4.78 (m, 1H), 4.51-4.65 (m, 2H), 4.23-4.40 (m, 3H), 3.25 (s, 3H), 2.85-3.60 (m, 8H), 2.65-2.73 (m, 1H), 2.38-2.48 (m, 1H), 2.35 (s, 3H), 1.32 (br dd, J=8.68, 7.46 Hz, 2H), 1.07-1.22 (m, 2H). m/z (ESI, +ve ion)=600.3 $[M+H]^+$.

Example 106. (S)-2-((4-(3-((2-chloro-4-methylphenyl)(methyl)amino)benzylidene)piperidin-1-yl)methyl)-1-(oxetan-2-ylmethyl)-1H-benzo[d]imidazole-6-carboxylic acid (106)

106

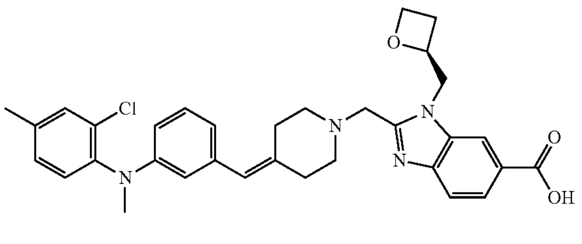

Step A. tert-Butyl 4-(3-bromobenzylidene)piperidine-1-carboxylate (106a)

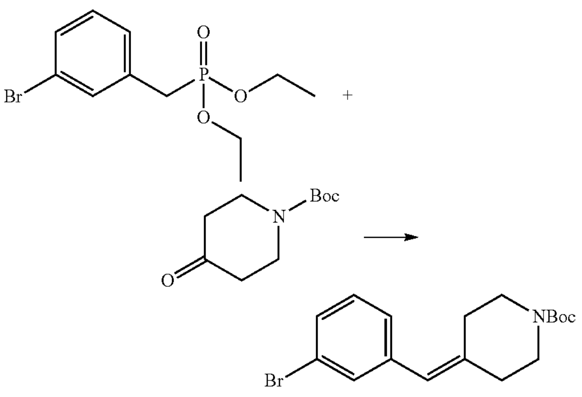

106a

A solution of diethyl(3-bromobenzyl)phosphonate (2 g, 6.5 mmol) in THF (15 mL) was added NaH (60% in mineral oil, 260 mg, 13.0 mmol) at 0° C. After stirring for 30 min at 0° C., a solution of tert-butyl 4-oxopiperidine-1-carboxylate (2.59 g, 13.0 mmol) in THF (5 mL) was added. The resulting mixture was stirred for 0.5 h at the same temperature, and then stirred another 8 h at 20° C. under a $N_2$ atmosphere. The mixture was quenched with $H_2O$ (10 mL), and extracted with EtOAc (10 mL×2). The combined organic layer were dried over $Na_2SO_4$, filtered, concentrated, and purified by silica gel column chromatography (EtOAc:petroleum ether=1:10) to give the title product (106a) (2.2 g. 96%) as a white solid. m/z (ESI, +ve ion)=374.1 $[M+Na]^+$.

Step B. tert-Butyl 4-(3-((2-chloro-4-methylphenyl)amino)benzylidene)piperidine-1-carboxylate (106b)

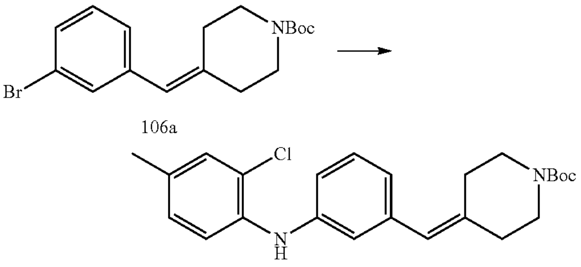

106a

106b

A solution of 106a (1.0 g, 2.84 mmol) in 1,4-dioxane (5 mL) was added 2-chloro-4-methylaniline (482 mg, 3.41 mmol), Ruphos-Pd-G2 (241 mg, 0.31 mmol), $Cs_2CO_3$ (1.85 g, 5.68 mmol) under $N_2$. The mixture was stirred for 7 h at 95° C. and then concentrated to give a crude residue, which was purified by silica gel column chromatography (EtOAc: petroleum ether=1:10) to give the title product (106b) (760 mg, 65%) as a light brown oil. m/z (ESI, +ve ion)=435.1 $[M+Na]^+$.

Step C. tert-Butyl 4-(3-((2-chloro-4-methylphenyl)(methyl)amino)benzylidene)piperidine-1-carboxylate (106c)

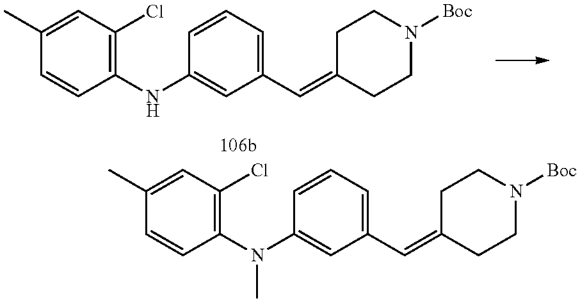

106b

106c

A solution of 106b (45 mg, 0.11 mol) in DMF (1 mL) was added KOH (78 mg, 0.54 mol) and iodomethane (232 mg, 1.6 mol). The mixture was stirred for 16 h at 20° C. The reaction was diluted with water (10 mL) and extracted with EtOAc (5 mL×3). The combined organic layers were dried over $Na_2SO_4$, filtered, concentrated, and purified by prep-TLC (EtOAc:petroleum ether=1:5) to give the title product (106c) (32 mg, 68%) as a colorless oil. m/z (ESI, +ve ion)=449.2 $[M+Na]^+$.

Step D. 2-Chloro-N,4-dimethyl-N-(3-(piperidin-4-ylidenemethyl)phenyl)aniline (106d)

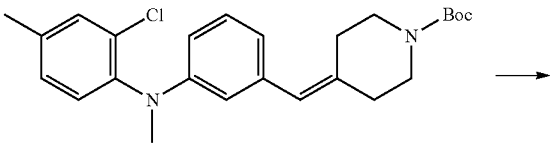

106c

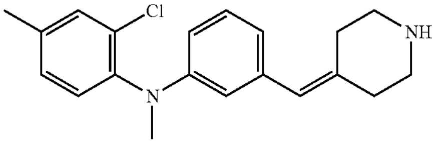

106d

A mixture of 106c (45 mg, 0.105 mmol) in DCM (3 mL) was added 4 N HCl in dioxane (0.3 mL). The mixture was stirred at 14° C. for 2 h. After completion, the reaction mixture was concentrated in vacuo to give the title product (106d) (46 mg, HCl salt) as a white solid, which was used in the next step without further purification. m/z (ESI, +ve ion)=327.1 $[M+H]^+$.

Step E. Methyl(S)-2-((4-(3-((2-chloro-4-methylphenyl)(methyl)amino)benzylidene)piperidin-1-yl)methyl)-1-(oxetan-2-ylmethyl)-1H-benzo[d]imidazole-6-carboxylate (106e)

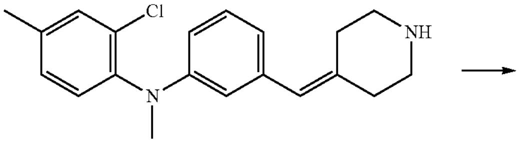

106d

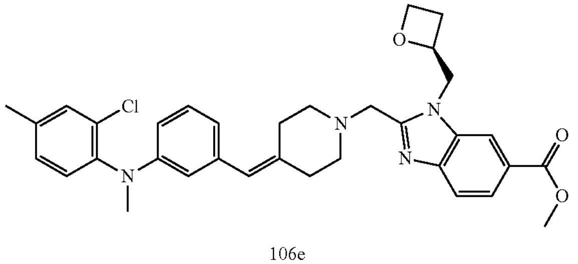

106e

A mixture of 106d (41 mg, 0.10 mmol), and potassium carbonate (56 mg, 0.41 mmol) in DMF (3 mL) was stirred at 16° C. for 0.5 h. Then potassium iodide (2 mg, 0.01 mmol) and 1h (30 mg, 0.10 mmol) in DMF (0.5 mL) were added to the above mixture. After stirring for 2.5 h, the mixture was poured into water (10 mL), and extracted with EtOAc (10 mL×2). The combined organic layers were dried over $Na_2SO_4$, filtered, concentrated, and purified by reverse phase HPLC (53% $CH_3CN$ in $H_2O$ with 0.05% TFA as a modifier) to give the title product (106e) (29 mg, 39%) as a white solid. m/z (ESI, +ve ion)=585.3 $[M+H]^+$.

Step F. (S)-2-((4-(3-((2-Chloro-4-methylphenyl)(methyl)amino)benzylidene)piperidin-1-yl)methyl)-1-(oxetan-2-ylmethyl)-1H-benzo[d]imidazole-6-carboxylic acid (106)

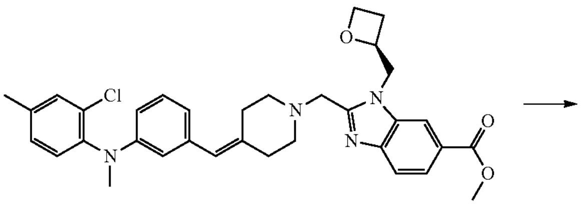

106e

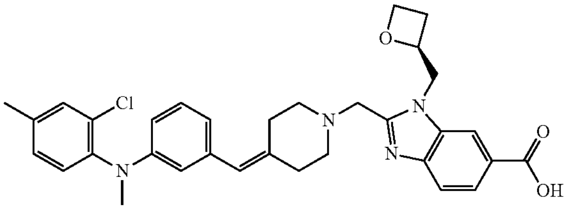

106

To a solution of 106e (29 mg, 0.05 mmol) in a mixed solvent of $CH_3OH$:$H_2O$=5:1 (3.5 mL) was added LiOH. $H_2O$ (40 mg, 0.95 mmol). The reaction was stirred at 16° C. for 18 h, adjusted to pH=7 with 1 N HCl, and extracted with EtOAc (10 mL×2). The combined organic layers were dried over $Na_2SO_4$, filtered, concentrated, and purified by reverse phase HPLC (42% $CH_3CN$ in $H_2O$ with 0.5% TFA as a modifier) to afford the title compound (106) (16.8 mg, 48.4%) as a white solid. $^1H$ NMR (400 MHZ, $CD_3OD$) δ ppm 8.35 (d, J=0.88 Hz, 1H), 8.02-8.09 (m, 1H), 7.82 (d, J=8.77 Hz, 1H), 7.36 (s, 1H), 7.11-7.23 (m, 3H), 6.59 (d, J=7.45 Hz, 1H), 6.46-6.55 (m, 2H), 6.29 (s, 1H), 5.22 (qd, J=7.16, 2.63 Hz, 1H), 4.61-4.83 (m, 5H), 4.42 (dt, J=9.43, 5.81 Hz, 1H), 3.55 (br s, 2H), 3.42 (br s, 2H), 3.21 (s, 3H), 2.72-2.89 (m, 3H), 2.67 (br t, J=5.92 Hz, 2H), 2.44-2.55 (m, 1H), 2.36 (s, 3H). m/z (ESI, +ve ion)=571.1 $[M+H]^+$.

Example 110. 1'-((6-(2H-Tetrazol-5-yl)pyridin-3-yl)methyl)-6-((2,4-dichlorobenzyl)oxy)-1',2',3',6'-tetrahydro-2,4'-bipyridine (110)

110

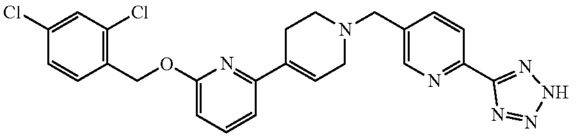

Step A. tert-Butyl 6-((2,4-dichlorobenzyl)oxy)-3',6'-dihydro-[2,4'-bipyridine]-1'(2'H)-carboxylate (110a)

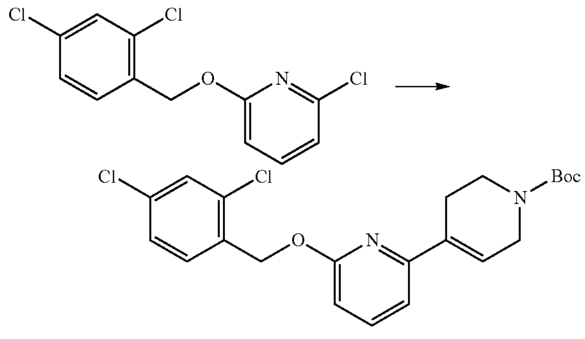

110a (1,1'-Bis(diphenylphosphino)ferrocene) palladium(II) dichloride (12.7 mg, 0.017 mmol), $Cs_2CO_3$ (113 mg, 0.35 mmol), and tert-butyl 4-(4,4,5,5-tetramethyl-1,3,2-dioxaborolan-2-yl)-1,2,3,6-tetrahydropyridine-1-carboxylate (53 mg 0.17 mmol) were added to 2-chloro-6-[(2,4-dichlorophenyl)methoxy]pyridine (50 mg, 0.17 mmol) in anhydrous 1,4-dioxane (0.9 mL) at room temperature. The mixture was flushed with argon for 10 min, then heated to 90° C. for 2 h. The reaction was partitioned between EtOAc and sat. aq. $NaHCO_3$. The organic layer was washed with brine, dried ($Na_2SO_4$), filtered, concentrated, and purified by silica gel column chromatography (gradient elution, EtOAc in hexanes 0-50%) to provide the title product (110a) (48 mg, 64%) as a white oil. m/z (ESI, +ve ion)=435.2 $[M+H]^+$.

Step B. 5-((6-((2,4-Dichlorobenzyl)oxy)-3',6'-dihydro-[2,4'-bipyridin]-1'(2'H)-yl)methyl) picolinonitrile (110b)

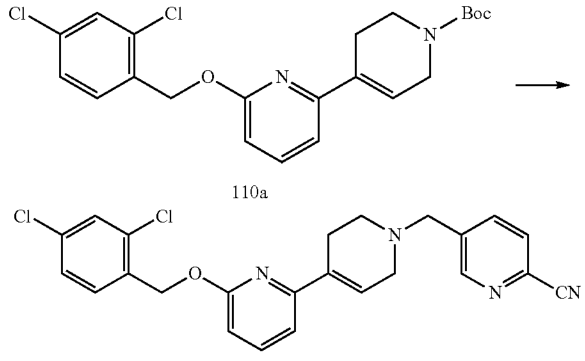

110a

110b

TFA (0.15 mL, 2.0 mmol) was added to 110a (44 mg, 0.1 mmol) in DCM (1 mL) at room temperature, and stirred for 30 min. The reaction was concentrated to give a crude TFA salt which was redissolved in anhydrous THF (0.1 M, 1.0 mL). 5-Formylpyridine-2-carbonitrile (45 mg, 0.15 mmol) was added. After stirring for 10 min, sodium triacetoxyborohydride (42 mg, 0.2 mmol) was added, and the reaction was stirred for 3 h. The reaction was partitioned between EtOAc and sat. aq. $NaHCO_3$. The organic layer was washed with brine, dried ($Na_2SO_4$), concentrated, and purified by silica gel column chromatography (gradient elution, MeOH in DCM 0-5%) to provide the title product (110b) (15 mg, 21%) as a white oil. m/z (ESI, +ve ion)=451.2 $[M+H]^+$.

Step C. 1'-((6-(2H-Tetrazol-5-yl)pyridin-3-yl)methyl)-6-((2,4-dichlorobenzyl)oxy)-1',2',3',6'-tetrahydro-2,4'-bipyridine (110)

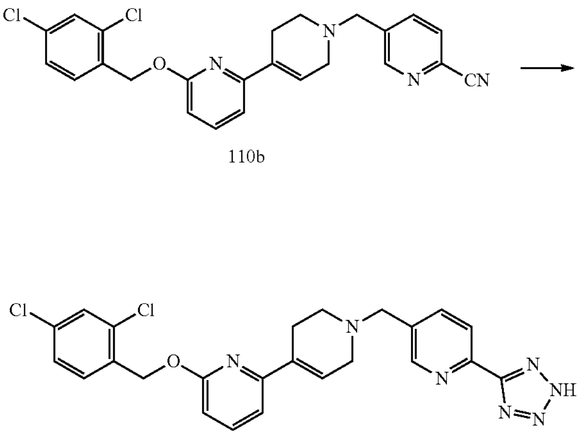

110b

110

$NaN_3$ (2 mg, 0.032 mmol), and $NH_4Cl$ (2 mg, 0.032 mmol) were added to 110b (13 mg, 0.029 mmol) in anhydrous DMF (0.3 mL) at room temperature. After stirring for 10 min, the reaction was heated to 100° C. for 40 h, and then cooled down. The crude mixture was directly purified by reverse phase HPLC (gradient elution, 0-90% $CH_3CN$ in water with 0.1% TFA as a modifier) to afford the title compound (110) (2.6 mg, 15%) as a white solid. $^1H$ NMR (600 MHz, $CD_3OD$) δ ppm 8.94 (br s, 1H), 8.38 (d, J=8.07 Hz, 1H), 8.23 (dd, J=7.89, 1.28 Hz, 1H), 7.72 (t, J=7.89 Hz, 1H), 7.45-7.50 (m, 2H), 7.31 (dd, J=8.25, 2.02 Hz, 1H), 7.18 (d, J=7.70 Hz, 1H), 6.84 (d, J=8.44 Hz, 1H), 6.70 (br s, 1H), 5.48 (s, 2H), 4.62 (s, 2H), 4.01 (br s, 2H), 3.65 (br s, 2H), 2.97 (br s, 2H). m/z (ESI, +ve ion)=494.2 $[M+H]^+$.

Example 111. (S)-2-((4-(3-((2-Chloro-4-methylphenyl)(methyl)amino)phenoxy)piperidin-1-yl)methyl)-1-(oxetan-2-ylmethyl)-1H-benzo[d]imidazole-6-carboxylic acid (111)

111

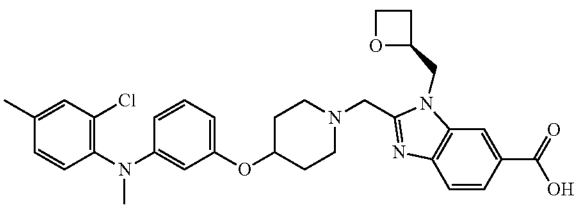

Step A. tert-Butyl 4-{3-[(2-chloro-4-methylphenyl)(methyl)amino]phenoxy}piperidine-1-carboxylate (111a)

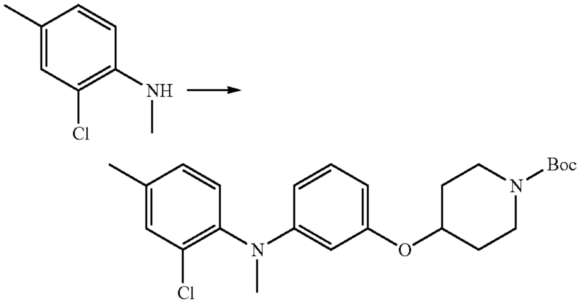

111a tert-Butyl 4-(3-bromophenoxy)piperidine-1-carboxylate (137 mg, 0.39 mmol), $Pd(OAc)_2$ (1.4 mg, 0.006 mmol), BINAP (4 mg, 0.006 mmol), and $Cs_2CO_3$ (157 mg, 0.48 mmol) were added to a flask charged with 2-chloro-N,4-dimethylaniline (50 mg, 0.32 mmol) in anhydrous toluene (0.2 M, 1.6 mL) at room temperature. The mixture was degassed with argon for 10 min, then heated to 120° C. for 2 h. The reaction was partitioned between EtOAc and sat. aq. $NaHCO_3$. The organic layer was washed with brine, dried ($Na_2SO_4$), filtered, concentrated, and purified by silica gel column chromatography (gradient elution, EtOAc in hexanes 0-20%) to provide an impure title product (111a) as a white oil (122 mg). m/z (ESI, +ve ion)=432.2 $[M+H]^+$.

Step B. 2-Chloro-N,4-dimethyl-N-(3-(piperidin-4-yloxy)phenyl)aniline (111b)

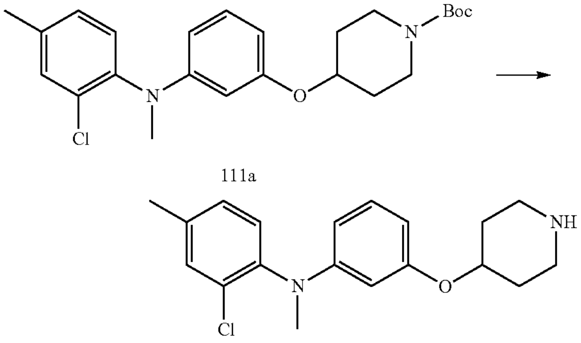

111a

111b

A flask was charged with 111a (30 mg, impure) in DCM (0.7 mL) at room temperature. TFA (0.1 mL, 1.4 mmol) was added. The reaction was stirred for 30 min, and then concentrated. The crude residue was partitioned between EtOAc and sat. aq. $NaHCO_3$. The organic layer was washed with brine, dried ($Na_2SO_4$), and concentrated to provide the crude title product (111b) (23 mg) as a colorless oil, which was used in the next step without further purification. m/z (ESI, +ve ion)=331.2 $[M+H]^+$.

Step C. (S)-2-((4-(3-((2-Chloro-4-methylphenyl)(methyl)amino)phenoxy)piperidin-1-yl)methyl)-1-(oxetan-2-ylmethyl)-1H-benzo[d]imidazole-6-carboxylic acid (111)

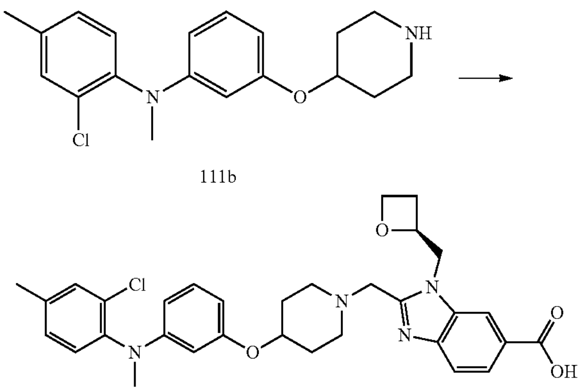

111b

111

DIPEA (0.012 mL, 0.07 mmol), and 1h (12 mg, 0.04 mmol) were added to 111b (23 mg, 0.07 mmol) in DCM (1.4 mL) at room temperature, and heated to 40° C. for 16 h. The reaction was concentrated to provide a crude ester, which was re-dissolved in THF:$H_2O$ (1:1, 0.4 mL). LiOH·$H_2O$ (2 mg, 0.045 mmol) was added. After stirring for 12 h at room temperature, the reaction was acidified with 1 N HCl. The mixture was partitioned between EtOAc and sat. aq. $NaHCO_3$. The organic layer was washed with brine, dried ($Na_2SO_4$), filtered, concentrated, and purified by reverse phase HPLC (0-70% $CH_3CN$ and water with 0.1% HOAc as a modifier, gradient elution) to provide the title product (111) as a white solid (2.5 mg, 6% over 3 steps). $^1H$ NMR (600 MHZ, $CD_3OD$) δ ppm 8.50 (s, 1H), 8.27 (s, 1H), 7.95 (dd, J=8.44, 1.47 Hz, 1H), 7.62 (d, J=8.44 Hz, 1H), 7.34 (s, 1H), 7.12-7.21 (m, 1H), 7.01 (t, J=8.25 Hz, 1H), 6.31 (dd, J=8.07, 1.83 Hz, 1H), 6.14 (dd, J=8.07, 2.20 Hz, 1H), 6.03 (t, J=2.38 Hz, 1H), 5.25 (qd, J=7.15, 2.38 Hz, 1H), 4.85-4.90 (m, 1H), 4.70 (dd, J=15.41, 2.93 Hz, 1H), 4.63 (td, J=7.89, 5.87 Hz, 1H), 4.46 (dt, J=9.17, 5.87 Hz, 1H), 4.23-4.31 (m, 1H), 3.85-4.03 (m, 2H), 3.17 (s, 3H), 2.72-2.84 (m, 3H), 2.47-2.57 (m, 1H), 2.39-2.46 (m, 2H), 2.37 (s, 3H), 1.91-2.01 (m, 2H), 1.74 (br s, 2H). m/z (ESI, +ve ion)=575.3 $[M+H]^+$.

Example 112. 2-((4-(3-(1-(2-Chloro-4-methylphenyl)ethyl)benzoyl)piperazin-1-yl)methyl)-1-(((S)-oxetan-2-yl)methyl)-1H-benzo[d]imidazole-6-carboxylic acid (112)

112

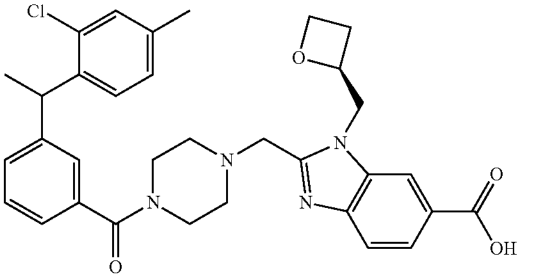

Step A. Methyl 3-(2-chloro-4-methylbenzoyl)benzoate (112a)

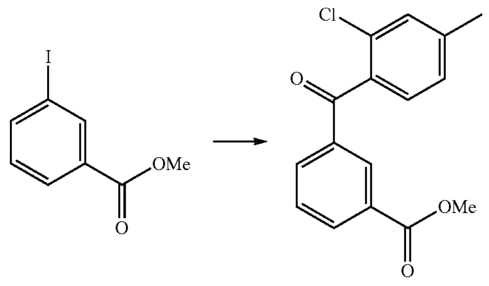

112a

To a mixture of methyl 3-iodobenzoate (400 mg, 1.53 mmol), (2-chloro-4-methylphenyl)boronic acid (260 mg, 1.53 mmol), $K_2CO_3$ (527 mg, 3.82 mmol), and Pd(dppf) $Cl_2$·DCM (125 mg, 0.15 mmol) was added anisole (12 mL) under a carbon monoxide (CO) atmosphere. The mixture was stirred at 80° C. for 12 h. After completion, the mixture was filtered, concentrated, and purified by silica gel column chromatography (EtOAc:petroleum ether=1:10) to afford the title product (112a) (291 mg, 59%) as a yellow solid. m/z (ESI, +ve ion)=289.0 $[M+H]^+$.

Step B. 3-(2-Chloro-4-methylbenzoyl)benzoic acid (112b)

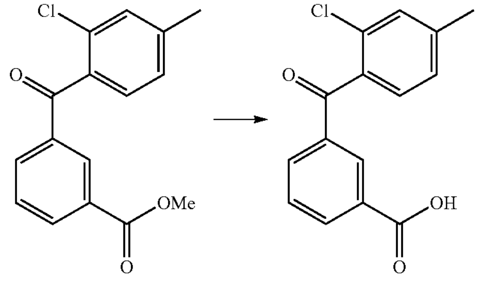

112a 112b

A flask was charged with 112a (150 mg, 0.52 mmol), and $CH_3OH$:$H_2O$=10:1 (8 mL) followed by the addition of sodium hydroxide (104 mg, 2.6 mmol). The mixture was stirred at 16° C. for 3 h. The mixture was then adjusted to pH=7 with 1N HCl, and extracted with EtOAc (30 mL×2). The combined organic layers were washed with $H_2O$ (5 mL), brine (5 mL), dried over $Na_2SO_4$, filtered, and concentrated in vacuo to give the title product (112b) (130 mg) as a gray solid, which was used in the next step without further purification. m/z (ESI, +ve ion)=274.9 $[M+H]^+$.

Step C. 3-(1-(2-Chloro-4-methylphenyl)-1-hydroxyethyl)benzoic acid (112c)

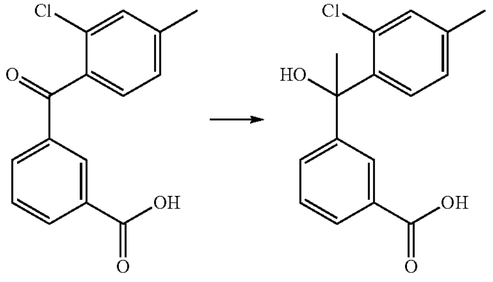

112b 112c

To a mixture of 112b (130 mg, 0.47 mmol) in THF (10 mL) was added $CH_3MgBr$ (3 M in hexanes, 0.6 mL, 1.66 mmol) at 0° C. The mixture was stirred at 0° C. for one hour. After completion, the mixture was quenched with sat. aq. $NH_4Cl$ (10 mL), diluted with $H_2O$ (10 mL), and extracted with EtOAc (20 mL×2). The combined organic layers were dried over $Na_2SO_4$, filtered, and concentrated in vacuo to give the title product (112c) (116 mg, crude) as a yellow oil, which was used in next step without further purification. m/z (ESI, +ve ion)=273.1 $[M-OH]^+$.

Step D. 3-(1-(2-Chloro-4-methylphenyl)ethyl)benzoic acid (112d)

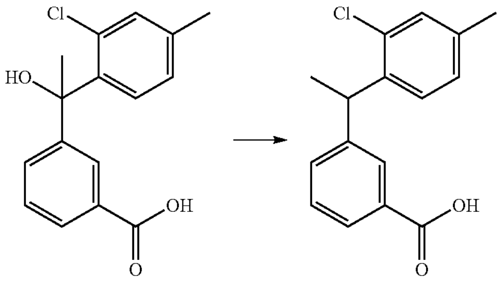

112c 112d

To a flask charged with 112c (116 mg, 0.4 mmol) was added triethylsilane (2 mL), followed by TFA (1 mL). The mixture was stirred at 16° C. for 3 h. After completion, the reaction mixture was poured into water (10 mL), and extracted with EtOAc (20 mL×2). The combined organic layers were dried over $Na_2SO_4$, filtered, and concentrated in vacuo. The crude residue was purified by reverse phase HPLC (61% $CH_3CN$ in $H_2O$ with 0.5% TFA as a modifier) to give the title product (112d) (69 mg, 60%) as a white solid. m/z (ESI, +ve ion)=275.1 $[M+H]^+$.

Step E. Methyl 2-((4-(3-(1-(2-chloro-4-methylphenyl)ethyl)benzoyl)piperazin-1-yl)methyl)-1-(((S)-oxetan-2-yl)methyl)-1H-benzo[d]imidazole-6-carboxylate (112e)

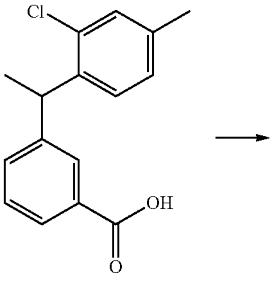

112d

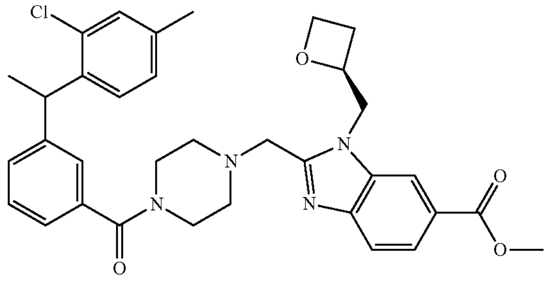

112e

The title compound was prepared from 112d, and 1j by procedures similar to those described in Example 102, Step D. m/z (ESI, +ve ion)=601.1 $[M+H]^+$.

Step F. 2-((4-(3-(1-(2-Chloro-4-methylphenyl)ethyl)benzoyl)piperazin-1-yl)methyl)-1-(((S)-oxetan-2-yl)methyl)-1H-benzo[d]imidazole-6-carboxylic acid (112)

112

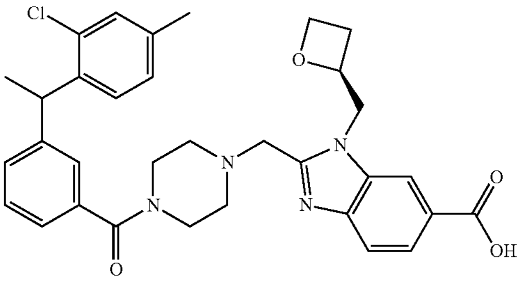

The title compound was prepared from 112e by procedures similar to those described in Example 106, Step F. $^1H$ NMR (400 MHZ, $CD_3OD$) δ ppm 8.47 (s, 1H), 8.14 (dd, J=8.33, 1.32 Hz, 1H), 7.81 (d, J=8.33 Hz, 1H), 7.34-7.45 (m, 2H), 7.22-7.31 (m, 3H), 7.19 (s, 1H), 7.12 (br d, J=7.89 Hz, 1H), 5.23 (qd, J=7.16, 2.19 Hz, 1H), 4.92 (br d, J=3.51 Hz, 1H), 4.74 (br dd, J=15.35, 2.63 Hz, 1H), 4.58-4.70 (m, 2H), 4.32-4.51 (m, 3H), 3.87 (br s, 2H), 3.57 (br s, 2H), 2.77-3.02 (m, 5H), 2.47-2.58 (m, 1H), 2.28 (s, 3H), 1.62 (d, J=7.45 Hz, 3H). m/z (ESI, +ve ion)=587.2 $[M+H]^+$.

Example 114. (S)-2-((4-((6-((2-Cyano-4-methylphenoxy)methyl)pyridin-2-yl)methyl)piperidin-1-yl)methyl)-1-(oxetan-2-ylmethyl)-1H-benzo[d]imidazole-6-carboxylic acid (114)

114

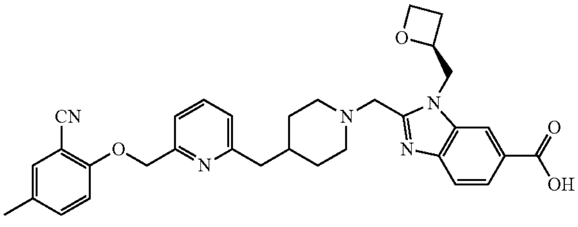

Step A. (E)-2-Hydroxy-5-methylbenzaldehyde oxime (114a)

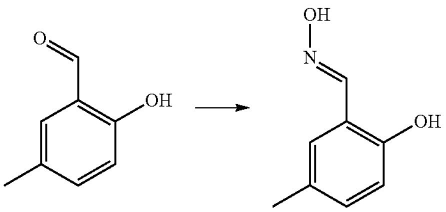

114a

A solution of 2-hydroxy-5-methylbenzaldehyde (5 g, 36.7 mmol), hydroxylamine hydrochloride (12.75 g, 183.5 mmol) and pyridine (5.81 g, 73.4 mmol) in EtOH (50 mL) was stirred at 60° C. for 3 h. After completion, the reaction mixture was concentrated to about 10 mL. EtOAc (150 mL) and 1 N HCl (50 mL) were added. The organic phase was washed with water (50 mL×2), brine (50 mL), dried with $Na_2SO_4$, filtered and concentrated to afford the title product (114a) (5.1 g, 87%) as a white solid. m/z (ESI, +ve ion)=152.2 $[M+H]^+$.

Step B. 2-Hydroxy-5-methylbenzonitrile (114b)

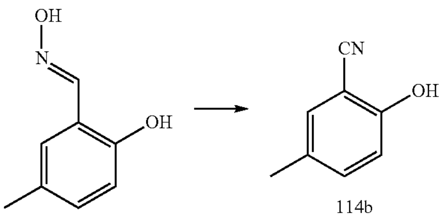

114a

114b

To a solution of 114a (100 mg, 0.66 mmol) and $PPh_3$ (433 mg, 1.65 mmol) in $CH_2Cl_2$ (2 mL) was added diethyl azodicarboxylate (334 mg, 1.65 mmol) dropwise at 17° C. The resulting mixture was stirred at 17° C. for 3 h. After completion, the reaction mixture was partitioned between $CH_2Cl_2$ (10 mL) and 0.1 N NaOH (10 mL). The aqueous layer was washed with $CH_2Cl_2$ (50 mL×3) and acidified with 1 N HCl (10 mL). The acidic aqueous layer was extracted with $CH_2Cl_2$ (50 mL×2). The combined organic layer was dried, filtered, and concentrated to afford the title product (114b) (51 mg, 52%) as a white solid. m/z (ESI, +ve ion)=134.2 $[M+H]^+$.

Step C. (6-(Chloromethyl)pyridin-2-yl)methanol (114c)

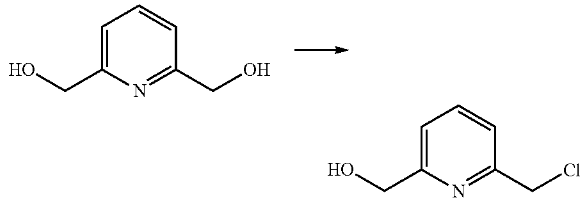

114c

To a solution of pyridine-2,6-diyldimethanol (20 g, 143 mmol) in DMF (100 mL) was added NaH (60% in mineral oil, 5.75 g, 143 mmol) at 0° C. The mixture was stirred at 0° C. for 0.5 h. Then tert-butyl(chloro) dimethylsilane (26 g, 172 mmol) was added dropwise. The mixture was stirred at 17° C. for 16 h. The reaction was diluted with EtOAc (200 ml) and washed with sat. $NaHCO_3$ (50 mL), and brine (50 mL). The EtOAc layer was dried, filtered, concentrated and the resulting crude residue was purified by silica gel column chromatography (5% MeOH in DCM) to afford the title product (114c) (3.5 g, 14.7%) as a colorless oil. m/z (ESI, +ve ion)=158.1 $[M+H]^+$.

Step D. tert-Butyl 4-((6-(hydroxymethyl)pyridin-2-yl)methyl)-3,6-dihydropyridine-1(2H)-carboxylate (114d)

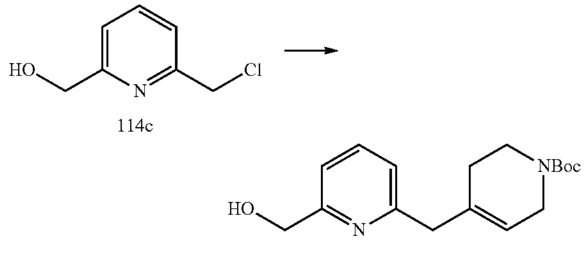

114c

114d

A flask was charged with 114c (3.3 g, 20.9 mmol), tert-butyl 4-(4,4,5,5-tetramethyl-1,3,2-dioxaborolan-2-yl)-3,6-dihydropyridine-1(2H)-carboxylate (7.13 g, 22.9 mmol), $K_2CO_3$ (8.67 g, 62.6 mmol) and Pd(dppf)$Cl_2$·DCM (0.85 g, 1.0 mmol) and added 3 mL of a mixed solvent of 1,4-dioxane/$H_2O$ (4:1). The mixture was degassed with nitrogen and stirred at 90° C. for 3 h under nitrogen. After completion, the reaction was diluted with $H_2O$ (100 mL) and extracted with EtOAc (100 mL×3). The organic layer was dried, filtered and concentrated. The crude residue was purified by silica gel column chromatography (petroleum ether:EtOAc=3:2) to afford the title product (114d) (3.8 g, 57%) as a yellow oil. m/z (ESI, +ve ion)=305.2 $[M+H]^+$.

Step E. tert-Butyl 4-((6-(hydroxymethyl)pyridin-2-yl)methyl)piperidine-1-carboxylate (114e)

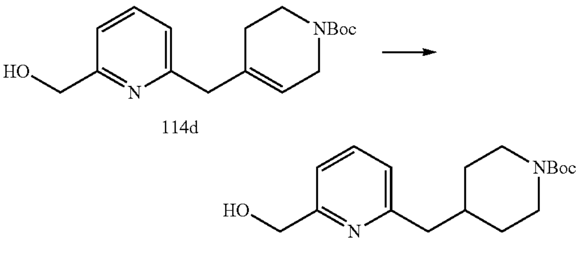

114d

114e

A solution of 114d (3.8 g, 12.5 mmol) and 10% Pd/C (380 mg) in MeOH (30 mL) was stirred under hydrogen at 17° C. for 12 h. After completion, the reaction was filtered through a pad of celite and rinsed with MeOH (50 mL×3). The organic layer was concentrated to afford the title product (114e) (3.5 g, 87%) as a yellow oil, which was used in the next step without further purification. m/z (ESI, +ve ion)=307.3 $[M+H]^+$.

Step F. tert-Butyl 4-((6-((2-cyano-4-methylphenoxy)methyl)pyridin-2-yl)methyl)piperidine-1-carboxylate (114f)

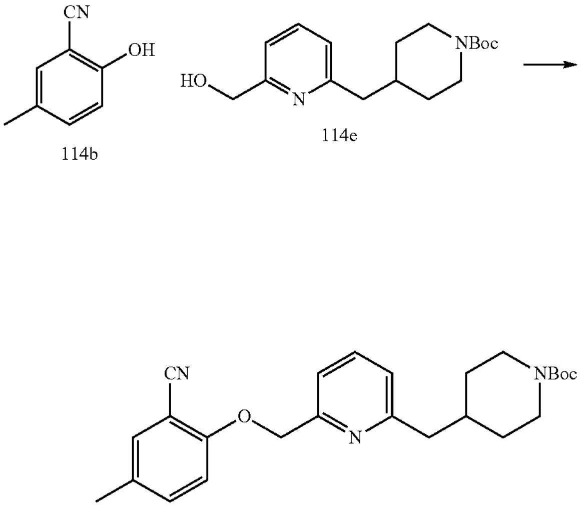

114b

114e

114f

A flask was charged with 114b (332 mg, 2.50 mmol), 114e (510 mg, 1.66 mmol), and $PPh_3$ (655 mg, 2.50 mmol). Anhydrous THF (10 mL) was added and the reaction was cooled down in an ice bath. Diethyl azodicarboxylate (435 mg, 2.50 mmol) was added dropwise and the resulting mixture was stirred at 0° C. for 1 h, then at 17° C. for 11 h under nitrogen. After completion, the organic layer was concentrated and purified by silica gel column chromatography (petroleum ether:EtOAc=4:1) to afford the title product (114f) (600 mg, 79%) as a yellow oil. m/z (ESI, +ve ion)=422.2 $[M+H]^+$.

Step G. 2-((2-Chloro-4-methylphenoxy)methyl)-6-(piperidin-4-ylmethyl)pyridine (114g)

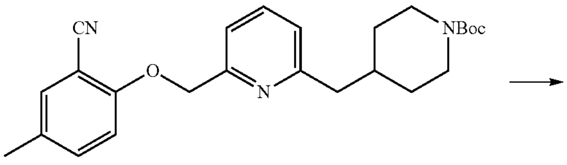

114f

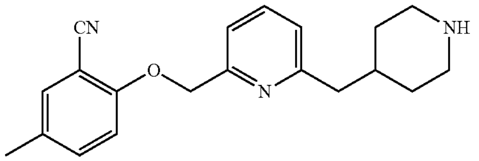

114g

A solution of 114f (523 mg, 1.24 mmol) and 2,6-lutidine (2.66 g, 24.8 mmol) in anhydrous DCM (10 mL) was stirred at 0° C. for 0.5 h. TMSOTf (2.76 g, 12.4 mmol) was added and the resulting mixture was stirred at 0° C. for 2 h. After completion, the reaction was quenched with saturated ammonium chloride solution (1 mL). The reaction mixture was diluted with $H_2O$ (10 mL) and extracted with EtOAc (10 mL×3). The organic layer was dried, filtered and concentrated to afford the title product (114g) (400 mg, 95%) as a yellow oil, which was used in the next step without further purification. m/z (ESI, +ve ion)=322.2 $[M+H]^+$.

Step H. Methyl(S)-2-((4-((6-((2-cyano-4-methylphenoxy)methyl)pyridin-2-yl)methyl)piperidin-1-yl)methyl)-1-(oxetan-2-ylmethyl)-1H-benzo[d]imidazole-6-carboxylate (114h)

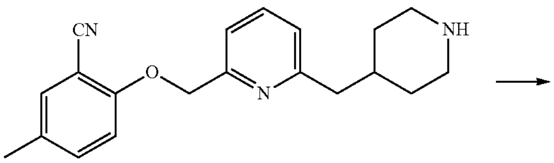

114g

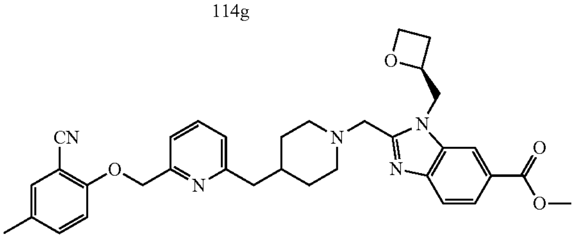

114h

A solution of 114g (98 mg, 0.30 mmol), 1h (90 mg, 0.30 mmol) and $K_2CO_3$ (126 mg, 0.91 mmol) in DMF (2 mL) was stirred at 17° C. for 6 h. After completion, the reaction was diluted with $H_2O$ (10 mL) and extracted with EtOAc (10 mL×3). The organic layer was dried, filtered and concentrated to give a crude residue, which was purified by silica gel column chromatography (DCM:MeOH=50:1) to afford the title product (114h) (158 mg) as a white solid with some impurity. m/z (ESI, +ve ion)=580.3 $[M+H]^+$.

Step I. (S)-2-((4-((6-((2-Cyano-4-methylphenoxy)methyl)pyridin-2-yl)methyl)piperidin-1-yl)methyl)-1-(oxetan-2-ylmethyl)-1H-benzo[d]imidazole-6-carboxylic acid (114)

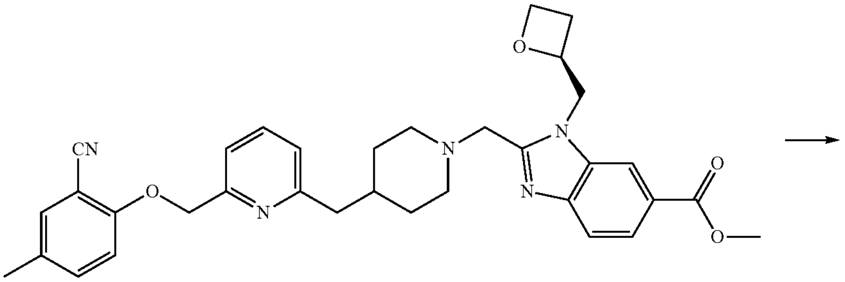

114h

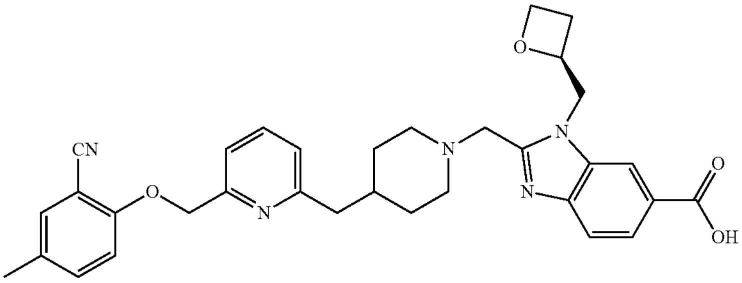

114

A solution of 114h (79 mg, 0.136 mmol) and LiOH (10 mg, 0.41 mmol) in THF:$H_2O$=1:1 (2 mL) was stirred at 30° C. for 6 h. After completion, 1 N HCl was added to the mixture to adjust pH=5 in an ice bath. The reaction mixture was then extracted with EtOAc (50 mL×3). The organic layer was dried, filtered and concentrated and the crude residue was purified by reverse phase HPLC (25% $CH_3CN$ in $H_2O$, with 0.05% TFA as a modifier) to afford the TFA salt of the title product (114) (16.4 mg, 18%) as a white solid. $^1H$ NMR (400 MHz, $CD_3OD$) δ ppm 8.33 (d, J=0.88 Hz, 1H), 8.04 (dd, J=8.55, 1.53 Hz, 1H), 7.88-7.94 (m, 1H), 7.80 (d, J=9.21 Hz, 1H), 7.57 (d, J=7.45 Hz, 1H), 7.42-7.48 (m, 2H), 7.38 (d, J=7.02 Hz, 1H), 7.13-7.17 (m, 1H), 5.29 (s, 2H), 5.20 (qd, J=7.09, 2.41 Hz, 1H), 4.76-4.82 (m, 2H), 4.71-4.75 (m, 1H), 4.60-4.69 (m, 2H), 4.41 (dt, J=9.43, 5.81 Hz, 1H), 3.73-3.84 (m, 2H), 3.15-3.28 (m, 2H), 2.89 (d, J=7.02 Hz, 2H), 2.79 (dtd, J=11.46, 8.19, 8.19, 5.92 Hz, 1H), 2.41-2.54 (m, 1H), 2.14-2.26 (m., 1H), 1.90-2.01 (m, 2H) 1.57-1.74 (m, 2H). m/z (ESI, +ve ion)=566.2 $[M+H]^+$.

Example compounds 118, 120, 140 were synthesized in similar procedures as described in Example 114. Example 123 was synthesized from methyl 5-fluoro-6-methylpicolinate as described in Example 60, Steps A, B, followed by as described in Example 72, Step C and Example 114, Steps E to I. Example 126, 133 were synthesized following the same synthetic sequence as Example 123. Example 135 was synthesized from as described in Example 60, Steps A to C, followed by as described in Example 72, Step C and Example 114, Steps F to I. Example 162 was synthesized in Example 60, Steps A to C, followed by as described in Example 72, Step C to D, Example 116, Step D and Example 114, Steps H to I.

Example 115. (S)-2-((4-(3-((4-Cyclopropyl-2-methylphenyl)(methyl)amino)benzoyl)piperazin-1-yl)methyl)-1-(oxetan-2-ylmethyl)-1H-benzo[d]imidazole-6-carboxylic acid (115)

115

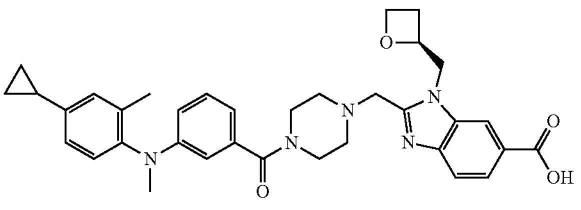

Step A. 4-Cyclopropyl-2-methylaniline (115a)

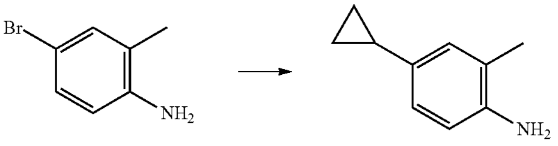

115a 1,1'-Bis(diphenylphosphino)ferrocene-palladium(II) dichloridedichloromethane complex (44 mg, 0.05 mmol) was added to a solution of 4-bromo-2-methylaniline (50 mg, 0.27 mmol), cesium carbonate (350 mg, 1.07 mmol), cyclopropylboronic acid (46 mg, 0.54 mmol) in 1,4-dioxane (2 mL) and $H_2O$ (0.1 mL). The resulting mixture was stirred at 100° C. for 5 h and was concentrated. Then the reaction was diluted with water (5 mL) and the mixture was extracted with EtOAc (5 mL×3). The organic layer was washed with water (5 mL), brine (5 mL), dried with anhydrous sodium sulfate, filtered and concentrated. The crude residue was purified by silica gel column chromatography (gradient elution, EtOAc in petroleum ether 0-10%) to afford the title product (115a) (30 mg, 68.3%) as a yellow oil. m/z (ESI, +ve ion)=148.2 $[M+H]^+$.

Step B. Methyl 3-((4-cyclopropyl-2-methylphenyl)amino)benzoate (115b)

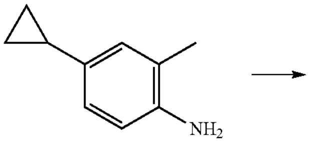

115a

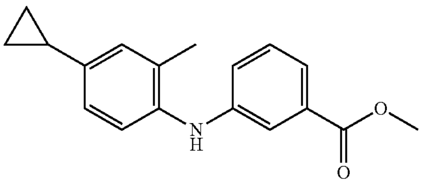

115b

Chloro(2-dicyclohexylphosphino-2',6'-di-i-propoxy-1,1'-biphenyl) (2-amino-1,1'-biphenyl-2-yl)palladiuM(II) (RuPhos Palladacycle) (16 mg, 0.02 mmol) was added to a solution of 115a (30 mg, 0.2 mmol), cesium carbonate (332 mg, 1 mmol), methyl 3-bromobenzoate (44 mg, 0.2 mmol) in 1,4-dioxane (3 mL). The resulting reaction mixture was stirred at 90° C. for 16 h and concentrated. The reaction was diluted with water (5 mL) and extracted with EtOAc (5 mL×3). The organic layer was washed with water (5 mL), brine (5 mL), dried with anhydrous sodium sulfate, filtered and concentrated. The crude residue was purified by silica gel column chromatography (gradient elution, EtOAc in petroleum ether 0)-10%) to afford an impure title product (115b) (32 mg, 80% purity) as a yellow oil. m/z (ESI, +ve ion)=282.1 $[M+H]^+$.

Step C. 3-((4-Cyclopropyl-2-methylphenyl)(methyl)amino)benzoic acid (115c)

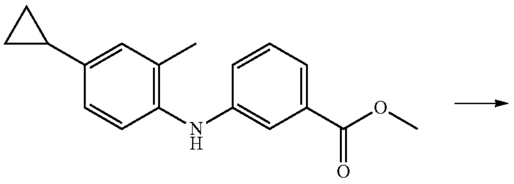

115b

-continued

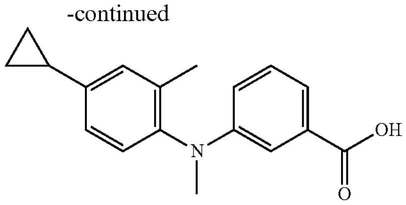

115b

The title product (115c) was prepared from 115b by procedures similar to those described in Example 46, Steps B and C.

Step D. Methyl(S)-2-((4-(3-((4-cyclopropyl-2-methylphenyl)(methyl)amino)benzoyl)piperazin-1-yl)methyl)-1-(oxetan-2-ylmethyl)-1H-benzo[d]imidazole-6-carboxylate (115d)

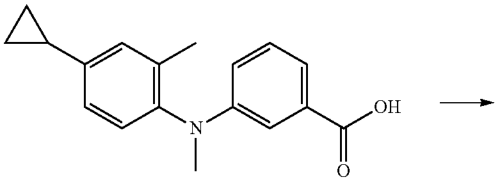

115c

-continued

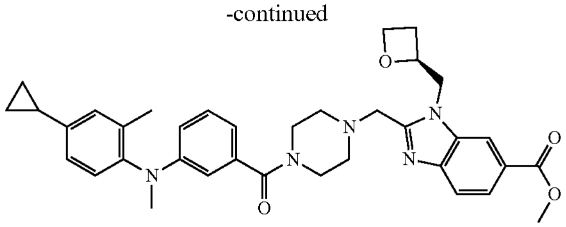

115d

Intermediate 1j (122 mg, 0.36 mmol) and 115c (100 mg, 0.36 mmol) were dissolved in DCM (3 mL). Diisopropylethylamine (184 mg, 1.42 mmol) and HATU (203 mg, 0.53 mmol) were added and the reaction was stirred at 20° C. for 1 h. After removal of the volatiles, the crude residue was purified with prep-TLC (MeOH in DCM 5-10%, with 0.5% $NH_3 \cdot H_2O$ as a modifier) to afford an impure title product (115d) (107 mg, 83% purity) as a yellow oil. m/z (ESI, +ve ion)=608.2 $[M+H]^+$.

Step E. (S)-2-((4-(3-((4-Cyclopropyl-2-methylphenyl)(methyl)amino)benzoyl)piperazin-1-yl)methyl)-1-(oxetan-2-ylmethyl)-1H-benzo[d]imidazole-6-carboxylic acid (115)

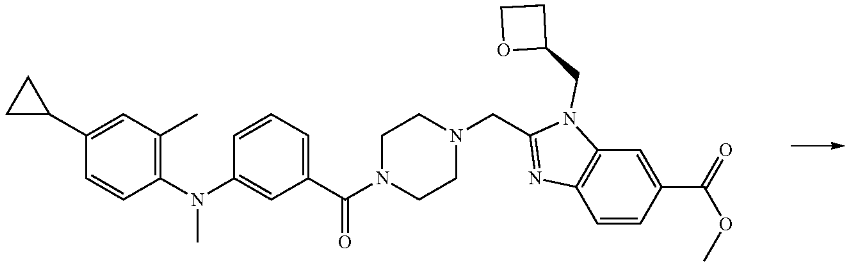

115d

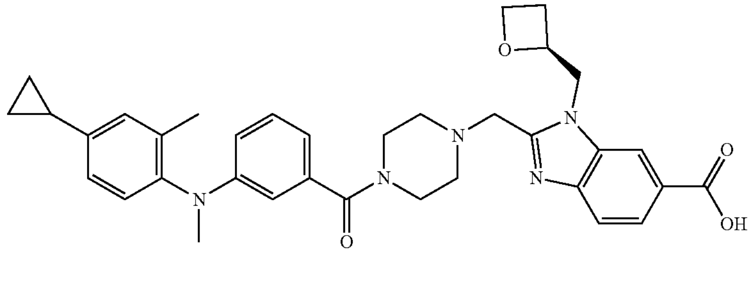

115

To a solution of the impure 115d (65 mg, 0.1 mmol) in MeOH:$H_2O$=5:1 (2.4 mL) was added sodium hydroxide (39 mg, 0.97 mmol) at 0° C. The reaction mixture was raised to room temperature and stirred at 20° C. for 16 h. After concentration, the mixture was diluted with water (5 mL), adjusted to pH=4 with 0.1 N HCl, and extracted with EtOAc (5 mL×3). The organic layer was washed with water (5 mL), brine (5 mL), dried with anhydrous sodium sulfate, filtered and concentrated. The crude residue was purified by reverse phase HPLC (gradient elution, 40-50% $CH_3CN$ in $H_2O$, with 0.1% formic acid as a modifier) to afford the title product (115) (19.2 mg) as a white solid. $^1H$ NMR (400 MHZ, $CD_3OD$) δ ppm 8.46 (s, 1H), 8.12 (dd, J=8.56, 1.47 Hz, 1H), 7.80 (d, J=8.56 Hz, 1H), 7.17-7.26 (m, 1H), 7.05 (s, 1H), 6.91-7.02 (m, 2H), 6.68 (d, J=7.34 Hz, 1H), 6.62 (dd, J=8.31, 2.20 Hz, 1H), 6.44 (s, 1H), 5.16-5.29 (m, 1H), 4.87-4.91 (m, 1H), 4.60-4.78 (m, 2H), 4.46 (dt, J=9.11, 6.08 Hz, 1H), 4.27-4.43 (m, 2H), 3.50-3.89 (m, 4H), 3.21 (s, 3H), 2.74-3.01 (m, 5H), 2.52 (ddd, J=16.38, 11.62, 7.21 Hz, 1H), 2.07 (s, 3H), 1.84-1.96 (m, 1H), 0.92-1.03 (m, 2H), 0.61-0.75 (m, 2H). m/z (ESI, +ve ion)=594.3 $[M+H]^+$.

Example 122 was synthesized in similar procedures as described in Example 115.

Example 116. (S)-2-((4-(3-((2-Chloro-4-methylphenyl)(methyl)amino)benzyl)piperidin-1-yl)methyl)-1-(oxetan-2-ylmethyl)-1H-benzo[d]imidazole-6-carboxylic acid (116)

116

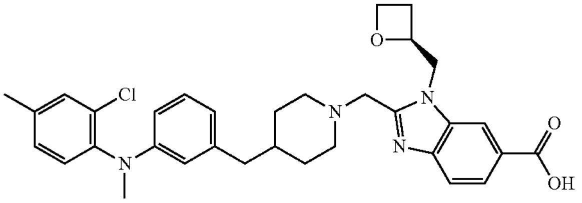

Step A. (3-((2-Chloro-4-methylphenyl)(methyl)amino)phenyl)methanol (116a)

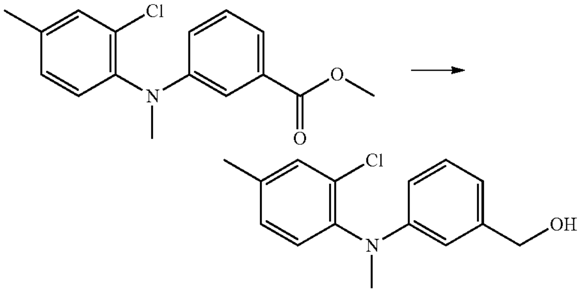

116a

To a solution of methyl 3-((2-chloro-4-methylphenyl)(methyl)amino)benzoate (650 mg, 2.2 mmol, prepared by a similar procedure as described in Example 115, Step B) in 10 mL anhydrous THF was added $LiAlH_4$ (256 mg, 6.7 mmol) at 0° C. The reaction was stirred at 0° C. for 1 h under $N_2$ and quenched with $Na_2SO_4 \cdot 10H_2O$. The mixture was filtered and the filtrate cake was rinsed with DCM (100 mL). The organic layer was concentrated to afford the title product (116a) (487 mg, 85%) as a colorless oil, which was used in the next step without further purification. m/z (ESI, +ve ion)=262.2 $[M+H]^+$.

Step B. N-(3-(Bromomethyl)phenyl)-2-chloro-N,4-dimethylaniline (116b)

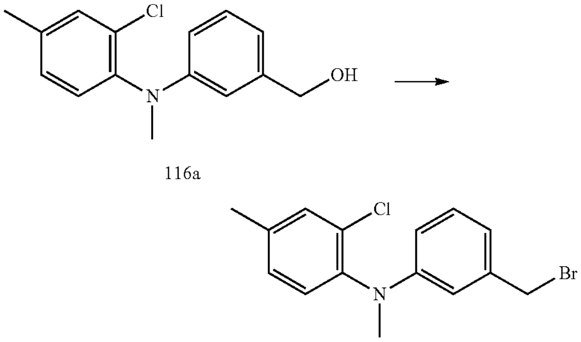

116a

116b

To a solution of 116a (487 mg, 1.9 mmol) in DCM (20 mL) was added $PBr_3$ (506 mg, 1.9 mmol) at 0° C. The mixture was stirred at 17° C. for 2 h. After completion, the mixture was diluted with $H_2O$ (30 mL), and extracted with EtOAc (30 mL×3). The organic layer was washed with $H_2O$ (30 mL), brine (30 mL), dried over anhydrous $Na_2SO_4$, filtered and concentrated in vacuo to give the crude title product (116b) (591 mg) as a colorless oil, which was used in the next step without further purification. m/z (ESI, +ve ion)=324.0 $[M+H]^+$.

Step C. tert-Butyl 4-(3-((2-chloro-4-methylphenyl)(methyl)amino)benzyl)piperidine-1-carboxylate (116c)

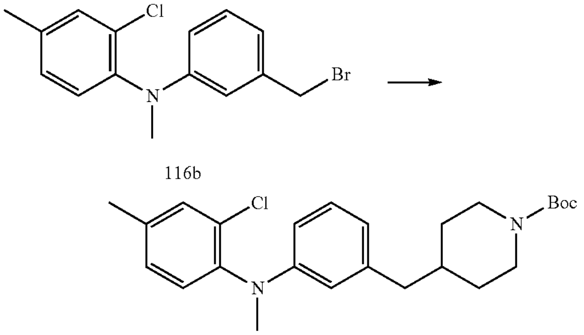

116b

116c

The title product (116c) was prepared by procedures similar to those described in Example 60, Steps B and C.

Step D. 2-Chloro-N,4-dimethyl-N-(3-(piperidin-4-ylmethyl)phenyl)aniline (116d)

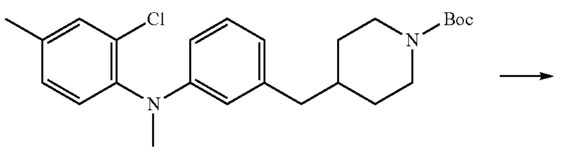

116c

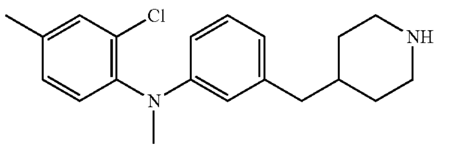

116d

To a solution of 116c (56 mg, 0.13 mmol) in DCM (8 mL) was added TFA (2 mL). The mixture was stirred at 17° C. for 1 h. After completion, the mixture was concentrated in vacuo to afford the crude title product (116d) (62 mg) as a colorless oil, which was used in the next step without further purification. m/z (ESI, +ve ion)=329.2 $[M+H]^+$.

Step E. Methyl(S)-2-((4-(3-((2-chloro-4-methylphenyl)(methyl)amino)benzyl)piperidin-1-yl)methyl)-1-(oxetan-2-ylmethyl)-1H-benzo[d]imidazole-6-carboxylate (116e)

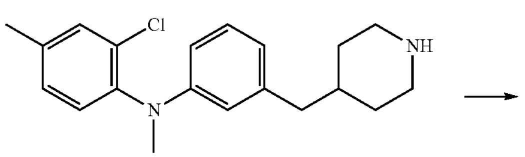

116d

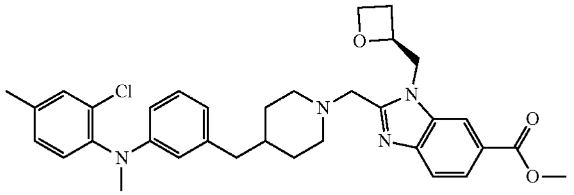

116e

A mixture of 116d (62 mg, 0.19 mmol) and $K_2CO_3$ (78 mg, 0.57 mmol) in DMF (5 mL) was added 1h (56 mg, 0.19 mmol) at 17° C. The mixture was stirred at 17° C. for 16 h. After completion, the reaction was quenched with $H_2O$ (5 mL) and extracted with DCM (20 mL×3). The organic layer was washed with brine (10 mL), dried over anhydrous $Na_2SO_4$, filtered and concentrated and the resulting crude residue was purified by silica gel column chromatography (2% MeOH in DCM) to afford the title product (116e) (45 mg, 40%) as a white solid. m/z (ESI, +ve ion)=587.3 $[M+H]^+$.

Step F. (S)-2-((4-(3-((2-Chloro-4-methylphenyl)(methyl)amino)benzyl)piperidin-1-yl)methyl)-1-(oxetan-2-ylmethyl)-1H-benzo[d]imidazole-6-carboxylic acid (116)

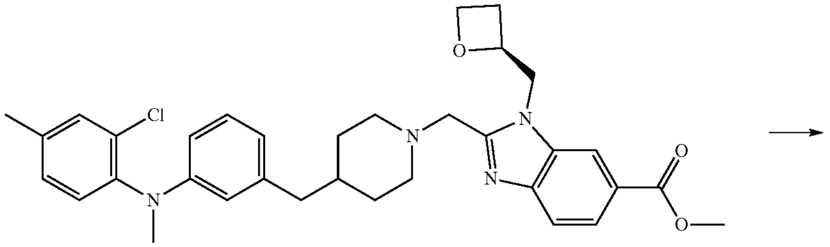

116e

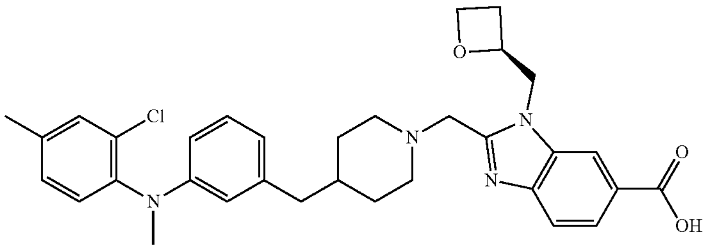

116

A mixture of 116e (45 mg, 0.07 mmol) in THF (3 ml) and $H_2O$ (1 mL) was added lithium hydroxide (18 mg, 0.70 mmol) at room temperature and heated at 30° C. for 2 h. After completion, the mixture was adjusted to pH=7 with 1 N HCl. The residue was purified by reverse phase HPLC ($CH_3CN$ in water, with 0.1% TFA as a modifier) to afford the TFA salt of the title product (116) (17.1 mg, 32%) as a white solid. $^1H$ NMR (400 MHZ, $CD_3OD$) δ ppm 8.32 (s, 1H), 8.03 (dd, J=8.56, 1.47 Hz, 1H), 7.80 (d, J=8.31 Hz, 1H), 7.34 (s, 1H), 7.12-7.20 (m, 2H), 7.08 (t, J=7.83 Hz, 1H), 6.55 (d, J=7.09 Hz, 1H), 6.43 (dd, J=8.31, 2.20 Hz, 1H), 6.33 (s, 1H), 5.15-5.27 (m, 1H), 4.74-4.80 (m, 2H), 4.72 (d, J=6.85 Hz, 1H), 4.58-4.69 (m, 2H), 4.39 (dt, J=9.29, 5.87 Hz, 1H), 3.76 (br s, 2H), 3.12-3.27 (m, 5H), 2.72-2.87 (m, 1H), 2.43-2.57 (m, 3H), 2.36 (s, 3H), 1.62-1.98 (m, 2H), 1.42-1.60 (m, 2H). m/z (ESI, +ve ion)=573.3 $[M+H]^+$.

Example 117 was synthesized in similar procedures as described in Example 116.

Example 121. (S)-2-((8-((4-Chloro-2-fluorobenzyl)oxy)-1,3,4,9-tetrahydro-2H-pyrido[3,4-b]indol-2-yl)methyl)-1-(oxetan-2-ylmethyl)-1H-benzo[d]imidazole-6-carboxylic acid (121)

121

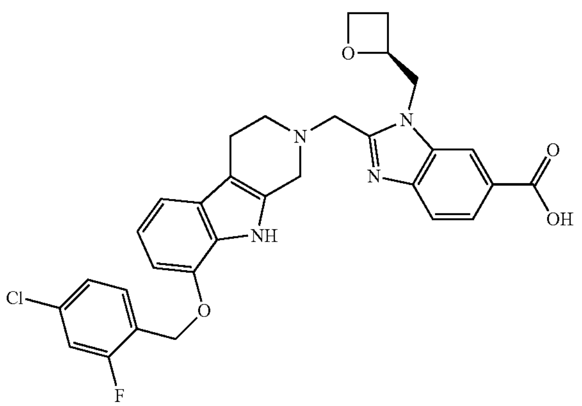

Step A. 7-Methoxy-1H-indole-3-carbaldehyde (121a)

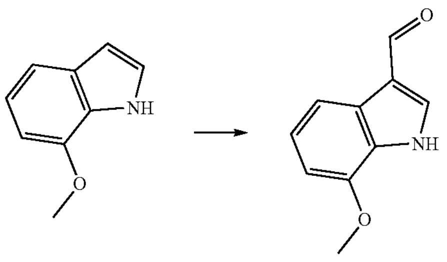

121a

Phosphoryl chloride (2.9 g, 19 mmol) was added drop-wise to a stirred mixture of 7-methoxy-1H-indole (2.5 g, 17 mmol) in DMF (25 ml) at 0° C. The reaction was raised to room temperature and stirred at 25° C. for 16 h under $N_2$. After completion, the reaction mixture was poured into crushed ice and neutralized with 2 N NaOH solution. The mixture was extracted with EtOAc (20 ml×6). The organic layer was washed with $H_2O$ (20 mL), brine (20 mL), dried over anhydrous $Na_2SO_4$, filtered and concentrated to give a crude residue, which was purified by silica gel column chromatography (petroleum ether:EtOAc=3:1) to afford the title product (121a) (2.2 g, 70%) as a colorless oil. m/z (ESI, +ve ion)=176.1 $[M+H]^+$.

Step B. (Z)-7-Methoxy-3-(2-nitrovinyl)-1H-indole (121b)

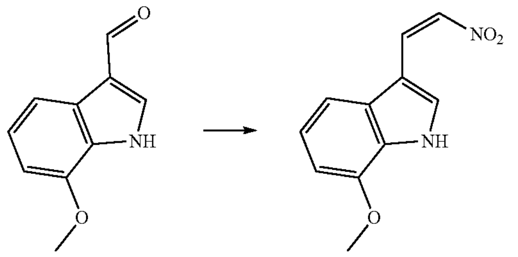

121a 121b

A mixture of 121a (2.2 g, 0.013 mol) in nitromethane (23 g, 0.38 mol) was added ammonium acetate (2.9 g, 0.038 mol) at 25° C. The reaction was stirred at 100° C. for 90 min under $N_2$. After completion, the reaction was quenched with $H_2O$ (20 mL) and extracted with EtOAc (20 mL×3). The organic layer was washed with $H_2O$ (20 mL), brine (20 mL), dried over anhydrous $Na_2SO_4$, filtered and concentrated to give a crude residue, which was purified by silica gel chromatography (petroleum ether:EtOAc=3:1) to afford the title product (121b) (2.5 g, 87%) as a yellow solid. m/z (ESI, +ve ion)=219.1 $[M+H]^+$.

Step C. 2-(7-Methoxy-1H-indol-3-yl) ethan-1-amine (121c)

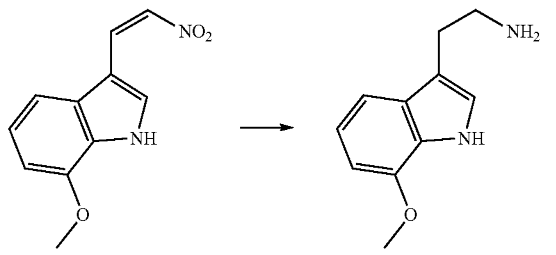

121b 121c

To a mixture of 121b (3.0 g, 14 mmol) in anhydrous THF (50 mL) was added $LiAlH_4$ (3.3 g, 82 mmol) in THF (20 mL) at 0° C. under $N_2$. The reaction was heated to reflux for 1 h, and then allowed to stir at 25° C. for 16 h under $N_2$. After completion, the reaction was quenched with $H_2O$ (50 mL), followed by addition of 15% NaOH solution. The mixture was extracted with EtOAc (50 mL×4). The organic layer was washed with $H_2O$ (50 mL), brine (50 mL), dried over anhydrous $Na_2SO_4$, filtered and concentrated to give a crude residue, which was purified by silica gel column chromatography (1% MeOH in DCM) to afford the title product (121c) (2.6 g, 89%) as a black oil. m/z (ESI, +ve ion)=191.1 [M+H].

Step D. 8-Methoxy-2,3,4,9-tetrahydro-1H-pyrido[3,4-b]indole (121d)

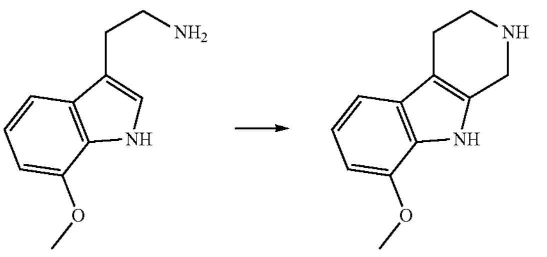

121c 121d

To a solution of 121c (2.0 g, 11 mmol) in MeOH (2 mL) was added HCHO (975 mg, 13 mmol, 40% in water) and HOAc (20 mL) at 0° C. The reaction was stirred at 0° C. for 1 h under $N_2$. After completion, the mixture was adjusted to pH=8 with 2 N NaOH, and extracted with EtOAc (20 mL×3). The organic layer was washed with $H_2O$ (20 mL), brine (20 mL), dried over anhydrous $Na_2SO_4$, filtered and concentrated to give a crude residue, which was purified by silica gel column chromatography (5% MeOH in DCM) to afford the title product (121d) (2.0 g, 85%) as a brown solid. m/z (ESI, +ve ion)=203.1 $[M+H]^+$.

Step E. 2,3,4,9-Tetrahydro-1H-pyrido[3,4-b]indol-8-ol (121e)

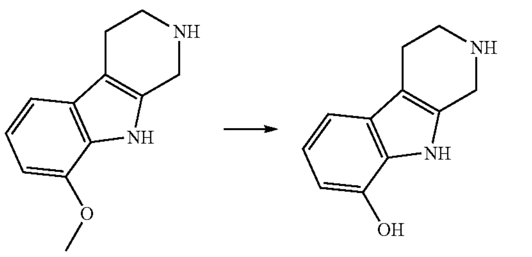

121d 121e

A flask was charged with 121d (2.0 g, 9.9 mmol) and added 40% HBr in $H_2O$ (5 mL) at 25° C. The reaction was stirred at 100° C. for 2 h under $N_2$. After completion, the reaction mixture was filtered and concentrated in vacuo to give a crude residue, which was purified by reverse phase HPLC (100% $H_2O$) to afford the title product (121e) (1.0 g, 46%) as a black solid. m/z (ESI, +ve ion)=189.1 $[M+H]^+$.

Step F. tert-Butyl 8-hydroxy-1,3,4,9-tetrahydro-2H-pyrido[3,4-b]indole-2-carboxylate (121f)

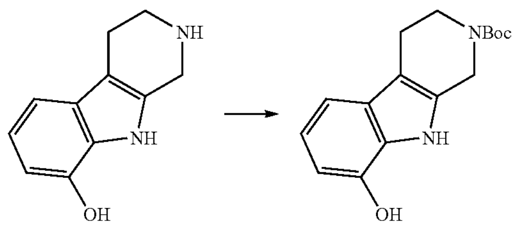

121e 121f

To a solution of 121e (400 mg, 2.1 mmol) in THF/$H_2O$ (30 mL) was added $(Boc)_2O$ (232 mg, 1.1 mmol) and $NaHCO_3$ (179 mg, 2.1 mmol) at 0° C. The mixture was stirred at 0° C. for 0.5 h under $N_2$. After completion, the reaction was diluted with $H_2O$ (20 mL) and extracted with EtOAc (30 mL×3). The organic layer was washed with $H_2O$ (20 mL), brine (20 mL), dried over anhydrous $Na_2SO_4$, filtered and concentrated to give a crude residue, which was purified by silica gel column chromatography (petroleum ether:EtOAc=1:1) to afford the title product (121f) (90 mg, 13%) as a white solid. m/z (ESI, +ve ion)=289.1 $[M+H]^+$.

Step G. tert-Butyl 8-((4-Chloro-2-fluorobenzyl)oxy)-1,3,4,9-tetrahydro-2H-pyrido[3,4-b]indole-2-carboxylate (121g)

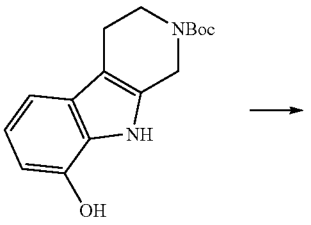

121f

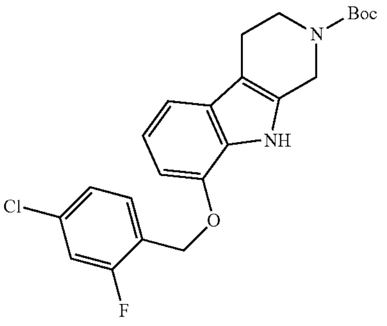

121g

To a solution of 121f (50 mg, 0.17 mmol) and 1-(bromomethyl)-4-chloro-2-fluorobenzene (43 mg, 0.19 mmol) in acetone (8 mL) was added $K_2CO_3$ (24 mg, 0.17 mmol) at 25° C. The reaction was then heated at 30° C. for 48 h under $N_2$. After completion, the reaction was quenched with $H_2O$ (8 mL) and extracted with EtOAc (10 mL×3). The organic layer was washed with $H_2O$ (10 mL), brine (10 mL), dried over anhydrous $Na_2SO_4$, filtered and concentrated to give a crude residue, which was purified by silica gel column chromatography (petroleum ether:EtOAc=10:1) to afford the title product (121g) (35 mg, 44%) as a colorless oil. m/z (ESI, +ve ion)=431.0 [M+H]$^+$.

Step H. 8-((4-Chloro-2-fluorobenzyl)oxy)-2,3,4,9-tetrahydro-1H-pyrido[3,4-b]indole (121h)

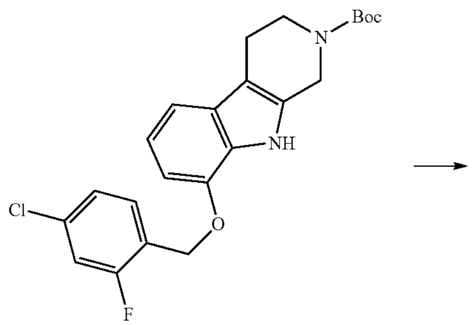

121g

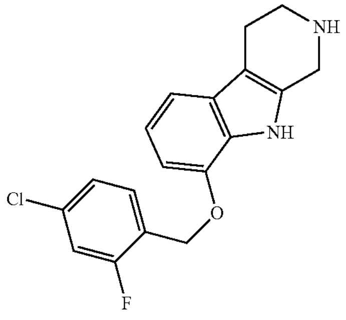

121h

To a solution of 121g (35 mg, 0.081 mmol) in DCM (3 mL) was added TFA (0.3 ml) at 0° C. The mixture was stirred at 0° C. for 1 h under $N_2$. After completion, the reaction was concentrated to afford the title product (121h) (20 mg, 71%) as a white solid, which was used in the next step without further purification. m/z (ESI, +ve ion)=331.1 [M+H]$^+$.

Step I. tert-Butyl(S)-2-((8-((4-chloro-2-fluorobenzyl)oxy)-1,3,4,9-tetrahydro-2H-pyrido[3,4-b]indol-2-yl)methyl)-1-(oxetan-2-ylmethyl)-1H-benzo[d]imidazole-6-carboxylate (121i)

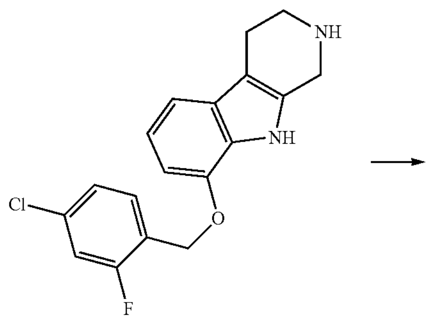

121h

-continued

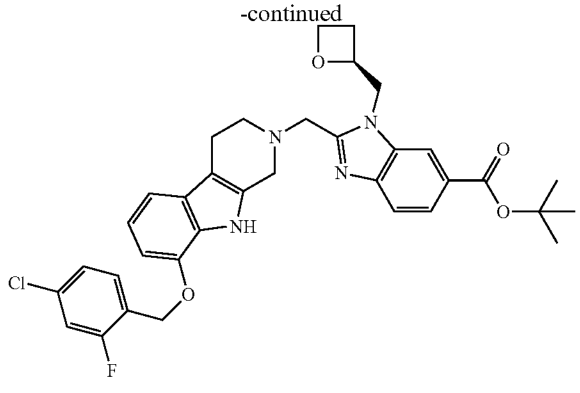

121i

To a solution of 121h (30 mg, 0.091 mmol) and tert-butyl 2-(chloromethyl)-3-[(2S)-oxetan-2-ylmethyl]-1,3-benzodiazole-5-carboxylate (34 mg, 0.10 mmol, prepared as described for 1h) in DMF (5 mL) was added $K_2CO_3$ (25 mg, 0.18 mmol) and KI (15 mg, 0.091 mmol) at 25° C. The reaction was stirred at 25° C. for 1 h under $N_2$. After completion, the reaction was quenched with $H_2O$ (5 mL) and extracted with EtOAc (5 mL×3). The organic layer was washed with $H_2O$ (5 mL), brine (5 mL), dried over anhydrous $Na_2SO_4$, filtered and concentrated to give a crude residue, which was purified by silica gel column chromatography (petroleum ether:EtOAc=3:1) to afford the title product (121i) (15 mg, 24%) as a yellow oil. m/z (ESI, +ve ion)=631.2 [M+H]$^+$.

Step J. (S)-2-((8-((4-Chloro-2-fluorobenzyl)oxy)-1,3,4,9-tetrahydro-2H-pyrido[3,4-b]indol-2-yl)methyl)-1-(oxetan-2-ylmethyl)-1H-benzo[d]imidazole-6-carboxylic acid (121)

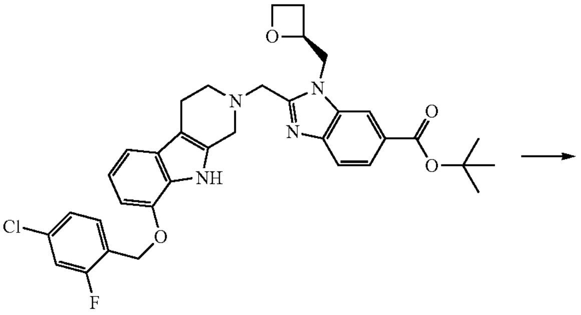

121i

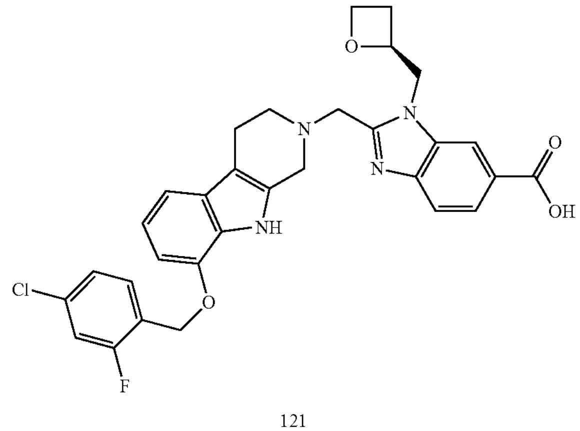

121

To a solution of 121i (10 mg, 0.016 mmol) in DCM (4 mL) was added TFA (0.8 ml) at 0° C. The reaction was raised to room temperature and stirred at 25° C. for 16 h under $N_2$. After completion, the reaction was concentrated to give a crude residue, which was purified by reverse phase HPLC (40% $CH_3CN$ in $H_2O$, with 0.05% TFA as modifier) to afford the TFA salt of the title compound (121) (6 mg, 55%) as a yellow solid. $^1H$ NMR (400 MHZ, $CD_3OD$) δ ppm 8.35 (d, J=0.88 Hz, 1H), 8.01-8.09 (m, 1H), 7.82 (d, J=8.77 Hz, 1H), 7.62 (t, J=8.11 Hz, 1H), 7.19-7.30 (m, 2H), 7.14 (d, J=7.89 Hz, 1H), 7.00 (t, J=7.67 Hz, 1H), 6.81 (d, J=7.89 Hz, 1H), 5.26 (s, 2H), 5.17 (qd, J=7.16, 2.19 Hz, 1H), 4.97 (s, 2H), 4.73-4.81 (m, 1H), 4.62-4.69 (m, 3H), 4.56 (dd, J=16.01, 5.92 Hz, 1H), 4.27-4.33 (m, 1H), 3.81-3.89 (m, 2H), 3.17 (t, J=5.92 Hz, 2H), 2.70-2.81 (m, 1H), 2.39-2.51 (m, 1H). m/z (ESI, +ve ion)=575.1 $[M+H]^+$.

Example 124, 125, 129, 141 were synthesized in similar procedures as described in Example 60.

Example 128. 2-((4-((2-((2,4-Dichlorophenoxy)methyl)pyridin-4-yl)methyl)piperidin-1-yl)methyl)-1-((1-ethyl-1H-imidazol-5-yl)methyl)-1H-benzo[d]imidazole-6-carboxylic acid (128)

128

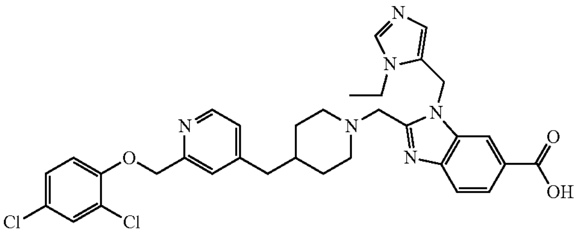

Step A. Methyl 4-((1-(tert-butoxycarbonyl)-1,2,3,6-tetrahydropyridin-4-yl)methyl)picolinate (128a)

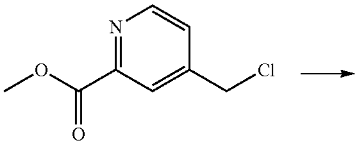

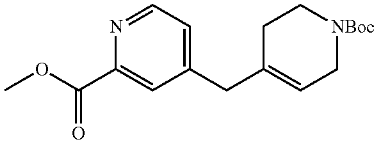

128a

To a mixture of methyl 4-(chloromethyl)pyridine-2-carboxylate (116 mg, 0.63 mmol), tert-butyl 4-(4,4,5,5-tetramethyl-1,3,2-dioxaborolan-2-yl)-1,2,3,6-tetrahydropyridine-1-carboxylate (194 mg, 0.63 mmol), Pd(dppf)$Cl_2$ (46 mg, 0.063 mmol) and $K_3PO_4$ (266 mg, 1.25 mmol) was added THF (6 mL) and water (6 mL). The resulting suspension was heated at reflux overnight. After being cooled to room temperature, the mixture was extracted with ethyl acetate (10 mL×3) and washed with brine. The combined organic phase was dried with anhydrous $Na_2SO_4$, filtered and concentrated. The resulting crude residue was purified by reverse phase HPLC (gradient elution, 20-100% $CH_3CN$ in water, with 0.1% TFA as modifier) to afford the title product (128a) (42 mg, 20%) as a white solid. m/z (ESI, +ve ion)=333.1 $[M+H]^+$.

Step B. Methyl 4-((1-(tert-butoxycarbonyl)piperidin-4-yl)methyl)picolinate (128b)

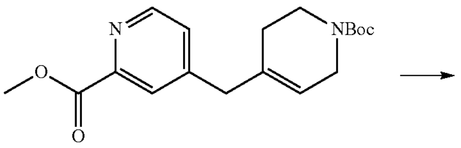

128a

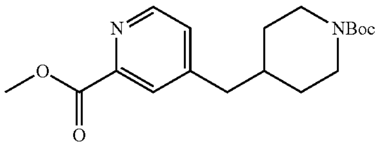

128b

A solution of 128a (42 mg, 0.12 mmol) and 10% Pd/C (8.4 mg) in MeOH (6 mL) was stirred under hydrogen at room temperature for 22 h. After completion, the reaction was filtered through a pad of celite and washed with MeOH (6 mL×3). The organic layer was concentrated to afford the title product (128b) (34 mg) as a colorless oil, which was used in the next step without further purification. m/z (ESI, +ve ion)=335.3 $[M+H]^+$.

Step C. tert-Butyl 4-((2-(hydroxymethyl)pyridin-4-yl)methyl)piperidine-1-carboxylate (128c)

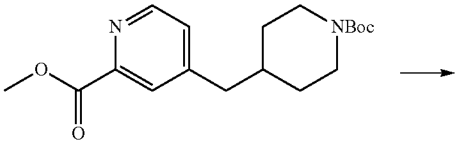

128b

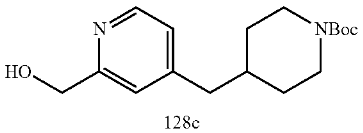

128c

To a mixture of 128b (34 mg, 0.1 mmol), $CaCl_2$) (23 mg, 0.2 mmol) and $NaBH_4$ (15 mg, 0.4 mmol) was added THF (10 mL). The resulting suspension was stirred at 60° C. overnight and cooled down. The reaction was quenched with water (10 mL), extracted with ethyl acetate (10 mL×3) and washed with brine. The combined organic phase was dried with anhydrous $Na_2SO_4$, filtered and concentrated to give a crude residue, which was purified by silica gel column chromatography (EtOAc in hexanes) to afford the title product (128c) (7 mg, 19% for 2 steps) as a colorless oil. m/z (ESI, +ve ion)=307.2 $[M+H]^+$.

Step D. tert-Butyl 4-((2-((2,4-dichlorophenoxy) methyl)pyridin-4-yl)methyl)piperidine-1-carboxylate (128d)

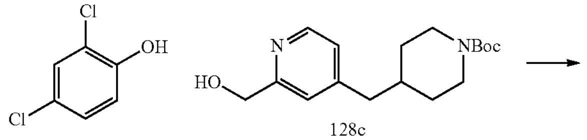

128c

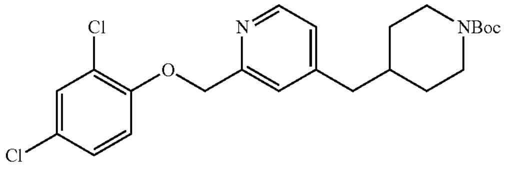

128d

A flask was charged with 2,4-dichlorophenol (7 mg, 0.043 mmol), 128c (12 mg, 0.039 mmol), and $PPh_3$ (12 mg, 0.047 mmol). Anhydrous THF (5 mL) was added and the reaction was cooled down in an ice bath. Diethyl azodicarboxylate (9.5 mg, 0.047 mmol) was added dropwise and the resulting mixture was stirred at 0° C. for 0.5 h, then at room temperature overnight. After completion, the reaction was quenched with water (20 mL), extracted with EtOAc (20 mL×3) and washed with brine. The combined organic layer was dried with anhydrous $Na_2SO_4$, filtered and concentrated to provide a crude residue, which was purified by silica gel column chromatography (EtOAc in hexanes) to afford the title product (128d) (12.6 mg) as a colorless oil with some impurity, which was used in next step without further purification. m/z (ESI, +ve ion)=451.3 $[M+H]^+$.

Step E. 2-((2,4-Dichlorophenoxy)methyl)-4-(piperidin-4-ylmethyl)pyridine (128e)

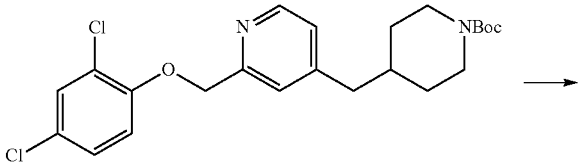

128d

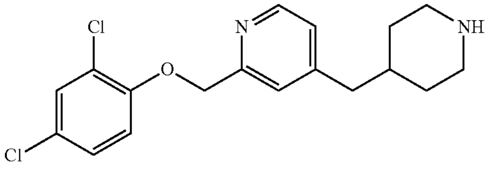

128e

A solution of 128d (12.6 mg, 0.02 mmol) in DCM (0.5 mL) was treated with TFA (0.5 mL) at room temperature for 10 min. After completion, the solvent was removed in vacuo, and the resulting crude residue was purified by reverse phase HPLC (gradient elution, 20-100% $CH_3CN$ in water, with 0.1% formic acid as a modifier) to afford the title product (128e) (5.9 mg, 44%) as a white solid. m/z (ESI, +ve ion)=351.3 $[M+H]^+$.

Step F. Methyl 2-((4-((2-((2,4-dichlorophenoxy) methyl)pyridin-4-yl)methyl)piperidin-1-yl)methyl)-1-((1-ethyl-1H-imidazol-5-yl)methyl)-1H-benzo[d] imidazole-6-carboxylate (128f)

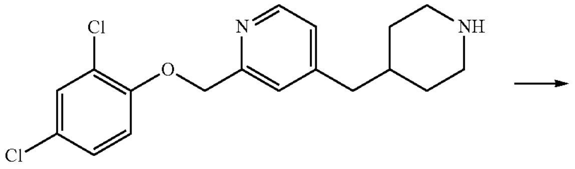

128e

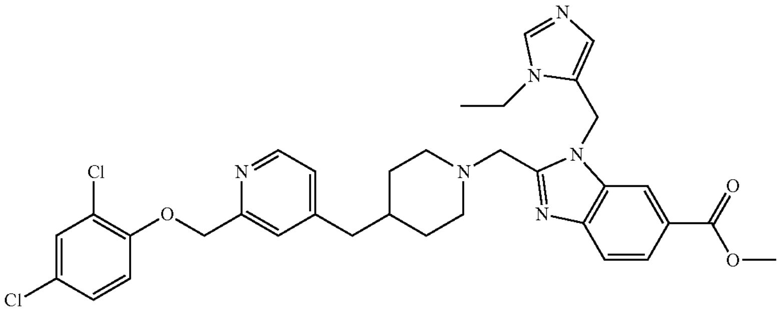

128f

A solution of 128e (4.8 mg, 0.014 mmol), 57f (5.5 mg, 0.016 mmol) and $Et_3N$ (14 mg, 0.14 mmol) in DMF (1 mL) was stirred at room temperature for 24 h. After completion, the reaction was purified by reverse phase HPLC (gradient elution, 0-90% $CH_3CN$ in water, with 0.1% TFA as a modifier) to provide the title product (128f) (14 mg) as a white solid with some impurity. m/z (ESI, +ve ion)=647.3 $[M+H]^+$.

Step G. 2-((4-((2-((2,4-Dichlorophenoxy)methyl) pyridin-4-yl)methyl)piperidin-1-yl)methyl)-1-((1-ethyl-1H-imidazol-5-yl)methyl)-1H-benzo[d]imidazole-6-carboxylic acid (128)

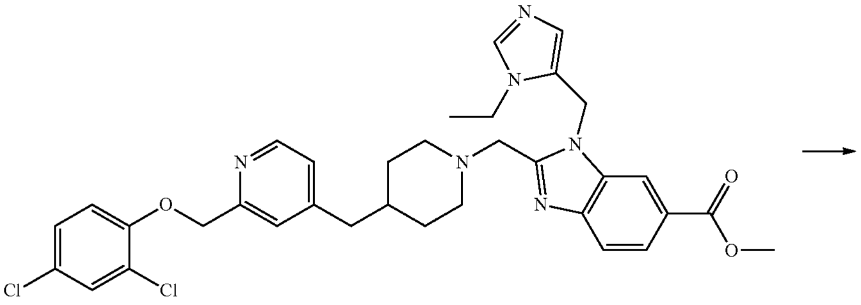

128f

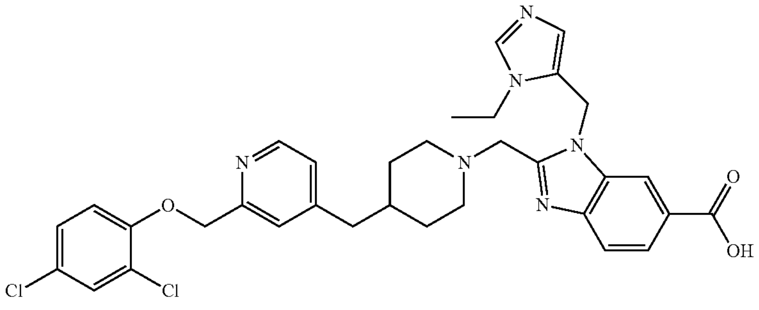

128

A solution of 128f (14 mg, impure) in THF (0.5 mL) was treated with 2 N NaOH (0.5 mL) and MeOH (2 drops). The resulting mixture was stirred at room temperature for 6 h. After completion, the reaction was purified by reverse phase HPLC (gradient elution, 0-90% $CH_3CN$ in water with 0.1% formic acid as a modifier) to provide the title product (128) (4.5 mg, 51%) as a white solid. $^1H$ NMR (600 MHZ, $CD_3OD$) δ ppm 8.41 (d, J=5.14 Hz, 1H), 8.13 (br d, J=1.10 Hz, 1H), 7.99 (dd, J=8.62, 1.65 Hz, 1H), 7.87 (s, 1H), 7.68-7.72 (m, 1H), 7.41-7.44 (m, 1H), 7.40 (s, 1H), 7.22 (dd, J=8.80, 2.57 Hz, 1H), 7.18 (br dd, J=5.14, 1.47 Hz, 1H), 7.07 (d, J=8.80 Hz, 1H), 6.60 (s, 1H), 5.76 (s, 2H), 5.24 (s, 2H), 4.08 (q, J=7.34 Hz, 2H), 3.84 (s, 2H), 2.81 (br d, J=11.37 Hz, 2H), 2.57 (br d, J=6.97 Hz, 2H), 2.04-2.12 (m, 2H), 1.57-1.64 (m, 1H), 1.51 (br d, J=12.47 Hz, 2H), 1.29 (t, J=7.34 Hz, 3H), 1.02-1.09 (m, 2H). m/z (ESI, +ve ion)=633.2 $[M+H]^+$.

Example compounds 137, 139, 148, 149, 151, 158, 159, 165, 166, 165, 166, 187, and 188 were synthesized in similar procedures as described in Example 128.

Example 130. 2-((4-((3-((2-Chloro-4-methylphenoxy)methyl)phenyl)(hydroxy)methyl)piperidin-1-yl)methyl)-1-((1-ethyl-1H-imidazol-5-yl)methyl)-1H-benzo[d]imidazole-6-carboxylic acid (130)

130

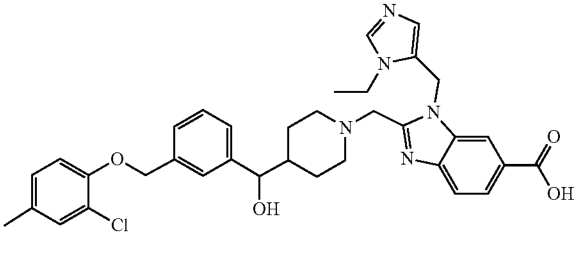

Step A. 1-[(3-Bromophenyl)methoxy]-2-chloro-4-methylbenzene (130a)

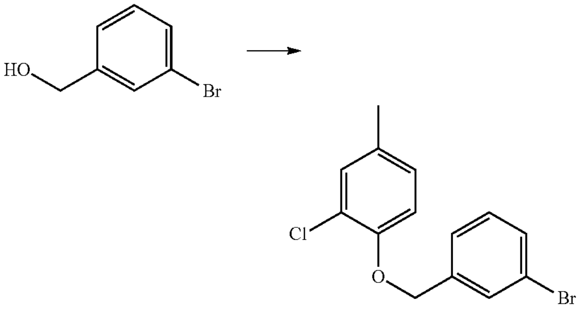

130a

A mixture of (3-bromophenyl)methanol (3.0 g, 0.016 mol), 2-chloro-4-methylphenol (2.7 g, 0.019 mol) and $PPh_3$ (4.6 g, 0.018 mol) in THF (50 mL) was added DEAD (3.1 g, 0.018 mol) at 0° C. The mixture was stirred at 25° C. for 8 h under $N_2$. After completion, the mixture was concentrated in vacuo to give a crude residue, which was purified by silica gel column chromatography (petroleum ether: EtOAc=10:1) to afford the title product (130a) (4.5 g, 86%) as a yellow oil. $^1H$ NMR (400 MHZ, DMSO-$d_6$) δ 7.67 (s, 1H), 7.50-7.56 (m, 1H), 7.46 (d, J=7.7 Hz, 1H), 7.36 (t, J=7.8 Hz, 1H), 7.26 (s, 1H), 7.09 (d, J=0.9 Hz, 2H), 5.18 (s, 2H), 2.23 (s, 3H).

Step B. tert-Butyl 4-((3-((2-chloro-4-methylphenoxy)methyl)phenyl)(hydroxy)methyl)piperidine-1-carboxylate (130b)

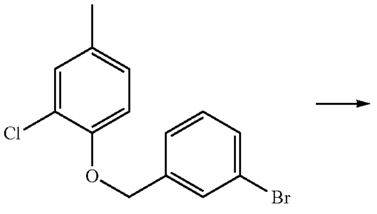

130a

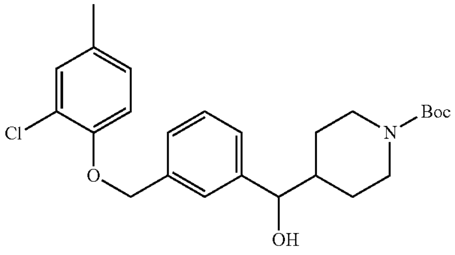

130b

To a mixture of 130a (3.0 g, 9.6 mmol, 1.0 eq) in THF (50 mL) was added nBuLi (2.6 M in hexanes) (5 ml, 13 mmol) at −65° C. After 30 min, tert-butyl 4-formylpiperidine-1-carboxylate (2.1 g, 9.6 mmol) was added dropwise and the reaction was stirred at −65° C. for 1 h under $N_2$. After completion, the mixture was quenched with $NH_4Cl$ (40 mL), and extracted with EtOAc (30 mL×3). The organic layer was washed with $H_2O$ (20 mL), brine (20 mL), dried over anhydrous $Na_2SO_4$, filtered and concentrated in vacuo to give a crude residue, which was purified by silica gel column chromatography (petroleum ether:EtOAc=10:1) to afford the title product (130b) (3.6 g, 75%) as a yellow oil. m/z (ESI, +ve ion)=468.2 $[M+Na]^+$.

Step C. Methyl 2-((4-((3-((2-chloro-4-methylphenoxy)methyl)phenyl)(hydroxy)methyl)piperidin-1-yl)methyl)-1-((1-ethyl-1H-imidazol-5-yl)methyl)-1H-benzo[d]imidazole-6-carboxylate (130c)

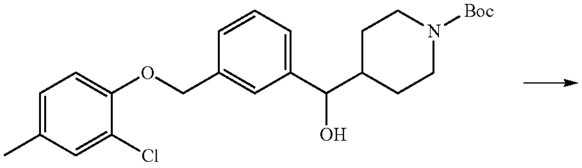

130b

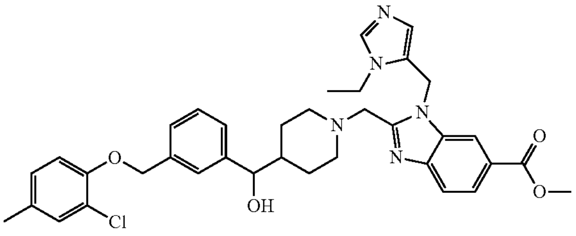

130c

To a solution of 130b (13 mg, 0.03 mmol) in anhydrous $CH_2Cl_2$ (0.3 mL) was added TFA (0.12 mL) at room temperature. After 1 h, the mixture was concentrated, and sat. $NaHCO_3$ (0.5 mL) was added. The reaction was extracted with EtOAc (2 mL×3). The organic layer was dried over $Na_2SO_4$, filtered, and concentrated to afford a crude amine (13 mg). To this crude amine (13 mg) in dichloroethane (0.3 mL) was added 57f (12 mg, 0.036 mmol) and DIPEA (0.01 mL) at room temperature. The reaction was then heated at 60° C. for 20 h. After cooling down to room temperature, the reaction was concentrated and purified by silica gel column chromatography (gradient elution, 0-10% MeOH in DCM) to afford the title product (130c) (16 mg, impure) as a colorless film. m/z (ESI, +ve ion)=642.3 $[M+H]^+$.

Step D. 2-((4-((3-((2-Chloro-4-methylphenoxy)methyl)phenyl)(hydroxy)methyl)piperidin-1-yl)methyl)-1-((1-ethyl-1H-imidazol-5-yl)methyl)-1H-benzo[d]imidazole-6-carboxylic acid (130)

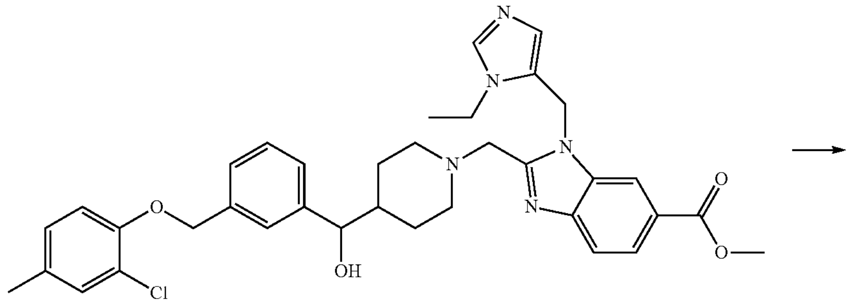

130c

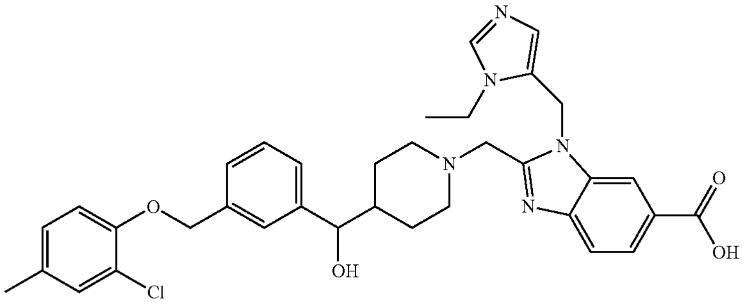

130

130c (16 mg, impure) was dissolved in a mixed solvent of THF and $H_2O$ (2:1, 0.25 mL) at room temperature. LiOH (2.1 mg, 0.05 mmol) was added. After 16 h of stirring, the reaction was acidified with 1 N HCl to pH=7 and concentrated. The crude residue was purified by reverse phase HPLC (gradient elution, 0-70% $CH_3CN$ in water, with 0.1% TFA as a modifier) to provide the TFA salt of the title product (130) as a white solid (12.5 mg, 58% over 2 steps, racemic). $^1H$ NMR (600 MHz, $CD_3OD$) δ ppm 8.92 (s, 1H), 8.22 (d, J=0.92 Hz, 1H), 8.05 (dd, J=8.54, 1.53 Hz, 1H), 7.82 (d, J=8.54 Hz, 1H), 7.46 (s, 1H), 7.35-7.41 (m, 2H), 7.30 (br d, J=6.41 Hz, 1H), 7.18 (d, J=1.53 Hz, 1H), 6.96-7.04 (m, 3H), 5.80 (s, 2H), 5.14 (s, 2H), 4.57 (br s, 2H), 4.47 (br d, J=6.71 Hz, 1H), 4.29 (q, J=7.22 Hz, 2H), 3.56-3.75 (m, 2H), 2.86-3.02 (m, 2H), 2.22 (s, 3H), 2.02-2.11 (m, 1H), 1.83-1.95 (m, 1H), 1.55-1.62 (m, 3H), 1.52 (t, J=7.32 Hz, 3H). m/z (ESI, +ve ion)=628.3 $[M+H]^+$.

Example 131. 2-((4-((3-((2-Chloro-4-methylphenoxy)methyl)phenyl)fluoromethyl)piperidin-1-yl)methyl)-1-((1-ethyl-1H-imidazol-5-yl)methyl)-1H-benzo[d]imidazole-6-carboxylic acid (131)

131

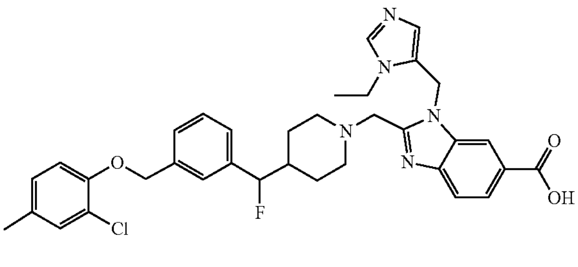

Step A. tert-Butyl 4-((3-((2-chloro-4-methylphenoxy)methyl)phenyl)fluoromethyl)piperidine-1-carboxylate (131a)

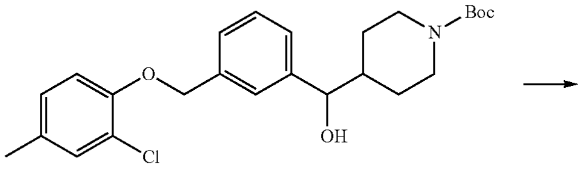

130b

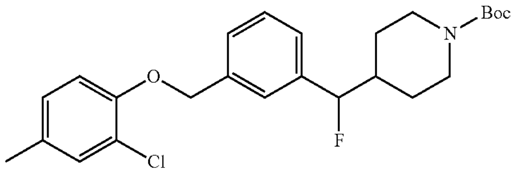

131a

To a solution of 130b (53 mg, 0.12 mmol) in anhydrous $CH_2Cl_2$ (1.2 mL) was added Deoxo-Fluor (70 mg, 0.14 mmol, 45% in THF) at 0° C. After 0.5 h, the reaction was warmed to room temperature and stirred for 16 h. Then sat. $NaHCO_3$ was added. The mixture was extracted with EtOAc (5 mL×3) and the organic layer was dried over $Na_2SO_4$, filtered, and concentrated. The resulting crude residue was purified by silica gel column chromatography (gradient elution, 0-40% EtOAc in hexanes) to afford the title product (131a) (19 mg, 35%) as a colorless film. m/z (ESI, +ve ion)=470.1 $[M+H]^+$.

Step B. 2-((4-((3-((2-Chloro-4-methylphenoxy)methyl)phenyl)fluoromethyl)piperidin-1-yl)methyl)-1-((1-ethyl-1H-imidazol-5-yl)methyl)-1H-benzo[d]imidazole-6-carboxylic acid (131)

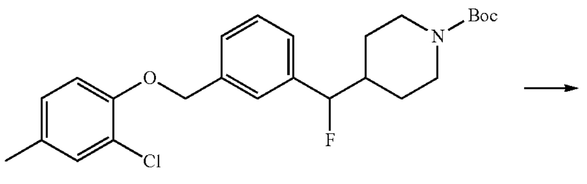

131a

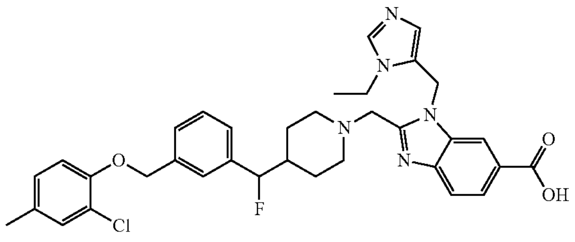

131

The title product (131) was synthesized in similar procedures from 131a as described in Example 130, Steps C and D as a racemic mixture. $^1$H NMR (600 MHZ, $CD_3OD$) δ ppm 9.04 (d, J=1.10 Hz, 1H), 8.20-8.26 (m, 1H), 8.06 (dd, J=8.62, 1.65 Hz, 1H), 7.80-7.90 (m, 1H), 7.35-7.51 (m, 3H), 7.25-7.35 (m, 1H), 7.19 (d, J=1.83 Hz, 1H), 6.92-7.08 (m, 3H), 5.79-5.90 (m, 2H), 5.37 (dd, J=46.8, 6.24 Hz, 1H), 5.13-5.17 (m, 2H), 4.59-4.69 (m, 2H) 4.33 (q, J=7.34 Hz, 2H) 3.65-3.85 (m, 2H), 3.06 (br s, 2H), 2.12-2.25 (m, 4H), 2.00-2.10 (m, 1H), 1.67-1.76 (m, 3H), 1.56 (t, J=7.3 Hz, 3H). m/z (ESI, +ve ion)=630.3 $[M+H]^+$.

Example 132. 2-((4-((3-((2-Chloro-4-methylphenoxy)methyl)phenyl)difluoromethyl)piperidin-1-yl)methyl)-1-((1-ethyl-1H-imidazol-5-yl)methyl)-1H-benzo[d]imidazole-6-carboxylic acid (132)

132

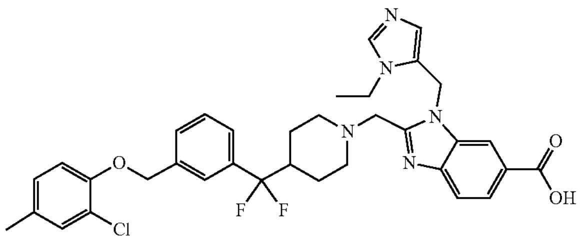

Step A. tert-Butyl 4-(3-((2-chloro-4-methylphenoxy)methyl)benzoyl)piperidine-1-carboxylate (132a)

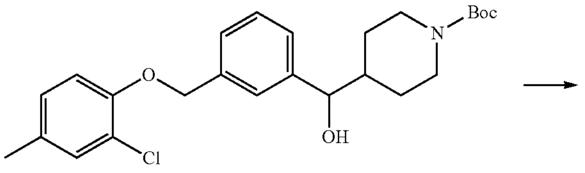

130b

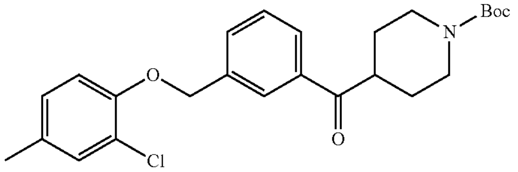

132a

To a solution of 130b (2.0 g, 4.5 mmol) in DCM (50 mL) was added Dess-Martin periodinane (3.8 g, 8.9 mmol) at 0° C. The reaction was heated at 30° C. for 16 h under $N_2$. After completion, the mixture was quenched with aq. $NaHCO_3$ (40 mL), and extracted with DCM (50 mL×3). The organic layer was washed with $H_2O$ (50 mL), brine (50 mL), dried over anhydrous $Na_2SO_4$, filtered and concentrated in vacuo to give a crude residue, which was purified by silica gel column chromatography (petroleum ether:EtOAc=3:1) to afford the title product (132a) (1.2 g, 58%) as a white solid. m/z (ESI, +ve ion)=466.2 $[M+Na]^+$.

Step B. tert-Butyl 4-((3-((2-chloro-4-methylphenoxy)methyl)phenyl)difluoromethyl)piperidine-1-carboxylate (132b)

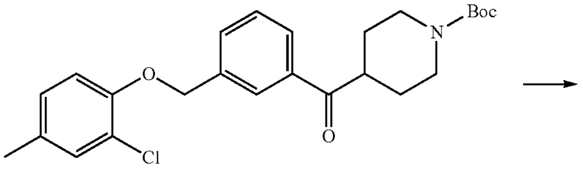

132a

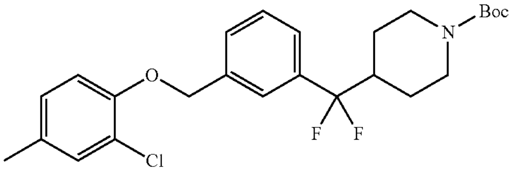

132b

Deoxo-Fluor (112 mg, 0.50 mmol, 45% in THF) was added to 132a (150 mg, 0.34 mmol) and heated to 80° C. After 40 h, the reaction was concentrated and the crude residue was purified by silica gel column chromatography (gradient elution, 0-40% EtOAc in hexanes) to afford the title compound (132b) (34 mg, 21%) as a colorless film. m/z (ESI, +ve ion)=466.2 $[M+H]^+$.

Step C. 2-((4-((3-((2-Chloro-4-methylphenoxy)methyl)phenyl)difluoromethyl)piperidin-1-yl)methyl)-1-((1-ethyl-1H-imidazol-5-yl)methyl)-1H-benzo[d]imidazole-6-carboxylic acid (132)

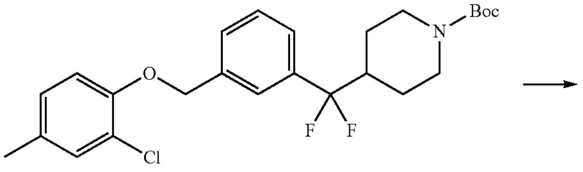

132b

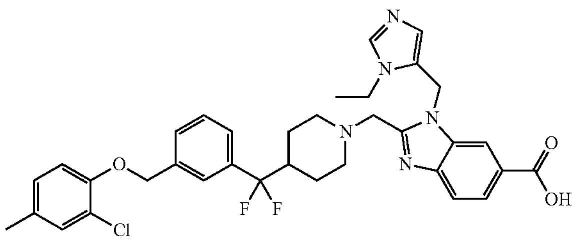

132

The title product (132) was synthesized in similar procedures from 132b as described in Example 130, Steps C and D.

$^1$H NMR (600 MHZ, MeOD) δ ppm 9.01 (d, J=1.10 Hz, 1H), 8.21 (d, J=1.10 Hz, 1H), 8.05 (dd, J=8.80, 1.47 Hz, 1H), 7.82 (d, J=8.80 Hz, 1H), 7.58-7.62 (m, 2H), 7.51 (1, J=7.70 Hz., 1H), 7.42 (br d, J=7.70 Hz., 1H), 7.20 (d, J=1.47 Hz, 1H), 6.99-7.07 (m, 3H), 5.82 (d, J=0.73 Hz, 2H), 5.19 (s, 2H), 4.46 (br s, 2H), 4.32 (q, J=7.34 Hz, 2H), 3.48-3.58

(m, 2H), 2.76-2.87 (m, 2H), 2.31-2.44 (m, 1H), 2.24 (s, 3H), 1.86 (br d, J=13.20 Hz, 2H), 1.51-1.64 (m, 5H). m/z (ESI, +ve ion)=648.3 $[M+H]^+$.

Example 161 was prepared in similar procedures as described in Example 132.

Example 136. (S)-2-((4-((2-(((3-Chloro-5-cyclopropylpyridin-2-yl)oxy)methyl)oxazol-5-yl)methyl)piperidin-1-yl)methyl)-1-(oxetan-2-ylmethyl)-1H-benzo[d]imidazole-6-carboxylic acid (136)

136

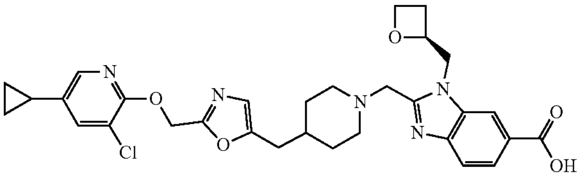

Step A. 2,3-Dichloro-5-cyclopropylpyridine (136a)

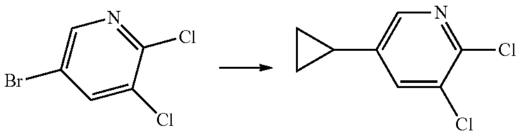

136a

A mixture of 5-bromo-2,3-dichloropyridine (2.2 g, 10.0 mmol), cyclopropylboronic acid (1.0 g, 12.0 mmol), $Pd(OAc)_2$ (112 mg, 0.5 mmol), tri(o-tolyl)phosphine (304 mg, 1.0 mmol) and $K_2CO_3$ (4.1 g, 30.0 mmol) in 20 mL toluene and 5 mL $H_2O$ was stirred at 80° C. for 4 h under $N_2$. After completion, the reaction was diluted with $H_2O$ (20 mL) and extracted with EtOAc (30 mL×3). The organic layer was dried over anhydrous $Na_2SO_4$, filtered, and concentrated to give a crude residue, which was purified by silica gel column chromatography (5% EtOAc in petroleum ether) to afford the title product (136a) (1.7 g, 91%) as a colorless oil. m/z (ESI, +ve ion)=188.1 $[M+H]^+$.

Step B. tert-Butyl 4-((2-(((3-chloro-5-cyclopropylpyridin-2-yl)oxy)methyl)oxazol-5-yl)methyl)piperidine-1-carboxylate (136b)

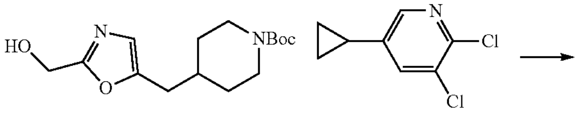

60d

136a

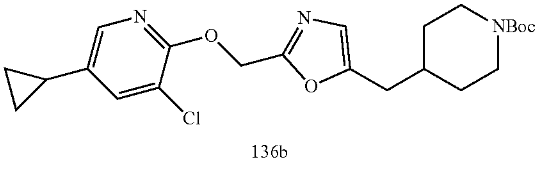

136b

A mixture of 136a (260 mg, 1.4 mmol), 60d (411 mg, 1.4 mmol) and $Cs_2CO_3$ (1.4 g, 4.2 mmol) in DMF (5 mL) was stirred at 80° C. for 16 h. After completion, the reaction was diluted with $H_2O$ (30 mL) and extracted with EtOAc (30 mL×3). The combined organic layer was washed with brine (30 mL×3), dried over anhydrous $Na_2SO_4$, filtered and concentrated to give a crude residue, which was purified by silica gel column chromatography (5% MeOH in DCM) to afford the title product (136b) (340 mg, 54%) as colorless oil. m/z (ESI, +ve ion)=448.2 $[M+H]^+$.

Step C. 2-(((3-Chloro-5-cyclopropylpyridin-2-yl)oxy)methyl)-5-(piperidin-4-ylmethyl)oxazole (136c)

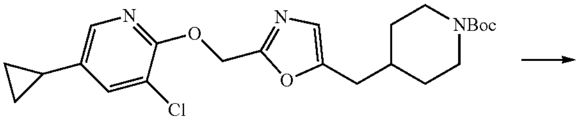

136b

-continued

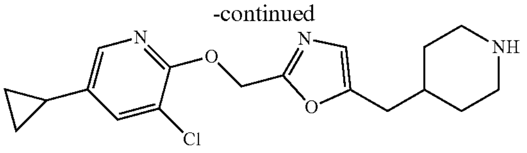

136c

To a mixture of 136b (100 mg, 0.22 mmol) in DCM (10 mL) was added 2,6-lutidine (523 mg, 4.4 mmol) and TMSOTf (488 mg, 2.2 mmol) at 0° C. The mixture was stirred at 0° C. for 1 h. After completion, the reaction was quenched with $NH_4Cl$ (10 mL) and extracted with EtOAc (20 mL×3). The combined organic layer was washed with $H_2O$ (20 mL), brine (20 mL), dried over anhydrous $Na_2SO_4$, filtered and concentrated to afford the crude title product (136c) (230 mg) as a yellow oil, which was used in the next step without further purification. m/z (ESI, +ve ion)=348.2 $[M+H]^+$.

Step D. Methyl(S)-2-((4-((2-(((3-chloro-5-cyclopropylpyridin-2-yl)oxy)methyl)oxazol-5-yl)methyl)piperidin-1-yl)methyl)-1-(oxetan-2-ylmethyl)-1H-benzo[d]imidazole-6-carboxylate (136d)

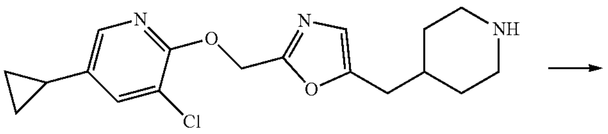

136c

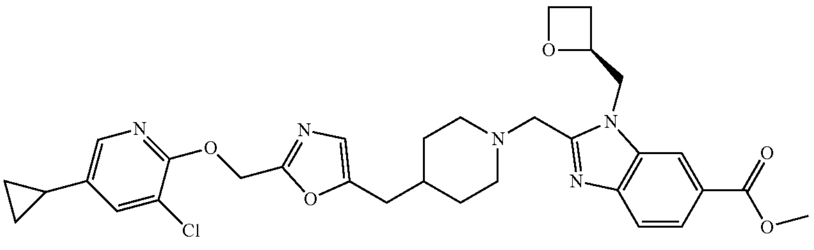

136d

To a stirred solution of 136c (230 mg, 0.22 mmol) and $K_2CO_3$ (93 mg, 0.66 mmol) in DMF (3 mL) was added 1h (65 mg, 0.22 mmol) at 15° C. The mixture was stirred at 15° C. for 16 h. After completion, the reaction was quenched with $H_2O$ (5 mL) and extracted with DCM (20 mL×3). The combined organic layer was washed with brine (10 mL), dried over anhydrous $Na_2SO_4$, filtered and concentrated to give a crude residue, which was purified by silica gel column chromatography (2% MeOH in DCM) to afford the title product (136d) (78 mg, 59%) as a white solid. m/z (ESI, +ve ion)=606.3 $[M+H]^+$.

Step E. (S)-2-((4-((2-(((3-Chloro-5-cyclopropylpyridin-2-yl)oxy)methyl)oxazol-5-yl)methyl)piperidin-1-yl)methyl)-1-(oxetan-2-ylmethyl)-1H-benzo[d]imidazole-6-carboxylic acid (136)

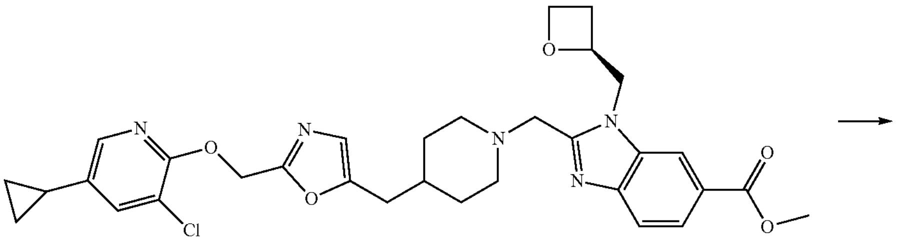

136d

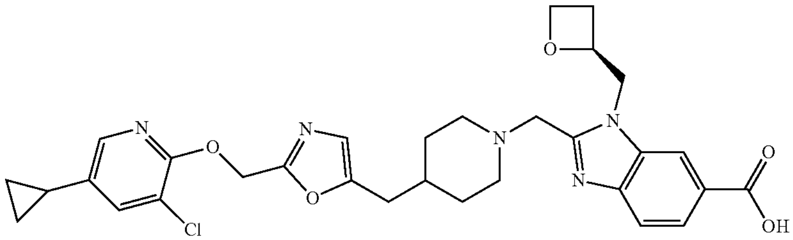

136

A mixture of 136d (78 mg, 0.1 mmol) in THF (3 mL) and $H_2O$ (1 mL) was added lithium hydroxide (24 mg, 1.0 mmol). The reaction was stirred at 17° C. for 16 h. After completion, the reaction was adjusted to pH=7 with 1 N HCl and extracted with EtOAc (20 mL×3). The organic layer was dried, filtered and concentrated and the crude residue was purified by reverse phase HPLC ($CH_3CN$ in $H_2O$, with 0.1% TFA as a modifier) to afford the TFA salt of the title product (136) (26.0 mg, 29%) as a white solid. $^1H$ NMR (400 MHZ, $CD_3OD$) δ ppm 8.33 (d, J=0.73 Hz, 1H), 8.04 (dd, J=8.56, 1.47 Hz, 1H), 7.86 (d, J=1.96 Hz, 1H), 7.80 (d, J=8.56 Hz, 1H), 7.45 (d, J=1.96 Hz, 1H), 6.92 (s, 1H), 5.44 (s, 2H), 5.14-5.25 (m, 1H), 4.80 (d, J=3.42 Hz, 2H), 4.71-4.78 (m, 1H), 4.56-4.71 (m, 2H), 4.40 (dt, J=9.23, 5.78 Hz, 1H), 3.78 (br s, 2H), 3.15-3.32 (m, 2H), 2.68-2.86 (m, 3H), 2.42-2.55 (m, 1H), 1.90-2.12 (m, 3H), 1.86 (tt, J=8.47, 5.10 Hz, 1H), 1.51-1.70 (m, 2H), 0.89-1.01 (m, 2H), 0.55-0.70 (m, 2H). m/z (ESI, +ve ion)=592.3 $[M+H]^+$.

Example 144 was synthesized in similar procedures as described in Example 136.

Example 138 was synthesized in similar procedures as described in Example 60.

Example 142 and Example 143 were synthesized from 4-iodophenol and (2,4-dichlorophenyl)methanol as described in Example 114, Step F, followed by similar procedures in Example 90, Steps C to E and Example 134, Steps A to B.

Example 145. 2-((4-((2-((2,4-Dichlorophenoxy)methyl)pyridin-4-yl)oxy)piperidin-1-yl)methyl)-1-((1-ethyl-1H-imidazol-5-yl)methyl)-1H-benzo[d]imidazole-6-carboxylic acid (145)

145

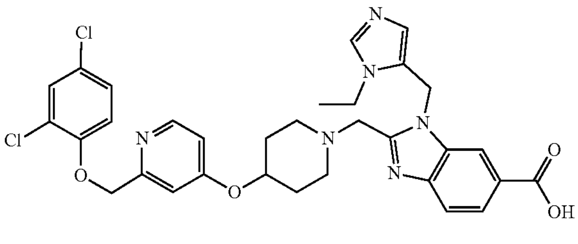

Step A. Methyl 4-((1-(tert-butoxycarbonyl)piperidin-4-yl)oxy)picolinate (145a)

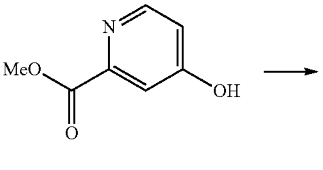

-continued

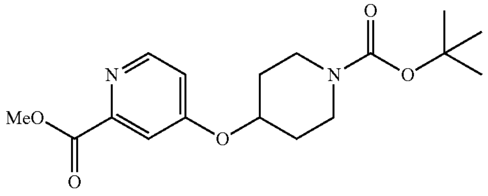

145a

To a stirred solution of methyl 4-hydroxypicolinate (400 mg, 2.61 mmol), 1-Boc-4-hydroxypiperidine (526 mg, 2.61 mmol) and triphenylphosphine (856 mg, 3.27 mmol) in THF (15 mL) was added diisopropyl azodicarboxylate (660 mg, 3.27 mmol) dropwise at room temperature. The mixture was heated at 55° C. for 23 h. After cooling down to room temperature, it was concentrated under reduced pressure. The crude residue was purified by silica gel column chromatography (gradient elution, 10% to 60% acetone in hexanes) to afford the title product (145a) (454 mg, 52%) as a yellow gum. m/z (ESI, +ve ion)=337.4 $[M+H]^+$.

Step B. tert-Butyl 4-((2-(hydroxymethyl)pyridin-4-yl)oxy)piperidine-1-carboxylate (145b)

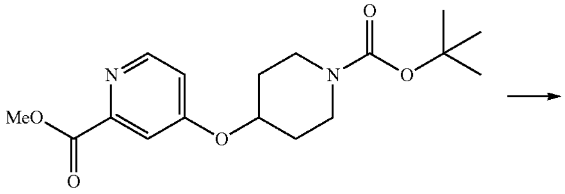

145a

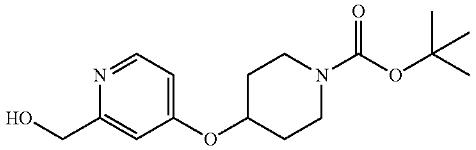

145b

To a stirred solution of 145a (420 mg, 1.25 mmol) in EtOH (6.2 mL) was added $CaCl_2$) (416 mg, 3.75 mmol) at 0° C., followed by the addition of $NaBH_4$ (134 mg, 3.75 mmol). The resulting mixture was allowed to warm to room temperature and stirred for 2.5 h. It was cooled back down to 0° C. and the reaction was quenched by adding saturated ammonium chloride. The reaction mixture was diluted with $H_2O$ and extracted with EtOAc (×3). The combined organic layer was washed with brine, dried over $Na_2SO_4$, filtered and concentrated under reduced pressure. The crude residue was purified by silica gel column chromatography (gradient elution, 0-10% MeOH in DCM) to afford the title product (145b) (313 mg, 81%) as a colorless gum. m/z (ESI, +ve ion)=309.5 $[M+H]^+$.

Step C. tert-Butyl 4-((2-((2,4-dichlorophenoxy)methyl)pyridin-4-yl)oxy)piperidine-1-carboxylate (145c)

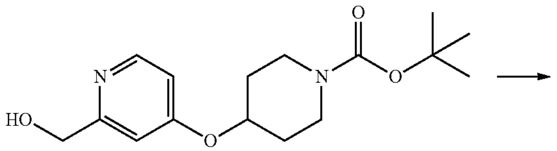

145b

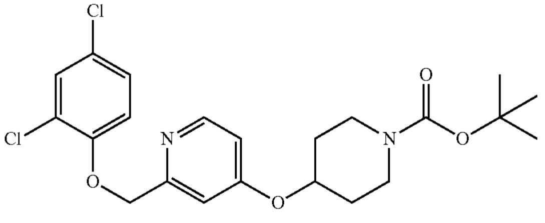

145c

To a stirred solution of 145b (50.0 mg, 0.162 mmol), 2,4-dichlorophenol (27.8 mg, 0.170 mmol) and triphenylphosphine (63.8 mg, 0.243 mmol) in THF (1.0 mL) at room temperature was added diisopropyl azodicarboxylate (49.2 mg, 0.243 mmol) dropwise. The mixture was stirred at room temperature for 6 h. The reaction mixture was concentrated under reduced pressure. The crude residue was purified by silica gel column chromatography (gradient elution, 20-40% acetone in hexanes) to afford the title product (145c) (62.2 mg, 85%) as a white solid. m/z (ESI, +ve ion)=453.3 $[M+H]^+$.

Step D. 2-((2,4-Dichlorophenoxy)methyl)-4-(piperidin-4-yloxy)pyridine (145d)

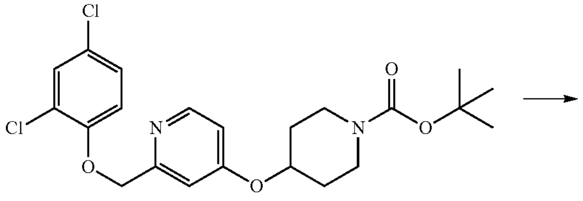

145c

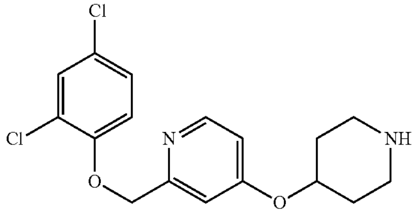

145d

A solution of 145c (60 mg, 0.132 mmol) in DCM/TFA (2:1, 2.0 mL) was stirred at room temperature for 2 h. The mixture was concentrated under reduced pressure and the residue was diluted with DCM, and washed with saturated sodium bicarbonate and brine. The organic layer was dried over $Na_2SO_4$, filtered and concentrated under reduced pressure to provide the title product (145d) (51.1 mg) as a white solid, which was used in the next step without further purification. m/z (ESI, +ve ion)=353.3 $[M+H]^+$.

Step E. Methyl 1-((1-ethyl-1H-imidazol-5-yl) methyl)-2-(hydroxymethyl)-1H-benzo[d]imidazole-6-carboxylate (145e)

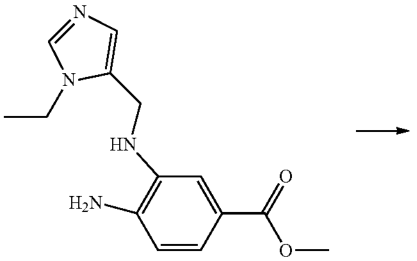

57e

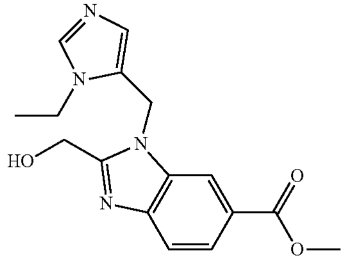

145e

A mixture of 57e (150 mg, 0.547 mmol) and glycolic acid (62.4 mg, 0.82 mmol) in 1,3,5-trimethylbenzene (1.5 mL) was heated at 140° C. for 19 h. It was cooled to room temperature and stirred at the same temperature for 3 h. The yellow solution was decanted off to give an orange residue that was dissolved in MeOH (5 mL) and concentrated under reduced pressure. The crude residue was purified by silica gel column chromatography (gradient elution, 0-15% MeOH in DCM) to afford the title product (145e) (32.4 mg, 19%) as a white foamy solid. m/z (ESI, +ve ion)=315.1 $[M+H]^+$.

Step F. Methyl 1-((1-ethyl-1H-imidazol-5-yl) methyl)-2-formyl-1H-benzo[d]imidazole-6-carboxylate (145f)

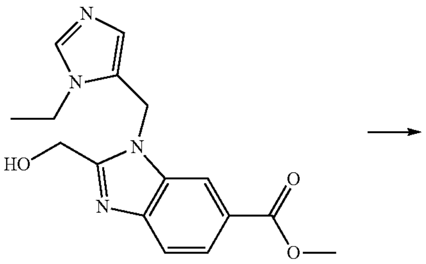

145e

-continued

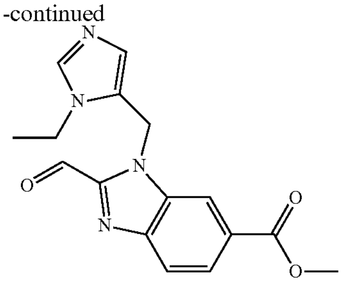

145f

To s stirred suspension of 145e (32.0 mg, 0.102 mmol) in DCM (2 mL) was added Dess-Martin periodinane (47.5 mg, 0.112 mmol) at room temperature. The mixture was stirred at the same temperature for 1 h. The reaction was quenched by the addition of 10% $Na_2S_2O_3$ aqueous solution (1 mL) and saturated sodium bicarbonate (0.6 mL). The resulting mixture was stirred at room temperature for 5 min, diluted with water and extracted with DCM (×3). The combined organic layer was washed with brine, dried over $Na_2SO_4$, filtered and concentrated under reduced pressure to provide the title product (145f) (40 mg) as a white foamy solid, which was used in the next step without further purification. m/z (ESI, +ve ion)=313.2 $[M+H]^+$.

Step G. Methyl 2-((4-((2-((2,4-dichlorophenoxy) methyl)pyridin-4-yl)oxy)piperidin-1-yl)methyl)-1-((1-ethyl-1H-imidazol-5-yl)methyl)-1H-benzo[d] imidazole-6-carboxylate (145g)

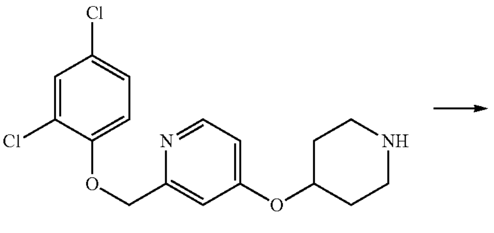

145d

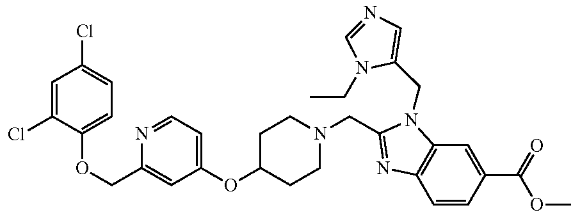

145g

To a stirred solution of 145d (10.0 mg, 0.032 mmol) and 145f (13.6 mg, 0.038 mmol) in 1,2-dichloroethane (0.3 mL) at room temperature was added AcOH (5.8 mg, 0.096 mmol), followed by addition of sodium triacetoxyborohydride (10.1 mg, 0.048 mmol). After stirring at the same temperature for 1 h, the reaction was quenched with saturated sodium bicarbonate and extracted with DCM (×3). The combined organic layer was washed with brine, dried over $Na_2SO_4$, filtered and concentrated under reduced pressure. The crude residue was purified by silica gel column chromatography (0-20% MeOH in DCM, gradient elution) to afford the title product (145g) (15.4 mg, 74%) as a off-white foamy solid. m/z (ESI, +ve ion)=651.3 $[M+H]^+$.

Step H. 2-((4-((2-((2,4-Dichlorophenoxy)methyl)pyridin-4-yl)oxy)piperidin-1-yl)methyl)-1-((1-ethyl-1H-imidazol-5-yl)methyl)-1H-benzo[d]imidazole-6-carboxylic acid (145)

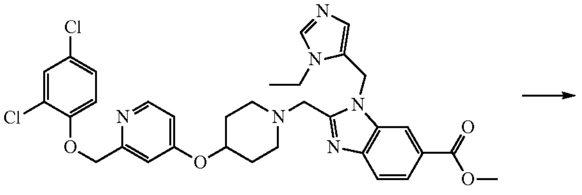

145g

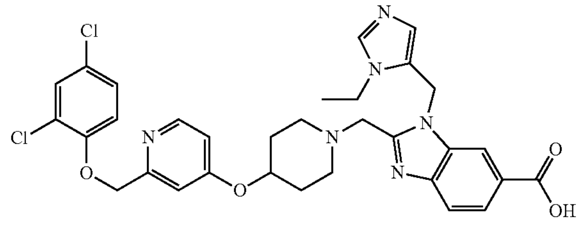

145

To a stirred solution of 145g (12.3 mg, 0.0189 mmol) in THE/MeOH/$H_2O$ (2:1:1, 0.4 mL) was added lithium hydroxide monohydrate (2.4 mg, 0.57 mmol) at room temperature. It was stirred for 4 h, then 1 N HCl was added to the mixture to adjust to pH=3. The solution was purified by reverse phase HPLC (gradient elution, 20-60% $CH_3CN$ in $H_2O$, with 0.1% TFA as a modifier) to give the TFA salt of the title compound (145) (8 mg, 56% yield) as a white solid. $^1H$ NMR (600 MHZ, $CD_3OD$) δ 9.07 (d, J=1.3 Hz, 1H), 8.56 (d, J=6.6 Hz, 1H), 8.22 (d, J=0.7 Hz, 1H), 8.06 (dd, J=8.4, 1.5 Hz, 1H), 7.81 (d, J=8.6 Hz, 1H), 7.50-7.53 (m, 2H), 7.31-7.36 (m, 2H), 7.19 (d, J=9.0 Hz, 1H), 7.08 (d, J=1.1 Hz, 1H), 5.91 (s, 2H), 5.35 (s, 2H), 4.93 (br s, 1H), 4.31-4.40 (m, 4H), 3.15-3.20 (m, 2H), 2.91-3.04 (m, 2H), 2.15-2.20 (m, 2H), 1.94 (br s, 2H), 1.56 (t, J=7.3 Hz, 3H). m/z (ESI, +ve ion)=635.0 $[M+H]^+$.

Example 146. (S)-2-((4-((6-((2-(Hydroxymethyl)-4-methylphenoxy)methyl)pyridin-2-yl)methyl)piperidin-1-yl)methyl)-1-(oxetan-2-ylmethyl)-1H-benzo[d]imidazole-6-carboxylic acid (146)

Step A. tert-Butyl 4-((6-((2-(methoxycarbonyl)-4-methylphenoxy)methyl)pyridin-2-yl)methyl)piperidine-1-carboxylate (146a)

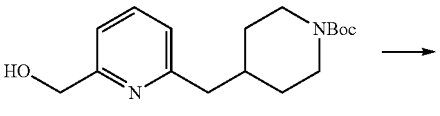

114e

-continued

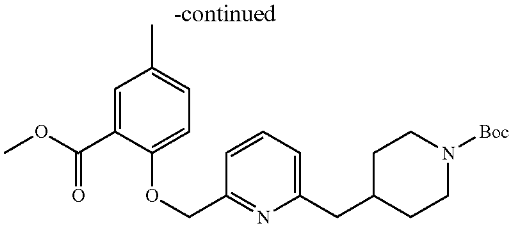

146a

To a solution of 114e (800 mg, 2.61 mmol), methyl 2-hydroxy-5-methylbenzoate (434 mg, 2.61 mmol) and $PPh_3$ (1.02 g, 3.92 mmol) in THF (20 mL) was added DEAD (682 mg, 3.92 mmol) dropwise at 0° C. The resulting mixture was stirred at 15° C. for 16 h. The reaction was diluted with EtOAc (50 mL) and washed with brine (50 mL). The EtOAc layer was dried over $Na_2SO_4$, filtered and concentrated. The crude residue was purified by silica gel column chromatography (20% EtOAc in petroleum ether) to afford the title product (146a) (260 mg, 21.8%) as a colorless oil. m/z (ESI, +ve ion)=455.2 $[M+H]^+$.

Step B. tert-Butyl 4-((6-((2-(hydroxymethyl)-4-methylphenoxy)methyl)pyridin-2-yl)methyl)piperidine-1-carboxylate (146b)

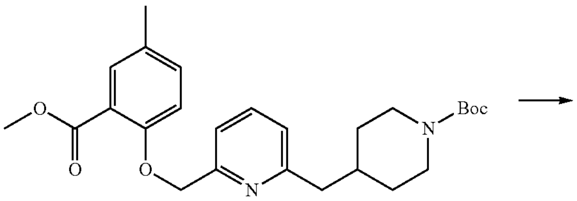

146a

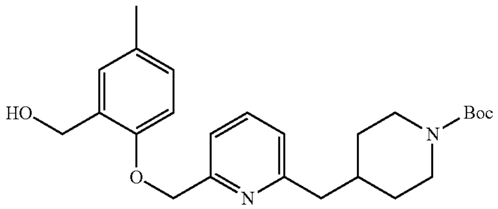

146b

To a solution of 146a (180 mg, 0.40 mmol) in THF (10 ml) was added $LiBH_4$ (43 mg, 1.98 mmol). The reaction was stirred at 15° C. for 16 h, quenched with saturated $NH_4Cl$ (30 ml), and extracted with EtOAc (50 ml×2). The combined EtOAc layer was dried, filtered and concentrated to give a crude residue, which was purified by silica gel column chromatography (15% MeOH in DCM) to afford the title product (146b) (150 mg, 91.7%) as a white solid. m/z (ESI, +ve ion)=427.3 $[M+H]^+$.

Step C. (S)-2-((4-((6-((2-(Hydroxymethyl)-4-methylphenoxy)methyl)pyridin-2-yl)methyl)piperidin-1-yl)methyl)-1-(oxetan-2-ylmethyl)-1H-benzo[d]imidazole-6-carboxylic acid (146)

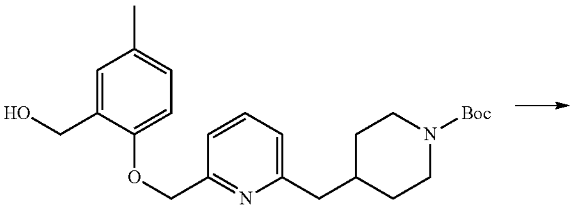

146b

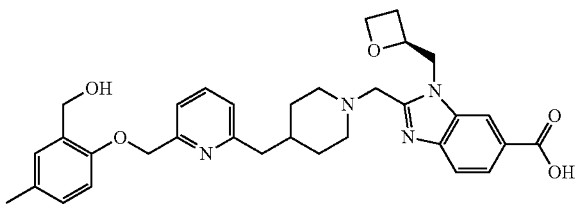

146

The title compound (146) was prepared from 146b as described in Example 114, Steps G-I. $^1$H NMR (400 MHZ, $CD_3OD$) δ ppm 8.18 (s, 1H), 7.93 (dd, J=8.33, 1.32 Hz, 1H), 7.73 (t, J=7.89 Hz, 1H), 7.55 (d, J=8.77 Hz, 1H), 7.40 (d, J=7.45 Hz, 1H), 7.13-7.24 (m, 2H), 6.99 (dd, J=8.55, 1.97 Hz, 1H), 6.83 (d, J=7.89 Hz, 1H), 5.24 (qd, J=7.09, 2.85 Hz, 1H), 5.16 (s, 2H), 4.80-4.87 (m, 1H), 4.55-4.74 (m, 4H), 4.45 (dt, J=9.10, 5.97 Hz, 1H), 3.94 (d, J=13.59 Hz, 1H), 3.82 (d, J=13.59 Hz, 1H), 2.91 (d, J=11.40 Hz, 1H), 2.68-2.84 (m, 4H), 2.45-2.59 (m, 1H), 2.24 (s, 3H), 1.97-2.19 (m, 2H), 1.71-1.83 (m, 1H), 1.51-1.66 (m, 2H), 1.23-1.46 (m, 2H). m/z (ESI, +ve ion)=571.3 [M+H]$^+$.

Example 150. 2-((4-((2-((2,4-Dichlorophenoxy)methyl)pyridin-4-yl)methyl)-4-(hydroxymethyl)piperidin-1-yl)methyl)-1-((1-ethyl-1H-imidazol-5-yl)methyl)-1H-benzo[d]imidazole-6-carboxylic acid (150)

150

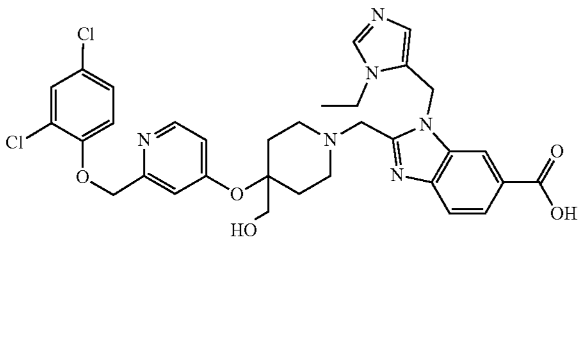

Step A. Methyl 2-((2,4-dichlorophenoxy)methyl)isonicotinate (150a)

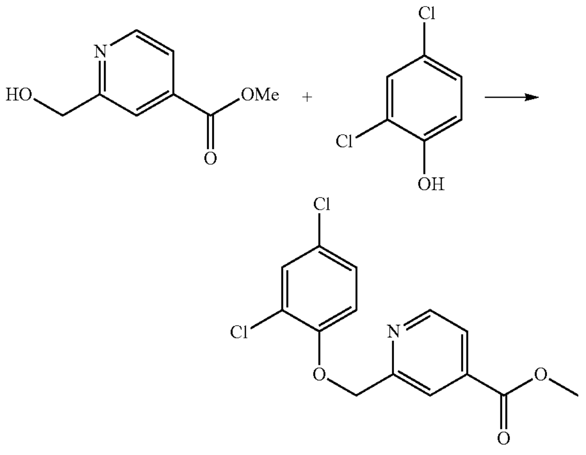

150a

To a solution of methyl 2-(hydroxymethyl)pyridine-4-carboxylate (0.5 g, 2.99 mmol), 2,4-dichlorophenol (0.51 g, 2.99 mmol) and $PPh_3$ (1.18 g, 4.49 mmol) in THF (15 mL) was added DIAD (0.88 mL, 4.49 mmol) dropwise. The resulting mixture was stirred at room temperature for 4 h. After completion, reaction was concentrated and the resulting crude residue was purified by silica gel column chromatography (gradient elution, 40-70% EtOAc in hexanes) to provide the title product (150a) (0.84 g, 90%) as a white solid. m/z (ESI, +ve ion)=312.1 [M+H]$^+$.

Step B. (2-((2,4-Dichlorophenoxy)methyl)pyridin-4-yl)methanol (150b)

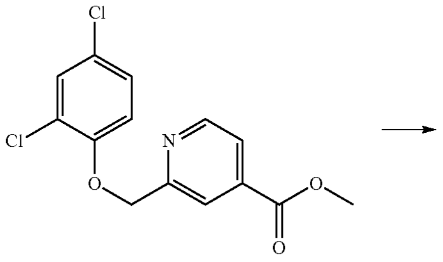

150a

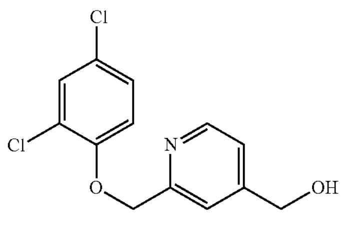

150b

To an ice cold suspension of 150a (1.9 g, 6.09 mmol) in EtOH (25 mL) and THF (25 mL) was added $CaCl_2$ (2.03 g, 18.3 mmol) and $NaBH_4$ (0.65 g, 18.3 mmol). The resulting reaction mixture was warmed to room temperature and stirred for 2 h. After completion, reaction was cooled to 0° C. and quenched with sat. $NH_4Cl$ (20 mL). EtOH and THF were removed under reduced pressure. The resulting aqueous phase was extracted with EtOAc (20 mL×3). The combined organic layer was washed with brine (20 mL), dried over $Na_2SO_4$, concentrated and purified by silica gel column chromatography (gradient elution, 70-100% EtOAc in hexanes) to provide the title product (150b) (1.02 g, 59%) as a white solid. m/z (ESI, +ve ion)=284.3 $[M+H]^+$.

Step C. 4-(Bromomethyl)-2-((2,4-dichlorophenoxy)methyl)pyridine (150c)

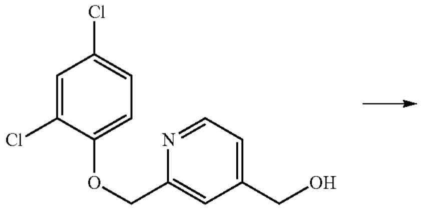

150b

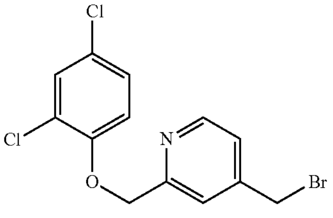

150c $PBr_3$ (0.18 mL, 1.94 mmol) was added dropwise to an ice cold solution of 150b (0.5 g, 1.76 mmol) in THF (8.8 mL). The resulting white suspension was stirred at room temperature for 1 h. After completion, the reaction was cooled to 0° C., and added ice water (10 mL). The reaction mixture was extracted with EtOAc (10 mL×3). The combined organic layer was washed with sat. $NaHCO_3$ solution (50 mL), brine (10 mL), dried over $Na_2SO_4$, filtered, and concentrated to provide the title product (150c) (0.63 g) as a white solid, which was used in the next step without further purification. m/z (ESI, +ve ion)=346.0 $[M+H]^+$.

Step 1-(tert-Butyl) 4-methyl 4-((2-((2,4-dichlorophenoxy)methyl)pyridin-4-yl)methyl)piperidine-1,4-dicarboxylate (150d)

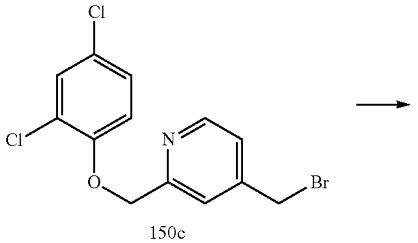

150c

-continued

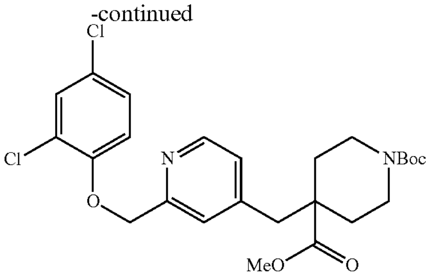

150d

To a solution of diisopropylamine (0.44 mL, 3.12 mmol) in THF (4 mL) at −78° C., n-butyllithium in hexanes (1.37 mL, 3.42 mmol) was added dropwise. The resulting solution was warmed to room temperature and stirred for 30 min before cooling down to −78° C. again. A solution of 1-tert-butyl 4-methyl piperidine-1,4-dicarboxylate (0.54 g, 2.23 mmol) in THF (3 mL) was added dropwise, and the reaction was stirred for an additional 30 min, followed by dropwise addition of 150c (0.52 g, 1.49 mmol) in THF. The reaction was warmed to room temperature slowly and stirred overnight. Then the reaction was quenched with sat. $NH_4Cl$ solution (10 mL) and extracted with EtOAc (10 mL×3). The combined organic layer was washed with brine (10 mL), dried over $Na_2SO_4$, filtered, concentrated and purified by silica gel column chromatography (gradient elution, 60-100% EtOAc in hexanes) to provide the title product (150d) (0.47 g, 62%) as a colorless oil. m/z (ESI, +ve ion)=509.3 $[M+H]^+$.

Step E. tert-Butyl 4-((2-((2,4-dichlorophenoxy)methyl)pyridin-4-yl)methyl)-4-(hydroxymethyl)piperidine-1-carboxylate (150e)

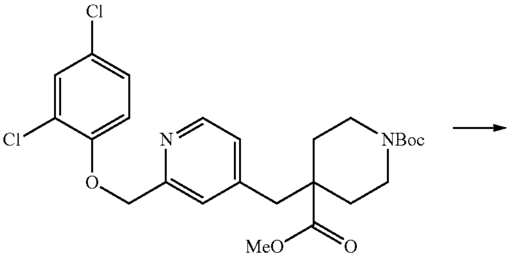

150d

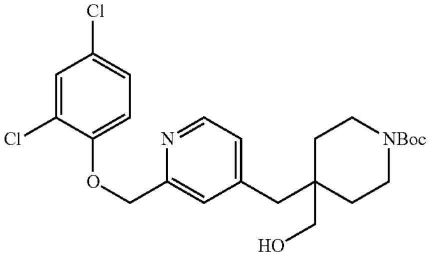

150e

Lithium aluminum hydride solution in THF (0.77 mL, 1.85 mmol) was added dropwise to an ice cold solution of 150d (0.47 g, 0.92 mmol) in THF (4.6 mL). The reaction was stirred at 0° C. for 10 min. and quenched with water (5 mL).

The resulting mixture was filtered through a pad of celite. The filtrate was extracted with EtOAc (×3). The combined organic layer was washed with brine (5 mL), dried over $Na_2SO_4$, filtered, concentrated and purified by silica gel column chromatography (gradient elution, 80-100% EtOAc in hexanes) to provide the title product (150e) (0.26 g, 59%) as a colorless oil. m/z (ESI, +ve ion)=481.3 $[M+H]^+$.

Step F. (4-((2-((2,4-Dichlorophenoxy)methyl)pyridin-4-yl)methyl)piperidin-4-yl)methanol (150f)

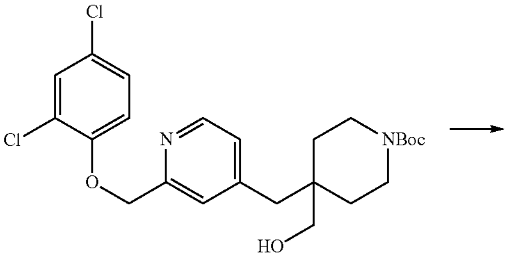

150e

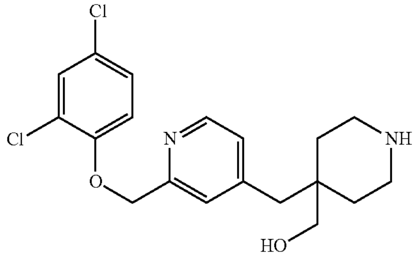

150f

A solution of 150e (15 mg, 0.031 mmol) in DCM (1 mL) and TFA (0.5 mL) was stirred at room temperature for 10 min. After completion, the reaction solvent was removed under reduced pressure and the resulting residue was diluted with EtOAc (3 mL). The organic layer was washed with sat. $NaHCO_3$ (5 mL), brine (3 mL), dried over $Na_2SO_4$, filtered and concentrated to afford the title product (150f) (12 mg) as a colorless oil, which was used in the next step without further purification. m/z (ESI, +ve ion)=381.1 $[M+H]^+$.

Step G. Methyl 2-((4-((2-((2,4-dichlorophenoxy)methyl)pyridin-4-yl)methyl)-4-(hydroxymethyl)piperidin-1-yl)methyl)-1-((1-ethyl-1H-imidazol-5-yl)methyl)-1H-benzo[d]imidazole-6-carboxylate (150g)

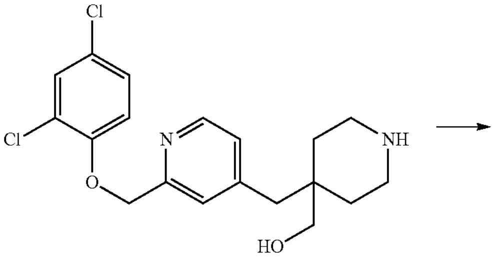

150f

-continued

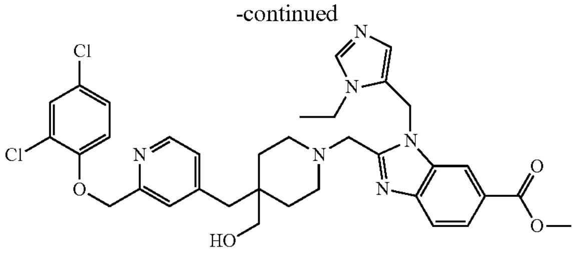

150g

A solution of 150f (11.5 mg, 0.03 mmol), 57f (16.7 mg, 0.045 mmol) and DIPEA (0.026 mL, 0.15 mmol) in DMF (0.5 mL) was stirred at room temperature overnight. After completion, the reaction mixture was diluted with EtOAc (5 mL). The organic layer was washed with water (3 mL×2), brine (3 mL), dried over $Na_2SO_4$, filtered and concentrated and the resulting crude residue was purified by silica gel column chromatography (gradient elution, 0-20% MeOH in DCM) to afford the title product (150g) (6.4 mg, 31%) as a pale-yellow oil. m/z (ESI, +ve ion)=677.2 $[M+H]^+$.

Step H. 2-((4-((2-((2,4-Dichlorophenoxy)methyl)pyridin-4-yl)methyl)-4-(hydroxymethyl)piperidin-1-yl)methyl)-1-((1-ethyl-1H-imidazol-5-yl)methyl)-1H-benzo[d]imidazole-6-carboxylic acid (150)

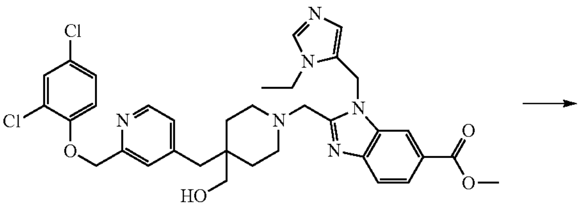

150g

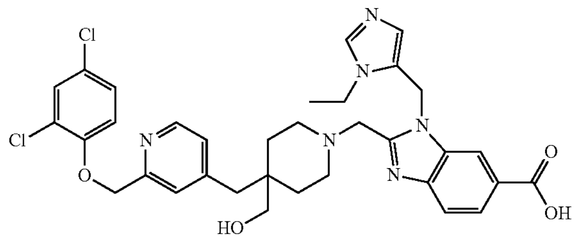

150

A solution of 150g (6.4 mg, 0.009 mmol) and LiOH (1.2 mg, 0.028 mmol) in THF:MeOH:$H_2O$=2:1:1 (0.4 mL) was stirred at 30° C. overnight. After completion, the reaction mixture was diluted with water to 1 mL and purified by reverse phase HPLC (gradient elution, 20-100% $CH_3CN$ in $H_2O$, with 0.1% formic acid as a modifier) to afford the title product (150) (3.1 mg, 49%) as a white solid. $^1H$ NMR (600 MHZ, $CD_3OD$) δ ppm 8.42 (d, J=5.1 Hz, 1H), 8.13 (s, 1H), 8.00 (dd, J=8.6, 1.7 Hz, 1H), 7.80 (s, 1H), 7.73 (d, J=8.4 Hz, 1H), 7.41 (s, 1H), 7.35 (d, J=2.6 Hz, 1H), 7.22 (dd, J=5.1, 1.5 Hz, 1H), 7.19 (dd, J=9.2, 2.6 Hz, 1H), 7.05 (d, J=9.2 Hz, 1H), 6.57 (s, 1H), 5.73 (s, 2H), 5.25 (s, 2H), 4.04 (q, J=7.2 Hz, 2H), 3.87 (s, 2H), 3.21 (s, 2H), 2.72 (s, 2H), 2.49-2.56 (m, 2H), 2.39-2.46 (m, 2H), 1.19-1.34 (m, 7H). m/z (ESI, +ve ion)=663.3 $[M+H]^+$.

Examples 168, 169, and 170 were synthesized from 145d in similar procedures as described in Example 150, Steps G and H. Example 171, 174, 182, 183 were synthesized in similar procedures as described in Example 168.

Example 152. (S)-2-((4-((6-((2-Chloro-4-cyclopropylphenoxy)methyl)pyridin-2-yl)methyl)piperidin-1-yl)methyl)-1-(oxetan-2-ylmethyl)-1H-benzo[d]imidazole-6-carboxylic acid (152)

152

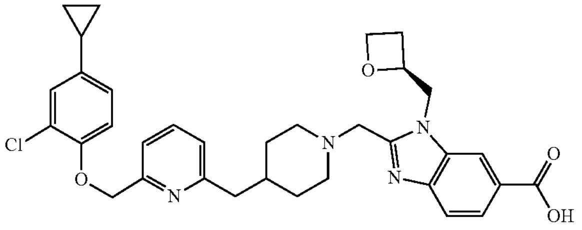

Step A. tert-Butyl 4-((6-((2-chloro-4-cyclopropylphenoxy)methyl)pyridin-2-yl)methyl)piperidine-1-carboxylate (152b)

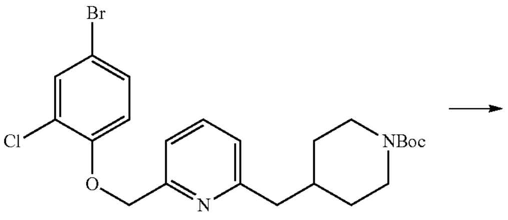

152a

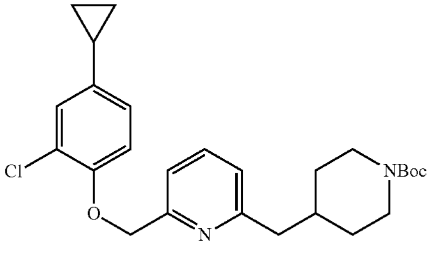

152b

A mixture of 152a (800 mg, 1.6 mmol, prepared in similar procedures as described in the synthesis of 114f), cyclopropylboronic acid (690 mg, 8 mmol), Pd(dppf)$Cl_2$ (130 mg, 0.1 mmol) in toluene (26 mL) was degassed with nitrogen and stirred at 10° C. A solution of $Cs_2CO_3$ (1.04 g, 3.2 mmol) in $H_2O$ (4 mL) was added and the resulting mixture was heated at 100° C. for 2 h under $N_2$. After cooling down, the reaction was filtered and diluted with EtOAc (50 mL), washed with $H_2O$ (15 mL), and brine (15 mL). The organic layer was concentrated and purified by silica gel column chromatography (EtOAc:petroleum ether=1:4) to provide the title product (152b) (0.52 g, 62.5%) as a yellow oil. m/z (ESI, +ve ion)=457.3 $[M+H]^+$.

Step B. 2-((2-Chloro-4-cyclopropylphenoxy)methyl)-6-(piperidin-4-ylmethyl)pyridine (152c)

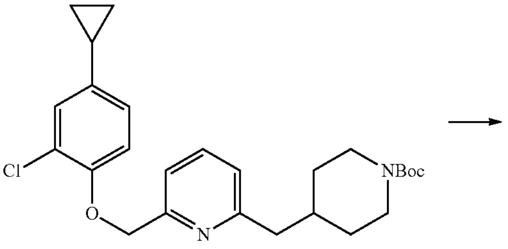

152b

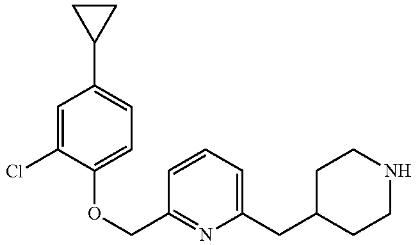

152c

A mixture of 152b (40 mg, 0.09 mmol) in DCM (3 mL) was added TFA (0.5 mL) at 0° C. The reaction was stirred at 0° C. for 1 h, and then diluted with DCM (15 mL), washed with aq. $NaHCO_3$ (8 mL×2), $H_2O$ (10 mL), and brine (10 mL). The organic layer was dried over $Na_2SO_4$, filtered and concentrated to afford the title product (152c) (25 mg, 72%) as a yellow oil. m/z (ESI, +ve ion)=357.1 $[M+H]^+$.

Step C. Methyl(S)-2-((4-((6-((2-chloro-4-cyclopropylphenoxy)methyl)pyridin-2-yl)methyl)piperidin-1-yl)methyl)-1-(oxetan-2-ylmethyl)-1H-benzo[d]imidazole-6-carboxylate (152d)

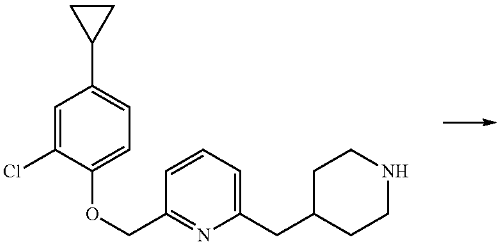

152c

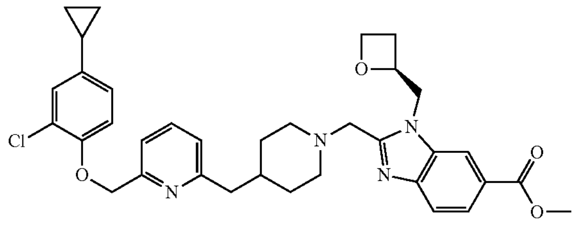

152d

To a mixture of 152c (50 mg, 0.14 mmol), 1h (41 mg, 0.14 mmol) in DMF (5 mL) was added $K_2CO_3$ (58 mg, 0.42 mg), and potassium iodide (12 mg, 0.7 mmol) at 0° C. The reaction was raised to room temperature and stirred for 1 h. The reaction was quenched with $H_2O$ (50 ml), and extracted with ethyl acetate (50 mL×3). The organic layer was dried over $Na_2SO_4$, filtered and concentrated to afford a crude residue, which was purified by reverse phase HPLC (65% $CH_3CN$ in $H_2O$, with 0.05% TFA as a modifier) to afford the title product (152d) (60 mg, 62.7%) as a white solid. m/z (ESI, +ve ion)=615.3 $[M+H]^+$.

Step D. (S)-2-((4-((6-((2-Chloro-4-cyclopropylphenoxy)methyl)pyridin-2-yl)methyl)piperidin-1-yl)methyl)-1-(oxetan-2-ylmethyl)-1H-benzo[d]imidazole-6-carboxylic acid (152)

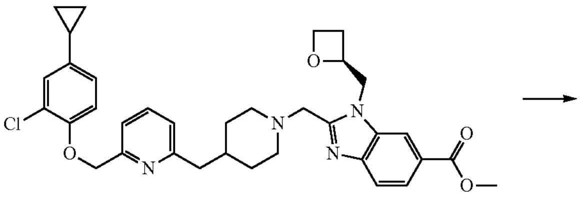

152d

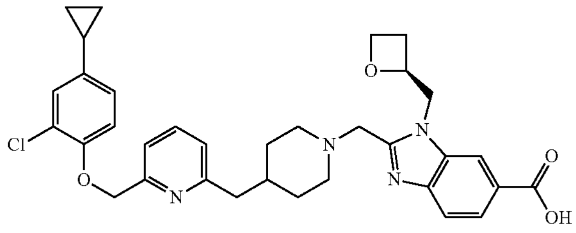

152

To a solution of 152d (30 mg, 0.05 mmol) in MeOH/$H_2O$=10:1 (5 ml) was added lithium hydroxide (23 mg, 0.98 mmol). The mixture was stirred for 48 h at 30° C. The reaction was quenched with $H_2O$ (50 ml), and then extracted with EtOAc (50 mL×3). The organic layer was dried over $Na_2SO_4$ and concentrated to afford a crude residue, which was purified by reverse HPLC (65% $CH_3CN$ in $H_2O$, with 0.05% TFA as a modifier) to afford the TFA salt of the title compound (152) (15 mg, 51%) as a white solid. $^1H$ NMR (400 MHZ, $CD_3OD$) δ 8.32 (d, J=0.91 Hz, 1H), 8.03 (dd, J=8.55, 1.51 Hz, 1H), 7.85 (t, J=7.75 Hz, 1H), 7.79 (d, J=8.56 Hz, 1H), 7.55 (d, J=7.56 Hz, 1H), 7.30 (d, J=7.66 Hz, 1H), 7.09 (d, J=2.06 Hz, 1H), 6.96 (dt, J=8.50, 5.25 Hz, 2H), 5.19 (s, 2H), 4.60-4.80 (m, 6H), 4.39 (dt, J=9.3, 5.9 Hz, 1H), 3.69-3.84 (m, 2H), 3.19-3.25 (m, 2H), 2.85 (d, J=7.04 Hz, 2H), 2.73-2.82 (m, 1H), 2.42-2.52 (m, 1H), 2.17 (br s, 1H), 1.88-1.98 (m, 2H), 1.82 (td, J=8.41, 4.20 Hz, 1H), 1.54-1.72 (m, 2H), 0.90 (ddd, J=8.41, 6.29, 4.38 Hz, 2H), 0.58 (dt, J=6.39, 4.51 Hz, 2H). m/z (ESI, +ve ion)=601.2 $[M+H]^+$.

Example 153 was synthesized in similar procedures as described in Example 152.

Example 154. (S)-2-((4-((2-(((4-Chloro-6-cyclopropylpyridin-3-yl)oxy)methyl)oxazol-5-yl)methyl)piperidin-1-yl)methyl)-1-(oxetan-2-ylmethyl)-1H-benzo[d]imidazole-6-carboxylic acid (154)

154

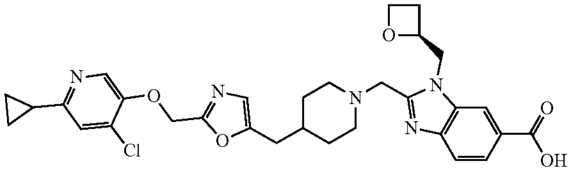

Step A. 2-Bromo-5-methoxypyridine 1-oxide (154a)

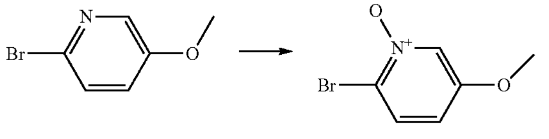

154a

To a solution of 2-bromo-5-methoxypyridine (15 g, 79.8 mmol) in DCE (200 ml) was added m-CPBA (20.6 g, 119.7 mmol). The reaction was stirred at 60° C. for 16 h. Then the reaction mixture was cooled down and washed with sat. $Na_2CO_3$ (200 mL×3). The DCE layer was dried, filtered, and concentrated to afford the title product (154a) (15.8 g, 96.9%) as a white solid. m/z (ESI, +ve ion)=206.0 $[M+H]^+$.

Step B. 2-Bromo-5-methoxy-4-nitropyridine 1-oxide (154b)

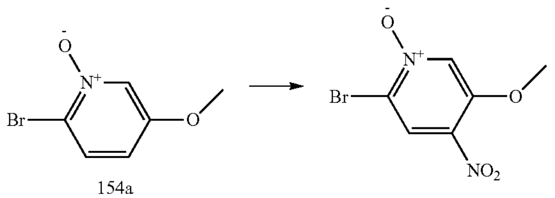

154a

154b

A flask was charged with sulfuric acid (40 mL) and added 154a (8 g, 39.2 mmol) followed by a dropwise addition of nitric acid (4.8 mL, 108 mmol). Then the reaction was cooled to 60° C. and the rest of nitric acid (19.2 mL, 432 mmol) was added. The resulting mixture was stirred at 60° C. for 30 min, then cooled and poured into ice/water mixture (800 mL). The solid was collected by filtration, washed with EtOAc (50 mL) and dried in an oven to afford the title compound (154b) (5.0 g, 49%) as a yellow solid, which was used in the next step without further purification. m/z (ESI, +ve ion)=248.9 $[M+H]^+$.

Step C. 2-Bromo-5-methoxypyridin-4-amine (154c)

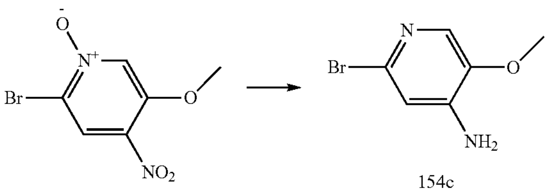

154b

154c

To a solution of 154b (4.5 g, 18.07 mmol) and iron powder (10.1 g, 180.72 mmol) in 75% $EtOH/H_2O$ (60 mL) was added $NH_4Cl$ (9.7, 180.72 mmol). The mixture was stirred at 70° C. for 3 h. Then the reaction mixture was filtered and the residue was washed with EtOH (50 mL×3). The combined filtrate was concentrated and redissolved in EtOAc (100 mL). The EtOAc layer was washed with water (20 mL), brine (20 mL), dried over $Na_2SO_4$, filtered and concentrated to afford the title compound (154c) (2.9 g, 75.3%) as a yellow solid, which was used in the next step without further purification. m/z (ESI, +ve ion)=205.1 $[M+H]^+$.

Step D. 2-Bromo-4-chloro-5-methoxypyridine (154d)

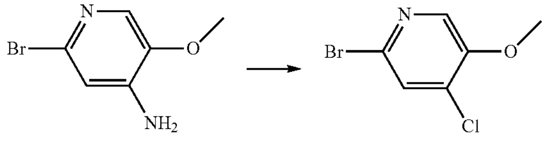

154c

154d

To a solution of 154c (3.3 g, 16.3 mmol) and 37% HCl (30 mL) at 0° C. was added a solution of sodium nitrite (1.2 g, 17.1 mmol) in water (5 mL) dropwise. The resulting mixture was stirred at 0° C. for 15 min, then a solution of copper(I) chloride (1.96 g, 19.51 mmol) in 37% HCl (60 mL) was added dropwise at the same temperature. The resulting mixture was raised to room temperature and stirred for 2 h. Then the reaction was diluted with water (500 ml) and solid precipitates crashed out. The solids were collected by filtration, washed with water (50 mL), and redissolved in EtOAc (100 mL). The EtOAc layer was washed with sat. $NaHCO_3$ (100 mL×2), brine (200 mL), dried over $Na_2SO_4$, and filtered. The filtrate was concentrated and the crude residue was purified by silica gel column chromatography (15% EtOAc in petroleum ether) to afford the title compound (154d) (1.9 g, 52.3%) as a yellow solid. $^1$H NMR (400 MHZ, $CD_3OD$) δ 8.15 (s, 1H), 7.67 (s, 1H), 4.00 (s, 3H).

Step E. 6-Bromo-4-chloropyridin-3-ol (154e)

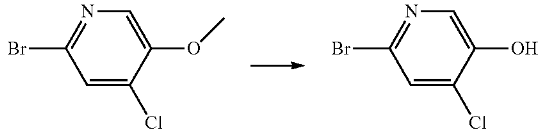

154d

154e

To a solution of 154d (550 mg, 2.47 mmol) in $CHCl_3$ (15 mL) was added $BBr_3$ (1.25 g, 4.95 mmol). The reaction was stirred at 50° C. for 16 h, cooled down, washed with sat. $NaHCO_3$ (20 ml) and brine (20 ml). The organic layer was dried over $Na_2SO_4$, filtered, and concentrated to provide a crude residue, which was purified by silica gel column chromatography (5% MeOH in DCM) to afford the title product (154e) (350 mg, 67.8%) as a white solid. m/z (ESI, +ve ion)=210.0 $[M+H]^+$.

Step F. tert-Butyl 4-((2-(((6-bromo-4-chloropyridin-3-yl)oxy)methyl)oxazol-5-yl)methyl)piperidine-1-carboxylate (154f)

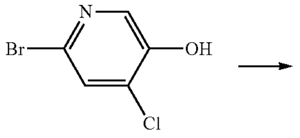

154e

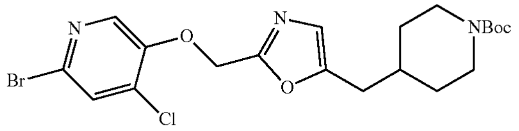

154f

To a solution of 60d (498 mg, 1.69 mmol) and DIPEA (524 mg, 4.06 mmol) in DCM (10 mL) was added MsCl (232 mg, 2.03 mmol) at 0° C. The reaction was stirred at 0° C. for 0.5 h and then washed with water (10 mL). The DCM layer was dried over $Na_2SO_4$, filtered and concentrated to provide a residue A. A separate flask was charged with 154e (350 mg, 1.69 mmol), $K_2CO_3$ (466 mg, 3.38 mmol). DMF (10 mL) was added. To this mixture was added a solution of residue A in DMF. The reaction was stirred at 50° C. for 2 h. After cooling down, the reaction mixture was diluted with EtOAc (50 ml), and washed with brine (50 mL×2). The EtOAc layer was dried, filtered, and concentrated to provide a crude residue, which was purified by silica gel column chromatography (30% EtOAc in petroleum ether) to afford the title product (154f) (540 mg, 65.7%) as a white solid. m/z (ESI, +ve ion)=510.1 $[M+Na]^+$.

Step G. (S)-2-((4-((2-(((4-Chloro-6-cyclopropylpyridin-3-yl)oxy)methyl)oxazol-5-yl)methyl)piperidin-1-yl)methyl)-1-(oxetan-2-ylmethyl)-1H-benzo[d]imidazole-6-carboxylic acid (154)

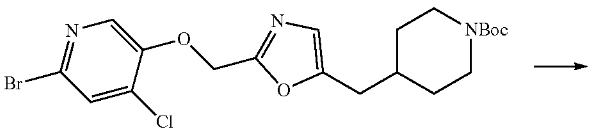

154f

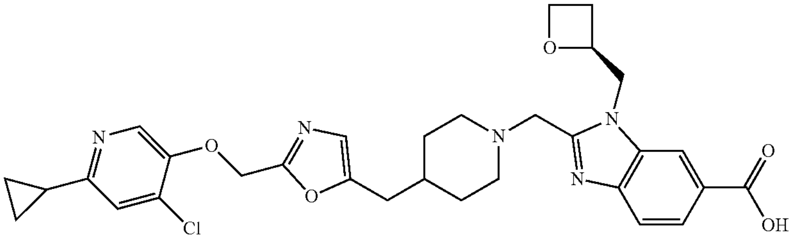

154

The title product (154) was synthesized in similar procedures as described in Example 114, Steps G to I. $^1H$ NMR (400 MHZ, $CD_3OD$) δ ppm 8.34 (d, J=0.88 Hz, 1H), 8.28 (s, 1H), 7.98-8.09 (m, 1H), 7.80 (d, J=8.77 Hz, 1H), 7.38 (s, 1H), 6.96 (s, 1H), 5.30 (s, 2H), 5.14-5.25 (m, 1H), 4.61-4.83 (m, 5H), 4.40 (dt, J=9.43, 5.81 Hz, 1H), 3.72-3.88 (m, 2H), 3.18-3.29 (m, 2H), 2.73-2.86 (m, 3H), 2.41-2.56 (m, 1H), 1.89-2.13 (m, 4H), 1.61 (br s, 2H), 0.97-1.06 (m, 2H), 0.85-0.97 (m, 2H). m/z (ESI, +ve ion)=592.2 $[M+Na]^+$.

Example 155. 2-((4-((2-((2,4-Dichlorophenoxy)methyl)pyridin-4-yl)methylene)piperidin-1-yl)methyl)-1-((1-ethyl-1H-imidazol-5-yl)methyl)-1H-benzo[d]imidazole-6-carboxylic acid (155)

155

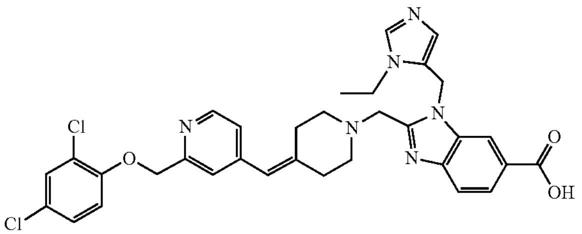

Step A. Methyl 4-((1-(tert-butoxycarbonyl)piperidin-4-ylidene)methyl)picolinate (155a)

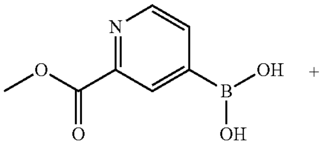

-continued

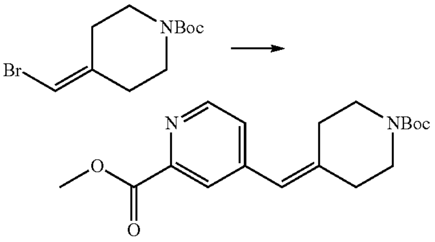

155a

A flask was charged with (2-(methoxycarbonyl)pyridin-4-yl)boronic acid (66 mg, 0.37 mmol), tert-butyl 4-(bromomethylidene)piperidine-1-carboxylate (101 mg, 0.37 mmol), $Cs_2CO_3$ (238 mg, 0.73 mmol) and Pd(dppf)$Cl_2$ (27 mg, 0.037 mmol) and added a mixed solvent of THF: $H_2O$=2:1 (18 mL). The mixture was degassed with nitrogen and stirred at 50° C. for 18 h under argon. After completion, the reaction was extracted with EtOAc (10 mL×3). The organic layer was dried, filtered and concentrated. The crude residue was purified by silica gel column chromatography (EtOAc in hexanes) to afford the title product (155a) (16.5 mg, 14%) as a colorless oil. m/z (ESI, +ve ion)=333.2 $[M+H]^+$.

Step B. tert-Butyl 4-((2-(hydroxymethyl)pyridin-4-yl)methylene)piperidine-1-carboxylate (155b)

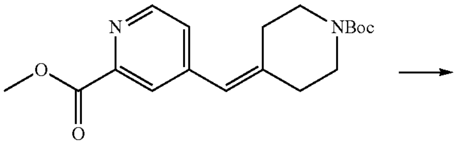

155a

-continued

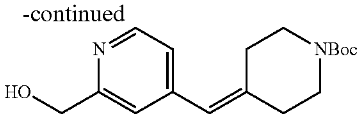

155b

To a mixture of 155a (17 mg, 0.05 mmol), $CaCl_2$) (11 mg, 0.1 mmol) and $NaBH_4$ (7 mg, 0.2 mmol) was added THF (10 mL). The resulting suspension was stirred at 60° C. overnight. After cooling down, the reaction was quenched with water (10 mL), extracted with ethyl acetate (10 mL×3) and washed with brine. The combined organic phase was dried with anhydrous $Na_2SO_4$, filtered and concentrated to give a crude product which was purified by silica gel column chromatography (EtOAc in hexanes) to afford the title product (155b) (9.5 mg, 63%) as a colorless oil. m/z (ESI, +ve ion)=305.1 $[M+H]^+$.

Step C. tert-Butyl 4-((2-((2,4-dichlorophenoxy) methyl)pyridin-4-yl)methylene)piperidine-1-carboxylate (155c)

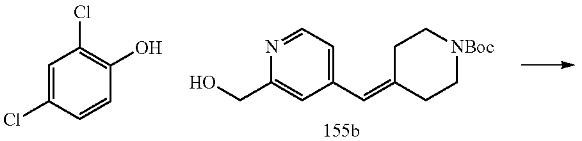

155b

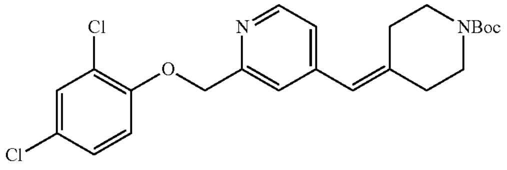

155c

A flask was charged with 2,4-dichlorophenol (5.6 mg, 0.034 mmol), 155b (9.5 mg, 0.031 mmol), and $PPh_3$ (9.8 mg, 0.038 mmol). Anhydrous THF (5 mL) was added and the reaction was cooled down in an ice bath. Diethyl azodicarboxylate (7.6 mg, 0.038 mmol) was added dropwise and the resulting mixture was stirred at 0° C. for 0.5 h, then at room temperature overnight. After completion, the reaction was quenched with water (5 mL), extracted with ethyl acetate (5 mL×3) and washed with brine. The combined organic phase was dried with anhydrous $Na_2SO_4$, filtered and concentrated to provide a crude residue, which was purified by silica gel column chromatography (EtOAc in hexanes) to afford the title product (155c) as a colorless oil with some impurity, which was used in next step without further purification. m/z (ESI, +ve ion)=451.1 $[M+H]^+$.

Step D. 2-((2,4-Dichlorophenoxy)methyl)-4-(piperidin-4-ylidenemethyl)pyridine (155d)

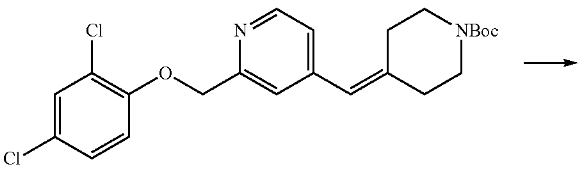

155c

-continued

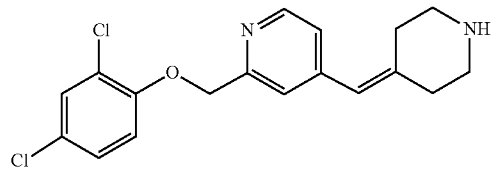

155d

A solution of 155c (impure) in DCM (2 mL) was treated with TFA (1 mL) at room temperature for 10 min. After completion, the solvent was removed in vacuo, and the resulting crude residue was purified by reverse phase HPLC (gradient elution, 0-90% $CH_3CN$ in water with 0.1% TFA as a modifier) to provide the title product (155d) (6.3 mg, 44% for 2 steps) as a white solid. m/z (ESI, +ve ion)=351.2 $[M+H]^+$.

Step E. Methyl 2-((4-((2-((2,4-dichlorophenoxy) methyl)pyridin-4-yl)methylene)piperidin-1-yl) methyl)-1-((1-ethyl-1H-imidazol-5-yl)methyl)-1H-benzo[d]imidazole-6-carboxylate (155e)

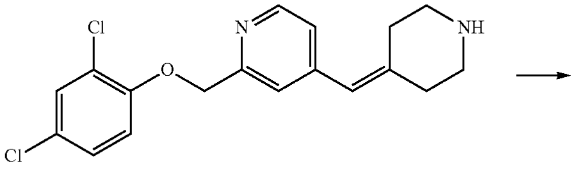

155d

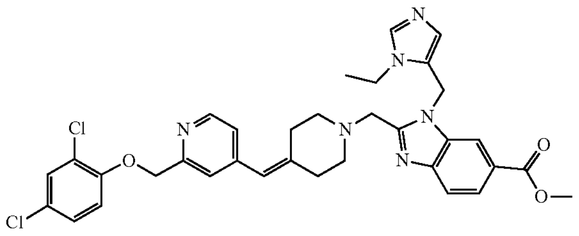

155e

A solution of 155d (6.2 mg, 0.018 mmol), 57f (5.9 mg, 0.018 mmol) and $Et_3N$ (18 mg, 0.18 mmol) in DMF (0.8 mL) was stirred at room temperature for 18 h. After completion, the reaction was purified by reverse phase HPLC (gradient elution, 0-90% $CH_3CN$ in water, with 0.1% TFA as a modifier) to provide the title product (155e) (4.4 mg, 39%) as a white solid. m/z (ESI, +ve ion)=645.3 $[M+H]^+$.

Step F. 2-((4-((2-((2,4-Dichlorophenoxy)methyl) pyridin-4-yl)methylene)piperidin-1-yl)methyl)-1-((1-ethyl-1H-imidazol-5-yl)methyl)-1H-benzo[d]imidazole-6-carboxylic acid (155)

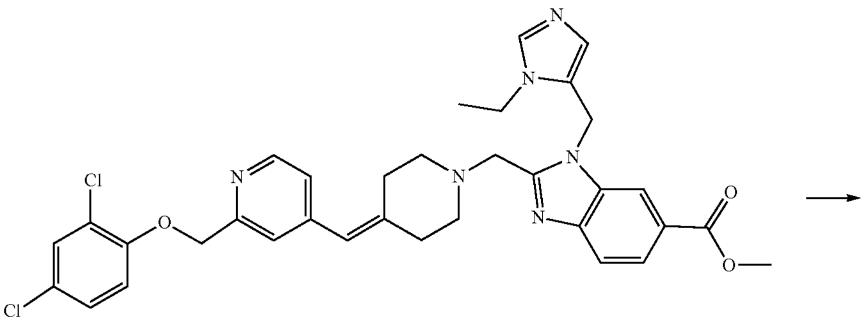

155e

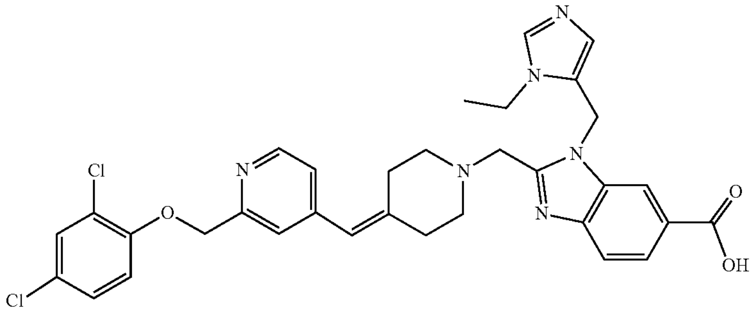

155

A solution of 155e (4.4 mg, 0.007 mmol) in $CH_3CN$ (0.4 mL) was treated with 2 N NaOH (0.4 mL). The resulting mixture was stirred at room temperature for 24 h. After completion, the reaction was purified by reverse phase HPLC (gradient elution, 0-75% $CH_3CN$ in water, with 0.1% formic acid as a modifier) to provide the title product (155) (2.7 mg, 63%) as a white solid. $^1H$ NMR (600 MHz, $CD_3OD$) δ ppm 8.44 (d, J=5.14 Hz, 1H), 8.16 (br d, J=0.73 Hz, 1H), 8.00 (br dd, J=8.62, 1.65 Hz, 1H), 7.79 (s, 1H), 7.69-7.73 (m, 1H), 7.42 (br d, J=2.57 Hz, 1H), 7.38 (s, 1H), 7.23 (br dd, J=8.80, 2.57 Hz, 1H), 7.16 (br dd, J=5.14, 1.10 Hz, 1H), 7.07 (br d, J=9.17 Hz, 1H), 6.58 (br d, J=0.73 Hz, 1H), 6.30 (s, 1H), 5.80 (s, 2H), 5.25 (s, 2H), 4.11 (q, J=7.34 Hz, 2H), 3.86 (s, 2H), 2.55-2.60 (m, 2H), 2.40-2.44 (m, 2H), 2.29 (dt, J=9.81, 5.18 Hz, 4H), 1.32 (t, J=7.34 Hz, 3H) m/z (ESI, +ve ion)=631.3 $[M+H]^+$.

Example 156 was synthesized from 102c and 57i as described in Example 57, Step J. Example 160 was synthesized in similar procedures as described in Example 156.

Example 157. 2-((4-(3-((2,4-Dichlorophenoxy) methyl)phenoxy)piperidin-1-yl)methyl)-1-((1-ethyl-1H-imidazol-5-yl)methyl)-1H-benzo[d]imidazole-6-carboxylic acid (157)

157

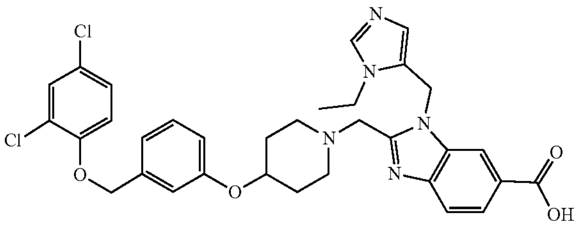

Step A. Methyl 2-((4-(3-((2,4-dichlorophenoxy)methyl)phenoxy)piperidin-1-yl)methyl)-1-((1-ethyl-1H-imidazol-5-yl)methyl)-1H-benzo[d]imidazole-6-carboxylate (157b)

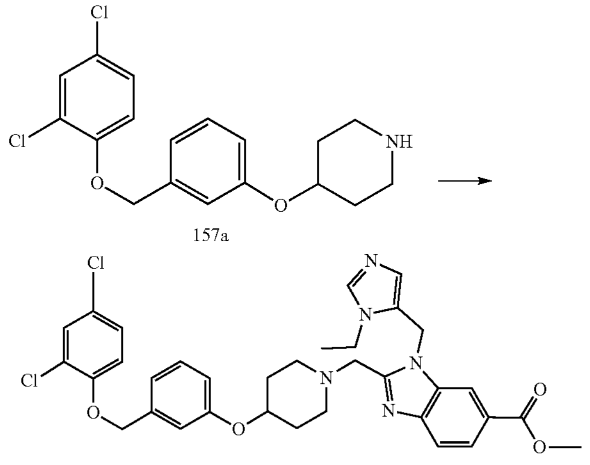

157a

157b

To a stirred solution of 157a (13.6 mg, 0.0386 mmol, prepared as described for the synthesis of 145d) and 145f (14.5 mg, 0.0463 mmol) in 1,2-dichloroethane (0.3 mL) was added HOAc (7.0 mg, 0.116 mmol) at room temperature, followed by addition of sodium triacetoxyborohydride (12.2 mg, 0.058 mmol). The mixture was stirred for 1 h at the same temperature. The reaction was quenched by addition of saturated sodium bicarbonate, and extracted with DCM (×3). The combined organic layer was washed with brine, dried over $Na_2SO_4$, filtered and concentrated under reduced pressure. The crude residue was purified by silica gel column chromatography (gradient elution, 1-8% MeOH in DCM) to afford the title product (157b) (11.5 mg, 46%) as a colorless gum. m/z (ESI, +ve ion)=648.3 $[M+H]^+$.

Step B. 2-((4-(3-((2,4-Dichlorophenoxy)methyl)phenoxy)piperidin-1-yl)methyl)-1-((1-ethyl-1H-imidazol-5-yl)methyl)-1H-benzo[d]imidazole-6-carboxylic acid (157)

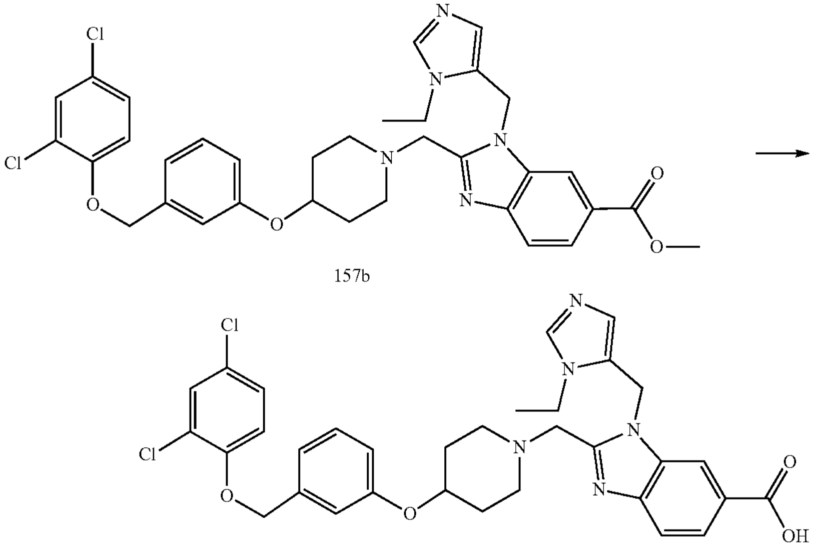

157b

157

To a stirred solution of 157b (11.5 mg, 0.0177 mmol) in THF/MeOH/$H_2O$ (2:1:11, 0.4 mL) was added lithium hydroxide monohydrate (2.23 mg, 0.053 mmol) at room temperature. After the mixture was stirred at the same temperature for 2 h, additional lithium hydroxide monohydrate (2.23 mg, 0.053 mmol) was added. After an additional 1.5 h, 1 N HCl was added to the mixture to adjust to pH=3. The solution was purified by reverse preparative HPLC (gradient elution, 20-60% MeCN in $H_2O$, with 0.1% TFA as a modifier) to provide the TFA salt of the title compound 157 (11.4 mg, 86%) as a white solid. $^1H$ NMR (600 MHZ, $CD_3OD$) δ 9.04 (s, 1H), 8.23 (d, J=0.9 Hz, 1H), 8.06 (dd, J=8.4, 1.5 Hz, 1H), 7.83 (d, J=8.4 Hz, 1H), 7.42 (d, J=2.6

Hz, 1H), 7.31 (t, J=7.9 Hz, 1H), 7.23 (dd, J=8.8, 2.6 Hz, 1H), 7.02-7.12 (m, 4H), 6.94 (dd, J=8.1, 2.0 Hz, 1H), 5.87 (s, 2H), 5.15 (s, 2H), 4.64 (br s, 1H), 4.54 (br s, 2H), 4.35 (q, J=7.3 Hz, 2H), 3.19-3.41 (m, 4H), 2.13-2.20 (m, 2H), 1.88-2.01 (m, 2H), 1.56 (t, J=7.2 Hz, 3H). m/z (ESI, +ve ion)=634.3 $[M+H]^+$.

Example 163. 2-((4-((2-((2,4-Dichlorophenoxy)methyl)pyridin-4-yl)methyl)-4-methylpiperidin-1-yl)methyl)-1-((1-ethyl-1H-imidazol-5-yl)methyl)-1H-benzo[d]imidazole-6-carboxylic acid (163)

163

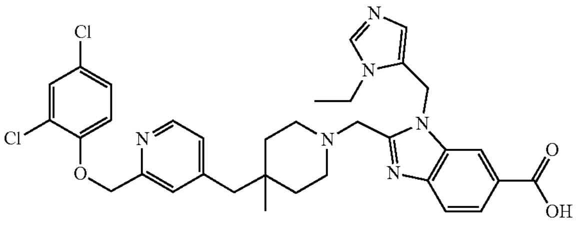

Step A. tert-Butyl 4-(((1H-imidazole-1-carbonothioyl)oxy)methyl)-4-((2-((2,4-dichlorophenoxy)methyl)pyridin-4-yl)methyl)piperidine-1-carboxylate (163a)

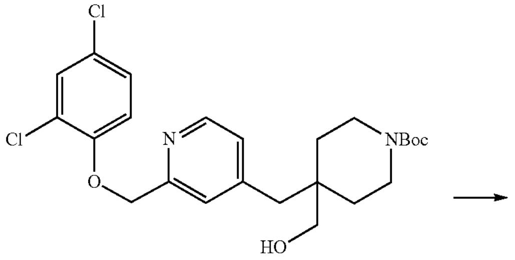

150e

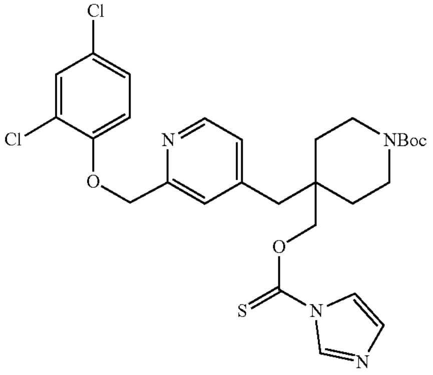

163a

Thiocarbonyldiimidazole (42.6 mg, 0.24 mmol) was added to a solution of 150e (23 mg, 0.048 mmol) in THF (0.24 mL) at room temperature. The resulting solution was heated at 60° C. for 2 h. After completion, the reaction was cooled down, diluted with water (1 mL) and EtOAc (1 mL), and was extracted with EtOAc (1 mL×3). The combined organic layer was washed with brine (1 mL), dried over $Na_2SO_4$, filtered, and concentrated to afford the crude title product (163a) (28 mg) as a yellow solid, which was used in the next step without further purification. m/z (ESI, +ve ion)=591.3 $[M+H]^+$.

Step B. tert-Butyl 4-((2-((2,4-dichlorophenoxy)methyl)pyridin-4-yl)methyl)-4-methylpiperidine-1-carboxylate (163b)

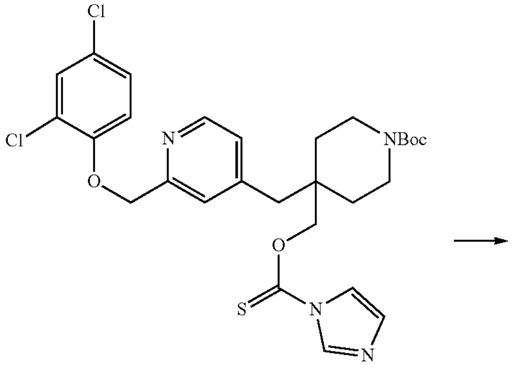

163a

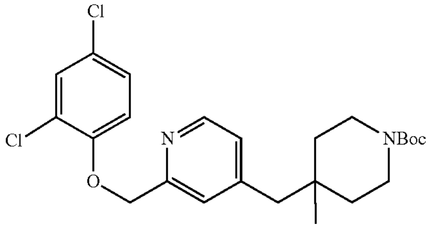

163b

AIBN (2.33 mg, 0.0142 mmol) and tributyltin hydride (0.064 mL, 0.24 mmol) were added to a solution of 163a (0.028 g, 0.047 mmol) in toluene (2.4 mL) under Ar at room temperature. The resulting solution was heated at 100° C. overnight. After completion, the reaction solvent was removed under reduced pressure to provide a crude title product (163b) (7.5 mg), which was used in the next step without further purification. m/z (ESI, +ve ion)=465.3 $[M+H]^+$.

Step C. 2-((4-((2-((2,4-Dichlorophenoxy)methyl)pyridin-4-yl)methyl)-4-methylpiperidin-1-yl)methyl)-1-((1-ethyl-1H-imidazol-5-yl)methyl)-1H-benzo[d]imidazole-6-carboxylic acid (163)

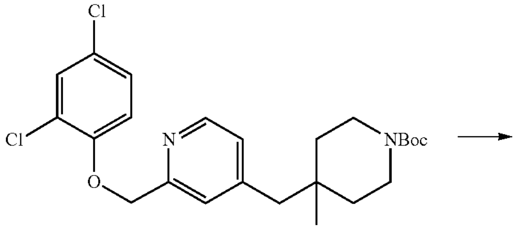

163b

-continued

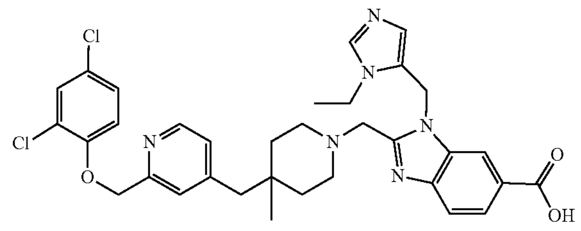

163

The title product (163) was synthesized in similar procedures as described in Example 150, Steps F—H. $^1H$ NMR (600 MHZ, $CD_3OD$) δ ppm 8.42 (d, J=5.1 Hz, 1H), 8.13 (d, J=0.7 Hz, 1H), 8.00 (dd, J=8.4, 1.5 Hz, 1H), 7.81 (s, 1H), 7.72 (d, J=8.4 Hz, 1H), 7.36-7.38 (m, 2H), 7.20 (dd, J=8.8, 2.6 Hz, 1H), 7.15 (dd, J=5.1, 1.5 Hz, 1H), 7.06 (d, J=8.8 Hz, 1H), 6.57 (s, 1H), 5.73 (s, 2H), 5.26 (s, 2H), 4.05 (q, J=7.3 Hz, 2H), 3.88 (s, 2H), 2.54-2.66 (m, 4H), 2.35-2.42 (m, 2H), 1.24-1.35 (m, 5H), 1.16-1.22 (m, 2H), 0.83 (s, 3H). m/z (ESI, +ve ion)=647.3 $[M+H]^+$.

Example 164. 2-((4-((2-((2,4-Dichlorophenoxy)methyl)pyridin-4-yl)methyl)-4-(fluoromethyl)piperidin-1-yl)methyl)-1-((1-ethyl-1H-imidazol-5-yl)methyl)-1H-benzo[d]imidazole-6-carboxylic acid (164)

164

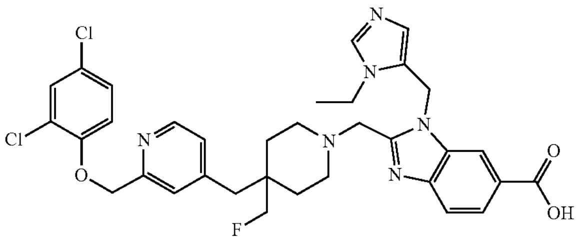

Step A. tert-Butyl 4-((2-((2,4-dichlorophenoxy)methyl)pyridin-4-yl)methyl)-4-(fluoromethyl)piperidine-1-carboxylate (164a)

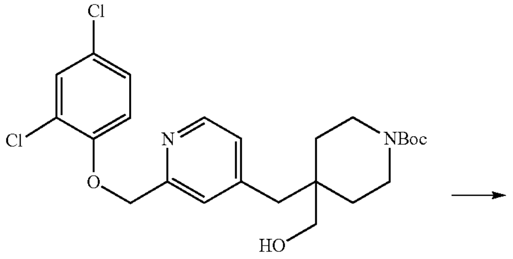

150e

-continued

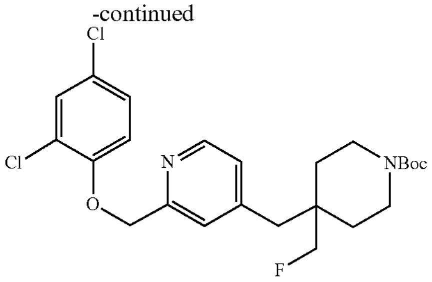

164a

Deoxo-fluor (0.104 mL, 0.254 mmol) was added dropwise to a solution of 150e (0.102 g, 0.212 mmol) in DCM (1.1 mL) at room temperature. Then the reaction was heated to 45° C. overnight. After completion, the reaction was quenched with sat. $NaHCO_3$ solution (5 mL) and extracted with EtOAc (5 mL×3). The combined organic layer was washed with brine (5 mL), dried over $Na_2SO_4$, filtered, and concentrated to give a crude residue, which was purified by silica gel column chromatography (gradient elution, 40-80% EtOAc in hexanes) to afford the title product (164a) (45.0 mg, 44%) as a yellow oil. m/z (ESI, +ve ion)=483.3 $[M+H]^+$.

Step B. 2-((4-((2-((2,4-Dichlorophenoxy)methyl)pyridin-4-yl)methyl)-4-(fluoromethyl)piperidin-1-yl)methyl)-1-((1-ethyl-1H-imidazol-5-yl)methyl)-1H-benzo[d]imidazole-6-carboxylic acid (164)

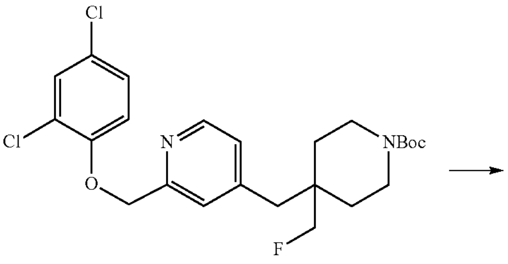

164a

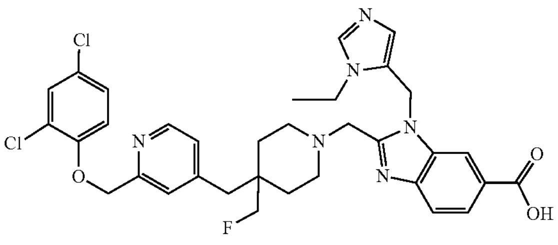

164

The title product (164) was synthesized in similar procedures from 164a as described in Example 150, Steps F—H. m/z (ESI, +ve ion)=665.3 $[M+H]^+$.

Example 178. (S)-2-((4-((4-((2,4-Dichlorophenoxy)methyl)pyridin-2-yl)oxy)piperidin-1-yl)methyl)-1-(oxetan-2-ylmethyl)-1H-benzo[d]imidazole-6-carboxylic acid (178)

178

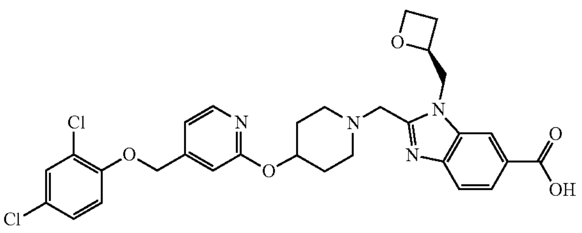

Step A. Methyl 4-((1-(tert-butoxycarbonyl)piperidin-4-yl)oxy)picolinate (178a)

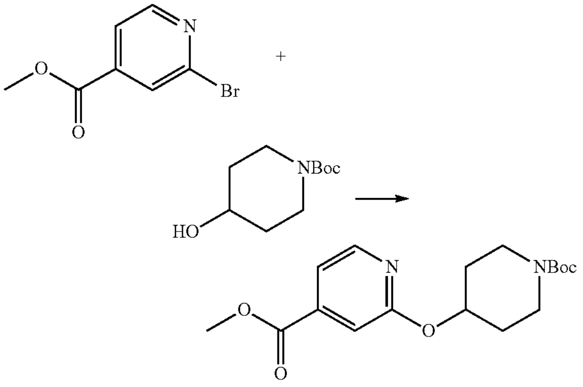

178a

A solution of $Pd_2(dba)_3$ (46 mg, 0.05 mmol) and BINAP (62 mg, 0.1 mmol) in toluene (2 mL) was heated at 120° C. for 5 min before transferred into a mixture of methyl 2-bromopyridine-4-carboxylate (216 mg, 1.0 mmol), tert-butyl 4-hydroxypiperidine-1-carboxylate (241 mg, 1.2 mmol) and $Cs_2CO_3$ (652 mg, 2.0 mmol) in 18 mL of toluene. The mixture was degassed with argon and stirred at 120° C. for 16 h under argon. After completion, the solvent was removed in vacuo and the residue was purified by silica gel column chromatography (EtOAc in hexanes) to afford the title product (178a) with impurities as a colorless oil, which was used in the next step without further purification. m/z (ESI, +ve ion)=337.3 $[M+H]^+$.

Step B. tert-Butyl 4-((2-(hydroxymethyl)pyridin-4-yl)oxy)piperidine-1-carboxylate (178b)

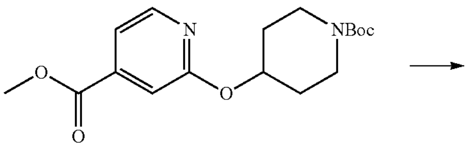

178a

-continued

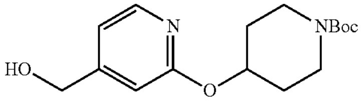

178b

To a mixture of 178a (77 mg, 0.23 mmol), $CaCl_2$) (51 mg, 0.46 mmol) and $NaBH_4$ (35 mg, 0.91 mmol) was added THF (10 mL). The resulting suspension was stirred at 60° C. overnight. After completion, the reaction was quenched with water (10 mL), extracted with ethyl acetate (10 mL×3). The combined organic phase was washed with brine, dried with anhydrous $Na_2SO_4$, filtered, and concentrated to give a crude residue which was purified by silica gel column chromatography (EtOAc in hexanes) to afford the title product (178b) (35 mg, 23% for 2 steps) as a colorless oil. m/z (ESI, +ve ion)=309.3 $[M+H]^+$.

Step C. tert-Butyl 4-((2-((2,4-dichlorophenoxy)methyl)pyridin-4-yl)oxy)piperidine-1-carboxylate (178c)

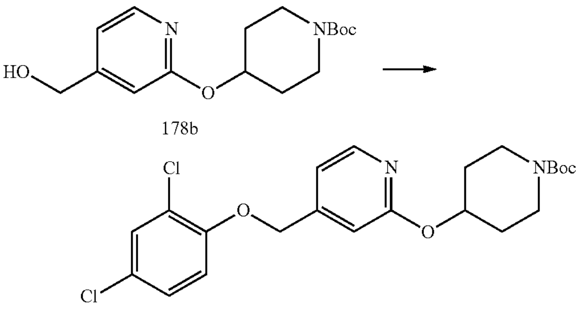

178b

178c

A flask was charged with 2,4-dichlorophenol (27 mg, 0.17 mmol), 178b (17 mg, 0.06 mmol), and $PPh_3$ (44 mg, 0.17 mmol). Anhydrous THF (5 mL) was added and the reaction was cooled down in an ice bath. Diethyl azodicarboxylate (34 mg, 0.17 mmol) was added dropwise and the resulting mixture was stirred at 0° C. for 0.5 h, then at room temperature overnight. After completion, the reaction was quenched with water (5 mL), and extracted with ethyl acetate (5 mL×3). The combined organic phase was washed with brine, dried with anhydrous $Na_2SO_4$, filtered, and concentrated to give a crude residue, which was purified by silica gel column chromatography (EtOAc in hexanes) to afford the title product (178c) as a colorless oil with some impurities, which was used in the next step without further purification. m/z (ESI, +ve ion)=453.3 $[M+H]^+$.

Step D. 2-((2,4-Dichlorophenoxy)methyl)-4-(piperidin-4-yloxy)pyridine (178d)

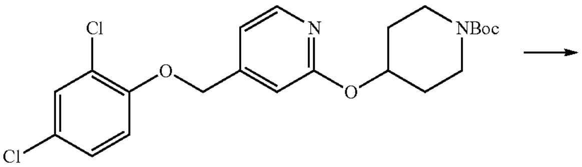

178c

-continued

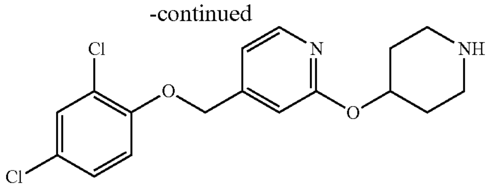

178d

A solution of 178c (15 mg, impure) in DCM (2 mL) was treated with TFA (1 mL) at room temperature for 10 min. After completion, the solvent was removed in vacuo, and the resulting crude was purified by reverse phase HPLC (gradient elution, 0-75% $CH_3CN$ in water, with 0.1% TFA as a modifier) to provide the title product (178d) (17 mg, 62% for 2 steps) as a white solid. m/z (ESI, +ve ion)=353.1 $[M+H]^+$.

Step E. Methyl(S)-2-((4-((2-((2,4-dichlorophenoxy)methyl)pyridin-4-yl)oxy)piperidin-1-yl)methyl)-1-(oxetan-2-ylmethyl)-1H-benzo[d]imidazole-6-carboxylate (178e)

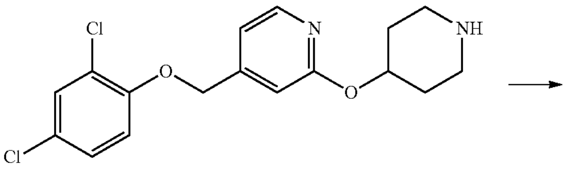

178d

-continued

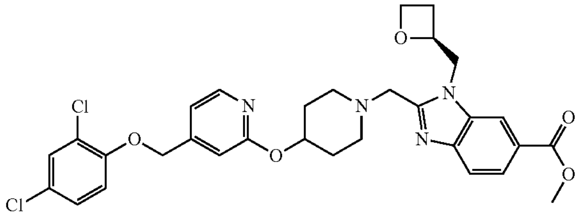

178e

A solution of 178d (4.6 mg, 0.01 mmol), 1h (3.2 mg, 0.011 mmol) and DIPEA (25.5 mg, 0.2 mmol) in DMF (1 mL) was stirred at room temperature for 22 h. After completion, the reaction was purified by reverse phase HPLC (gradient elution, 20-100% $CH_3CN$ in water with 0.1% TFA as a modifier) to provide the title product (178e) (5.6 mg, impure) as a white solid, which was used in the next step without further purification. m/z (ESI, +ve ion)=611.3 $[M+H]^+$.

Step F. (S)-2-((4-((2-((2,4-Dichlorophenoxy)methyl)pyridin-4-yl)oxy)piperidin-1-yl)methyl)-1-(oxetan-2-ylmethyl)-1H-benzo[d]imidazole-6-carboxylic acid (178)

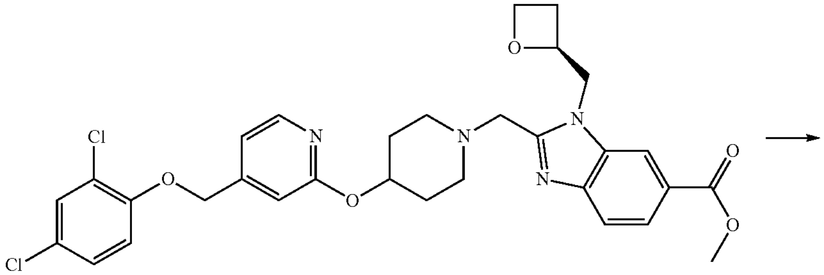

178e

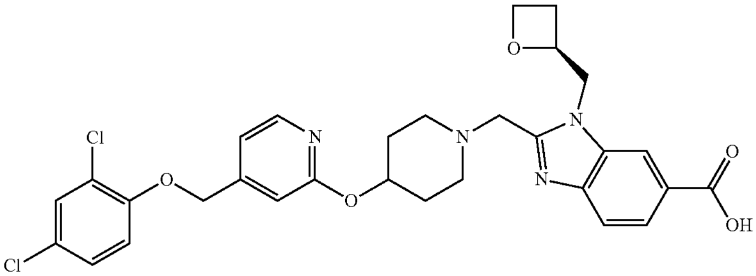

178

A solution of 178e (5.6 mg, 0.008 mmol, impure) in $CH_3CN$ (0.5 mL) was treated with 2 N NaOH (0.5 mL). The resulting mixture was stirred at room temperature for 26 h. After completion, the reaction was purified by reverse phase HPLC (gradient elution, 0-90% $CH_3CN$ in water, with 0.1% formic acid as a modifier) to provide the title product (178) (3.5 mg, 59% for 2 steps) as a white solid. $^1H$ NMR (600 MHZ, $CD_3OD$) δ ppm 8.32-8.37 (m, 1H), 8.10 (d, J=5.13 Hz, 1H), 7.97 (br dd, J=8.44, 1.47 Hz, 1H), 7.68 (d, J=8.44 Hz, 1H), 7.46 (d, J=2.57 Hz, 1H), 7.26 (br dd, J=8.80, 2.57 Hz, 1H), 7.08 (d, J=8.80 Hz, 1H), 6.98-7.03 (m, 1H), 6.88 (s, 1H), 5.26 (qd, J=7.34, 2.57 Hz, 1H), 5.18 (s, 2H), 5.09 (m, 1H), 4.85-4.90 (m, 1H), 4.72 (br dd, J=15.59, 2.75 Hz, 1H), 4.65 (td, J=7.89, 5.87 Hz, 1H), 4.47 (dt, J=9.17, 6.05 Hz, 1H), 4.10 (br d, J=13.94 Hz, 1H), 4.00 (br d, J=13.94 Hz, 1H), 2.91-2.96 (m, 1H), 2.88 (br d, J=3.67 Hz, 1H), 2.81 (m, 1H), 2.49-2.61 (m, 3H), 2.05-2.11 (m, 2H), 1.80-1.90 (m, 2H). m/z (ESI, +ve ion)=597.3 $[M+H]^+$.

Example 179 was synthesized in similar procedures as described in Example 178.

Example 186. 2-(((S)-4-(2-((2,4-Dichlorophenoxy)methyl)oxazole-5-carbonyl)-2-methylpiperazin-1-yl)methyl)-1-(((S)-oxetan-2-yl)methyl)-1H-benzo[d]imidazole-6-carboxylic acid (186)

186

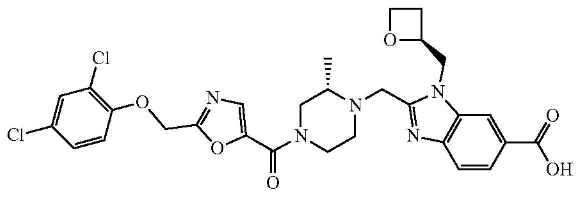

Step A. tert-Butyl(S)-4-(2-((2,4-dichlorophenoxy)methyl)oxazole-5-carbonyl)-2-methylpiperazine-1-carboxylate (186a)

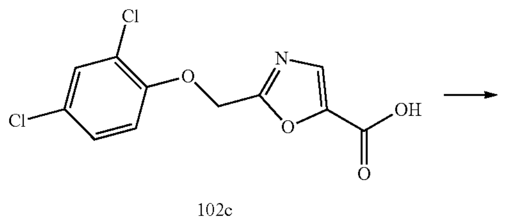

102c

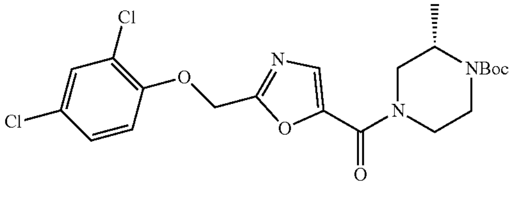

186a

To a solution of 102c (49 mg, 0.17 mmol), tert-butyl(2S)-2-methylpiperazin-1-yl formate (34 mg, 0.17 mmol) and $T_3P$ (178 mg, 0.26 mmol) in DMF (2 ml) was added triethylamine (51 mg, 0.51 mmol). The mixture was stirred at 15° C. for 16 h, diluted with EtOAc (20 ml) and washed with brine (20 mL×3). The organic layer was dried, filtered and evaporated to dryness to afford the title product (186a) (80 mg) as a colorless oil, which was used in the next step without further purification. m/z (ESI, +ve ion)=470.1 $[M+H]^+$.

Step B. (S)-(2-((2,4-Dichlorophenoxy)methyl)oxazol-5-yl) (3-methylpiperazin-1-yl)methanone (186b)

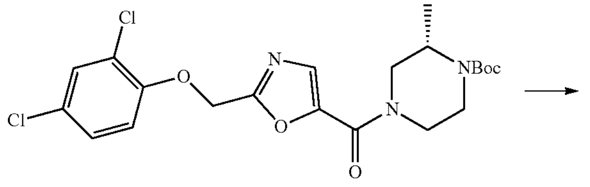

186a

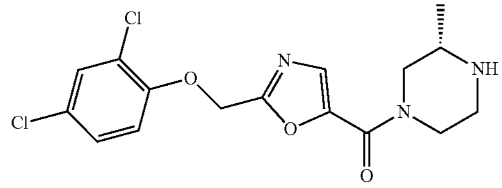

186b

To a solution of 186a (100 mg, 0.21 mmol) in DCM (5 ml) was added TFA (1 mL). The reaction was stirred at 20° C. for 2 h and concentrated. The crude was redissolved in DCM and washed with sat. $NaHCO_3$ (5 mL×2). The DCM layer was dried, filtered, and concentrated to afford the title product (186b) (78 mg) as a colorless oil, which was used in the next step without further purification. m/z (ESI, +ve ion)=370.1 $[M+H]^+$.

Step C. (S)-2-(Chloromethyl)-1-(oxetan-2-ylmethyl)-1H-benzo[d]imidazole-6-carboxylic acid (186c)

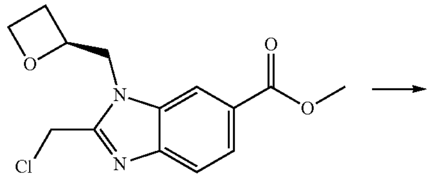

1h

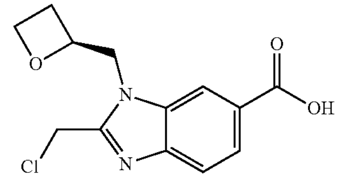

186c

To a solution of 1h (390 mg, 1.33 mmol) in 2 mL of THF/$H_2O$ (1:1) was added LiOH (64 mg, 2.66 mmol). The mixture was stirred at 25° C. for 2 h. After completion, the mixture was adjusted to pH=5-6 with 1 N HCl and extracted with EtOAc (20 mL×3). The combined organic layer was dried, filtered and concentrated. The crude residue was purified by Prep-TLC (10% MeOH in DCM) to provide the title product (186c) (290 mg, 74%) as a white solid. m/z (ESI, +ve ion)=281.1 [M+H]$^+$.

Step D. 2-(((S)-4-(2-((2,4-Dichlorophenoxy)methyl) oxazole-5-carbonyl)-2-methylpiperazin-1-yl) methyl)-1-(((S)-oxetan-2-yl)methyl)-1H-benzo[d] imidazole-6-carboxylic acid (186)

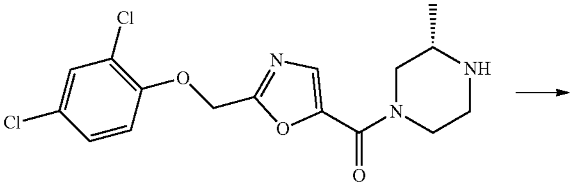

186b

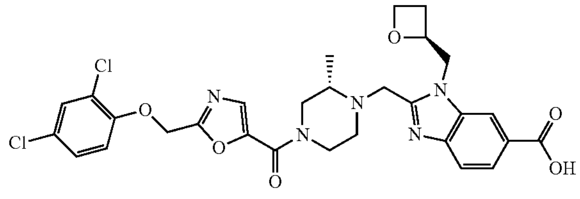

186

To a solution of 186b (78 mg, 0.21 mmol) and 186c (61 mg, 0.22 mmol) in DMF (3 mL) was added DIPEA (85 mg, 0.66 mmol). The mixture was stirred at 50° C. for 16 h. The mixture was purified by reversed phase HPLC (45% $CH_3CN$ in $H_2O$, with 0.05% TFA as a modifier) to afford the TFA salt of the title product (186) (6.5 mg, 4.2%) as a white solid. 1H NMR (400 MHZ, $CD_3OD$) δ 8.49 (s, 1H), 8.17 (dd, J=8.6, 1.3 Hz, 1H), 7.83 (d, J=8.6 Hz, 1H), 7.70 (s, 1H), 7.42 (s, 1H), 7.26 (dt, J=22.0, 5.6 Hz, 2H), 5.36 (s, 2H), 5.31-5.17 (m, 1H), 4.77-4.85 (m, 2H), 4.61-4.70 (m, 2H), 4.45 (dt, J=9.2, 5.9 Hz, 1H), 4.22 (d, J=16.4 Hz, 1H), 3.98-4.17 (m, 2H), 3.65 (br s, 1H), 3.48 (br s, 1H), 2.91-3.16 (m, 2H), 2.77-2.90 (m, 1H), 2.65-2.81 (m, 1H), 2.52 (ddd, J=16.4, 11.5, 7.3 Hz, 1H), 1.20 (s, 3H). m/z (ESI, +ve ion)=614.1 [M+H]$^+$.

Example 189. 2-((4-Cyano-4-((2-((2,4-dichlorophenoxy)methyl)pyridin-4-yl)methyl)piperidin-1-yl) methyl)-1-((1-ethyl-1H-imidazol-5-yl)methyl)-1H-benzo[d]imidazole-6-carboxylic acid (189)

189

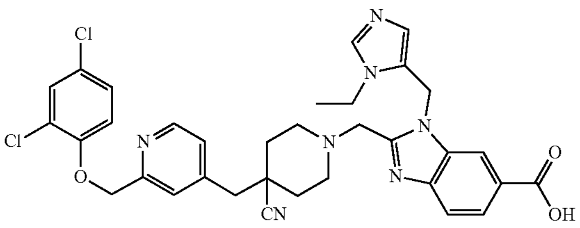

Step A. tert-Butyl 4-cyano-4-((2-((2,4-dichlorophenoxy)methyl)pyridin-4-yl)methyl)piperidine-1-carboxylate (189a)

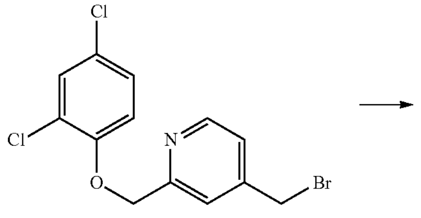

150c

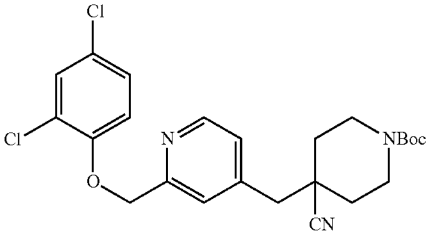

189a

To a solution of diisopropylamine (0.20 mL, 1.39 mmol) in THF (2 mL) at −78° C., n-butyllithium in hexanes (0.61 mL, 1.52 mmol) was added dropwise. The resulting solution was warmed to room temperature and stirred for 30 min before cooling to −78° C. again. A solution of tert-butyl 4-cyanopiperidine-1-carboxylate (0.21 g, 0.99 mmol) in THF (1.5 mL) was added dropwise. The reaction was stirred for 30 min, followed by the careful addition of 150c (0.23 g, 0.66 mmol). The reaction was allowed to slowly warm to room temperature and stirred overnight. Saturated $NH_4Cl$ solution (10 mL) was added and the reaction was extracted with EtOAc (10 mL×3). The combined organic layer was washed with brine (10 mL), dried over $Na_2SO_4$, concentrated and purified by silica gel column chromatography (gradient elution, 60-100% EtOAc in hexanes) to afford the title product (150d) (0.027 g, 9%) as a colorless oil. m/z (ESI, +ve ion)=476.3 [M+H]$^+$.

Step B. 4-((2-((2,4-Dichlorophenoxy)methyl)pyridin-4-yl)methyl)piperidine-4-carbonitrile (189b)

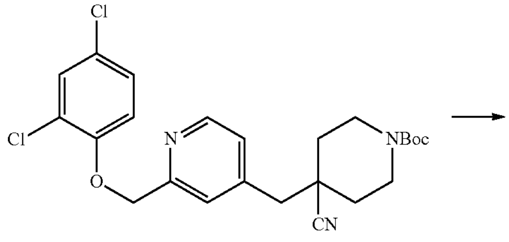

189a

-continued

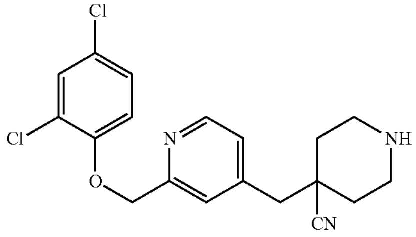

189b

A solution of 189a (9.3 mg, 0.020 mmol) in DCM (1 mL) and TFA (0.5 mL) was stirred at room temperature for 10 min. After completion, the solvent was removed under reduced pressure. The resulting residue was diluted with EtOAc (3 mL) and washed with sat. $NaHCO_3$ (5 mL), brine (3 mL), dried with $Na_2SO_4$, filtered, and concentrated to afford the crude title product (189b) (6.8 mg) as a yellow oil, which was used in the next step without further purification. m/z (ESI, +ve ion)=376.3 $[M+H]^+$.

Step C. 2-((4-Cyano-4-((2-((2,4-dichlorophenoxy)methyl)pyridin-4-yl)methyl)piperidin-1-yl)methyl)-1-((1-ethyl-1H-imidazol-5-yl)methyl)-1H-benzo[d]imidazole-6-carboxylic acid (189)

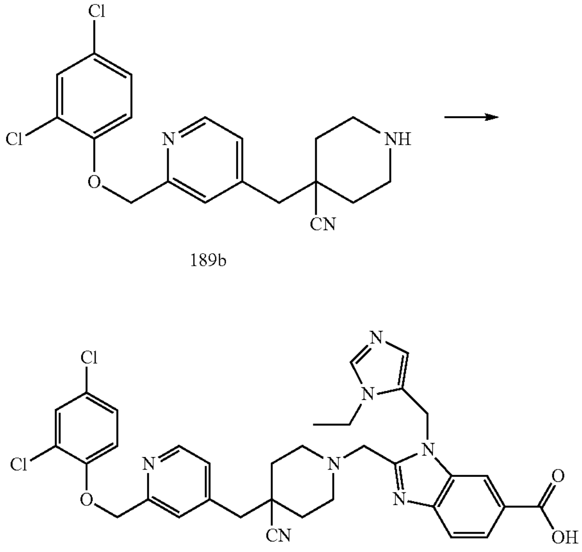

189b

189

The title product (189) was prepared in similar procedures as described in Example 150, Steps G and H. $^1H$ NMR (600 MHZ, $CD_3OD$) δ ppm 9.06 (d, J=1.5 Hz, 1H), 8.56 (d, J=5.1 Hz, 1H), 8.22 (d, J=1.1 Hz, 1H), 8.06 (dd, J=8.6, 1.7 Hz, 1H), 7.80 (d, J=8.1 Hz, 1H), 7.63 (s, 1H), 7.42 (d, J=2.6 Hz, 1H), 7.41 (dd, J=5.3, 1.7 Hz, 1H), 7.25 (dd, J=8.8, 2.6 Hz, 1H), 7.11 (d, J=8.8 Hz, 1H), 7.10 (d, J=1.5 Hz, 1H), 5.90 (s, 2H), 5.30 (s, 2H), 4.34 (q, J=7.3 Hz, 2H), 4.17 (s, 2H), 3.13 (br d, J=11.7 Hz, 2H), 3.03 (s, 2H), 2.64 (t, J=11.9 Hz, 2H), 1.88 (br d, J=12.8 Hz, 2H), 1.67 (dd, J=1.0, 1.0 Hz, 2H), 1.53 (t, J=7.3 Hz, 3H). m/z (ESI, +ve ion)=658.3 $[M+H]^+$.

Example 198. (S)-2-((4-((6-((2,4-Dichlorophenoxy)methyl)pyridin-2-yl)oxy)piperidin-1-yl)methyl)-1-(oxetan-2-ylmethyl)-1H-benzo[d]imidazole-6-carboxylic acid (198)

198

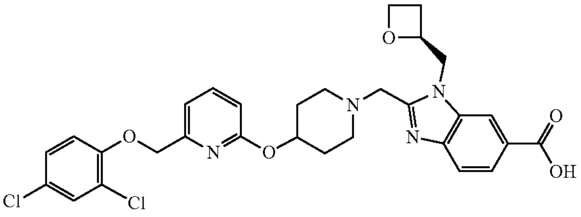

Step A. 2-Bromo-6-((2,4-dichlorophenoxy)methyl)pyridine (198a)

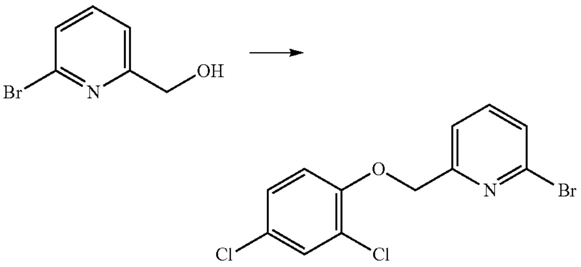

198a

To a solution of (6-bromopyridin-2-yl)methanol (1.57 g, 8.35 mmol) in anhydrous THF (16.7 mL) at 0° C. was added DIAD (2.53 g, 12.5 mmol), $PPh_3$ (3.29 g, 12.5 mmol) and 2,4-dichlorophenol (1.36 g, 8.35 mmol). The resulting mixture was stirred at room temperature for 1.5 h and sat. $NaHCO_3$ (10 mL) was added. The mixture was extracted with EtOAc (10 mL×3), washed with brine (10 mL), dried over $Na_2SO_4$, filtered, concentrated and the crude residue was purified by silica gel column chromatography (gradient elution, 0-20% EtOAc in hexanes) to provide the title product (198a) (738 mg, 27%). m/z (ESI, +ve ion)=334.0 $[M+H]^+$.

Step B. tert-Butyl 4-((6-((2,4-dichlorophenoxy)methyl)pyridin-2-yl)oxy)piperidine-1-carboxylate (198b)

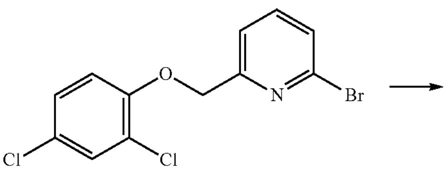

198a

-continued

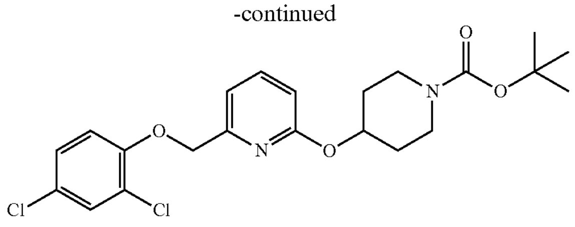

198b

To a solution of tert-butyl 4-hydroxypiperidine-1-carboxylate (44 mg, 0.22 mmol) in anhydrous DMF (1.1 mL) was added NaH (13 mg, 0.33 mmol, 60% dispersion in mineral oil) at 0° C. After stirring for 10 min, the reaction was heated to 50° C. and a solution of 198a (80 mg, 0.24 mmol) in DMF (0.6 mL) was added dropwise. After stirring for 8 h, the reaction mixture was cooled down to room temperature and quenched with $H_2O$ (1 mL). The crude mixture was extracted with EtOAc (3 mL×2), washed with brine (3 mL), dried over $Na_2SO_4$, filtered, concentrated and the crude residue was purified by silica gel column chromatography (gradient elution, 0-50% EtOAc in hexanes) to afford the title product (198b) (39 mg, 40%). m/z (ESI, +ve ion)=453.3 $[M+H]^+$.

Step C. 2-((2,4-Dichlorophenoxy)methyl)-6-(piperidin-4-yloxy)pyridine (198c)

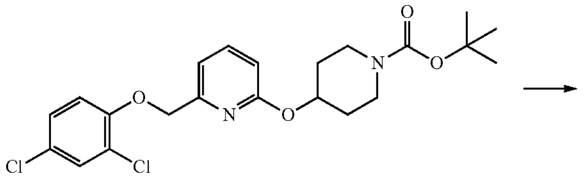

198b

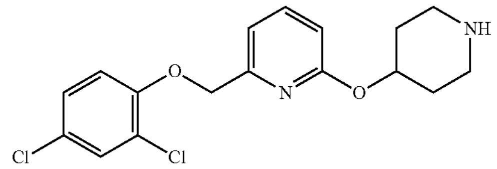

198c

To a solution of 198b (37 mg, 0.082 mmol) in anhydrous $CH_2Cl_2$ (0.8 mL) was added TFA (0.3 mL, 4.1 mmol) at room temperature. After stirring for 1 h, the reaction was concentrated and sat. $NaHCO_3$ (0.5 mL) was added to neutralize the TFA. The mixture was extracted with EtOAc (2 mL×3) and the combined organic layer was dried over $Na_2SO_4$, filtered, and concentrated to afford the crude title product (198c) (28 mg), which was used in the next step without further purification. m/z (ESI, +ve ion)=353.3 $[M+H]^+$.

Step D. Methyl(S)-2-((4-((6-((2,4-dichlorophenoxy)methyl)pyridin-2-yl)oxy)piperidin-1-yl)methyl)-1-(oxetan-2-ylmethyl)-1H-benzo[d]imidazole-6-carboxylate (198d)

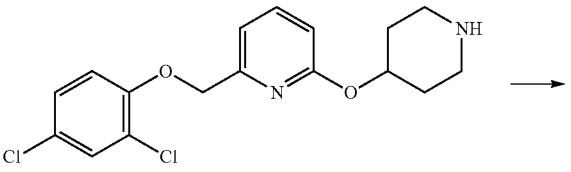

198c

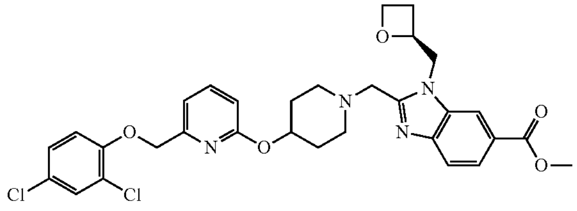

198d

To a solution of crude 198c (8 mg, 0.023 mmol) in dichloroethane (0.2 mL) was added 1h (8 mg, 0.027 mmol) and DIPEA (0.01 mL, 8.8 mg, 0.068 mmol) at room temperature. The reaction was heated to 60° C. After 20 h, the reaction was cooled down to room temperature and concentrated to provide the crude title product (198d), which was used in the next step without further purification. m/z (ESI, +ve ion)=611.3 $[M+H]^+$.

Step E. (S)-2-((4-((6-((2,4-Dichlorophenoxy)methyl)pyridin-2-yl)oxy)piperidin-1-yl)methyl)-1-(oxetan-2-ylmethyl)-1H-benzo[d]imidazole-6-carboxylic acid (198)

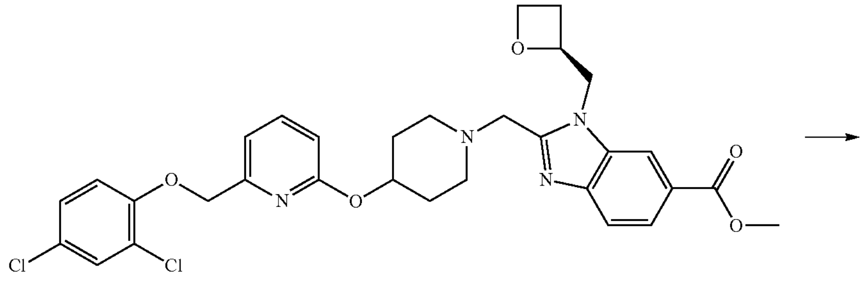

198d

-continued

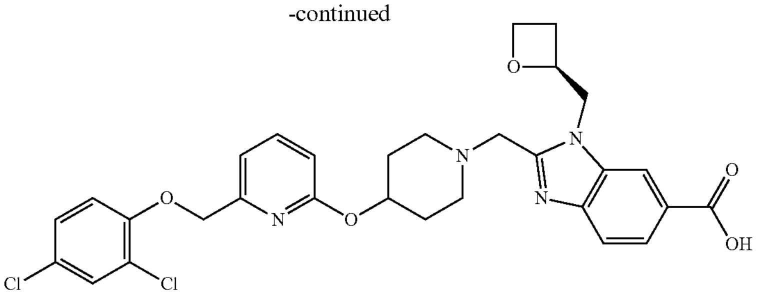

198

The crude 198d was dissolved in THF/$H_2O$ (1:1, 0.4 mL) at room temperature. LiOH·$H_2O$ (5 mg, 0.11 mmol) and a few drops of MeOH were added to the mixture and heated to 50° C. After stirring for 1 h, the reaction was acidified with 1 N HCl to adjust to pH=5. The mixture was concentrated and purified by reverse phase HPLC (gradient elution, 0-70% $CH_3CN$ in water with 0.1% TFA as a modifier) to provide the title product (198) (13.8 mg, 86% over 3 steps) as a white solid. m/z (ESI, +ve ion)=597.3 $[M+H]^+$. $^1H$ NMR (600 MHZ, $CD_3OD$) δ ppm 8.35 (s, 1H), 8.05 (dd, J=8.62, 1.28 Hz, 1H), 7.81 (d, J=8.44 Hz, 1H), 7.74 (t, J=7.89 Hz, 1H), 7.44 (d, J=2.57 Hz, 1H), 7.25 (dd, J=8.99, 2.38 Hz, 1H), 7.17 (d, J=6.97 Hz, 1H), 7.11 (d, J=8.80 Hz, 1H), 6.79 (br d, J=8.07 Hz, 1H), 5.36 (br s, 1H), 5.22 (ddd, J=14.49, 7.15, 2.20 Hz, 1H), 5.17 (s, 2H), 4.87 (s, 2H), 4.63-4.71 (m, 3H), 4.43 (dt, J=9.17, 5.87 Hz, 1H), 3.57-3.78 (m, 4H), 2.77-2.84 (m, 1H), 2.50 (ddd, J=16.69, 11.55, 7.34 Hz, 1H), 2.16-2.36 (m, 4H).

Examples 199, 214, 246, 247, and 264 were synthesized in similar procedures as described in Example 198.

Examples 248, 249 were synthesized in similar procedures as described in Example 198, with $NH_4OH$ used as the modifier for the last step purification.

Example 200 was synthesized in similar procedures as described in Example 114.

Examples 202 and 203 (stereochemistry arbitrarily assigned) were synthesized from (3-bromophenyl)methanol and 2,4-dichlorophenol in similar procedures as described in Example 131, Step A, then Example 152, step B to step C, then chiral separation by UPCC (Daicel CHIRALPAK AD_3, 3*150 mm, $CO_2$/MeOH (0.1% DEA)=50/50), followed by Example 152, Step D.

Examples 204 and 205. (R)-2-((4-((3-((2,4-dichlorophenoxy)methyl)phenyl)(methoxy)methyl)piperidin-1-yl)methyl)-1-((1-ethyl-1H-imidazol-5-yl)methyl)-1H-benzo[d]imidazole-6-carboxylic acid (204) and(S)-2-((4-((3-((2,4-dichlorophenoxy)methyl)phenyl)(methoxy)methyl)piperidin-1-yl)methyl)-1-((1-ethyl-1H-imidazol-5-yl)methyl)-1H-benzo[d]imidazole-6-carboxylic acid (205)

204

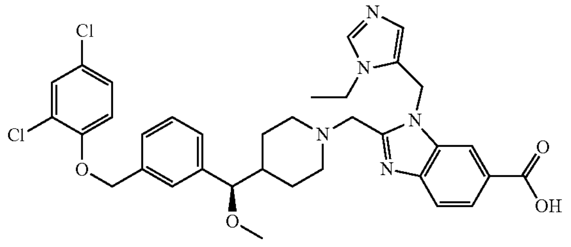

205

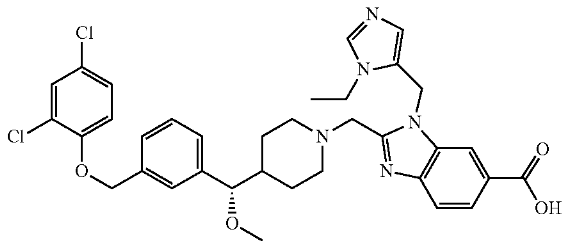

Step A. tert-Butyl 4-((3-((2,4-dichlorophenoxy)methyl)phenyl)(methoxy)methyl)piperidine-1-carboxylate (204a)

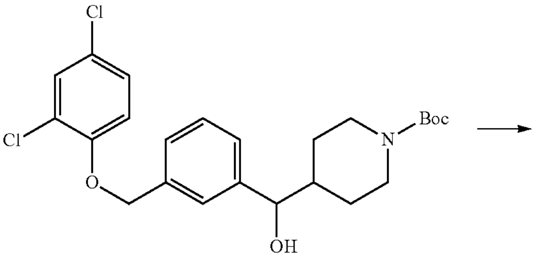

204a

-continued

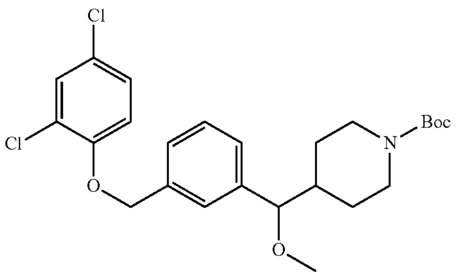

204b

To a mixture of NaH (86 mg, 2.1 mmol, 60% dispersion in mineral oil) in THF (15 mL) was added a THF (20 mL) solution of 204a (made by following similar procedures as 130b) (500 mg, 1.1 mmol). The reaction was stirred at 0° C. for 30 min. Then $CH_{31}$ (759 mg, 5.3 mmol) was added. The reaction was allowed to warm to room temperature and stirred for 48 h under $N_2$. After completion, the reaction was quenched with $H_2O$ (20 mL), extracted with EtOAc (20 mL×3). The combined organic layer was washed with $H_2O$ (10 mL), brine (10 mL), dried over anhydrous $Na_2SO_4$, filtered and concentrated to give a crude residue, which was purified by silica gel column chromatography (petroleum ether:EtOAc=10:1) to afford the title product (204b) (400 mg, 74%) as a yellow oil. m/z (ESI, +ve ion)=502.2 $[M+Na]^+$.

Step B. tert-Butyl(R)-4-((3-((2,4-dichlorophenoxy)methyl)phenyl)(methoxy)methyl)piperidine-1-carboxylate (204b-P1) and tert-butyl(R)-4-((3-((2,4-dichlorophenoxy)methyl)phenyl)(methoxy)methyl)piperidine-1-carboxylate (204b-P2)

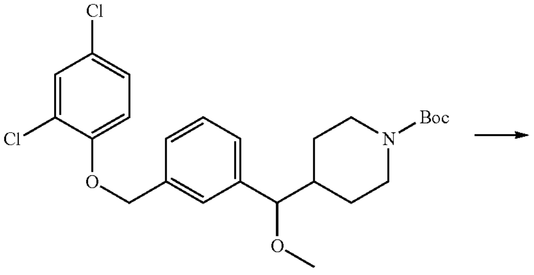

204b

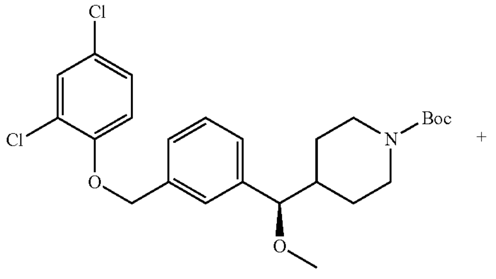

204b-P1

-continued

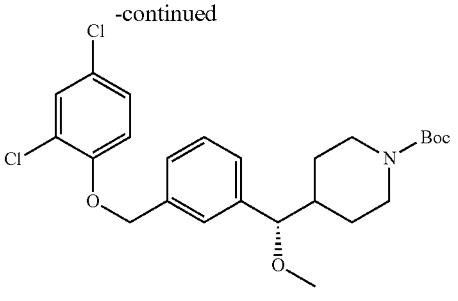

204b-P2

The title products (204b-P1 and 204b-P2) were obtained through chiral separation of 204b by UPCC (Daicel CHIRALPAK IA 4.6*250 mm, $CO_2$/MeOH (0.1% DEA)=80:20). 204b-P1: 130 mg, RT=1.186 min, white solid; 204b-P2: 140 mg, RT=1.441 min, white solid. The stereochemistry is arbitrarily assigned.

Step C. (R)-2-((4-((3-((2,4-Dichlorophenoxy)methyl)phenyl)(methoxy)methyl)piperidin-1-yl)methyl)-1-((1-ethyl-1H-imidazol-5-yl)methyl)-1H-benzo[d]imidazole-6-carboxylic acid (204) and(S)-2-((4-((3-((2,4-dichlorophenoxy)methyl)phenyl)(methoxy)methyl)piperidin-1-yl)methyl)-1-((1-ethyl-1H-imidazol-5-yl)methyl)-1H-benzo[d]imidazole-6-carboxylic acid (205)

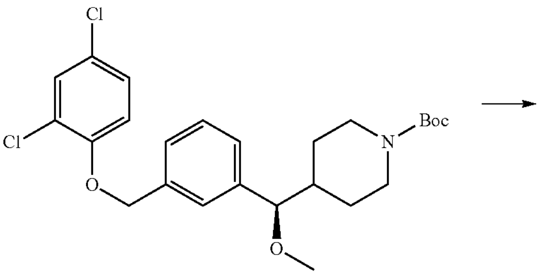

204b-P1

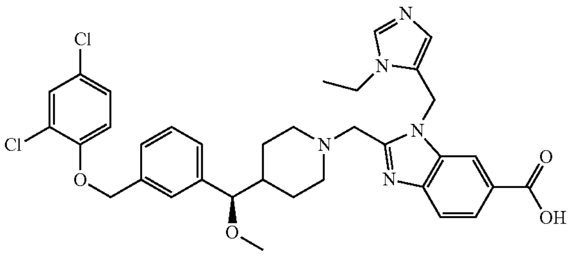

204

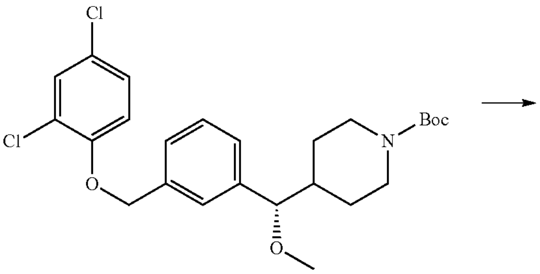

204b-P2

-continued

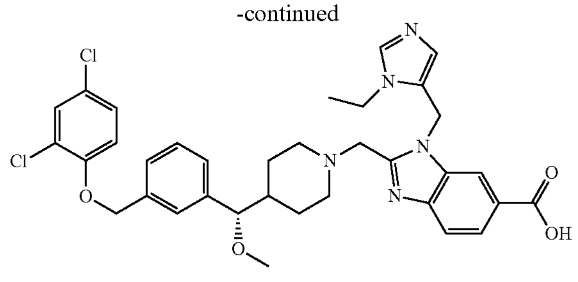

205

The title compound 204 was synthesized in similar procedures from 204b-P1 as described in Example 152, Step B to D. m/z (ESI, +ve ion)=662.3 $[M+H]^+$. $^1H$ NMR (400 MHz, $CD_3OD$) δ ppm 8.89-8.97 (m, 2H), 8.23 (s, 1H), 8.05 (dd, J=8.5, 1.5 Hz, 1H), 7.83 (d, J=8.3 Hz, 1H), 7.37-7.46 (m, 3H), 7.20-7.29 (m, 2H), 7.12 (d, J=8.7 Hz, 1H), 6.99 (br s, 1H), 5.82 (s, 2H), 5.21 (s, 2H), 4.45-4.65 (m, 2H), 4.30 (q, J=7.3 Hz, 2H), 4.02 (br d, J=7.0 Hz, 1H), 3.50-3.74 (m, 2H), 3.20 (s, 3H), 2.78-3.05 (m, 2H), 2.10 (br s, 1H), 1.88 (br s, 1H), 1.45-1.67 (m, 6H). m/z (ESI, +ve ion)=662.3.

The title compound 205 was synthesized in similar procedures from 204b-P2 as described in Example 152, Step B to D. m/z (ESI, +ve ion)=662.3 $[M+H]^+$. $^1H$ NMR (400 MHz, $CD_3OD$) δ ppm 8.12 (s, 1H), 7.97 (dd, J=8.5, 1.1 Hz, 1H), 7.74 (s, 1H), 7.64 (d, J=8.7 Hz, 1H), 7.41 (d, J=2.2 Hz, 1H), 7.18-7.29 (m, 2H), 7.08 (d, J=8.7 Hz, 1H), 6.82-6.88 (m, 2H), 6.85 (dd, J=8.2 Hz, 1H), 6.52 (s, 1H), 5.76 (s, 2H), 5.14 (s, 2H), 4.31-4.39 (m, 1H), 4.09 (q, J=7.4 Hz, 2H), 4.83 (s, 2H), 3.30 (s, 3H), 2.66-2.78 (m, 2H), 2.35 (br t, J=8.9 Hz, 2H), 1.81-1.93 (m, 2H), 1.52-1.77 (m, 2H), 1.22-1.38 (m, 4H).

Example 206. (S)-2-((4-(3-((2-Cyano-4-fluorophenoxy)methyl)phenoxy)piperidin-1-yl)methyl)-1-(oxetan-2-ylmethyl)-1H-benzo[d]imidazole-6-carboxylic acid (206)

206

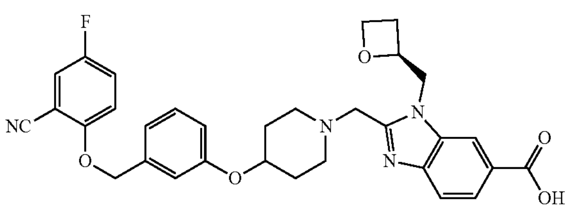

Step A. tert-Butyl 4-(3-(methoxycarbonyl)phenoxy) piperidine-1-carboxylate (206a)

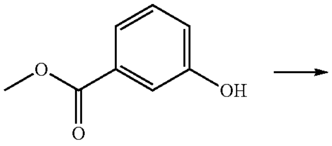

-continued

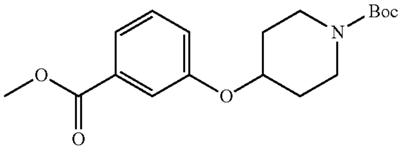

206a

A mixture of methyl 3-hydroxybenzoate (4.88 g, 32.1 mmol), tert-butyl(4-hydroxypiperidin-1-yl) formate (6.5 g, 32.1 mmol), $PPh_3$ (12.63 g, 48.1 mmol) in THF (30 mL) was added DEAD (8.39 g, 48.1 mmol) at 0° C. under $N_2$. The mixture was stirred at 20° C. for 18 h and concentrated in vacuo. The crude residue was purified by silica gel column chromatography (petroleum ether:EtOAc=10:1) to afford the title product (206a) (4.3 g) with some impurity as a white solid. m/z (ESI, +ve ion)=358.1 $[M+Na]^+$.

Step B. tert-Butyl 4-(3-(hydroxymethyl)phenoxy) piperidine-1-carboxylate (206b)

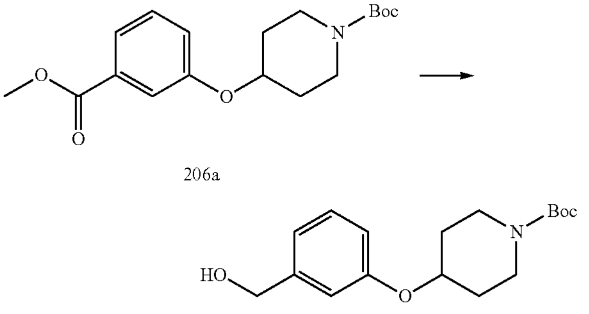

206a

206b

A solution of 206a (4.3 g, 12.8 mmol) in THF (40 mL) was cooled down to 0° C. Lithium aluminum hydride (15.4 mL, 15.3 mmol, 1 N in THF) was added and the reaction was stirred at 0° C. for 1.5 h. The reaction was quenched with $Na_2SO_4 \cdot 10H_2O$ (15 g) at 0° C. After stirring at the same temperature for 20 min, the mixture was filtered and concentrated in vacuo to give a crude residue, which was purified by silica gel column chromatography (petroleum ether:EtOAc=3:1) to provide the title product (206b) (3.2 g, 77%) as a colorless oil. m/z (ESI, +ve ion)=330.1 $[M+Na]^+$.

Step C. tert-Butyl 4-(3-((2-cyano-4-fluorophenoxy) methyl)phenoxy)piperidine-1-carboxylate (206c)

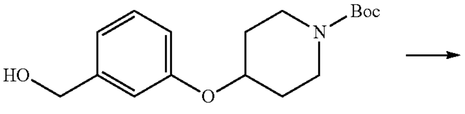

206b

-continued

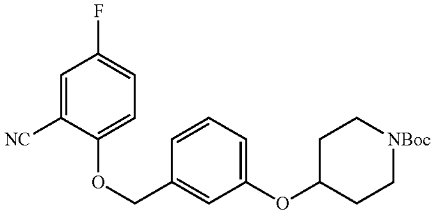

206c

To a solution of 206b (50 mg, 0.16 mmol, 1.0 eq) in DMF (1.5 mL) was added NaH (10 mg, 0.24 mmol, 60% dispersion in mineral oil) at 0° C. and stirred for 30 min at the same temperature. A solution of 2,5-difluorobenzonitrile (23 mg, 0.17 mmol) in DMF (0.5 mL) was added. After stirring at 20° C. for 2 h, the mixture was poured into ice water (8 mL), and extracted with EtOAc (8 mL×2). The combined organic layer was washed with $H_2O$ (3 mL), brine (3 mL), dried over $Na_2SO_4$, filtered and concentrated in vacuo to give the title product (206c) (65 mg) with some impurity as a white solid. m/z (ESI, +ve ion)=449.1 $[M+Na]^+$.

Step D. 5-Fluoro-2-((3-(piperidin-4-yloxy)benzyl)oxy)benzonitrile (206d)

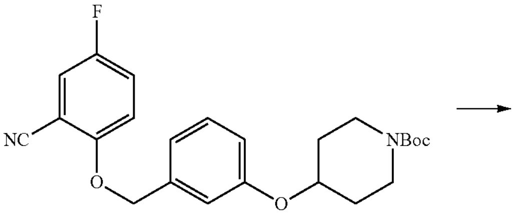

206c

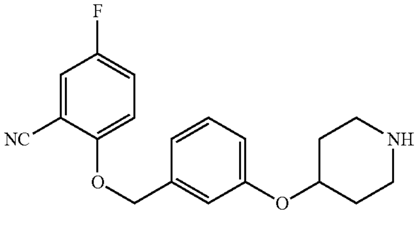

206d

To a solution of 206c (65 mg, 0.13 mmol) in DCM (1 mL) was added TFA (0.5 mL). The reaction was stirred at 18° C. for 1.5 h and was concentrated to give the crude title product (206d) (45 mg) as a yellow oil, which was used in the next step without further purification. m/z (ESI, +ve ion)=327.1 $[M+H]^+$.

Step E. Methyl(S)-2-((4-(3-((2-cyano-4-fluorophenoxy)methyl)phenoxy)piperidin-1-yl)methyl)-1-(oxetan-2-ylmethyl)-1H-benzo[d]imidazole-6-carboxylate (206e)

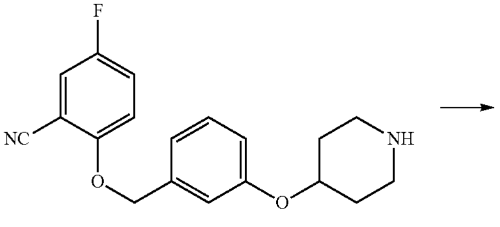

206d

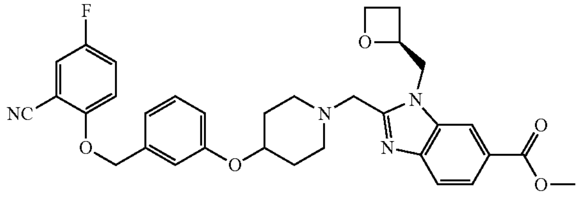

206e

A mixture of 206d (45 mg, 0.14 mmol), $K_2CO_3$ (56 mg, 0.41 mmol) in $CH_3CN$ (4 mL) was stirred at 20° C. for 20 min. KI (3 mg, 0.01 mmol) and 1h (40 mg, 0.14 mmol) were added and the reaction was stirred at 18° C. for another 1.5 h. The reaction was then diluted with EtOAc (15 mL), washed with $H_2O$ (5 mL), and brine (5 mL). The organic layer was dried over $Na_2SO_4$, filtered and concentrated in vacuo to provide the title product (206e) (20 mg, 20%) as a white solid which was used in the next step without further purification. m/z (ESI, +ve ion)=585.2 $[M+H]^+$.

Step F. (S)-2-((4-(3-((2-Cyano-4-fluorophenoxy)methyl)phenoxy)piperidin-1-yl)methyl)-1-(oxetan-2-ylmethyl)-1H-benzo[d]imidazole-6-carboxylic acid (206)

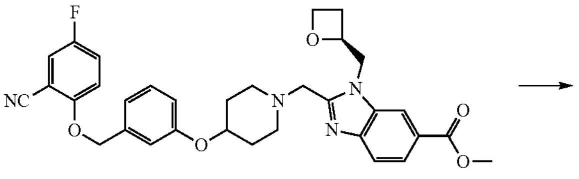

206e

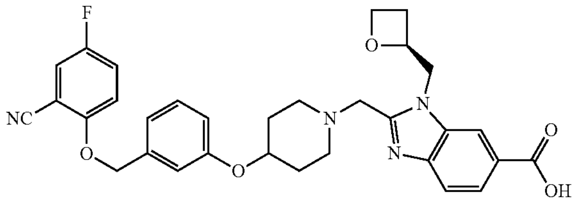

206

To a solution of 206e (20 mg, 0.03 mmol) in $CH_3OH/H_2O$ (3 mL, 1:1) was added LiOH (10 mg, 0.3 mmol). The reaction was stirred at 30° C. for 18 h, adjusted to pH=7 with 1 N HCl, and extracted with DCM/$CH_3OH$ (10:1) (5 mL×2).

The organic layer was concentrated in vacuo to give a crude residue, which was purified by prep-TLC (silica gel, DCM/$CH_3OH$=10:1) to provide the title product (206) (7.2 mg, 35.1%) as a white solid. m/z (ESI, +ve ion)=571.2 $[M+H]^+$. $^1$H NMR (400 MHz, $CD_3OD$) δ ppm 8.33 (d, J=0.9 Hz, 1H), 7.97 (dd, J=8.5, 1.5 Hz, 1H), 7.67 (d, J=8.3 Hz, 1H), 7.46 (dd, J=8.1, 3.3 Hz, 1H), 7.37 (ddd, J=9.3, 8.0, 3.3 Hz, 1H), 7.21-7.31 (m, 2H), 7.09 (s, 1H), 7.01 (d, J=7.4 Hz, 1H), 6.90 (dd, J=8.1, 2.0 Hz, 1H), 5.20-5.29 (m, 3H), 4.86-4.93 (m, 1H), 4.72 (dd, J=15.7, 2.6 Hz, 1H), 4.65 (td, J=7.6, 6.1 Hz, 1H), 4.46 (dt, J=9.2, 5.9 Hz, 2H), 3.92-4.09 (m, 2H), 2.75-2.93 (m, 3H), 2.47-2.58 (m, 3H), 1.98-2.09 (m, 2H), 1.81 (ddd, J=12.5, 8.4, 4.4 Hz, 2H).

Examples 317 were synthesized in similar procedures as described in Example 206, with THF used as the solvent in the last step.

Examples 207, 221 were synthesized in similar procedures as described in the synthesis of 157a, followed by Example 152, Steps C to D.

Example 208. 2-((4-(3-((2,4-Dichlorophenoxy)methyl)phenoxy)piperidin-1-yl)methyl)-1-(isoxazol-5-ylmethyl)-1H-benzo[d]imidazole-6-carboxylic acid (208)

208

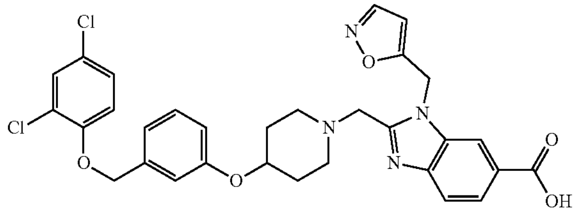

Step A. tert-Butyl 2-((4-(3-((2,4-dichlorophenoxy)methyl)phenoxy)piperidin-1-yl)methyl)-1-(isoxazol-5-ylmethyl)-1H-benzo[d]imidazole-6-carboxylate (208a)

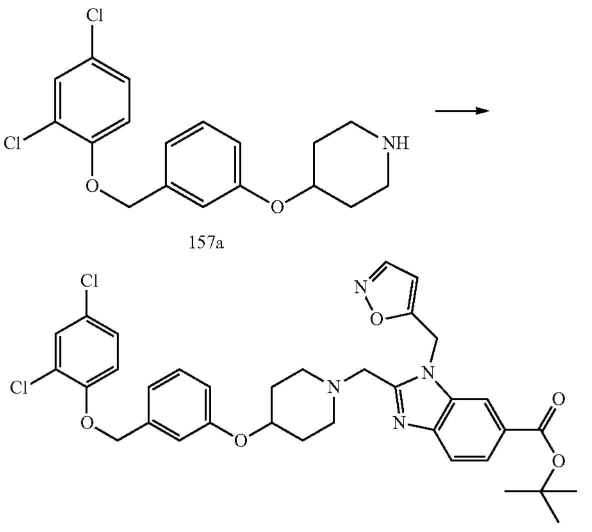

157a

208a

To a mixture of tert-butyl 2-(chloromethyl)-3-(1,2-oxazol-5-ylmethyl)-1,3-benzodiazole-5-carboxylate (30 mg, 0.086 mmol, synthesized in similar procedures as 57f), 157a (33 mg, 0.095 mmol) and potassium carbonate (36 mg, 0.259 mmol) in DMF (1 mL) was added potassium iodide (29 mg, 0.173 mmol). The reaction was stirred at 20° C. for 3 h. After completion, the reaction was diluted with $H_2O$ (5 mL) and extracted with EtOAc (10 mL×3). The combined organic layer was dried, filtered, concentrated and purified by silica gel column chromatography (petroleum ether: EtOAc=3:1) to afford the title product (208a) (35 mg, 58%) as a white solid. m/z (ESI, +ve ion)=663.2 $[M+H]^+$.

Step B. 2-((4-(3-((2,4-Dichlorophenoxy)methyl)phenoxy)piperidin-1-yl)methyl)-1-(isoxazol-5-ylmethyl)-1H-benzo[d]imidazole-6-carboxylic acid (208)

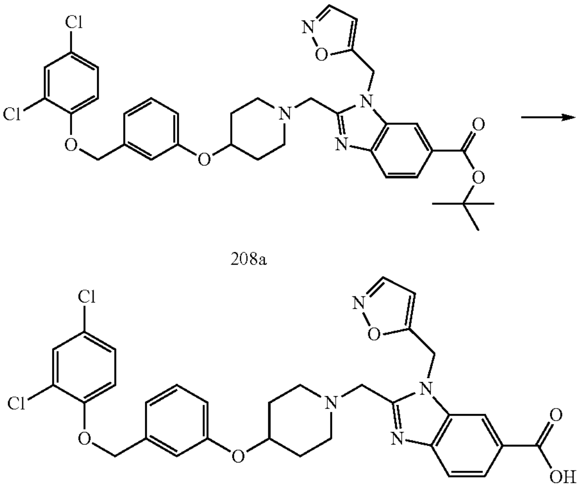

208a

208

A solution of 208a (20 mg, 0.03 mmol) in 4 N HCl in dioxane (1 mL) was stirred at 18° C. for 2 h. After completion, the reaction was cooled down in an ice bath. 1 N NaOH was added to the mixture to adjust to pH=5. The reaction mixture was then extracted with EtOAc (5 mL×3). The combined organic layer was dried, filtered, concentrated and purified by silica gel column chromatography (petroleum ether:EtOAc=2:1) to afford the title product (208) (9.4 mg, 51%) as a white solid. m/z (ESI, +ve ion)=607.2 $[M+H]^+$. $^1$H NMR (400 MHZ, $CD_3OD$) δ 8.35 (d, J=1.80 Hz, 1H), 8.20 (s, 1H), 7.99 (d, J=8.44 Hz, 1H), 7.67 (d, J=8.44 Hz, 1H), 7.41 (d, J=2.52 Hz, 1H), 7.18-7.28 (m, 2H), 7.07 (d, J=8.88 Hz, 1H), 6.96-7.03 (m, 2H), 6.86 (dd, J=8.12, 2.1 Hz, 1H), 6.30 (d, J=1.72 Hz, 1H), 5.95 (s, 2H), 5.13 (s, 2H), 4.36 (s, 1H), 3.94 (s, 2H), 2.76 (s, 2H), 2.41 (t, J=8.64 Hz, 2H), 1.88 (s, 2H), 1.65 (d, J=8.9 Hz, 2H)

Examples 257, 280 were synthesized from 145d in similar procedures as described in Example 208. tert-Butyl 1-((1-(tert-butoxycarbonyl)azetidin-3-yl)methyl)-2-(chloromethyl)-1H-benzo[d]imidazole-6-carboxylate was used for Example 280 at the last step.

Example 215 was synthesized in similar procedures as described in Example 145.

Example 216. 2-((4-(3-((2,4-Dichlorophenoxy)methyl)phenoxy)piperidin-1-yl)methyl)-1-(oxazol-5-ylmethyl)-1H-benzo[d]imidazole-6-carboxylic acid (216)

216

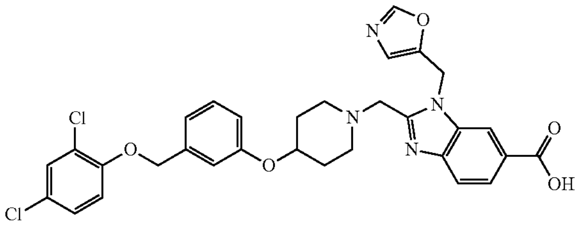

Step A. tert-Butyl 2-((4-(3-((2,4-dichlorophenoxy)methyl)phenoxy)piperidin-1-yl)methyl)-1-(oxazol-5-ylmethyl)-1H-benzo[d]imidazole-6-carboxylate (216a)

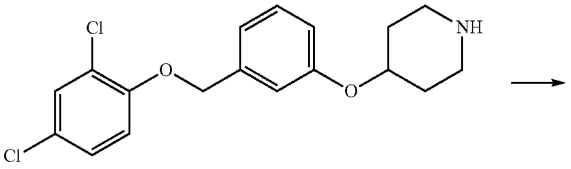

157a

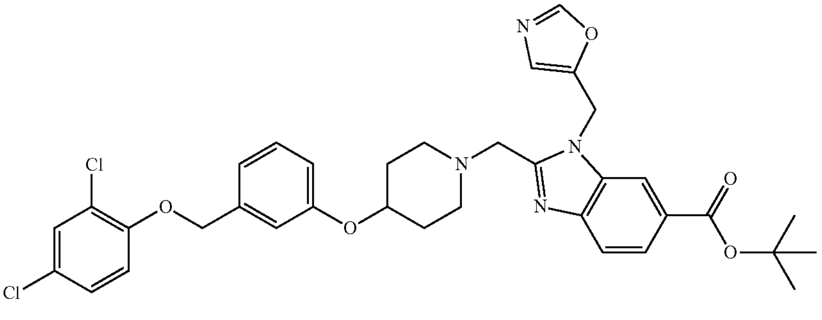

216a

To a solution of 157a (10 mg, 0.028 mmol) and tert-butyl 2-(chloromethyl)-1-(oxazol-5-ylmethyl)-1H-benzo[d]imidazole-6-carboxylate (9.9 mg, 0.028 mmol) in DMF (1 mL) was added $Et_3N$ (57.5 mg, 0.57 mmol). The resulting mixture was stirred at room temperature overnight. The crude mixture was directly purified by reverse phase HPLC (gradient elution, $CH_3CN$ in $H_2O$ containing 0.1% TFA as a modifier, 20-100%) to afford the title product (216a) (17 mg, 90%) as a white solid. m/z (ESI, +ve ion)=663.3 $[M+H]^+$.

Step B. 2-((4-(3-((2,4-Dichlorophenoxy)methyl) phenoxy)piperidin-1-yl)methyl)-1-(oxazol-5-ylmethyl)-1H-benzo[d]imidazole-6-carboxylic acid (216)

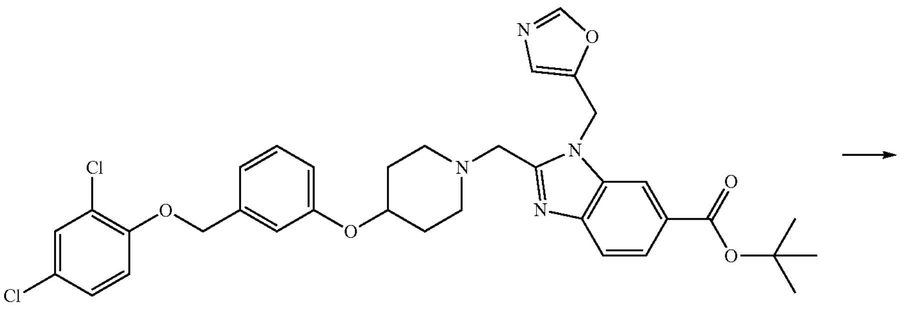

216a

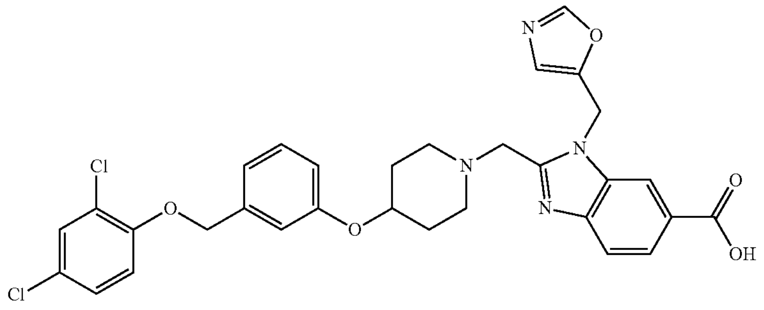

216

216a (17 mg, 0.026 mmol) was dissolved in a mixture containing TFA:triisopropylsilane:$H_2O$ (3.7 mL:0.1 mL:0.2 mL) in DCM (4 mL). The reaction was stirred at room temperature for 1 h. After completion, the reaction was concentrated in vacuo and redissolved in DMSO (1 mL) before reverse phase HPLC purification (gradient elution, $CH_3CN$ in $H_2O$ containing 0.1% TFA as a modifier, 0-90%) to afford the title product (216) as a white solid (13.4 mg, 72.5%). $^1H$ NMR (600 MHZ,) δ ppm 8.40 (d, J=1.10 Hz, 1H), 8.16 (s, 1H), 8.03 (dd, J=8.62, 1.65 Hz, 1H), 7.79 (d, J=8.44 Hz, 1H), 7.42 (d, J=2.57 Hz, 1H), 7.31-7.39 (m, 2H), 7.24 (dd, J=8.80, 2.57 Hz, 1H), 7.15 (s, 1H), 7.07-7.13 (m, 2H), 7.01 (dd, J=8.25, 2.38 Hz, 1H), 5.76 (s, 2H), 5.17 (s, 2H), 4.93 (s, 2H), 4.80 (br s, 1H), 3.72 (br s, 2H), 3.67 (br s, 2H), 2.32 (m, 2H), 2.24 (, 2H). m/z (ESI, +ve ion)=607.2 $[M+H]^+$.

Examples 217 and 232 were synthesized in similar procedures as described in Example 216.

Example 220. (S)-2-((4-((2-((2-Chloro-4-fluorophenoxy)methyl)pyridin-4-yl)oxy)piperidin-1-yl) methyl)-1-(oxetan-2-ylmethyl)-1H-benzo[d]imidazole-6-carboxylic acid (220)

220

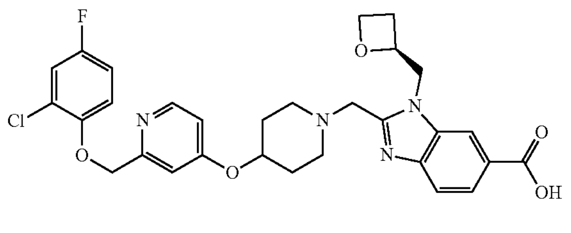

Step A. tert-Butyl 4-((2-(((methylsulfonyl)oxy) methyl)pyridin-4-yl)oxy)piperidine-1-carboxylate (220a)

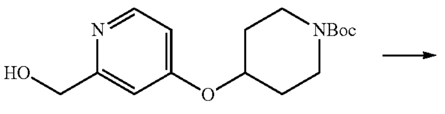

145b

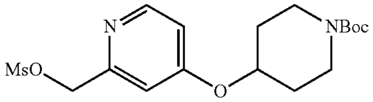

220a

To a solution of 145b (50 mg, 0.16 mmol) in DCM (3 mL) was added $Ms_2O$ (157 mg, 0.48 mmol) and $Et_3N$ (80 mg, 0.8 mmol) at 0° C. The mixture was stirred at 5° C. for 1 h. After completion, the mixture was quenched with $H_2O$ (2 ml) and extracted with EtOAc (5 ml×3). The combined organic layer was dried over anhydrous $Na_2SO_4$, filtered and concentrated to afford the crude title product (220a) (80 mg), which was used in the next step without further purification.

Step B. tert-Butyl 4-((2-((2-chloro-4-fluorophenoxy)methyl)pyridin-4-yl)oxy)piperidine-1-carboxylate (220b)

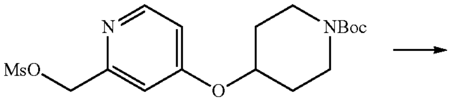

220a

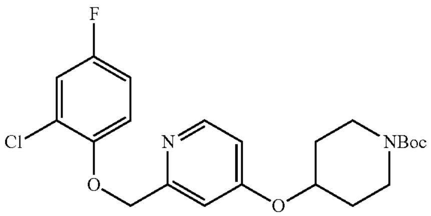

220b

To a solution of crude 220a (80 mg, 0.21 mmol) in DMF (5 mL) was added 2-chloro-4-fluorophenol (30 mg, 0.21 mmol) and $Cs_2CO_3$ (105 mg, 0.32 mmol) at 20° C. The mixture was heated at 50° C. for 5 h. After completion, the reaction was quenched by $H_2O$ (10 mL) and extracted with EtOAc (5 mL×3). The combined organic layer was dried over anhydrous $Na_2SO_4$, filtered, and concentrated to afford a crude residue, which was purified by silica gel column chromatography (petroleum ether:EtOAc=1:1) to afford the title product 220b (80 mg, 87%). m/z (ESI, +ve ion)=437.1 $[M+H]^+$.

Step C. 2-((2-Chloro-4-fluorophenoxy)methyl)-4-(piperidin-4-yloxy)pyridine (220c)

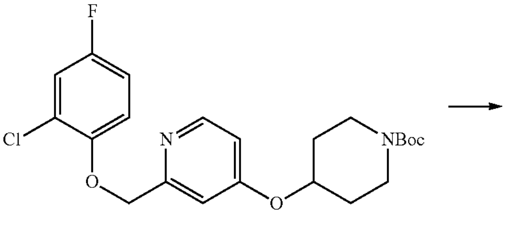

220b

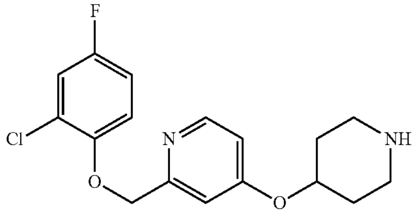

220c

To a solution of 220b (80 mg, 0.18 mmol) in DCM (3 mL) was added TFA (0.6 mL) at 0° C. The resulting mixture was stirred at 20° C. for 1 h. After completion, the reaction was concentrated to afford the crude title product (220c) (100 mg), which was used in the next step without further purification. m/z (ESI, +ve ion)=337.1 $[M+H]^+$.

Step D. Methyl(S)-2-((4-((2-((2-chloro-4-fluorophenoxy)methyl)pyridin-4-yl)oxy)piperidin-1-yl) methyl)-1-(oxetan-2-ylmethyl)-1H-benzo[d]imidazole-6-carboxylate (220d)

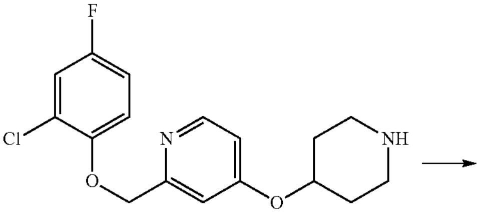

220c

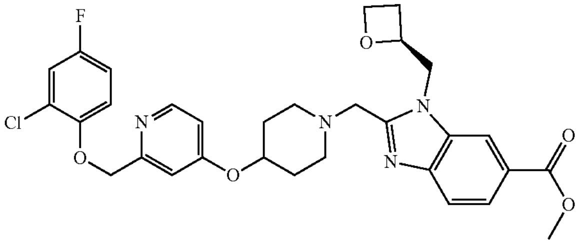

220d

To a solution of 220c (50 mg, 0.15 mmol) in $CH_3CN$ (3 mL) was added 1h (44 mg, 0.15 mmol) and $K_2CO_3$ (124 mg, 0.9 mmol) at 0° C. The resulting mixture was stirred at 20° C. for 4 h. After completion, the reaction was concentrated and purified by prep-TLC (EtOAc:MeOH=10:1) to afford the title product (220d) (40 mg, 38%). m/z (ESI, +ve ion)=595.2 $[M+H]^+$.

Step E. (S)-2-((4-((2-((2-Chloro-4-fluorophenoxy) methyl)pyridin-4-yl)oxy)piperidin-1-yl)methyl)-1-(oxetan-2-ylmethyl)-1H-benzo[d]imidazole-6-carboxylic acid (220)

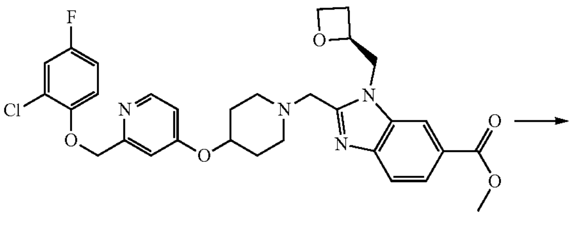

220d

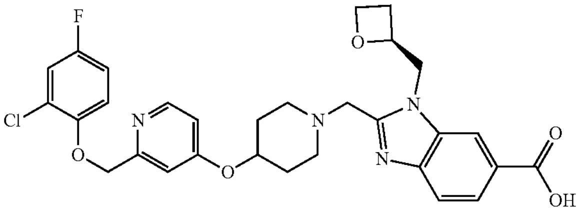

220

To a solution of 220d (15 mg, 0.03 mmol) in MeOH/THF/$H_2O$ (1:1:1, 3 mL) was added LiOH (7.3 mg, 0.3 mmol). The resulting mixture was stirred at 20° C. for 3 h. After completion, the mixture was quenched with 1 N HCl aq. (0.5 mL) to adjust to pH=6, extracted with EtOAc (5 mL×3). The combined organic layer was dried over anhydrous $Na_2SO_4$, filtered and concentrated to provide a crude product, which was purified by reverse phase HPLC ($CH_3CN$ in $H_2O$, with 0.05% TFA as a modifier) to afford the title product (220) (7.4 mg, 48%). m/z (ESI, +ve ion) =581.2 $[M+H]^+$. $^1H$ NMR (400 MHZ, $CD_3OD$) δ ppm 8.56 (d, J=6.54 Hz, 1H), 8.36 (d, J=0.87 Hz, 1H) 8.05 (dd, J=8.50, 1.53 Hz, 1H), 7.80 (d, J=8.72 Hz, 1H), 7.53 (d, J=2.18 Hz, 1H), 7.35 (dd, J=6.32, 2.40 Hz, 1H), 7.29 (dd, J=7.85, 3.05 Hz, 1H), 7.21 (dd, J=9.16, 4.80 Hz, 1H), 7.08 (ddd, J=9.05, 7.96, 3.05 Hz, 1H), 5.32 (s, 2H), 5.18-5.26 (m, 1H), 5.07 (br s, 1H), 4.78-4.83 (m, 3H), 4.63-4.72 (m, 2H), 4.45 (dt, J=9.37, 5.78 Hz, 1H), 3.46-3.70 (m, 4H), 2.76-2.87 (m, 1H), 2.45-2.56 (m, 1H), 2.14-2.42 (m, 4H).

Examples 308, 352, 356, 357, 358, 359 were synthesized from 220a in similar procedures as described in Example 220. Examples 309, 318 were synthesized from 206b in similar procedures as described in Example 220. Example 316, 321, 322, 333, 354 were synthesized in similar procedures as described in Example 220. For all these compounds following Example 220 synthesis, DMF could be used as the solvent at the second to last step and THE used as the solvent in last step. Last step purification can have the option of no modifier in the reverse phase purification.

Example 378, 379 were synthesized in similar procedures as described in Example 220, except DIPEA/DMF was used in the second to last step instead of $K_2CO_3$. $NH_4OH$ was used as the modifier for the last step purification.

Example 288 was synthesized from 206b in similar procedures as described in Example 220. 4 N HCl in dioxane was used to remove the Boc group (Step C) instead of TFA. Example 294 was synthesized in similar procedures as described in Example 288. The mesylate analog of 57f derived from 145e was used in the second to last step.

Example 290 was synthesized from methyl 6-hydroxypicolinate and tert-butyl(2S,4S)-4-hydroxy-2-methylpiperidine-1-carboxylate as described in Example 271, Steps A to B, followed by Example 220, Steps A to E. Example 291 was synthesized in similar procedures as described in Example 290.

Example 224 was synthesized from 157a in similar procedures as described in Example 155, Steps E and F.

Example 227 is the side product of the last step hydrolysis of Example 168.

Example 230. 2-((4-((2-((4-Chloro-2-fluorophenoxy)methyl)pyridin-4-yl)oxy)piperidin-1-yl) methyl)-1-((1-ethyl-1H-imidazol-5-yl)methyl)-1H-benzo[d]imidazole-6-carboxylic acid (230)

230

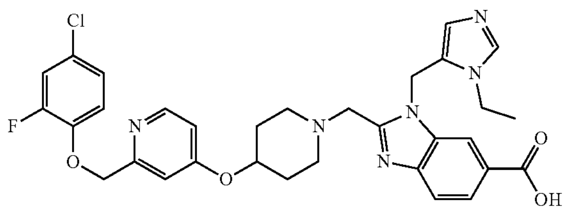

Step A. Methyl 2-((4-((2-((4-chloro-2-fluorophenoxy)methyl)pyridin-4-yl)oxy)piperidin-1-yl) methyl)-1-((1-ethyl-1H-imidazol-5-yl)methyl)-1H-benzo[d]imidazole-6-carboxylate (230b)

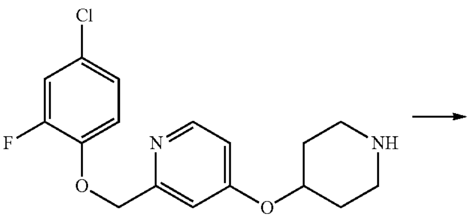

230a

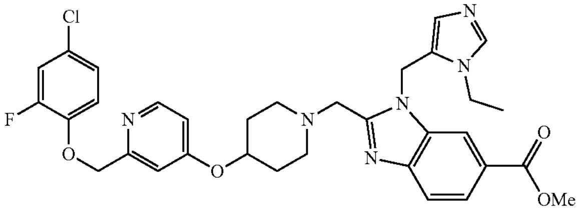

230b

A solution of 230a (prepared in similar procedures as 145d, 19.0 mg, 0.056 mmol), 57f (25.2 mg, 0.056 mmol) and DIPEA (0.02 mL, 1.13 mmol) in DMF (0.3 mL) was stirred at room temperature overnight. After completion, the reaction mixture was diluted with EtOAc (5 mL). The organic layer was washed with water (3 mL×2), brine (3 mL), dried over $Na_2SO_4$, filtered and concentrated and the resulting crude residue was purified by silica gel column chromatography (gradient elution, 0-20% MeOH in DCM) to afford the title product (230b) (7.6 mg, 21%) as a pale-yellow oil. m/z (ESI, +ve ion)=633.3 $[M+H]^+$.

Step B. 2-((4-((2-((4-Chloro-2-fluorophenoxy)methyl)pyridin-4-yl)oxy)piperidin-1-yl)methyl)-1-((1-ethyl-1H-imidazol-5-yl)methyl)-1H-benzo[d]imidazole-6-carboxylic acid (230)

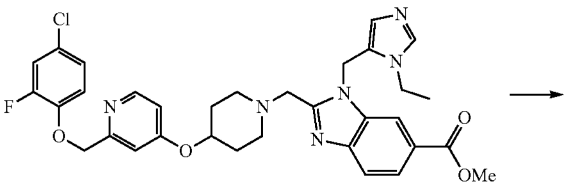

230b

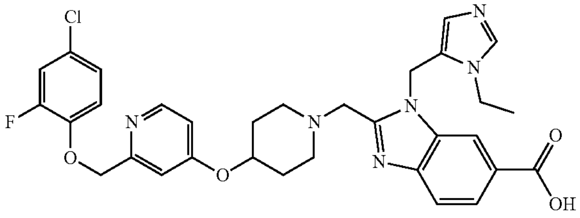

230

A solution of 230b (7.6 mg, 0.012 mmol) and LiOH (2.5 mg, 0.060 mmol) in THF:MeOH:$H_2O$=2:1:1 (0.4 mL) was stirred at 30° C. overnight. After completion, the reaction mixture was diluted with water to 1 mL and purified by reverse phase HPLC (gradient elution, 20-50% $CH_3CN$ in $H_2O$, with 0.1% TFA as a modifier) to afford the title product (230) (8.7 mg, 99%) as a white solid. m/z (ESI, +ve ion)=619.3 $[M+H]^+$. $^1H$ NMR (600 MHZ, $CD_3OD$) δ ppm 9.11 (d, J=1.1 Hz, 1H), 8.63 (d, J=7.0 Hz, 1H), 8.26 (s, 1H), 8.09 (dd, J=8.4, 1.5 Hz, 1H), 7.85 (d, J=8.8 Hz, 1H), 7.60 (d, J=2.6 Hz, 1H), 7.48 (dd, J=6.8, 2.8 Hz, 1H), 7.32 (dd, J=11.0, 2.2 Hz, 1H), 7.23-7.27 (m, 2H), 7.11 (d, J=1.1 Hz, 1H), 5.93 (s, 2H), 5.42 (s, 2H), 5.06 (br s, 1H), 4.50 (br s, 2H), 4.39 (q, J=7.2 Hz, 2H), 3.30-3.37 (m, 2H), 3.15-3.25 (m, 2H), 2.22-2.30 (m, 2H), 2.06 (br s, 2H), 1.59 (t, J=7.3 Hz, 3H).

Examples 259, 267 were synthesized in similar procedures as described in Example 230.

Example 250 was synthesized in similar procedures as described in Example 230, with the last step reverse phase HPLC purification using 0.05% $NH_4OH$ as a modifier.

Examples 336, 344, 345, 362, 365 were synthesized in similar procedures as described in Example 250. Example 346 is the side product isolated in the last step synthesis of Example 345. Example 364 was synthesized from 274c in similar procedures as described in Example 250.

Example 277 was synthesized in similar procedures as described in Example 230, with the last step product purified through normal phase silica gel column chromatography.

Example 302, 335, 337, and 363 was synthesized in similar procedures as described in Example 277.

Example 231 was synthesized from 4-(3-((4-chloro-2-fluorophenoxy)methyl)phenoxy)piperidine (following similar procedures of 145d) and 57f as described in Example 155, Steps E and F.

Examples 242 and 243 were synthesized in similar procedures as described in Example 231.

Example 239. 2-((4-((2-((4-Chloro-2-isocyanophenoxy)methyl)pyridin-4-yl)oxy)piperidin-1-yl)methyl)-1-(oxazol-2-ylmethyl)-1H-benzo[d]imidazole-6-carboxylic acid (239)

239

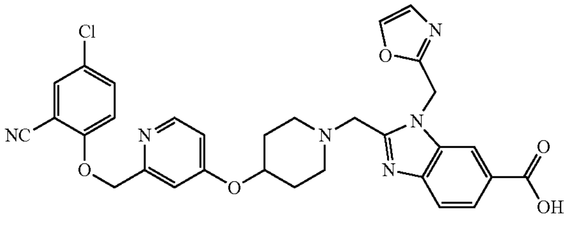

Step A. tert-Butyl 2-((4-((2-((4-chloro-2-isocyanophenoxy)methyl)pyridin-4-yl)oxy)piperidin-1-yl)methyl)-1-(oxazol-2-ylmethyl)-1H-benzo[d]imidazole-6-carboxylate (239b)

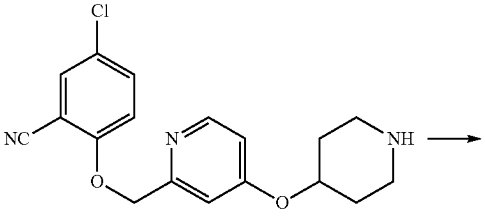

239a

-continued

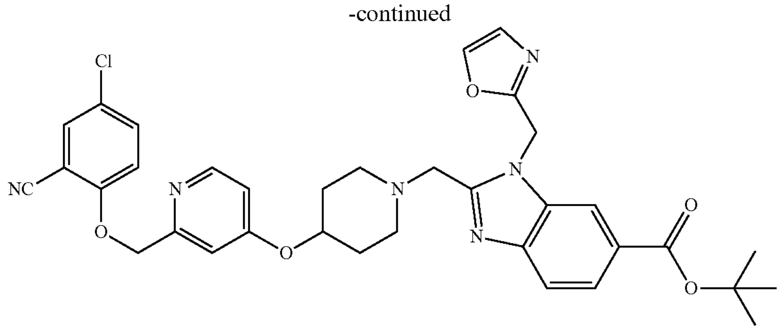

239b

A solution of 239a (prepared in similar procedures as 145d, 13.0 mg, 0.038 mmol), tert-butyl 2-(chloromethyl)-1-(oxazol-2-ylmethyl)-1H-benzo[d]imidazole-6-carboxylate (13.2 mg, 0.038 mmol) and DIPEA (132.0 μL, 0.76 mmol) in DMF (0.4 mL) was stirred at room temperature for 2 h. After completion, the reaction mixture was diluted with EtOAc (5 mL). The organic layer was washed with water (3 mL×2), brine (3 mL), dried over $Na_2SO_4$, filtered and concentrated and the resulting crude residue was purified by silica gel column chromatography (gradient elution, 80-100% EtOAc/hexanes then 0-20% MeOH in DCM) to afford the title product (239b) (20.9 mg, 84%) as a colorless oil. m/z (ESI, +ve ion)=655.1 $[M+H]^+$.

Step B. 2-((4-((2-((4-Chloro-2-isocyanophenoxy)methyl)pyridin-4-yl)oxy)piperidin-1-yl)methyl)-1-(oxazol-2-ylmethyl)-1H-benzo[d]imidazole-6-carboxylic acid (239)

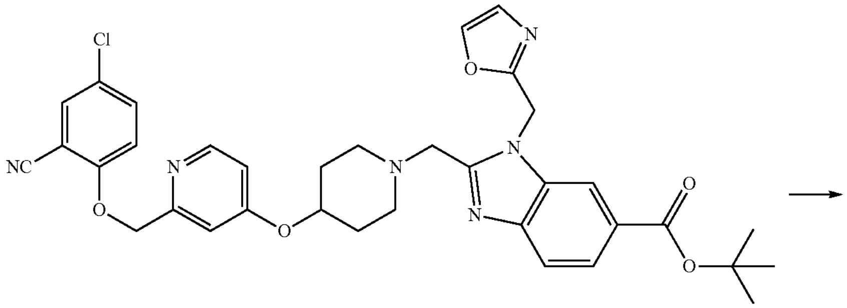

239b

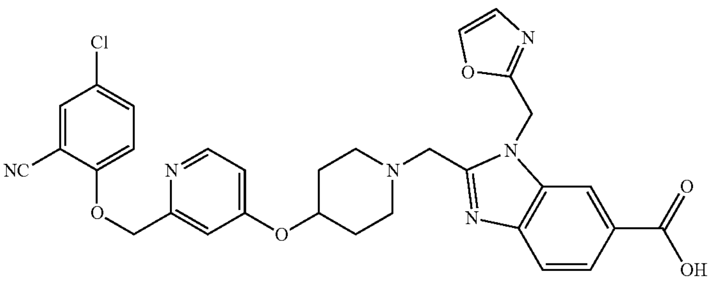

239

A solution of 239b (20.9 mg, 0.032 mmol) in DCM (1.0 mL) and TFA (1.0 mL) was stirred at room temperature overnight. After completion, the reaction solvent was removed under reduced pressure and the resulting residue was diluted with water to 1 mL and purified by reverse phase HPLC (gradient elution, 20-60% $CH_3CN$ in $H_2O$, with 0.1% TFA as a modifier) to afford the title product (239) (22.7 mg, 100%) as a white solid. m/z (ESI, +ve ion)=599.3 $[M+H]^+$. $^1H$ NMR (600 MHZ, $CD_3OD$) δ ppm 8.57 (d, J=8.2 Hz, 1H), 8.35 (d, J=1.1 Hz, 1H), 8.05 (dd, J=8.6, 1.7 Hz, 1H), 7.96 (d, J=1.1 Hz, 1H), 7.80 (d, J=8.1 Hz, 1H), 7.78 (d, J=2.6 Hz, 1H), 7.70 (dd, J=8.8, 2.6 Hz, 1H), 7.61 (d, J=2.6 Hz, 1H), 7.31-7.34 (m, 2H), 7.19 (d, J=1.1 Hz, 1H), 5.86 (s, 2H), 5.42 (s, 2H), 5.06 (br s, 1H), 4.75 (s, 2H), 3.55 (br s, 2H), 3.37-3.48 (m, 2H), 2.28-2.39 (m, 2H), 2.12-2.24 (m, 2H).

Examples 240, 241, 258, 265, 266 were synthesized in similar procedures as described in Example 239. Examples 268, 269, 270 were synthesized from the corresponding analogs of 198c in similar procedures as described in Example 239.

Examples 251, 252, 253 were synthesized in similar procedures as described in Example 198, Steps A to C, followed by Example 219, Steps A to B.

Example 254 was synthesized from methyl 3-hydroxybenzoate and tert-butyl(2S,4S)-4-hydroxy-2-methylpiperidine-1-carboxylate in similar procedures as described in Example 145, Steps A to D, followed by Example 155, Steps E and F.

Example 255 was synthesized from 157a in similar procedures as described in Example 152, Steps C and D.

Example 256 was synthesized from 186b and t-butyl ester analog of 57f in similar procedures as described in Example 208, Steps A and B.

Examples 260 and 263. (R)-2-((4-((3-((4-Chloro-2-cyanophenoxy)methyl)phenyl)fluoromethyl)piperidin-1-yl)methyl)-1-((1-ethyl-1H-imidazol-5-yl)methyl)-1H-benzo[d]imidazole-6-carboxylic acid (260) and(S)-2-((4-((3-((4-chloro-2-cyanophenoxy)methyl)phenyl)fluoromethyl)piperidin-1-yl)methyl)-1-((1-ethyl-1H-imidazol-5-yl)methyl)-1H-benzo[d]imidazole-6-carboxylic acid (263)

260

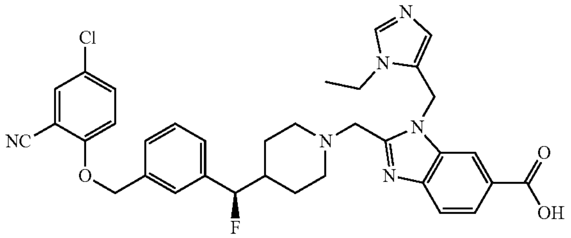

263

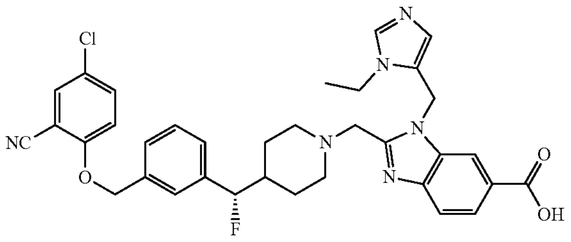

Step A. tert-Butyl 4-(hydroxy(3-(methoxycarbonyl)phenyl)methyl)piperidine-1-carboxylate (260a)

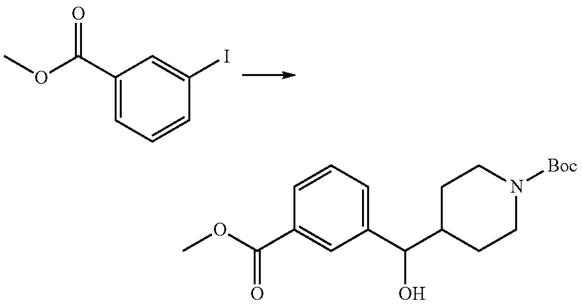

260a

A solution of methyl 3-iodobenzoate (3.5 g, 13.4 mmol) and isopropyl magnesium chloride (2 M in THF) (7.35 mL, 14.7 mmol) in anhydrous THF (30 mL) was stirred at −65° C. for 0.5 h. Then tert-butyl(4-formylpiperidin-1-yl) formate (3.16 g, 14.7 mmol) was added to the mixture. After stirring at 17° C. for 1 h, the reaction was quenched with saturated $NH_4Cl$ solution (100 mL) and extracted with ethyl acetate (100 mL×3). The organic layer was dried over $Na_2SO_4$, filtered, concentrated and purified by silica gel column chromatography (petroleum ether:EtOAc=7:3) to afford the title product (260a) (4.2 g, 85%) as a colorless oil. m/z (ESI, +ve ion)=372.2 $[M+Na]^+$.

Step B. tert-Butyl 4-(fluoro (3-(methoxycarbonyl)phenyl)methyl)piperidine-1-carboxylate (260b)

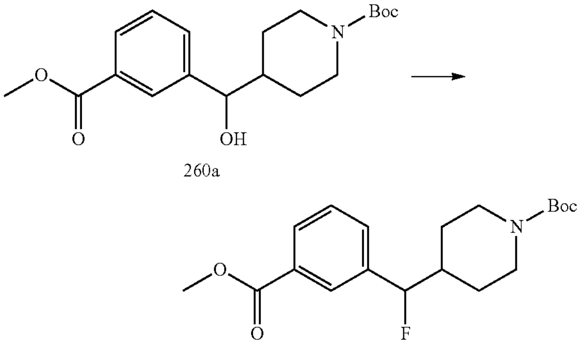

260a

260b

To a solution of 260a (4.2 g, 12 mmol, 1.0 eq) in THF (45 mL) was added Deoxo-Fluor (3.18 g, 14.4 mmol) at 0° C. The mixture was stirred at 0° C. for 2 h under $N_2$. After completion, saturated aqueous sodium bicarbonate solution was added to the mixture to adjust to pH=7 in ice bath. Then the reaction was diluted with $H_2O$ (100 mL) and extracted with EtOAc (100 mL×3). The combined organic layer was dried over $Na_2SO_4$, filtered, concentrated and purified by silica gel column chromatography (petroleum:EtOAc=8:2) to afford the title product (260b) (2.8 g, 62%) as a colorless oil. m/z (ESI, +ve ion)=374.2 $[M+Na]^+$.

Step C. tert-Butyl 4-(fluoro (3-(hydroxymethyl) phenyl)methyl)piperidine-1-carboxylate (260c)

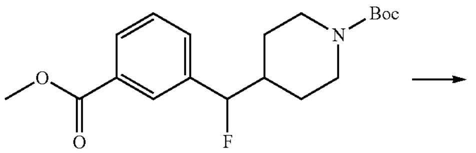

260b

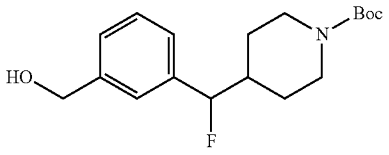

260c

A solution of 260b (2.7 g, 7.7 mmol) and $LiAlH_4$ (440 mg, 11.5 mmol) in THF (30 mL) was stirred at 0° C. for 1 h. After completion, the reaction was quenched with sodium sulfate decahydrate and the precipitates were rinsed with THF (50 mL×3). The combined organic layer was dried over $Na_2SO_4$, filtered, concentrated and purified by silica gel column chromatography (petroleum ether:EtOAc=7:3) to afford the title product (260c) (2.1 g, 79%) as colorless oil. m/z (ESI, +ve ion)=346.1 [M+Na].

Step D. tert-Butyl 4-((3-((4-chloro-2-cyanophenoxy)methyl)phenyl)fluoromethyl)piperidine-1-carboxylate (260d)

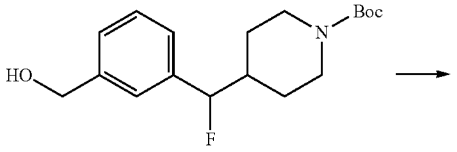

260c

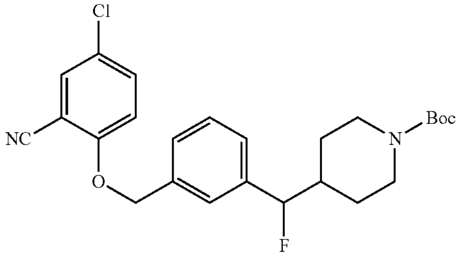

260d

A solution of 260c (2.17 g, 6.7 mmol), 5-chloro-2-hydroxybenzonitrile (1.03 g, 6.7 mmol), $PPh_3$ (2.64 g, 10.0 mmol) and DEAD (1.75 g, 10.0 mmol) in THF (20 mL) was stirred at 0° C. for 1 h and 25° C. for 12 h. After completion, the reaction was diluted with $H_2O$ (50 mL) and extracted with EtOAc (50 mL×3). The organic layer was dried over anhydrous $Na_2SO_4$, filtered, concentrated and purified by silica gel column chromatography (petroleum ether: EtOAc=9:1) to afford the title product (260d) (1.5 g, 46%) as a colorless oil. m/z (ESI, +ve ion)=481.2 $[M+Na]^+$.

Step E. tert-Butyl(R)-4-((3-((4-chloro-2-cyanophenoxy)methyl)phenyl)fluoromethyl)piperidine-1-carboxylate (260d-P1) and tert-butyl(S)-4-((3-((4-chloro-2-cyanophenoxy)methyl)phenyl) fluoromethyl)piperidine-1-carboxylate (260d-P2)

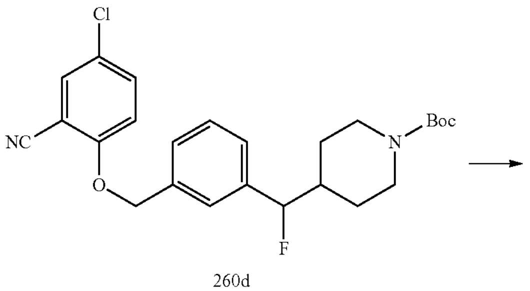

260d

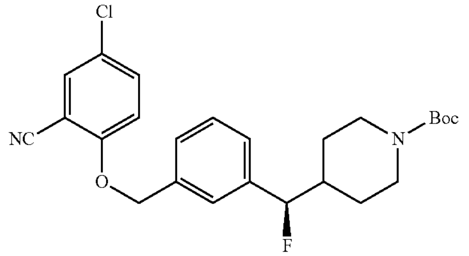

+

260d-P1

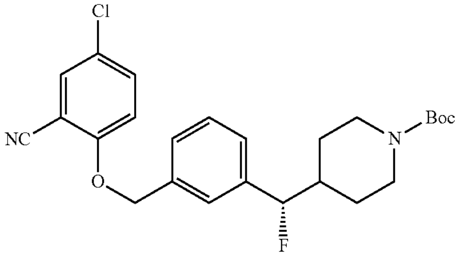

260d-P2

The title products (260d-P1 and 260d-P2) were obtained through chiral separation of 260d by UPCC (Daicel CHIRALPAK OJ=3 3*150 mm, $CO_2$/MeOH (0.1% DEA)=85/15) to afford 260d-P1 (130 mg, RT=2.911m) and 260d-P2 (140 mg, RT=3.321m) as a colorless oil. The stereochemistry of 260d-P1 and 260d-P2 are arbitrarily assigned.

Step F. (R)-2-((4-((3-((4-Chloro-2-cyanophenoxy)methyl)phenyl)fluoromethyl)piperidin-1-yl)methyl)-1-((1-ethyl-1H-imidazol-5-yl)methyl)-1H-benzo[d]imidazole-6-carboxylic acid (260) and(S)-2-((4-((3-((4-chloro-2-cyanophenoxy)methyl)phenyl)fluoromethyl)piperidin-1-yl)methyl)-1-((1-ethyl-1H-imidazol-5-yl)methyl)-1H-benzo[d]imidazole-6-carboxylic acid (263)

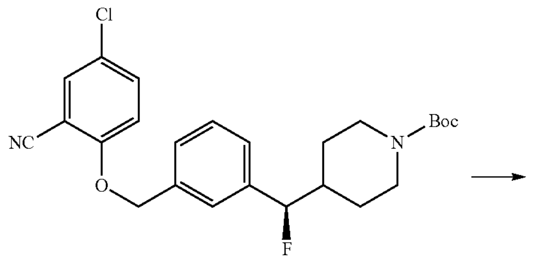

260d-P1

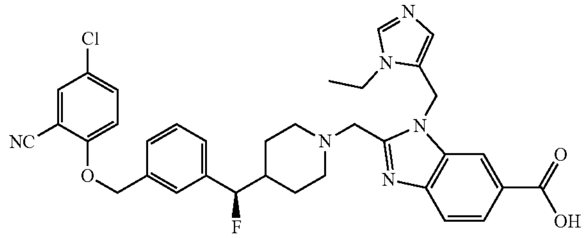

260

The title compound (260) was synthesized in similar procedures from 260d-P1 as described in Example 152, Step B to D. A 1:1 THF:$H_2O$ mixed solvent was used for the last step. m/z (ESI, +ve ion)=641.2 $[M+H]^+$. $^1H$ NMR (400 MHZ, $CD_3OD$) δ ppm 8.98 (d, J=1.0 Hz, 1H), 8.23 (d, J=0.7 Hz, 1H), 8.05 (dd, J=8.6, 1.7 Hz, 1H), 7.82 (d, J=8.3 Hz, 1H), 7.69 (d, J=2.7 Hz, 1H), 7.62 (dd, J=9.1, 2.7 Hz, 1H), 7.42-7.54 (m, 3H), 7.31-7.37 (m, 1H), 7.28 (d, J=9.1 Hz, 1H), 7.00 (d, J=1.2 Hz, 1H), 5.83 (s, 2H), 5.36 (dd, J=48.0, 8.0 Hz, 1H), 5.28-5.31 (m, 2H), 4.48 (br s, 2H), 4.32 (q, J=7.3 Hz, 2H), 3.45-3.63 (m, 2H), 2.73-2.92 (m, 2H), 2.02-2.20 (m, 2H), 1.97 (br d, J=15.4 Hz, 1H), 1.44-1.72 (m, 5H).

The title compound (263) was synthesized in similar procedures from 260d-P2 as described in Example 152, Step B to D. A 1:1 THF:$H_2O$ mixed solvent was used for the last step. m/z (ESI, +ve ion)=641.3 $[M+H]^+$. $^1H$ NMR (400 MHz, $CD_3OD$) δ=8.23 (d, J=0.73 Hz, 1H), 8.05 (dd, J=8.4, 1.6 Hz, 1H), 7.83 (d, J=8.6 Hz, 1H), 7.69 (d, J=2.7 Hz, 1H), 7.62 (dd, J=9.1, 2.7 Hz, 1H), 7.51 (s, 1H), 7.43-7.49 (m, 3H), 7.22-7.38 (m, 1H), 7.28 (d, J=9.1 Hz, 1H), 7.01 (s, 1H), 5.83 (s, 2H), 5.37 (dd, J=48.0, 8.0 Hz, 1H), 5.28 (s, 2H), 4.53 (br s, 2H), 4.33 (q, J=7.3 Hz, 2H), 3.50-3.68 (m, 2H), 2.79-2.99 (m, 2H), 2.05-2.22 (m, 1H), 1.99 (br d, J=13.5 Hz, 1H), 1.45-1.73 (m, 6H).

Example 261. 2-((4-((2-((4-Cyano-2-fluorophenoxy)methyl)pyrimidin-4-yl)oxy)piperidin-1-yl)methyl)-1-((1-ethyl-1H-imidazol-5-yl)methyl)-1H-benzo[d]imidazole-6-carboxylic acid (261)

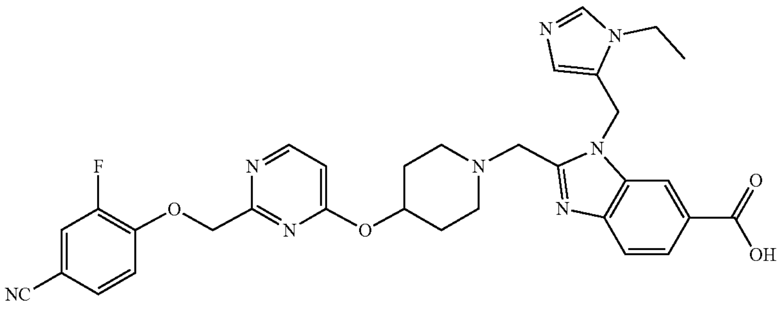 [SMILES: CCn1cncc1Cn1c(CN2CCC(Oc3ccnc(COc4ccc(C#N)cc4F)n3)CC2)nc2ccc(C(=O)O)cc21]

Step A. 4-((4-Chloropyrimidin-2-yl)methoxy)-3-fluorobenzonitrile (261a)

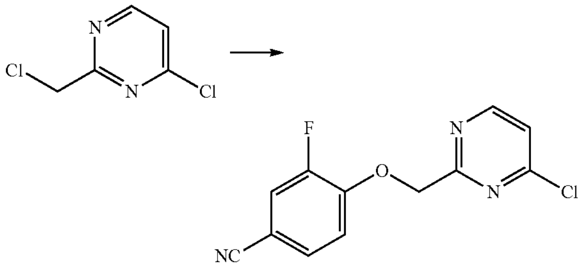

261a

A mixture of 3-fluoro-4-hydroxybenzonitrile (81.8 mg, 0.6 mmol) and 4-chloro-2-(chloromethyl)pyrimidine (81 mg, 0.5 mmol) in DMF (4 mL) was treated with $Cs_2CO_3$ (324 mg, 1 mmol) at room temperature. The reaction mixture was stirred for 2 h before quenched with water (50 mL) and extracted with EtOAc (20 mL×3). The combined organic layer was washed with brine, dried with $Na_2SO_4$, filtered and concentrated in vacuo. The crude residue was purified by silica gel column chromatography (EtOAc in hexanes) to provide the title product (261a) (93 mg, 71%) as a white solid. m/z (ESI, +ve ion)=264.1 $[M+H]^+$.

Step B. tert-Butyl 4-((2-((4-cyano-2-fluorophenoxy)methyl)pyrimidin-4-yl)oxy)piperidine-1-carboxylate (261b)

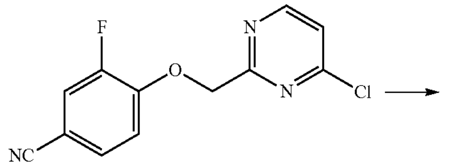

261a

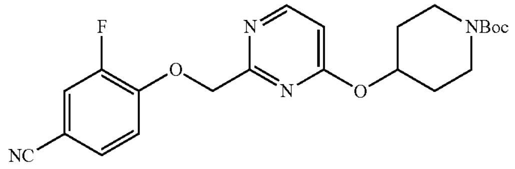

261b

A reaction vial was charged with 261a (18.7 mg, 0.071 mmol), tert-butyl 4-hydroxypiperidine-1-carboxylate (17.1 mg, 0.085 mmol), $Cs_2CO_3$ (46.2 mg, 0.14 mmol) and degassed with Ar, followed by addition of dry toluene (4 mL) under an Ar balloon. The same preparation was applied to a separate vial containing a solution of $Pd_2(dba)_3$ (2.9 mg, 0.004 mmol) and BINAP (4.4 mg, 0.0071 mmol) in dry toluene (2 mL), heated up to 110° C. for 5 min, which was then transferred to the first reaction vial using syringe. The resulting reaction mixture was heated at 110° C. overnight. Upon completion, the reaction solvent was removed in vacuo, and the residue was diluted with EtOAc/$H_2O$ and extracted with EtOAc. The organic layer was dried over $Na_2SO_4$, filtered, concentrated and purified by silica gel column chromatography to provide the title product (261b) (25 mg, 82%). m/z (ESI, +ve ion)=429.3 $[M+H]^+$.

Step C. 3-Fluoro-4-((4-(piperidin-4-ylmethyl)pyrimidin-2-yl)methoxy)benzonitrile (261c)

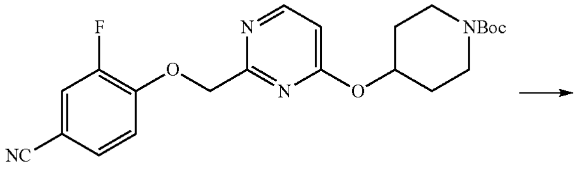

261b

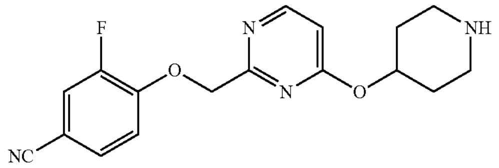

261c 261b (149 mg, 0.35 mmol) was dissolved in a solution of TFA (2 mL) in DCM (5 mL). After stirring for 10 min, the reaction was concentrated in vacuo. The resulting residue was re-dissolved in DMSO (1 mL) and purified by reverse phase HPLC (gradient elution, 0-60% $CH_3CN$ in $H_2O$ containing 0.1% TFA as a modifier) to afford the title product (261c) (117 mg, 76%) as a white solid. m/z (ESI, +ve ion)=329.3 $[M+H]^+$.

Step D. Methyl 2-((4-((2-((4-cyano-2-fluorophenoxy)methyl)pyrimidin-4-yl)oxy)piperidin-1-yl)methyl)-1-((1-ethyl-1H-imidazol-5-yl)methyl)-1H-benzo[d]imidazole-6-carboxylate (261d)

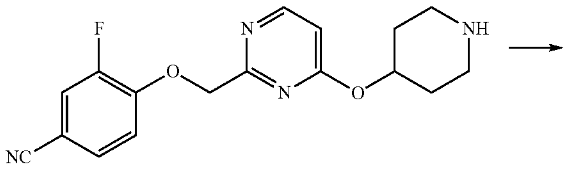

261c

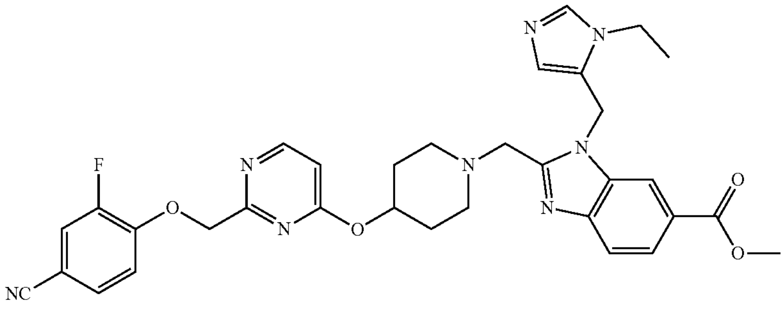

261d

To a solution of 261c (TFA salt, 7.3 mg, 0.017 mmol) and 57f (6.6 mg, 0.02 mmol) in DMF (1 mL) was added $Et_3N$ (33.4 mg, 0.33 mmol). The resulting mixture was stirred at room temperature overnight then purified by reverse phase HPLC (gradient elution, 0-75% $CH_3CN$ in $H_2O$ containing 0.1% TFA as a modifier) to provide the title product (261d) (9.2 mg, 75%) as a white solid. m/z (ESI, +ve ion)=625.3 $[M+H]^+$.

Step E. 2-((4-((2-((4-Cyano-2-fluorophenoxy)methyl)pyrimidin-4-yl)oxy)piperidin-1-yl)methyl)-1-((1-ethyl-1H-imidazol-5-yl)methyl)-1H-benzo[d]imidazole-6-carboxylic acid (261)

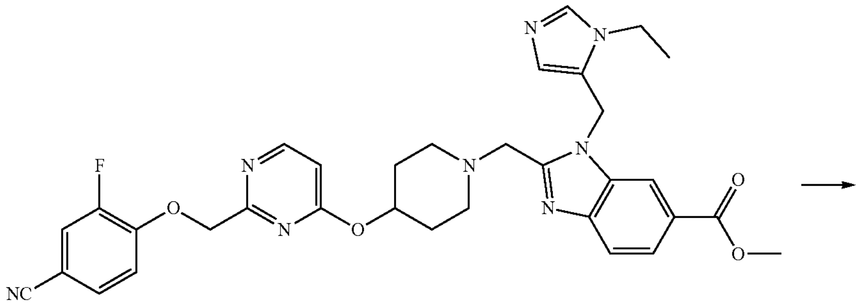

261d

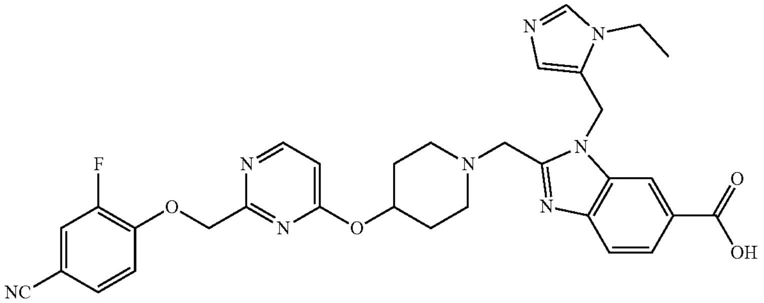

261

261d (9.2 mg, 0.012 mmol) was dissolved in $CH_3CN$ (0.5 mL) and treated with 2 N NaOH (0.5 mL). The mixture was stirred at room temperature for 24 h, then purified by reverse phase HPLC (gradient elution, 0-75% $CH_3CN$ in $H_2O$ containing 0.1% TFA as a modifier) to provide the title product (261) as a white solid (7.8 mg, 86%). m/z (ESI, +ve ion)=611.4 $[M+H]^+$. $^1H$ NMR (600 MHZ, $CD_3OD$) δ ppm 9.08 (s, 1H), 8.50 (br d, J=5.87 Hz, 1H), 8.24 (br s, 1H), 8.07 (dd, J=8.80, 1.47 Hz, 1H), 7.85 (br d, J=8.44, 1H), 7.56-7.61 (m, 1H), 7.45-7.48 (m, 1H), 7.25 (br t, J=8.44 Hz, 1H), 7.07 (s, 1H), 6.82 (m, 1H), 5.87 (s, 2H), 5.40 (s, 2H), 4.65-4.74 (m, 2H), 4.57-4.64 (m, 1H), 4.35 (q, J=7.34 Hz, 2H), 3.47-3.58 (m, 2H), 3.33-3.45 (m, 2H), 2.10-2.22 (m, 2H), 1.94-2.10 (m, 2H), 1.57 (t, J=7.34 Hz, 3H).

Example 262. (S)-2-((4-((2-((4-Cyano-2-fluorophenoxy)methyl)pyrimidin-4-yl)oxy)piperidin-1-yl)methyl)-1-(oxetan-2-ylmethyl)-1H-benzo[d]imidazole-6-carboxylic acid (262)

262

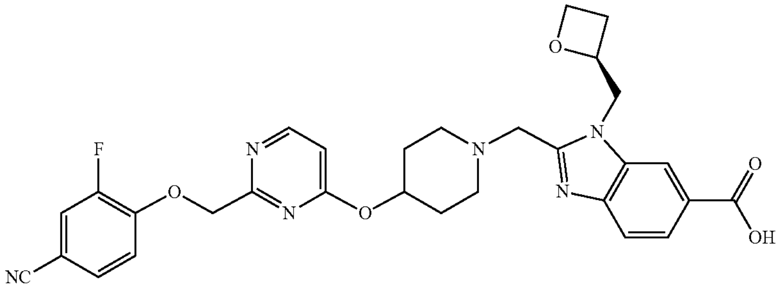

Step A. Methyl(S)-2-((4-((2-((4-cyano-2-fluorophenoxy)methyl)pyrimidin-4-yl)oxy)piperidin-1-yl)methyl)-1-(oxetan-2-ylmethyl)-1H-benzo[d]imidazole-6-carboxylate (262a)

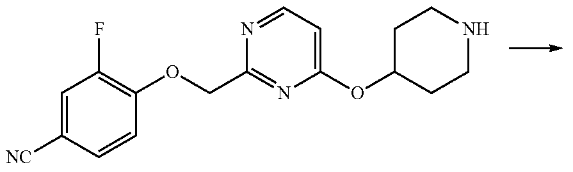

261c

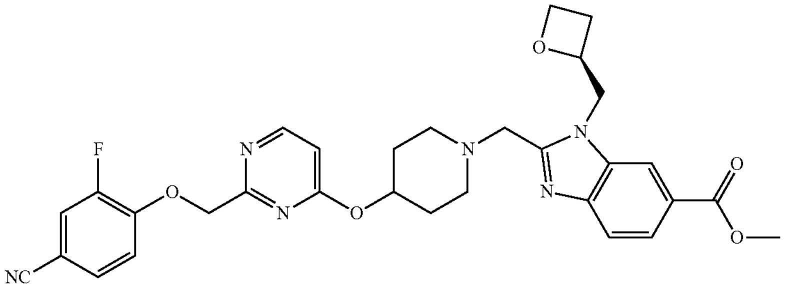

262a

To a solution of 261c (7.3 mg, 0.017 mmol) and 1h (5.8 mg, 0.02 mmol) in DMF (1 mL) was added $Et_3N$ (33.4 mg, 0.33 mmol). The resulting mixture was stirred at room temperature overnight then purified by reverse phase HPLC (gradient elution, 0-75% $CH_3CN$ in $H_2O$ containing 0.1% TFA as a modifier) to provide the title product (262a) (11.9 mg, with impurities) as a white solid. m/z (ESI, +ve ion)=587.4 $[M+H]^+$.

Step B. (S)-2-((4-((2-((4-Cyano-2-fluorophenoxy)methyl)pyrimidin-4-yl)oxy)piperidin-1-yl)methyl)-1-(oxetan-2-ylmethyl)-1H-benzo[d]imidazole-6-carboxylic acid (262)

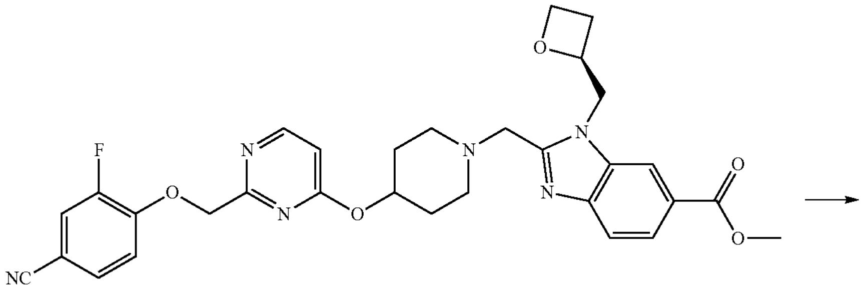

262a

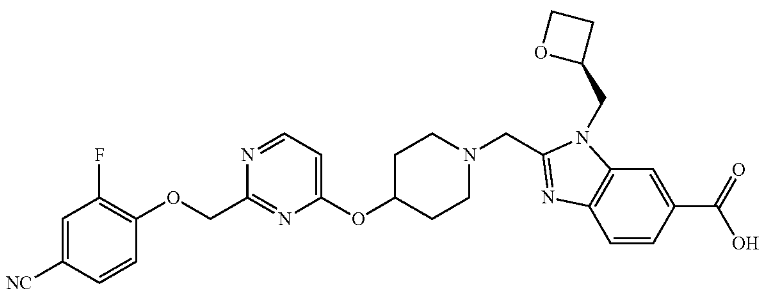

262

262a (12 mg, 0.017 mmol) was dissolved in $CH_3CN$ (0.5 mL) and treated with 2 N NaOH (0.5 mL). The mixture was stirred at room temperature for 24 h, then directly purified by reverse phase HPLC (gradient elution, 0-75% $CH_3CN$ in $H_2O$ containing 0.05% $NH_4OH$ as a modifier) to afford the title product (262) as a white solid (5.5 mg, 55%). m/z (ESI, +ve ion)=573.3 $[M+H]^+$. $^1H$ NMR (600 MHZ, $CD_3OD$) δ ppm 8.43 (d, J=5.87 Hz, 1H), 8.31 (d, J=1.10 Hz, 1H), 7.97 (dd, J=8.44, 1.47 Hz, 1H), 7.67 (d, J=8.44 Hz, 1H), 7.59 (dd, J=11.00, 1.83 Hz, 1H), 7.43-7.50 (m, 1H), 7.22 (t, J=8.44 Hz, 1H), 6.75 (d, J=5.87 Hz, 1H), 5.39 (s, 2H), 5.25 (qd, J=7.07, 2.89 Hz, 1H), 4.96-5.03 (m, 1H), 4.85-4.90 (m, 1H), 4.70 (br dd, J=15.41, 2.93 Hz, 1H), 4.64 (td, J=7.89, 5.87 Hz, 1H), 4.46 (dt, J=9.08, 5.91 Hz, 1H), 4.01 (br d, J=13.57 Hz, 1H), 3.90 (br d, J=13.57 Hz, 1H), 2.77-2.84 (m, 2H), 2.71-2.77 (m, 1H), 2.49-2.55 (m, 1H), 2.30-2.38 (m, 2H), 1.87-1.94 (m, 2H), 1.68-1.77 (m, 2H).

Example 374 was synthesized from 4-chloro-2-(chloromethyl)-5-fluoropyrimidine in similar procedures as described in Example 262.

Examples 296, 315, 328, 331, 339, 343 were synthesized in similar procedures as described in Example 262.

Example 271. 2-((4-((2-((2,4-Dichlorophenoxy)methyl)pyridin-3-yl)oxy)piperidin-1-yl)methyl)-1-((1-ethyl-1H-imidazol-5-yl)methyl)-1H-benzo[d]imidazole-6-carboxylic acid (271)

271

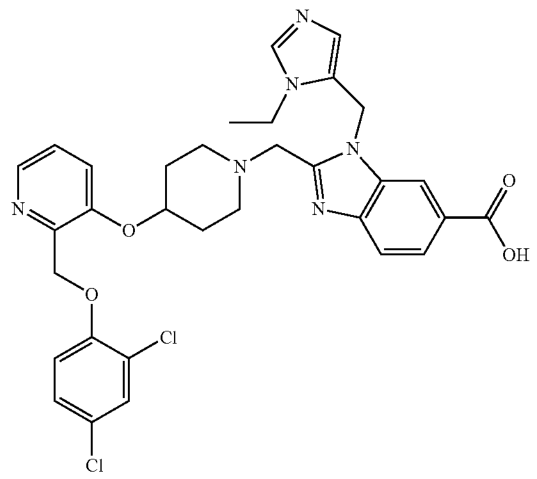

Step A. Methyl 3-((1-(tert-butoxycarbonyl)piperidin-4-yl)oxy)picolinate (271a)

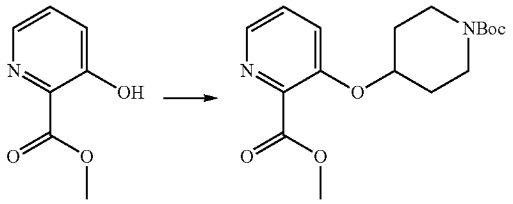

271a

A solution of methyl 3-hydroxypyridine-2-carboxylate (1.5 g, 9.8 mmol), tert-butyl 4-hydroxypiperidine-1-carboxylate (1.97 g, 9.8 mmol), $PPh_3$ (3.86 g, 14.7 mmol) and DEAD (2.56 g, 14.7 mmol) in anhydrous THF (15 mL) was stirred at 0° C. for 1 h under $N_2$. The resulting mixture was stirred at 17° C. for 11 h. After completion, the reaction was diluted with $H_2O$ (100 mL) and extracted with EtOAc (100 mL×3). The organic layer was dried over $Na_2SO_4$, concentrated and purified by silica gel column chromatography (petroleum ether:EtOAc=7:3) to afford the crude product (271a) (5.1 g) which contained some $PPh_3O$ as a colorless oil. m/z (ESI, +ve ion)=337.1 $[M+H]^+$.

Step B. tert-Butyl 4-((2-(hydroxymethyl)pyridin-3-yl)oxy)piperidine-1-carboxylate (271b)

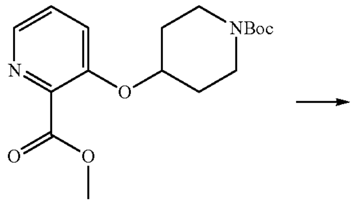

271a

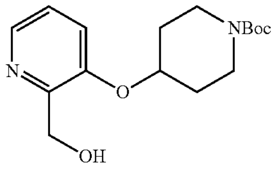

271b

A solution of crude 271a (5.1 g) and $LiBH_4$ (330 mg, 1.5 mmol) in THF/MeOH (50 mL/10 mL) was stirred at 0° C. for 1 h. After completion, the reaction was quenched with sodium sulfate decahydrate and filtered. The filter cake was further rinsed with THF (100 mL×3). The combined organic layer was dried over $Na_2SO_4$, filtered, concentrated and purified by reverse phase HPLC (27% $CH_3CN$ in $H_2O$, with 0.05% TFA as a modifier) to afford the title product (271b) (1.3 g, 26.3%) as a colorless oil. m/z (ESI, +ve ion)=309.2 $[M+H]^+$.

Step C. tert-Butyl 4-((2-((2,4-dichlorophenoxy)methyl)pyridin-3-yl)oxy)piperidine-1-carboxylate (271c)

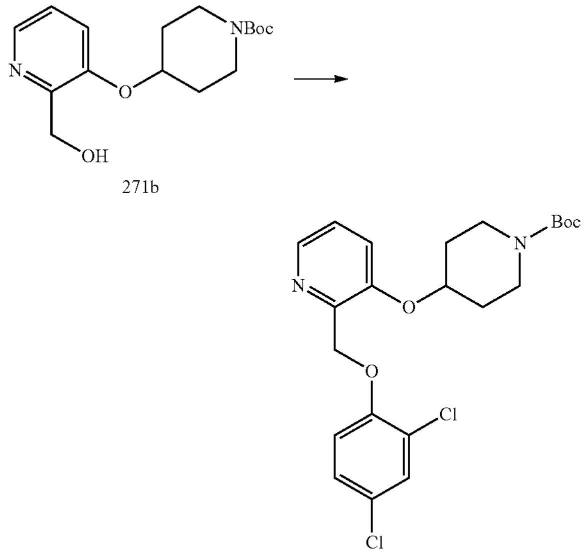

271b

271c

A solution of 271b (303 mg, 1.02 mmol), 2,4-dichlorophenol (167 mg, 1.02 mmol), $PPh_3$ (403 mg, 1.54 mmol) and DEAD (268 mg, 1.54 mmol) in anhydrous THF (6 mL) was stirred at 0° C. for 1 h under $N_2$. Then the resulting mixture was stirred at 17° C. overnight. After completion, the reaction solution was diluted with $H_2O$ (20 mL) and extracted with EtOAc (20 mL×3). The combined organic layer was dried over $Na_2SO_4$, filtered, concentrated and purified by silica gel column chromatography (petroleum ether:EtOAc=7:3) to afford the title product (271c) (180 mg, 38%) as a colorless oil. m/z (ESI, +ve ion)=453.1 $[M+H]^+$.

Step D. 2-((4-((2-((2,4-Dichlorophenoxy)methyl)pyridin-3-yl)oxy)piperidin-1-yl)methyl)-1-((1-ethyl-1H-imidazol-5-yl)methyl)-1H-benzo[d]imidazole-6-carboxylic acid (271)

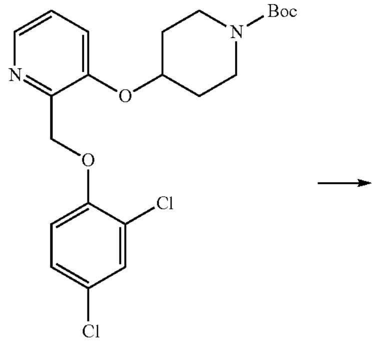

271c

-continued

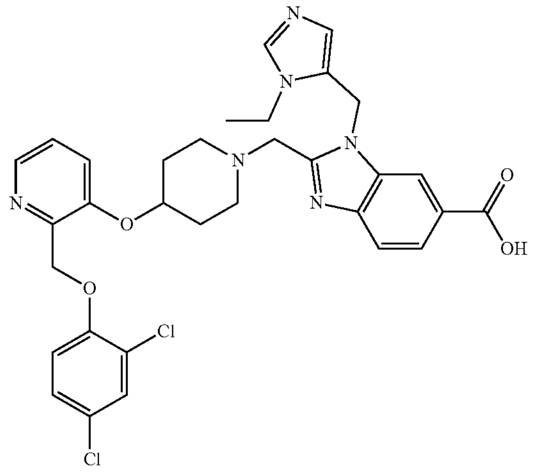

271

The title compound 271 was synthesized in similar procedures from 271c as described in Example 152, Step B to D. A 1:1 THF:$H_2O$ mixed solvent was used for the last step. m/z (ESI, +ve ion)=635.1 $[M+H]^+$. $^1H$ NMR (400 MHZ, $CD_3OD$) δ ppm 8.23 (d, J=1.7 Hz, 1H), 8.05 (dd, J=8.6, 1.5 Hz, 1H), 7.83 (d, J=8.6 Hz, 1H), 7.79 (d, J=7.8 Hz, 1H), 7.56 (dd, J=8.6, 4.9 Hz, 1H), 7.42 (d, J=2.2 Hz, 1H), 7.22-7.30 (m, 2H), 7.04 (d, J=1.2 Hz, 1H), 5.86 (s, 2H), 5.37 (s, 2H), 4.73 (s, 2H), 4.35 (q, J=7.3 Hz, 2H), 3.50-3.70 (m, 5H), 2.28-2.40 (m, 2H), 2.12-2.27 (m, 2H), 1.57 (t, J=7.3 Hz, 3H).

Example 286 was synthesized in similar procedures as described in Example 271.

Example 272 was synthesized in similar procedures from methyl 2-hydroxybenzoate as described in Example 271, Step A, then Example 60, Steps D and E, followed by Example 106, Steps D to F.

Example 284 was synthesized in similar procedures as described in Example 272.

Example 274. 2-(((2S,4S)-4-((2-((2,4-Dichlorophenoxy)methyl)pyridin-4-yl)oxy)-2-methylpiperidin-1-yl)methyl)-1-((1-ethyl-1H-imidazol-5-yl)methyl)-1H-benzo[d]imidazole-6-carboxylic acid (274)

274

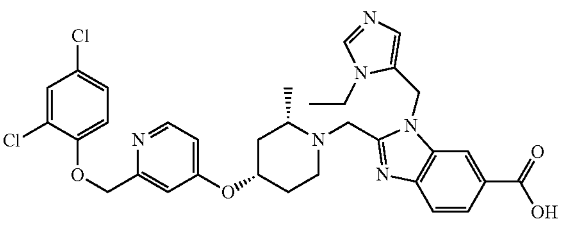

Step A. tert-Butyl(2S,4R)-2-methyl-4-((methylsulfonyl)oxy)piperidine-1-carboxylate (274a)

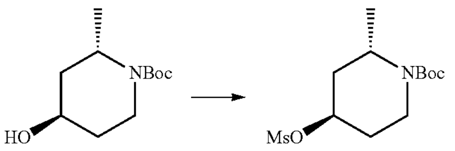

274a

To a mixture of tert-butyl(2S,4R)-4-hydroxy-2-methylpiperidine-1-carboxylate (400 mg, 1.86 mmol), DIPEA (960 mg, 7.43 mmol) in DCM (10 mL) was added a solution of methanesulfonic anhydride (809 mg, 4.64 mmol) in DCM (2.5 mL). After stirring at 0° C. for 2 h, the reaction was diluted with EtOAc (100 mL) and washed with $H_2O$ (40 mL×2). The organic layer was dried over $Na_2SO_4$, filtered and concentrated in vacuo to afford the title product (274a) (550 mg) as a colorless oil, which was used in the next step without further purification. m/z (ESI, +ve ion)=316.1 $[M+Na]^+$.

Step B. Methyl 4-(((2S,4S)-1-(tert-butoxycarbonyl)-2-methylpiperidin-4-yl)oxy)picolinate (274b)

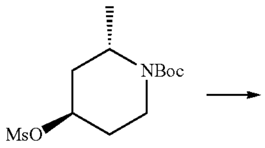

274a

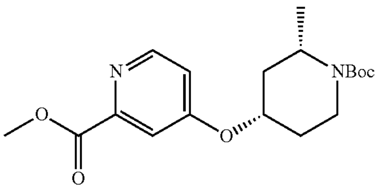

274b

A mixture of 274a (460 mg, 1.55 mmol), methyl 4-hydroxypyridine-2-carboxylate (238 mg, 1.55 mmol), $Cs_2CO_3$ (608 mg, 1.86 mmol) in DMF (4 mL) was stirred at 90° C. for 3 h. The mixture was poured into water (20 mL), and extracted with EtOAc (20 mL×3). The organic layer was washed with $H_2O$ (10 mL), brine (10 mL), dried over $Na_2SO_4$, filtered and concentrated in vacuo to give a crude residue, which was purified by prep-TLC (EtOAc/petroleum ether=2:1) to afford the title product (274b) (317 mg, 52.4%) as a colorless oil. m/z (ESI, +ve ion)=351.1 $[M+H]^+$.

Step C. tert-Butyl(2S,4S)-4-((2-(hydroxymethyl)pyridin-4-yl)oxy)-2-methylpiperidine-1-carboxylate (274c)

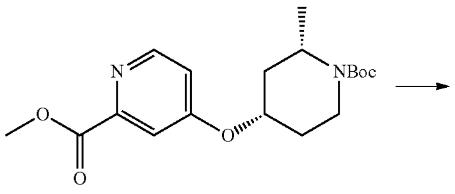

274b

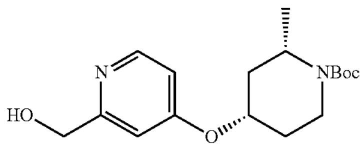

274c

A mixture of 274b (300 mg, 0.86 mmol) in THF (4 mL) was added $LiAlH_4$ (1 mL, 1.03 mmol) at 0° C. The mixture was stirred at 0° C. for 1 h and quenched with $Na_2SO_4 \cdot 10H_2O$. After stirring at 20° C. for 30 min, the reaction was filtered and concentrated in vacuo to afford the title product (274c) (229 mg, 75%) as a colorless oil, which was used in the next step without further purification. m/z (ESI, +ve ion)=323.1 $[M+H]^+$.

Step D. 2-(((2S,4S)-4-((2-((2,4-Dichlorophenoxy)methyl)pyridin-4-yl)oxy)-2-methylpiperidin-1-yl)methyl)-1-((1-ethyl-1H-imidazol-5-yl)methyl)-1H-benzo[d]imidazole-6-carboxylic acid (274)

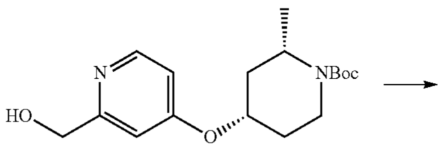

274c

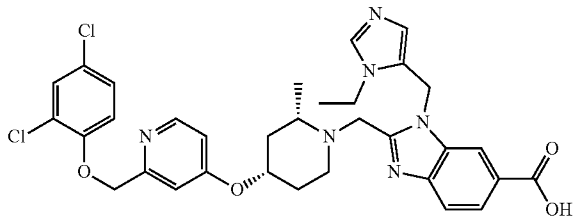

274

The title product (274) was synthesized in similar procedures from 274c as described in Example 220, Steps A to E. DMF was used as the solvent at the second to last step. m/z (ESI, +ve ion)=649.1 $[M+H]^+$. $^1H$ NMR (400 MHZ, MeOD) δ ppm $^1H$ NMR (400 MHz, $CD_3OD$) 9.10 (d, J=1.47 Hz, 1H) 8.57 (d, J=6.60 Hz, 1H) 8.22 (d, J=0.73 Hz, 1H), 8.08 (dd, J=8.56, 1.47 Hz, 1H), 7.83 (d, J=8.31 Hz, 1H), 7.53 (d, J=2.45 Hz, 2H), 7.32-7.41 (m, 2H), 7.20 (d, J=8.80 Hz, 1H), 7.08 (d, J=1.22 Hz, 1H), 5.95 (br d, J=3.42 Hz, 2H), 5.37 (s, 2H), 4.76 (br d, J=15.16 Hz, 1H), 4.41 (q, J=7.34 Hz, 2H), 4.17-4.08 (m, 1H), 3.23-3.31 (m, 2H), 3.23-3.13 (m, 1H), 2.90-2.78 (m, 1H), 2.17-2.41 (m, 2H), 1.66-1.82 (m, 2H), 1.62 (t, J=7.34 Hz, 3H), 1.40 (d, J=6.11 Hz, 3H).

Examples 283 was synthesized in similar procedures as described in Example 274. Example 295 was synthesized from tert-butyl(2S,4S)-4-hydroxy-2-methylpiperidine-1-carboxylate in similar procedures as described in Example 274. $LiBH_4$ was the reducing agent at Step C. These compounds all used silica gel column or prep-TLC for purification at the last step.

Example 366 was synthesized in similar procedures as described in Example 274, with the last step purification using reverse phase HPLC ($NH_4OH$ as modifier).

Example 275 was synthesized in similar procedures as described in Example 145.

Example 276. 2-((4-((2-((4-Chloro-2-cyanophenoxy)methyl)pyridin-4-yl)oxy)-2,2-dimethylpiperidin-1-yl)methyl)-1-((1-ethyl-1H-imidazol-5-yl)methyl)-1H-benzo[d]imidazole-6-carboxylic acid (276)

276

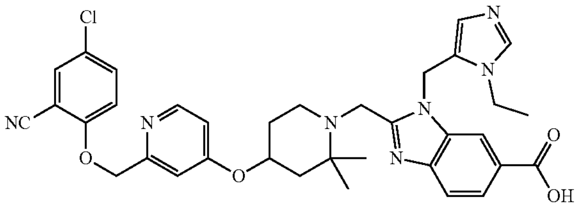

Step A. tert-Butyl 4-((2-(bromomethyl)pyridin-4-yl)oxy)-2,2-dimethylpiperidine-1-carboxylate (276b)

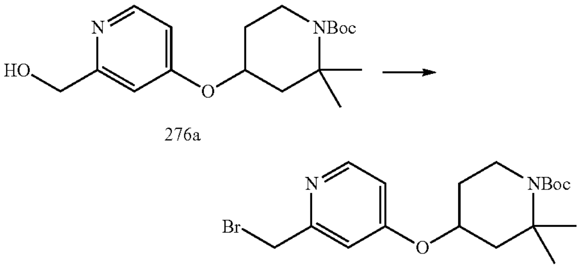

276a

276b

To a solution of 276a (prepared in similar procedures as 145a, 70.7 mg, 0.21 mmol), $PPh_3$ (82.7 mg, 0.32 mmol) in DCM (2.1 mL) was added $CBr_4$ (105 mg, 0.32 mmol). The reaction was stirred at room temperature for 35 min. Upon completion, the reaction was concentrated in vacuo and the resulting crude residue was purified by silica gel column chromatography (gradient elution, 5-40% acetone in hexanes) to afford the title product (276b) (57.7 mg, 69%) as a pale-yellow oil. m/z (ESI, +ve ion)=399.3 $[M+H]^+$.

Step B. tert-Butyl 4-((2-((4-chloro-2-cyanophenoxy)methyl)pyridin-4-yl)oxy)-2,2-dimethylpiperidine-1-carboxylate (276c)

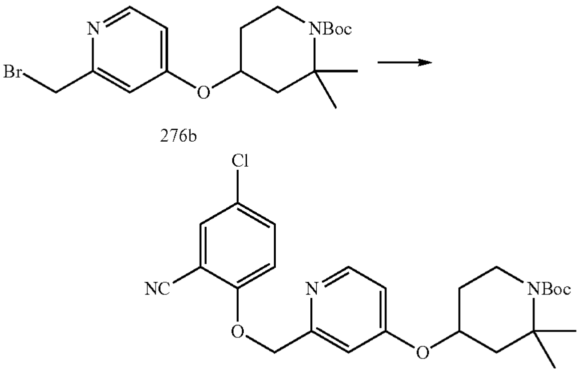

276b

276c

To a solution of 276b (57.7 mg, 0.14 mmol) and 5-chloro-2-hydroxybenzonitrile (44.4 mg, 0.29 mmol) in DMF (0.72 mL) was added $Cs_2CO_3$ (118 mg, 0.36 mmol). It was stirred at room temperature for 1 h. Upon completion, the reaction was quenched by water (5 mL). The aqueous layer was extracted with EtOAc (5 mL×3). The combined organic layer was washed with water (5 mL), brine (5 mL×3), dried over $Na_2SO_4$, filtered, concentrated and the resulting crude residue was purified by silica gel column chromatography (gradient elution, 20-100% EtOAc in hexanes) to afford the title product (276c) (53.8 mg, 79%) as a white solid. m/z (ESI, +ve ion)=472.4 $[M+H]^+$.

Step C. 5-Chloro-2-((4-((2,2-dimethylpiperidin-4-yl)oxy)pyridin-2-yl)methoxy)benzonitrile (276d)

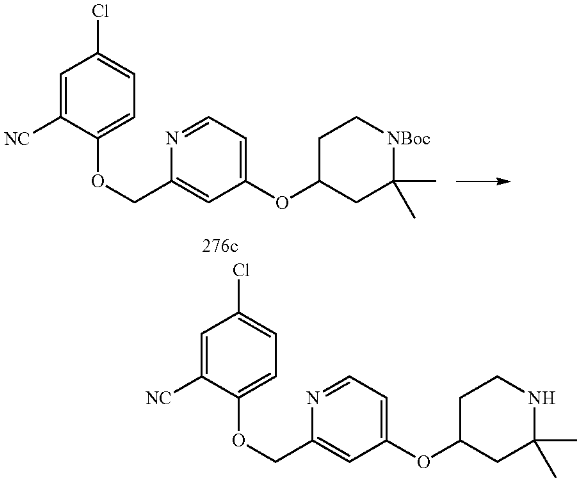

276c

276d

A solution of 276c (53.8 mg, 0.114 mmol) in DCM (1.14 mL) and TFA (0.57 mL) was stirred at room temperature for 30 min. After completion, the reaction solvent was removed under reduced pressure and the resulting residue was diluted with EtOAc (3 mL). The organic layer was washed with sat.

$NaHCO_3$ (5 mL), brine (3 mL), dried over $Na_2SO_4$, filtered and concentrated to afford the title product (276d) (20 mg) as a colorless oil, which was used in the next step without further purification. m/z (ESI, +ve ion)=372.3 $[M+H]^+$.

Step D. Methyl 2-((4-((2-((4-chloro-2-cyanophenoxy)methyl)pyridin-4-yl)oxy)-2,2-dimethylpiperidin-1-yl)methyl)-1-((1-ethyl-1H-imidazol-5-yl)methyl)-1H-benzo[d]imidazole-6-carboxylate (276e)

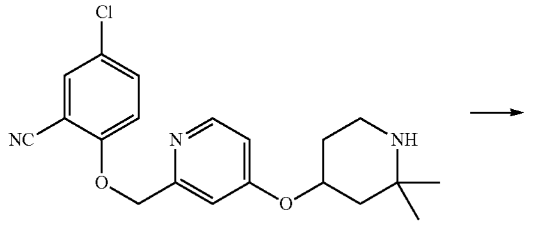

276d

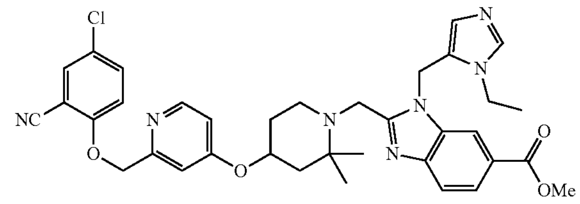

276e

A solution of 276d (20.0 mg, 0.054 mmol), 57f (46.2 mg, 0.10 mmol) and $Et_3N$ (75 μL, 0.54 mmol) in DMF (0.3 mL) was stirred at 80° C. After completion, the reaction mixture was diluted with EtOAc (5 mL). The organic layer was washed with water (3 mL×2), brine (3 mL), dried over $Na_2SO_4$, filtered and concentrated and the resulting crude residue was purified by silica gel column chromatography (gradient elution, 0-10% MeOH in DCM) to afford the title product (276e) (9.2 mg, 26%) as a white solid. m/z (ESI, +ve ion)=668.4 $[M+H]^+$.

Step E. 2-((4-((2-((4-Chloro-2-cyanophenoxy)methyl)pyridin-4-yl)oxy)-2,2-dimethylpiperidin-1-yl)methyl)-1-((1-ethyl-1H-imidazol-5-yl)methyl)-1H-benzo[d]imidazole-6-carboxylic acid (276)

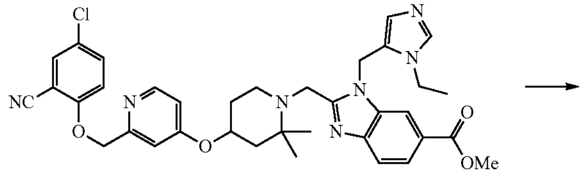

276e

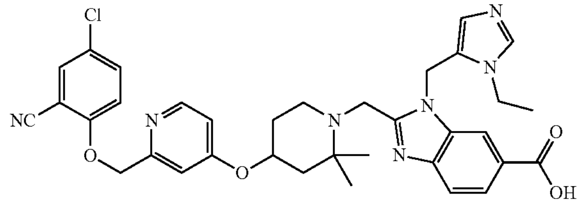

276

A solution of 276e (9.2 mg, 0.014 mmol) and LiOH (1.7 mg, 0.041 mmol) in THF:MeOH:$H_2O$=2:1:1 (0.4 mL) was stirred at 30° C. overnight. After completion, the reaction mixture was diluted with water to 1 mL and purified by reverse phase HPLC (gradient elution, 15-40% $CH_3CN$ in $H_2O$, with 0.1% TFA as a modifier) to afford the title product (276) (5.8 mg, 55%) as a white solid. $^1H$ NMR (600 MHZ, $CD_3OD$) δ ppm 9.07 (s, 1H), 8.49 (d, J=6.2 Hz, 1H), 8.17 (s, 1H), 8.07 (d, J=8.4 Hz, 1H), 7.82 (d, J=8.4 Hz, 1H), 7.76 (d, J=2.6 Hz, 1H), 7.69 (dd, J=9.2, 2.6 Hz, 1H), 7.49 (d, J=2.2 Hz, 1H), 7.31 (d, J=9.2 Hz, 1H), 7.18 (dd, J=6.4, 2.4 Hz, 1H), 7.04 (s, 1H), 5.87-5.98 (m, 2H), 5.37 (s, 2H), 4.96-5.03 (m, 1H), 4.61 (d, J=15.4 Hz, 1H), 4.40 (q, J=7.1 Hz, 2H), 4.17-4.28 (m, 1H), 3.20-3.27 (m, 1H), 3.05-3.17 (m, 1H), 2.25 (dd, J=8.8, 1.5 Hz, 1H), 2.15-2.21 (m, 1H), 1.92-2.00 (m, 1H), 1.70-1.80 (m, 1H), 1.62 (t, J=7.3 Hz, 3H), 1.46 (s, 3H), 1.42 (s, 3H). m/z (ESI, +ve ion)=654.5 $[M+H]^+$.

Examples 278 and 279 were synthesized from methyl 5-((diethoxyphosphoryl)methyl)oxazole-2-carboxylate and tert-butyl(S)-2-methyl-4-oxopiperidine-1-carboxylate in similar procedures as described in Example 106, Step A, then Example 128, Step B to C ($LiBH_4$ was used in Step C), followed by Example 220, Steps A to E. Chiral separation was performed after Step B of Example 220.

Example 285. (S)-2-((4-((6-((4-Cyano-2-fluorophenoxy)methyl)pyridin-2-yl)oxy)piperidin-1-yl)methyl)-1-(oxetan-2-ylmethyl)-1H-benzo[d]imidazole-6-carboxylic acid (285)

285

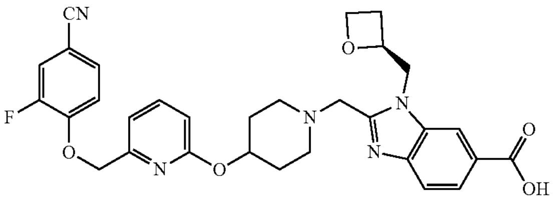

Step A. tert-Butyl 4-((methylsulfonyl)oxy)piperidine-1-carboxylate (285a)

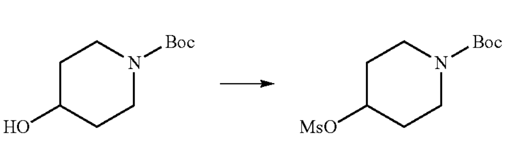

285a

To a solution of tert-butyl 4-hydroxypiperidine-1-carboxylate (8 g, 0.0396 mol), methanesulfonic anhydride (17.25 g, 0.099 mol) in DCM (100 mL) was added DIPEA (20.47 g, 0.1584 mol). The reaction was stirred at 23° C. for 2 h. After completion, the reaction was diluted with $H_2O$ (30 mL) and extracted with EtOAc (60 mL×3). The organic layer was dried, filtered and concentrated to afford the crude title product (285a) (10 g) as a colorless oil. m/z (ESI, +ve ion)=302.1 $[M+Na]^+$.

Step B. Methyl 6-((1-(tert-butoxycarbonyl)piperidin-4-yl)oxy)picolinate (285b)

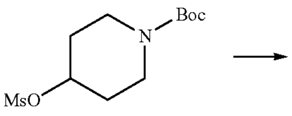

285a

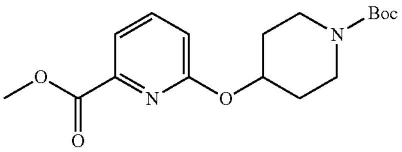

285b

To a solution of 285a (5.03 g, 17.9 mmol), methyl 6-hydroxypicolinate (2.5 g, 16.3 mmol) in DMF (50 mL) was added $Cs_2CO_3$ (15.93 g, 48.9 mmol). The reaction was stirred at 90° C. for 10 h. After completion, the reaction was diluted with $H_2O$ (15 mL) and extracted with EtOAc (30 mL×3). The combined organic layer was dried, filtered, concentrated and purified by silica gel column chromatography (petroleum ether:EtOAc=6:1) to afford the title product (285b) (2.1 g, 36%) as a white solid. m/z (ESI, +ve ion)=337.2 $[M+H]^+$.

Step C. tert-Butyl 4-((6-(hydroxymethyl)pyridin-2-yl)oxy)piperidine-1-carboxylate (285c)

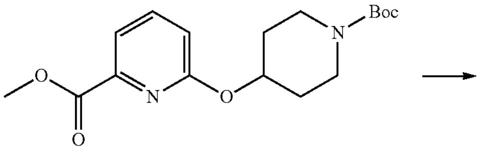

285b

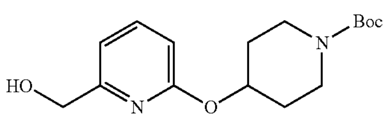

285c

A flask was charged with 285b (2.1 g, 6.2 mmol) and added $LiAlH_4$ (1 M in THF, 10 mL, 10 mmol). The reaction was stirred at 0° C. for 2 h. After completion, the reaction was diluted with $H_2O$ (15 mL) and extracted with EtOAc (20 mL×3). The organic layer was dried, filtered, concentrated and purified by silica gel column chromatography (petroleum ether:EtOAc=2:1) to afford the title product (285c) (1.0 g, 52%) as a white solid. m/z (ESI, +ve ion)=309.2 $[M+H]^+$.

Step D. tert-Butyl 4-((6-((4-cyano-2-fluorophenoxy)methyl)pyridin-2-yl)oxy)piperidine-1-carboxylate (285d)

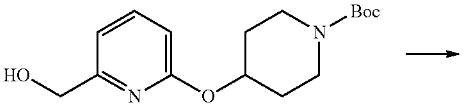

285c

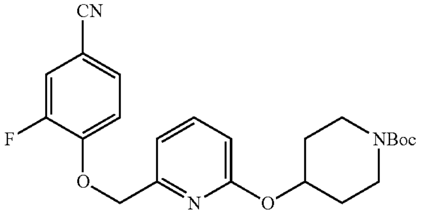

285d

To a solution of 285c (100 mg, 0.32 mmol), 3-fluoro-4-hydroxybenzonitrile (45 mg, 0.32 mmol), $PPh_3$ (128 mg, 0.49 mmol)) in anhydrous DCM (1.6 mL) at 0° C. was added slowly N-({[(4-chlorophenyl)methoxy]carbonyl}imino)[(4-chlorophenyl)methoxy]formamide (DCAD) (179 mg, 0.49 mmol) in $CH_2Cl_2$ (2.5 mL). The reaction was allowed to warm to room temperature and white precipitate was formed. After 1.5 h, reaction mixture was filtered and the filtrate was concentrated to provide a crude residue, which was purified by silica gel column chromatography (gradient elution, 0-40% EtOAc in hexanes) to provide the title product (285d) (140 mg, 100%). m/z (ESI, +ve ion)=450.3 $[M+Na]^+$.

Step E. (S)-2-((4-((6-((4-Cyano-2-fluorophenoxy)methyl)pyridin-2-yl)oxy)piperidin-1-yl)methyl)-1-(oxetan-2-ylmethyl)-1H-benzo[d]imidazole-6-carboxylic acid (285)

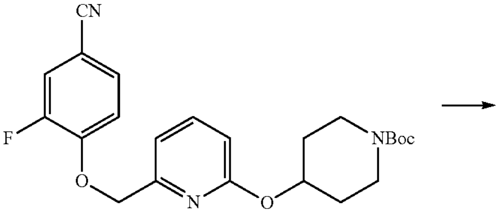

285d

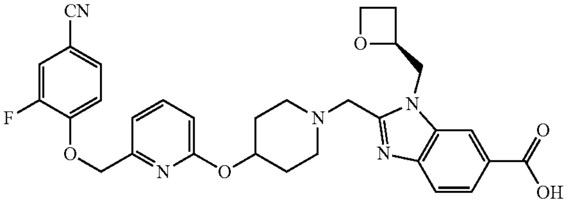

285

The title product (285) was synthesized in similar procedures as described in Example 198, Steps C to E. m/z (ESI, +ve ion)=572.4 $[M+H]^+$. $^1H$ NMR (600 MHZ, $CD_3OD$) δ ppm 8.31 (s, 1H), 7.97 (br dd, J=8.44, 1.10 Hz, 1H), 7.63-7.71 (m, 2H), 7.57 (br dd, J=10.82, 2.02 Hz, 1H), 7.50 (br d, J=8.44 Hz, 1H), 7.33 (br t, J=8.44 Hz, 1H), 7.05 (d, J=7.34 Hz, 1H), 6.69 (d, J=8.07 Hz, 1H), 5.23-5.30 (m, 3H), 5.02-5.07 (m, 1H) 4.93-4.85 (m, 1H), 4.72 (br dd, J=15.41, 2.57 Hz, 1H), 4.65 (br dd, J=13.76, 7.89 Hz, 1H), 4.47 (dt, J=9.08, 5.91 Hz, 1H), 3.90-4.07 (m, 2H), 2.77-2.90 (m, 3H), 2.40-2.57 (m, 3H), 1.97-2.04 (m, 2H), 1.73-1.85 (m, 2H).

Example 297. (S)-2-((4-((2-((4-(Difluoromethyl)-2-fluorophenoxy)methyl)pyridin-4-yl)oxy)piperidin-1-yl)methyl)-1-(oxetan-2-ylmethyl)-1H-benzo[d]imidazole-6-carboxylic acid (297)

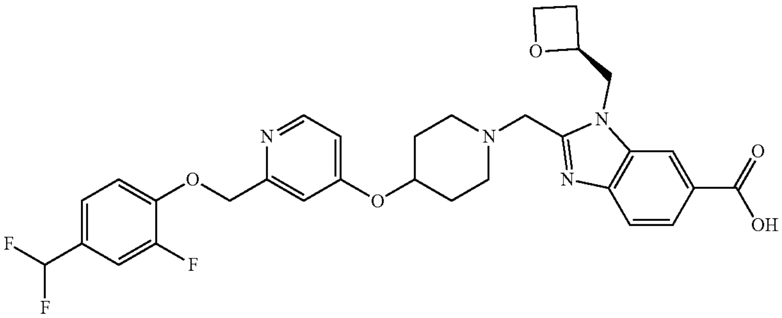

Step A. 4-(Difluoromethyl)-2-fluorophenol (297a)

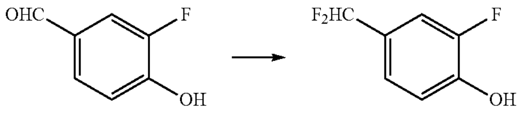

297a

To a solution of 3-fluoro-4-hydroxybenzaldehyde (3 g, 21.4 mmol) in anhydrous $CH_2Cl_2$ (107 mL) at 0° C. was added Deoxo-Fluor (15.8 g, 32.1 mmol, 45% in THF) dropwise. The reaction was warmed to room temperature and stirred for 24 h. After completion, the reaction was cooled down to 0° C., quenched with sat. $NaHCO_3$ dropwise, and extracted with EtOAc. The combined organic layer was washed with water, brine, dried over $Na_2SO_4$, filtered, concentrated and purified by silica gel column chromatography (gradient elution, 0-30% EtOAc in hexanes) to afford the title product (297a) (1.88 g, 54%) as a colorless oil. A stock solution of 297a in toluene (18.8 mL, 100 mg/mL) was prepared and stored in freezer for further use. m/z (ESI, −ve ion)=161.1 $[M-H]^-$.

Step B. (S)-2-((4-((2-((4-(Difluoromethyl)-2-fluorophenoxy)methyl)pyridin-4-yl)oxy)piperidin-1-yl)methyl)-1-(oxetan-2-ylmethyl)-1H-benzo[d]imidazole-6-carboxylic acid (297)

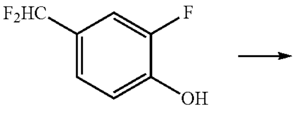

297a

297

-continued

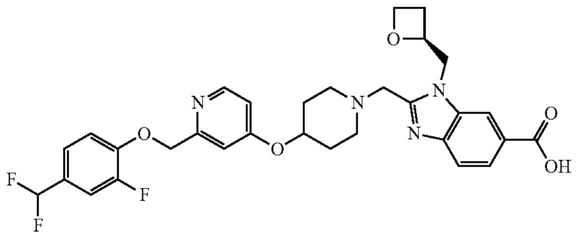

297

The title product (297) was prepared from 297a in similar procedures as described in Example 277. m/z (ESI, +ve ion)=597.3 $[M+H]^+$. $^1$H NMR (600 MHZ, DMSO-$d_6$) δ ppm 8.37 (d, J=5.7 Hz, 1H), 8.26 (d, J=1.3 Hz, 1H), 7.79 (dd, =8.4, 1.5 Hz, 1H), 7.64 (d, J=8.4 Hz, 1H), 7.48 (d, J=11.7 Hz, 1H), 7.34-7.38 (m, 2H), 7.07 (d, J=2.6 Hz, 1H), 6.97 (dd, J=5.9, 2.6 Hz, 1H), 6.96 (t, J=40.0 Hz, 1H), 5.24 (s, 2H), 5.08 (qd, J=7.2, 2.8 Hz, 1H), 4.78 (dd, J=15.3, 7.2 Hz, 1H), 4.63 (dd, J=15.2, 2.8 Hz, 1H), 4.54-4.60 (m, 1H), 4.46-4.52 (m, 1H), 4.37 (dt, J=9.0, 5.9 Hz, 1H), 3.94 (d, J=13.8 Hz, 1H), 3.79 (d, J=13.6 Hz, 1H), 2.74-2.81 (m, 1H), 2.66-2.74 (m, 2H), 2.34-2.45 (m, 3H), 1.91-1.98 (m, 2H), 1.58-1.68 (m, 2H).

Example 299. (S)-2-((4-((2-((4-Chloro-2-(fluoromethyl)phenoxy)methyl)pyridin-4-yl)oxy)piperidin-1-yl)methyl)-1-(oxetan-2-ylmethyl)-1H-benzo[d]imidazole-6-carboxylic acid (299)

299

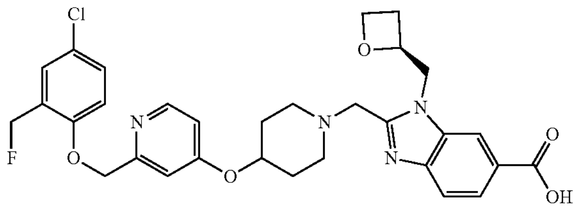

Step A. tert-Butyl 4-((2-((4-chloro-2-(methoxycarbonyl)phenoxy)methyl)pyridin-4-yl)oxy)piperidine-1-carboxylate (299a)

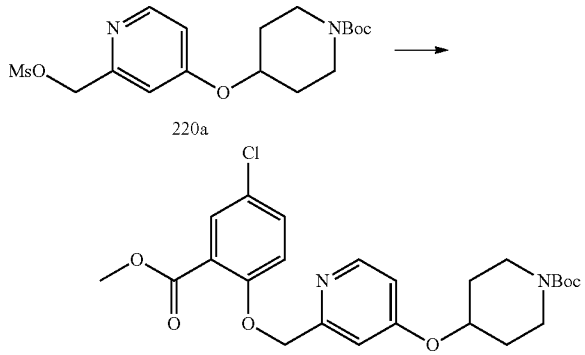

220a

299a

A solution of 220a (1.0 g, 2.6 mmol), methyl 5-chloro-2-hydroxybenzoate (490 mg, 2.6 mmol) and $K_2CO_3$ (2.54 g, 7.8 mmol) in DMF (10 mL) was stirred at 50° C. for 5 h. After completion, the reaction was diluted with $H_2O$ (30 mL) and extracted with EtOAc (30 mL×3). The combined organic layer was dried over $Na_2SO_4$, filtered, concentrated and purified by silica gel column chromatography (petroleum ether:EtOAc=7:3) to afford the title product (299a) (1.0 g, 77%) as a yellow oil. m/z (ESI, +ve ion)=477.1 $[M+H]^+$.

Step B. tert-Butyl 4-((2-((4-chloro-2-(hydroxymethyl)phenoxy)methyl)pyridin-4-yl)oxy)piperidine-1-carboxylate (299b)

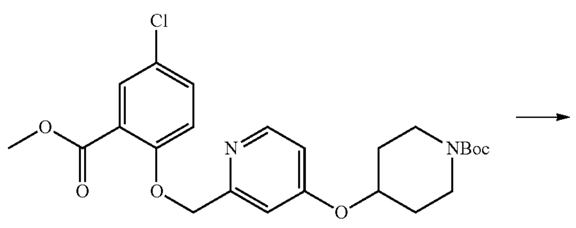

299a

-continued

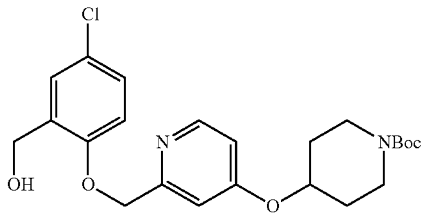

299b

A solution of 299a (1.0 g, 2.1 mmol) and $LiAlH_4$ (240 mg, 6.3 mmol) in THF (12 mL) was stirred at 0° C. for 1 h. After completion, the reaction was quenched with sodium sulfate decahydrate, filtered and the filter cake was rinsed by DCM (50 mL×3). The combined organic layer was dried over $Na_2SO_4$, filtered, concentrated and purified by silica gel column chromatography (petroleum ether:EA=1:1) to afford the title product (299b) (712 mg, 71%) as yellow solid. m/z (ESI, +ve ion)=449.1 $[M+H]^+$.

Step C. tert-Butyl 4-((2-((4-chloro-2-(fluoromethyl)phenoxy)methyl)pyridin-4-yl)oxy)piperidine-1-carboxylate (299c)

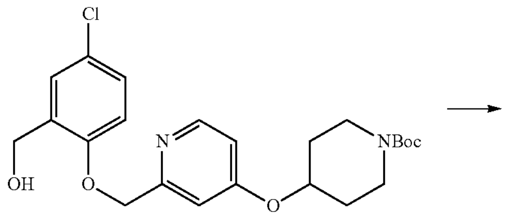

299b

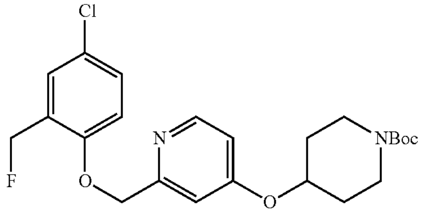

299c

To a mixture of 299b (200 mg, 0.445 mmol) in DCM (2 mL) was added DAST (144 mg, 0.891 mmol) at 0° C. The mixture was stirred at 20° C. for 12 h under $N_2$. After completion, the reaction was diluted with EtOAc (10 mL) and $H_2O$ (5 mL). The organic phase was separated and concentrated. The crude residue was purified with prep-TLC plate (EtOAc:petroleum ether=1:5) to give the title product (299c) (90 mg, 53.8%) as an oil. m/z (ESI, +ve ion)=451.2 $[M+H]^+$.

Step D. 2-((4-Chloro-2-(fluoromethyl)phenoxy)methyl)-4-(piperidin-4-yloxy)pyridine (299d)

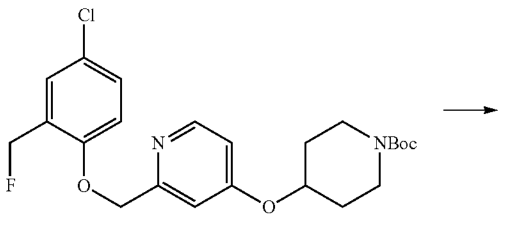

299c

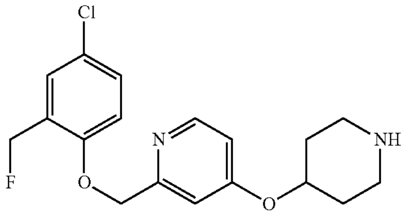

299d

To a mixture of 299c (120 mg, 0.266 mmol) in dioxane (1 mL) was added 4 N HCl in dioxane (0.33 mL, 1.33 mmol) at 0° C. The mixture was stirred at 20° C. for 1 h under $N_2$. After completion, the mixture was concentrated to give the crude title product (299d) (90 mg) as a colorless oil. m/z (ESI, +ve ion)=351.2 $[M+H]^+$.

Step E. (S)-2-((4-((2-((4-Chloro-2-(fluoromethyl)phenoxy)methyl)pyridin-4-yl)oxy)piperidin-1-yl)methyl)-1-(oxetan-2-ylmethyl)-1H-benzo[d]imidazole-6-carboxylic acid (299)

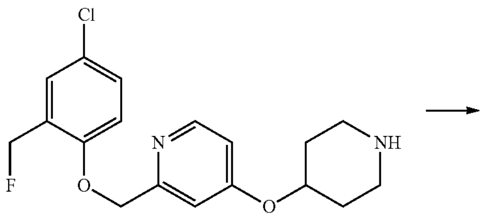

299d

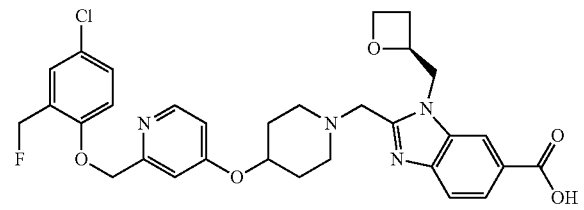

299

The title product (299) was synthesized from 299d in similar procedures as described in Example 72, Steps F and G. m/z (ESI, +ve ion)=595.2 $[M+H]^+$. $^1$H NMR (400 MHz, DMSO-$d_6$) δ ppm 8.35 (d, J=5.9 Hz, 1H), 8.16 (s, 1H), 7.78 (br d, J=8.3 Hz, 1H), 7.53 (br d, J=8.3 Hz, 1H), 7.47 (br s, 1H), 7.41 (br dd, J=8.8, 2.0 Hz, 1H), 7.13 (br d, J=8.8 Hz, 1H), 7.06 (br d, J=2.0 Hz, 1H), 6.94 (br dd, J=5.4, 2.5 Hz, 1H), 5.50 (d, J=48.0 Hz, 2H), 5.18 (s, 2H), 5.03-5.12 (m, 1H), 4.73 (br dd, J=15.2, 6.9 Hz, 1H), 4.44-4.65 (m, 3H), 4.36 (dt, J=8.8, 5.9 Hz, 1H), 3.73-3.97 (m, 2H), 2.63-2.83 (m, 3H), 2.30-2.47 (m, 3H), 1.87-2.03 (m, 2H), 1.55-1.69 (m, 2H).

Examples 287 and 292 were synthesized in similar procedures from 299b as described in Example 299, Steps D to E. The mesylate analog of 57f derived from 145e was used in the second to last step for 287.

Example 300. 2-((4-(3-((4-Cyano-2-fluorophenoxy)methyl)phenoxy)piperidin-1-yl)methyl)-4-fluoro-1-((1-(fluoromethyl)cyclopropyl)methyl)-1H-benzo[d]imidazole-6-carboxylic acid (300)

300

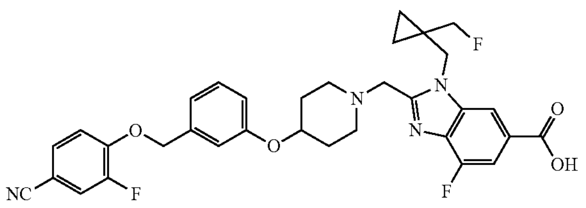

Step A. Methyl 3-fluoro-5-(((1-(fluoromethyl)cyclopropyl)methyl)amino)-4-nitrobenzoate (300a)

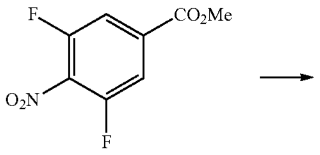

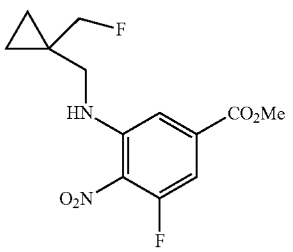

300a

To a solution of methyl 3,5-difluoro-4-nitrobenzoate (500 mg, 2.3 mmol) and [1-(fluoromethyl)cyclopropyl]methanamine trifluoroacetic Acid (500 mg, 2.3 mmol) in anhydrous DMF (7.7 mL) was added DIPEA (1.0 mL, 5.8 mmol) at room temperature. After stirring for 0.5 h, the reaction was diluted with EtOAc (20 mL) and washed with brine (10 mL×2). The organic layer was dried over $Na_2SO_4$, filtered, concentrated and purified by silica gel column chromatography (gradient elution, 0-40% EtOAc in hexanes) to afford the title product (300a) (481 mg, 70%) as an orange solid. m/z (ESI, +ve ion)=301.4 $[M+H]^+$.

Step B. Methyl 4-amino-3-fluoro-5-(((1-(fluoromethyl)cyclopropyl)methyl)amino)benzoate (300b)

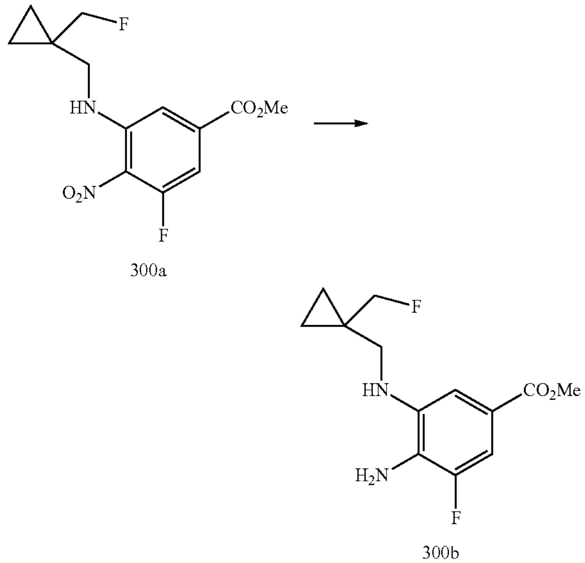

300a

300b

10% Pd/C (33 mg, 0.031 mmol) was added to 300a (186 mg, 0.62 mmol) in EtOH (6.2 mL) at room temperature. The mixture was purged with hydrogen for 10 min, then stirred under a $H_2$ balloon for 1 h. The reaction was filtered through a pad of celite, rinsed with EtOAc, and concentrated to provide the crude title product (300a) (167 mg). m/z (ESI, +ve ion)=271.4 $[M+H]^+$.

Step C. Methyl 2-(chloromethyl)-4-fluoro-1-((1-(fluoromethyl)cyclopropyl)methyl)-1H-benzo[d]imidazole-6-carboxylate (300c)

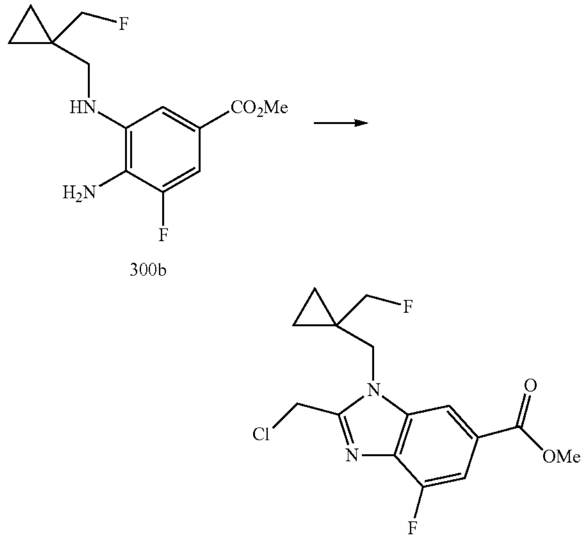

300b

300c

To a solution of crude 300b (167 mg, 0.62 mmol) and 2-chloro-1,1,1-trimethoxyethane (0.25 mL, 287 mg, 1.86 mmol) in anhydrous $CH_3CN$ (3.1 mL) at room temperature was added PTSA (6 mg, 0.03 mmol) and heated to 60° C. After stirring for 30 min, the mixture was concentrated and purified by silica gel column chromatography (gradient elution, 0-80% EtOAc in hexanes) to afford the title product (300c) (194 mg, 95% over 2 steps) as a light brown oil. m/z (ESI, +ve ion)=329.3 $[M+H]^+$.

Step D. tert-Butyl 4-(3-((4-cyano-2-fluorophenoxy)methyl)phenoxy)piperidine-1-carboxylate (300d)

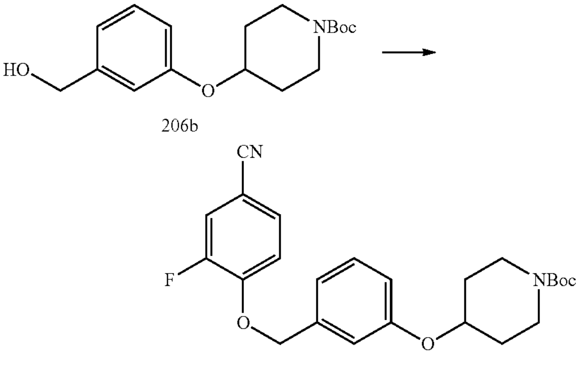

206b

300d

To a solution of 206b (100 mg, 0.33 mmol) in anhydrous $CH_2Cl_2$ (1.6 mL) at 0° C. was added $PPh_3$ (3.29 g, 12.5 mmol), 3-fluoro-4-hydroxybenzonitrile (1.36 g, 8.35 mmol) followed by addition of a solution of DCAD (2.53 g, 12.5 mmol) in anhydrous $CH_2Cl_2$ (1.6 mL) dropwise. The resulting mixture was warmed to room temperature, stirred for 1 h, filtered and concentrated. The crude residue was purified by silica gel column chromatography (gradient elution, 0-40% EtOAc in hexanes) to provide the title product (300d) (130 mg) with some triphenylphosphine oxide impurities (130 mg). m/z (ESI, +ve ion)=449.3 $[M+Na]^+$.

Step E. 3-Fluoro-4-((3-(piperidin-4-yloxy)benzyl)oxy)benzonitrile (300e)

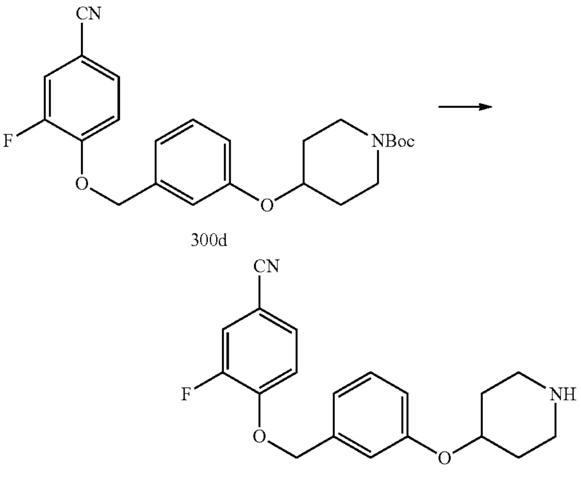

300d

300e

To a solution of 300d (28 mg, 0.066 mmol) in anhydrous $CH_2Cl_2$ (0.66 mL) was added TFA (0.25 mL, 3.3 mmol) at room temperature. After stirring for 1 h, the mixture was concentrated and azeotroped with (2 mL×2) to afford the crude title product (300e) (21 mg), which was used in the next step without further purification. m/z (ESI, +ve ion) =327.3 $[M+H]^+$.

Step F. Methyl 2-((4-(3-((4-cyano-2-fluorophenoxy) methyl)phenoxy)piperidin-1-yl)methyl)-4-fluoro-1-((1-(fluoromethyl)cyclopropyl)methyl)-1H-benzo[d] imidazole-6-carboxylate (300f)

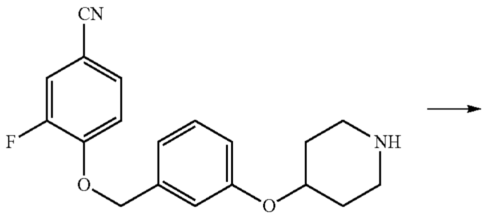

300e

-continued

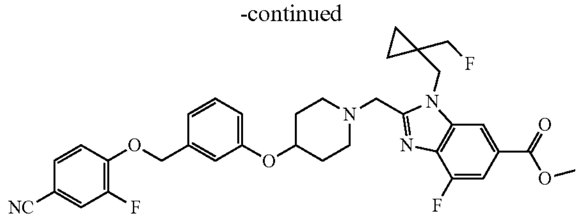

300f

To a solution of crude 300e (21 mg, 0.066 mmol) in dichloroethane (0.66 mL) was added 1h (8 mg, 0.059 mmol) and DIPEA (0.034 mL, 0.20 mmol) at room temperature. The reaction was heated to 60° C. After 20 h, the reaction was cooled down to room temperature, concentrated and purified by silica gel column chromatography (gradient elution, 0-60% EtOAc in hexanes) to afford the title product (300f) (24 mg, 59% over 2 steps) as a light brown oil. m/z (ESI, +ve ion)=619.3 $[M+H]^+$.

Step G. 2-((4-(3-((4-Cyano-2-fluorophenoxy) methyl)phenoxy)piperidin-1-yl)methyl)-4-fluoro-1-((1-(fluoromethyl)cyclopropyl)methyl)-1H-benzo[d] imidazole-6-carboxylic acid (300)

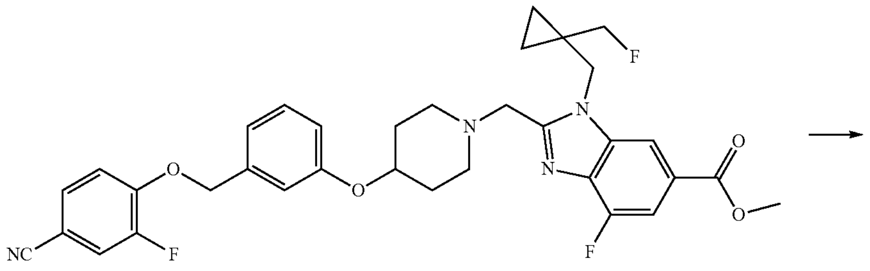

300f

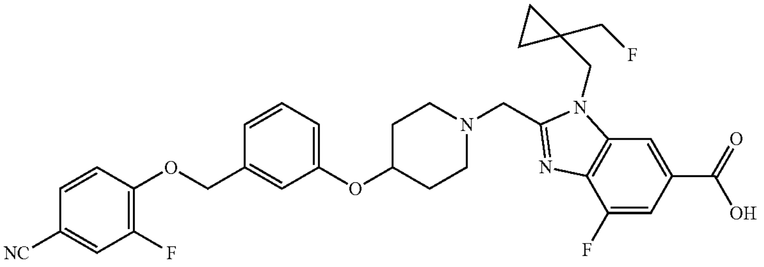

300

A flask charged with 300f (24 mg, 0.039 mmol) was dissolved in THF/$H_2O$ (1:1, 0.8 mL) at room temperature. LiOH·$H_2O$ (8 mg, 0.19 mmol) and a few drops of MeOH were added to the mixture and heated to 40° C. After 2.5 h, the reaction was cooled down and acidified with acetic acid to pH=5. The solution was diluted with EtOAc (3 mL) and washed with brine (2 mL). The organic layer was dried over $Na_2SO_4$, filtered, concentrated and purified by silica gel column chromatography (gradient elution, 0-5% MeOH/DCM) to afford the title product (300) as a colorless film, which was further lyophilized to provide a white solid (11.6 mg, 49%). m/z (ESI, +ve ion)=605.3 $[M+H]^+$. $^1H$ NMR (600 MHZ, $CD_3OD$) δ ppm 8.16 (d, J=0.73 Hz, 1H), 7.64 (d, J=11.00 Hz, 1H), 7.55 (dd, J=10.82, 2.02 Hz, 1H), 7.50 (dd, J=8.44, 1.47 Hz, 1H), 7.29 (td, J=8.16, 1.65 Hz, 2H), 6.99-7.06 (m, 2H), 6.92 (dd, J=8.25, 2.38 Hz, 1H), 5.23 (s, 2H), 4.70 (s, 2H), 4.46 (br dd, J=7.15, 3.85 Hz, 1H), 4.08-4.22 (m, 2H), 3.99 (s, 2H), 2.81-2.87 (m, 2H), 2.47-2.54 (m, 2H), 1.98-2.07 (m, 2H), 1.77-1.84 (m, 2H), 0.89 (q, J=5.26 Hz, 2H), 0.77-0.82 (m, 2H). m/z (ESI, +ve ion) =605.3 $[M+H]^+$.

Examples 301, 303, 310 were synthesized in similar procedures as described in Example 300, except HCl in dioxane was used in deprotecting the Boc group at Step E.

Example 304. (S)-2-((4-((2-((2,4-Dichlorophenoxy) methyl)pyrimidin-4-yl)oxy)piperidin-1-yl)methyl)-1-(oxetan-2-ylmethyl)-1H-benzo[d]imidazole-6-carboxylic acid (304)

304

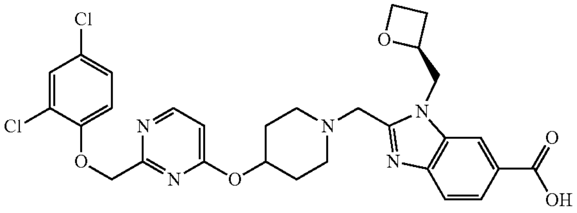

Step A. Methyl(S)-2-((4-((2-((2,4-dichlorophenoxy) methyl)pyrimidin-4-yl)oxy)piperidin-1-yl)methyl)-1-(oxetan-2-ylmethyl)-1H-benzo[d]imidazole-6-carboxylate (304b)

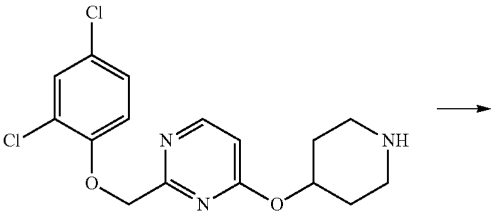

304a

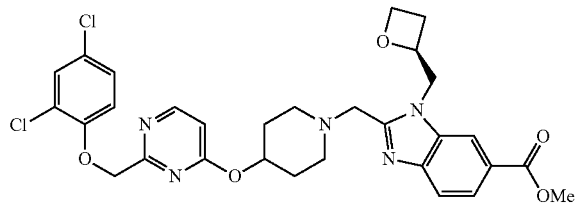

304b

A solution of 304a (TFA salt, prepared in similar procedures as 261c, 24.0 mg, 0.051 mmol), 1h (18.1 mg, 0.062 mmol) and DIPEA (170 μL, 1.03 mmol) in DMF (0.5 mL) was stirred at room temperature overnight. After completion, the reaction mixture was diluted with EtOAc (5 mL). The organic layer was washed with water (3 mL×2), brine (3 mL), dried over $Na_2SO_4$, filtered and concentrated and the resulting crude residue was purified by silica gel column chromatography (gradient elution, 80-100% EtOAc/hexanes then 0-20% MeOH in DCM) to afford the title product (304b) (11.9 mg, 38%) as a pale-yellow oil. m/z (ESI, +ve ion)=612.3 $[M+H]^+$.

Step B. (S)-2-((4-((2-((2,4-Dichlorophenoxy) methyl)pyrimidin-4-yl)oxy)piperidin-1-yl)methyl)-1-(oxetan-2-ylmethyl)-1H-benzo[d]imidazole-6-carboxylic acid (304)

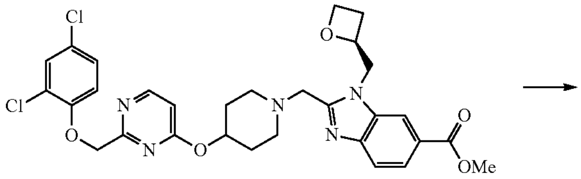

304b

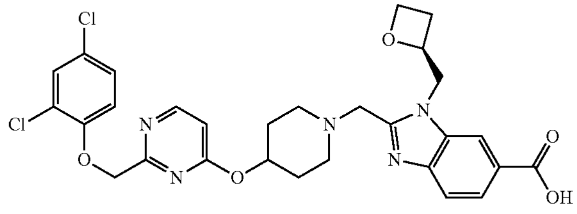

304

A solution of 304b (11.9 mg, 0.019 mmol) and LiOH (4.1 mg, 0.097 mmol) in THF:MeOH:$H_2O$=2:1:1 (0.4 mL) was stirred at 30° C. overnight. After completion, the reaction mixture was diluted with water to 1 mL and purified by reverse phase HPLC (gradient elution, 20-45% $CH_3CN$ in $H_2O$, with 0.05% $NH_4OH$ as a modifier) to afford the title product (304) (10.5 mg, 88%) as a white solid. $^1H$ NMR (600 MHZ, DMSO-$d_6$) δ ppm 8.49 (d, J=5.9 Hz, 1H), 8.22 (s, 1H), 7.79 (dd, J=8.4, 1.5 Hz, 1H), 7.60 (d, J=8.4 Hz, 1H), 7.57 (d, J=2.6 Hz, 1H), 7.28 (dd, J=8.8, 2.6 Hz, 1H), 7.11 (d, J=8.8 Hz, 1H), 6.8 (d, J=5.9 Hz, 1H), 5.37 (s, 2H), 5.07 (qd, J=7.2, 3.1 Hz, 1H), 4.85 (dt, J=8.7, 4.6 Hz, 1H), 4.75 (br dd, J=15.2, 7.2 Hz, 1H), 4.61 (br dd, J=15.2, 2.8 Hz, 1H), 4.46-4.51 (m, 1H), 4.36 (dt, J=8.8, 5.9 Hz, 1H), 3.91 (d, J=13.6 Hz, 1H), 3.76 (d, J=13.6 Hz, 1H), 2.65-2.80 (m, 2H), 2.36-2.46 (m, 2H), 2.14-2.25 (m, 2H), 1.76-1.85 (m, 2H), 1.50-1.60 (m, 2H). m/z (ESI, +ve ion)=598.2 $[M+H]^+$.

Examples 305, 306, 307, 338, 340, 341, 342, 348, 349 were synthesized in similar procedures as described in Example 304.

Example 369, 370, 371, 373 were synthesized in similar procedures as described in Example 304, except used a silica gel column to purify at the last step.

Example 313. 2-(((2S,4S)-4-((2-((4-Cyano-2-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid (313)

313

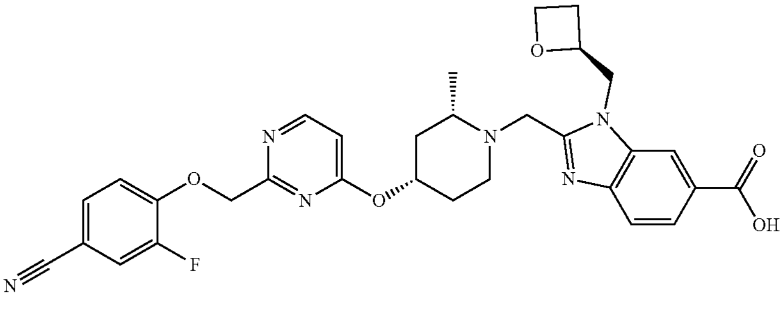

Step A. tert-Butyl(2S,4S)-4-((2-((4-cyano-2-fluorophenoxy)methyl)pyrimidin-4-yl)oxy)-2-methylpiperidine-1-carboxylate (313a)

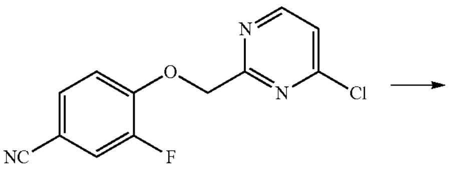

261a

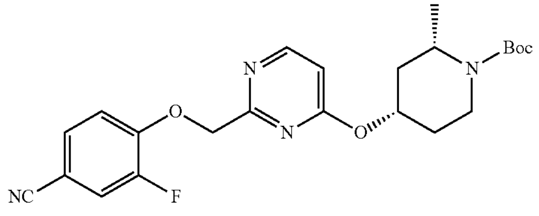

313a

To a solution of 261a (50 mg, 0.19 mmol), tert-butyl(2S, 4S)-4-hydroxy-2-methylpiperidine-1-carboxylate (49 mg, 0.23 mmol) in anhydrous toluene (1.9 mL) was added $Pd_2(dba)_3$ (7.7 mg, 0.0095 mmol), BINAP (11.8 mg, 0.019 mmol), and $Cs_2CO_3$ (124 mg, 0.38 mmol) at room temperature. The mixture was flushed with argon for 15 min, then was heated to 90° C. After 12 h, the reaction was cooled down to room temperature and $H_2O$ (2 mL) was added. The reaction was extracted with EtOAc (3 mL×3) and the combined organic layer was dried over $Na_2SO_4$, filtered, concentrated and the crude residue was purified by silica gel column chromatography (gradient elution, 0-50% EtOAc in hexanes) to afford the title product (313a) (89 mg, quantitative) m/z (ESI, +ve ion)=443.3 $[M+H]^+$.

Step B. 2-(((2S,4S)-4-((2-((4-Cyano-2-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid (313)

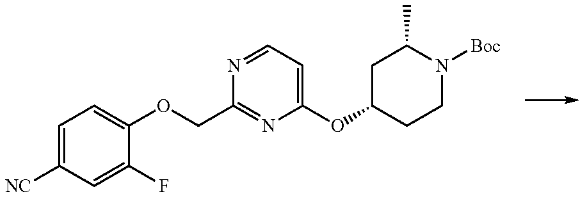

313a

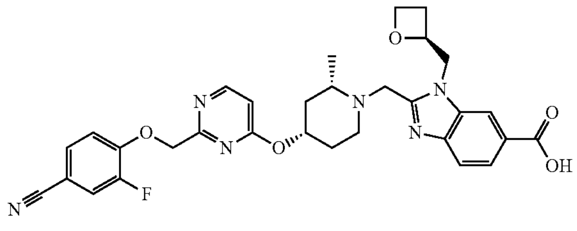

313

The title product (313) was synthesized in similar procedures as described in Example 300, Steps E to G. m/z (ESI, +ve ion)=587.4 $[M+H]^+$. $^1H$ NMR (400 MHZ, $CD_3OD$) δ ppm 8.42 (d, J=5.87 Hz, 1H), 8.31 (d, J=0.98 Hz, 1H), 7.97 (dd, J=8.56, 1.47 Hz, 1H), 7.69 (d, J=8.56 Hz, 1H), 7.60 (dd, J=11.00, 1.96 Hz, 1H), 7.47 (dt, J=8.56, 1.59 Hz, 1H), 7.22 (t, J=8.56 Hz, 1H), 6.70 (d, J=5.87 Hz, 1H), 5.40 (s, 2H), 5.24-5.32 (m, 1H), 4.91-4.96 (m, 1H), 4.73 (dd, J=15.53, 5.75 Hz, 1H), 4.56-4.65 (m, 3H), 4.31 (dt, J=9.29, 5.87 Hz, 1H), 3.60 (d, J=13.94 Hz, 1H), 2.70-2.83 (m, 2H), 2.35-2.51 (m, 2H), 2.19 (td, J=12.23, 1.96 Hz, 1H), 1.82-2.01 (m, 2H), 1.40-1.65 (m, 2H), 1.20 (d, J=6.11 Hz, 3H).

Examples 311, 312, 314, 323, 324, 325, 326, 327, 329, 353, 375, 376, 377 were synthesized in similar procedures as described in Example 313. HCl in dioxane was used to remove Boc group for Examples 311 and 312.

Example 319 was synthesized from methyl 3-hydroxybenzoate and tert-butyl(2S,4R)-4-hydroxy-2-methylpiperidine-1-carboxylate in similar procedures as described in Example 206, Steps A and B, followed by Example 300, Steps D to G.

Example 320 was synthesized in similar procedures as described in Example 319.

Example 330. (S)-2-((4-((6-((4-Cyano-2-fluorophenoxy)methyl)-3-fluoropyridin-2-yl)oxy)piperidin-1-yl)methyl)-1-(oxetan-2-ylmethyl)-1H-benzo[d]imidazole-6-carboxylic acid (330)

330

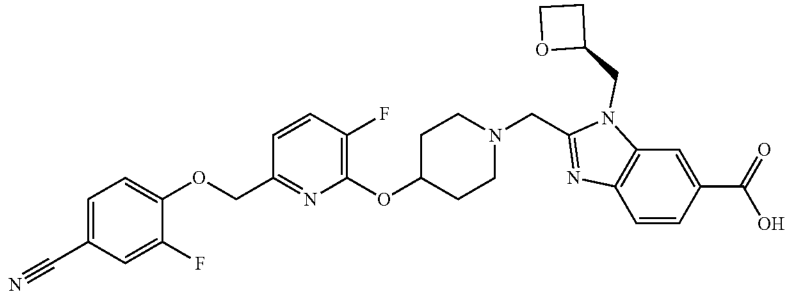

Step A. Methyl 6-((1-(tert-butoxycarbonyl)piperidin-4-yl)oxy)-5-fluoropicolinate (330a)

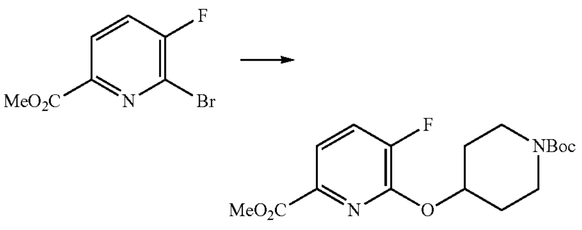

330a

To a solution of methyl 6-bromo-5-fluoropyridine-2-carboxylate (100 mg, 0.43 mmol), tert-butyl 4-hydroxypiperidine-1-carboxylate (103 mg, 0.51 mmol) in anhydrous toluene (4.3 mL) was added $Pd_2(dba)_3$ (17 mg, 0.021 mmol), BINAP (27 mg, 0.043 mmol), and $Cs_2CO_3$ (278 mg, 0.86 mmol) at room temperature. The reaction was flushed with argon for 15 min, then heated to 90° C. After 12 h, the reaction was cooled down to room temperature and $H_2O$ (2 mL) was added. The reaction mixture was extracted with EtOAc (3 mL×3) and the combined organic layer was dried over $Na_2SO_4$, filtered, concentrated and the crude residue was purified by silica gel column chromatography (gradient elution, 0-50% EtOAc in hexanes) to afford the title product (330a) (105 mg, 69%) as a colorless oil. m/z (ESI, +ve ion)=377.3 $[M+Na]^+$.

Step B. tert-Butyl 4-((3-fluoro-6-(hydroxymethyl)pyridin-2-yl)oxy)piperidine-1-carboxylate (330b)

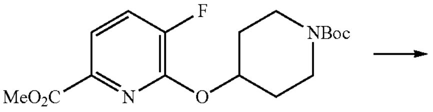

330a

-continued

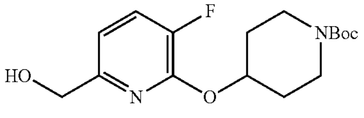

330b

To a solution of 330a (103 mg, 0.29 mmol) in anhydrous THF (2.9 mL) was added $LiAlH_4$ (0.44 mL, 0.44 mmol, 1 M in THF) at 0° C. After 0.5 h, EtOAc (3 mL) was added dropwise and the reaction was diluted with half-saturated Rochelle salt solution (2 mL). The reaction mixture was extracted with EtOAc (5 mL×3) and the combined organic layer was dried over $Na_2SO_4$, filtered, concentrated and the crude residue was purified by silica gel column chromatography (gradient elution, 0-60% EtOAc in hexanes) to afford the title product (330b) (78 mg, 82%) as a colorless oil. m/z (ESI, +ve ion)=349.4 $[M+Na]^+$.

Step C. (S)-2-((4-((6-((4-Cyano-2-fluorophenoxy)methyl)-3-fluoropyridin-2-yl)oxy)piperidin-1-yl)methyl)-1-(oxetan-2-ylmethyl)-1H-benzo[d]imidazole-6-carboxylic acid (330)

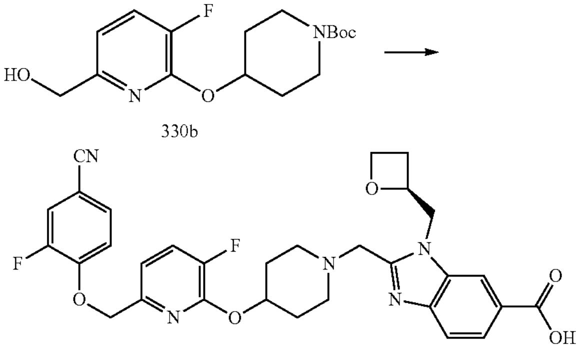

330b

330

The title product (330) was synthesized in similar procedures as described in Example 300, Steps D to G. m/z (ESI, +ve ion)=590.3 $[M+H]^+$. $^1H$ NMR (600 MHZ, $CD_3OD$) δ ppm 8.33 (d, J=1.10 Hz, 1H), 7.97 (dd, J=8.62, 1.65 Hz, 1H), 7.67 (d, J=8.44 Hz, 1H), 7.57 (dd, J=10.82, 2.02 Hz, 1H), 7.45-7.53 (m, 2H), 7.34 (t, J=8.44 Hz, 1H), 7.07 (dd, J=8.07, 2.93 Hz, 1H), 5.26 (qd, J=7.21, 2.57 Hz, 1H), 5.23 (s, 2H), 5.14 (dt, J=7.79, 3.99 Hz, 1H), 4.88 (dd, J=15.41, 7.34 Hz, 1H), 4.72 (dd, J=15.41, 2.57 Hz, 1H), 4.65 (td, J=7.89, 5.87 Hz, 1H), 4.47 (dt, J=9.17, 6.05 Hz, 1H), 3.92-4.08 (m, 2H), 2.78-2.91 (m, 3H) 2.44-2.57 (m, 3H), 2.00-2.07 (m, 2H), 1.79-1.90 (m, 2H).

Example 347 was synthesized in similar procedures as described in Example 330.

Example 355. 2-(((2S,4S)-4-((2-((2-cyano-4-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid (355)

355

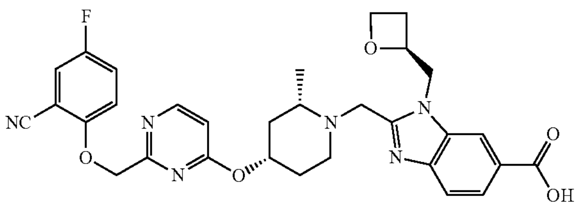

Step A. tert-Butyl(2S,4S)-4-((2-chloropyrimidin-4-yl)oxy)-2-methylpiperidine-1-carboxylate (355a)

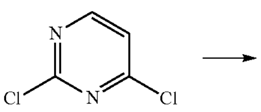

-continued

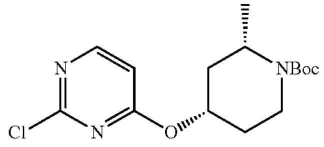

355a

To a solution of 2,4-dichloropyrimidine (5.20 g, 34.90 mmol) and tert-butyl(2S,4S)-4-hydroxy-2-methyl-piperidine-1-carboxylate (7.51 g, 34.90 mmol) in DMF (50 mL) was added $Cs_2CO_3$ (17.06 g, 52.4 mmol). The reaction was stirred at 80° C. for 3 h. After completion, the reaction was diluted with $H_2O$ (200 mL) and extracted with EtOAc (200 mL×3). The combined organic layer was dried over $Na_2SO_4$ and concentrated to afford a crude residue, which was purified by silica gel column chromatography (gradient elution, 2.5 to 5% EtOAc in petroleum ether) to afford the title product (355a) (5.65 g, 48%) as a white solid. m/z (ESI, +ve ion)=328.1 $[M+H]^+$.

Step B. Methyl 4-(((2S,4S)-1-(tert-butoxycarbonyl)-2-methylpiperidin-4-yl)oxy)pyrimidine-2-carboxylate (355b)

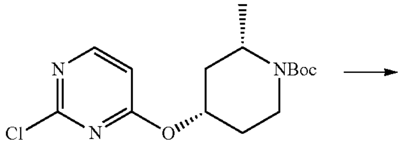

355a

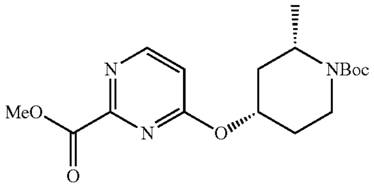

355b

A mixture of 355a (7.20 g, 21.96 mmol), $Pd(dppf)Cl_2$ (803.57 mg, 1.10 mmol), $Et_3N$ (3.06 mL, 21.96 mmol) in MeOH (70 mL) and DMSO (35 mL) was degassed and purged with $N_2$ 3 times. The reaction was heated at 60° C. for 16 h under a CO (50 Psi) atmosphere. After completion, the reaction was concentrated, diluted with $H_2O$ (200 mL) and extracted with EtOAc (200 mL×3). The combined organic layer was washed with brine (100 mL×3), dried over $Na_2SO_4$, filtered, concentrated and purified by silica gel column chromatography (gradient elution, 2-20% EtOAc in petroleum ether) to afford the title product (355b) (4.0 g, 52%) as a white solid. m/z (ESI, +ve ion)=352.2 $[M+H]^+$.

Step C. tert-Butyl(2S,4S)-4-((2-(hydroxymethyl) pyrimidin-4-yl)oxy)-2-methylpiperidine-1-carboxylate (355c)

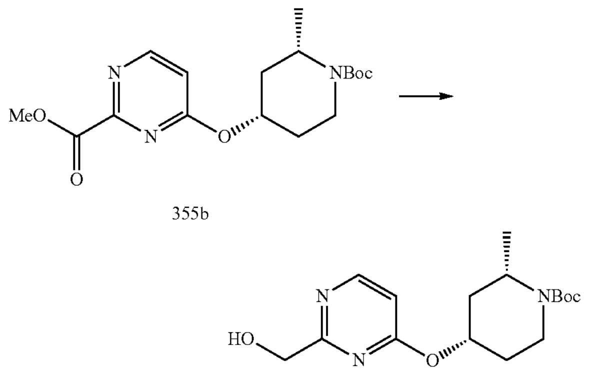

355b

355c

A mixture of 355b (4.50 g, 12.81 mmol), $CaCl_2$) (1.42 g, 12.81 mmol) in EtOH (90 mL) was degassed and purged with $N_2$ 3 times followed by addition of $NaBH_4$ (484.45 mg, 12.81 mmol) at 0° C. It was allowed to stir at 20° C. for 1 h under a $N_2$ atmosphere. After completion, reaction mixture was cooled to 0° C., followed by addition of MeOH (50 mL), and then concentrated. The resulting residue was diluted with $H_2O$ (100 mL) and the aqueous layer was extracted with EtOAc (100 mL×3). The combined organic layer was dried over $Na_2SO_4$, filtered, concentrated and purified by silica gel column chromatography (gradient elution, 5-100% EtOAc in hexanes) to afford the title product (355c) (2.7 g, 65% yield) as a white solid, m/z (ESI, +ve ion)=324.1 $[M+H]^+$.

Step D. tert-Butyl(2S,4S)-2-methyl-4-((2-(((methylsulfonyl)oxy)methyl)pyrimidin-4-yl)oxy)piperidine-1-carboxylate (355d)

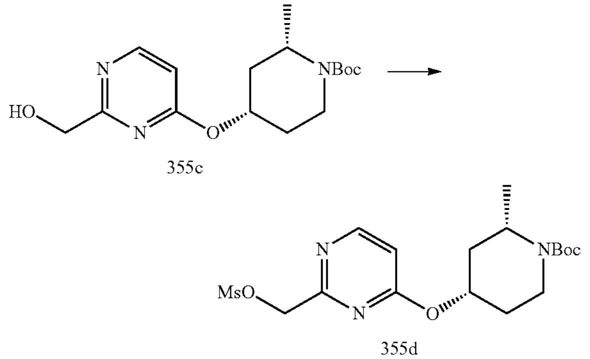

355c

355d $Et_3N$ (174 μL, 1.24 mmol) and MsCl (57.4 μL, 0.74 mmol) were added to an ice-cold solution of 355c (200.0 mg, 0.062 mmol) in dichloromethane (3.1 mL). The reaction was stirred at 0° C. for 1 h. After completion, reaction was quenched with saturated aqueous $NaHCO_3$ (10 mL) and extracted with EtOAc (10 mL×3). The combined organic layer was washed with brine (10 mL), dried over $Na_2SO_4$, filtered and concentrated to afford the crude title product (355d) (248.0 mg) as a pale-yellow oil, which was used in the next step without further purification. m/z (ESI, +ve ion)=402.3 $[M+H]^+$.

Step E. tert-Butyl(2S,4S)-4-((2-((2-cyano-4-fluorophenoxy)methyl)pyrimidin-4-yl)oxy)-2-methylpiperidine-1-carboxylate (355e)

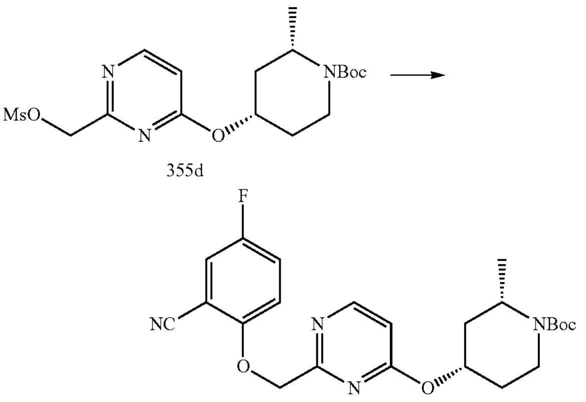

355d

355e

To a solution of 355d (248.0 mg, 0.62 mmol) and 5-fluoro-2-hydroxybenzonitrile (88.9 mg, 0.65 mmol) in DMF (3.1 mL) was added $K_2CO_3$ (171.0 mg, 1.24 mmol). The reaction was stirred at room temperature for 2 h. Upon completion, the reaction was quenched by addition of water (5 mL) and extracted with EtOAc (10 mL×3). The combined organic layer was washed with water (10 mL), brine (10 mL×3), dried over $Na_2SO_4$, filtered, concentrated and the resulting crude residue was purified by silica gel column chromatography (gradient elution, 0-40% EtOAc in hexanes) to afford the title product (355e) (164.0 mg, 60%) as a yellow. m/z (ESI, +ve ion)=443.4 $[M+H]^+$.

Step F. 5-Fluoro-2-((4-(((2S,4S)-2-methylpiperidin-4-yl)oxy)pyrimidin-2-yl)methoxy)benzonitrile (355f)

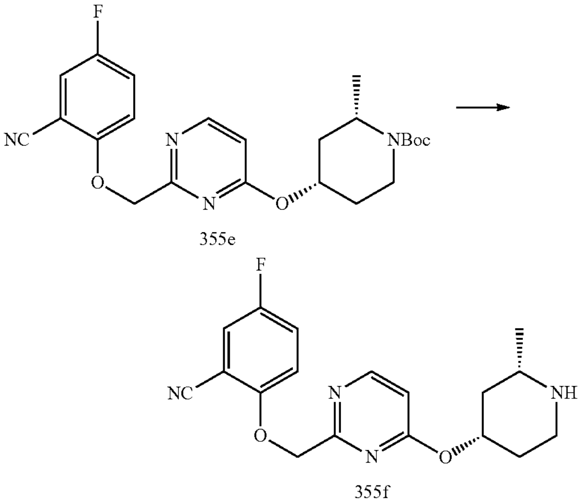

355e

355f

A solution of 355e (164.0 mg, 0.37 mmol) in DCM (6 mL) and TFA (3 mL) was stirred at room temperature for 10 min. After completion, the reaction solvent was removed under reduced pressure and the resulting residue was diluted with EtOAc (10 mL). The organic layer was washed with sat. $NaHCO_3$ (5 mL), brine (3 mL), dried over $Na_2SO_4$, filtered and concentrated to afford the title product (355f) (127 mg) as a colorless oil, which was used in the next step without further purification. m/z (ESI, +ve ion)=343.4 $[M+H]^+$.

Step G. Methyl 2-(((2S,4S)-4-((2-((2-cyano-4-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylate (355g)

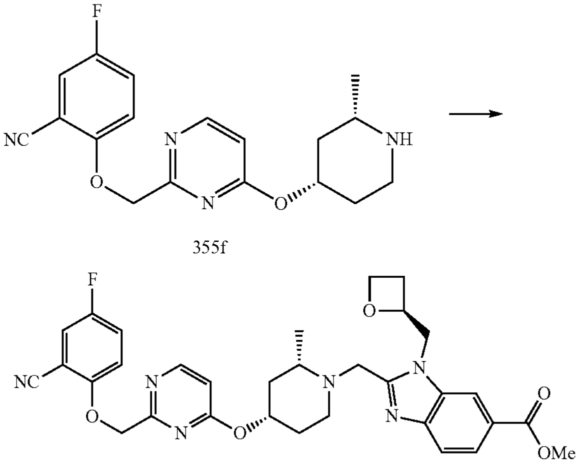

355f

355g

A solution of 355d (127.0 mg, 0.37 mmol), 1h (186.0 mg, 0.63 mmol) and DIPEA (323 μL, 1.85 mmol) in DMF (1.2 mL) was stirred at 70° C. overnight. After completion, the reaction mixture was diluted with EtOAc (20 mL). The organic layer was washed with water (10 mL×2), brine (10 mL×3), dried over $Na_2SO_4$, filtered and concentrated and the resulting crude residue was purified by silica gel column chromatography (gradient elution, 0-20% acetone in DCM) to afford the title product (355g) (160.0 mg, 72%) as a colorless oil. m/z (ESI, +ve ion)=601.3 $[M+H]^+$.

Step H. 2-(((2S,4S)-4-((2-((2-Cyano-4-fluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid (355)

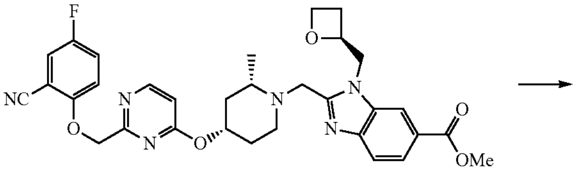

355g

-continued

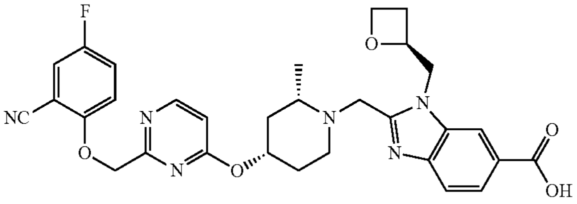

355

A solution of 355g (160.0 mg, 0.27 mmol) and LiOH (112.0 mg, 2.66 mmol) in THF:MeOH:$H_2O$=2:1:1 (12 mL) was stirred at 30° C. for 2 h. After completion, the reaction mixture was diluted with water (20 mL) and neutralized with glacial acetic acid (0.16 mL) until pH=7. Then the reaction was extracted with 30% IPA in chloroform (30 mL×3). The combined organic layer was dried over $Na_2SO_4$, filtered, concentrated and purified by silica gel column chromatography (gradient elution, 0-10% MeOH in DCM) to afford the title product (355) (122.0 mg, 76%) as a colorless oil. m/z (ESI, +ve ion)=587.2 $[M+H]^+$. $^1H$ NMR (400 MHZ, DMSO-$d_6$) δ ppm 8.48 (d, J=5.8 Hz, 1H), 8.24 (s, 1H), 7.80 (dd, J=8.3, 1.5 Hz, 1H), 7.76 (dd, J=8.0, 3.3 Hz, 1H), 7.65 (d, J=8.3, Hz, 1H), 7.48 (ddd, J=9.4, 8.3, 3.1 Hz, 1H), 7.22 (dd, J=9.5, 4.0 Hz, 1H), 6.77 (d, J=5.8 Hz, 1H), 5.75 (s, 2H), 5.46 (s, 2H), 5.08-5.18 (m, 1H), 4.65-4.85 (m, 2H), 4.36-4.51 (m, 2H), 4.20-4.29 (m, 1H), 3.55 (br d, J=14.1 Hz, 1H), 2.58-2.77 (m, 2H), 2.29-2.44 (m, 2H), 2.05-2.22 (m, 1H), 1.73-1.90 (m, 1H), 1.36-1.52 (m, 1H), 1.20-1.34 (m, 1H), 1.09 (d, J=6.3 Hz, 3H).

Example 367. (S)-2-((4-((2-((4-Cyano-2-fluorophenoxy)methyl)-5-fluoropyridin-4-yl)oxy)piperidin-1-yl)methyl)-1-(oxetan-2-ylmethyl)-1H-benzo[d]imidazole-6-carboxylic acid (367)

367

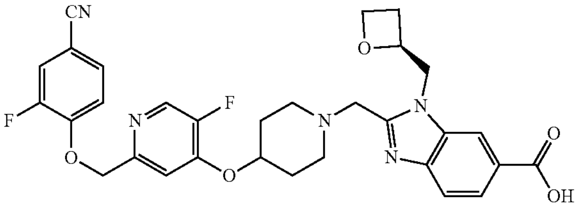

Step A. Methyl 4-((1-(tert-butoxycarbonyl)piperidin-4-yl)oxy)-5-fluoropicolinate (367b)

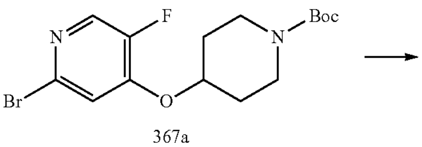

367a

-continued

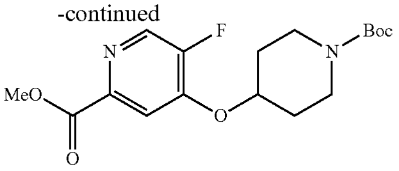

367b

To a solution of 367a (prepared similar to 145a from 2-bromo-5-fluoropyridin-4-ol, 360 mg, 0.96 mmol), palladium diacetate (43 mg, 0.19 mmol) and DPPP (79 mg, 0.19 mmol) in DMSO/MeOH (15 mL) was added $Et_3N$ (968 mg, 9.57 mmol). The reaction mixture was purged with CO and stirred at 80° C. for 4 h. After completion, the reaction was diluted with $H_2O$ (25 mL) and extracted with EtOAc (30 mL×3). The combined organic layer was dried, filtered, concentrated and purified by silica gel column chromatography (DCM:MeOH=20:1) to afford the title product (367b) (230 mg, 64%) as a white solid. m/z (ESI, +ve ion)=355.2 $[M+H]^+$.

Step B. tert-Butyl 4-((5-fluoro-2-(hydroxymethyl) pyridin-4-yl)oxy)piperidine-1-carboxylate (367b)

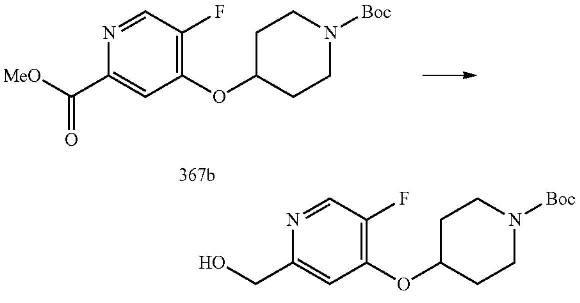

367b

367c

A flask was charged with 367b (200 mg, 0.56 mmol) and added THF (10 mL). $LiAlH_4$ (1.1 mL, 1 M in THF) was added at 0° C. under nitrogen. The reaction was stirred at 0° C. for 2 h. After completion, the reaction was quenched with saturated $NH_4Cl$ aqueous solution (15 mL) and extracted with EtOAc (20 mL×3). The organic layer was dried, filtered and concentrated to afford the crude title product (367c) (93 mg, 48%) as a white solid, which was used in the next step without further purification. m/z (ESI, +ve ion)=327.1 $[M+H]^+$.

Step C. tert-Butyl 4-((5-fluoro-2-(((methylsulfonyl) oxy)methyl)pyridin-4-yl)oxy)piperidine-1-carboxylate (367d)

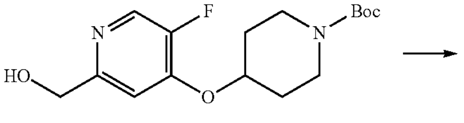

367c

-continued

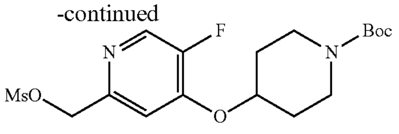

367d

To a solution of 367c (40 mg, 0.12 mmol), methanesulfonic anhydride (53 mg, 0.31 mmol) in DCM (2 mL) was added DIPEA (47 mg, 0.37 mmol). The reaction mixture was stirred at 25° C. for 2 h. After completion, the reaction solution was diluted with $H_2O$ (10 mL) and extracted with EtOAc (10 mL×3). The organic layer was dried, filtered and concentrated to afford the crude title product (367d) (43 mg, 82%) as a yellow oil. m/z (ESI, +ve ion)=405.1 $[M+H]^+$.

Step D. tert-Butyl 4-((2-((4-cyano-2-fluorophenoxy) methyl)-5-fluoropyridin-4-yl)oxy)piperidine-1-carboxylate (367e)

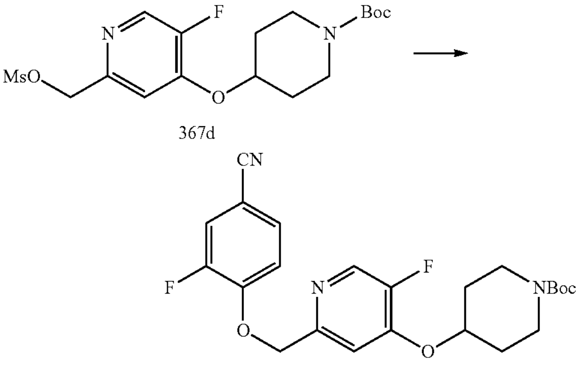

367d

367e

To a solution of 367d (50 mg, 0.12 mmol), 3-fluoro-4-hydroxybenzonitrile (20 mg, 0.15 mmol) in DMF (2 mL) was added $K_2CO_3$ (51 mg, 0.37 mmol). The reaction was stirred at 80° C. for 2 h. After completion, the reaction was diluted with $H_2O$ (15 mL) and extracted with EtOAc (20 mL×3). The combined organic layer was dried, filtered, concentrated and purified by silica gel column chromatography (DCM:MeOH=30:1) to afford the title product (367e) (48 mg, 83%) as a white solid. m/z (ESI, +ve ion)=446.1 $[M+H]^+$.

Step E. 3-Fluoro-4-((5-fluoro-4-(piperidin-4-yloxy) pyridin-2-yl)methoxy)benzonitrile (367f)

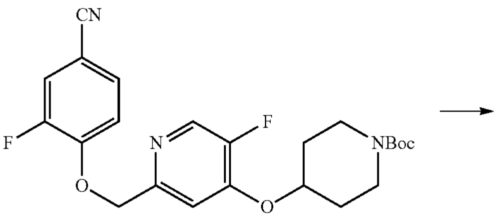

367e

-continued

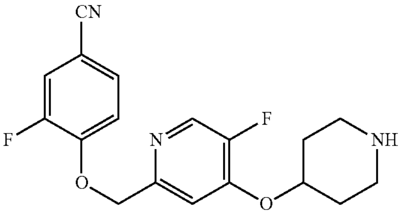

367f

A solution of 367e (40 mg, 0.09 mmol) in 4 N HCl in dioxane (1 mL) was stirred at 25° C. for 2 h. After completion, 1 N NaOH was added to the mixture to adjust to pH=8 in an ice bath. The reaction mixture was then extracted with EtOAc (15 mL×3). The organic layer was dried, filtered, concentrated and purified by silica gel column chromatography (DCM:MeOH=20:1) to afford the title product (367f) (30 mg, 92%) as a white solid, which was used in the next step without further purification. m/z (ESI, +ve ion)=346.1 $[M+H]^+$.

Step F. Methyl(S)-2-((4-((2-((4-Cyano-2-fluorophenoxy)methyl)-5-fluoropyridin-4-yl)oxy)piperidin-1-yl)methyl)-1-(oxetan-2-ylmethyl)-1H-benzo[d]imidazole-6-carboxylate (367g)

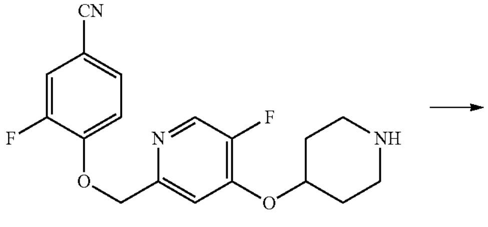

367f

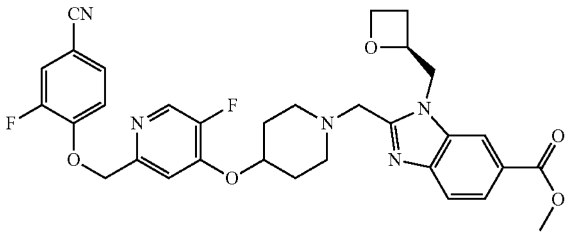

367g

To a solution of 367f (30 mg, 0.09 mmol), 1h (31 mg, 0.11 mmol) in DMF (1 mL) was added $K_2CO_3$ (36 mg, 0.26 mmol). The reaction mixture was stirred at 25° C. for 2 h. After completion, the reaction solution was diluted with $H_2O$ (15 mL) and extracted with EtOAc (20 mL×3). The combined organic layer was dried, filtered, concentrated and purified by silica gel column chromatography (DCM: MeOH=20:1) to afford the title product (367g) (34 mg, 62%) as a white solid. m/z (ESI, +ve ion)=604.3 $[M+H]^+$.

Step G. (S)-2-((4-((2-((4-Cyano-2-fluorophenoxy)methyl)-5-fluoropyridin-4-yl)oxy)piperidin-1-yl)methyl)-1-(oxetan-2-ylmethyl)-1H-benzo[d]imidazole-6-carboxylic acid (367)

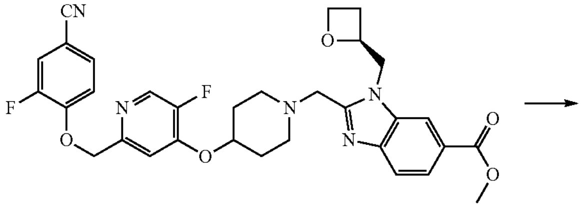

367g

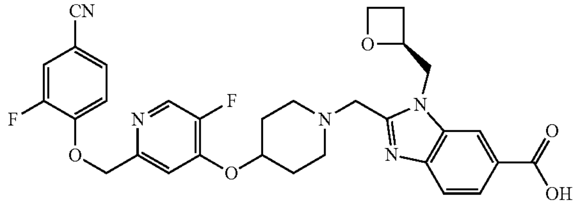

367

To a solution of 367g (30 mg, 0.05 mmol) in THF (1.5 mL) was added a solution of lithium hydroxide (12 mg, 0.5 mmol) in $H_2O$ (0.5 mL). The reaction was stirred at 25° C. for 2 h. After completion, 1 N HCl was added to the reaction to adjust to pH=5 in an ice bath. The reaction mixture was then extracted with EtOAc (15 mL×3). The organic layer was dried, filtered, concentrated and purified by silica gel column chromatography (EtOAc in petroleum ether, 20-30%) to afford the title product (367) (24 mg, 78% yield) as a white solid. m/z (ESI, +ve ion)=590.3 $[M+H]^+$. $^1H$ NMR (400 MHZ, $CD_3OD$) δ ppm 8.27-8.37 (m, 2H), 7.96 (d, J=8.56 Hz, 1H), 7.66 (d, J=8.31 Hz, 1H), 7.57 (dd, J=10.88, 1.83 Hz, 1H), 7.52 (br d, J=8.56 Hz, 1H), 7.38 (d, J=6.85 Hz, 1H) 7.33 (t, J=8.44 Hz, 1H), 5.18-5.34 (m, 3H), 4.65-4.75 (m, 3H), 4.46 (dt, J=9.05, 5.87 Hz, 1H) 3.89-4.09 (m, 2H), 3.68-3.78 (m, 1H), 2.72-2.91 (m, 3H), 2.24-2.58 (m, 3H), 1.98-2.13 (m, 2H), 1.79-1.94 (m, 2H).

Example 380 was synthesized in similar procedure as described in Example 367.

Example 368. 2-((4-((2-((4-Chloro-2-fluorophenoxy)methyl)pyridin-4-yl)oxy)piperidin-1-yl)methyl)-1-((1-methoxycyclopropyl)methyl)-1H-benzo[d]imidazole-6-carboxylic acid (368)

368

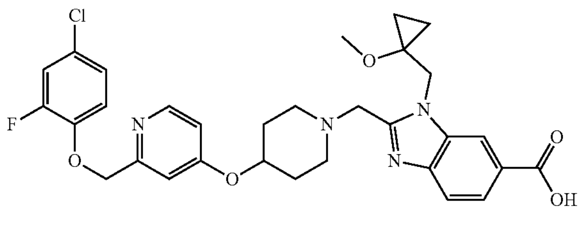

Step A. Methyl 2-((4-((2-((4-chloro-2-fluorophenoxy)methyl)pyridin-4-yl)oxy)piperidin-1-yl)methyl)-1-((1-methoxycyclopropyl)methyl)-1H-benzo[d]imidazole-6-carboxylate (368b)

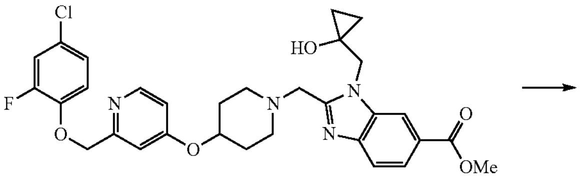

368a

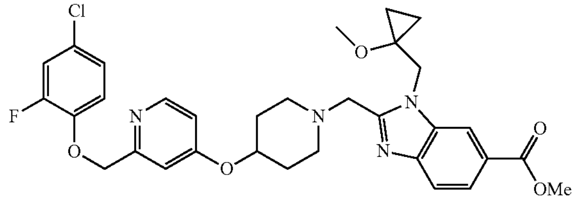

368b

An ice-cold solution of 368a (an intermediate in the synthesis of 345, 200 mg, 0.34 mmol) in DMF (1 mL) was degassed and purged with $N_2$ for 3 times, and NaH (26.89 mg, 0.67 mmol, 60% dispersion in mineral oil) was added. After stirring for 30 min at 0° C., MeI (25.1 μL, 0.40 mmol) was added. The reaction was warmed to room temperature and stirred for 3.5 h under a $N_2$ atmosphere. After completion, reaction was quenched with saturated aqueous $NH_4Cl$ (20 mL) and extracted with EtOAc (30 mL×3). The combined organic layer was dried over $Na_2SO_4$, filtered, concentrated and purified by reverse phase HPLC (gradient elution, 35-65% $CH_3CN$ in $H_2O$, with 0.05% $NH_4HCO_3$ as a modifier) to afford the title product (368b) (80.0 mg, 39%) as a white solid. m/z (ESI, +ve ion)=609.2.

Step B. 2-((4-((2-((4-Chloro-2-fluorophenoxy)methyl)pyridin-4-yl)oxy)piperidin-1-yl)methyl)-1-((1-methoxycyclopropyl)methyl)-1H-benzo[d]imidazole-6-carboxylic acid (368)

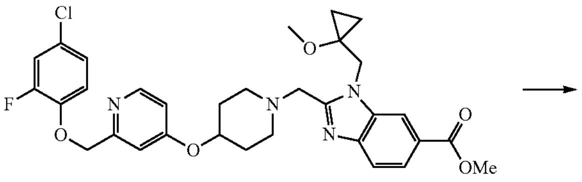

368b

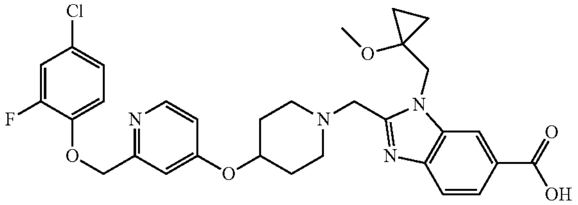

368

To a solution of 368b (25 mg, 0.041 mmol) in THF (0.6 mL), MeOH (0.3 mL) and $H_2O$ (0.3 mL) was added $LiOH \cdot H_2O$ (5.17 mg, 0.12 mmol). The reaction was stirred at 20° C. for 16 h. After completion, the reaction solvent was removed under reduced pressure. The resulting residue was diluted with water (2.0 mL) and then neutralized with saturated aqueous citric acid until pH=7. A white precipitation was formed. It was filtered and dried to afford the title product (368) (13.5 mg, 55% yield) as a white solid. m/z (ESI, +ve ion)=595.2. 1H NMR (400 MHZ, DMSO-$d_6$) δ ppm 8.36 (d, J=5.5 Hz, 1H), 8.27 (s, 1H), 7.80 (d, J=8.5 Hz, 1H), 7.65 (d, J=8.5 Hz, 1H), 7.46 (dd, J=11.0, 2.5 Hz, 1H), 7.17-7.30 (m, 2H), 7.05 (d, J=2.0 Hz, 1H), 6.97 (dd, J=5.6, 2.3 Hz, 1H), 5.18 (s, 2H), 4.73 (s, 2H), 4.59 (br s, 1H), 3.92 (br s, 2H), 3.21 (s, 3H), 2.69-2.84 (m, 2H), 2.57-2.65 (m, 2H), 1.91-2.04 (m, 2H), 1.66 (br d, J=9.5 Hz, 2H), 0.83 (br d, J=10.5 Hz, 4H).

Example 372. (S)-2-((4-((6-((4-Cyano-2-fluorophenoxy)methyl)pyridin-2-yl)oxy)piperidin-1-yl)methyl)-3-(oxetan-2-ylmethyl)-3H-imidazo[4,5-b]pyridine-5-carboxylic acid (372)

372

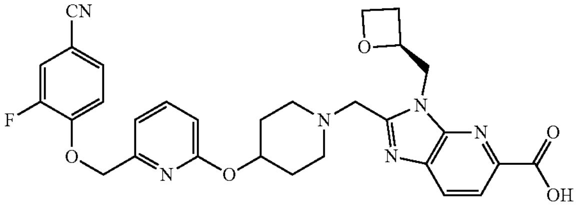

Step A. 4-((6-Bromopyridin-2-yl)methoxy)-3-fluorobenzonitrile (372a)

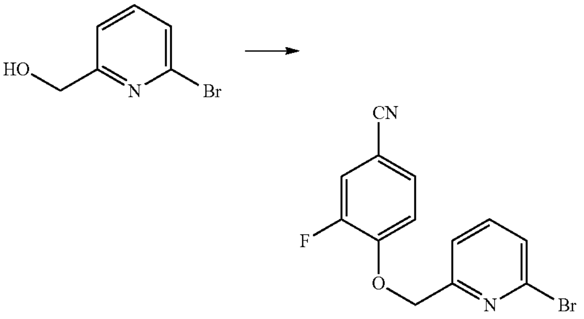

372a

To a solution of (6-bromopyridin-2-yl)methanol (1.53 g, 8.14 mmol), 3-fluoro-4-hydroxybenzonitrile (1 g, 7.32 mmol) and $PPh_3$ (3.2 g, 12.2 mmol) in THF (33 mL) was added DIAD (2.4 mL, 12.2 mmol) dropwise. The resulting mixture was stirred at room temperature for 2 h. After completion, reaction was concentrated and the resulting crude residue was purified by silica gel column chromatography (gradient elution, 0-50% EtOAc in hexanes) to provide an impure product, which was triturated with MeOH. Product precipitated out as a white solid. After stirring for an additional 10 min at 0° C., the mixture was filtered and rinsed with MeOH. The solid was dried on high vacuum pump to afford the title product (372a) (1.59 g, 63.6%) as a white solid. m/z (ESI, +ve ion)=307.1 $[M+H]^+$.

Step B. tert-Butyl 4-((6-((4-cyano-2-fluorophenoxy)methyl)pyridin-2-yl)oxy)piperidine-1-carboxylate-tert-butyl 4-((6-((4-cyano-2-fluorophenoxy)methyl)pyridin-2-yl)oxy)piperidine-1-carboxylate (372b)

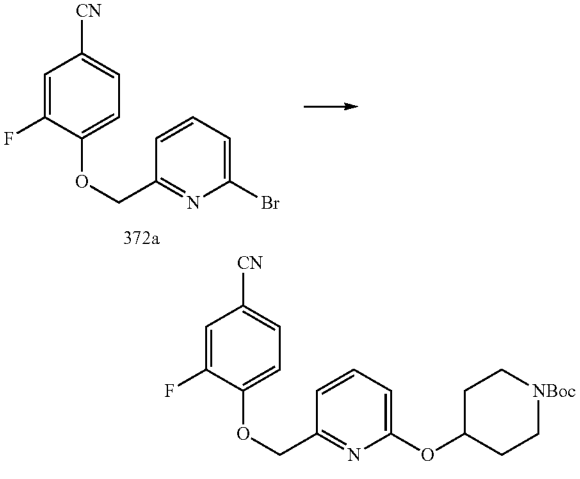

372a

372b

A flask was charged with 372a (1.59 g, 5.2 mmol), tert-butyl 4-hydroxypiperidine-1-carboxylate (1.25 g, 6.2 mmol), $Pd_2(dba)_3$ (209 mg, 0.26 mmol), BINAP (322 mg, 0.52 mmol) and $Cs_2CO_3$ (3.37 g, 10.4 mmol) and added toluene (52 mL). The resulting mixture was degassed with Ar for 5 min and then heated at 110° C. overnight under Ar. After completion, the solvent was removed in vacuo and the residue was diluted with EtOAc and water. The aqueous layer was extracted with EtOAc (3×) and the combined organic layer was washed with brine, dried, filtered, concentrated and purified by silica gel column chromatography (gradient elution, 0-40% EtOAc in hexanes) to afford the title product (372b) (1.65 g, 75%). m/z (ESI, +ve ion)=450.3 $[M+Na]^+$.

Step C. (S)-2-((4-((6-((4-Cyano-2-fluorophenoxy)methyl)pyridin-2-yl)oxy)piperidin-1-yl)methyl)-3-(oxetan-2-ylmethyl)-3H-imidazo[4,5-b]pyridine-5-carboxylic acid (372)

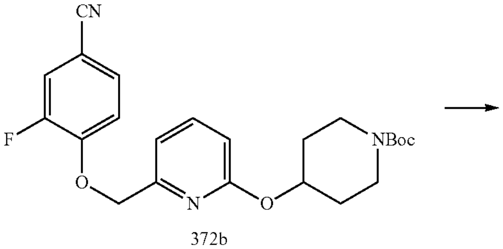

372b

-continued

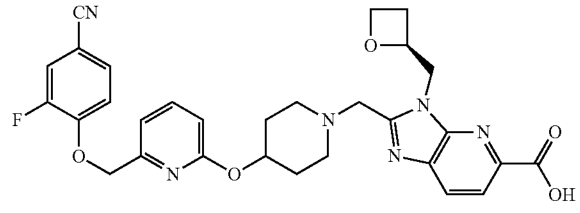

372

The title product (372) was synthesized from 372b in similar procedures as described in Example 300, Steps E to G. m/z (ESI, +ve ion)=573.3. $^1H$ NMR (400 MHZ, DMSO-$d_6$) δ ppm 13.06 (br s, 1H), 8.14 (d, J=8.3 Hz, 1H), 7.99 (d, J=8.3 Hz, 1H), 7.88 (dd, J=11.3, 2.0 Hz, 1H), 7.73 (dd, J=8.3, 7.3 Hz, 1H), 7.64-7.69 (m, 1H), 7.45 (1, J=8.7 Hz, 1H), 7.06 (d, J=7.3 Hz, 1H), 6.74 (d, J=8.0 Hz, 1H), 5.76 (s, 1H), 5.31 (s, 2H), 5.12-5.20 (m, 1H), 4.88-4.96 (m, 1H), 4.84 (dd, J=14.7, 6.4 Hz, 1H), 4.66-4.76 (m, 1H), 4.49 (ddd, J=8.4, 7.2, 5.8 Hz, 1H), 4.37 (dt, J=9.0, 6.1 Hz, 1H), 3.88-4.02 (m, 2H), 2.63-2.82 (m, 3H), 2.26-2.38 (m, 2H), 1.86-1.96 (m, 2H), 1.56-1.70 (m, 2H).

Example 381. (S)-2-((4-((2-((4-Chloro-2-fluorophenoxy)methyl)pyrimidin-4-yl)amino)piperidin-1-yl)methyl)-1-(oxetan-2-ylmethyl)-1H-benzo[d]imidazole-6-carboxylic acid (381)

381

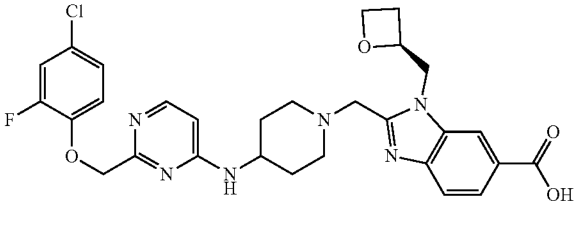

Step A. tert-Butyl 4-((2-((4-chloro-2-fluorophenoxy)methyl)pyrimidin-4-yl)amino)piperidine-1-carboxylate (381a)

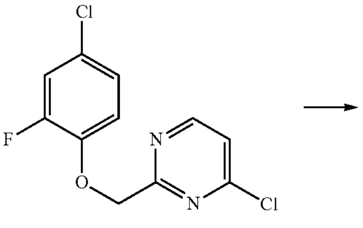

360a

-continued

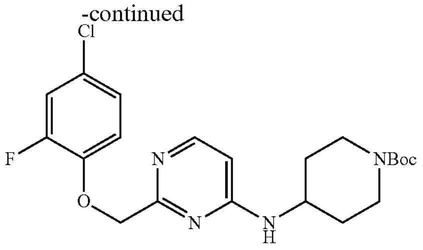

381a

A solution of 360a (27.3 mg, 0.1 mmol), tert-butyl 4-aminopiperidine-1-carboxylate (22 mg, 110 μmol), and DIPEA (34.8 μL, 0.2 mmol) in DMF (0.5 mL) was heated to 40° C. for 24 h. Upon completion, the reaction mixture was diluted with $H_2O$ (5 mL) and stirred 30 min. The aqueous layer was decanted and the residue was rinsed with $H_2O$ (1 mL) and dried to provide the title product (381a) (8 mg), which was used directly in the next step without further purification. m/z (ESI, +ve ion)=437.4 [M+H]$^+$.

Step B. 2-((4-Chloro-2-fluorophenoxy)methyl)-N-(piperidin-4-yl)pyrimidin-4-amine (381b)

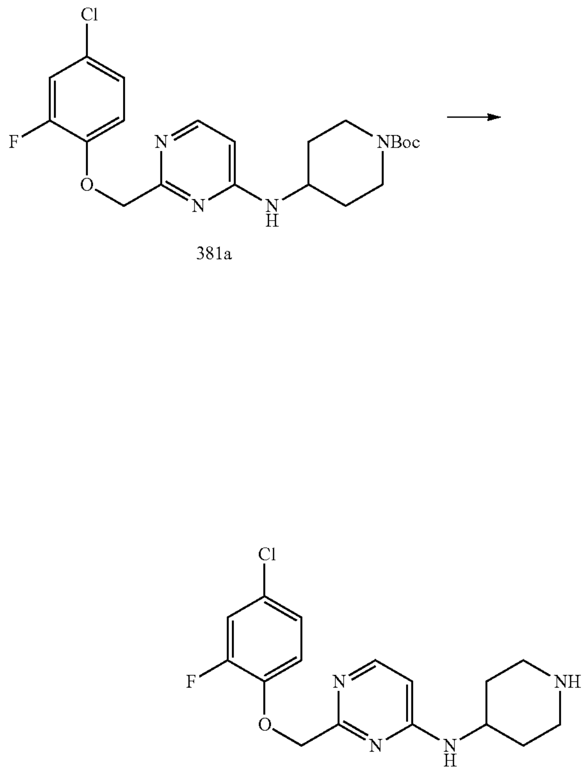

381a

381b

A solution of 381a (8 mg, 18.3 μmol) and trifluoroacetic acid (0.5 mL) in DCM (1 mL) was stirred at 21° C. for 2 h. Upon completion, the reaction was concentrated and co-evaporated with DCE (3×2 mL) to provide the title product (381b) (8 mg), which was used directly in the next step without further purification. m/z (ESI, +ve ion)=337.3 [M+H]$^+$.

Step C. Methyl(S)-2-((4-((2-((4-chloro-2-fluorophenoxy)methyl)pyrimidin-4-yl)amino)piperidin-1-yl)methyl)-1-(oxetan-2-ylmethyl)-1H-benzo[d]imidazole-6-carboxylate (381c)

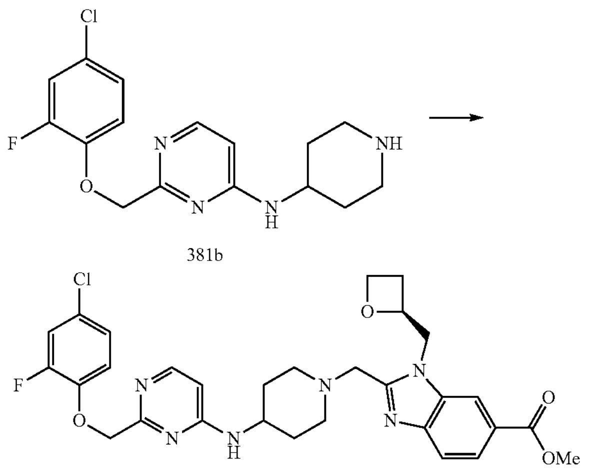

381b

381c

A solution of crude 381b (8 mg), 1h (7 mg, 23.8 μmol) and DIPEA (41.4 μL, 238 μmol) in DMF (0.5 mL) was stirred at 21° C. for 24 h. Upon completion, the reaction mixture was diluted with $H_2O$ (10 mL), stirred for 30 min and the aqueous layer was decanted. The residue was dried to provide the title product (381c) (14 mg), which was used directly in the next step without further purification. m/z (ESI, +ve ion)=595.3 [M+H]$^+$.

Step D. (S)-2-((4-((2-((4-chloro-2-fluorophenoxy)methyl)pyrimidin-4-yl)amino)piperidin-1-yl)methyl)-1-(oxetan-2-ylmethyl)-1H-benzo[d]imidazole-6-carboxylic acid (381)

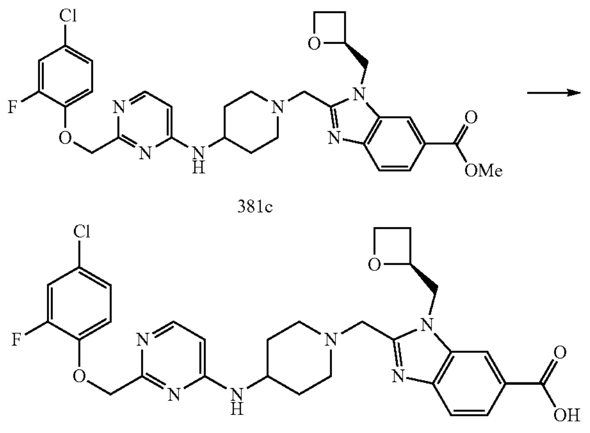

381c

381

A mixture of 381c (14 mg, 23.5 μmol) and LiOH (1 M) (118 μL, 118 μmol) in THF (235 μL), and MeOH (235 μL) were stirred at 21° C. for 4 h. Upon completion, the reaction mixture was diluted with $H_2O$ (2 mL) and purified directly by reverse phase HPLC (Gemini 5 μm C18 110 Å, 250×21.2 mm AXIA packed) (gradient elution, 10-40% $CH_3CN$ in $H_2O$, with 0.05% $NH_4OH$ as a modifier) to provide the title product (381) (7.1 mg, 52%) as a colorless solid. m/z (ESI, +ve ion)=581.3 $[M+H]^+$. $^1H$ NMR (400 MHZ, $CD_3OD$) δ ppm: 8.19 (s, 1H), 7.90-8.03 (m, 2H), 7.59 (d, J=8.44 Hz, 1H), 7.19-7.23 (m, 1H), 7.02-7.08 (m, 2H), 6.36 (br s, 1H), 5.28 (qd, J=7.03, 2.87 Hz, 1H), 5.11 (s, 2H), 4.91-4.93 (m, 1H), 4.84-4.87 (m, 1H), 4.68-4.74 (m, 1H), 4.61-4.68 (m, 1H), 4.48 (dt, J=9.17, 5.99 Hz, 1H), 4.00 (d, J=13.69 Hz, 1H), 3.85-3.97 (m, 1H), 2.88-2.95 (m, 1H), 2.74-2.86 (m, 2H), 2.48-2.60 (m, 1H), 2.15-2.31 (m, 2H), 1.85 (br s, 2H), 1.52 (br d, J=12.84 Hz, 2H).

Example 382 was synthesized in similar procedures as described in Example 381.

Example 475 was synthesized in similar procedures starting from 4-bromo-2-fluorophenol as described in Example 355, Steps A to E, then a step of cyclopropanation similar as described in Example 136, Step A ($Pd(OAc)_2$, $PPh_3$, $K_3PO_4$), followed by Example 480, Steps F to H, with LiOH used at the last step.

Examples 476, 508, 509, and 510 were synthesized in similar procedures as described in Example 475.

Example 477 was synthesized in similar procedures as described in Example 300, Step D, followed by similar procedures as described in Example 355, Steps F to H.

Example 478 was synthesized in similar procedures as described in Example 367.

Example 479 was synthesized from 367f in similar procedures as described in Example 355.

Example 480. 2-((4-((2-(1-(4-Cyano-2-fluorophenoxy)ethyl)pyrimidin-4-yl)oxy)piperidin-1-yl)methyl)-1-(((S)-oxetan-2-yl)methyl)-1H-benzo[d]imidazole-6-carboxylic acid (480)

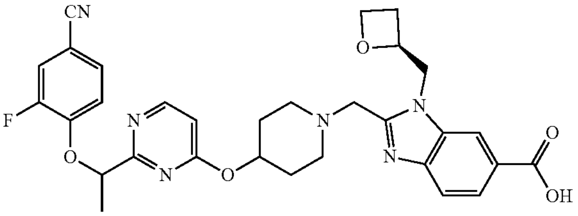 [SMILES: CC(Oc1ccc(C#N)cc1F)c1nccc(OC2CCN(Cc3nc4ccc(C(=O)O)cc4n3C[C@@H]3CCO3)CC2)n1]

Step A. tert-Butyl 4-((2-(1-ethoxyvinyl)pyrimidin-4-yl)oxy)piperidine-1-carboxylate (480b)

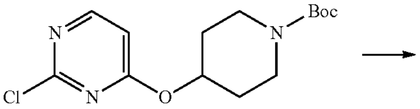

480a

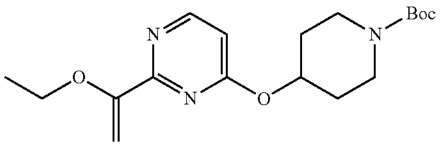

480b

A solution of 480a (synthesized in similar procedures as 355a) (1 g, 3.2 mmol) and tributyl(1-ethoxyethenyl)stannane (1.39 g, 3.8 mmol) in NMP (10 mL) was added $Pd(PPh_3)_2Cl_2$ (0.22 g, 0.3 mmol). After heating at 110° C. for 6 h under $N_2$, the mixture was filtered, poured into $H_2O$ (50 mL) and extracted with EtOAc (35 mL×3). The combined organic layer was washed with $H_2O$ (25 mL), dried over $Na_2SO_4$, filtered and concentrated in vacuo. The resulting crude residue was purified by Prep-TLC (EtOAc:petroleum ether=1:10) to afford the impure title product (480b) (0.53 g) as a colorless oil. m/z (ESI, +ve ion)=350.1 $[M+Na]^+$.

Step B. tert-Butyl 4-((2-acetylpyrimidin-4-yl)oxy)piperidine-1-carboxylate (480c)

A mixture of 480b (530 mg, 1.51 mmol) in acetone (10 mL) was added 1 N HCl (6 mL, 6.05 mmol) at 25° C. After stirring at 25° C. for 18 h, acetone was removed under reduced pressure and the residue was diluted with a mixed solution of THF/$H_2O$ (5 mL/5 mL). $Na_2CO_3$ (1.6 g, 15.1 mmol) was added to the residue. The resulting mixture was stirred at 25° C. for 1 h and extracted with EtOAc (10 mL×2). The combined organic layer was dried over $Na_2SO_4$, filtered and concentrated in vacuo, which was purified by Prep-TLC (EtOAc:petroleum ether=1:4) to afford the title product (480c) (240 mg, 44%) as a colorless oil. m/z (ESI, +ve ion)=322.1 $[M+H]^+$.

Step C. tert-Butyl 4-((2-(1-hydroxyethyl)pyrimidin-4-yl)oxy)piperidine-1-carboxylate (480d)

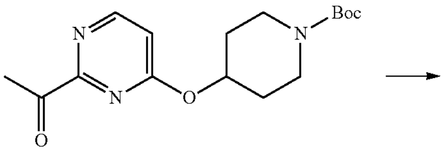

480c

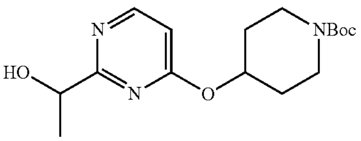

480d

To a mixture of 480c (260 mg, 0.806 mmol) in $CH_3OH$ (8 mL) was added $NaBH_4$ (61 mg, 1.6 mmol) at 0° C. After stirring at 0° C. for 1 h, the mixture was poured into water (20 mL) and extracted with EtOAc (35 mL×3). The combined organic layer was dried over $Na_2SO_4$, filtered and concentrated in vacuo to afford a crude title product (480d, racemic) (210 mg, 72%) as a colorless oil, which was used in the next step without further purification. m/z (ESI, +ve ion)=324.3 $[M+H]^+$.

Step D. tert-Butyl 4-((2-(1-((methylsulfonyl)oxy)ethyl)pyrimidin-4-yl)oxy)piperidine-1-carboxylate (480e)

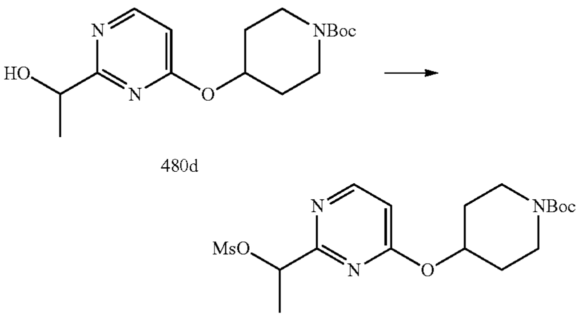

480d

480e

A solution of 480d (216 mg, 0.0928 mmol) and DIPEA (345 mg, 2.67 mmol) in DCM (6 mL) was added methanesulfonic anhydride (291 mg, 1.67 mmol) at 0° C. After stirring at 0° C. for 1 h, the reaction was diluted with DCM (20 mL) and washed with $H_2O$ (10 mL×2). The combined organic layer was dried over $Na_2SO_4$, filtered and concentrated in vacuo to afford the crude title product (480e) (250 mg) as a colorless oil, which was used in the next step without further purification. m/z (ESI, +ve ion)=402.2 $[M+H]^+$.

Step E. tert-Butyl 4-((2-(1-(4-cyano-2-fluorophenoxy)ethyl)pyrimidin-4-yl)oxy)piperidine-1-carboxylate (480f)

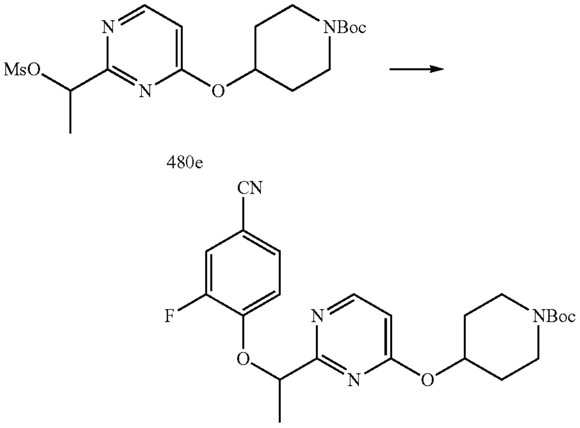

480e

480f

A mixture of 480e (250 mg, 0.56 mmol), 3-fluoro-4-hydroxybenzonitrile (77 mg, 0.56 mmol) and $K_2CO_3$ (232 mg, 1.68 mmol) in DMF (5 mL) was heated at 80° C. for 2 h. The mixture was poured into water (30 mL) and extracted with EtOAc (25 mL×2). The combined organic layer was dried over $Na_2SO_4$, filtered and concentrated to give a crude residue, which was purified by Prep-TLC (EtOAc:petroleum ether=2:1) to afford the title product (480f) (180 mg, 65%) with about 90% purity as a colorless oil. m/z (ESI, +ve ion)=443.1 $[M+H]^+$.

Step F. 3-Fluoro-4-(1-(4-(piperidin-4-yloxy)pyrimidin-2-yl) ethoxy)benzonitrile (480g)

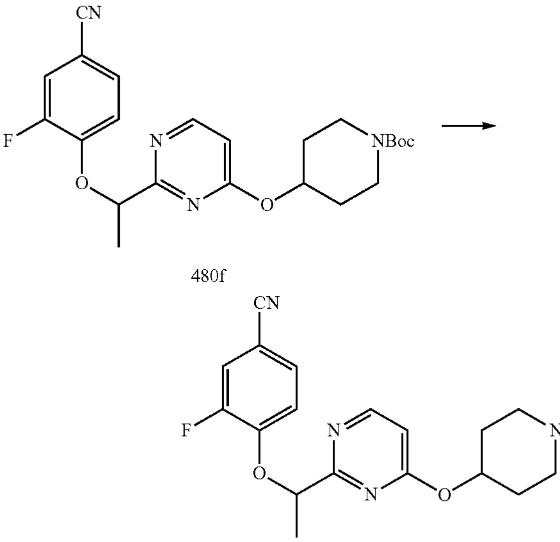

480f

480g

A solution of 480f (180 mg, 0.41 mmol) in DCM (3 mL) was added TFA (1 mL). After stirring at 25° C. for 1 h, the reaction was concentrated to afford the crude title product (480g) (130 mg) as a yellow oil, which was used in the next step without further purification. m/z (ESI, +ve ion)=343.1 $[M+H]^+$.

Step G. Methyl 2-((4-((2-(1-(4-cyano-2-fluorophenoxy)ethyl)pyrimidin-4-yl)oxy)piperidin-1-yl)methyl)-1-(((S)-oxetan-2-yl)methyl)-1H-benzo[d]imidazole-6-carboxylate (480h)

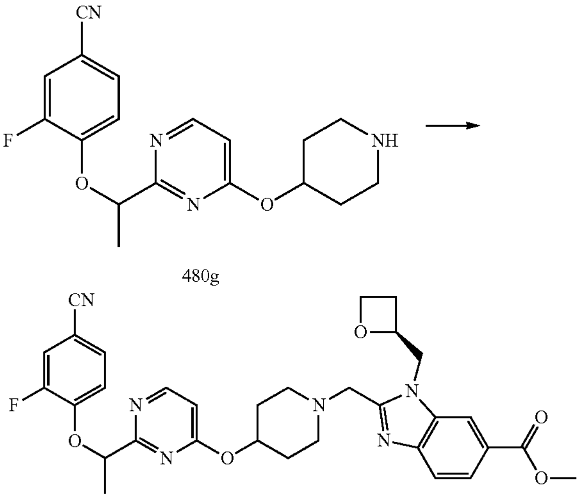

480g

480h

A mixture of 480g (143 mg, 0.42 mmol), 1h (123 mg, 0.42 mmol), and $K_2CO_3$ (173 mg, 1.25 mmol) in DMF (5 mL) was stirred at 25° C. for 4 h. The mixture was poured into water (35 mL) and extracted with EtOAc (25 ml×2). The combined organic layer was washed with $H_2O$ (20 mL), dried over $Na_2SO_4$, filtered and concentrated in vacuo to give a crude residue, which was purified by Prep-TLC (EtOAc:petroleum ether=2:1) to afford the title product (480h) (180 mg, 64.6%) as a yellow oil. m/z (ESI, +ve ion)=601.3 $[M+H]^+$.

Step H. 2-((4-((2-(1-(4-Cyano-2-fluorophenoxy) ethyl)pyrimidin-4-yl)oxy)piperidin-1-yl)methyl)-1-(((S)-oxetan-2-yl)methyl)-1H-benzo[d]imidazole-6-carboxylic acid (480)

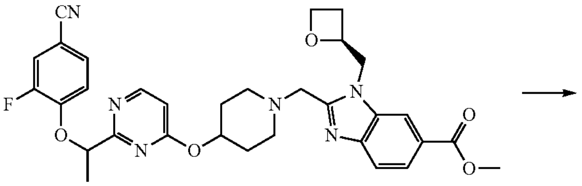

480h

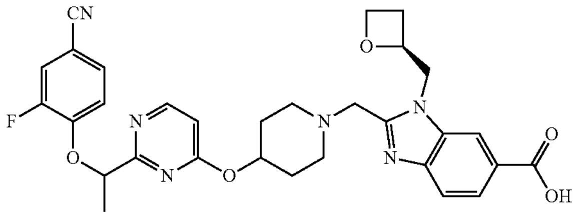

480

To a mixture of 480h (20 mg, 0.033 mmol) in THF/$H_2O$ (1 mL/1 mL) was added NaOH (27 mg, 0.66 mmol). After stirring at 25° C. for 18 h, the reaction was adjusted to pH=7~8 with 1 N HCl, and extracted with DCM/$CH_3OH$ (10/1) (15 mL×2). The combined organic layer was dried over $Na_2SO_4$, filtered, concentrated and purified by Prep-TLC (DCM:$CH_3OH$=10:1) to afford the title product (480) (5.1 mg, 24%, diastereomer mixture) as a white solid. $^1H$ NMR (400 MHZ, $CD_3OD$) δ ppm 8.42 (d, J=5.75 Hz, 1H), 8.30 (s, 1H), 7.97 (br d, J=8.50 Hz, 1H), 7.66 (d, J=8.50 Hz, 1H), 7.53-7.58 (m, 1H), 7.36 (br t, J=7.38 Hz, 1H), 7.01 (t, J=8.38 Hz, 1H), 6.72 (d, J=6.00 Hz, 1H), 5.58 (q, J=6.50 Hz, 1H), 5.22-5.38 (m, 2H), 5.03-5.11 (m, 1H), 4.56-4.77 (m, 2H), 4.42-4.51 (m, 1H), 4.02 (br dd, J=13.88, 4.38 Hz, 1H), 3.91 (br dd, J=13.76, 4.00 Hz, 1H), 2.71-2.89 (m, 3H), 2.41-2.60 (m, 2H), 2.30-2.39 (m, 1H), 1.95-2.10 (m, 2H), 1.70-1.89 (m, 4H), 1.55-1.69 (m, 1H). m/z (ESI, +ve ion) =587.2 $[M+H]^+$.

Example 481 was synthesized in similar procedures from tert-butyl 4-hydroxypiperidine-1-carboxylate as described in Example 355, Steps A to E, followed by Example 360, Steps C to E.

Example 482 was synthesized in similar procedures as described in Example 481, except TFA was used to remove the Boc protecting group.

Example 483. (R)-2-((4-((2-((2-Chloro-4-fluorophenoxy)methyl)pyrimidin-4-yl)oxy)piperidin-1-yl) methyl)-1-((1-(isoxazole-3-carbonyl)azetidin-2-yl) methyl)-1H-benzo[d]imidazole-6-carboxylic acid (483)

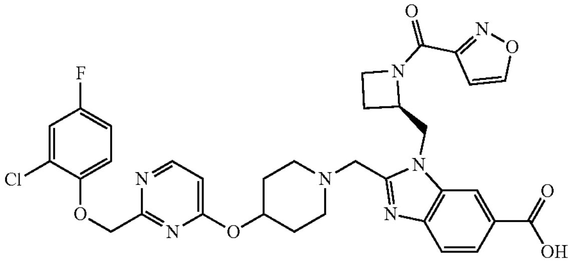 [SMILES: O=C(O)c1ccc2nc(CN3CCC(Oc4ccnc(COc5ccc(F)cc5Cl)n4)CC3)n(C[C@H]3CCN3C(=O)c3ccon3)c2c1]

Step A. (R)-1-(Azetidin-2-ylmethyl)-2-((4-((2-((2-chloro-4-fluorophenoxy)methyl)pyrimidin-4-yl)oxy) piperidin-1-yl)methyl)-1H-benzo[d]imidazole-6-carboxylic acid (483b)

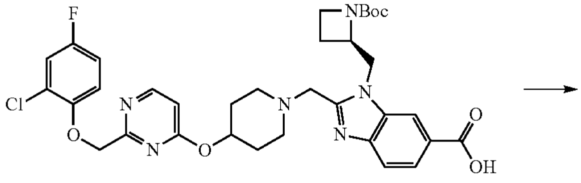

483a

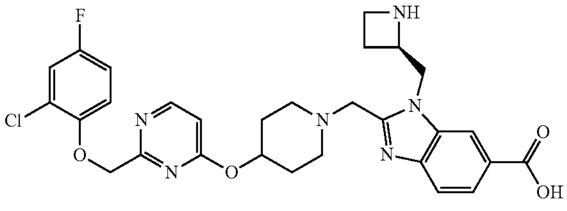

483b

A mixture of 483a (synthesized in similar procedures as described in Example 355) (64 mg, 0.094 mmol) in DCM (2 mL) was added TFA (0.5 mL). After stirring at 25° C. for 2 h, the reaction was concentrated to afford the crude title product (483b), which was used in the next step without further purification. m/z (ESI, +ve ion)=581.2 $[M+H]^+$.

Step B. (R)-2-((4-((2-((2-Chloro-4-fluorophenoxy)methyl)pyrimidin-4-yl)oxy)piperidin-1-yl)methyl)-1-((1-(isoxazole-3-carbonyl)azetidin-2-yl)methyl)-1H-benzo[d]imidazole-6-carboxylic acid (483)

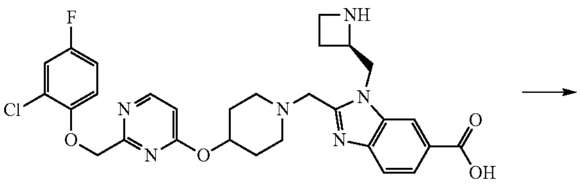

483b

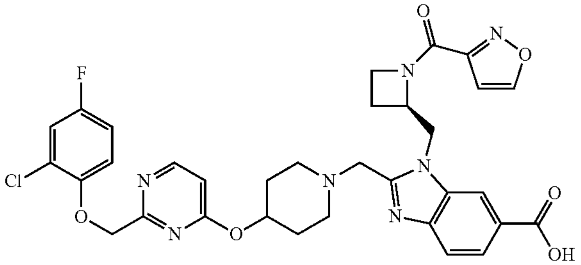

483

A solution of 1,2-oxazole-3-carboxylic acid (15 mg, 0.133 mmol) and DIPEA (86 mg, 0.664 mmol) in DCM (2.5 mL) was added HATU (55 mg, 0.146 mmol) at 25° C. After stirring for 30 min, a solution of 483b (54 mg, 0.093 mmol) in DCM (0.5 mL) was added to the above mixture. After stirring for another 30 min, the reaction was concentrated and purified by reverse phase HPLC (37% $CH_3CN$ in $H_2O$, with 0.5% $NH_4OH$ as a modifier) to afford the title product (483) (4.7 mg, 5.0%) as a white solid. m/z (ESI, +ve ion)=676.2 $[M+H]^+$.

Example 484 was synthesized from 261c in similar procedures as described in Example 360, Steps D and E, with NaI added in Step D.

Example 485 was synthesized from 2-(bromomethyl)-4-chloropyrimidine in similar procedures as described in Example 216, Steps A to C, followed by Example 304, Steps A and B.

Example 486. (S)-2-((4-((2-((4-Cyano-2-fluorophenoxy)methyl)pyrimidin-4-yl)oxy)piperidin-1-yl)methyl)-1-(oxetan-2-ylmethyl)-1H-imidazo[4,5-b]pyridine-6-carboxylic acid (486)

486

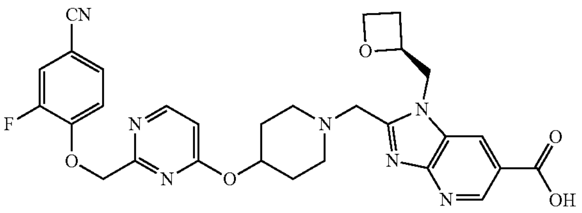

Step A. (S)-5-Bromo-2-nitro-N-(oxetan-2-ylmethyl)pyridin-3-amine (486a)

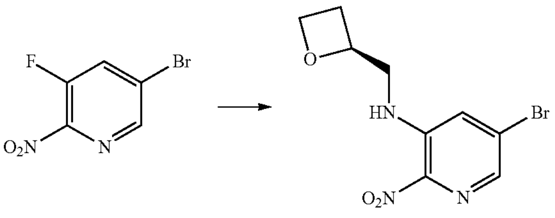

486a

To a mixture of 5-bromo-3-fluoro-2-nitropyridine (750 mg, 3.39 mmol) and $K_2CO_3$ (935 mg, 6.78 mmol) in DMF (10 mL) was added 1e (1.48 g, 16.97 mmol). After stirring at 25° C. for 16 h, the reaction was diluted with EtOAc (50 mL) and washed with brine (50 mL×2). The combined organic layer was dried and evaporated to dryness to afford the crude title product (486a) (950 mg) as a yellow solid. m/z (ESI, +ve ion)=288.0 $[M+H]^+$.

Step B. (S)-5-Bromo-$N_3$-(oxetan-2-ylmethyl)pyridine-2,3-diamine (486b)

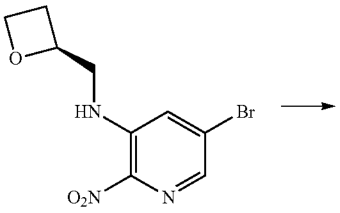

486a

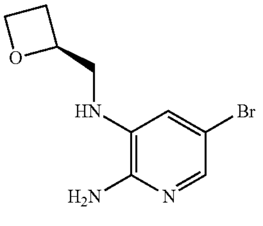

486b

To a solution of 486a (220 mg, 0.76 mmol) in acetic acid (5 ml) was added Fe (128 mg, 2.3 mmol). After stirring at 25° C. for 2 h, the reaction was filtered and the filtrate was diluted with EtOAc (30 ml) and washed with brine (30 mL×3). The combined organic layer was dried, evaporated to dryness to afford the crude title product (486b) (185 mg) as a brown solid. m/z (ESI, +ve ion)=258.0 $[M+H]^+$.

Step C. (S)-6-Bromo-2-(chloromethyl)-1-(oxetan-2-ylmethyl)-1H-imidazo[4,5-b]pyridine (486c)

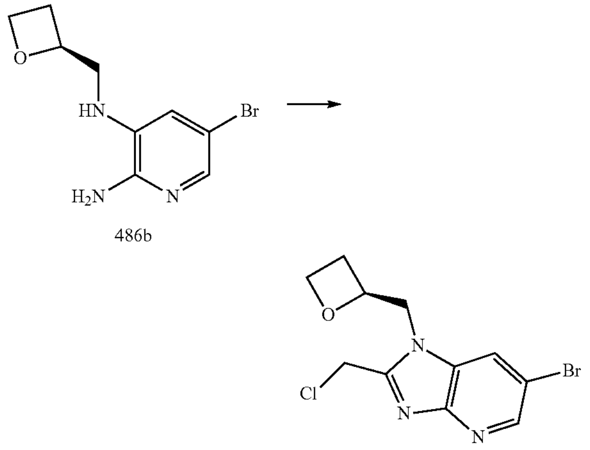

486b

486c

To a solution of 486b (70 mg, 0.27 mmol) and 2-chloro-1,1,1-trimethoxyethane (125.7 mg, 0.81 mmol) in $CH_3CN$ (3 ml) was added TsOH (17.2 mg, 0.02 mmol). After stirring under $N_2$ at 60° C. for 16 h, the reaction was diluted with EtOAc (20 mL) and washed with brine (20 mL×2). The combined organic layer was dried and evaporated to dryness to afford the crude title product (486c) (70 mg) as a yellow solid. m/z (ESI, +ve ion)=316.0 $[M+H]^+$.

Step D. (S)-4-((4-((1-((6-Bromo-1-(oxetan-2-ylmethyl)-1H-imidazo[4,5-b]pyridin-2-yl)methyl)piperidin-4-yl)oxy)pyrimidin-2-yl)methoxy)-3-fluorobenzonitrile (486d)

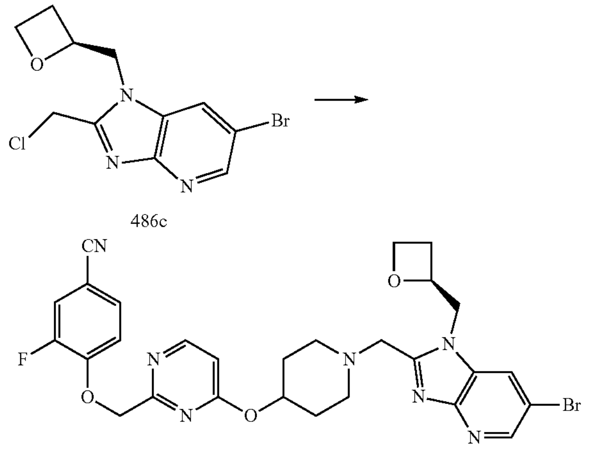

486c

486d

To a solution of 261c (40 mg, 0.12 mmol) and $K_2CO_3$ (49.7 mg, 0.36 mmol) in $CH_3CN$ (5 ml) was added 486c (38.5 mg, 0.122 mmol). After stirring at 25° C. for 16 h, the reaction was diluted with EtOAc (20 mL) and washed with brine (20 mL×2). The combined organic layer was dried and evaporated to dryness and the resulting residue was purified by Prep-TLC (5% MeOH/DCM) to afford the title product (486d) (70 mg, 85%) as a yellow solid. m/z (ESI, +ve ion)=608.1 $[M+H]^+$.

Step E. Methyl(S)-2-((4-((2-((4-cyano-2-fluorophenoxy)methyl)pyrimidin-4-yl)oxy)piperidin-1-yl)methyl)-1-(oxetan-2-ylmethyl)-1H-imidazo[4,5-b]pyridine-6-carboxylate (486e)

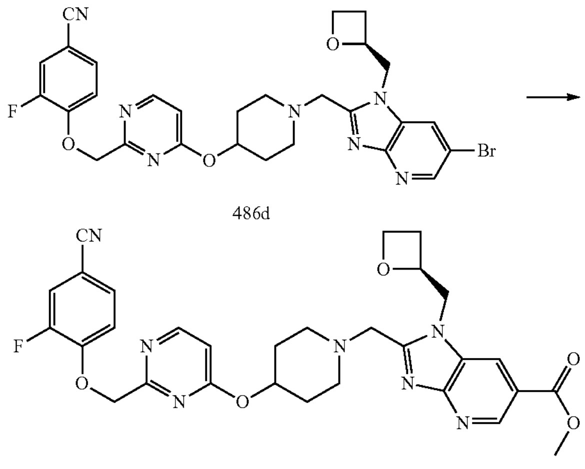

486d

486e

To a solution of 486d (100 mg, 0.16 mmol) and $Et_3N$ (49.7 mg, 0.49 mmol) in 50% DMSO/MeOH (5 ml) was added Pd(dppf)$Cl_2$ (12 mg, 0.016 mmol). The reaction was stirred under CO (1 atm) at 75° C. for 16 h. Then the reaction was diluted with EtOAc (50 mL) and washed with brine (50 mL×3). The combined organic layer was dried, evaporated to dryness and the resulting crude residue was purified by Prep-TLC (5% MeOH/DCM) to afford the title product (486e) (50 mg, 47%) as a yellow solid. m/z (ESI, +ve ion)=588.2 $[M+H]^+$.

Step F. (S)-2-((4-((2-((4-Cyano-2-fluorophenoxy)methyl)pyrimidin-4-yl)oxy)piperidin-1-yl)methyl)-1-(oxetan-2-ylmethyl)-1H-imidazo[4,5-b]pyridine-6-carboxylic acid (486)

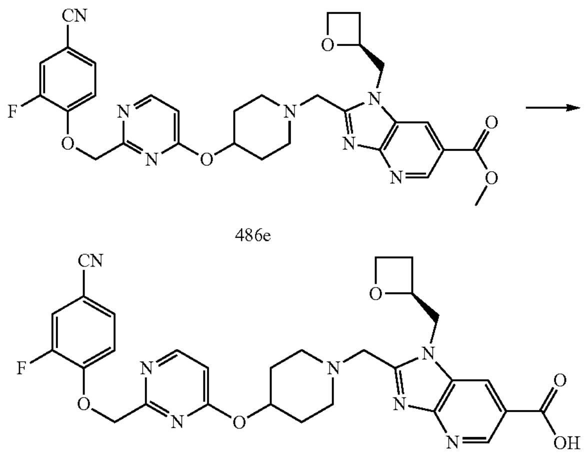

486e

486

To a solution of 486e (50 mg, 0.085 mmol) in 50% $THF/H_2O$ (2 mL) was added LiOH (4 mg, 0.17 mmol). After stirring at 20° C. for 2 h, the reaction was adjusted to pH=6 and purified by reverse phase HPLC ($CH_3CN$ in $H_2O$) to afford the title product (2.8 mg, 5.6%) as a white solid. $^1H$ NMR (400 MHZ, $CD_3OD$) δ ppm 9.06 (d, J=1.71 Hz, 1H), 8.68 (d, J=1.71 Hz, 1H), 8.44 (d, J=5.87 Hz, 1H), 7.56-7.65 (m, 1H), 7.47 (br d, J=8.56 Hz, 1H), 7.23 (1, J=8.56 Hz, 1H), 6.76 (d, J=5.87 Hz, 1H), 5.39 (s, 2H), 5.15-5.32 (m, 1H), 5.02 (br d, J=4.16 Hz, 1H), 4.84-4.86 (m, 1H), 4.59-4.80 (m, 2H), 4.48 (dt, J=9.11, 5.96 Hz., 1H), 4.08 (br d, J=14.18 Hz, 1H), 3.97 (br d, J=13.94 Hz, 1H), 2.69-2.95 (m, 3H), 2.37-2.57 (m, 3H), 1.85-2.04 (m, 2H), 1.68-1.82 (dt, J=8.44, 4.10 Hz, 2H). m/z (ESI, +ve ion)=574.1 $[M+H]^+$.

Examples 512 and 513 were synthesized in similar procedures as described in Example 355, Steps A to F, followed by similar procedures described in Example 486, with KI added at Step D of 486 synthesis.

Example 487 and 488 were synthesized from 261a following similar procedures as described in Example 313.

Example 489 was synthesized from 355d in similar procedures as described in Example 355, Steps E and F, followed by Example 367, Steps F and G.

Example 490. 2-(((2R,4S)-4-((2-((4-Cyano-2-fluorophenoxy)methyl)pyrimidin-4-yl)oxy)-2-(fluoromethyl)piperidin-1-yl)methyl)-1-(((S)-oxetan-2-yl)methyl)-1H-benzo[d]imidazole-6-carboxylic acid (490)

490

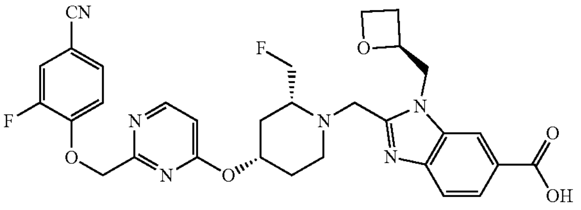

Step A. tert-Butyl(2R,4S)-4-((2-((4-cyano-2-fluorophenoxy)methyl)pyrimidin-4-yl)oxy)-2-(hydroxymethyl)piperidine-1-carboxylate (490b)

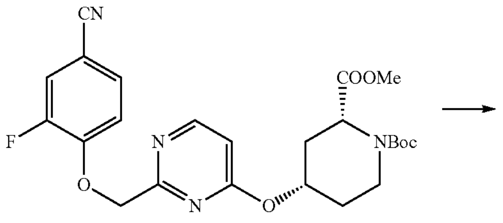

490a

-continued

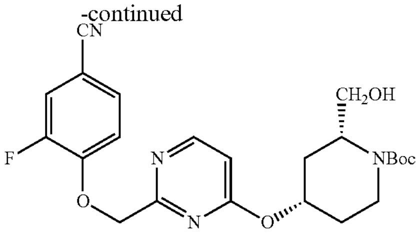

490b

To a solution of 490a (synthesized in similar procedures as 261b, 144 mg, 0.30 mmol) in anhydrous EtOH (3.0 mL) at 0° C. was added $NaBH_4$ (32 mg, 0.89 mmol) and $CaCl_2$) (99 mg, 0.89 mmol). The reaction was raised to room temperature, stirred for 12 h and quenched with 1 N HCl (1 mL) dropwise at 0° C. The reaction was extracted with EtOAc (5 mL×3) and the combined organic layer was dried over $Na_2SO_4$, filtered, concentrated and purified by silica gel column chromatography (gradient elution, 0-5% MeOH in $CH_2Cl_2$) to provide the title product (490b) (24 mg, 18%). m/z (ESI, +ve ion)=459.3 $[M+H]^+$.

Step B. Methyl 2-(((2R,4S)-4-((2-((4-cyano-2-fluorophenoxy)methyl)pyrimidin-4-yl)oxy)-2-(hydroxymethyl)piperidin-1-yl)methyl)-1-(((S)-oxetan-2-yl)methyl)-1H-benzo[d]imidazole-6-carboxylate (490c)

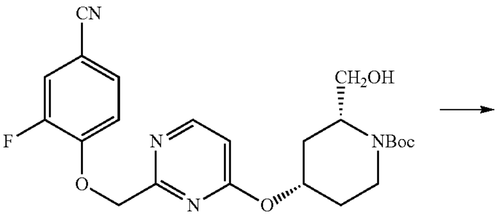

490b

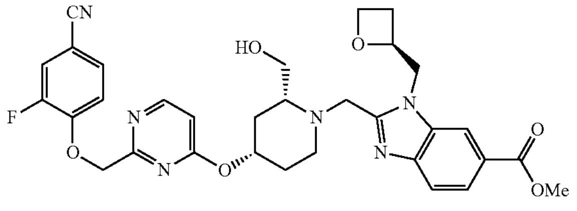

490c

The title product (490c) was synthesized from 490b in similar procedures as described in Example 355, Step F and G.

Step C. Methyl 2-(((2R,4S)-4-((2-((4-Cyano-2-fluorophenoxy)methyl)pyrimidin-4-yl)oxy)-2-(fluoromethyl)piperidin-1-yl)methyl)-1-(((S)-oxetan-2-yl)methyl)-1H-benzo[d]imidazole-6-carboxylate (490d)

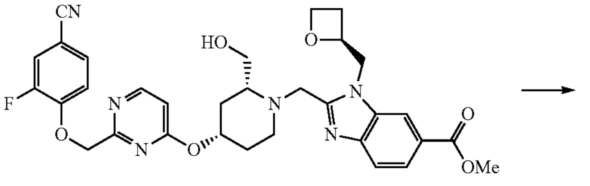

490c

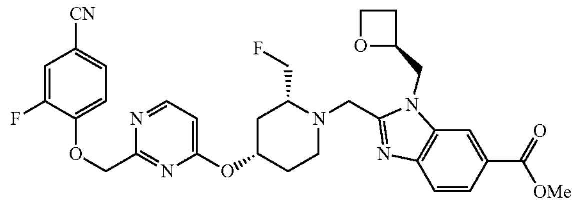

490d

To a solution of 490c (23 mg, 0.037 mmol) in anhydrous $CH_2Cl_2$ (0.37 mL) at 0° C. was added Deoxo-Fluor (22 mg, 0.045 mmol, 45% in THF) dropwise. The reaction was allowed to warm to room temperature and stirred for 1 h. Additional Deoxo-Fluor (22 mg, 0.045 mmol, 45% in THF) was added. After completion, the reaction was cooled down to 0° C. and quenched with dropwise addition of sat. $NaHCO_3$. The reaction was extracted with EtOAc, and washed with water and brine. The organic layer was dried over $Na_2SO_4$, filtered, concentrated and purified by silica gel column chromatography (gradient elution, 0-5% MeOH in $CH_2Cl_2$) to afford the title product (490d) (8 mg, 35%) as a colorless oil. m/z (ESI, +ve ion)=619.3 $[M+H]^+$.

Step D. 2-(((2R,4S)-4-((2-((4-Cyano-2-fluorophenoxy)methyl)pyrimidin-4-yl)oxy)-2-(fluoromethyl)piperidin-1-yl)methyl)-1-(((S)-oxetan-2-yl)methyl)-1H-benzo[d]imidazole-6-carboxylic acid (490)

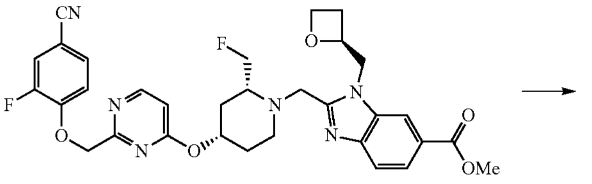

490d

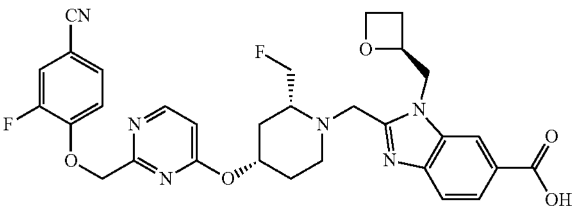

490

To a solution of 490d (8 mg, 0.013 mmol) in THF/$H_2O$ (1/1, 0.3 mL) was added $LiOH \cdot H_2O$ (3 mg, 0.065 mmol) and a few drops of MeOH. After heating at 40° C. for 4 h, the reaction was acidified with acetic acid to adjust to pH=5. The reaction mixture was diluted with EtOAc (3 mL) and washed with brine (2 mL). The organic layer was then dried over $Na_2SO_4$, filtered, concentrated and purified by silica gel column chromatography (gradient elution, 0-5% MeOH in DCM) to afford the title product (490) (3 mg, 38%) as a colorless film. NMR showed a pair of rotamers. $^1$H NMR (400 MHZ, $CD_3OD$) δ ppm 8.43 (dd, J=5.87, 1.71 Hz, 1H), 8.34-8.30 (m, 1H), 8.01-7.93 (m, 1H), 7.71-7.65 (m, 1H), 7.64-7.50 (m, 1H), 7.49-7.40 (m, 1H), 7.27-7.11 (m, 1H), 6.77-6.71 (m, 1H), 5.48 (s, 1H), 5.42-5.34 (m, 1H), 5.30-5.19 (m, 1H) 5.18-4.97 (m, 1H), 5.30-4.91 (m, 1H), 4.96-4.89 (m, 1H), 4.81-4.30 (m, 5H), 4.21-4.06 (m, 1H), 3.14-2.44 (m, 5H), 2.31-1.52 (m, 4H). m/z (ESI, +ve ion)=605.4 $[M+H]^+$.

Example 491 was synthesized from 3,5-dichloropyridazine in similar procedures as described in Example 355, with the first step using NaH as a base and reaction run at 0 to 20° C. for 2 h.

Example 492 and 493, 494, and 495 were synthesized in similar procedures as described in Example 355.

Example 496 was synthesized from 220a in similar procedures as described in Example 367, Step D, followed by Example 355, Steps F to H.

Example 497 was synthesized from 274c in similar procedures as described in Example 367, Steps C to G.

Example 498. (S)-2-((4-((2-((4-Cyano-2,5-difluorophenoxy)methyl)pyrimidin-4-yl)oxy)piperidin-1-yl)methyl)-1-(oxetan-2-ylmethyl)-1H-benzo[d]imidazole-6-carboxylic acid (498)

498

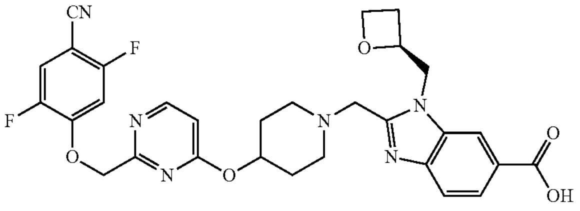

Step A. 2,5-Difluoro-4-hydroxybenzonitrile (498a)

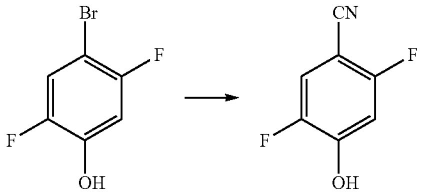

498a

To a solution of 4-bromo-2,5-difluorophenol (300 mg, 1.4 mmol) in DMF (10 mL) was added CuCN (514 mg, 5.7 mmol). After heating at 100° C. for 12 h, the reaction was cooled down, quenched with $H_2O$ (30 mL) and extracted with EtOAc (50 mL×3). The combined organic layer was dried over anhydrous $Na_2SO_4$, filtered, concentrated and purified by reverse phase HPLC (gradient elution, 0-70% $CH_3CN$ in $H_2O$) to afford the title product (498a) (200 mg, 85%) as a white solid. m/z (ESI, −ve ion)=154.1 $[M-H]^-$.

Step B. tert-Butyl 4-((2-(((methylsulfonyl)oxy)methyl)pyrimidin-4-yl)oxy)piperidine-1-carboxylate (498c)

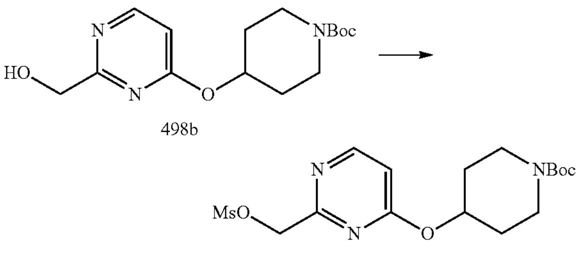

498b

498c

To a solution of 498b (synthesized in similar procedures as 355c, 400 mg, 1.2 mmol) in DCM (10 mL) was added DIPEA (1000 mg, 7.7 mmol). After stirring for 3 min at 0° C.), methanesulfonic anhydride (675 mg, 3.8 mmol) was added and the resulting mixture was stirred at 20° C. for 2 h. The reaction was quenched with $H_2O$ (8 mL) and extracted with EtOAc (5 mL×3). The combined organic layer was dried over anhydrous $Na_2SO_4$, filtered and concentrated to afford the crude title product (498c), which was used in the next step without further purification. m/z (ESI, +ve ion)=388.2 $[M+H]^+$.

Step C. tert-Butyl 4-((2-((4-cyano-2,5-difluorophenoxy)methyl)pyrimidin-4-yl)oxy)piperidine-1-carboxylate (498d)

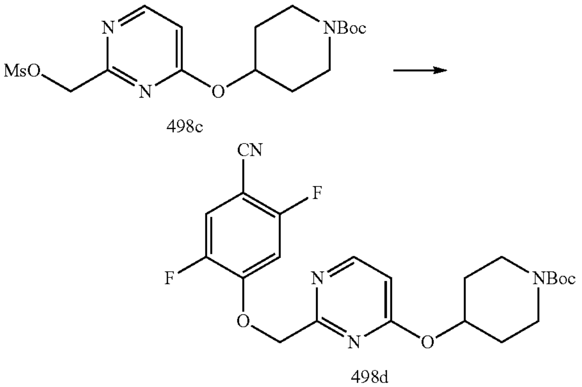

498c

498d

To a solution of 498c (100 mg, 0.25 mmol) in DMF (10 mL) was added 498a (44 mg, 0.28 mmol) and $K_2CO_3$ (178 mg, 1.29 mmol). After heating at 80° C. for 5 h, the reaction was quenched with $H_2O$ (40 mL) and extracted with EtOAc (15 mL×3). The combined organic layer was dried over anhydrous $Na_2SO_4$, filtered, concentrated and purified by reverse phase HPLC (gradient elution, 0-80% $CH_3CN$ in $H_2O$) to afford the title product (498d) (100 mg, 82%) as a light-yellow solid. m/z (ESI, +ve ion)=447.2 $[M+H]^+$.

Step D. (S)-2-((4-((2-((4-Cyano-2,5-difluorophenoxy)methyl)pyrimidin-4-yl)oxy)piperidin-1-yl)methyl)-1-(oxetan-2-ylmethyl)-1H-benzo[d]imidazole-6-carboxylic acid (498)

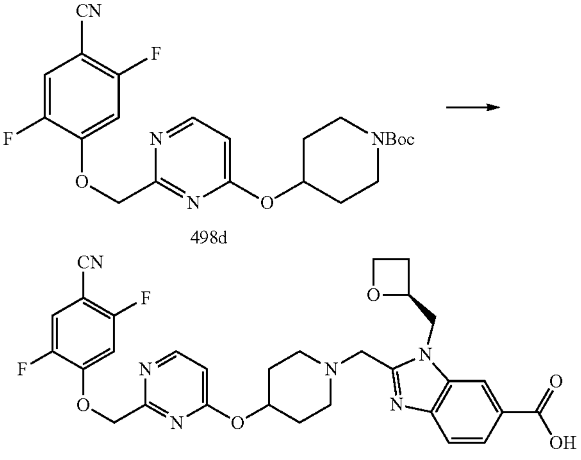

498d

498

The title compound (498) was synthesized from 498d in similar procedures as described in Example 220, Steps C to E, with Step D heating to 90° C. for 12 h. $^1H$ NMR (400 MHz, $CD_3OD$) δ ppm 8.44 (d, J=5.87 Hz, 1H), 8.21 (s, 1H), 7.95 (dd, J=8.31, 1.47 Hz, 1H), 7.64 (dd, J=10.51, 6.11 Hz, 1H), 7.60 (d, J=8.56 Hz, 1H), 7.25 (dd, J=11.00, 6.85 Hz, 1H), 6.77 (d, J=5.87 Hz, 1H), 5.40 (s, 2H), 5.26 (qd, J=7.13, 2.81 Hz, 1H), 5.02 (br d, J=4.16 Hz, 1H), 4.83-4.87 (m, 1H), 4.60-4.73 (m, 2H), 4.46 (dt, J=9.17, 5.93 Hz, 1H), 3.96-4.02 (m, 1H), 3.85-3.93 (m, 1H), 2.73-2.84 (m, 3H), 2.48-2.57 (m, 1H), 2.29-2.39 (m, 2H), 1.87-2.01 (m, 2H), 1.76 (td, J=8.80, 4.40 Hz, 2H). m/z (ESI, +ve ion)=589.1 $[M+H]^+$.

Example 500 was synthesized in similar procedures as described in Example 498, with KI added at the second to last step and reaction run at room temperature.

Example 499 was synthesized in similar procedures as described in Example 220.

Examples 501, 503 were synthesized in similar procedures as described in Example 363.

Example 502 was synthesized from 498d in similar procedures as described in Example 206, Steps D to F, with THE as the solvent for the last step.

Example 504 was synthesized in similar procedures from 498c as described in Example 498, Step D, followed by Example 355, Step F and Example 304, Steps A and B. Isopropanol was used as solvent to replace MeOH at the last step.

Example 505 was synthesized in similar procedures as described in Example 504.

Example 506, Example 507 were synthesized from 261a in similar procedures as described in Example 313. DMF was used as solvent for the second to last step and THF/$H_2O$/isopropanol (2:1:1) was used as solvent for the last step.

Example 511 was synthesized in similar procedures as described in Example 382.

Example 514 was synthesized in similar procedures as described in Example 261,

Steps A to C, followed by Example 367, Steps F and G, with KI added at the second to last step.

Example 515 was synthesized in similar procedures as described in Example 355, Steps A to F, followed by Example 367, Steps F and G, with KI added at the second to last step.

Biological Example 1

GLP-1R CAMP Assay

CAMP accumulation was measured in Chinese hamster ovary (CHO) cells stably overexpressing the human GLP-1 receptor using the HitHunter CAMP Assay for Small Molecules Kit (Eurofins). Briefly, cells were grown in Ham's F12 Nutrient Mix with 10% FBS, and lifted with Cell Dissociation Buffer, Enzyme free, PBS based (ThermoFisher). Cells were pelleted, and resuspended in Hank's buffered saline solution with 10 mM HEPES, and 625 μM 3-isobutyl-1-methylxanthine. The anti-cAMP antibody reagent was then added to cells at a 1:2 ratio and 5 μL of mixture was seeded in 384-well small volume white assay plates, at 10,000 cells/well. Cells were then treated with 50 nL compound using an ECHO 550 acoustic dispenser (Labcyte) in a 20-point dose response format in triplicate for 30 min. Cells were then lysed, and detection reagents added according to the manufacturer's protocol. After overnight incubation, luminescence was measured using a Perkin Elmer Envision plate reader. Dose response curves were analyzed using GraphPad Prism 9.0.

Results are reported in Table 1 below. In the Table, $EC_{50}$ values are +++≤50 nM<++≤500 nM<+. Molecular weights are calculated by standard techniques, and mass spectrometry results are reported according to the Examples above.

| Example Compound | EC50 | MW Calc. | $[M + H]^+$ Found |
|---|---|---|---|
| 1 | ++ | 479.54 | 480.2 |
| 2 | + | 629.03 | 629.3 |
| 3 | + | 542.61 | 543.3 |
| 4 | + | 551.6 | 552.3 |
| 5 | + | 540.62 | 541.3 |
| 6 | + | 556.62 | 557.4 |
| 7 | + | 561.04 | 561.2 |
| 8 | ++ | 565.07 | 565.3 |
| 9 | ++ | 585.48 | 585.3 |
| 10 | + | 569.59 | 570.2 |
| 11 | + | 595.48 | 595.3 |
| 12 | + | 579.03 | 579.5 |
| 13 | + | 544.58 | 545.3 |
| 14 | + | 540.62 | 541.4 |
| 15 | ++ | 575.06 | 575.2 |
| 16 | + | 558.61 | 559.3 |
| 17 | + | 540.62 | 541.2 |
| 18 | ++ | 554.65 | 555.2 |
| 19 | ++ | 579.05 | 579.2 |
| 20 | + | 516.6 | 517.2 |
| 21 | + | 540.62 | 541.4 |
| 22 | + | 540.62 | 541.3 |
| 23 | + | 589.09 | 589.3 |
| 24 | + | 593.08 | 593.2 |
| 25 | + | 539.64 | 540.3 |
| 26 | ++ | 599.47 | 599.1 |
| 27 | + | 605.52 | 605.2 |
| 28 | + | 589.06 | 589.2 |
| 29 | ++ | 553.66 | 554.3 |
| 30 | + | 530.58 | 531.3 |
| 31 | + | 565.02 | 565.2 |
| 32 | ++ | 573.09 | 573.2 |
| 33 | + | 538.65 | 539.3 |
| 34 | +++ | 542.6 | 543.3 |
| 35 | + | 526.64 | 527.3 |
| 36 | + | 583.01 | 583.2 |
| 37 | + | 573.58 | 574.2 |
| 38 | + | 579.05 | 579.2 |

-continued

| Example Compound | EC50 | MW Calc. | $[M + H]^+$ Found |
|---|---|---|---|
| 39 | + | 565.02 | 565.2 |
| 40 | + | 565.02 | 565.2 |
| 41 | ++ | 558.64 | 559.3 |
| 42 | + | 544.61 | 545.3 |
| 43 | + | 544.61 | 545.3 |
| 44 | ++ | 566.61 | 567.2 |
| 45 | +++ | 567.69 | 568.3 |
| 46 | ++ | 591.72 | 592.4 |
| 47 | +++ | 637.52 | 637.2 |
| 48 | ++ | 593.51 | 593.2 |
| 49 | + | 619.65 | 620.4 |
| 50 | + | 574.08 | 574.3 |
| 51 | +++ | 588.11 | 588.4 |
| 52 | +++ | 602.13 | 602.4 |
| 53 | + | 500.48 | 501.2 |
| 54 | ++ | 626.16 | 626.4 |
| 55 | +++ | 596.69 | 597.3 |
| 56 | ++ | 611.14 | 611.4 |
| 57 | ++ | 613.12 | 613.3 |
| 58 | + | 612.13 | 612.4 |
| 59 | ++ | 583.47 | 583.2 |
| 60 | +++ | 585.48 | 585.3 |
| 61 | + | 547.66 | 548.2 |
| 62 | + | 541.61 | 542.3 |
| 63 | +++ | 623.54 | 625.2 |
| 64 | ++ | 589.09 | 589.3 |
| 65 | ++ | 627.14 | 627.4 |
| 66 | + | 583.62 | 584.3 |
| 67 | + | 621.67 | 622.4 |
| 68 | + | 583.62 | 584.3 |
| 69 | + | 621.67 | 622.3 |
| 70 | + | 603.69 | 604.3 |
| 71 | + | 653.58 | 653.2 |
| 72 | +++ | 584.49 | 584.2 |
| 73 | + | 599.47 | 599.1 |
| 74 | + | 585.48 | 585.2 |
| 75 | +++ | 602.13 | 602.4 |
| 76 | +++ | 640.19 | 640.4 |
| 77 | + | 640.19 | 640.4 |
| 78 | + | 602.13 | 602.4 |
| 79 | + | 626.16 | 626.4 |
| 80 | + | 588.11 | 588.4 |
| 81 | ++ | 605.09 | 605.3 |
| 82 | + | 484.5 | 485.2 |
| 83 | +++ | 484.5 | 485.2 |
| 84 | +++ | 582.48 | 582.1 |
| 85 | ++ | 589.09 | 589.3 |
| 86 | + | 624.15 | 624.2 |
| 87 | ++ | 614.14 | 614.2 |
| 88 | + | 589.09 | 589.2 |
| 89 | ++ | 582.7 | 583.3 |
| 90 | + | 575.04 | 575.1 |
| 91 | + | 460.47 | 461.2 |
| 92 | ++ | 485.48 | 486.1 |
| 93 | ++ | 628.17 | 628.4 |
| 94 | + | 613.49 | 613.2 |
| 95 | ++ | 606.1 | 606.3 |
| 96 | + | 613.49 | 613.1 |
| 97 | + | 514.37 | 514.2 |
| 98 | +++ | 606.1 | 606.3 |
| 99 | ++ | 589.09 | 589.2 |
| 100 | +++ | 606.1 | 606.2 |
| 101 | ++ | 589.09 | 589.2 |
| 102 | ++ | 600.45 | 600.1 |
| 103 | +++ | 594.53 | 594.2 |
| 104 | +++ | 632.59 | 632.2 |
| 105 | + | 600.16 | 600.3 |
| 106 | ++ | 571.12 | 571.3 |
| 107 | + | 513.38 | 513.2 |
| 108 | +++ | 623.54 | 623.2 |
| 109 | +++ | 622.55 | 622.2 |
| 110 | ++ | 494.38 | 494.2 |
| 111 | ++ | 575.11 | 575.3 |
| 112 | ++ | 587.12 | 587.2 |
| 113 | + | 600.45 | 600.1 |
| 114 | +++ | 565.674 | 566.2 |

-continued

| Example Compound | EC50 | MW Calc. | [M + H]+ Found |
|---|---|---|---|
| 115 | +++ | 593.728 | 594.3 |
| 116 | +++ | 573.13 | 573.3 |
| 117 | ++ | 571.12 | 571.2 |
| 118 | +++ | 575.11 | 575.2 |
| 120 | +++ | 613.16 | 613.3 |
| 121 | + | 575.04 | 575.1 |
| 122 | +++ | 614.14 | 614.3 |
| 123 | +++ | 593.1 | 593.2 |
| 124 | +++ | 623.54 | 623.2 |
| 125 | +++ | 624.52 | N/A |
| 126 | ++ | 612.52 | 612.3 |
| 128 | +++ | 633.57 | 633.2 |
| 129 | +++ | 586.47 | 586.2 |
| 130 | +++ | 628.17 | 628.3 |
| 131 | +++ | 630.16 | 630.3 |
| 132 | +++ | 648.15 | 648.3 |
| 133 | +++ | 650.58 | 650.3 |
| 135 | ++ | 612.52 | 612.1 |
| 136 | +++ | 592.09 | 592.3 |
| 137 | +++ | 650.58 | 650.3 |
| 138 | +++ | 614.1 | 614.4 |
| 139 | +++ | 633.57 | 633.3 |
| 140 | +++ | 633.57 | 633.3 |
| 141 | +++ | 603.12 | 603.3 |
| 142 | + | 591.49 | 591 |
| 143 | ++ | 629.54 | 629 |
| 144 | +++ | 630.15 | 630.2 |
| 145 | +++ | 635.55 | 635 |
| 146 | +++ | 570.69 | 571.3 |
| 148 | +++ | 608.56 | 608.3 |
| 149 | +++ | 605.52 | 605.3 |
| 150 | +++ | 663.6 | 663.3 |
| 151 | +++ | 608.56 | 608.4 |
| 152 | +++ | 601.14 | 601.2 |
| 153 | +++ | 639.2 | 639.2 |
| 154 | ++ | 592.09 | 592.2 |
| 155 | +++ | 631.56 | 631.3 |
| 156 | +++ | 638.51 | 638.3 |
| 157 | +++ | 634.56 | 634.3 |
| 158 | +++ | 599.13 | 599.4 |
| 159 | +++ | 596.08 | 596.3 |
| 160 | +++ | 644.13 | 644.3 |
| 161 | +++ | 668.57 | 668.3 |
| 162 | +++ | 612.52 | 612.3 |
| 163 | +++ | 647.6 | 647.3 |
| 164 | +++ | 665.59 | 665.3 |
| 165 | +++ | 623.15 | 623.3 |
| 166 | +++ | 585.1 | 585.3 |
| 168 | +++ | 597.49 | 597.3 |
| 169 | +++ | 611.52 | 611.3 |
| 170 | +++ | 608.48 | 608.3 |
| 171 | +++ | 626.11 | 626.4 |
| 174 | +++ | 596.51 | 596.3 |
| 178 | ++ | 597.49 | 597.3 |
| 179 | +++ | 635.55 | 635.3 |
| 182 | +++ | 588.06 | 588.3 |
| 183 | +++ | 571.609 | 572.4 |
| 186 | +++ | 614.48 | 614.1 |
| 187 | +++ | 568.649 | 569.4 |
| 188 | +++ | 606.702 | 607.4 |
| 189 | +++ | 658.58 | 658.3 |
| 198 | +++ | 597.49 | 597.3 |
| 199 | +++ | 635.55 | 635.3 |
| 200 | +++ | 595.52 | 595.2 |
| 202 | +++ | 650.58 | 650.2 |
| 203 | +++ | 650.58 | 650.2 |
| 204 | ++ | 662.61 | 662.3 |
| 205 | ++ | 662.61 | 662.3 |
| 206 | +++ | 570.621 | 571.2 |
| 207 | +++ | 580.05 | 580.2 |
| 208 | +++ | 607.49 | 607.2 |
| 214 | +++ | 625.51 | 625.2 |
| 215 | +++ | 625.13 | 625.3 |
| 216 | +++ | 607.49 | 607.2 |
| 217 | +++ | 607.49 | 607.3 |
| 220 | +++ | 581.04 | 581.2 |

-continued

| Example Compound | EC50 | MW Calc. | [M + H]+ Found |
|---|---|---|---|
| 221 | +++ | 580.05 | 580.1 |
| 224 | +++ | 614.5 | 632.3 (ammonium + H) |
| 227 | +++ | 615.51 | 615.3 |
| 230 | +++ | 619.09 | 619.3 |
| 231 | +++ | 618.11 | 618.3 |
| 232 | +++ | 598.06 | 598.3 |
| 239 | +++ | 599.04 | 599.3 |
| 240 | +++ | 599.04 | 599.3 |
| 241 | +++ | 599.04 | 599.3 |
| 242 | +++ | 596.51 | 596.3 |
| 243 | +++ | 596.51 | 596.3 |
| 246 | +++ | 626.11 | 626.3 |
| 247 | +++ | 619.09 | 619.3 |
| 248 | ++ | 588.06 | 588.3 |
| 249 | +++ | 581.04 | 581.3 |
| 250 | +++ | 581.04 | 581.3 |
| 251 | + | 599.04 | 599.3 |
| 252 | + | 599.04 | 599.3 |
| 253 | + | 599.04 | 599.3 |
| 254 | +++ | 610.53 | 610.2 |
| 255 | +++ | 620.53 | 620.1 |
| 256 | +++ | 652.53 | 652.2 |
| 257 | +++ | 608.48 | 608.1 |
| 258 | +++ | 592.02 | 592.3 |
| 259 | +++ | 612.09 | 612.3 |
| 260 | +++ | 641.14 | 641.2 |
| 261 | +++ | 610.65 | 611.4 |
| 262 | +++ | 572.597 | 573.3 |
| 263 | +++ | 641.14 | 641.3 |
| 264 | +++ | 605.07 | 605.3 |
| 265 | +++ | 592.02 | 592.3 |
| 266 | +++ | 592.02 | 592.3 |
| 267 | +++ | 605.07 | 605.3 |
| 268 | +++ | 592.02 | 592.3 |
| 269 | +++ | 592.02 | 592.3 |
| 270 | +++ | 592.02 | 592.3 |
| 271 | ++ | 635.55 | 635.1 |
| 272 | ++ | 634.56 | 634.2 |
| 274 | +++ | 649.57 | 649.2 |
| 275 | +++ | 609.662 | 610.3 |
| 276 | +++ | 654.17 | 654.3 |
| 277 | +++ | 571.609 | 572.4 |
| 278 | +++ | 637.56 | 637.2 |
| 279 | +++ | 637.56 | 637.2 |
| 280 | +++ | 596.51 | 596.2 |
| 283 | +++ | 611.52 | 611.1 |
| 284 | + | 596.51 | 596.2 |
| 285 | +++ | 571.609 | 572.4 |
| 286 | + | 597.49 | 597.2 |
| 287 | +++ | 631.13 | 631.2 |
| 288 | + | 581.04 | 581.2 |
| 290 | +++ | 595.07 | 595.2 |
| 291 | +++ | 595.07 | 595.2 |
| 292 | +++ | 593.08 | 593.3 |
| 294 | ++ | 619.09 | 619.2 |
| 295 | +++ | 611.52 | 611.1 |
| 296 | +++ | 582.03 | 582.3 |
| 297 | +++ | 596.607 | 597.3 |
| 299 | +++ | 595.07 | 595.2 |
| 300 | +++ | 604.63 | 605.3 |
| 301 | +++ | 595.619 | 596.3 |
| 302 | +++ | 614.598 | 615.3 |
| 303 | +++ | 629.628 | 630.3 |
| 304 | +++ | 598.48 | 598.2 |
| 305 | +++ | 616.47 | 616.2 |
| 306 | +++ | 572.597 | 573.3 |
| 307 | +++ | 590.588 | 591.3 |
| 308 | +++ | 582.03 | 582.2 |
| 309 | +++ | 588.612 | 589.1 |
| 310 | +++ | 613.61 | 614.4 |
| 311 | +++ | 597.595 | 598.3 |
| 312 | +++ | 615.586 | 616.3 |
| 313 | +++ | 586.624 | 587.4 |
| 314 | +++ | 606.606 | 607.3 |
| 315 | +++ | 600.02 | 600.3 |
| 316 | +++ | 620.08 | 620.1 |

-continued

| Example Compound | EC50 | MW Calc. | $[M + H]^+$ Found |
|---|---|---|---|
| 317 | +++ | 588.612 | 589.2 |
| 318 | +++ | 570.621 | 571.3 |
| 319 | +++ | 584.648 | 585.3 |
| 320 | +++ | 602.639 | 603.3 |
| 321 | +++ | 597.06 | 597.2 |
| 322 | +++ | 614.598 | 615.1 |
| 323 | +++ | 604.615 | 605.3 |
| 324 | +++ | 616.04 | 616.3 |
| 325 | +++ | 605.07 | 605.3 |
| 326 | +++ | 582.03 | 582.3 |
| 327 | +++ | 616.04 | 616.3 |
| 328 | +++ | 590.588 | 591.3 |
| 329 | +++ | 600.02 | 600.3 |
| 330 | +++ | 589.6 | 590.3 |
| 331 | +++ | 595.635 | 596.3 |
| 333 | +++ | 607.08 | 607.2 |
| 335 | +++ | 599.03 | 599.1 |
| 336 | +++ | 599.03 | 599.1 |
| 337 | +++ | 604.08 | 604.1 |
| 338 | +++ | 615.586 | 616.3 |
| 339 | +++ | 613.626 | 614.4 |
| 340 | +++ | 621.52 | 621.3 |
| 341 | +++ | 639.51 | 639.3 |
| 342 | +++ | 615.586 | 616.3 |
| 343 | +++ | 588.616 | 589.3 |
| 344 | +++ | 587.02 | 587.3 |
| 345 | +++ | 581.04 | 581.1 |
| 346 | +++ | 581.04 | 581.1 |
| 347 | +++ | 589.6 | 590.4 |
| 348 | +++ | 595.635 | 596.4 |
| 349 | +++ | 613.626 | 614.4 |
| 352 | +++ | 563.05 | 563.3 |
| 353 | +++ | 609.662 | 610.3 |
| 354 | +++ | 623.12 | 623.2 |
| 355 | +++ | 586.624 | 587.3 |
| 356 | +++ | 614.598 | 615.2 |
| 357 | +++ | 596.607 | 597.2 |
| 358 | +++ | 588.06 | 588.1 |
| 359 | +++ | 606.05 | 606.1 |
| 362 | +++ | 619.645 | 620.3 |
| 363 | +++ | 585.636 | 586.3 |
| 364 | +++ | 610.634 | 611.4 |
| 365 | +++ | 589.6 | 590.4 |
| 366 | +++ | 602.09 | 602.1 |
| 367 | +++ | 589.6 | 590.3 |
| 368 | +++ | 595.07 | 595.1 |
| 369 | +++ | 589.05 | 589.3 |
| 370 | +++ | 583.02 | 583.3 |
| 371 | +++ | 616.574 | 617.3 |
| 372 | +++ | 572.597 | 573.3 |
| 373 | +++ | 573.585 | 574.3 |
| 374 | +++ | 590.588 | 591.3 |
| 375 | +++ | 587.612 | 588.3 |
| 376 | +++ | 629.613 | 630.2 |
| 377 | +++ | 630.601 | 631.1 |
| 378 | +++ | 582.03 | 582.3 |
| 379 | +++ | 572.597 | 573.3 |
| 380 | +++ | 599.03 | 599.2 |
| 381 | +++ | 581.05 | 581.3 |
| 382 | +++ | 595.07 | 595.3 |
| 475 | +++ | 587.652 | 588.2 |
| 476 | +++ | 594.672 | 595.3 |
| 477 | +++ | 603.08 | 603.3 |
| 478 | +++ | 607.59 | 608.2 |
| 479 | +++ | 565.578 | 566.3 |
| 480 | ++ | 586.624 | 587.2 |
| 481 | +++ | 589.05 | 589.1 |
| 482 | +++ | 583.568 | 584.2 |
| 483 | +++ | 676.1 | 676.2 |
| 484 | +++ | 586.624 | 587.3 |
| 485 | +++ | 579.605 | 580.3 |
| 486 | +++ | 573.585 | 574.1 |
| 487 | ++ | 598.635 | 599.4 |
| 488 | ++ | 598.635 | 599.4 |
| 489 | +++ | 603.08 | 603.1 |
| 490 | +++ | 604.615 | 605.4 |

-continued

| Example Compound | EC50 | MW Calc. | $[M + H]^+$ Found |
|---|---|---|---|
| 491 | +++ | 572.597 | 573.3 |
| 492 | +++ | 604.615 | 605.3 |
| 493 | +++ | 604.615 | 605.3 |
| 494 | +++ | 601.559 | 602.2 |
| 495 | +++ | 583.568 | 584.1 |
| 496 | +++ | 582.58 | 583.1 |
| 497 | +++ | 578.617 | 579.3 |
| 498 | +++ | 590.588 | 591.2 |
| 499 | +++ | 585.636 | 586.3 |
| 500 | +++ | 586.624 | 587.2 |
| 501 | +++ | 603.627 | 604.3 |
| 502 | +++ | 608.578 | 609.2 |
| 503 | +++ | 599.663 | 600.3 |
| 504 | +++ | 590.588 | 591.3 |
| 505 | +++ | 608.578 | 609.3 |
| 506 | +++ | 584.608 | 585.3 |
| 507 | +++ | 584.608 | 585.3 |
| 508 | +++ | 613 | 613.3 |
| 509 | +++ | 627 | 627.3 |
| 510 | +++ | 609 | 609.3 |
| 511 | +++ | 653.13 | 653.1 |
| 512 | + | 580.593 | 581.2 |
| 513 | +++ | 587.612 | 588.2 |
| 514 | +++ | 597.595 | 598.2 |
| 515 | +++ | 600.651 | 601.2 |

Intravenous Glucose Tolerance Test (IVGTT) in Cynomolgus Monkeys

Aged (<8 years old) cynomolgus monkeys (*Macaca fascicularis*; N=4-5/test article) were fasted overnight and anesthetized with ketamine prior to the intravenous glucose tolerance test (IVGTT). The test articles were formulated at 6 mg/mL in vehicle (5% polyethylene glycol 400: 95% (12% (w/v) sulfobutylether-β-cyclodextrin in deionized water) (v/v)]) and administered by intravenous bolus into a peripheral vein 1-6 minutes prior to the IVGTT. The IVGTT was initiated by administration of an IV bolus of glucose (0.5 g/kg as a 50% glucose solution). Blood samples were collected from a peripheral vein 0, 1, 3, 5, 10, 20, 40 and 60 minutes upon completion of the IV bolus glucose injection. The blood samples were collected directly into potassium ethylene diamine tetra-acetic acid tubes and plasma separated by centrifugation at 2,500 g for 10 minutes within 30 minutes of collection. The plasma from all time points was analyzed for insulin concentrations (μU/mL) using a Cobas e411 Immunology analyzer. Insulin area-under-the-curve (AUC) was calculated using GraphPad Prism software (v 9). As shown in FIG. 1, an increase in insulin secretion was observed, consistent with the substantial increase of insulin AUC following administration of compounds 145, 171, 313, 326, 335, 355, and 338 respectively.

EQUIVALENTS

The disclosure set forth above may encompass multiple distinct embodiments with independent utility. Although each of these embodiments has been disclosed, the specific embodiments thereof as disclosed and illustrated herein are not to be considered in a limiting sense, because numerous variations are possible. The subject matter of the embodiments includes all novel and nonobvious combinations and subcombinations of the various elements, features, functions, and/or properties disclosed herein. The following claims particularly point out certain combinations and subcombinations regarded as novel and nonobvious. Alternative embodiments as in other combinations and subcombinations of features, functions, elements, and/or properties may be claimed in this application, in applications claiming priority from this application, or in related applications. Such claims, whether directed to a different embodiment or to the same embodiment, and whether broader, narrower, equal, or different in scope in comparison to the original claims, also are regarded as included within the subject matter of this disclosure.

One or more features from any embodiments described herein or in the FIGURES may be combined with one or more features of any other embodiments described herein or in the FIGURES without departing from the scope of this disclosure.

All publications, patents and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed is:

1. A compound which is 2-(((2S,4S)-4-((2-((2,4-difluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid:

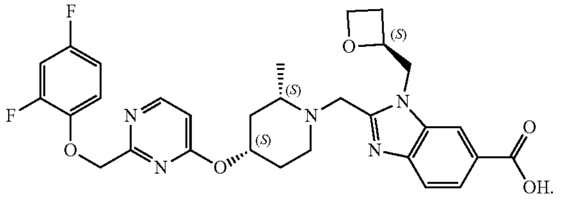

or a pharmaceutically acceptable salt thereof.

2. The compound of claim 1, which is 2-(((2S,4S)-4-((2-((2,4-difluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid:

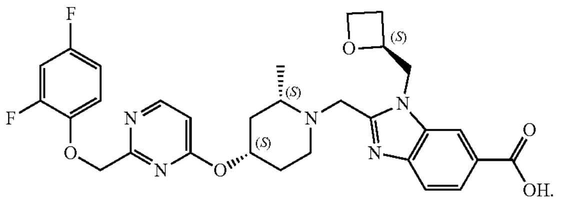

3. The compound of claim 1, which is a pharmaceutically acceptable salt of 2-(((2S,4S)-4-((2-((2,4-difluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid:

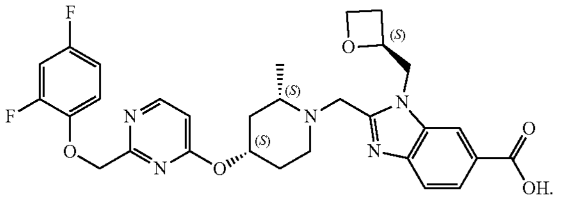

4. A pharmaceutical composition comprising 2-(((2S,4S)-4-((2-((2,4-difluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid:

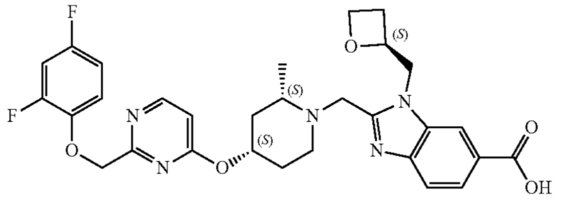

or a pharmaceutically acceptable salt thereof, and one or more pharmaceutically acceptable excipients.

5. The pharmaceutical composition of claim 4, comprising 2-(((2S,4S)-4-((2-((2,4-difluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid:

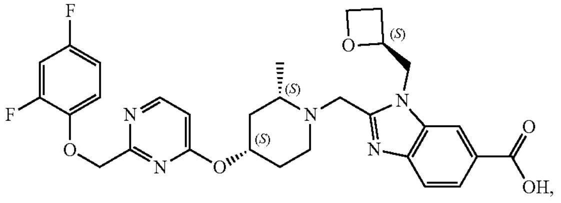

and one or more pharmaceutically acceptable excipients.

6. The pharmaceutical composition of claim 4, comprising a pharmaceutically acceptable salt of 2-(((2S,4S)-4-((2-((2,4-difluorophenoxy)methyl)pyrimidin-4-yl)oxy)-2-methylpiperidin-1-yl)methyl)-1-(((S)-oxetan-2-yl)methyl)-1H-benzo[d]imidazole-6-carboxylic acid:

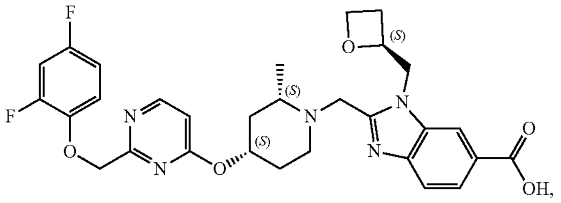

and one or more pharmaceutically acceptable excipients.

* * * * *